(12) United States Patent
Ganguly et al.

(10) Patent No.: US 11,999,777 B2
(45) Date of Patent: *Jun. 4, 2024

(54) METHODS FOR TREATING OR PREVENTING SARS-COV-2 INFECTIONS AND COVID-19 WITH ANTI-SARS-COV-2 SPIKE GLYCOPROTEIN ANTIBODIES

(71) Applicant: Regeneron Pharmaceuticals, Inc., Tarrytown, NY (US)

(72) Inventors: Samit Ganguly, Elmsford, NY (US); Jennifer Hamilton, Ridgefield, CT (US); Gary Herman, Princeton, NJ (US); Andrea Hooper, Port Chester, NY (US); Flonza Isa, Yonkers, NY (US); Meagan O'Brien, New York, NY (US); Sumathi Sivapalasingam, Brooklyn, NY (US); Kenneth Turner, Ridgefield, CT (US); Eduardo Forleo Neto, Greenwich, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 106 days.

This patent is subject to a terminal disclaimer.

(21) Appl. No.: 17/337,396

(22) Filed: Jun. 2, 2021

(65) Prior Publication Data
US 2021/0395345 A1    Dec. 23, 2021

Related U.S. Application Data

(60) Provisional application No. 63/186,029, filed on May 7, 2021, provisional application No. 63/185,301, filed on May 6, 2021, provisional application No. 63/173,468, filed on Apr. 11, 2021, provisional application No. 63/166,187, filed on Mar. 25, 2021, provisional application No. 63/165,654, filed on Mar. 24, 2021, provisional application No. 63/164,488, filed on Mar. 22, 2021, provisional application No. 63/162,996, filed on Mar. 18, 2021, provisional application No. 63/162,504, filed on Mar. 17, 2021, provisional application No. 63/150,978, filed on Feb. 18, 2021, provisional application No. 63/144,789, filed on Feb. 2, 2021, provisional application No. 63/142,471, filed on Jan. 27, 2021, provisional application No. 63/141,952, filed on Jan. 26, 2021, provisional application No. 63/141,423, filed on Jan. 25, 2021, provisional application No. 63/131,627, filed on Dec. 29, 2020, provisional application No. 63/124,980, filed on Dec. 14, 2020, provisional application No. 63/120,065, filed on Dec. 1, 2020, provisional application No. 63/119,593, filed on Nov. 30, 2020, provisional application No. 63/116,773, filed on Nov. 20, 2020, provisional application No. 63/112,140, filed on Nov. 10, 2020, provisional application No. 63/106,696, filed on Oct. 28, 2020, provisional application No. 63/105,779, filed on Oct.

(Continued)

(51) Int. Cl.
| | | |
|---|---|---|
| C07K 16/10 | (2006.01) | |
| A61K 9/00 | (2006.01) | |
| A61K 31/706 | (2006.01) | |
| A61K 39/42 | (2006.01) | |
| A61K 45/06 | (2006.01) | |
| A61P 31/14 | (2006.01) | |
| C07K 16/28 | (2006.01) | |
| A61K 39/00 | (2006.01) | |

(52) U.S. Cl.
CPC ............ *C07K 16/10* (2013.01); *A61K 9/0019* (2013.01); *A61K 31/706* (2013.01); *A61K 39/42* (2013.01); *A61K 45/06* (2013.01); *A61P 31/14* (2018.01); *C07K 16/2866* (2013.01); *A61K 2039/507* (2013.01); *A61K 2039/54* (2013.01); *C07K 2317/33* (2013.01); *C07K 2317/565* (2013.01); *C07K 2317/76* (2013.01)

(58) Field of Classification Search
CPC ............. C07K 16/10; C07K 2317/565; C07K 16/2866; A61K 39/42; A61K 2039/507
See application file for complete search history.

(56) References Cited

U.S. PATENT DOCUMENTS

| | | | | |
|---|---|---|---|---|
| 10,787,501 B1 * | 9/2020 | Babb | ...................... | A61K 39/15 |
| 10,822,379 B1 | 11/2020 | Dimitrov et al. | | |

(Continued)

FOREIGN PATENT DOCUMENTS

| | | |
|---|---|---|
| CN | 111088283 A | 5/2020 |
| CN | 111285933 A | 6/2020 |

(Continued)

OTHER PUBLICATIONS

Wang Y. Evaluation of the efficacy and safety of intravenous remdesivir in adult patients with severe COVID-19: study protocol for a phase 3 randomized, double-blind, placebo-controlled, multicentre trial. Trials. May 24, 2020;21(1):422. (Year: 2020).*

(Continued)

*Primary Examiner* — Aurora M Fontainhas
*Assistant Examiner* — Jennifer A Benavides
(74) *Attorney, Agent, or Firm* — Schwabe, Williamson & Wyatt PC; Gabe Amodeo

(57) ABSTRACT

The present invention provides methods for preventing and treating SARS-CoV-2 infections, COVID-19, or symptoms thereof. The methods of the invention feature the administration of one or more antigen-binding molecules (e.g., antibodies) that bind a surface protein of SARS-CoV-2 (e.g., spike protein).

68 Claims, 125 Drawing Sheets
Specification includes a Sequence Listing.

Related U.S. Application Data 26, 2020, provisional application No. 63/094,133, filed on Oct. 20, 2020, provisional application No. 63/090,690, filed on Oct. 12, 2020, provisional application No. 63/089,399, filed on Oct. 8, 2020, provisional application No. 63/084,881, filed on Sep. 29, 2020, provisional application No. 63/085,066, filed on Sep. 29, 2020, provisional application No. 63/065,799, filed on Aug. 14, 2020, provisional application No. 63/062,961, filed on Aug. 7, 2020, provisional application No. 63/060,592, filed on Aug. 3, 2020, provisional application No. 63/043,336, filed on Jun. 24, 2020, provisional application No. 63/038,274, filed on Jun. 12, 2020, provisional application No. 63/036,956, filed on Jun. 9, 2020, provisional application No. 63/034,348, filed on Jun. 3, 2020.

(56) References Cited

U.S. PATENT DOCUMENTS

| | | | |
|---|---|---|---|
| 10,954,289 | B1 | 3/2021 | Babb et al. |
| 10,975,139 | B1 | 4/2021 | Babb et al. |
| 11,020,474 | B1 | 6/2021 | Xiang et al. |
| 11,021,531 | B1 | 6/2021 | Glanville et al. |
| 11,021,532 | B1 | 6/2021 | Glanville et al. |
| 11,028,150 | B1 | 6/2021 | Glanville et al. |
| 11,028,167 | B1 | 6/2021 | Glanville et al. |
| 2006/0240551 | A1 | 10/2006 | Jiang et al. |
| 2017/0096455 | A1 | 4/2017 | Baric et al. |
| 2021/0031123 | A1 | 2/2021 | Liu et al. |
| 2021/0093709 | A1 | 4/2021 | Wu et al. |
| 2021/0260201 | A1 | 8/2021 | Chukly et al. |
| 2021/0275665 | A1 | 9/2021 | Cho |
| 2021/0277093 | A1 | 9/2021 | Mond et al. |
| 2021/0388065 | A1* | 12/2021 | Lu .................... C07K 16/10 |

FOREIGN PATENT DOCUMENTS

| | | |
|---|---|---|
| CN | 111303254 A | 6/2020 |
| CN | 111303279 A | 6/2020 |
| CN | 111303280 A | 6/2020 |
| CN | 111333704 B | 6/2020 |
| CN | 111333722 A | 6/2020 |
| CN | 111420048 A | 7/2020 |
| CN | 111423508 A | 7/2020 |
| CN | 111440229 A | 7/2020 |
| CN | 111471105 A | 7/2020 |
| CN | 111499692 A | 8/2020 |
| CN | 111499765 A | 8/2020 |
| CN | 111518773 A | 8/2020 |
| CN | 111560399 A | 8/2020 |
| CN | 111574614 A | 8/2020 |
| CN | 111592594 A | 8/2020 |
| CN | 111592595 B | 8/2020 |
| CN | 111607003 A | 9/2020 |
| CN | 111620945 B | 9/2020 |
| CN | 111620946 B | 9/2020 |
| CN | 111647053 A | 9/2020 |
| CN | 111647076 B | 9/2020 |
| CN | 111647077 B | 9/2020 |
| CN | 111662379 B | 9/2020 |
| CN | 111690058 B | 9/2020 |
| CN | 111690059 A | 9/2020 |
| CN | 111690060 A | 9/2020 |
| CN | 111714621 B | 9/2020 |
| CN | 111718411 A | 9/2020 |
| CN | 111732654 B | 10/2020 |
| CN | 111732655 A | 10/2020 |
| CN | 111732664 B | 10/2020 |
| CN | 111748032 B | 10/2020 |
| CN | 111778218 A | 10/2020 |
| CN | 111793129 A | 10/2020 |
| CN | 111825762 A | 10/2020 |
| CN | 111825771 A | 10/2020 |
| CN | 111848750 A | 10/2020 |
| CN | 111848751 A | 10/2020 |
| CN | 111848789 A | 10/2020 |
| CN | 111875701 A | 11/2020 |
| CN | 111909260 A | 11/2020 |
| CN | 111909261 A | 11/2020 |
| CN | 111909262 A | 11/2020 |
| CN | 111909263 A | 11/2020 |
| CN | 111925439 A | 11/2020 |
| CN | 111925440 A | 11/2020 |
| CN | 111925441 A | 11/2020 |
| CN | 111925442 A | 11/2020 |
| CN | 111925443 A | 11/2020 |
| CN | 111925444 A | 11/2020 |
| CN | 111944026 A | 11/2020 |
| CN | 111978377 A | 11/2020 |
| CN | 111978395 A | 11/2020 |
| CN | 111978396 A | 11/2020 |
| CN | 111978397 A | 11/2020 |
| CN | 111978398 A | 11/2020 |
| CN | 111978399 A | 11/2020 |
| CN | 111995672 A | 11/2020 |
| CN | 111995674 A | 11/2020 |
| CN | 111995678 B | 11/2020 |
| CN | 112010962 A | 12/2020 |
| CN | 112010963 A | 12/2020 |
| CN | 112010964 A | 12/2020 |
| CN | 112010967 B | 12/2020 |
| CN | 112062838 B | 12/2020 |
| CN | 112062839 A | 12/2020 |
| CN | 112062840 A | 12/2020 |
| CN | 112062859 A | 12/2020 |
| CN | 112076316 A | 12/2020 |
| CN | 112094326 A | 12/2020 |
| CN | 112094327 A | 12/2020 |
| CN | 112094340 A | 12/2020 |
| CN | 112094342 A | 12/2020 |
| CN | 112094343 A | 12/2020 |
| CN | 112125973 A | 12/2020 |
| CN | 112159469 A | 1/2021 |
| CN | 112175071 A | 1/2021 |
| CN | 112175073 A | 1/2021 |
| CN | 112194711 A | 1/2021 |
| CN | 112210004 A | 1/2021 |
| CN | 112250763 A | 1/2021 |
| CN | 112251414 A | 1/2021 |
| CN | 112300274 A | 2/2021 |
| CN | 112341541 A | 2/2021 |
| CN | 112341542 B | 2/2021 |
| CN | 112390879 B | 2/2021 |
| CN | 112409479 A | 2/2021 |
| CN | 112409488 A | 2/2021 |
| CN | 112430265 A | 3/2021 |
| CN | 112442120 A | 3/2021 |
| CN | 112485455 A | 3/2021 |
| CN | 112500480 A | 3/2021 |
| CN | 112500481 A | 3/2021 |
| CN | 112513076 A | 3/2021 |
| CN | 112521494 A | 3/2021 |
| CN | 112521496 A | 3/2021 |
| CN | 112522203 A | 3/2021 |
| CN | 112538111 A | 3/2021 |
| CN | 112552399 A | 3/2021 |
| CN | 112574299 A | 3/2021 |
| CN | 112574300 A | 3/2021 |
| CN | 112625125 A | 4/2021 |
| CN | 112625136 A | 4/2021 |
| CN | 112626030 A | 4/2021 |
| CN | 112626089 A | 4/2021 |
| CN | 112646005 A | 4/2021 |
| CN | 112661841 A | 4/2021 |
| CN | 112724247 A | 4/2021 |
| CN | 112724248 A | 4/2021 |
| CN | 112794898 A | 5/2021 |
| CN | 112794899 A | 5/2021 |
| CN | 112851804 A | 5/2021 |
| CN | 112980885 A | 6/2021 |
| CN | 113045647 A | 6/2021 |

(56) References Cited

FOREIGN PATENT DOCUMENTS

| | | |
|---|---|---|
| CN | 113072640 A | 7/2021 |
| CN | 113150129 A | 7/2021 |
| CN | 113150130 A | 7/2021 |
| CN | 113150132 A | 7/2021 |
| CN | 113150135 A | 7/2021 |
| CN | 113151184 A | 7/2021 |
| CN | 113173995 A | 7/2021 |
| CN | 113185609 A | 7/2021 |
| CN | 113214389 A | 8/2021 |
| CN | 113215106 A | 8/2021 |
| CN | 113234148 A | 8/2021 |
| CN | 113234149 A | 8/2021 |
| CN | 113234150 A | 8/2021 |
| CN | 113234151 A | 8/2021 |
| CN | 113248579 A | 8/2021 |
| CN | 113248581 A | 8/2021 |
| CN | 113264998 A | 8/2021 |
| CN | 113292649 A | 8/2021 |
| CN | 113292650 A | 8/2021 |
| CN | 113307865 A | 8/2021 |
| CN | 113336846 A | 9/2021 |
| CN | 113354731 A | 9/2021 |
| CN | 113354733 A | 9/2021 |
| DE | 202020105116 | 11/2020 |
| EP | 3872091 A1 | 9/2021 |
| EP | 3885361 A1 | 9/2021 |
| KR | 102205028 B1 | 1/2021 |
| KR | 102229225 B1 | 3/2021 |
| KR | 102233689 B1 | 3/2021 |
| RU | 2744274 C1 | 3/2021 |
| WO | 05/060520 A2 | 7/2005 |
| WO | 2015/179535 A1 | 11/2015 |
| WO | 2019/147831 A1 | 8/2019 |
| WO | 21/001388 A1 | 1/2021 |
| WO | 21/026074 A1 | 2/2021 |
| WO | 21/035177 A2 | 2/2021 |
| WO | 21/045836 A1 | 3/2021 |
| WO | 21/058521 A1 | 4/2021 |
| WO | 21/072399 A1 | 4/2021 |
| WO | 21/096980 A1 | 5/2021 |
| WO | 21/148884 A1 | 7/2021 |
| WO | 21/151100 A1 | 7/2021 |
| WO | 21/155639 A1 | 8/2021 |
| WO | 21/163265 A1 | 8/2021 |
| WO | 21/168483 A2 | 8/2021 |
| WO | 21/173879 A1 | 9/2021 |
| WO | 21/180602 A1 | 9/2021 |
| WO | 21/183790 A1 | 9/2021 |
| WO | 2021/183195 A1 | 9/2021 |
| WO | 2021/183359 A1 | 9/2021 |
| WO | 2021/190980 A1 | 9/2021 |
| WO | 2021/203053 A1 | 10/2021 |
| WO | 2021/222935 A2 | 11/2021 |
| WO | 2021/226560 A1 | 11/2021 |
| WO | 2021/233834 A1 | 11/2021 |
| WO | 21/242815 A1 | 12/2021 |
| WO | 21/247779 A1 | 12/2021 |
| WO | 2021/239935 A1 | 12/2021 |
| WO | 2021/245184 A1 | 12/2021 |
| WO | 2021/249547 A1 | 12/2021 |
| WO | 2022/090353 A1 | 5/2022 |
| WO | 2022/162587 A1 | 8/2022 |

OTHER PUBLICATIONS

Lagadinou M et al. Prognosis of COVID-19: Changes in laboratory parameters. Infez Med. Jun. 1, 2020;28 (Year: 2020).*
Rudikoff S et al. Single amino acid substitution altering antigen-binding specificity. Proc Natl Acad Sci U S A. Mar. 1982;79(6):1979-83. (Year: 1982).*
Almagro JC, Fransson J. Humanization of antibodies. Front Biosci. Jan. 1, 2008;13:1619-33. (Year: 2008).*
Kussie et al. A single engineered amino acid substitution changes antibody fine specificity.J Immunol. Jan. 1, 1994;152(1):146-52. (Year: 1994).*
Edwards et al. The remarkable flexibility of the human antibody repertoire; isolation of over one thousand different antibodies to a single protein, BLyS. J Mol Biol Nov. 14, 2003;334(1):103-18. (Year: 2003).*
Andreano et al., "Identification of neutralizing human monoclonal antibodies from Italian Covid-19 convalescent patients," bioRxiv 2020.05.05.078154; (2020) doi: https://doi.org/10.1101/2020.05.05.078154.
Barnes et al., "Structures of human antibodies bound to SARS-CoV-2 spike reveal common epitopes and recurrent features of antibodies," Structures of human antibodies bound to SARS-CoV-2 spike reveal common epitopes and recurrent features of antibodies, Cell (2020), doi: https://doi.org/10.1016/j.cell.2020.06.025.
Barnes et al., "Structures of Human Antibodies Bound to SARS-CoV-2 Spike Reveal Common Epitopes and Recurrent Features of Antibodies," Cell, vol. 182, Issue 4): 828-842, Jun. 23, 2020 (2020).
Baum A, Copin R, Ajithdoss D, et al. REGN-COV2 antibody cocktail prevents and treats SARS-CoV-2 infection in rhesus macaques and hamsters. bioRxiv 2020:2020.08.02.233320.
Baum et al., "Antibody cocktail to SARS-CoV-2 spike protein prevens rapid mutational escape seen with individual antibodies," Science, pp. 1-8, (Jun. 15, 2020). [Retrieved from the Internet Jun. 23, 2020 from http://science.sciencemag.org/].
Baum A, Fulton BO, Wloga E, et al. Antibody cocktail to SARS-CoV-2 spike protein prevents rapid mutational escape seen with individual antibodies. Science 2020.
Baum et al., "Antibody cocktail to SARS-CoV-2 spike protein prevents rapid mutational escape seen with individual antibodies," Science, vol. 1:1-17, (2020). [Retrieved from the Internet Jun. 30, 2020: <URL: http://science.sciencemag.org].
Bertoglio et al., "SARS-CoV-2 neutralizing human recombinant antibodies selected from pre-pandemic healthy donors binding at RBD-ACE2 interface," bioRxiv 2020.06.05.135921; (2020) doi: https://doi.org/10.1101/2020.06.05.135921.
Blanco-Melo D, Nilsson-Payant BE, Liu WC, et al. Imbalanced Host Response to SARS-CoV-2 Drives Development of COVID-19. Cell 2020;181:1036-45 e9.
Brouwer et al., "Potent neutralizing antibodies from COVID-19 patients define multiple targets of vulnerability" Science 10.1126/Science.abc5902 (2020).
Brouwer et al., "Potent neutralizing antibodies from COVID-19 patients define multiple targets of vulnerability" bioRxiv 2020.05.12.088716; doi: https://doi.org/10.1101/2020.05.12.088716.
Brouwer et al., "Potent neutralizing antibodies from COVID-19 patients define multiple targets of vulnerability," bioRxiv 2020.05.12.088716; (2020) doi: https://doi.org/10.1101/2020.05.12.088716.
Cao et al., "Potent Neutralizing Antibodies against SARS-CoV-2 identified by high-throughput single-cell sequencing of convalescent patients' B cells," Cell (2020), doi: https://doi.org/10.1016/j.cell.2020.05.025.
Cao et al., "Potent Neutralizing Antibodies against SARS-CoV-2 Identified by High-Throughput Single-Cell Sequencing of Convalescent Pateitns'B Cells," Cell, vol. 182: 73-84, (2020). [https://doi.org/10.1016/j.cell.2020.05.025].
Case et al., "Neutralizing antibody and soluble ACE2 inhibition of a replication-competent VSV-SARS-CoV-2 and a clinical isolate of SARS-CoV-2," bioRxiv 2020.05.18.102038; (2020) doi: https://doi.org/10.1101/2020.05.18.102038.
Chen et al., "Human monoclonal antibodies block the binding of SARS-CoV-2 spike protein to angiotensin converting enzyme 2 receptor," Cellular & Molecular Immunology (2020) https://doi.org/10.1038/s41423-020-0426-7.
Cheng et al., "An insertion unique to SARS-CoV-2 exhibits superantigenic character strengthened by recent mutations," bioRxiv 2020.05.21.109272; (2020) doi: https://doi.org/10.1101/2020.05.21.109272.
Chi et al., "A neutralizing human antibody binds to the N-terminal domain of the Spike protein of SARS-CoV-2," Science 11.1126/science.abc6952 (2020).

(56) References Cited

OTHER PUBLICATIONS

Chi et al., "A potent neutralizing human antibody reveals the N-terminal domain in the Spike protein of SARS-CoV-2 as a site of vulnerability," bioRxiv 2020.05.08.083964; (2020) doi: https://doi.org/10.1101/2020.05.08.083964.

Chi et al., "Humanized Single Domain Antibodies Neutralize SARS-CoV-2 by Targeting Spike Receptor Binding Domain," bioRxiv 2020.04.14.042010; (2020) doi: https://doi.org/10.1101/2020.04.14.042010.

Choi et al., "Characterization of a human monoclonal antibody generated from a B-cell specific for a prefusion-stabilized spike protein of Middle East respiratory syndrome coronavirus," PLoS ONE 15(5): e0232757. https://doi.org/10.1371/journal.pone.0232757.

Choudhury et al., "In silico studies on the comparative characterization of the interactions of SARS-CoV-2 spike glycoprotein with ACE-2 receptor homologs and humans TLRs," (2020) doi: 10.1002/jmv.25987.

Crooke et al., "Immunoinformatic identification of B cell and T cell epitopes in the SARS-CoV-2 proteome," bioRxiv 2020.05.14.093757; (2020) doi: https://doi.org/10.1101/2020.05.14.093757.

Custodio et al., "Selection, biophysical and structural analysis of synthetic nanobodies that effectively neutralize SARS-CoV-2," bioRxiv 2020.06.23.165415; (2020) doi: https://doi.org/10.1101/2020.06.23.165415.

Coronavirus Disease 2019 (COVID-19) Situation Report—101. 2020. (Accessed Oct. 6, 2020, at https://www.who.int/docs/default-source/coronaviruse/situation-reports/20200430-sitrep-101-covid-19.pdf?sfvrsn=2ba4e093_2.).

Copin et al., "The monoclonal antibody combination REGEN-COV protects against SARS-CoV-2 mutational escape in preclinical and human studies" Cell, vol. 184: 3949-3961, (Jul. 22, 2021). [https://doi.org/10.1016/j.cell.2021.06.002].

Davidson et al., "Mechanism of Binding to Ebola Virus Glycoprotein by the ZMapp, ZMAb, and MB-003 Cocktail Antibodies," Journal of Virology, vol. 89.21: 10982-10992, (2015).

Dinnon, III et al., "A mouse-adapter SARS-CoV-2 model for the evaluation of COVID-19 medical countermeasures," bioRxiv 2020.05.06.081497; (2020) doi: https://doi.org/10.1101/2020.05.06.081497.

Dong et al., "Development of multi-specific humanized llama antibodies blocking SARS-CoV-2/ACE2 interaction with high affinity and avidity," Emerging Microbes & Infections, 9:1, 1034-1036, DOI: 10.1080/22221751.2020.1768806.

Ejemel et al., "IgA Mab blocks SARS-CoV-2 Spike-ACE2 interaction providing mucosal immunity," bioRxiv 2020.05.15.096719; doi: https://doi.org/10.1101/2020.05.15.096719.

Galson et al., "Deep sequencing of B cell receptor repertoires from COVID-19 patients reveal strong convergent immune signature," bioRxiv 2020.05.20.106294; doi: https://doi.org/10.1101/2020.05.20.106294.

Garde et al., "In the race to develop a coronavirus treatment, Regeneron thinks it has the inside track," STAT, pp. 1-7, Feb. 5, 2020 (2020). [https://www.statnews.com/2020/02/05/in-the-race-to-develop-a-coronavirus-treatment-regeneron-thinks-it-has-the-inside-track/].

Giron et al., "On the Interactions of the receptor-binging domain of SARS-CoV-1 and SARS-CoV-2 spike proteins with monoclonal antibodies and the receptor ACE2," Virus Research 285 (2020) 198021.

Goncalves et al., "SARS-CoV-2 mutations and where to find them: An in silico perspective of structural changes and antigenicity of the Spike protein," bioRxiv 2020.05.21.108563; (2020) doi: https://doi.org/10.1101/2020.05.21.108563.

Goyal P, Choi JJ, Pinheiro LC, et al. Clinical Characteristics of Covid-19 in New York City. N Engl J Med 2020.

Grifoni et al., "Targets of T cell responses to SARS-CoV-2 coronavirus in humans with COVID-19 disease and unexposed individuals," Cell (2020), doi: https://doi.org/10.1016/j.cell.2020.05.015.

Group RC, Horby P, Lim WS, et al. Dexamethasone in Hospitalized Patients with Covid-19—Preliminary Report. N Engl J Med 2020.

Guan WJ, Ni ZY, Hu Y, et al. Clinical Characteristics of Coronavirus Disease 2019 in China. N Engl J Med 2020;382:1708-20.

Gudbjartsson DF, Helgason A, Jonsson H, et al. Spread of SARS-CoV-2 in the Icelandic Population. N Engl J Med 2020;382:2302-15.

Hanke et al., "An alpaca nanobody neutralizes SARS-CoV-2 by blocking receptor interaction," bioRxiv 2020.06.02.130161; (2020) doi: https://doi.org/10.1101/2020.06.02.130161.

Hansen et al., "Studies in humanized mice and convalescent humans yield a SARS-CoV-2 antibody cocktail," Science, vol. 1:1-47, (2020). [Retrieved from the Internet Jun. 30, 2020: <URL: http://science.sciencemag.org].

Hansen et al., "Studies in humanized mice and convalescent humans yield a SARS-CoV-2 antibody cocktail," Science, 1-10, (2020). [Retrieved from the Internet Jul. 29, 2020: <http://science.sciencemag.org>].

Hansen et al., "Studies in humanized mice and convalescent humans yield a SARS-CoV-2 antibody cocktail," Science, pp. 1-10, (Jun. 15, 2020). [Retrieved from the Internet Jun. 23, 2020 from http://science.sciencemag.org/].

Hansen et al., supplementary materials for "Studies in humanized mice and convalescent humans yield a SARS-CoV-2 antibody cocktail," Science, pp. 1-30, (Jun. 15, 2020). [science.scieocemag.org/cgi/conrent/fu1Vscience.abd0827/DCJ].

Hansen J, Baum A, Pascal KE, et al. Studies in humanized mice and convalescent humans yield a SARS-CoV-2 antibody cocktail. Science 2020.

Heurich et al., "TMPRSS2 and ADAM17 Cleave ACE2 Differentially and Only Proteolysis by TMPRSS2 Augments Entry Driven by the Severe Acute Respiratory Syndrome Coronavirus Spike Protein," Journal of Virology, vol. 88, No. 2; Jan. 2014; p. 1293-1307.

Hsieh et al., "Structure-based design of prefusion-stabilized SARS-CoV-2 Spikes," bioRxiv 2020.05.30.125484; (2020) doi: https://doi.org/10.1101/2020.05.30.125484.

Huibin et al., "Cross-reactive Antibody Response between SARS-CoV-2 and SARS-CoV Infections," Cell Reports 31, 107725; Jun. 2, 2020. https://doi.org/10.1016/j.celrep.2020.107725.

Hulburt et al., "Structural basis for potent neurtralization of SARS-CoV-2 and role of antibody affinity maturation," bioRxiv 2020.06.12.148692; doi: https://doi.org/10.1101/2020.06.12.148692.

Huo et al., "Neutralization of SARS-CoV-2 by destruction of the prefusion Spike," bioRxiv 2020.05.05.079202; (2020) doi: https://doi.org/10.1101/2020.05.05.079202.

Jacobs et al., "Neutralizing antibodies mediate virus-immune pathology of COVID-19," Science Direct, Medical Hypotheses 143; 109884, pp. 1-4. (2020).

Ju et al., "Human neutralizing antibodies elicited by SARS-CoV-2 infection," Nature https://doi.org/10.1038/s41586-020-2380-z (2020).

Ju et al., "Potent human neutralizing antibodies elicited by SARS-CoV-2 infection," bioRxiv 2020.03.21.990770; (2020) doi: https://doi.org/10.1101/2020.03.21.990770.

Keeffe et al., "A Combination of Two Human Monoclonal Antibodies Prevents Zika Virus Escape Mutations in Non-human Primates," Cell Reports, vol. 25: 1385-1394, (2018). [https://doi.org/10.1016/j.celrep.2018.10.031].

Kreer et al., "Longitudinal isolation of potent near-germline SARS-CoV-2-neutralizing antibodies from COVID-19 patients," bioRxiv 2020.06.12.146290; doi: https://doi.org/10.1101/2020.06.12.146290.

Kugelman et al., "Emergence of Ebola Virus Escape Variants in Infected Nonhuman Primates Treated with the MB-003 Antibody Cocktail," Cell Reports, vol. 12: 2111-2120, (2015). [http://dx.doi.org/10.1016/j.celrep.2015.08.038].

Interim Clinical Guidance for Management of Patients with Confirmed Coronavirus Disease (COVID-19)—Clinical Care Guidance—Updated Sep. 10, 2020. 2020. (Accessed Oct. 6, 2020).

Joyner MJ, Senefeld JW, Klassen SA, et al. Effect of Convalescent Plasma on Mortality among Hospitalized Patients with COVID-19: Initial Three-Month Experience. medRxiv 2020:2020.08.12.20169359.

(56) References Cited

OTHER PUBLICATIONS

Lan et al., "Structure of the SARS-CoV-2 spike receptor-binding domain bound to the ACE2 receptor," Nature, vol. 581, May 14, 2020.
Larsen et al., "Afucosylated immunoglobulin G resposnes are a hallmark of enveloped virus infections and show an exacerbated phenotype in COVID-19," bioRxiv 2020.05.18.099507; doi: https://doi.org/10.1101/2020.05.18.099507.
Lavezzo E, Franchin E, Ciavarella C, et al. Suppression of a SARS-CoV-2 outbreak in the Italian municipality of Vo'. Nature 2020;584:425-9.
Lee et al., "CD-8+ T cell cross-reactivity against SARS-CoV-2 conferred by toerh coronavirus strains and influenza virus," bioRxiv 2020.05.20.107292; doi: https://doi.org/10.1101/2020.05.20.107292.
Lee S, Kim T, Lee E, et al. Clinical Course and Molecular Viral Shedding Among Asymptomatic and Symptomatic Patients With SARS-CoV-2 Infection in a Community Treatment Center in the Republic of Korea. JAMA Intern Med 2020.
Li et al., "Potent neutralization of SARS-CoV-2 in vitro and in an animal model by a human monoclonal antibody," bioRxiv 2020. 05.13.093088; doi: https://doi.org/10.1101/2020.05.13.093088.
Li et al., "Potent synthetic nanobodies against SARS-CoV-2 and molecular basis for neutralization," bioRxiv 2020.06.09.143438; doi: https://doi.org/10.1101/2020.06.09.143438.
Li L, Zhang W, Hu Y, et al. Effect of Convalescent Plasma Therapy on Time to Clinical Improvement in Patients With Severe and Life-threatening COVID-19: A Randomized Clinical Trial. JAMA 2020;324:460-70.
Lou et al., "Cross-neutralization antibodies against SARS-cOv-2 and RBD mutations from convalescent patient antibody libraries," bioRxiv 2020.06.06.137513; doi: https://doi.org/10.1101/2020.06.06.137513.
Lui et al., "Trimeric SARS-CoV-2 Spike interacts with dimeric ACE2 with limited intra-Spike avidity," bioRxiv 2020.05.21. 109157; doi: https://doi.org/10.1101/2020.05.21.109157.
Lotfi et al., "covid-19: Transmission, prevention, and potential therapeutic opportunities," Science Direct, Clinica Chimica Acta (508): 254-266, (2020).
Lv et al., "Structural basis for neutralization of SARS-CoV-2 and SARS-CoV by a potent therapeutic antibody," bioRxiv 2020.06.02. 129098; doi: https://doi.org/10.1101/2020.06.02.129098.
Magleby R, Westblade LF, Trzebucki A, et al. Impact of SARS-CoV-2 Viral Load on Risk of Intubation and Mortality Among Hospitalized Patients with Coronavirus Disease 2019. Clin Infect Dis 2020.
Meirson et al., "Structural basis of SARS-CoV-2 spike protein induced by ACE2," bioRxiv 2020.05.24.113175; doi: https://doi.org/10.1101/2020.05.24.113175.
Meulen et al., "Human Monoclonal Antibody Combination against SARS Coronavirus: Synergy and Coverage of Escape Mutants," PLoS Medicine, vol. (3.7): 1071-1079, (2006). [www.plosmedicine.org].
Miersch et al., "Synthetic Antibodies neutralized SARS-CoV-2 infection of mammalian cells," bioRxiv 2020.06.05.137349; doi: https://doi.org/10.1101/2020.06.05.137349.
Mossel et al., "Exogenous ACE2 Expression Allows Refractory Cell Lines to Support Severe Acute Respiratory Syndrome Coronavirus Replication," Journal of Virology, vol. 79, No. 6; Mar. 2005; pp. 3846-3850.
Nascimento Jr. et al., "SARS, MERS and SARS-CoV-2 (COVI19) treatment: a patent review," Expert Opinion on Therapeutic Patents, DOI: 10.1080/13543776.2020.1772231.
Ng et al., "Pre-existing and de novo humoral immunity to SARS-CoV-2 in humans," bioRxiv 2020.05.14.095414; doi: https://doi.org/10.1101/2020.05.14.095414.
Ni et al., "Detection of SARS-CoV-2-Specific Humoral and Cellular Immunity in COVID-19 Convalescent Individuals," Immunity 52, 1-7; Jun. 16, 2020.

Nieto et al., "Fast isolation of sub-nanomolar affinity alpaca nanobody against the Spike RBD of SARSCoV-2 by combining bacterial display and a simple single-step density gradient selection," bioRxiv, vol. (1):1-27, (2020). [https://doi.org/10.1101/2020.06.09.137935].
Noy-Porat et al., "Tiger team: a panel of human neutralizing mAbs targeting SARS-CoV-2 spike at multiple epitopes," bioRxiv 2020. 05.20.106609; https://doi.org/10.1101/2020.05.20.106609.
Okba et al., "Severe Acute Respiratory Syndrome Coronavirus 2-Specific Antibody Responses in Coronavirus Disease 2019 Patients," Research vol. 26, No. 7; Apr. 8, 2020.
Oran DP, Topol EJ. Prevalence of Asymptomatic SARS-CoV-2 Infection : A Narrative Review. Ann Intern Med 2020;173:362-7.
Park et al., "Spike protein binding prediction with neutralizing antibodies of SARS-CoV-2", bioRxiv 2020.02.22.951178; (2020) doi: https://doi.org/10.1101/2020.02.22.951178.
Pascal et al., "Pre- and postexposure efficacy of fully human antibodies against Spike protein in a novel humanized mouse model of MERS-CoV infection," PNAS, vol. (112 No. 28):8738-8743, (2015). [www.pnas.org/cgi/doi/10.1073/pnas.1510830112].
Pascal et al., "Development of Clinical-Stage Human Monoclonal Antibodies That Treat Advanced Ebola Virus Disease in Nonhuman Primates," The Journal of Infectious Diseases, vol. 218: S612-S626, (2018).
Pinto et al., "Cross-neutralization of SARS-CoV-2 by a human monoclonal SARS-CoV antibody," Nature https://doi.org/10.1038/s41586-020-2349-y (2020).
Pinto et al., "Cross-neutralization of SARS-CoV-2 by a human monoclonal SARS-CoV antibody," Nature, vol. 583: 290-308, (2020). [https://doi.org/10.1038/s41586-020-2 349-y].
Poh et al., "Two linear epitopes on the SARS-CoV-2 spike protein that elicit neutralising antibodies in COVID-19 patients," Nature Communications (2020)11:2806. https://doi.org/10.1038s41467-020-16638-2.
Qiang et al., "Monoclonal Antibodies Capable of Binding SARS-CoV-2 Spike Protein Receptor Binding Motif Specifically Prevent GM-CSF Induction," bioRxiv, pp. 1-27, Sep. 4, 2020 (2020).
Ravichandran et al., "Antibody repertoire induced by SARS-CoV-2 spike protein immunogens," bioRxiv 2020.05.12.091918; doi: https://doi.org/10.1101/2020.05.12.091918.
Raybould et al., "CoV-AbDab: the Coronavirus Antibody Database," bioRxiv 2020.05.15.077313; doi: https://doi.org/10.1101/2020.05.15.077313.
Regeneron. Regeneron and Sanofi Provide Update on Kevzara (Sarilumab) Phase 3 U.S. Trial in COVID-19 Patients. 2020.
Richardson S, Hirsch JS, Narasimhan M, et al. Presenting Characteristics, Comorbidities, and Outcomes Among 5700 Patients Hospitalized With COVID-19 in the New York City Area. JAMA 2020.
Robbiani et al., "Convergent antibody responses to SARS-CoV-2 in convalescent individuals," Nature https://doi.org/10.1038/s41586-020-2456-9 (2020).
Robbiani et al., "Convergent Antibody Responses to SARS-CoV-2 Infection in Convalescent Individuals," bioRxiv 2020.05.13. 092619; (2020) doi: https://doi.org/10.1101/2020.05.13.092619.
Roche. Roche Provides an Update on the Phase III Covacta Trial of Actemra/Roactemra in Hospitalized Patients with Severe COVID-19 Associated Pneumonia. 2020.
Rockx et al., "Escape from Human Monoclonal Antibody Neutralization Affects in Vitro and In Vivo Fitness of Severe Acute Respiratory Syndrome Coronavirus," The Journal of Infectious Diseases, vol. 201: 946-955, (2010). [DOI: 10.1086/651022].
Rogers et al., "Isolation of potent SARS-CoV-2 neutralizing antibodies and protection from disease in a small animal model," Science 10.1126/scienec.abc7520 (2020).
Rogers et al., "Rapid isolation of potent SARS-CoV-2 neutralizing antibodies and protection in a small animal model," bioRxiv 2020. 05.11.088674; doi: https://doi.org/10.1101/2020.05.11.088674.
Rosas I, Brau N, Waters M, et al. Tocilizumab in Hospitalized Patients With COVID-19 Pneumonia. medRxiv 2020:2020.08.27. 20183442.
Seydoux et al., "Analysis of a SARS-CoV-2 infected individual reveals development of potent neutralizing antibodies to distinct epitopes with limited somatic mutation ," Immunity 4384; https://doi.org/10.1016/j.immuni.2020.06.001.

(56) References Cited

OTHER PUBLICATIONS

Seydoux et al., "Characterization of neutralizing antibodies from a SARS-CoV-2 infected individual," bioRxiv 2020.05.12.091298; doi: https://doi.org/10.1101/2020.05.12.091298.
Shi et al., "A Human neutralizing antibody targets the receptor binding cite of SARS-CoV-2," Nature https://doi.org/10.1038/s41586-020-2381-y (2020).
Simoes EAF, Forleo-Neto E, Geba GP, et al. Suptavumab for the Prevention of Medically Attended Respiratory Syncytial Virus Infection in Preterm Infants. Clin Infect Dis 2020.
Suthar et al., "Rapid generation of neutralizing antibody responses in COVID-19 patients," Cell Reports Medicine, 1-36 pages (2020). [https://doi.org/10.1016/j.xcrm.2020.100040].
Tai et al., "Identification of SARS-CoV RBD-targeting monoclonal antibodies with crossreactive or neutralizing activity against SARS-CoV-2," Antiviral Research, Science Direct, vol. 179:1-6, (2020). [www.elsevier.com/locate/antiviral].
Teng et al., "Systemic Effects of Missense Mutations on SARS-CoV-2 Spike Glycoprotein Stability and Receptor Binding Affinity," bioRxiv, vol. 1:1-36, (2020). [https://doi.org/10.1101/2020.05.21.109835].
Tenforde MW, Kim SS, Christopher J. Lindsell, et al. Symptom Duration and Risk Factors for Delayed Return to Usual Health Among Outpatients with COVID-19 in a Multistate Health Care Systems Network—United States, Mar.-Jun. 2020. MMWR Morb Mortal Wkly Rep 2020;60:993-8.
Tian et al., "Potent binding of 2019 novel coronavirus spike protein by a SARS coronavirus-specific human monoclonal antibody," Emerging Microbes & Infections, vol. 17: 647-649, Feb. 17, 2020 (2020).
U.S. Appl. No. 16/912,678, Notice of Allowance dated Jul. 29, 2020.
U.S. Appl. No. 16/996,297, Non-Final Office Action dated Dec. 8, 2020.
U.S. Appl. No. 17/021,286, Non-Final Office Action dated Dec. 23, 2020.
U.S. Appl. No. 17/021,286, Notice of Allowance dated Jan. 22, 2021.
U.S. Appl. No. 16/996,297, Notice of Allowance dated Jan. 25, 2021.
Vandergaast et al., "Development and validation of Immuno-Covtm: a high-throughput clinical assay for detecting antibodies that neutralize SARS-CoV-2," bioRxiv, pp. 1-32, (2020). [https://doi.org/10.1101/2020.05.26.117549].
Wan et al., "Human IgG cell neutralizing monoclonal antibodies block SARS-CoV-2 infect," bioRxiv, vol. 1:1-25, (2020). [https://doi.org/10.1101/2020.05.19.104117].
Wan et al., "Human IgG cell neutralizing monoclonal antibodies block SARS-CoV-2 infection," bioRxiv, pp. 1-28, (May 21, 2020). [doi:https://doi.org/10.1101/2020.05.19.104117].
Wang et al., "A human monoclonal antibody blocking SARS-CoV-2 infection," bioRxiv, pp. 1-24, (Mar. 12, 2020). [doi:https://doi.org/10.1101/2020.03.11.987958].
Wang et al., "A human monoclonal antibody blocking SARS-CoV-2 infection," Supplemental information, 1-13 pages (2020).
Wang et al., "A human monoclonal antibody blocking SARS-CoV-2 infection," Nature Communications, 1-7, (2020). [https://doi.org/10.1038/s41467-020-16256-y | www.nature.com/naturecommunications].
Wang et al., "SARS-CoV-2 Neutralizing Antibody Responses are More Robust in Patients with Severe Disease," bioRxiv, vol. 1:1-9, (2020). [https://doi.org/10.1101/2020.06.13.150250].
Wang et al., "Structural and Functional Basis of SARS-CoV-2 Entry by Using Human ACE2," Cell, vol. 181:894-904, (2020). [https://doi.org/10.1016/j.cell.2020.03.045].
Wang et al., "Importance of Neutralizing Monoclonal Antibodies Targeting Multiple Antigenic Sites on the Middle East Respiratory Syndrome Coronavirus Spike Glycoproein to Avoid Neutralization Escape," Vaccines and Antiviral Agents, Journal of Virology, vol. 92 No. 10: 1-21, ( May 2018). [Retrieved from the Internet May 5, 2020: <URL: http://jvi.asm.org>].
Watanabe et al., "Site-specific glycan analysis of the SARS-CoV-2 spike," Science, vol. 1:1-9, (2020). [Retrieved from the Internet May 13, 2020: <URL: http://science.sciencemag.org>; Y. Watanabe et al., Science 10.1126/science.abb9983 (2020)].
Watanabe et al., "Vulnerabilities in coronavirus glycan shields despite extensive glycosylation," Nature Communications, vol. 11:1-10, (2020). [https://doi.org/10.1038/s41467-020-16567-0].
Wec et al., "Broad neutralization of SARS-related viruses by human monoclonal antibodies," Science, vol. 1:1-12, (2020). [Retrieved from the Internet Jun. 17, 2020: <URL: http://science.sciencemag.org>; A. Z. Wec et al., Science 10.1126/science.abc7424 (2020)].
Wec et al., "Broad neutralization of SARS-related viruses by human monoclonal antibodies," Science, vol. 1:1-30, (2020). [science.sciencemag.org/cgi/content/full/science.abc7424/DC1>].
Wec et al., "Broad sarbecovirus neutralizing antibodies define a key site of vulnerability on the SARS-CoV-2 spike protein," bioRxiv, 1-18, (2020). [https://doi.org/10.1101/2020.05.15.096511].
WHO Director-General's Opening Remarks at the Media Briefing on COVID-19—Mar. 11, 2020. 2020. (Accessed Jun. 9, 2020, at https://www.who.int/dg/speeches/detail/who-director-general-s-opening-remarks-at-the-media-briefing-on-covid-19---11-march-2020.).
WIPO Application No. PCT/US2020/039707, PCT International Search Report and Written Opinion of the International Searching Authority dated Nov. 9, 2020.
WIPO Application No. PCT/US2021/035556, PCT International Search Report and Written Opinion of the International Searching Authority dated Sep. 10, 2021.
WIPO Application No. PCT/US2021/034187, PCT International Search Report and Written Opinion of the International Searching Authority dated Nov. 2, 2021.
Wolfel R, Corman VM, Guggemos W, et al. Virological assessment of hospitalized patients with COVID-2019. Nature 2020;581:465-9.
Wrapp et al., "Structural Basis for Potent Neutralization of Betacoronaviruses by Single-Domain Camelid Antibodies," Cell, vol. 181:1-12, (2020). [https://doi.org/10.1016/j.cell.2020.04.031].
Wrapp et al., "Cryo-EM structure of the 2019-nCoV spike in the prefusion conformation," Science, vol. 367:1260-1263, (2020). [Retrieved from the Internet Jul. 29, 2020: <http://science.sciencemag.org>].
Wu et al., "A noncompeting pair of human neutralizing antibodies block COVID-19 virus binding to its receptor ACE2," Science, 1-8, (2020). [Retrieved from the Internet May 14, 2020: <URL: http://science.sciencemag.org>; Y. Wu et al., Science 10.1126/science.abc2241 (2020)].
Wu et al., "Fully human single-domain antibodies against SARS-CoV-2," bioRxiv 2020.03.30.015990; (2020) doi: https://doi.org/10.1101/2020.03.30.015990.
Wu et al., "Identification of Human Single-Domain Antibodies against SARS-CoV-2," Cell Host & Microbe, vol. 27:1-8, (2020). [https://doi.org/10.1016/j.chom.2020.04.023].
Wu et al., "Identification of Human Single-Domain Antibodies against SARS-CoV-2," Cell Host & Microbe, vol. 27:S 891-898, (2020).
Yi et al., "Key residues of the receptor binding motif in the spike protein of SARS-CoV-2 that interact with ACE2 and neutralizing antibodies," Cellular & Molecular Immunology, vol. 17: 621-630, (2020). [www.nature.com/cmi].
Yi et al., "Key residues of the receptor binding motif in the spike protein of SARS-CoV-2 that interact with ACE2 and neutralizing antibodies," Cellular & Molecular Immunology, 1-10, (2020).
Yu et al., "DNA vaccine protection against SARS-CoV-2 in rhesus macaques," Science, 1-11, (2020). [Retrieved from the Internet May 22, 2020: <URL: http://science.sciencemag.org>; J. Yu et al., *Science* 10.1126/science.abc6284 (2020)].
Yuan et al., "A highly conserved cryptic epitope in the receptor binding domains of SARS-CoV-2 and SARS-CoV," Science, vol. 368:630-633, (2020). [Retrieved from the Internet May 20, 2020: <URL: http://science.sciencemag.org>].

(56) References Cited

OTHER PUBLICATIONS

Yuan et al., "Isolation of and Characterization of Neutralizing Antibodies to Covid-19 from a Large Human Naïve scFv Phage Display Library," bioRxiv, 1-15, (2020). [https://doi.org/10.1101/2020.05.19.104281].

Zhang et al., "Immunization with the receptor-binding domain of SARS-CoV-2 elicits antibodies cross-neutralizing SARS-CoV-2 and SARS-CoV without antibody-dependent enhancement," bioRxiv, 1-33, (2020). [https://doi.org/10.1101/2020.05.21.107565].

Zheng et al., "Isolation of a human monoclonal antibody specific for the receptor binding domain of SARS-CoV-2 using a competitive phage biopanning strategy," Antibody Therapeutics, vol. 3.2:95-100, (2020). [Retrieved from the Internet May 27, 2020: <URL: https://academic.oup.com/abt/article-abstract/3/2/95/5827124>].

Zheng et al., "Novel antibody epitopes dominate the antigenicity of spike glycoprotein in SARS-CoV-2 compared to SARS-CoV," Cellular & Molecular Immunology, vol. 17:536-538, (2020). [https://doi.org/10.1038/s41423-020-0385-z].

Zhu et al., "Safety, tolerability, and immunogenicity of a recombinant adenovirus type-5 vectored COVID-19 vaccine: a dose-escalation, open-label, non-randomised, first-in-human trial ," the lancet, vol. 395: 1845-1854, (May 22, 2020). [https://doi.org/10.1016/ 50140-6736(20)31208-3].

Zhou et al., "A pneumonia outbreak associated with a new coronavirus of probable bat origin," Nature, vol. 579: 270-289, (2020). [https://doi.org/10.1038/s41586-020-2012-7].

Zost et al., "Potently neutralizing human antibodies that block SARS-CoV-2 receptor binding and protect animals," bioRxiv, 1-35, (2020). [https://doi.org/10.1101/2020.05.22.111005].

Zost et al., "Rapid isolation and profiling of a diverse panel of human monoclonal antibodies targeting the SARS-CoV-2 spike protein," bioRxiv, 1-48, (2020). [https://doi.org/10.1101/2020.05.12.091462].

Chen et al., "Resistance of SARS-CoV-2 variants to neutralization by monoclonal and serum-derived polyclonal antibodies," Nature Medicine, vol. 7: 717-726, (2021). [https://doi.org/10.1038/s41591-021-01294-w].

Cheng et al., "Impact of South African 501.V2 Variant on SARS-CoV-2 Spike Infectivity and Neutrlization: A Structure-based Computational Assessment," Bioinformatics, pp. 1-7, (2021). [https://doi.org/10.1101/2021.01.10.426143].

Li et al., "Repurposing host-based therapeutics to control coronavirus and influenza virus," Drug Discovery Today, vol. 24 (No. 3): 726-736, (Mar. 2019). [https://doi.org/10.1016/j.drudis.2019.01.018].

Matsuyama et al., "Enhanced isolation of SARS-CoV-2 by TMPRSS2-expressing cells," PNAS, vol. 117 (No. 13), pp. 7001-7003, (Mar. 31, 2020). [<www.pnas.org/cgi/doi/10.1073/pnas.2002589117>].

Reichert, "Coronavirus in the crosshairs, Part 1—The Antibody Society," pp. 1-7, (2020). [https://www.antibodysociety.org/coronavirus/coronavirus-in-the-crosshairs/].

Reichert, "Coronavirus in the crosshairs, Part 4: Antibody therapeutics —The Antibody Society," pp. 1-10, (2020). [https://www.antibodysociety.org/covid-19/coronavirus-in-the-crosshairs-part-4-antibody-therapeutics/].

Rouet et al., "Potent SARS-CoV-2 binding and neutralization through maturation of iconic SARS-CoV-1 antibodies," bioRxiv, pp. 1-52, (2020). [https://doi.org/10.1101/2020.12.14.422791].

Shen et al., "TMPRSS2: A potential target for treatment of influenza virus and coronavirus infections," Biochimie at ScienceDirect, vol. 142: 1-10, (2017). [http://dx.doi.org/10.1016/j.biochi.2017.07.016].

Stave et al., "Antibody and Antigen Contact Residues Define Epitope and Paratope Size and Structure," The Journal of Immunology, vol. 191: 1428-1435, (2013). [www.jimmunol.org/cgi/doi/10.4049/jimmunol.1203198].

Supasa et al., "Reduced neutralization of SARS-CoV-2 B.1.1.7 variant by convalescent and vaccine sera," Cell, vol. 184: 2201-2211, (2021). Https://doi.org/10.1016/j.cell.2021.02.033].

Walker et al., "Passive immunotherapy of viral infections: 'super-antibodies' enter the fray," Nature Reviews at Immunology, vol. 18: 297-308, (2018). [doi:10.1038/nri.2017.148].

Wang et al., "E484K mutation in SARS-CoV-2 RBD enahnces binding affinity with hACE2 but reduces interactions with neutralizing antibodies and nanobodies: Binding free energy calculation studies," bioRxiv, pp. 1-18, (2021).

WIPO Application No. PCT/US2020/039707, PCT Third Party Observation Communication dated May 2, 2022.

WIPO Application No. PCT/US2022/018918, PCT International Search Report and Written Opinion of the International Searching Authority dated Jun. 17, 2022.

Yuan et al., "Structural and functional ramifications of antigenic drift in recent SARS-CoV-2 variants," bioRxiv, pp. 1-50, (2021). [https://doi.org/10.1101.2021.02.16.430500].

Zhang et al., "The use of anti-inflammatory drugs in the treatment of people with severe coronavirus disease 2019 (COVID-19): The Perspectives of clinical immunologists from China," Clinical Immunology at ScienceDirect, vol. 214, (2020). [https://doi.org/10.1016/j.clim.2020.108393].

Zhou et al., "Evidence of escape of SARS-CoV-2 variant B.1.351 from natural and vaccine-induced sera," Cell, vol. 189: 2348-2361, (2021). [https://doi.org/10.1016/j.cell.2021.02.037].

U.S. Appl. No. 63/165,654, filed Mar. 24, 2021, Expired.

U.S. Appl. No. 17/863,864, filed Jul. 13, 2022, Pending.

U.S. Appl. No. 17/927,649, filed Nov. 23, 2022, Pending.

Barnes et al., "SARS-CoV-2 neutralizing antibody structures inform therapeutic strategies," Nature, vol. 588, No. 7839, pp. 682-687, (2020). [Retrieved from the Internet: <URL: http://www.nature.com/articles/s41586-020-2852-1>].

Baum et al., "REGN-CoV2 antibodies prevent and treat SARS-CoV-2 infection in rhesus macaques and hamsters," Science, vol. 370, No. 6520:1110-1115, (2020).

Deshpande et al., "Epitope Classification and RBD Binding Properties of Neutralizing Antibodies Against SARS-CoV-2 Variants of Concern," Frontiers in Immunology, vol. 12, Jun. 4, 2021; 30 pages.

Jones et al., "LY-CoV555, a rapidly isolated potent neutralizing antibody, provides protection in a non-human primate model of SARS-CoV-2 infection," bioRxiv, Oct. 9, 2020; 29 pages. [Retrieved from the Internet May 23, 2021: <URL: http://www.biorxiv.org/content/10.1101/2020.09.30.318972x3>].

Tortorici et al., "Ultrapotent human antobodies protect against SARS-CoV-2 challenge via multiple mechanisms," Science, vol. 370:950-957, (2020). [Retrieved from the Internet Apr. 14, 2021: <URL: http://www.science.sciencemag.org/content/sci/370/6519/950.full.pdf>].

U.S. Appl. No. 17/207,524, Requirement for Restriction/Election dated Sep. 7, 2022.

U.S. Appl. No. 17/207,524, Non-Final Office Action dated Nov. 22, 2022.

Van Blargan et al., "A potently neutralizing SARS-CoV-2 antibody inhibits variants of concern by utilizing unique binding residues in a highly conserved epitope," Immunity, vol. 54, No. 10, pp. 2399-2416, (2021).

Weinreich et al., "REGN-CoV, a Neutralizing Antibody Cocktail, in Outpatients with Covid-19," The New England Journal of Medicine, vol. 384(3):238-251, (2020). [Retrieved from the Internet: <URL: http://www.nehm.org/doi/pds/10.1056/NEJMao2035002?articleTools=true>].

WIPO Application No. PCT/US2022/036950, PCT International Search Report and Written Opinion of the International Searching Authority dated Nov. 29, 2022; 30 pages.

WIPO Application No. PCT/US2022/036950, PCT Invitation to Pay Additional Fees, and Where Applicable, Protest Fee, dated Oct. 7, 2022.

Zhiqiang Ku et al., "Molecular determinants and mechanism for antibody cocktail preventing SARS-CoV-2 escape," Nature Communications, vol. 12(469), 13 pages (2021). [Retrieved from the Internet Apr. 14, 2022 <URL: http://www.nature.com.articles/s41467-020-20789-7.pdf>].

Bruel et al., "Serum neutralization of SARS-CoV-2 Omicron sublineages BA.1 and BA.2 in patients receiving monoclonal antibodies," Nature Medicine, Nature Publishing Group US, vol. 28 No. 6:

(56) References Cited

OTHER PUBLICATIONS 1297-1302, (2022). [Retrieved from the Internet Mar. 23, 2022; ISSN: 1078-8956, DOI:10.1038/S41591-022-01792-5].

Deeks et al., "Casirivimab/Imdevimab: First Approval," Drugs, vol. 81 No. 17: 2047-2055, (2021). [URL: https://link.springer.com/article/10.1007/s40265-021-01620-z/fulltext.html].

European Medicines Agency (EMA), "Assesment report Regeneron Ireland DAC use of casirivimab and imdevimab for the treatment of COVID-19," Chapter 2.2, (2021). [Retrieved from the Internet URL:https://www.ema.europa.eu/en/documents/referral/regn-cov2-antibody-combination-casirivimab/imdevimab-covid19-article-53-procedure-assessment-report_en.pdf].

Mazzaferri et al., "Exploratory data on the clinical efficacy of monoclonal antibodies against SARS-DOV-2 Omicron Variant of Concern," medRxiv, pp. 1-21, (2022). [Retrieved from the Internet Jun. 27, 2022: <URL: http://www.medrxiv.org/content/10.1101/2022.05.06.22274613v1>].

Tatham et al., "Lack of Ronapreve (REGN-COV;casirivimab and imdevimab) virological efficacy against the SARS-COV-2 Omicron variant (B.1.1.529) in K18-hACE2 mice," bioRxiv, (2022). [Retrieved from the Internet Feb. 14, 2023 URL:https://www.biorxiv.org/content/10.1101.2022.01.23.477397v1].

Uraki et al., "Characterization and antiviral susceptibility of SARS-COV-2 Omicron BA.2," Nature, Nature Publishing Group UK, London, vol. 607 No. 7917: 119-127, (2022). [Retrieved from the Internet May 16, 2022, ISSN: 0028-0836, DOI: 10.1038/S41586-022-04856-1].

U.S. Appl. No. 17/207,524, Notice of Allowance dated Mar. 30, 2023.

Wiegang et al., "The Rise and Fall of SARS-COV-2 Variants and Ongoing Diversification of Omicron," Viruses, vol. 14 No. 9 : p. 2009, (2022). [URL: http://www.mdpi.com/1999-4915/14/9/20/09>].

WIPO Application No. PCT/US2022/049069, PCT Invitation to Pay Additional Fees and, where Applicable, Protest Fee of the International Searching Authority dated Mar. 2, 2023.

WIPO Application No. PCT/US2022/049069, PCT International Search Report and Written Opinion of the International Searching Authority dated Apr. 26, 2023.

U.S. Appl. No. 16/912,678, filed Jun. 25, 2020, U.S. Pat. No. 10,787,501, Issued.

U.S. Appl. No. 16/996,297, filed Aug. 18, 2020, U.S. Pat No. 10,975,139, Issued.

U.S. Appl. No. 17/021,286, filed Sep. 15, 2020, U.S. Pat No. 10,954,289, Issued.

U.S. Appl. No. 17/207,524, filed Mar. 19, 2021, US-2022-0356230, Published.

* cited by examiner

FIG. 3B

The time to negative RT-qPCR in NP swabs with no subsequent positive RT-qPCR for analysis group 2 is shown above. IV, intravenous(ly); NP, nasopharyngeal; RT-qPCR, quantitative real-time RT-PCR.

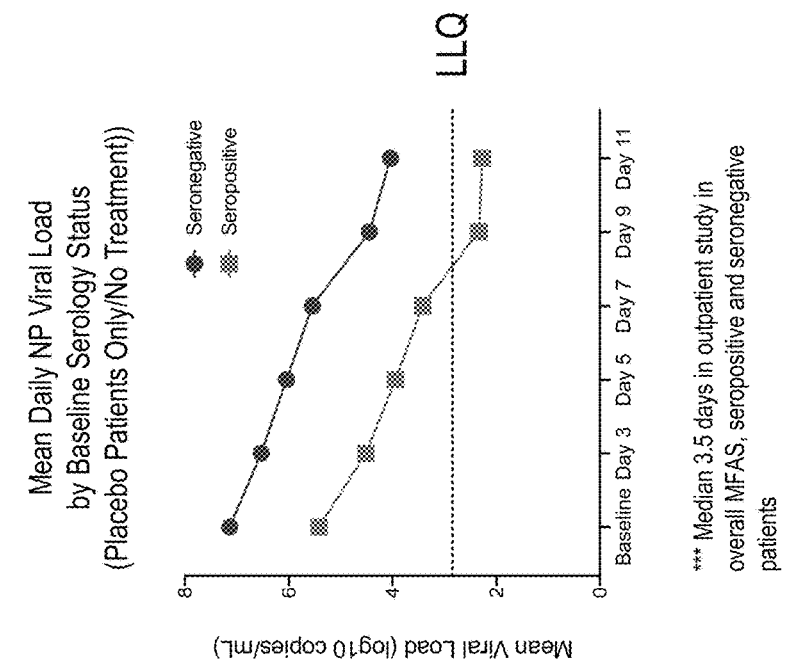

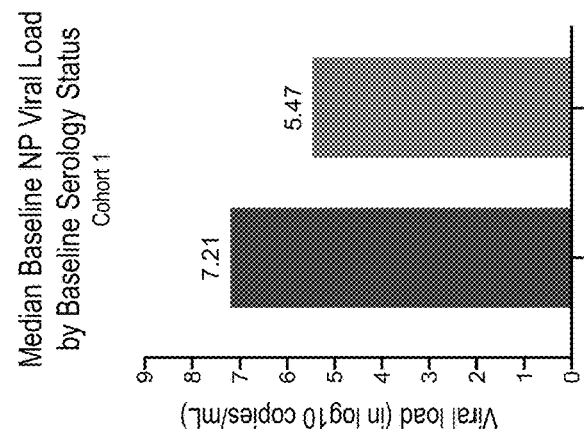

Baseline serostatus*
Seronegative: 217/533 (40.7%)
Seropositive: 270/533 (50.7%)
Other: 46/533 (8.6%)

Baseline Viral Load in NP swabs**
Seroneg: 7.21 log10 copies/mL
Seropos: 5.47 log10 copies/mL

Median days of COVID-19 symptoms before treatment***:
All: 6 days (Q1-Q3 4-8days)
Seroneg: 5 days (3-7 days)
Seropos: 7 days (5-8 days)

**2067 (outpatient study):
Seronegative: 113/275 (41%)
Seropositive*: 123/275 (45%)

***2067 (outpatient study):
Seroneg: 7.18 log10 copies/mL
Seropos: 3.49 log10 copies/mL

*** Median 3.5 days in outpatient study in overall MFAS, seropositive and seronegative patients

FIG. 16

| By serostatus | Placebo seronegative N=68 | Placebo seropositive N=96 |
|---|---|---|
| Death or mechanical Ventilation | | |
| Event number | 14 | 8 |
| Cumulative incidence (%) (80%CI) | 23.0 (16.9, 30.9) | 9.3 (6.0, 14.4) |
| Death | | |
| Event number | 12 | 6 |
| Cumulative incidence (%) (80%CI) | 20.4 (14.3, 28.7) | 6.2 (3.5, 10.7) |
| Mechanical Ventilation | | |
| Event number | 9 | 6 |
| Cumulative incidence (%) (80%CI) | 14.5 (9.7, 21.4) | 7.3 (4.3, 12.0) |
| Discharge | | |
| Event number | 51 | 84 |
| Cumulative incidence (%) (80%CI) | 75.0 (67.9, 81.6) | 88.5 (83.7, 92.5) |

| By baseline viral load | mFAS VL>10^6 N=97 | mFAS VL<10^6 N=80 |
|---|---|---|
| Death or mechanical Ventilation | | |
| Event number | 18 | 5 |
| Cumulative incidence (%) (80%CI) | 20.7 (15.7, 26.9) | 7.3% (4.1%, 12.7%) |
| Death | | |
| Event number | 15 | 4 |
| Cumulative incidence (%) (80%CI) | 16.5 (11.9, 22.8) | 6.3% (3.3%, 11.9%) |
| Mechanical Ventilation | | |
| Event number | 12 | 4 |
| Cumulative incidence (%) (80%CI) | 13.7 (9.7, 19.3) | 6.1% (3.2%, 11.4%) |
| Discharge | | |
| Event number | 75 | 72 |
| Cumulative incidence (%) (80%CI) | 77.5 (71.6, 82.9) | 91.1% (86.4%, 94.8%) |

FIG. 18

| # | Hypothesis Testing Hierarchy (all analyses in mFAS) | Comparison | Treatment effect |
|---|---|---|---|
| 1. | Proportion of patients with ≥1 COVID-19-related hospitalization or all-cause death through day 29 | 2400 mg vs PBO | 71.3% reduction; 18/1355 (1.3%) vs 62/1341 (4.6%) 95% CI (51.7%, 82.9%); p<0.0001 |
| 2. | Proportion of patients with ≥1 COVID-19-related hospitalization or all-cause death through day | 1200 mg vs PBO | 70.4% reduction; 7/736 (1.0%) vs 24/748 (3.2%) 95% CI (31.6%, 87.1%); p=0.0024 |
| 3. | Proportion of patients with ≥1 COVID-19-related hospitalization or all-cause death through day 29 in patients with *baseline viral load > 10⁶ copies/mL* | 2400 mg vs PBO | 77.6% reduction; 13/924 (1.4%) vs 55/876 (6.3%) 95% CI (59.3%, 87.7%); p<0.0001 |
| 4. | Proportion of patients with ≥1 COVID-19-related hospitalization or all-cause death through day 29 in patients who are *seronegative at baseline* | 2400 mg vs PBO | 75.8% reduction; 12/940 (1.3%) vs 49/930 (5.3%) 95% CI (54.7%, 87.0%); p<0.0001 |
| 5. | Proportion of patients with ≥1 COVID-19-related hospitalization or all-cause death through day 29 in patients with *baseline viral load > 10⁶ copies/mL* | 1200 mg vs PBO | 70.7% reduction; 6/482 (1.2%) vs 20/471 (4.2%) 95% CI (27.6%, 88.1%); p=0.0045 |
| 6. | Proportion of patients with ≥1 COVID-19-related hospitalization or all-cause death through day 29 in patients who are *seronegative at baseline* | 1200 mg vs PBO | 82.7% reduction; 3/500 (0.6%) vs 18/519 (3.5%) 95% CI (41.6%, 94.9%); p=0.0014 |
| 7. | Proportion of patients with ≥1 COVID-19-related hospitalization or all-cause death - *day 4 through day 29* | 2400 mg vs PBO | 89.2% reduction; 5/1351 (0.4%) vs 46/1340 (3.4%) 95% CI (73.0%, 95.7%); p<0.0001 |
| 8. | Proportion of patients with ≥1 COVID-19-related hospitalization or all-cause death - *day 4 through day 29* | 1200 mg vs PBO | 71.7% reduction; 5/735 (0.7%) vs 18/748 (2.4%) 95% CI (24.3%, 89.4%); p=0.0101 |
| 9. | Time to COVID-19 symptoms resolution | 2400 mg vs PBO | 4-day faster resolution (Median 10 vs 14 days; p<0.0001) |
| 10. | Time to COVID-19 symptoms resolution | 1200 mg vs PBO | 4-day faster resolution (Median 10 vs 14 days; p<0.0001) |

FAS: all randomized patients (includes patients with and without risk factors for severe COVID-19)

mFAS: all randomized patients with a positive SARS-CoV-2 RT-qPCR test from NP swabs at randomization and ≥1 risk factor for severe COVID-19

FIG. 33

| Baseline Characteristic | Phase 1/2 (high-risk) N=408 | 2400 mg (pooled) N=1355 | PBO (2400 mg) (concurrent) N=1341 | 1200 mg N=736 | PBO (1200 mg) (concurrent) N=748 | 600 mg N=645 |
|---|---|---|---|---|---|---|
| Mean Age (range) | 48.3 (18-89) | 49.3 (18-96) | 47.8 (18-92) | 47.6 (18-90) | 47.1 (18-93) | 49.7 (18-90) |
| Age ≥50 years (%) | 48.0% | 52.8% | 50.6% | 48.5% | 47.6% | 56.2% |
| Male (%) | 46.1% | 48.4% | 47.2% | 49.5% | 47.1% | 51.8% |
| Hispanic/Latino (%) | 47.3% | 34.2% | 35.1% | 42.4% | 39.4% | 28.3% |
| Black/AA (%) | 11.3% | 4.9% | 4.9% | 5.2% | 5.1% | 5.3% |
| BMI ≥30 kg/m² (%) | 61.8% | 58.1% | 57.6% | 55.7% | 57.1% | 61.4% |
| ≥1 Risk Factor (%) | 100% | 100% | 100% | 100% | 100% | 100% |
| Median days of symptoms prior to baseline (IQR) | 3 (2-5) | 3 (2-5) | 3 (2-5) | 3 (2-4) | 3 (2-5) | 3 (2-5) |
| Median Viral Load (log₁₀ copies/m) | 6.48 | 7.01 | 6.95 | 6.92 | 6.65 | 7.00 |
| Median Viral Load (million copies/mL) | 3.04 | 10.3 | 9.0 | 8.4 | 7.1 | 10.1 |
| Viral load >10⁶, (%) | 54.4% | 68% | 65% | 65% | 63% | 68% |
| Seronegative, (%) | 55.1% | 69% | 69% | 68% | 69% | 66% |
| Seropositive, (%) | 33.6% | 24% | 22% | 24% | 22% | 26% | mFAS: all randomized patients with a positive SARS-CoV-2 RT-qPCR test from NP swabs at randomization and ≥1 risk factor for severe COVID-19

FIG. 34

| | PBO (N=1843) | 1200 mg IV (N=827) | 2400 mg IV (N=1849) | 8000 mg IV (N=1012) |
|---|---|---|---|---|
| AESI Infusion-related rxn ≥ Grade 2 thru Day 4 | 0 | 2 (0.2%) | 1 (<0.1%) | 3 (0.4%) |
| AESI Hypersensitivity rxn ≥ Grade 2 thru Day 29 | 1 (<0.1%) | 0 | 1 (<0.1%) | 0 |
| Patients with any SAE | 74 (4.0%) | 9 (1.1%) | 24 (1.3%) | 17 (1.7%) |
| Deaths | 5 (0.3%) | 1 (0.1%) | 1 (<0.1%) | 0 |

FIG. 40

| Primary System Organ Class Preferred Term | Placebo (N=1843) | 1.2 g IV (N=827) | 2.4 g IV (N=1849) | 8.0 g IV (N=1012) | Total (N=5531) |
|---|---|---|---|---|---|
| Patients with any SAE | 74 (4.0%) | 9 (1.1%) | 24 (1.3%) | 17 (1.7%) | 124 (2.2%) |
| Respiratory, thoracic & mediastinal disorders | 22 (1.2%) | 1 (0.1%) | 7 (0.4%) | 5 (0.5%) | 35 (0.6%) |
| Hypoxia | 6 (0.3%) | 1 (0.1%) | 1 (<0.1%) | 1 (<0.1%) | 9 (0.2%) |
| Dyspnea | 7 (0.4%) | 0 | 1 (<0.1%) | 1 (0.1%) | 9 (0.2%) |
| Acute respiratory failure | 3 (0.2%) | 0 | 2 (0.1%) | 1 (<0.1%) | 6 (0.1%) |
| Respiratory distress | 2 (0.1%) | 0 | 0 | 0 | 2 (<0.1%) |
| Infections and infestations | 48 (2.6%) | 5 (0.6%) | 14 (0.8%) | 12 (1.2%) | 79 (1.4%) |
| COVID-19 | 18 (1.0%) | 1 (0.1%) | 5 (0.3%) | 5 (0.5%) | 29 (0.5%) |
| COVID-19 pneumonia | 14 (0.8%) | 2 (0.2%) | 4 (0.2%) | 5 (0.5%) | 25 (0.5%) |
| Pneumonia | 17 (0.9%) | 2 (0.2%) | 3 (0.2%) | 1 (<0.1%) | 23 (0.4%) |
| Metabolism and nutrition disorders | 4 (0.2%) | 0 | 0 | 0 | 4 (<0.1%) |
| Dehydration | 2 (0.1%) | 0 | 0 | 0 | 2 (<0.1%) |
| Hyponatremia | 2 (0.1%) | 0 | 0 | 0 | 2 (<0.1%) |

FIG. 41

| Primary System Organ Class<br>Preferred Term | Placebo<br>(N=1843) | 1.2 g IV<br>(N=827) | 2.4 g IV<br>(N=1849) | 8.0 g IV<br>(N=1012) | Total<br>(N=5531) |
|---|---|---|---|---|---|
| Patients with any Infusion Related Rxn | 0 | 2 (0.2%) | 1 (<0.1%) | 3 (0.4%) | 6 (0.1%) |
| Infusion related reaction | 0 | 1 (0.1%) | 1 (<0.1%) | 1 (<0.1%) | 3 (<0.1%) |
| Nausea | 0 | 1 (0.1%) | 0 | 1 (<0.1%) | 2 (<0.1%) |
| Dizziness | 0 | 1 (0.1%) | 0 | 0 | 1 (<0.1%) |
| Headache | 0 | 1 (0.1%) | 0 | 0 | 1 (<0.1%) |
| Hyperhidrosis | 0 | 0 | 0 | 1 (<0.1%) | 1 (<0.1%) |
| Hyporesponsive to stimuli | 0 | 0 | 0 | 1 (<0.1%) | 1 (<0.1%) |
| Rash | 0 | 0 | 0 | 1 (<0.1%) | 1 (<0.1%) |
| Vomiting | 0 | 0 | 0 | 1 (<0.1%) | 1 (<0.1%) |
| Patients with any Hypersensitivity Rxn | 1 (<0.1%) | 0 | 1 (<0.1%) | 0 | 2 (<0.1%) |
| Urticaria | 1 (<0.1%) | 0 | 1 (<0.1%) | 0 | 2 (<0.1%) |

FIG. 42

| Analysis Set | | Pre PA6 Placebo | Pre PA6 2400 mg | Pre PA6 1200 mg | PA6 or later Placebo | PA6 or later 1200 mg | PA6 or later 2400 mg |
|---|---|---|---|---|---|---|---|
| mFAS | N | N=589 | N=617 | N=625 | N=744 | N=734 | N=736 |
| | Baseline, mean (SD) | 6.70 (1.664) | 6.62 (1.630) | 6.64 (1.671) | 6.63 (1.823) | 6.73 (1.863) | 6.80 (1.765) |
| | MEAN (SD) Day 7 | 3.87 (2.077) | 2.95 (1.858) | 2.97 (1.859) | 3.48 (2.163) | 2.85 (1.854) | 2.70 (1.916) |
| | Mean change from baseline at D7 | -2.84 (1.921) | -3.65 (1.833) | -3.67 (1.901) | -3.14 (1.964) | -3.90 (2.027) | -4.09 (2.002) |
| With hospitalization /deaths | N | N=37 | N=7 | N=13 | N=24 | N=7 | N=11 |
| | Baseline, mean (SD) | 7.56 (1.225) | 6.72 (1.044) | 6.15 (1.735) | 7.50 (1.120) | 7.62 (1.425) | 6.22 (1.976) |
| | MEAN (SD) Day 7 | 5.54 (1.462) | 2.66 (1.808) | 3.10 (2.524) | 5.03 (1.106) | 3.70 (2.493) | 3.14 (2.262) |
| | Mean change from baseline at D7 | -2.12 (1.348) | -4.08 (2.294) | -2.25 (1.907) | -2.69 (1.421) | -4.29 (2.136) | -2.28 (3.379) |
| Without hospitalization /deaths | N | N=552 | N=610 | N=612 | N=720 | N=727 | N=725 |
| | Baseline, mean (SD) | 6.65 (1.674) | 6.62 (1.636) | 6.65 (1.669) | 6.60 (1.836) | 6.72 (1.865) | 6.81 (1.762) |
| | MEAN (SD) Day 7 | 3.80 (2.071) | 2.95 (1.860) | 2.97 (1.853) | 3.45 (2.168) | 2.84 (1.850) | 2.70 (1.916) |
| | Mean change from baseline at D7 | -2.86 (1.936) | -3.65 (1.832) | -3.68 (1.897) | -3.14 (1.972) | -3.89 (2.028) | -4.10 (1.991) |

FIG. 44

| | Pooled Placebo (N=77) | REGEN-COV 300 mg IV (N=80) | REGEN-COV 600 mg IV (N=68) | REGEN-COV 1200 mg IV (N=72) | REGEN-COV 2400 mg IV (N=62) | Total (N=359) |
|---|---|---|---|---|---|---|
| Age (years) Mean (SD) | 35.1 (9.97) | 33.8 (8.90) | 33.9 (9.16) | 34.1 (10.51) | 36.3 (9.16) | 34.6 (9.55) |
| Sex, n (%) | | | | | | |
| Male | 31 (40.3%) | 33 (41.3%) | 39 (57.4%) | 29 (40.3%) | 28 (45.2%) | 160 (44.6%) |
| Female | 46 (59.7%) | 47 (58.8%) | 29 (42.6%) | 43 (59.7%) | 34 (54.8%) | 199 (55.4%) |
| Ethnicity, n (%) | | | | | | |
| Hispanic or Latino | 27 (35.1%) | 28 (35%) | 16 (23.5%) | 26 (36.1%) | 24 (38.7) | 121 (33.7%) |
| Not Hispanic or Latino | 50 (64.9%) | 52 (65%) | 52 (76.5%) | 43 (59.7) | 38 (61.3%) | 235 (65.5%) |
| Not Reported | 0 | 0 | 0 | 3 (4.2%) | 0 | 3 (0.8%) |
| Weight (kg) Mean (SD) | 74.04 (16.05) | 73.12 (14.01) | 73.12 (13.45) | 73.12 (13.54) | 73.21 (12.33) | 73.33 (13.94) |

FIG. 45

| | Pooled Placebo (N=77) | REGEN-COV 600 mg SC (N=75) | REGEN-COV 1200 mg SC (N=73) | Total (N=225) |
|---|---|---|---|---|
| Age (years) | | | | |
| Mean (SD) | 35.1 (9.97) | 33.5 (9.18) | 33.5 (10.88) | 34.1 (10.00) |
| Sex, n (%) | | | | |
| Male | 31 (40.3%) | 36 (48.0%) | 35 (47.9%) | 102 (45.3%) |
| Female | 46 (59.7%) | 39 (52.0%) | 38 (52.1%) | 123 (54.7%) |
| Ethnicity, n (%) | | | | |
| Hispanic or Latino | 27 (35.1%) | 30 (40.0%) | 21 (28.8%) | 78 (34.7%) |
| Not Hispanic or Latino | 50 (64.9%) | 44 (58.7%) | 50 (68.5%) | 144 (64.0%) |
| Not Reported | 0 | 1 (1.3%) | 2 (2.7%) | 3 (1.3%) |
| Weight (kg) | | | | |
| Mean (SD) | 74.04 (16.05) | 72.77 (12.48) | 74.51 (13.48) | 73.77 (14.06) |

FIG. 46

| | Placebo IV (N=57) | REGEN-COV 300 mg IV (N=115) | REGEN-COV 600 mg IV (N=114) | REGEN-COV 1200 mg IV (N=116) | REGEN-COV 2400 mg IV (N=115) |
|---|---|---|---|---|---|
| Total number of TEAE | 11 | 13 | 17 | 25 | 9 |
| Total number of grade 3 or 4 TEAE | 1 | 0 | 1 | 1 | 0 |
| Total number of SAE | 0 | 0 | 0 | 1 | 1 |
| Total number of AESI | 2 | 0 | 1 | 2 | 0 |
| Patients with any TEAE | 10 (17.5%) | 10 (8.7%) | 16 (14.0%) | 22 (19.0%) | 9 (7.8%) |
| Patients with any grade 3 or 4 TEAE | 1 (1.8%) | 0 | 1 (0.9%) | 1 (0.9%) | 0 |
| Patients with any SAE | 0 | 0 | 0 | 1 (0.9%) | 1 (0.9%) |
| Patients with any AESI | 1 (1.8%) | 0 | 1 (0.9%) | 2 (1.7%) | 0 |
| Patients with infusion-related reaction (grade >=2) through day 4 | 0 | 0 | 0 | 0 | 0 |
| Patients with injection-site reactions (grade >=3) through day 4 | 0 | 0 | 0 | 0 | 0 |
| Patients with hypersensitivity reactions (grade >=2) through day 4 | 0 | 0 | 0 | 0 | 0 |
| Patients with any TEAE leading to death | 0 | 0 | 0 | 0 | 0 |
| Patients with any TEAE leading to withdrawal from the study medication | 0 | 0 | 0 | 0 | 1 (0.9%) |
| Patients with any TEAE leading to study infusion interruption | 0 | 0 | 0 | 0 | 0 |

AESI include all grade ≥2 IRR, grade ≥3 ISR, grade ≥2 hypersensitivity reactions, and any TEAE that led to hospitalization of ER visit regardless of relation to COVID-19

FIG. 49

| | Placebo SC (N=58) | REGEN-COV 600 mg SC (N=114) | REGEN-COV 1200 mg SC (N=114) |
|---|---|---|---|
| Total number of TEAE | 11 | 5 | 14 |
| Total number of grade 3 or 4 TEAE | 0 | 0 | 0 |
| Total number of SAE | 0 | 0 | 0 |
| Total number of AESI | 0 | 0 | 1 |
| Patients with any TEAE | 6 (10.3%) | 5 (4.4%) | 12 (10.5%) |
| Patients with any grade 3 or 4 TEAE | 0 | 0 | 0 |
| Patients with any SAE | 0 | 0 | 0 |
| Patients with any AESI | 0 | 0 | 1 (0.9%) |
| Patients with infusion-related reaction (grade >=2) through day 4 | 0 | 0 | 0 |
| Patients with injection-site reactions (grade >=3) through day 4 | 0 | 0 | 0 |
| Patients with hypersensitivity reactions (grade >= 2) through day 4 | 0 | 0 | 0 |
| Patients with any TEAE leading to death | 0 | 0 | 0 |
| Patients with any TEAE leading to withdrawal from the study medication | 0 | 0 | 0 |
| Patients with any TEAE leading to study infusion interruption | 0 | 0 | 0 |

FIG. 50

| 2067 Analysis Set (symptomatic, ≥1 risk factor) | | Original Ph3 Placebo | Original Ph3 2400 mg IV | Original Ph3 1200 mg IV | Amended Ph3 Placebo | Amended Ph3 1200 mg IV | Amended Ph3 600 mg IV |
|---|---|---|---|---|---|---|---|
| mFAS | Baseline, mean (SD) | 6.70 (1.664) | 6.62 (1.630) | 6.64 (1.671) | 6.63 (1.823) | 6.73 (1.863) | 6.80 (1.765) |
| | LSMEAN Change (SE) | -2.63 (0.09) | -3.49 (0.09) | -3.49 (0.09) | -2.64 (0.09) | -3.35 (0.09) | -3.51 (0.09) |
| | Difference from Placebo | | -0.87 (0.10) | -0.87 (0.10) | | -0.71 (0.09) | -0.87 (0.09) |
| | p-value | | <0.0001 | <0.0001 | | <0.0001 | <0.0001 |
| Seronegative | Baseline, mean (SD) | 7.19 (1.370) | 7.10 (1.346) | 7.20 (1.337) | 7.18 (1.550) | 7.27 (1.611) | 7.23 (1.560) |
| | LSMEAN Change (SE) | -2.69 (0.11) | -3.79 (0.10) | -3.84 (0.11) | -2.70 (0.11) | -3.56 (0.11) | -3.70 (0.11) |
| | Difference from Placebo | | -1.10 (0.12) | -1.15 (0.12) | | -0.86 (0.11) | -1.00 (0.11) |
| | p-value | | <0.0001 | <0.0001 | | <0.0001 | <0.0001 |
| Seropositive | Baseline, mean (SD) | 5.18 (1.634) | 5.35 (1.661) | 5.30 (1.696) | 5.07 (1.671) | 5.27 (1.728) | 5.32 (1.695) |
| | LSMEAN Change (SE) | -2.08 (0.19) | -2.49 (0.18) | -2.36 (0.18) | -2.36 (0.16) | -2.53 (0.15) | -2.85 (0.15) |
| | Difference from Placebo | | -0.41 (0.21) | -0.28 (0.21) | | -0.16 (0.19) | -0.49 (0.19) |
| | p-value | | 0.0527 | 0.1802 | | 0.3799 | 0.0094 |

| 20145 Analysis Set (symptomatic, no risk factor or asymptomatic) | | 20145 Placebo (IV/SC) | 20145 2400 mg IV | 20145 1200 mg IV | 20145 600 mg IV | 20145 300 mg IV | 20145 1200 mg SC | 20145 600 mg SC |
|---|---|---|---|---|---|---|---|---|
| mFAS | Baseline, mean (SD) | 6.81 (1.509) | 6.43 (1.948) | 6.56 (1.745) | 6.94 (1.847) | 6.88 (1.784) | 6.73 (1.790) | 6.86 (1.822) |
| | LSMEAN Change (SE) | -3.39 (0.18) | -4.08 (0.17) | -3.83 (0.17) | -3.62 (0.18) | -3.87 (0.17) | -3.94 (0.17) | -3.86 (0.17) |
| | Difference from Placebo | | -0.69 (0.24) | -0.44 (0.24) | -0.22 (0.25) | -0.48 (0.24) | -0.54 (0.25) | -0.47 (0.24) |
| | p-value | | 0.0053 | 0.0714 | 0.3775 | 0.0505 | 0.0331 | 0.0547 |
| Seronegative | Baseline, mean (SD) | 7.02 (1.389) | 7.25 (1.602) | 7.15 (1.518) | 7.43 (1.451) | 7.22 (1.578) | 7.18 (1.564) | 7.40 (1.540) |
| | LSMEAN Change (SE) | -3.48 (0.19) | -4.28 (0.21) | -3.84 (0.20) | -3.85 (0.21) | -4.08 (0.19) | -4.09 (0.20) | -4.19 (0.20) |
| | Difference from Placebo | | -0.81 (0.29) | -0.36 (0.28) | -0.37 (0.28) | -0.60 (0.27) | -0.62 (0.28) | -0.71 (0.28) |
| | p-value | | 0.0052 | 0.1975 | 0.1901 | 0.0270 | 0.0261 | 0.0101 |
| Seropositive | Baseline, mean (SD) | 5.75 (1.758) | 4.88 (1.525) | 5.18 (1.650) | 4.83 (1.865) | 5.71 (2.137) | 4.95 (1.795) | 4.90 (1.519) |
| | LSMEAN Change (SE) | -3.46 (0.49) | -3.54 (0.31) | -3.23 (0.34) | -2.63 (0.41) | -3.00 (0.41) | -3.70 (0.42) | -3.03 (0.45) |
| | Difference from Placebo | | -0.08 (0.58) | 0.24 (0.60) | 0.83 (0.64) | 0.46 (0.64) | -0.24 (0.65) | 0.43 (0.67) |
| | p-value | | 0.8939 | 0.6921 | 0.1971 | 0.4714 | 0.7167 | 0.5157 |

FIG. 51

| Baseline Serology | EVENT | Baseline Viral Load (Log10 Copies/mL) | Day 7 Viral Load (Log10 Copies/mL) | Change to Day 7 in Viral Load (Log10 Copies/mL) |
|---|---|---|---|---|
| All | No | 6.60 | 3.45 | -3.14 |
| All | Yes | 7.50 (n=62) | 5.03 (n=43) | -2.69 |
| SeroNeg | No | 7.14 (n=905) | 4.04 (n=861) | -3.02 |
| SeroNeg | Yes | 7.61 (n=50) | 5.40 (n=35) | -1.83 |
| SeroPos | No | 5.06 (n=289) | 2.47 (n=282) | -2.52 |
| SeroPos | Yes | 7.06 (n=12) | 5.08 (n=8) | -1.56 |

Results not QC'd

FIG. 58

| Hypothesis Testing Hierarchy | Comparison | Treatment Effect |
|---|---|---|
| 1. Incidence of Symptomatic Infection [broad term(%)] | REGEN-COV vs PBO | 81% rel. risk reduction:11/753 (1.5%) vs 59/752 (7.8%)<br>Odds ratio (95% CI)*: 0.17 (0.09, 0.33); p<0.0001 |
| 2. Incidence of Viral Load >10⁴ (copies/mL) (%) | REGEN-COV vs PBO | 86% rel. risk reduction:12/745 (1.6%) vs 85/749 (11.3%)<br>Odds ratio (95% CI)*: 0.13 (0.07, 0.24); p<0.0001 |
| 3. Number of weeks of symptomatic infection | REGEN-COV vs PBO | 93% reduction: 12.9 vs 187.7 (weeks);<br>Per 1000 subjects: 17 vs 249.6 (weeks), p<0.0001 |
| 4. Number of weeks of Viral Load >10⁴ (copies/mL) | REGEN-COV vs PBO | 90% reduction: 14 vs 136 (weeks)<br>Per 1000 subjects: 18.8 vs 181.6 (weeks), p<0.0001 |
| 5. Number of weeks of infection regardless of symptoms | REGEN-COV vs PBO | 82% reduction: 41 vs 231 (weeks)<br>Per 1000 subjects: 54.4 vs 307.2 (weeks), p<0.0001 |
| 6. Incidence of any RT-qPCR positive Infection (%) | REGEN-COV vs PBO | 66% reduction:36/753 (4.8%) vs 107/752 (14.2%)<br>Odds ratio (95% CI)*: 0.31 (0.21, 0.46), p<0.0001 |
| 7. Index linkage to 2067 for incidence of qPCR positive infection (%)[(index case placebo vs index case REGEN-COV) | Index Case (2067):<br>REGEN-COV vs PBO | No reduction: 23/116 (19.8%) vs 10/51 (19.6%)<br>Not significant |

*Based on the logistic regression model adjusted by region (US vs ex-US) and age group (12 to <50 vs >=50 years)
Note: Duration of disease burden endpoints are based on stratified Wilcoxon rank sum test (Van Elteren test) with region (US vs ex-US) and age group (12 to <50 vs >=50 years) as strata.

FIG. 59

| Symptomatic Infection Endpoints | Placebo N=752 | REGEN-COV N=753 | Observed Risk Reduction (%) | Odds Ratio (95% CI)* | p-Value |
|---|---|---|---|---|---|
| Broad term Symptomatic infection rate (%) (primary) | 59 (7.8%) | 11 (1.5%) | 80.8% | 0.17 (0.09, 0.33) | <0.0001 |
| CDC Definition Symptomatic infection rate (%) | 46 (6.1%) | 6 (0.8%) | 86.9% | 0.12 (0.05, 0.29) | <0.0001** |
| Strict term Symptomatic infection rate (%) | 22 (2.9%) | 2 (0.3%) | 89.7% | 0.09 (0.02, 0.37) | 0.0010** |

Prevention Cohort (Cohort A); asymptomatic, RT-PCR negative, seronegative at baseline
*Based on the logistic regression model adjusted by region (US vs ex-US) and age group (12 to <50 vs >=50 years)
** Nominal p-Value

FIG. 60

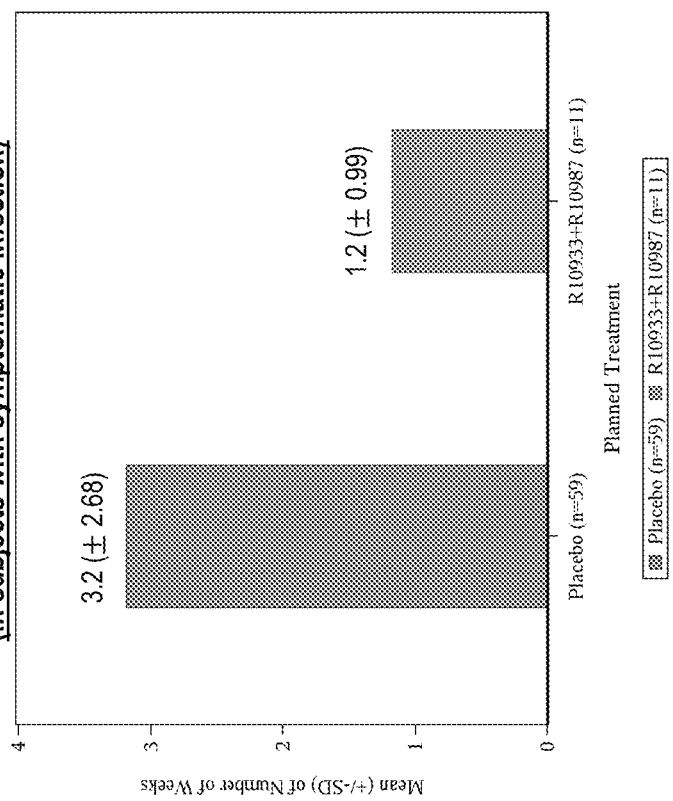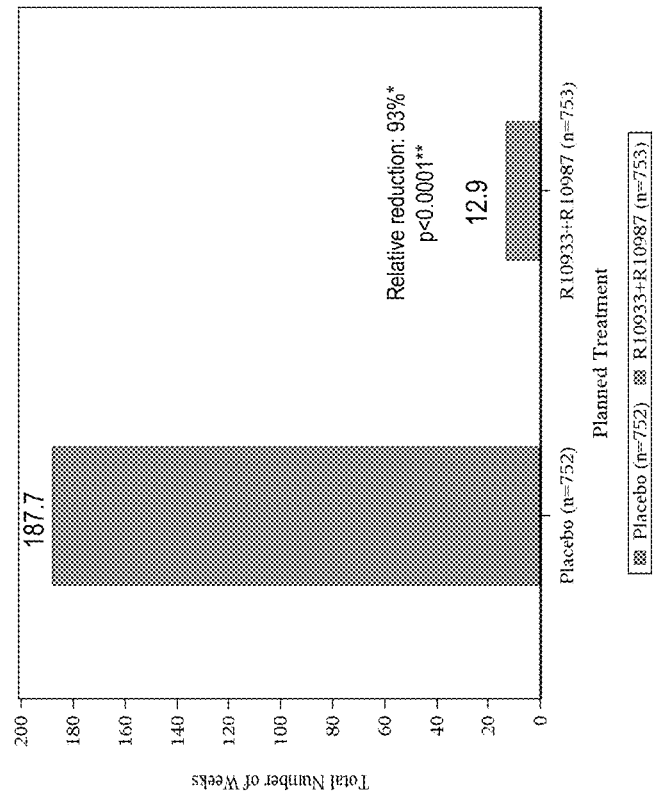
FIG. 63

| Hypothesis Testing Hierarchy | Comparison | Treatment Effect |
|---|---|---|
| 1. Symptomatic infection rate (%) | REGEN-COV vs PBO | 31.4% relative risk reduction; 29/100 (29.0%) vs 44/104 (42.3%)<br>Odds ratio (95% CI):* 0.54 (0.30, 0.97); p=0.0380 |
| 2. Weeks of symptomatic infection | REGEN-COV vs PBO | 45.3% relative risk reduction; 89.6 vs 170.3 (weeks)<br>Per 1000 subjects: 895.7 vs 1637.4 (weeks), p=0.0273 |
| 3. Weeks of Viral Load >10⁴ (copies/mL) | REGEN-COV vs PBO | 39.7% relative risk reduction; 48 vs 82 (weeks)<br>Per 1000 subjects: 489.8 vs 811.9 (weeks); p=0.0010 |

| Seronegative Pre-emptive therapy Cohort | Placebo | REGEN-COV | Risk Reduction | p-Value |
|---|---|---|---|---|
| All subjects | 44/104 (42.3%) | 29/100 (29.0%) | 31.4% | 0.0380 |
| Day 2 and beyond | 37/97 (38.1%) | 19/90 (21.1%) | 44.6% | 0.0094 |
| Day 3 and beyond | 22/82 (26.8%) | 8/79 (10.1%) | 62.3% | 0.0075 |
| Day 4 and beyond | 22/82 (26.8%) | 5/76 (6.6%) | 75.4% | 0.0014 |

*Based on the logistic regression model adjusted by region (US vs ex-US) and age group (12 to <50 vs >=50 years)

Note: Duration of disease burden endpoints are based on stratified Wilcoxon rank sum test (Van Elteren test) with region (US vs ex-US) and age group (12 to <50 vs >=50 years) as strata.

FIG. 66

| Overall study period, including seronegative and seropositive subjects | Prevention Cohort (Cohort A) | | Pre-emptive therapy Cohort (Cohort B) | |
|---|---|---|---|---|
| | Placebo N=1306 | REGEN-COV N=1311 | Placebo N=156 | REGEN-COV N=155 |
| Subjects with any TEAEs | 379 (29.0%) | 265 (20.2%) | 75 (48.1%) | 52 (33.5%) |
| Subjects with any AESI (grade 3 or greater injection site reaction or hypersensitivity reaction) | 0 | 0 | 0 | 0 |
| Subjects with any serious TEAE | 15 (1.1%) | 10 (0.8%) | 4 (2.6%) | 0 |
| Deaths | 2 (0.2%) | 2 (0.2%) | 0 | 0 |
| Injection site reaction | 19 (1.5%) | 55 (4.2%) | 1 (0.6%) | 6 (3.9%) |
| Subjects with treatment/study withdrawn due to TEAEs | 0 | 0 | 0 | 0 |

Comparatively more subjects experienced TEAEs in placebo groups in both Cohort A and B in comparison with study treatment Injection site reactions reported with REGEN-COV were mild to moderate in severity.

FIG. 69

| Overall study period, including seronegative and seropositive subjects | Prevention Cohort (Cohort A) | | Pre-emptive therapy cohort (Cohort B) | |
|---|---|---|---|---|
| | Placebo N=1306 | REGEN-COV N=1311 | Placebo N=156 | REGEN-COV N=155 |
| COVID-19 | 112 (8.6%) | 15 (1.1%) | 49 (31.4%) | 34 (21.9%) |
| Asymptomatic COVID-19 | 108 (8.3%) | 54 (4.1%) | 12 (7.7%) | 7 (4.5%) |
| Headache | 46 (3.5%) | 24 (1.8%) | 1 (0.6%) | 0 |
| Injection site reaction | 19 (1.5%) | 55 (4.2%) | 1 (0.6%) | 6 (3.9%) |

- Most frequent TEAEs were COVID-19 related
- TEAEs occurred more frequently in the placebo group, consistent with the benefit of REGEN-COV

FIG. 70

| | Prevention Cohort (Cohort A) Subjects with at least 1 SAE | | Pre-emptive therapy Cohort (Cohort B) Subjects with at least 1 SAE | |
|---|---|---|---|---|
| Overall study period including seronegative and seropositive subjects | Placebo N=1,306 | REGEN-COV N=1,311 | Placebo N=155 | REGEN-COV N=155 |
| Patients with any SAE by SOC/PT | 15 (1.1%)<br>• Sepsis<br>• Pneumonia (not related to COVID-19)<br>• Appendicitis<br>• Scrotal abscess + UTI<br>• Cardiac arrest<br>• Abdominal pain<br>• Gun shot wound<br>• Breast cancer<br>• Mania + Suicidal ideation<br>• Essential hypertension<br>• COVID-19 x 4<br>• COVID-19 pneumonia x 2 | 10 (0.8%)<br>• Gastroenteritis<br>• Pneumonia (not related to COVID-19)<br>• Sepsis<br>• Soft tissue infection<br>• Appendicitis<br>• Cardiac failure congestive + Acute myocardial infarction + Cholecystitis acute<br>• Abdominal pain upper<br>• Sudden death<br>• Ankle+ Tibia+ Foot fracture<br>• Cervix carcinoma recurrent | 4 (2.6%)<br>• Acute pancreatitis<br>• COVID-19 x 2<br>• COVID-19 pneumonia | 0 |
| Deaths by SOC/PT | 2 (0.2%)<br>• Cardiac arrest (not related to COVID-19)<br>• Gunshot wound | 2 (0.2%)<br>• Cardiac failure congestive<br>• Sudden death in subject with multiple comorbidities (not related to COVID-19) | 0 | 0 |

FIG. 71

Demographic and Baseline Medical Characteristics* (mFAS)

| Characteristic | REGEN-COV 2400 mg (n=1355) | Placebo (2400 mg) (concurrent) (n=1341) | REGEN-COV 1200 mg (n=736) | Placebo (1200 mg) (concurrent) (n=748) | Total (n=4057) |
|---|---|---|---|---|---|
| Demographics | | | | | |
| Median age (IQR) — year | 50.0 (39.0–60.0) | 50.0 (37.0–58.0) | 48.5 (37.0–57.5) | 48.0 (35.0–57.0) | 50.0 (38.0–59.0) |
| Baseline age category — no. (%) | | | | | |
| Age ≥50 years | 715 (52.8) | 679 (50.6) | 357 (48.5) | 356 (47.6) | 2101 (51.8) |
| Age ≥65 years | 214 (15.8) | 144 (10.7) | 93 (12.6) | 88 (11.8) | 548 (13.5) |
| Male sex — no. (%) | 656 (48.4) | 633 (47.2) | 364 (49.5) | 352 (47.1) | 1977 (48.7) |
| Hispanic or Latino ethnic group — no. (%)† | 464 (34.2) | 471 (35.1) | 312 (42.4) | 295 (39.4) | 1424 (35.1) |
| Race — no. (%)† | | | | | |
| White | 1161 (85.7) | 1136 (84.7) | 595 (80.8) | 611 (81.7) | 3426 (84.4) |
| Black or African American | 67 (4.9) | 66 (4.9) | 38 (5.2) | 38 (5.1) | 204 (5.0) |
| Asian | 52 (3.8) | 56 (4.2) | 38 (5.2) | 36 (4.8) | 172 (4.2) |
| American Indian or Alaska Native | 19 (1.4) | 13 (1.0) | 17 (2.3) | 10 (1.3) | 52 (1.3) |

FIG. 78

| | | | | | |
|---|---|---|---|---|---|
| Unknown | 28 (2.1) | 43 (3.2) | 36 (4.9) | 37 (4.9) | 122 (3.0) |
| Not reported | 24 (1.8) | 26 (1.9) | 10 (1.4) | 15 (2.0) | 74 (1.8) |
| Median weight (IQR) — kg | 87.50 (75.15-102.10) | 87.90 (74.30-103.00) | 86.20 (74.40-102.10) | 86.20 (72.80-102.40) | 87.80 (74.80-103.00) |
| Body-mass index‡ | 31.09±6.331 | 31.19±6.638 | 31.54±7.309 | 31.07±6.457 | 31.33±6.761 |
| Obesity — no. (%)§ | 787 (56.1) | 772 (57.6) | 410 (55.7) | 427 (57.1) | 2353 (56.0) |
| At least one risk factor for severe Covid-19 — no. (%)¶ | 1355 (100) | 1341 (100) | 736 (100) | 748 (100) | 4057 (100) |
| Medical Clinical Characteristics | | | | | |
| Positive baseline qualitative RT-PCR — no. (%) | 1353 (99.9) | 1333 (99.4) | 734 (99.7) | 744 (99.5) | 4045 (99.7) |
| Baseline viral load in nasopharyngeal swab (raw values) | | | | | |
| No. of patients | 1353 | 1333 | 734 | 744 | 4045 |
| Mean viral load — (10^6) copies/ml | 250.74± 764.3 | 293.66± 1061.1 | 439.04± 1703.6 | 372.54± 1380.5 | 286.58± 1070.8 |
| Median viral load (range) — (10^6) copies/ml | 10.30 (0-10600) | 9.01 (0-16100) | 6.37 (0-29700) | 7.12 (0-16100) | 8.55 (0-29700) |
| Baseline viral load in nasopharyngeal swab (log₁₀ scale) | | | | | |
| No. of patients | 1353 | 1333 | 734 | 744 | 4045 |

FIG. 78 (Cont.)

| | | | | | |
|---|---|---|---|---|---|
| Mean viral load — log₁₀ copies/ml | 6.72±1.707 | 6.66±1.754 | 6.73±1.863 | 6.63±1.823 | 6.69±1.746 |
| Median viral load (range) — log₁₀ copies/ml | 7.01 (2.6–10.0) | 6.95 (2.6–10.2) | 6.92 (2.6–10.5) | 6.85 (2.6–10.2) | 6.98 (2.6–10.5) |
| Baseline serum C-reactive protein level | | | | | |
| No. of patients | 1242 | 1243 | 713 | 724 | 3742 |
| Mean level — mg/l | 11.992±23.2378 | 12.971±24.5365 | 13.244±23.7685 | 13.097±24.9732 | 12.677±24.5170 |
| Median level (range) — mg/l | 4.615 (0.11–354.16) | 4.940 (0.10–242.73) | 4.910 (0.11–238.53) | 4.865 (0.16–227.45) | 4.850 (0.10–354.16) |
| Baseline serum antibody status — no. (%) | | | | | |
| Negative | 940 (69.4) | 930 (68.4) | 588 (67.9) | 519 (69.4) | 2782 (68.6) |
| Positive | 323 (23.8) | 297 (22.1) | 177 (24.0) | 164 (21.9) | 959 (23.6) |
| Other | 92 (6.8) | 114 (8.5) | 59 (8.0) | 65 (8.7) | 316 (7.8) |
| Median time from symptom onset to randomization (IQR) — days | 3.0 (2–5) | 3.0 (2–5) | 3.0 (2–5) | 3.0 (2–4) | 3.0 (2–5) |

\* Plus-minus values are means ±SD. Percentages may not total 100 because of rounding. IQR denotes interquartile range, RT-PCR reverse-transcriptase polymerase chain reaction, and SD standard deviation.
† Race and ethnic group were reported by the patients.
‡ The body-mass index is the weight in kilograms divided by the square of the height in meters.
§ Obesity is defined as a body-mass index of greater than or equal to 30.
¶ Risk factors for hospitalization include an age of more than 50 years, obesity, cardiovascular disease (including hypertension), chronic lung disease (including asthma), chronic metabolic disease (including diabetes), chronic kidney disease (including receipt of dialysis), chronic liver disease, and immunocompromised (immunosuppression or receipt of immunosuppressants).

FIG. 78 (Cont.)

Hierarchical End Points

| Hypothesis Testing Hierarchy* | Comparison | Treatment Effect | P value |
|---|---|---|---|
| 1. Proportion of patients with ≥1 Covid-19-related hospitalization or all-cause death through day 29 | 2400 mg vs placebo | 18/1355 (1.3%) vs 62/1341 (4.6%); 71.3% reduction (95% CI: 51.7%, 82.9%) | <0.0001 |
| 2. Proportion of patients with ≥1 Covid-19-related hospitalization or all-cause death through day 29 | 1200 mg vs placebo | 7/736 (1.0%) vs 24/748 (3.2%); 70.4% reduction (95% CI: 31.6%, 87.1%) | 0.0024 |
| 3. Proportion of patients with ≥1 Covid-19-related hospitalization or all-cause death through day 29 in patients with baseline viral load >10⁶ copies/mL | 2400 mg vs placebo | 13/924 (1.4%) vs 55/876 (6.3%); 77.6% reduction (95% CI: 59.3%, 87.7%) | <0.0001 |
| 4. Proportion of patients with ≥1 Covid-19-related hospitalization or all-cause death through day 29 in patients who are serum antibody negative at baseline | 2400 mg vs placebo | 12/940 (1.3%) vs 49/930 (5.3%); 75.8% reduction (95% CI: 54.7%, 87.0%) | <0.0001 |
| 5. Proportion of patients with ≥1 Covid-19-related hospitalization or all-cause death through day 29 in patients with baseline viral load >10⁶ copies/mL | 1200 mg vs placebo | 6/482 (1.2%) vs 20/471 (4.2%); 70.7% reduction (95% CI: 27.6%, 88.1%) | 0.0045 |
| 6. Proportion of patients with ≥1 Covid-19-related hospitalization or all-cause death through day 29 in patients who are serum antibody negative at baseline | 1200 mg vs placebo | 3/508 (0.6%) vs 18/519 (3.5%); 82.7% reduction (95% CI: 41.6%, 94.9%) | 0.0014 |
| 7. Proportion of patients with ≥1 Covid-19-related hospitalization or all-cause death from day 4 through day 29 | 2400 mg vs placebo | 5/1351 (0.4%) vs 46/1340 (3.4%); 89.2% reduction (95% CI: 73.0%, 95.7%) | <0.0001 |
| 8. Proportion of patients with ≥1 Covid-19-related hospitalization or all-cause death from day 4 through day 29 | 1200 mg vs placebo | 5/735 (0.7%) vs 18/748 (2.4%); 71.7% reduction (95% CI: 24.3%, 89.4%) | 0.0101 |
| 9. Time to Covid-19 symptoms resolution | 2400 mg vs placebo | Median 10 vs 14 days, 4-day faster resolution | <0.0001 |
| 10. Time to Covid-19 symptoms resolution | 1200 mg vs placebo | Median 10 vs 14 days, 4-day faster resolution | <0.0001 |

* All analyses in mFAS; all randomized patients with a positive SARS-CoV-2 RT-qPCR test from nasopharyngeal swabs at randomization and ≥1 risk factor for severe COVID-19.

CI, confidence interval; mFAS, modified full analysis set; RT-qPCR, reverse transcriptase quantitative polymerase chain reaction.

FIG. 79

Overview of Serious Adverse Events and Adverse Events of Special Interest in the Safety Population

| Event | Placebo (n=1843) | REGEN-COV 1200 mg IV (n=827) | REGEN-COV 2400 mg IV (n=1849) | REGEN-COV 8000 mg IV (n=1012) | Total (n=5531) |
|---|---|---|---|---|---|
| | | no. of patients (percent) | | | |
| Serious adverse event | | | | | |
| Any serious adverse event | 74 (4.0) | 9 (1.1) | 24 (1.3) | 17 (1.7) | 124 (2.2) |
| Any serious adverse event of special interest* | 6 (0.3) | 1 (0.1) | 1 (<0.1) | 1 (<0.1) | 9 (0.2) |
| Adverse events of special interest that occurred or worsened during the observation period† | | | | | |
| Grade ≥2 infusion-related reaction within 4 days | 0 | 2 (0.2) | 1 (<0.1) | 3 (0.3) | 6 (0.1) |
| Grade ≥2 hypersensitivity reaction within 29 days | 1 (<0.1) | 0 | 1 (<0.1) | 0 | 2 (<0.1) |
| Adverse events that occurred or worsened during the observation period† | | | | | |
| Patients with event | 189 (10.3) | 59 (7.1) | 142 (7.7) | 85 (8.4) | 475 (8.6) |
| Patients with grade 3 or 4 event | 62 (3.4) | 11 (1.3) | 18 (1.0) | 15 (1.5) | 106 (1.9) |
| Patients with event that led to death | 5 (0.3) | 1 (0.1) | 1 (<0.1) | 0 | 7 (0.1) |
| Patients with event that led to withdrawal from the trial | 1 (<0.1) | 0 | 1 (<0.1) | 2 (0.2) | 4 (<0.1) |
| Patients with event that led to infusion interruption^ | 0 | 1 (0.1) | 0 | 1 (<0.1) | 2 (<0.1) |

* Events were hypersensitivity reactions (grade ≥2), infusion-related reactions (grade ≥2), or medically-attended visits, regardless of relation to Covid-19
† Events listed here were not present at baseline or were an exacerbation of a preexisting condition that occurred during the observation period, which is defined as the time from administration of REGEN-COV or placebo to the final follow-up visit

CI, confidence interval; HR, hazard ratio; IV, intravenous.

FIG. 86A
FIG. 86B
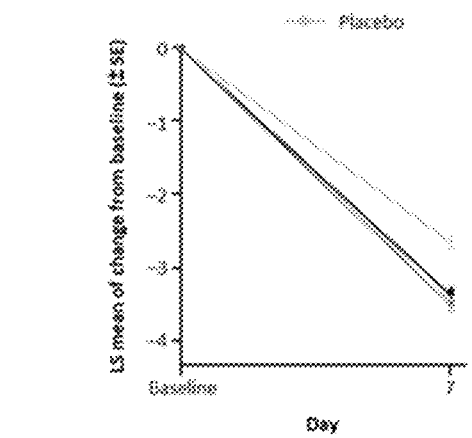
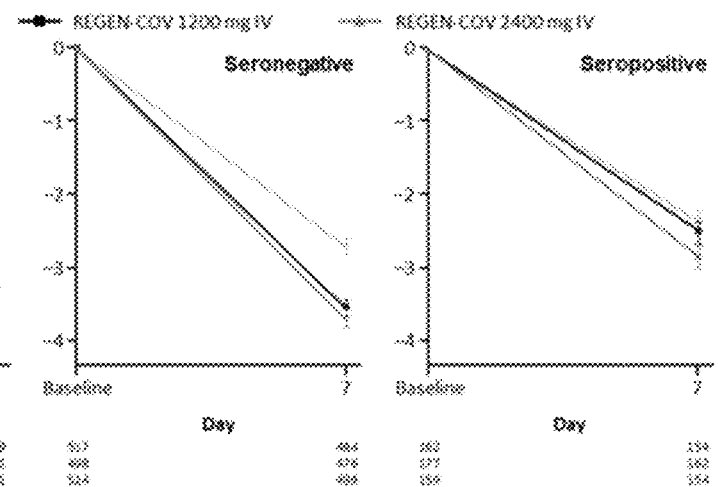
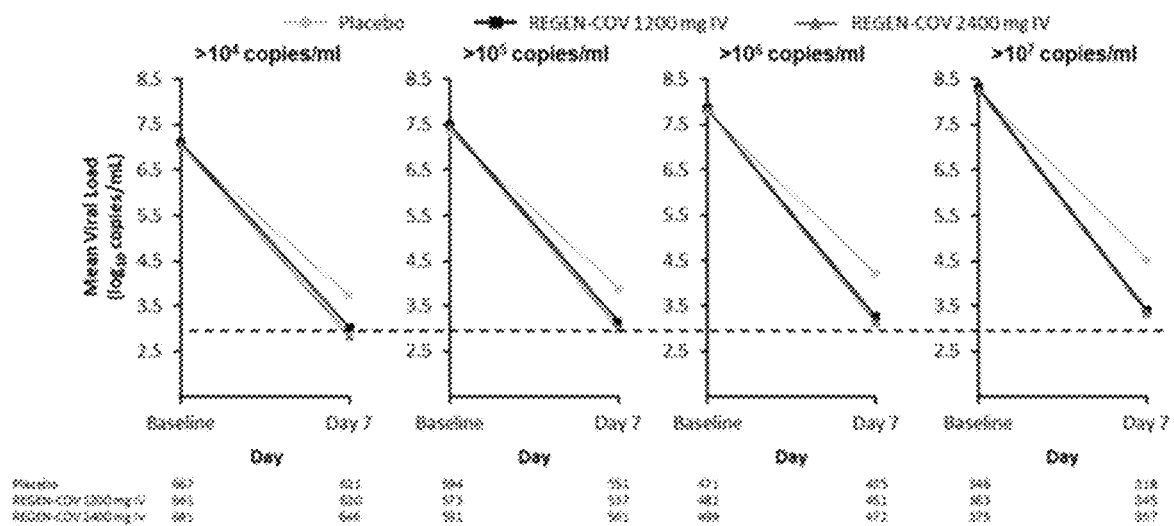
FIG. 86C

FIG. 88A
FIG. 88B
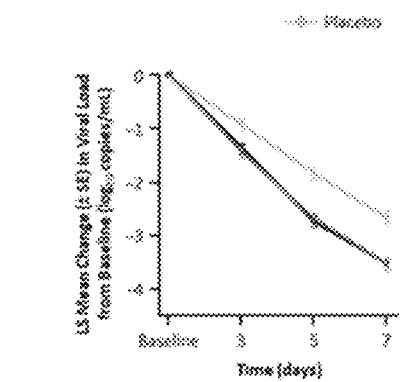
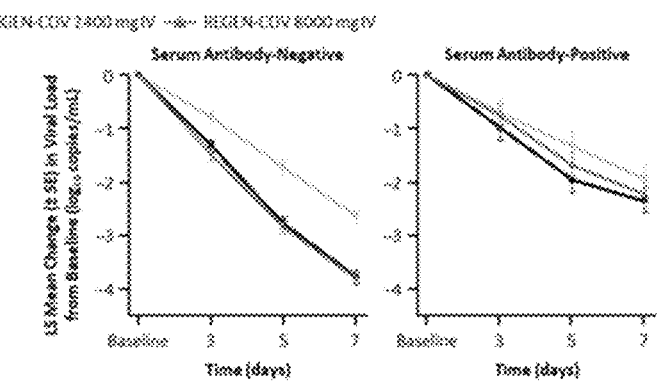
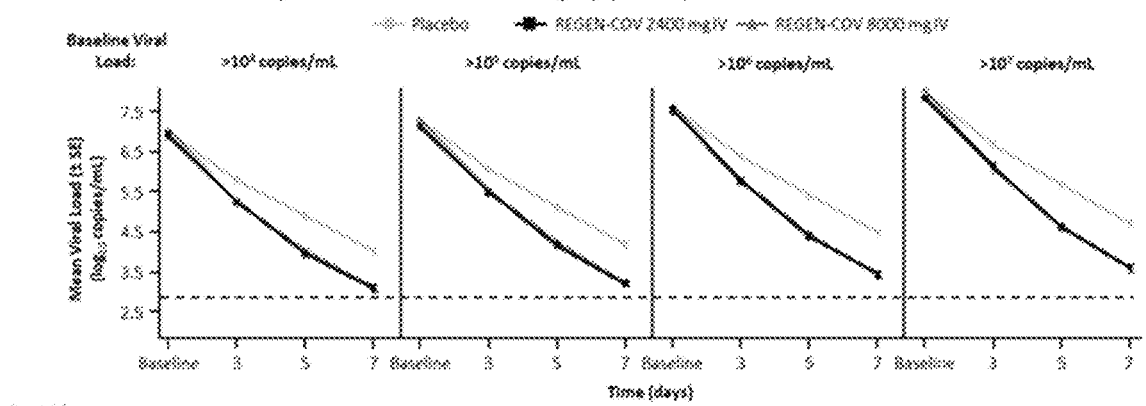
FIG. 88C

Phase 3 Primary Analysis Hierarchical Testing Order

The analysis of the primary endpoint (proportion of patients with ≥1 COVID-19-related hospitalization or all-cause death through day 29) and key secondary endpoint (time to symptom resolution) will be conducted at the overall α=0.05. The endpoints will be tested hierarchically in the following order, adjusting for interim analysis:

| Hierarchy Number | Description |
| --- | --- |
| 1 | Proportion of patients with ≥1 COVID-19-related hospitalization or all-cause death through day 29 in the mFAS for REGEN-COV 2400 mg group versus placebo |
| 2 | Proportion of patients with ≥1 COVID-19-related hospitalization or all-cause death through day 29 in the mFAS for REGEN-COV 1200 mg group versus placebo |
| 3 | Proportion of patients with ≥1 COVID-19-related hospitalization or all-cause death through day 29 in the mFAS patients with baseline viral load >10$^6$ copies/mL for REGEN-COV 2400 mg group versus placebo |
| 4 | Proportion of patients with ≥1 COVID-19-related hospitalization or all-cause death through day 29 in the mFAS patients who are seronegative at baseline for REGEN-COV 2400 mg group versus placebo |
| 5 | Proportion of patients with ≥1 COVID-19-related hospitalization or all-cause death through day 29 in the mFAS patients with baseline viral load >10$^6$ copies/mL for REGEN-COV 1200 mg group versus placebo |
| 6 | Proportion of patients with ≥1 COVID-19-related hospitalization or all-cause death through day 29 in the mFAS patients who are seronegative at baseline for REGEN-COV 1200 mg group versus placebo |
| 7 | Proportion of patients with ≥1 COVID-19-related hospitalization or all-cause death from day 4 through day 29 in the mFAS for REGEN-COV 2400 mg group versus placebo |
| 8 | Proportion of patients with ≥1 COVID-19-related hospitalization or all-cause death from day 4 through day 29 in the mFAS for REGEN-COV 1200 mg group versus placebo |
| 9 | Time to COVID-19 symptoms resolution in the mFAS for REGEN-COV 2400 mg group versus placebo |
| 10 | Time to COVID-19 symptoms resolution in the mFAS for REGEN-COV 1200 mg group versus placebo | mFAS, modified full analysis set.

FIG. 89

Protocol-Defined Risk Factors for Severe Covid-19 (mFAS)

| Protocol-defined risk factor — no. (%)[a] | Placebo (n=1341) | REGEN-COV 1200 mg (n=736) | REGEN-COV 2400 mg (n=1355) | REGEN-COV 8000 mg (n=625) | Total (n=4057) |
|---|---|---|---|---|---|
| Age ≥50 years | 678 (50.6) | 357 (48.5) | 715 (52.8) | 351 (56.2) | 2101 (51.8) |
| Obesity (BMI ≥30 kg/m²) | 772 (57.6) | 410 (55.7) | 787 (58.1) | 384 (61.4) | 2353 (58.0) |
| Cardiovascular disease, including hypertension | 473 (35.3) | 282 (38.3) | 520 (38.4) | 196 (31.4) | 1471 (36.3) |
| Chronic lung disease, including asthma | 219 (16.3) | 139 (18.9) | 216 (15.9) | 92 (14.7) | 666 (16.4) |
| Type 1 or 2 diabetes mellitus | 210 (15.7) | 94 (12.8) | 202 (14.9) | 97 (15.5) | 603 (14.9) |
| Chronic kidney disease, including those on dialysis | 9 (0.7) | 8 (1.1) | 19 (1.4) | 9 (1.4) | 45 (1.1) |
| Chronic liver disease | 8 (0.6) | 3 (0.4) | 14 (1.0) | 11 (1.8) | 36 (0.9) |
| Immunocompromised[a] | 34 (2.5) | 24 (3.3) | 46 (3.4) | 16 (2.6) | 120 (3.0) |

BMI, body mass index; mFAS, modified full analysis set

[a] The most common immunosuppressive conditions were rheumatoid arthritis, HIV/AIDS, and systemic lupus erythematosus; the most common immunosuppressive medications were hydroxychloroquine, antimetabolites, and TNF inhibitors.

FIG. 90

Demographic and Baseline Medical Characteristics (mFAS) – 8000 mg REGEN-COV

| Characteristic | REGEN-COV 8000 mg (n=625) | Placebo (8000 mg) (concurrent) (n=593) |
|---|---|---|
| Demographics | | |
| Median age (IQR) — year | 51.0 (40.0-59.0) | 50.0 (39.0-58.0) |
| Baseline age category — no. (%) | | |
| Age ≥50 years | 351 (56.2) | 322 (54.3) |
| Age ≥65 years | 97 (15.5) | 56 (9.4) |
| Male sex — no. (%) | 324 (51.8) | 281 (47.4) |
| Hispanic or Latino ethnic group — no. (%)† | 177 (28.3) | 176 (29.7) |
| Race — no. (%)† | | |
| White | 534 (85.4) | 525 (88.5) |
| Black or African American | 33 (5.3) | 28 (4.7) |
| Asian | 26 (4.2) | 20 (3.4) |
| American Indian or Alaska Native | 3 (0.5) | 3 (0.5) |
| Unknown | 15 (2.4) | 6 (1.0) |
| Not reported | 14 (2.2) | 11 (1.9) |
| Median weight (IQR) — kg | 89.85 (76.20-106.60) | 89.50 (75.00-104.00) |

FIG. 91

| | | |
|---|---|---|
| Body-mass index‡ | 31.94±7.229 | 31.35±6.846 |
| Obesity — no. (%)§ | 384 (61.4) | 345 (58.2) |
| At least one risk factor for severe Covid-19 — no. (%)¶ | 625 (100) | 593 (100) |
| Medical Clinical Characteristics | | |
| Positive baseline qualitative RT-PCR — no. (%) | 625 (100) | 589 (99.3) |
| Baseline viral load in nasopharyngeal swab (raw values) | | |
| No. of patients | 625 | 589 |
| Mean viral load — (10^6) copies/ml | 170.03 ± 555.7 | 194.01 ± 628.9 |
| Median viral load (range) — (10^6) copies/ml | 10.10 (0–6090) | 11.20 (0–6780) |
| Baseline viral load in nasopharyngeal swab (log₁₀ scale) | | |
| No. of patients | 625 | 589 |
| Mean viral load — log₁₀ copies/ml | 6.64 ± 1.671 | 6.70 ± 1.664 |
| Median viral load (range) — log₁₀ copies/ml | 7.00 (2.6–9.8) | 7.05 (2.6–9.8) |
| Baseline serum C-reactive protein level | | |
| No. of patients | 544 | 519 |
| Mean level — mg/l | 14.206 ± 28.0260 | 12.794 ± 23.9368 |
| Median level (range) — mg/l | 5.065 (0.16–228.07) | 5.020 (0.10–242.73) |

FIG. 91 (Cont.)

| Baseline serum antibody status — no. (%) | | |
|---|---|---|
| Negative | 412 (65.9) | 411 (69.3) |
| Positive | 162 (25.9) | 133 (22.4) |
| Other | 51 (8.2) | 49 (8.3) |
| Median time from symptom onset to randomization (IQR) — days | 3.0 (2–5) | 3.0 (2–5) |

* Plus–minus values are means ±SD. Percentages may not total 100 because of rounding. IQR denotes interquartile range, RT-PCR reverse-transcriptase polymerase chain reaction, and SD standard deviation.
† Race and ethnic group were reported by the patients.
‡ The body-mass index is the weight in kilograms divided by the square of the height in meters.
§ Obesity is defined as a body-mass index of greater than or equal to 30.
¶ Risk factors for hospitalization include an age of more than 50 years, obesity, cardiovascular disease (including hypertension), chronic lung disease (including asthma), chronic metabolic disease (including diabetes), chronic kidney disease (including receipt of dialysis), chronic liver disease, and immunocompromised (immunosuppression or receipt of immunosuppressants).

FIG. 91 (Cont.)

Proportion of Patients in the Placebo Arm with ≥1 Covid-19-related Hospitalization or All-cause Death by Baseline Viral Load Category

| End Point | Placebo (concurrent with REGEN-COV 2400 mg) | Placebo (concurrent with REGEN-COV 1200 mg) |
|---|---|---|
| Proportion of patients with ≥1 Covid 19-related hospitalization or all-cause death | | |
| Baseline viral load category: high viral load (>10⁶ copies/mL) | | |
| No. of patients | 876 | 471 |
| Patients with event within 29 days — no. (%) | 55 (6.3) | 20 (4.2) |
| Baseline viral load category: low viral load (≤10⁶ copies/mL) | | |
| No. of patients | 457 | 273 |
| Patients with event within 29 days — no. (%) | 6 (1.3) | 4 (1.5) |

FIG. 92

Viral Load in the Placebo Arm by With and Without Hospitalization or Death and by Baseline Serum Antibody Status

| Baseline Serum Antibody Status: | Covid-19-related Hospitalization or Death | Baseline SARS-CoV-2 Viral Load (log₁₀ copies/ml) (Mean ± SD) | Day 7 SARS-CoV-2 Viral Load (log₁₀ copies/ml) (Mean ± SD) |
|---|---|---|---|
| All | | | |
| n=1272 | No | 6.62 ± 1.77 | 3.60 ± 2.13 |
| n=61 | Yes | 7.54 ± 1.18 | 5.36 ± 1.35 |
| Negative | | | |
| n=877 | No | 7.16 ± 1.49 | 4.03 ± 2.01 |
| n=48 | Yes | 7.61 ± 1.09 | 5.41 ± 1.36 |
| Positive | | | |
| n=283 | No | 5.04 ± 1.62 | 2.46 ± 2.04 |
| n=12 | Yes | 7.06 ± 1.35 | 5.08 ± 1.39 |

SD, standard deviation.

FIG. 93

Proportion of Patients with ≥1 Covid-19-related Hospitalization or All-cause Death

| End Point | REGEN-COV 2400 mg (n=1355) | Placebo (2400 mg) (concurrent) (n=1341) | REGEN-COV 1200 mg (n=736) | Placebo (1200 mg) (concurrent) (n=748) |
|---|---|---|---|---|
| Proportion of patients with ≥1 Covid-19-related hospitalization or all-cause death | | | | |
| Patients with event within 29 days — no. (%) | 18 (1.3) | 62 (4.6) | 7 (1.0) | 24 (3.2) |
| Relative risk reduction vs placebo — percentage points | 71.3 | | 70.4 | |
| 95% CI† | 51.7, 82.9 | | 31.6, 87.1 | |
| Proportion of patients with hospitalization | | | | |
| Patients with event within 29 days — no. (%) | 17 (1.3) | 59 (4.4) | 6 (0.8) | 23 (3.1) |
| Relative risk reduction vs placebo — percentage points | 71.5 | | 73.5 | |
| 95% CI† | 51.3, 83.3 | | 35.3, 89.1 | |
| Proportion of patients with all-cause death | | | | |
| Patients with event within 29 days — no. (%) | 1 (<0.1) | 3 (0.2) | 1 (0.1) | 1 (0.1) |
| Relative risk reduction vs placebo — percentage points | 67.0 | | -1.6 | |
| 95% CI† | -216.7, 96.6 | | -1522, 93.6 | |

CI, confidence interval
† 95% CI used the Farrington-Manning method

FIG. 94

Proportion of Patients with ≥1 Covid-19-related MAV or All-cause Death

| End Point | REGEN-COV 2400 mg (n=1355) | Placebo (2400 mg) (concurrent) (n=1341) | REGEN-COV 1200 mg (n=736) | Placebo (1200 mg) (concurrent) (n=748) |
|---|---|---|---|---|
| Proportion of patients with ≥1 Covid-19 related MAV or all-cause death | | | | |
| Patients with event within 29 days — no. (%) | 43 (3.2) | 109 (8.1) | 20 (2.7%) | 51 (6.8) |
| Relative risk reduction vs placebo — percentage points | 61.8 | | 60.1 | |
| 95% CI | 44.9, 72.3 | | 33.8, 76.0 | |
| Proportion of patients with hospitalization | | | | |
| Patients with event within 29 days — no. (%) | 17 (1.3) | 59 (4.4) | 6 (0.8) | 23 (3.1) |
| Relative risk reduction vs placebo — percentage points | 71.5 | | 73.5 | |
| 95% CI | 51.3, 83.3 | | 35.3, 89.1 | |
| Proportion of patients with emergency room visit | | | | |
| Patients with event within 29 days — no. (%) | 9 (0.7) | 16 (1.2) | 2 (0.3) | 10 (1.3) |
| Relative risk reduction vs placebo — percentage points | 44.3 | | 79.7 | |
| 95% CI | -25.5, 75.3 | | 7.5, 95.5 | |
| Proportion of patients with urgent care visit | | | | |
| Patients with event within 29 days — no. (%) | 3 (0.2) | 7 (0.5) | 1 (0.1) | 5 (0.7) |
| Relative risk reduction vs placebo — percentage points | 57.6 | | 79.7 | |
| 95% CI | -63.7, 89.0 | | -73.6, 97.6 | |

FIG. 95

| Proportion of patients with physician office/telemedicine visit | | | |
|---|---|---|---|
| Patients with event within 29 days — no. (%) | 13 (1.0) | 24 (1.8) | 10 (1.4) | 12 (1.6) |
| Relative risk reduction vs placebo — percentage points | 46.4 | | 15.3 | |
| 95% CI† | -4.9, 72.6 | | -94.8, 63.2 | |
| Proportion of patients with all-cause death | | | |
| Patients with event within 29 days — no. (%) | 1 (<0.1) | 3 (0.2) | 1 (0.1) | 1 (0.1) |
| Relative risk reduction vs placebo — percentage points | 67.0 | | -1.6 | |
| 95% CI† | -216.7, 96.6 | | -1522, 93.6 | |

CI, confidence interval; MAV, medically-attended visit

* A patient with multiple types of events was only counted to the worst level event, following this decreasing order: all-cause death, hospitalization, ER, urgent care, physician office visit/telemedicine.
† 95% CI used the Farrington-Manning method.

FIG. 95 (Cont.)

Hospitalization Outcomes: Length of Stay, ICU, and Mechanical Ventilation

| End Point | REGEN-COV 2400 mg (n=1355) | Placebo (2400 mg) (concurrent) (n=1341) | REGEN-COV 1200 mg (n=736) | Placebo (1200 mg) (concurrent) (n=748) |
|---|---|---|---|---|
| Days of hospitalization due to COVID-19 per patient | | | | |
| No. of patients | 18 | 62 | 7 | 24 |
| Mean (SD) | 8.6 ± 7.07 | 10.0 ± 7.16 | 7.0 ± 8.04 | 8.4 ± 6.74 |
| Median (IQR) | 6.0 (3.0–11.0) | 7.0 (5.0–13.0) | 4.0 (3.0–6.0) | 5.5 (4.0–10.5) |
| Proportion of patients admitted to an ICU | | | | |
| Patients with event within 29 days — no. (%) | 6 (0.4) | 18 (1.3) | 3 (0.4) | 7 (0.9) |
| Relative risk reduction vs placebo — percentage points | 67.0 | | 56.4 | |
| 95% CI* | 17.2, 86.9 | | -67.8, 88.7 | |
| Proportion of patients requiring mechanical ventilation | | | | |
| Patients with event within 29 days — no. (%) | 1 (<0.1) | 6 (0.4) | 1 (0.1) | 2 (0.3) |
| Relative risk reduction vs placebo — percentage points | 83.5 | | 49.2 | |
| 95% CI* | -36.8, 98.0 | | -459.2, 95.4 | |

CI, confidence interval; ICU, intensive care unit; IQR, interquartile range; SD, standard deviation

* 95% CI used the Farrington-Manning method

FIG. 96

Proportion of Patients with ≥1 Covid-19-related Hospitalization, Emergency Room Visits, or All-cause Death

| End Point | REGEN-COV 2400 mg (n=1355) | Placebo (2400 mg) (concurrent) (n=1341) | REGEN-COV 1200 mg (n=736) | Placebo (1200 mg) (concurrent) (n=748) |
|---|---|---|---|---|
| Proportion of patients with events | | | | |
| Patients with event within 29 days — no. (%) | 27 (2.0) | 78 (5.8) | 9 (1.2) | 34 (4.5) |
| Relative risk reduction vs placebo — percentage points | 65.7 | | 73.1 | |
| 95% CI* | 47.3, 77.7 | | 44.3, 87.0 | |

CI, confidence interval.
* 95% CI used the Farrington-Manning method.

FIG. 97

Proportion of Patients with ≥1 Covid-19-related Hospitalization or All-cause Death – 8000 mg REGEN-COV

| End Point | REGEN-COV 8000 mg (n=625) | Placebo (8000 mg) (concurrent) (n=593) |
|---|---|---|
| Proportion of patients with ≥1 COVID-19-related hospitalization or all-cause death | | |
| Patients with event within 29 days — no. (%) | 13 (2.1) | 38 (6.4) |
| Relative risk reduction vs placebo — percentage points | 67.5 | |
| 95% CI† | 39.7, 82.5 | |
| Proportion of patients with hospitalization | | |
| Patients with event within 29 days — no. (%) | 13 (2.1) | 36 (6.1) |
| Relative risk reduction vs placebo — percentage points | 65.7 | |
| 95% CI† | 36.0, 81.6 | |
| Proportion of patients with all-cause death | | |
| Patients with event within 29 days — no. (%) | 0 | 2 (0.3) |
| Relative risk reduction vs placebo — percentage points | 100.0 | |
| 95% CI† | n/a | |

CI, confidence interval

† 95% CI used the Farrington-Manning method.

FIG. 98

Proportion of Patients with ≥1 Covid-19-related MAV or All-cause Death – 8000 mg REGEN-COV

| End Point | REGEN-COV 8000 mg (n=625) | Placebo (8000 mg) (concurrent) (n=593) |
|---|---|---|
| Proportion of patients with ≥1 Covid-19-related MAV or all-cause death | | |
| Patients with event within 29 days — no. (%) | 26 (4.2) | 58 (9.8) |
| Relative risk reduction vs placebo — percentage points | 57.5 | |
| 95% CI | 33.4, 72.8 | |
| Proportion of patients with hospitalization | | |
| Patients with event within 29 days — no. (%) | 13 (2.1) | 36 (6.1) |
| Relative risk reduction vs placebo — percentage points | 65.7 | |
| 95% CI | 36.0, 81.6 | |
| Proportion of patients with emergency room visit | | |
| Patients with event within 29 days — no. (%) | 3 (0.5) | 6 (1.0) |
| Relative risk reduction vs placebo — percentage points | 52.6 | |
| 95% CI | -88.8, 89.1 | |
| Proportion of patients with urgent care visit | | |
| Patients with event within 29 days — no. (%) | 2 (0.3) | 2 (0.3) |
| Relative risk reduction vs placebo — percentage points | 5.1 | |
| 95% CI | -571.4, 86.6 | |

FIG. 99

| | | |
|---|---|---|
| Proportion of patients with physician office/telemedicine visit | | |
| Patients with event within 29 days — no. (%) | 8 (1.3) | 12 (2.0) |
| Relative risk reduction vs placebo — percentage points | 36.7 | |
| 95% CI† | -53.6, 74.0 | |
| Proportion of patients with all-cause death | | |
| Patients with event within 29 days — no. (%) | 0 | 2 (0.3) |
| Relative risk reduction vs placebo — percentage points | 100.0 | |
| 95% CI† | n/a | |

CI, confidence interval; MAV, medically-attended visit.

* A patient with multiple types of events was only counted to the worst level event, following this decreasing order: all-cause death, hospitalization, ER, urgent care, physician office visit/telemedicine.
† 95% CI used the Farrington-Manning method.

FIG. 99 (Cont.)

Treatment-Emergent Adverse Events Leading to Death

| System Organ Class<br>Preferred Term | Placebo<br>(n=1476) | REGEN-COV<br>1200 mg IV<br>(n=827) | REGEN-COV<br>2400 mg IV<br>(n=1512) | REGEN-COV<br>8000 mg IV<br>(n=689) | Total<br>(n=4504) |
|---|---|---|---|---|---|
| | | no. of patients (percent) | | | |
| Number of patients with at least one treatment-emergent adverse event leading to death | 5 (0.3) | 1 (0.1) | 1 (<0.1) | 0 | 7 (0.2) |
| Treatment-emergent adverse event leading to death by system organ class and preferred term | | | | | |
| Respiratory, thoracic and mediastinal disorders | | | | | |
| Dyspnoea | 1 (<0.1) | 0 | 1 (<0.1) | 0 | 2 (<0.1) |
| Acute respiratory distress syndrome | 1 (<0.1) | 0 | 0 | 0 | 1 (<0.1) |
| Hypoxia | 0 | 1 (0.1) | 0 | 0 | 1 (<0.1) |
| Respiratory failure | 1 (<0.1) | 0 | 0 | 0 | 1 (<0.1) |
| Infections and infestations | | | | | |
| COVID-19 | 1 (<0.1) | 0 | 0 | 0 | 1 (<0.1) |
| COVID-19 pneumonia | 1 (<0.1) | 0 | 0 | 0 | 1 (<0.1) |
| Pneumonia | 1 (<0.1) | 0 | 0 | 0 | 1 (<0.1) |
| Neoplasms benign, malignant and unspecified (including cysts and polyps) | | | | | |
| Tumor obstruction | 1 (<0.1) | 0 | 0 | 0 | 1 (<0.1) |

FIG. 100

Treatment-Emergent Serious Adverse Events and Adverse Events of Special Interest

| System Organ Class<br>Preferred Term* | Placebo<br>(n=1843) | REGEN-COV<br>1200 mg IV<br>(n=827) | REGEN-COV<br>2400 mg IV<br>(n=1849) | REGEN-COV<br>8000 mg IV<br>(n=1012) | Total<br>(n=5531) |
|---|---|---|---|---|---|
| | no. of patients (percent)† | | | | |
| Serious treatment-emergent adverse events by system organ class and preferred term | | | | | |
| Infections and infestations | | | | | |
| COVID-19 | 18 (1.0%) | 1 (0.1%) | 5 (0.3%) | 5 (0.5%) | 29 (0.5%) |
| COVID-19 pneumonia | 14 (0.8%) | 2 (0.2%) | 4 (0.2%) | 5 (0.5%) | 25 (0.5%) |
| Pneumonia | 17 (0.9%) | 2 (0.2%) | 3 (0.2%) | 1 (<0.1%) | 23 (0.4%) |
| Respiratory, thoracic and mediastinal disorders | | | | | |
| Dyspnoea | 7 (0.4%) | 0 | 1 (<0.1%) | 1 (<0.1%) | 9 (0.2%) |
| Hypoxia | 6 (0.3%) | 1 (0.1%) | 1 (<0.1%) | 1 (<0.1%) | 9 (0.2%) |
| Acute respiratory failure | 3 (0.2%) | 0 | 2 (0.1%) | 1 (<0.1%) | 6 (0.1%) |
| Respiratory distress | 2 (0.1%) | 0 | 0 | 0 | 2 (<0.1%) |
| Metabolism and nutrition disorders | | | | | |
| Dehydration | 2 (0.1%) | 0 | 0 | 0 | 2 (<0.1%) |
| Hyponatraemia | 2 (0.1%) | 0 | 0 | 0 | 2 (<0.1%) |
| Adverse events of special interest by preferred term | | | | | |
| COVID-19 | 11 (0.6%) | 2 (0.2%) | 4 (0.2%) | 2 (0.2%) | 19 (0.3%) |
| Dyspnoea | 9 (0.5%) | 3 (0.4%) | 3 (0.2%) | 1 (<0.1%) | 16 (0.3%) |
| Cough | 2 (0.1%) | 3 (0.4%) | 2 (0.1%) | 1 (<0.1%) | 8 (0.1%) |
| Pneumonia | 6 (0.3%) | 2 (0.2%) | 0 | 0 | 8 (0.1%) |
| COVID-19 pneumonia | 4 (0.2%) | 2 (0.2%) | 0 | 1 (<0.1%) | 7 (0.1%) |
| Headache | 2 (0.1%) | 2 (0.2%) | 1 (<0.1%) | 1 (<0.1%) | 6 (0.1%) |
| Dizziness | 1 (<0.1%) | 2 (0.2%) | 1 (<0.1%) | 0 | 4 (<0.1%) |
| Nausea | 0 | 2 (0.2%) | 0 | 1 (<0.1%) | 3 (<0.1%) |
| Pulmonary congestion | 1 (<0.1%) | 0 | 0 | 2 (0.2%) | 3 (<0.1%) |
| Nasal congestion | 2 (0.1%) | 0 | 0 | 0 | 2 (<0.1%) |

* Term included if ≥2 patients in any of the individual dose groups.
† A patient who reported 2 or more adverse events with different preferred terms within the same system organ class is counted only once in that system organ class. A patient who reported 2 or more adverse events with the same preferred term is counted only once for that term. A patient who reported 2 or more adverse events with the same preferred term is counted only once for that term. If a patient had more than one occurrence in the same event category, only the most related was counted.

FIG. 101

Adverse Events of Special Interest – Patients Requiring Medical Attention at a Healthcare Facility

| | Placebo (n=1476) | REGEN-COV 1200 mg IV (n=827) | REGEN-COV 2400 mg IV (n=1512) | REGEN-COV 8000 mg IV (n=689) | Total (n=4504) |
|---|---|---|---|---|---|
| | | | no. of patients (percent) | | |
| Patients requiring medical attention at a healthcare facility | | | | | |
| Related to Covid-19 | 44 (3.0) | 15 (1.8) | 19 (1.3) | 10 (1.5) | 88 (2.0) |
| Not related to Covid-19 | 5 (0.3) | 0 | 7 (0.5) | 0 | 12 (0.3) |

FIG. 102

Mean (SD) [N] Pharmacokinetic Parameters of REGN10933 and REGN10987 in Serum

| Pharmacokinetic Parameter | REGN10933 (casirivimab)* | | | REGN10987 (imdevimab)* | | |
|---|---|---|---|---|---|---|
| | 600 mg | 1200 mg | 4000 mg | 600 mg | 1200 mg | 4000 mg |
| $C_{eoi}$ (mg/L)† | 185 (74.5) [158] | 321 (106) [553] | 1049 (317) [388] | 192 (78.9) [171] | 321 (112) [580] | 1049 (308) [400] |
| $C_{28}$ (mg/L)‡ | 46.4 (22.5) [127] | 73.2 (27.2) [609] | 238 (86.1) [482] | 38.3 (19.6) [127] | 60.0 (22.9) [610] | 192 (70.2) [469] |
| Estimated $t_{1/2}$ in days (90% CI)§ | 28.8 (16.5, 41.1) | | | 25.5 (17.4, 33.7) | | |

C, concentration; eoi, end of infusion; IV, intravenous; SD, standard deviation; $t_{1/2}$, half-life.

\* Mean (SD) [N], where N is number of observations
† Concentration at the end of infusion (1 hour)
‡ Observed concentration 28 days after dosing, i.e., on day 29
§ Based on 2-compartment population pharmacokinetic models developed for casirivimab and imdevimab from approximately 3700 patients across different REGEN-COV clinical trials, including this study (2067). Half-life estimates represent values for the 1200 mg IV, 2400 mg IV, and 8000 mg IV doses combined.

FIG. 103

```
                        SEQUENCE LISTING

<160> NUMBER OF SEQ ID NOS: 91

<210> SEQ ID NO 1
<211> LENGTH: 360
<212> TYPE: DNA
<213> ORGANISM: Artificial Sequence
<220> FEATURE:
<223> OTHER INFORMATION: Synthetic

<400> SEQUENCE: 1
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attacttata gtggtagtac catatactac     180
gcagactctg tgaagggccg attcaccatc tccagggaca acgccaagag ctcactgtat     240
ctgcaaatga acagcctgag agccgaggac acggccgtgt attactgtgc gagagatcgc     300
ggtacaacta tggtcccctt tgactactgg ggccagggaa ccctggtcac cgtctcctca     360

<210> SEQ ID NO 2
<211> LENGTH: 120
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Thr Tyr Ser Gly Ser Thr Ile Tyr Tyr Ala Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Thr Thr Met Val Pro Phe Asp Tyr Trp Gly Gln
            100                 105                 110

Gly Thr Leu Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcacct tcagtgacta ctac                                              24

<210> SEQ ID NO 4
<211> LENGTH: 8
<212> TYPE: PRT
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ser Asp Tyr Tyr
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
attacttata gtggtagtac cata                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Thr Tyr Ser Gly Ser Thr Ile
1               5

<210> SEQ ID NO 7
<211> LENGTH: 39
<212> TYPE: DNA
<213> ORGANISM: Artificial Sequence
<220> FEATURE:
<223> OTHER INFORMATION: Synthetic

<400> SEQUENCE: 7
gcgagagatc gcggtacaac tatggtcccc tttgactac                          39

<210> SEQ ID NO 8
<211> LENGTH: 13
<212> TYPE: PRT
<213> ORGANISM: Artificial Sequence
<220> FEATURE:
<223> OTHER INFORMATION: Synthetic

<400> SEQUENCE: 8

Ala Arg Asp Arg Gly Thr Thr Met Val Pro Phe Asp Tyr
1               5                   10

<210> SEQ ID NO 9
<211> LENGTH: 321
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccatcctcc ctgtctgcat ctgtaggaga cagagtcacc    60
atcacttgcc aggcgagtca ggacattacc aactatttaa attggtatca gcagaaacca   120
gggaaagccc ctaagctcct gatctacgct gcatccaatt tggaaacagg ggtcccatca   180
aggttcagtg gaagtggatc tgggacagat tttactttca ccatcagcgg cctgcagcct   240
gaagatattg caacatatta ctgtcaacag tatgataatc tccctctcac tttcggcgga   300
gggaccaagg tggagatcaa a     321

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Glu Thr Gly Val Pro Ser Arg Phe Ser Gly
    50                  55                  60

Ser Gly Ser Gly Thr Asp Phe Thr Phe Thr Ile Ser Gly Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
caggacatta ccaactat     18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Asp Ile Thr Asn Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gctgcatcc     9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caacagtatg ataatctccc tctcact                                        27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Tyr Asp Asn Leu Pro Leu Thr
1               5

<210> SEQ ID NO 17
<211> LENGTH: 1353
<212> TYPE: DNA
<213> ORGANISM: Artificial Sequence
<220> FEATURE:
<223> OTHER INFORMATION: Synthetic

<400> SEQUENCE: 17
caggtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg gctggagtg gtttcatac attacttata gtggtagtac catatactac    180
gcagactctg tgaagggccg attcaccatc tccagggaca cgccaagag ctcactgtat   240
ctgcaaatga acagcctgag agccgaggac acggccgtgt attactgtgc gagagatcgc   300
ggtacaacta tggtcccctt tgactactgg ggccagggaa ccctggtcac cgtctcctca   360
gcctccacca agggcccatc ggtcttcccc ctggcaccct cctccaagag cacctctggg   420
ggcacagcgg ccctgggctg cctggtcaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacccagacc   600
tacatctgca acgtgaatca caagcccagc aacaccaagg tggacaagaa agttgagccc   660
aaatcttgtg acaaaactca cacatgccca ccgtgcccag cacctgaact cctggggga   720
ccgtcagtct tcctcttccc cccaaaaccc aaggacaccc tcatgatctc ccggacccct   780
gaggtcacat gcgtggtggt ggacgtgagc cacgaagacc ctgaggtcaa gttcaactgg   840
tacgtggacg gcgtggaggt gcataatgcc aagacaaagc cgcgggagga gcagtacaac   900
agcacgtacc gtgtggtcag cgtcctcacc gtcctgcacc aggactggct gaatggcaag   960
gagtacaagt gcaaggtctc caacaaagcc ctcccagccc ccatcgagaa aaccatctcc  1020
aaagccaaag gcagccccg agaaccacag gtgtacaccc tgcccccatc ccgggatgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200

-continued

```
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagtccc tctccctgtc tccgggtaaa tga                                 1353
```

<210> SEQ ID NO 18
<211> LENGTH: 450
<212> TYPE: PRT
<213> ORGANISM: Artificial Sequence
<220> FEATURE:
<223> OTHER INFORMATION: Synthetic

<400> SEQUENCE: 18

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Thr Tyr Ser Gly Ser Thr Ile Tyr Tyr Ala Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Thr Thr Met Val Pro Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 19
<211> LENGTH: 645
<212> TYPE: DNA
<213> ORGANISM: Artificial Sequence
<220> FEATURE:
<223> OTHER INFORMATION: Synthetic

<400> SEQUENCE: 19
gacatccaga tgacccagtc tccatcctcc ctgtctgcat ctgtaggaga cagagtcacc      60
atcacttgcc aggcgagtca ggacattacc aactatttaa attggtatca gcagaaacca     120
gggaaagccc ctaagctcct gatctacgct gcatccaatt tggaaacagg ggtcccatca     180
aggttcagtg gaagtggatc tgggacagat tttactttca ccatcagcgg cctgcagcct     240
gaagatattg caacatatta ctgtcaacag tatgataatc tccctctcac tttcggcgga     300
gggaccaagg tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                    645

<210> SEQ ID NO 20
<211> LENGTH: 214
<212> TYPE: PRT
<213> ORGANISM: Artificial Sequence
<220> FEATURE:
<223> OTHER INFORMATION: Synthetic

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Glu Thr Gly Val Pro Ser Arg Phe Ser Gly
    50                  55                  60

Ser Gly Ser Gly Thr Asp Phe Thr Phe Thr Ile Ser Gly Leu Gln Pro

Glu Asp Ile Ala Thr Tyr Tyr Cys Gln Gln Tyr Asp Asn Leu Pro Leu
65                  70                  75                  80

Thr Phe Gly Gly Gly Thr Lys Val Glu Ile Lys Arg Thr Val Ala Ala
            85                  90                  95

Pro Ser Val Phe Ile Phe Pro Pro Ser Asp Glu Gln Leu Lys Ser Gly
        100                 105                 110

Thr Ala Ser Val Val Cys Leu Leu Asn Asn Phe Tyr Pro Arg Glu Ala
    115                 120                 125

Lys Val Gln Trp Lys Val Asp Asn Ala Leu Gln Ser Gly Asn Ser Gln
130                 135                 140

Glu Ser Val Thr Glu Gln Asp Ser Lys Asp Ser Thr Tyr Ser Leu Ser
145                 150                 155                 160

Ser Thr Leu Thr Leu Ser Lys Ala Asp Tyr Glu Lys His Lys Val Tyr
            165                 170                 175

Ala Cys Glu Val Thr His Gln Gly Leu Ser Ser Pro Val Thr Lys Ser
        180                 185                 190

Phe Asn Arg Gly Glu Cys
    195                 200             205

Phe Asn Arg Gly Glu Cys
210

<210> SEQ ID NO 21
<211> LENGTH: 360
<212> TYPE: DNA
<213> ORGANISM: Artificial Sequence
<220> FEATURE:
<223> OTHER INFORMATION: Synthetic

<400> SEQUENCE: 21
caggtgcagc tggtggagtc tgggggaggc gtggtccagc ctggggaggtc cctgagactc    60 tcctgtgcag cctctggatt caccttcagt aactatgcta tgtactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag aactgaggac acggctgtgt attactgtgc gagtggctcc   300
gactacggtg actactttat tggtttactgg ggccagggaa ccctggtcac cgtctcctca   360

<210> SEQ ID NO 22
<211> LENGTH: 120
<212> TYPE: PRT
<213> ORGANISM: Artificial Sequence
<220> FEATURE:
<223> OTHER INFORMATION: Synthetic

<400> SEQUENCE: 22

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met Tyr Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
            85                  90                  95

```
Ala Ser Gly Ser Asp Tyr Gly Asp Tyr Leu Leu Val Tyr Trp Gly Gln
            100                 105                 110
Gly Thr Leu Val Thr Val Ser Ser
        115                 120
```

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23
ggattcacct tcagtaacta tgct                                    24

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Gly Phe Thr Phe Ser Asn Tyr Ala
1               5

<210> SEQ ID NO 25
<211> LENGTH: 24
<212> TYPE: DNA
<213> ORGANISM: Artificial Sequence
<220> FEATURE:
<223> OTHER INFORMATION: Synthetic

<400> SEQUENCE: 25
atatcatatg atggaagtaa taaa                                    24

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Ile Ser Tyr Asp Gly Ser Asn Lys
1               5

<210> SEQ ID NO 27
<211> LENGTH: 39
<212> TYPE: DNA
<213> ORGANISM: Artificial Sequence
<220> FEATURE:
<223> OTHER INFORMATION: Synthetic

<400> SEQUENCE: 27
gcgagtggct ccgactacgg tgactactta ttggtttac                    39

<210> SEQ ID NO 28
<211> LENGTH: 13
<212> TYPE: PRT
<213> ORGANISM: Artificial Sequence
<220> FEATURE:
<223> OTHER INFORMATION: Synthetic

<400> SEQUENCE: 28

Ala Ser Gly Ser Asp Tyr Gly Asp Tyr Leu Leu Val Tyr

<210> SEQ ID NO 29
<211> LENGTH: 330
<212> TYPE: DNA
<213> ORGANISM: Artificial Sequence
<220> FEATURE:
<223> OTHER INFORMATION: Synthetic

<400> SEQUENCE: 29

```
cagtctgccc tgactcagcc tgcctccgtg tctgggtctc ctggacagtc gatcaccatc    60
tcctgcactg gaaccagcag tgacgttggt ggttataact atgtctcctg gtaccaacaa   120
cacccaggca aagcccccaa actcatgatt tatgatgtca gtaagcggcc ctcagggggtt   180
tctaatcgct ctctggctc caagtctggc aacacggcct ccctgaccat ctctgggctc    240
cagtctgagg acgaggctga ttattactgc aactctttga caagcatcag cacttgggtg   300
ttcggcggag ggaccaagct gaccgtccta                                    330
```

<210> SEQ ID NO 30
<211> LENGTH: 110
<212> TYPE: PRT
<213> ORGANISM: Artificial Sequence
<220> FEATURE:
<223> OTHER INFORMATION: Synthetic

<400> SEQUENCE: 30

Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
            20                  25                  30
Asn Tyr Val Ser Trp Tyr Gln Gln His Pro Gly Lys Ala Pro Lys Leu
        35                  40                  45
Met Ile Tyr Asp Val Ser Lys Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Ser Glu Asp Glu Ala Asp Tyr Tyr Cys Asn Ser Leu Thr Ser Ile
                85                  90                  95
Ser Thr Trp Val Phe Gly Gly Gly Thr Lys Leu Thr Val Leu
            100                 105                 110

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31

```
agcagtgacg ttggtggtta taactat                                        27
```

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Ser Ser Asp Val Gly Gly Tyr Asn Tyr
1               5

<210> SEQ ID NO 33
<211> LENGTH: 9
<212> TYPE: DNA
<213> ORGANISM: Artificial Sequence
<220> FEATURE:
<223> OTHER INFORMATION: Synthetic

<400> SEQUENCE: 33 gatgtcagt                                                                 9

<210> SEQ ID NO 34
<211> LENGTH: 3
<212> TYPE: PRT
<213> ORGANISM: Artificial Sequence
<220> FEATURE:
<223> OTHER INFORMATION: Synthetic

<400> SEQUENCE: 34

Asp Val Ser
1

<210> SEQ ID NO 35
<211> LENGTH: 30
<212> TYPE: DNA
<213> ORGANISM: Artificial Sequence
<220> FEATURE:
<223> OTHER INFORMATION: Synthetic

<400> SEQUENCE: 35
aactctttga caagcatcag cacttgggtg                                         30

<210> SEQ ID NO 36
<211> LENGTH: 10
<212> TYPE: PRT
<213> ORGANISM: Artificial Sequence
<220> FEATURE:
<223> OTHER INFORMATION: Synthetic

<400> SEQUENCE: 36

Asn Ser Leu Thr Ser Ile Ser Thr Trp Val
1               5                   10

<210> SEQ ID NO 37
<211> LENGTH: 1353
<212> TYPE: DNA
<213> ORGANISM: Artificial Sequence
<220> FEATURE:
<223> OTHER INFORMATION: Synthetic

<400> SEQUENCE: 37
caggtgcagc tggtggagtc tgggggaggc gtggtccagc ctggggaggtc cctgagactc        60 tcctgtgcag cctctggatt caccttcagt aactatgcta tgtactgggt ccgccaggct       120
ccaggcaagg ggctggagtg ggtggcagtt atatcatatg atggaagtaa taatactat        180 gcagactccg tgaagggccg attcaccatc tccagagaca attccaagaa cacgctgtat       240
ctgcaaatga acagcctgag aactgaggac acggctgtgt attactgtgc gagtggctcc       300
gactacggtg actacttatt ggtttactgg ggccagggaa ccctggtcac cgtctcctca       360
gcctccacca agggcccatc ggtcttcccc ctggcaccct cctccaagag cacctctggg       420
ggcacagcgg ccctgggctg cctggtcaag gactacttcc ccgaaccggt gacggtgtcg       480
tggaactcag gcgccctgac cagcggcgtg cacaccttcc cggctgtcct acagtcctca       540

```
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagtccc tctccctgtc tccgggtaaa tga                                1353
```

<210> SEQ ID NO 38
<211> LENGTH: 450
<212> TYPE: PRT
<213> ORGANISM: Artificial Sequence
<220> FEATURE:
<223> OTHER INFORMATION: Synthetic

<400> SEQUENCE: 38

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met Tyr Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Ser Gly Ser Asp Tyr Gly Asp Tyr Leu Leu Val Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220
```

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 39
<211> LENGTH: 651
<212> TYPE: DNA
<213> ORGANISM: Artificial Sequence
<220> FEATURE:
<223> OTHER INFORMATION: Synthetic

<400> SEQUENCE: 39
cagtctgccc tgactcagcc tgcctccgtg tctgggtctc ctggacagtc gatcaccatc      60
tcctgcactg gaaccagcag tgacgttggt ggttataact atgtctcctg gtaccaacaa     120
cacccaggca agcccccaa actcatgatt tatgatgtca gtaagcggcc ctcagggggtt     180 tctaatcgct tctctggctc caagtctggc aacacggcct ccctgaccat ctctgggctc     240
cagtctgagg acgaggctga ttattactgc aactctttga caagcatcag cacttgggtg     300
ttcggcggag ggaccaagct gaccgtccta ggccagccca aggccgcccc ctccgtgacc     360
ctgttccccc cctcctccga ggagctgcag gccaacaagg ccaccctggt gtgcctgatc     420
tccgacttct accccggcgc cgtgaccgtg gcctggaagg ccgactcctc ccccgtgaag     480
gccggcgtgg agaccaccac ccctccaag cagtccaaca acaagtacgc cgcctcctcc     540
tacctgtccc tgacccccga gcagtggaag tcccaccggt cctactcctg ccaggtgacc     600
cacgagggct ccaccgtgga agaccgtg gccccaccg agtgctcctg a                 651

<210> SEQ ID NO 40
<211> LENGTH: 216
<212> TYPE: PRT
<213> ORGANISM: Artificial Sequence
<220> FEATURE:
<223> OTHER INFORMATION: Synthetic

<400> SEQUENCE: 40

```
Gln Ser Ala Leu Thr Gln Pro Ala Ser Val Ser Gly Ser Pro Gly Gln
1               5                   10                  15

Ser Ile Thr Ile Ser Cys Thr Gly Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Asn Ser Leu Thr Ser Ile
                85                  90                  95

Ser Thr Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 41
<211> LENGTH: 369
<212> TYPE: DNA
<213> ORGANISM: Artificial Sequence
<220> FEATURE:
<223> OTHER INFORMATION: Synthetic

<400> SEQUENCE: 41

```
caggtgcagc tggtgcagtc tggggctgag gtgaagaagc ctggggcctc agtgaaggtc      60
tcctgcaagg cttctggata catcttcacc ggctactata tgcactgggt gcgacaggcc     120
cctggacagg gcttgagtg gatgggatgg atcaaccccta acagtggtgg cgcaaactat     180
gcacagaagt ttcagggcag ggtcaccctg accagggaca cgtccatcac cacagtctac     240
atggaactga gcaggctgag atttgacgac acggccgtgt attactgtgc gagaggatcc     300
cggtatgact ggaaccagaa caactggttc gaccctgggg ccagggaac cctggtcacc       360 gtctcctca                                                              369
```

<210> SEQ ID NO 42
<211> LENGTH: 123
<212> TYPE: PRT

<213> ORGANISM: Artificial Sequence
<220> FEATURE:
<223> OTHER INFORMATION: Synthetic

<400> SEQUENCE: 42

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ile Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Asn Ser Gly Gly Ala Asn Tyr Ala Gln Lys Phe
    50                  55                  60
Gln Gly Arg Val Thr Leu Thr Arg Asp Thr Ser Ile Thr Thr Val Tyr
65                  70                  75                  80
Met Glu Leu Ser Arg Leu Arg Phe Asp Asp Thr Ala Val Tyr Tyr Cys
                85                  90                  95
Ala Arg Gly Ser Arg Tyr Asp Trp Asn Gln Asn Asn Trp Phe Asp Pro
            100                 105                 110
Trp Gly Gln Gly Thr Leu Val Thr Val Ser Ser
        115                 120
```

<210> SEQ ID NO 43
<211> LENGTH: 24
<212> TYPE: DNA
<213> ORGANISM: Artificial Sequence
<220> FEATURE:
<223> OTHER INFORMATION: Synthetic

<400> SEQUENCE: 43
ggatacatct tcaccggcta ctat                                              24

<210> SEQ ID NO 44
<211> LENGTH: 8
<212> TYPE: PRT
<213> ORGANISM: Artificial Sequence
<220> FEATURE:
<223> OTHER INFORMATION: Synthetic

<400> SEQUENCE: 44

```
Gly Tyr Ile Phe Thr Gly Tyr Tyr
1               5
```

<210> SEQ ID NO 45
<211> LENGTH: 24
<212> TYPE: DNA
<213> ORGANISM: Artificial Sequence
<220> FEATURE:
<223> OTHER INFORMATION: Synthetic

<400> SEQUENCE: 45
atcaacccta acagtggtgg cgca                                              24

<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

```
Ile Asn Pro Asn Ser Gly Gly Ala
1               5
```

<210> SEQ ID NO 47
<211> LENGTH: 48
<212> TYPE: DNA
<213> ORGANISM: Artificial Sequence
<220> FEATURE:
<223> OTHER INFORMATION: Synthetic

<400> SEQUENCE: 47
gcgagaggat cccggtatga ctggaaccag aacaactggt tcgacccc            48

<210> SEQ ID NO 48
<211> LENGTH: 16
<212> TYPE: PRT
<213> ORGANISM: Artificial Sequence
<220> FEATURE:
<223> OTHER INFORMATION: Synthetic

<400> SEQUENCE: 48

Ala Arg Gly Ser Arg Tyr Asp Trp Asn Gln Asn Asn Trp Phe Asp Pro
1               5                   10                  15

<210> SEQ ID NO 49
<211> LENGTH: 330
<212> TYPE: DNA
<213> ORGANISM: Artificial Sequence
<220> FEATURE:
<223> OTHER INFORMATION: Synthetic

<400> SEQUENCE: 49
cagtctgccc tgactcagcc tgcctccgtg tctgggtctc ctggacagtc gatcaccatc      60
tcctgcactg gaaccagcag tgacgttggt acttataact atgtctcctg gtaccaacaa     120
cacccaggca aagcccccaa actcatgatt tttgatgtca gtaatcggcc ctcagggggtt    180 tctgatcgct tctctggctc caagtctggc aacacggcct ccctgaccat ctctgggctc     240
caggctgagg acgaggctga ttattactgc agctcattta caaccagcag cactgtggtt     300
ttcggcggag ggaccaagct gaccgtccta                                      330

<210> SEQ ID NO 50
<211> LENGTH: 110
<212> TYPE: PRT
<213> ORGANISM: Artificial Sequence
<220> FEATURE:
<223> OTHER INFORMATION: Synthetic

<400> SEQUENCE: 50

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Thr Tyr
            20                  25                  30

Asn Tyr Val Ser Trp Tyr Gln Gln His Pro Gly Lys Ala Pro Lys Leu
        35                  40                  45

Met Ile Phe Asp Val Ser Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Thr Thr Ser
                85                  90                  95

Ser Thr Val Val Phe Gly Gly Gly Thr Lys Leu Thr Val Leu
            100                 105                 110

```
<210> SEQ ID NO 51
<211> LENGTH: 27
<212> TYPE: DNA
<213> ORGANISM: Artificial Sequence
<220> FEATURE:
<223> OTHER INFORMATION: Synthetic

<400> SEQUENCE: 51
agcagtgacg ttggtactta taactat                                          27

<210> SEQ ID NO 52
<211> LENGTH: 9
<212> TYPE: PRT
<213> ORGANISM: Artificial Sequence
<220> FEATURE:
<223> OTHER INFORMATION: Synthetic

<400> SEQUENCE: 52

Ser Ser Asp Val Gly Thr Tyr Asn Tyr
1               5

<210> SEQ ID NO 53
<211> LENGTH: 30
<212> TYPE: DNA
<213> ORGANISM: Artificial Sequence
<220> FEATURE:
<223> OTHER INFORMATION: Synthetic

<400> SEQUENCE: 53
agctcattta caaccagcag cactgtggtt                                       30

<210> SEQ ID NO 54
<211> LENGTH: 10
<212> TYPE: PRT
<213> ORGANISM: Artificial Sequence
<220> FEATURE:
<223> OTHER INFORMATION: Synthetic

<400> SEQUENCE: 54

Ser Ser Phe Thr Thr Ser Ser Thr Val Val
1               5                   10

<210> SEQ ID NO 55
<211> LENGTH: 1362
<212> TYPE: DNA
<213> ORGANISM: Artificial Sequence
<220> FEATURE:
<223> OTHER INFORMATION: Synthetic

<400> SEQUENCE: 55
caggtgcagc tggtgcagtc tggggctgag gtgaagaagc ctggggcctc agtgaaggtc      60
tcctgcaagg cttctggata catcttcacc ggctactata tgcactgggt gcgacaggcc    120
cctggacagg gcttgagtg gatgggatgg atcaaccctact acagtggtgg cgcaaactat    180
gcacagaagt tcagggcag ggtcaccctg accaggaca cgtccatcac cacagtctac       240
atggaactga gcaggctgag atttgacgac acggccgtgt attactgtgc gagaggatcc    300
cggtatgact ggaaccagaa caactggttc gaccccttggg gccagggaac cctggtcacc   360
gtctcctcag cctccaccaa gggcccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
```

-continued

```
acccagacct acatctgcaa cgtgaatcac aagcccagca acaccaaggt ggacaagaaa    660
gttgagccca atcttgtga caaaactcac acatgcccac cgtgcccagc acctgaactc    720
ctgggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca agccaaagg gcagcccga gaaccacagg tgtacaccct gcccccatcc    1080
cgggatgagc tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctaca gcaagctcac cgtggacaag   1260
agcaggtggc agcaggggaa cgtcttctca tgctccgtga tgcatgaggc tctgcacaac   1320
cactacacgc agaagtccct ctccctgtct ccgggtaaat ga                     1362
```

<210> SEQ ID NO 56
<211> LENGTH: 453
<212> TYPE: PRT
<213> ORGANISM: Artificial Sequence
<220> FEATURE:
<223> OTHER INFORMATION: Synthetic

<400> SEQUENCE: 56

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Ala Asn Tyr Ala Gln Lys Phe
    50                  55                  60

Gln Gly Arg Val Thr Leu Thr Arg Asp Thr Ser Ile Thr Thr Val Tyr
65                  70                  75                  80

Met Glu Leu Ser Arg Leu Arg Phe Asp Asp Thr Ala Val Tyr Tyr Cys
                85                  90                  95

Ala Arg Gly Ser Arg Tyr Asp Trp Asn Gln Asn Asn Trp Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220
```

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 57
<211> LENGTH: 651
<212> TYPE: DNA
<213> ORGANISM: Artificial Sequence
<220> FEATURE:
<223> OTHER INFORMATION: Synthetic

<400> SEQUENCE: 57
cagtctgccc tgactcagcc tgcctccgtg tctgggtctc ctggacagtc gatcaccatc        60
tcctgcactg gaaccagcag tgacgttggt acttataact atgtctcctg gtaccaacaa       120
cacccaggca agcccccaa actcatgatt tttgatgtca gtaatcggcc ctcaggggtt        180
tctgatcgct tctctggctc caagtctggc aacacggcct ccctgaccat ctctgggctc       240
caggctgagg acgaggctga ttattactgc agctcattta caaccagcag cactgtggtt       300
ttcggcggag ggaccaagct gaccgtccta ggccagccca aggccgcccc ctccgtgacc       360
ctgttccccc cctcctccga ggagctgcag gccaacaagg ccaccctggt gtgcctgatc       420
tccgacttct accccggcgc cgtgaccgtg gcctggaagg ccgactcctc ccccgtgaag       480
gccggcgtgg agaccaccac ccctccaag cagtccaaca caagtacgc cgcctcctcc        540 tacctgtccc tgaccccga gcagtggaag tccaccggt cctactcctg ccaggtgacc        600
cacgagggct ccaccgtgga gaagaccgtg gcccccaccg agtgctcctg a                651

<210> SEQ ID NO 58

```
<211> LENGTH: 216
<212> TYPE: PRT
<213> ORGANISM: Artificial Sequence
<220> FEATURE:
<223> OTHER INFORMATION: Synthetic

<400> SEQUENCE: 58

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Thr Tyr
            20                  25                  30

Asn Tyr Val Ser Trp Tyr Gln Gln His Pro Gly Lys Ala Pro Lys Leu
        35                  40                  45

Met Ile Phe Asp Val Ser Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Thr Thr Ser
                85                  90                  95

Ser Thr Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 59
<211> LENGTH: 1273
<212> TYPE: PRT
<213> ORGANISM: Artificial Sequence
<220> FEATURE:
<223> OTHER INFORMATION: Synthetic

<400> SEQUENCE: 59

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
```

```
                    100                 105                 110
Lys Thr Gln Ser Leu Leu Ile Val Asn Asn Ala Thr Asn Val Val Ile
            115                 120                 125
Lys Val Cys Glu Phe Gln Phe Cys Asn Asp Pro Phe Leu Gly Val Tyr
            130                 135                 140
Tyr His Lys Asn Asn Lys Ser Trp Met Glu Ser Glu Phe Arg Val Tyr
145                 150                 155                 160
Ser Ser Ala Asn Asn Cys Thr Phe Glu Tyr Val Ser Gln Pro Phe Leu
                165                 170                 175
Met Asp Leu Glu Gly Lys Gln Gly Asn Phe Lys Asn Leu Arg Glu Phe
            180                 185                 190
Val Phe Lys Asn Ile Asp Gly Tyr Phe Lys Ile Tyr Ser Lys His Thr
            195                 200                 205
Pro Ile Asn Leu Val Arg Asp Leu Pro Gln Gly Phe Ser Ala Leu Glu
            210                 215                 220
Pro Leu Val Asp Leu Pro Ile Gly Ile Asn Ile Thr Arg Phe Gln Thr
225                 230                 235                 240
Leu Leu Ala Leu His Arg Ser Tyr Leu Thr Pro Gly Asp Ser Ser Ser
                245                 250                 255
Gly Trp Thr Ala Gly Ala Ala Ala Tyr Tyr Val Gly Tyr Leu Gln Pro
            260                 265                 270
Arg Thr Phe Leu Leu Lys Tyr Asn Glu Asn Gly Thr Ile Thr Asp Ala
            275                 280                 285
Val Asp Cys Ala Leu Asp Pro Leu Ser Glu Thr Lys Cys Thr Leu Lys
            290                 295                 300
Ser Phe Thr Val Glu Lys Gly Ile Tyr Gln Thr Ser Asn Phe Arg Val
305                 310                 315                 320
Gln Pro Thr Glu Ser Ile Val Arg Phe Pro Asn Ile Thr Asn Leu Cys
                325                 330                 335
Pro Phe Gly Glu Val Phe Asn Ala Thr Arg Phe Ala Ser Val Tyr Ala
            340                 345                 350
Trp Asn Arg Lys Arg Ile Ser Asn Cys Val Ala Asp Tyr Ser Val Leu
            355                 360                 365
Tyr Asn Ser Ala Ser Phe Ser Thr Phe Lys Cys Tyr Gly Val Ser Pro
            370                 375                 380
Thr Lys Leu Asn Asp Leu Cys Phe Thr Asn Val Tyr Ala Asp Ser Phe
385                 390                 395                 400
Val Ile Arg Gly Asp Glu Val Arg Gln Ile Ala Pro Gly Gln Thr Gly
            405                 410                 415
Lys Ile Ala Asp Tyr Asn Tyr Lys Leu Pro Asp Asp Phe Thr Gly Cys
            420                 425                 430
Val Ile Ala Trp Asn Ser Asn Asn Leu Asp Ser Lys Val Gly Gly Asn
            435                 440                 445
Tyr Asn Tyr Leu Tyr Arg Leu Phe Arg Lys Ser Asn Leu Lys Pro Phe
            450                 455                 460
Glu Arg Asp Ile Ser Thr Glu Ile Tyr Gln Ala Gly Ser Thr Pro Cys
465                 470                 475                 480
Asn Gly Val Glu Gly Phe Asn Cys Tyr Phe Pro Leu Gln Ser Tyr Gly
                485                 490                 495
Phe Gln Pro Thr Asn Gly Val Gly Tyr Gln Pro Tyr Arg Val Val Val
            500                 505                 510
Leu Ser Phe Glu Leu Leu His Ala Pro Ala Thr Val Cys Gly Pro Lys
            515                 520                 525
```

```
Lys Ser Thr Asn Leu Val Lys Asn Lys Cys Val Asn Phe Asn Phe Asn
            530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
                675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
                835                 840                 845

Leu Ile Cys Ala Gln Lys Phe Asn Gly Leu Thr Val Leu Pro Pro Leu
            850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
            930                 935                 940
```

```
Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
        980                 985                 990

Ile Asp Arg Leu Ile Thr Gly Arg Leu Gln Ser Leu Gln Thr Tyr Val
    995                1000                1005

Thr Gln Gln Leu Ile Arg Ala Ala Glu Ile Arg Ala Ser Ala Asn Leu
1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
        1075                1080                1085

Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
        1155                1160                1165

Ile Ser Gly Ile Asn Ala Ser Val Val Asn Ile Gln Lys Glu Ile Asp
    1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
                1205                1210                1215

Trp Leu Gly Phe Ile Ala Gly Leu Ile Ala Ile Val Met Val Thr Ile
            1220                1225                1230

Met Leu Cys Cys Met Thr Ser Cys Cys Ser Cys Leu Lys Gly Cys Cys
        1235                1240                1245

Ser Cys Gly Ser Cys Cys Lys Phe Asp Glu Asp Asp Ser Glu Pro Val
    1250                1255                1260

Leu Lys Gly Val Lys Leu His Tyr Thr
1265                1270
```

<210> SEQ ID NO 60
<211> LENGTH: 47
<212> TYPE: PRT
<213> ORGANISM: Artificial Sequence
<220> FEATURE:
<223> OTHER INFORMATION: Synthetic

<400> SEQUENCE: 60

```
Asp Ile Ser Thr Glu Ile Tyr Gln Ala Gly Ser Thr Pro Cys Asn Gly
1               5                   10                  15

Val Glu Gly Phe Asn Cys Tyr Phe Pro Leu Gln Ser Tyr Gly Phe Gln
            20                  25                  30
```

Pro Thr Asn Gly Val Gly Tyr Gln Pro Tyr Arg Val Val Leu
         35                  40                  45

<210> SEQ ID NO 61
<211> LENGTH: 21
<212> TYPE: PRT
<213> ORGANISM: Artificial Sequence
<220> FEATURE:
<223> OTHER INFORMATION: Synthetic

<400> SEQUENCE: 61

Cys Val Ile Ala Trp Asn Ser Asn Asn Leu Asp Ser Lys Val Gly Gly
1               5                   10                  15

Asn Tyr Asn Tyr Leu
            20

<210> SEQ ID NO 62
<211> LENGTH: 44
<212> TYPE: PRT
<213> ORGANISM: Artificial Sequence
<220> FEATURE:
<223> OTHER INFORMATION: Synthetic

<400> SEQUENCE: 62

Asp Ile Ser Thr Glu Ile Tyr Gln Ala Gly Ser Thr Pro Cys Asn Gly
1               5                   10                  15

Val Glu Gly Phe Asn Cys Tyr Phe Pro Leu Gln Ser Tyr Gly Phe Gln
            20                  25                  30

Pro Thr Asn Gly Val Gly Tyr Gln Pro Tyr Arg Val
         35                  40

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
gaccccaaaa tcagcgaaat                                          20

<210> SEQ ID NO 64
<211> LENGTH: 24
<212> TYPE: DNA
<213> ORGANISM: Artificial Sequence
<220> FEATURE:
<223> OTHER INFORMATION: Synthetic

<400> SEQUENCE: 64
tctggttact gccagttgaa tctg                                     24

<210> SEQ ID NO 65
<211> LENGTH: 24
<212> TYPE: DNA
<213> ORGANISM: Artificial Sequence
<220> FEATURE:
<223> OTHER INFORMATION: Synthetic

<400> SEQUENCE: 65
accccgcatt acgtttggtg gacc                                     24

<210> SEQ ID NO 66
<211> LENGTH: 30
<212> TYPE: DNA
<213> ORGANISM: Artificial Sequence

```
<220> FEATURE:
<223> OTHER INFORMATION: Synthetic

<400> SEQUENCE: 66
cgatcttgta gatctgttcc tcaaacgaac                                       30

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
atattgcagc agtacgcaca caca                                             24

<210> SEQ ID NO 68
<211> LENGTH: 26
<212> TYPE: DNA
<213> ORGANISM: Artificial Sequence
<220> FEATURE:
<223> OTHER INFORMATION: Synthetic

<400> SEQUENCE: 68
acactagcca tccttactgc gcttcg                                           26

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
accccgcatt acgtttggtg gacc                                             24

<210> SEQ ID NO 70
<211> LENGTH: 23
<212> TYPE: DNA
<213> ORGANISM: Artificial Sequence
<220> FEATURE:
<223> OTHER INFORMATION: Synthetic

<400> SEQUENCE: 70
cgatctcttg tagatctgtt ctc                                              23

<210> SEQ ID NO 71
<211> LENGTH: 22
<212> TYPE: DNA
<213> ORGANISM: Artificial Sequence
<220> FEATURE:
<223> OTHER INFORMATION: Synthetic

<400> SEQUENCE: 71
atattgcagc agtacgcaca ca                                               22

<210> SEQ ID NO 72
<211> LENGTH: 384
<212> TYPE: DNA
<213> ORGANISM: Artificial Sequence
<220> FEATURE:
<223> OTHER INFORMATION: Synthetic

<400> SEQUENCE: 72
gaagtgcagc tggtggagtc tgggggaggc ttggtacagc ctggcaggtc cctgagactc      60
```

```
tcctgtgcag cctctggatt cacctttgat gattatgcca tgcactgggt ccggcaagct    120
ccagggaagg gcctggagtg ggtctcaggt attagttgga ataggggtag cataggctat    180
gcggactctg tgaagggccg attcaccatc tccagagaca acgccaagaa ctccctgtat    240
ctgcaaatga gcagtctgag agctgaggac acggccttgt attactgcgc aaaagatggc    300
gagagatggg atagtgtagt agtaccatct gctaggaacg gtatggacgt ctggggccaa    360
gggaccacgg tcaccgtctc ctca                                           384
```

<210> SEQ ID NO 73
<211> LENGTH: 128
<212> TYPE: PRT
<213> ORGANISM: Artificial Sequence
<220> FEATURE:
<223> OTHER INFORMATION: Synthetic

<400> SEQUENCE: 73

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Arg Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Leu Tyr Tyr Cys
                85                  90                  95

Ala Lys Asp Gly Glu Arg Trp Asp Ser Val Val Val Pro Ser Ala Arg
            100                 105                 110

Asn Gly Met Asp Val Trp Gly Gln Gly Thr Thr Val Thr Val Ser Ser
        115                 120                 125
```

<210> SEQ ID NO 74
<211> LENGTH: 24
<212> TYPE: DNA
<213> ORGANISM: Artificial Sequence
<220> FEATURE:
<223> OTHER INFORMATION: Synthetic

<400> SEQUENCE: 74

```
ggattcacct ttgatgatta tgcc                                            24
```

<210> SEQ ID NO 75
<211> LENGTH: 8
<212> TYPE: PRT
<213> ORGANISM: Artificial Sequence
<220> FEATURE:
<223> OTHER INFORMATION: Synthetic

<400> SEQUENCE: 75

```
Gly Phe Thr Phe Asp Asp Tyr Ala
1               5
```

<210> SEQ ID NO 76
<211> LENGTH: 24
<212> TYPE: DNA
<213> ORGANISM: Artificial Sequence
<220> FEATURE:
<223> OTHER INFORMATION: Synthetic

<400> SEQUENCE: 76
attagttgga ataggggtag cata                                               24

<210> SEQ ID NO 77
<211> LENGTH: 8
<212> TYPE: PRT
<213> ORGANISM: Artificial Sequence
<220> FEATURE:
<223> OTHER INFORMATION: Synthetic

<400> SEQUENCE: 77

Ile Ser Trp Asn Arg Gly Ser Ile
1               5

<210> SEQ ID NO 78
<211> LENGTH: 63
<212> TYPE: DNA
<213> ORGANISM: Artificial Sequence
<220> FEATURE:
<223> OTHER INFORMATION: Synthetic

<400> SEQUENCE: 78
gcaaaagatg gcgagagatg ggatagtgta gtagtaccat ctgctaggaa cggtatggac        60
gtc                                                                      63

<210> SEQ ID NO 79
<211> LENGTH: 21
<212> TYPE: PRT
<213> ORGANISM: Artificial Sequence
<220> FEATURE:
<223> OTHER INFORMATION: Synthetic

<400> SEQUENCE: 79

Ala Lys Asp Gly Glu Arg Trp Asp Ser Val Val Val Pro Ser Ala Arg
1               5                   10                  15

Asn Gly Met Asp Val
            20

<210> SEQ ID NO 80
<211> LENGTH: 336
<212> TYPE: DNA
<213> ORGANISM: Artificial Sequence
<220> FEATURE:
<223> OTHER INFORMATION: Synthetic

<400> SEQUENCE: 80
cagtctgtgc tgacgcagcc gccctcagtg tctggggccc cagggcagag ggtcaccatc        60
tcctgcactg ggagcagctc aacatcggg gcaggttatg atgtacattg gtaccagcag       120
cttccaggaa cagcccccaa actcctcatc tatggtaaca gcaatcggcc ctcaggggtc       180
cctgaccgat tctctggctc caagtctggc acctcagcct ccctggccat cactgggctc       240
caggctgagg atgaggctga ttattactgc cagtcctatg acagcagcct gagtggctct       300
tatgtcttcg gaactgggac caaggtcacc gtccta                                 336

<210> SEQ ID NO 81
<211> LENGTH: 112
<212> TYPE: PRT
<213> ORGANISM: Artificial Sequence
<220> FEATURE:
<223> OTHER INFORMATION: Synthetic

<400> SEQUENCE: 81

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Tyr Val Phe Gly Thr Gly Thr Lys Val Thr Val Leu
            100                 105                 110
```

<210> SEQ ID NO 82
<211> LENGTH: 27
<212> TYPE: DNA
<213> ORGANISM: Artificial Sequence
<220> FEATURE:
<223> OTHER INFORMATION: Synthetic

<400> SEQUENCE: 82
agctccaaca tcggggcagg ttatgat    27

<210> SEQ ID NO 83
<211> LENGTH: 9
<212> TYPE: PRT
<213> ORGANISM: Artificial Sequence
<220> FEATURE:
<223> OTHER INFORMATION: Synthetic

<400> SEQUENCE: 83

Ser Ser Asn Ile Gly Ala Gly Tyr Asp
1               5

<210> SEQ ID NO 84
<211> LENGTH: 9
<212> TYPE: DNA
<213> ORGANISM: Artificial Sequence
<220> FEATURE:
<223> OTHER INFORMATION: Synthetic

<400> SEQUENCE: 84 ggtaacagc    9

<210> SEQ ID NO 85
<211> LENGTH: 3
<212> TYPE: PRT
<213> ORGANISM: Artificial Sequence
<220> FEATURE:
<223> OTHER INFORMATION: Synthetic

<400> SEQUENCE: 85

Gly Asn Ser
1

<210> SEQ ID NO 86
<211> LENGTH: 36
<212> TYPE: DNA
<213> ORGANISM: Artificial Sequence
<220> FEATURE:
<223> OTHER INFORMATION: Synthetic

<400> SEQUENCE: 86
cagtcctatg acagcagcct gagtggctct tatgtc        36

<210> SEQ ID NO 87
<211> LENGTH: 12
<212> TYPE: PRT
<213> ORGANISM: Artificial Sequence
<220> FEATURE:
<223> OTHER INFORMATION: Synthetic

<400> SEQUENCE: 87

Gln Ser Tyr Asp Ser Ser Leu Ser Gly Ser Tyr Val
1               5                   10

<210> SEQ ID NO 88
<211> LENGTH: 1377
<212> TYPE: DNA
<213> ORGANISM: Artificial Sequence
<220> FEATURE:
<223> OTHER INFORMATION: Synthetic

<400> SEQUENCE: 88
gaagtgcagc tggtggagtc tgggggaggc ttggtacagc ctggcaggtc cctgagactc        60
tcctgtgcag cctctggatt cacctttgat gattatgcca tgcactgggt ccggcaagct       120
ccagggaagg gcctggagtg ggtctcaggt attagttgga ataggggtag cataggctat       180
gcggactctg tgaagggccg attcaccatc tccagagaca acgccaagaa ctccctgtat       240
ctgcaaatga gcagtctgag agctgaggac acggccttgt attactgcgc aaaagatggc       300
gagagatggg atagtgtagt agtaccatct gctaggaacg gtatggacgt ctggggccaa       360
gggaccacgg tcaccgtctc ctcagcctcc accaagggcc catcggtctt ccccctggca       420
ccctcctcca agagcacctc tgggggcaca gcggccctgg gctgcctggt caaggactac       480
ttccccgaac cggtgacggt gtcgtggaac tcaggcgccc tgaccagcgg cgtgcacacc       540
ttcccggctg tcctacagtc ctcaggactc tactccctca gcagcgtggt gaccgtgccc       600
tccagcagct tgggcaccca gacctacatc tgcaacgtga atcacaagcc cagcaacacc       660
aaggtggaca agaaagttga gcccaaatct tgtgacaaaa ctcacacatg cccaccgtgc       720
ccagcacctg aactcctggg gggaccgtca gtcttcctct tccccccaaa acccaaggac       780
accctcatga tctcccggac ccctgaggtc acatgcgtgg tggtggacgt gagccacgaa       840
gaccctgagg tcaagttcaa ctggtacgtg gacggcgtgg aggtgcataa tgccaagaca       900
aagccgcggg aggagcagta caacagcacg taccgtgtgg tcagcgtcct caccgtcctg       960
caccaggact ggctgaatgg caaggagtac aagtgcaagg tctccaacaa agccctccca      1020
gcccccatcg agaaaaccat ctccaaagcc aagggcagc cccgagaacc acaggtgtac       1080
accctgcccc catcccggga tgagctgacc aagaaccagg tcagcctgac ctgcctggtc      1140
aaaggcttct atcccagcga catcgccgtg gagtgggaga gcaatgggca gccggagaac      1200
aactacaaga ccacgcctcc cgtgctggac tccgacggct ccttcttcct ctacagcaag      1260
ctcaccgtgg acaagagcag gtggcagcag gggaacgtct tctcatgctc cgtgatgcat      1320
gaggctctgc acaaccacta cacgcagaag tccctctccc tgtctccggg taaatga        1377

<210> SEQ ID NO 89
<211> LENGTH: 458
<212> TYPE: PRT
<213> ORGANISM: Artificial Sequence
<220> FEATURE:

<223> OTHER INFORMATION: Synthetic

<400> SEQUENCE: 89

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Arg Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Leu Tyr Tyr Cys
                85                  90                  95

Ala Lys Asp Gly Glu Arg Trp Asp Ser Val Val Pro Ser Ala Arg
            100                 105                 110

Asn Gly Met Asp Val Trp Gly Gln Gly Thr Thr Val Thr Val Ser Ser
            115                 120                 125

Ala Ser Thr Lys Gly Pro Ser Val Phe Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400
```

```
Asn Tyr Lys Thr Thr Pro Pro Val Leu Asp Ser Asp Gly Ser Phe Phe
                405                 410                 415
Leu Tyr Ser Lys Leu Thr Val Asp Lys Ser Arg Trp Gln Gln Gly Asn
            420                 425                 430
Val Phe Ser Cys Ser Val Met His Glu Ala Leu His Asn His Tyr Thr
        435                 440                 445
Gln Lys Ser Leu Ser Leu Ser Pro Gly Lys
    450                 455
```

<210> SEQ ID NO 90
<211> LENGTH: 657
<212> TYPE: DNA
<213> ORGANISM: Artificial Sequence
<220> FEATURE:
<223> OTHER INFORMATION: Synthetic

<400> SEQUENCE: 90

| | | | | | |
|---|---|---|---|---|---|
| cagtctgtgc | tgacgcagcc | gccctcagtg | tctggggccc | cagggcagag | ggtcaccatc | 60 |
| tcctgcactg | ggagcagctc | caacatcggg | gcaggttatg | atgtacattg | gtaccagcag | 120 |
| cttccaggaa | cagcccccaa | actcctcatc | tatggtaaca | gcaatcggcc | ctcaggggtc | 180 |
| cctgaccgat | tctctggctc | caagtctggc | acctcagcct | ccctggccat | cactgggctc | 240 |
| caggctgagg | atgaggctga | ttattactgc | cagtcctatg | acagcagcct | gagtggctct | 300 |
| tatgtcttcg | gaactgggac | caaggtcacc | gtcctaggcc | agcccaaggc | cgccccctcc | 360 |
| gtgaccctgt | tccccccctc | ctccgaggag | ctgcaggcca | acaaggccac | cctggtgtgc | 420 |
| ctgatctccg | acttctaccc | cggcgccgtg | accgtggcct | ggaaggccga | ctcctccccc | 480 |
| gtgaaggccg | gcgtggagac | caccaccccc | tccaagcagt | ccaacaacaa | gtacgccgcc | 540 |
| tcctcctacc | tgtccctgac | ccccgagcag | tggaagtccc | accggtccta | ctcctgccag | 600 |
| gtgacccacg | agggctccac | cgtggagaag | accgtggccc | ccaccgagtg | ctcctga | 657 |

<210> SEQ ID NO 91
<211> LENGTH: 218
<212> TYPE: PRT
<213> ORGANISM: Artificial Sequence
<220> FEATURE:
<223> OTHER INFORMATION: Synthetic

<400> SEQUENCE: 91

```
Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30
Tyr Asp Val His Trp Tyr Gln Gln Leu Pro Gly Thr Ala Pro Lys Leu
        35                  40                  45
Leu Ile Tyr Gly Asn Ser Asn Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Asp Ser Ser
                85                  90                  95
Leu Ser Gly Ser Tyr Val Phe Gly Thr Gly Thr Lys Val Thr Val Leu
            100                 105                 110
Gly Gln Pro Lys Ala Ala Pro Ser Val Thr Leu Phe Pro Pro Ser Ser
        115                 120                 125
Glu Glu Leu Gln Ala Asn Lys Ala Thr Leu Val Cys Leu Ile Ser Asp
```

-continued

```
            130                 135                 140
Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

METHODS FOR TREATING OR PREVENTING SARS-COV-2 INFECTIONS AND COVID-19 WITH ANTI-SARS-COV-2 SPIKE GLYCOPROTEIN ANTIBODIES

CROSS-REFERENCE TO RELATED APPLICATIONS

This application claims the benefit under 35 USC § 119(e) of U.S. Provisional Application Nos.: 63/034,348, filed Jun. 3, 2020; 63/036,956, filed Jun. 9, 2020; 63/038,274, filed Jun. 12, 2020; 63/043,336, filed Jun. 24, 2020; 63/060,592, filed Aug. 3, 2020; 63/062,961, filed Aug. 7, 2020; 63/065,799, filed Aug. 14, 2020; 63/084,881, filed Sep. 29, 2020; 63/085,066, filed Sep. 29, 2020; 63/089,399, filed Oct. 8, 2020; 63/090,690, filed Oct. 12, 2020; 63/094,133, filed Oct. 20, 2020; 63/105,779, filed Oct. 26, 2020; 63/106,696, filed Oct. 28, 2020; 63/112,140, filed Nov. 10, 2020; 63/116,773, filed Nov. 20, 2020; 63/119,593, filed Nov. 30, 2020; 63/120,065, filed Dec. 1, 2020; 63/124,980, filed Dec. 14, 2020; 63/131,627, filed Dec. 29, 2020; 63/141,423, filed Jan. 25, 2021; 63/141,952, filed Jan. 26, 2021; 63/142,471, filed Jan. 27, 2021; 63/144,789, filed Feb. 2, 2021; 63/150,978, filed Feb. 18, 2021; 63/162,504, filed Mar. 17, 2021; 63/162,996, filed Mar. 18, 2021; 63/164,488, filed Mar. 22, 2021; 63/165,654, filed Mar. 24, 2021; 63/166,187, filed Mar. 25, 2021; 63/173,468, filed Apr. 11, 2021; 63/185,301, filed May 6, 2021; and 63/186,029, filed May 7, 2021, each of which is incorporated herein by reference in its entirety for all purposes.

FEDERALLY SPONSORED RESEARCH OR DEVELOPMENT

This invention was made with Government support under Agreement HHSO100201700020C, awarded by the U.S. Department of Health and Human Services. The Government has certain rights in the invention.

REFERENCE TO A SEQUENCE LISTING

This application incorporates by reference the Sequence Listing submitted in Computer Readable Form as file 10807US01-Sequence, created on Jun. 2, 2021, and containing 72,328 bytes.

FIELD OF THE INVENTION

The present invention resides in the field of medicine, and relates to methods and pharmaceutical compositions for treating SARS-CoV-2 infections and COVID-19 via administration of antigen-binding molecules that bind a surface protein of SARS-CoV-2 (e.g., anti-SARS-CoV-2 spike glycoprotein antibodies and antigen-binding fragments thereof, or combinations of such antibodies or antigen-binding fragments).

BACKGROUND

Coronaviruses are a family of enveloped, single-stranded RNA viruses. In recent decades, two highly pathogenic strains of coronavirus were identified in humans: severe acute respiratory syndrome coronavirus (SARS-CoV) and Middle East respiratory syndrome coronavirus (MERS-CoV). These viruses were found to cause severe, and sometimes fatal, respiratory illness.

In December 2019, pneumonia of unknown cause was identified in clusters of patients in Wuhan City, China. A novel enveloped RNA betacoronavirus—severe acute respiratory syndrome coronavirus 2 (SARS-CoV-2)—was identified in these patients, and the disease caused by SARS-CoV-2 infection was later designated coronavirus disease 2019 (COVID-19) by the World Health Organization. As of May 2020, more than 5.5 million confirmed cases of COVID-19 have been reported globally. The rapidly spreading, worldwide outbreak has prompted the World Health Organization to declare COVID-19 a pandemic and public health emergency of international concern.

Patients with COVID-19 are at risk for developing a variety of respiratory conditions, ranging from relatively mild respiratory symptoms to severe respiratory failure and death. Among hospitalized patients, intensive care and/or oxygen supplementation (e.g., mechanical ventilation) is often required, and reported fatality rates are high. In a report from the Chinese Center for Disease Control and Prevention that included 44,500 confirmed infections, nearly 20% of the patients presented with advanced respiratory symptoms (14% with dyspnea, hypoxia, or >50% lung involvement on imaging; 5% in respiratory failure, shock, or multiorgan failure). Another analysis of patients with COVID-19 in China found that, among 1,099 hospitalized patients, 5% had been admitted to an intensive care unit (ICU), 2.3% required invasive mechanical ventilation, and 1.4% died. Among patients with advanced disease on admission (defined as pneumonia, hypoxemia, and tachypnea) reported in China, these negative outcomes rose to 19%, 14.5%, and 8.1%, respectively. A report of 2,634 hospitalized patients with COVID-19 in the United States identified similar clinical outcomes: 14.2% were admitted to an ICU, 12.2% required invasive mechanical ventilation, and 21% died. Other reports have found that approximately 20% to 30% of hospitalized patients with COVID-19 and pneumonia require intensive care for respiratory support.

Coronaviruses have an RNA genome packaged in nucleocapsid (N) protein surrounded by an outer envelope. The envelope is comprised of membrane (M) protein and envelope (E) protein, which are involved in virus assembly, and spike (S) protein, which mediates entry into host cells. S proteins form large trimeric projections, providing the hallmark crown-like appearance of coronaviruses. S protein trimers bind to a host receptor and, after priming by cellular proteases, mediate host-virus membrane fusion. S protein appears to be central to viral infectivity by SARS-CoV-2. SARS-CoV-2 S protein binds the host receptor angiotensin-converting enzyme 2 (ACE2) with high affinity, and in cell assays and animal models can utilize ACE2 as a functional receptor for host cell entry.

In light of the likely pivotal role of S protein in the pathogenesis of SARS-CoV-2, a number of efforts are underway to develop antibodies and vaccines that target this protein.

BRIEF SUMMARY OF THE INVENTION

The present disclosure provides methods for improving one or more clinical parameters of COVID-19. In some cases, the method comprises administering a therapeutic composition to a subject in need thereof, wherein the therapeutic composition comprises at least one antigen-binding molecule that binds a surface protein of SARS-CoV-2. In some embodiments, the subject is a human patient with laboratory-confirmed SARS-CoV-2 and one or more COVID-19 symptom(s). In some cases, the one or more COVID-19 symptom(s) comprise fever, cough, or shortness of breath.

In some embodiments, the subject is selected from the group consisting of: (a) a human COVID-19 patient requiring low-flow oxygen supplementation; (b) a human COVID-19 patient requiring high-intensity oxygen therapy but not on mechanical ventilation; and (c) a human COVID-19 patient requiring mechanical ventilation. In some cases, the subject is hospitalized due to one or more COVID-19 symptom(s). In some cases, the subject is an outpatient (i.e., treated on an outpatient basis).

The present disclosure also provides methods for preventing a SARS-CoV-2 infection or COVID-19 in a subject. In some cases, the method comprises administering a prophylactic composition to the subject, wherein the prophylactic composition comprises at least one antigen-binding molecule that binds a surface protein of SARS-CoV-2, e.g., SARS-CoV-2 spike protein.

In some embodiments, the subject is an uninfected individual at high risk of SARS-CoV-2 infection. In some embodiments, the subject at high risk of SARS-CoV-2 infection is a healthcare worker, a first responder, or a household member of an individual with a positive test for a SARS-CoV-2 infection.

In some embodiments, the therapeutic or prophylactic composition comprises a first antigen-binding molecule that binds a first epitope on a surface protein of SARS-CoV-2, and a second antigen-binding molecule that binds a second epitope on a surface protein of SARS-CoV-2, wherein the first epitope and the second epitope are structurally non-overlapping.

In some embodiments, the therapeutic or prophylactic composition further comprises a third antigen-binding molecule that binds a third epitope on a surface protein of SARS-CoV-2, wherein the third epitope is structurally non-overlapping with the first epitope and the second epitope.

In some embodiments, the therapeutic or prophylactic composition comprises a first antigen-binding molecule that binds a first epitope on a surface protein of SARS-CoV-2, and a second antigen-binding molecule that binds a second epitope on a surface protein of SARS-CoV-2, wherein the first antigen-binding molecule and the second antigen-binding molecule are capable of simultaneously binding the surface protein of SARS-CoV-2. In some embodiments, the therapeutic or prophylactic composition further comprises a third antigen-binding molecule that binds a third epitope on a surface protein of SARS-CoV-2, wherein the first antigen-binding molecule, the second antigen-binding molecule, and the third antigen-binding molecule are capable of simultaneously binding the surface protein of SARS-CoV-2. In some embodiments, a) the first antigen-binding molecule comprises three heavy chain complementarity determining regions (CDRs) (HCDR1, HCDR2 and HCDR3) contained within a heavy chain variable region (HCVR) comprising the amino acid sequence set forth in SEQ ID NO: 2, and three light chain complementarity determining regions (CDRs) (LCDR1, LCDR2 and LCDR3) contained within a light chain variable region (LCVR) comprising the amino acid sequence set forth in SEQ ID NO: 10; b) the second antigen-binding molecule comprises three heavy chain complementarity determining regions (CDRs) (HCDR1, HCDR2 and HCDR3) contained within a heavy chain variable region (HCVR) comprising the amino acid sequence set forth in SEQ ID NO: 22, and three light chain complementarity determining regions (CDRs) (LCDR1, LCDR2 and LCDR3) contained within a light chain variable region (LCVR) comprising the amino acid sequence set forth in SEQ ID NO: 30; and c) the third antigen-binding molecule comprises three heavy chain complementarity determining regions (CDRs) (HCDR1, HCDR2 and HCDR3) contained within a heavy chain variable region (HCVR) comprising the amino acid sequence set forth in SEQ ID NO: 73, and three light chain complementarity determining regions (CDRs) (LCDR1, LCDR2 and LCDR3) contained within a light chain variable region (LCVR) comprising the amino acid sequence set forth in SEQ ID NO: 81.

In any of the various embodiments, the surface protein of SARS-CoV-2 is a spike (S) protein comprising a receptor binding domain comprising an amino acid sequence at least 80% identical to SEQ ID NO: 59.

In some embodiments, the antigen-binding molecule is an anti-SARS-CoV-2 spike glycoprotein antibody or antigen-binding fragment thereof comprising six complementarity determining regions, HCDR1-HCDR2-HCDR3-LCDR1-LCDR2-LCDR3, contained within a heavy chain variable region (HCVR) and light chain variable region (LCVR) amino acid sequence pair comprising the amino acid sequences selected from the group consisting of SEQ ID NOs: 2/10, 22/30, 42/50, and 73/81. In some cases, the anti-SARS-CoV-2 spike glycoprotein antibody or antigen-binding fragment comprises six complementarity determining regions, HCDR1-HCDR2-HCDR3-LCDR1-LCDR2-LCDR3, comprising the amino acid sequences, respectively, selected from the group consisting of SEQ ID NOs: 4-6-8-12-14-16, 24-26-28-32-34-36, 44-46-48-52-34-54, and 75-77-79-83-85-87. In some cases, the anti-SARS-CoV-2 spike glycoprotein antibody or antigen-binding fragment comprises a HCVR/LCVR amino acid sequence pair comprising the amino acid sequences selected from the group consisting of SEQ ID NOs: 2/10, 22/30, 42/50, and 73/81. In some embodiments, the anti-SARS-CoV-2 spike glycoprotein antibody comprises a human IgG heavy chain constant region. In some cases, the anti-SARS-CoV-2 spike glycoprotein antibody comprises a heavy chain constant region of IgG1 or IgG4 isotype. In some cases, the anti-SARS-CoV-2 spike glycoprotein antibody comprises a heavy chain and light chain amino acid sequence pair selected from the group consisting of SEQ ID NOs: 18/20, 38/40, 56/58, and 89/91.

In some embodiments, the antigen-binding molecule is an anti-SARS-CoV-2 spike glycoprotein antibody that has the same binding and/or blocking properties as a reference antibody comprising a HCVR/LCVR amino acid sequence pair comprising the amino acid sequences selected from the group consisting of SEQ ID NOs: 2/10, 22/30, 42/50, and 73/81. In some embodiments, the antigen-binding molecule is an anti-SARS-CoV-2 spike glycoprotein antibody that has the same binding and/or blocking properties as a reference antibody comprising a heavy chain and light chain amino acid sequence pair selected from the group consisting of SEQ ID NOs: 18/20, 38/40, 56/58, and 89/91.

In some embodiments, the first antigen-binding molecule is a first anti-SARS-CoV-2 spike glycoprotein antibody or antigen-binding fragment thereof comprising six complementarity determining regions, HCDR1-HCDR2-HCDR3-LCDR1-LCDR2-LCDR3, contained within a heavy chain variable region (HCVR) and light chain variable region (LCVR) amino acid sequence pair comprising the amino acid sequences of SEQ ID NOs: 2/10, and the second antigen-binding molecule is a second anti-SARS-CoV-2 spike glycoprotein antibody or antigen-binding fragment thereof comprising six complementarity determining regions, HCDR1-HCDR2-HCDR3-LCDR1-LCDR2-LCDR3, contained within a heavy chain variable region (HCVR) and light chain variable region (LCVR) amino acid sequence pair comprising the amino acid sequences of SEQ ID NOs: 22/30. In some cases, the first anti-SARS-CoV-2 spike glycoprotein antibody or antigen-binding fragment comprises six complementarity determining regions, HCDR1-HCDR2-HCDR3-LCDR1-LCDR2-LCDR3, comprising the amino acid sequences, respectively, of SEQ ID NOs: 4-6-8-12-14-16, and the second anti-SARS-CoV-2 spike glycoprotein antibody or antigen-binding fragment comprises six complementarity determining regions, HCDR1-HCDR2-HCDR3-LCDR1-LCDR2-LCDR3, comprising the amino acid sequences, respectively, of SEQ ID NOs: 24-26-28-32-34-36. In some cases, the first anti-SARS-CoV-2 spike glycoprotein antibody or antigen-binding fragment comprises a HCVR/LCVR amino acid sequence pair comprising the amino acid sequences of SEQ ID NOs: 2/10, and the second anti-SARS-CoV-2 spike glycoprotein antibody or antigen-binding fragment comprises a HCVR/LCVR amino acid sequence pair comprising the amino acid sequences of SEQ ID NOs: 22/30. In some embodiments, the first and the second anti-SARS-CoV-2 spike glycoprotein antibodies comprises human IgG heavy chain constant regions. In some cases, the first and the second anti-SARS-CoV-2 spike glycoprotein antibodies comprises heavy chain constant regions of IgG1 or IgG4 isotype. In some cases, the first anti-SARS-CoV-2 spike glycoprotein antibody comprises a heavy chain comprising the amino acid sequence of SEQ ID NO: 18 and a light chain comprising the amino acid sequence of SEQ ID NO: 20, and the second anti-SARS-CoV-2 spike glycoprotein antibody comprises a heavy chain comprising the amino acid sequence of SEQ ID NO: 38 and a light chain comprising the amino acid sequence of SEQ ID NO: 40.

In some embodiments, the first antigen-binding molecule is a first anti-SARS-CoV-2 spike glycoprotein antibody or antigen-binding fragment thereof that has the same binding and/or blocking properties as a reference antibody comprising a HCVR/LCVR amino acid sequence pair comprising the amino acid sequences of SEQ ID NOs: 2/10, and the second antigen-binding molecule is a second anti-SARS-CoV-2 spike glycoprotein antibody or antigen-binding fragment thereof that has the same binding and/or blocking properties as a reference antibody comprising a HCVR/LCVR amino acid sequence pair comprising the amino acid sequences of SEQ ID NOs: 22/30. In some embodiments, the first antigen-binding molecule is a first anti-SARS-CoV-2 spike glycoprotein antibody or antigen-binding fragment thereof that has the same binding and/or blocking properties as a reference antibody comprising a heavy chain and a light chain pair comprising the amino acid sequences of SEQ ID NOs: 18/20, and the second antigen-binding molecule is a first anti-SARS-CoV-2 spike glycoprotein antibody or antigen-binding fragment thereof that has the same binding and/or blocking properties as a reference antibody comprising a heavy chain and a light chain pair comprising the amino acid sequences of SEQ ID NOs: 38/40.

In some embodiments, the antigen-binding molecule is an anti-SARS-CoV-2 spike glycoprotein antibody or antigen-binding fragment thereof comprising six complementarity determining regions, HCDR1-HCDR2-HCDR3-LCDR1-LCDR2-LCDR3, contained within a heavy chain variable region (HCVR) comprising the amino acid sequence of SEQ ID NO: 42 and light chain variable region (LCVR) comprising the amino acid sequence of SEQ ID NO: 50. In some cases, the anti-SARS-CoV-2 spike glycoprotein antibody or antigen-binding fragment comprises six complementarity determining regions, HCDR1-HCDR2-HCDR3-LCDR1-LCDR2-LCDR3, comprising the amino acid sequences, respectively, of SEQ ID NOs: 44-46-48-52-34-54. In some cases, the anti-SARS-CoV-2 spike glycoprotein antibody or antigen-binding fragment comprises a HCVR comprising the amino acid sequence of SEQ ID NO: 42, and a LCVR comprising the amino acid sequence of SEQ ID NOs: 50. In some embodiments, the anti-SARS-CoV-2 spike glycoprotein antibody comprises a human IgG heavy chain constant region. In some cases, the anti-SARS-CoV-2 spike glycoprotein antibody comprises a heavy chain constant region of IgG1 or IgG4 isotype. In some cases, the anti-SARS-CoV-2 spike glycoprotein antibody comprises a heavy chain comprising the amino acid sequence of SEQ ID NO: 56, and a light chain comprising the amino acid sequence of SEQ ID NO: 58.

In some embodiments, the antigen-binding molecule is an anti-SARS-CoV-2 spike glycoprotein antibody that has the same binding and/or blocking properties as a reference antibody comprising a HCVR/LCVR amino acid sequence pair comprising the amino acid sequences of SEQ ID NOs: 42/50. In some embodiments, the antigen-binding molecule is an anti-SARS-CoV-2 spike glycoprotein antibody that has the same binding and/or blocking properties as a reference antibody comprising a heavy chain and light chain pair comprising the amino acid sequences of SEQ ID NOs: 56/58.

In any of the various embodiments of the methods discussed above or herein, the therapeutic or prophylactic composition comprises 1 mg to 10 g of the antigen-binding molecule(s). In some cases, the therapeutic or prophylactic composition comprises about 1.2 g of mAb10933 and about 1.2 g of mAb10987. In some cases, the therapeutic or prophylactic composition comprises about 1.2 g of mAb10985. In some cases, the therapeutic or prophylactic composition comprises about 4.0 g of mAb10933 and about 4.0 g of mAb10987. In some cases, the therapeutic or prophylactic composition comprises about 150 mg of mAb10933 and about 150 mg of mAb10987. In some cases, the therapeutic or prophylactic composition comprises about 150 mg of mAb10985. In some cases, the therapeutic or prophylactic composition comprises about 300 mg of mAb10933 and about 300 mg of mAb10987. In some cases, the therapeutic or prophylactic composition comprises about 300 mg of mAb10985. In some cases, the therapeutic or prophylactic composition comprises about 600 mg of mAb10933 and about 600 mg of mAb10987. In some cases, the therapeutic or prophylactic composition comprises about 600 mg of mAb10985. In some case, the therapeutic or prophylactic composition comprises from 150 mg to 1200 mg of mAb10933 and from 150 mg to 1200 mg of mAb10987. In some cases, the therapeutic or prophylactic composition further comprises from 150 mg to 1200 mg of mAb10985. In some cases, the therapeutic or prophylactic composition comprises about 1.2 g of mAb10989.

In some embodiments, the therapeutic or prophylactic composition is administered to the subject by intravenous infusion or subcutaneous injection. In some embodiments, the present disclosure provides a method for treating a subject infected with SARS-CoV-2, comprising administering 1.2 g of mAb10987 and 1.2 g of mAb10933 via intravenous infusion. In some embodiments, the present disclosure provides a method for treating a subject with COVID-19, comprising administering 1.2 g of mAb10987 and 1.2 g of mAb10933 via intravenous infusion. In some embodiments, the present disclosure provides a method for treating a subject infected with SARS-CoV-2, comprising administering 600 mg of mAb10987 and 600 mg of mAb10933 via intravenous infusion. In some embodiments, the present disclosure provides a method for treating a subject with COVID-19, comprising administering 600 mg of mAb10987 and 600 mg of mAb10933 via intravenous infusion. In some embodiments, the present disclosure provides a method for treating a subject infected with SARS-CoV-2, comprising administering 4 g of mAb10987 and 4 g of mAb10933 via intravenous infusion. In some embodiments, the present disclosure provides a method for treating a subject with COVID-19, comprising administering 4 g of mAb10987 and 4 g of mAb10933 via intravenous infusion. In some embodiments, the present disclosure provides a method for treating a subject infected with SARS-CoV-2, comprising administering 300 mg of mAb10987 and 300 mg of mAb10933 via intravenous infusion. In some embodiments, the present disclosure provides a method for treating a subject with COVID-19, comprising administering 300 mg of mAb10987 and 300 mg of mAb10933 via intravenous infusion. In some embodiments, the present disclosure provides a method for treating a subject infected with SARS-CoV-2, comprising administering 150 mg of mAb10987 and 150 mg of mAb10933 via intravenous infusion. In some embodiments, the present disclosure provides a method for treating a subject with COVID-19, comprising administering 150 mg of mAb10987 and 150 mg of mAb10933 via intravenous infusion. In some embodiments, the present disclosure provides a method for treating a subject infected with SARS-CoV-2, comprising administering 600 mg of mAb10987 and 600 mg of mAb10933 via subcutaneous injection. In some embodiments, the present disclosure provides a method for treating a subject with COVID-19, comprising administering 600 mg of mAb10987 and 600 mg of mAb10933 via subcutaneous injection. In some embodiments, the present disclosure provides a method for treating a subject infected with SARS-CoV-2, comprising administering 300 mg of mAb10987 and 300 mg of mAb10933 via subcutaneous injection. In some embodiments, the present disclosure provides a method for treating a subject with COVID-19, comprising administering 300 mg of mAb10987 and 300 mg of mAb10933 via subcutaneous injection. In the above embodiments, mAb10987 and mAb10933 may be co-administered simultaneously, e.g., by combining the antibodies in an IV bag prior to a single infusion, or by combining the antibodies into a syringe prior to a single injection. Alternatively, the two antibodies may be administered as two separate subcutaneous injections. In the above embodiments, the subject may be at high risk for clinical complications.

In any of the various embodiments, the subject exhibits one or more efficacy parameters, following administration of the therapeutic composition, selected from the group consisting of: (a) reduction from baseline in SARS-CoV-2 viral shedding; (b) at least 1 point improvement in clinical status using the 7-point ordinal scale; (c) reduction or elimination of need for oxygen supplementation; (d) reduction or elimination of need for mechanical ventilation; (e) prevention of COVID-19-related mortality; (f) prevention of all-cause mortality; and (g) change in serum concentration of one or more disease-related biomarkers. In some cases, the 7-point ordinal scale is: [1] Death; [2] Hospitalized, requiring invasive mechanical ventilation or extracorporeal membrane oxygenation; [3] Hospitalized, requiring non-invasive ventilation or high flow oxygen devices; [4] Hospitalized, requiring supplemental oxygen; [5] Hospitalized, not requiring supplemental oxygen—requiring ongoing medical care (COVID-19-related or otherwise); [6] Hospitalized, not requiring supplemental oxygen—no longer requires ongoing medical care; and [7] Not hospitalized. In some cases, the one or more efficacy parameters are measured 21 days after administration of a first dose of the therapeutic composition. In some cases, the reduction from baseline in SARS-CoV-2 viral shedding is determined by real-time quantitative PCR (RT-qPCR) in nasopharyngeal swab samples, nasal samples, or saliva samples. In some cases, the change in serum concentration of one or more disease-related biomarkers is a change in c-reactive protein, lactate dehydrogenase, D-dimer, or ferritin.

In any of the various embodiments, the subject exhibits less than 5 COVID-19 related medically-attended visits, telemedicine visits, hospital admissions, and/or intensive care unit (ICU) admissions, following administration of the therapeutic composition. In some cases, the less than 5 COVID-19 related medically-attended visits, telemedicine visits, hospital admissions, and/or intensive care unit (ICU) admissions are exhibited by the subject within 29 days following administration of a first dose of the therapeutic composition. In some cases, the subject exhibits less than 4, less than 3, less than 2, or less than 1 COVID-19 related medically-attended visits, telemedicine visits, hospital admissions, and/or intensive care unit (ICU) admissions.

In some embodiments, the subject tests negative for SARS-CoV-2 within 2 days to 3 weeks following first administration of the therapeutic composition. In some cases, the negative test for SARS-CoV-2 is determined by RT-qPCR in nasopharyngeal swab samples, nasal samples, or saliva samples.

In some embodiments, the methods further comprise administering an additional therapeutic agent to the subject. In some cases, the additional therapeutic agent is an antiviral compound. In some embodiments, the antiviral compound is remdesivir. In some cases, the additional therapeutic agent is an IL-6 or IL-6R blocker. In some embodiments, the additional therapeutic agent is tocilizumab or sarilumab. In some cases, the additional therapeutic agent is a steroid. In some embodiments, the additional therapeutic agent is administered prior to the therapeutic composition. In some embodiments, the additional therapeutic agent is administered after or concurrent with the therapeutic composition. In any of the various embodiments of the methods discussed above or herein, the subject may be seronegative for SARS-CoV-2 infection.

In one aspect, the present disclosure provides a method for improving one or more clinical parameters of a SARS-CoV-2 infection, the method comprising administering a therapeutic composition to a subject with a SARS-CoV-2 infection, wherein the therapeutic composition comprises a first anti-SARS-CoV-2 spike glycoprotein antibody or antigen-binding fragment thereof comprising three heavy chain complementarity determining regions (HCDRs) and three light chain complementarity determining regions (LCDRs) contained within a heavy chain variable region (HCVR) and light chain variable region (LCVR) amino acid sequence pair comprising the amino acid sequences of SEQ ID NOs: 2/10, and a second anti-SARS-CoV-2 spike glycoprotein antibody or antigen-binding fragment thereof comprising three HCDRs and three LCDRs contained within an HCVR and an LCVR amino acid sequence pair comprising the amino acid sequences of SEQ ID NOs: 22/30, wherein said therapeutic composition alleviates at least one symptom of SARS-CoV-2 infection more rapidly when administered to a population of seronegative subjects as compared to a comparable population of seronegative subjects administered a placebo.

In one aspect, the present disclosure provides a method for improving one or more clinical parameters of a SARS-CoV-2 infection, wherein the method comprises administering a therapeutic composition to a subject with a SARS-CoV-2 infection, wherein the therapeutic composition comprises a first anti-SARS-CoV-2 spike glycoprotein antibody or antigen-binding fragment thereof comprising three heavy chain complementarity determining regions (HCDRs) and three light chain complementarity determining regions (LCDRs) contained within a heavy chain variable region (HCVR) and light chain variable region (LCVR) amino acid sequence pair comprising the amino acid sequences of SEQ ID NOs: 2/10, and a second anti-SARS-CoV-2 spike glycoprotein antibody or antigen-binding fragment thereof comprising three HCDRs and three LCDRs contained within an HCVR and an LCVR amino acid sequence pair comprising the amino acid sequences of SEQ ID NOs: 22/30, wherein said therapeutic composition alleviates at least one symptom of SARS-CoV-2 infection more rapidly when administered to a population of seronegative subjects as compared to a comparable population of seropositive subjects.

In one aspect, the present disclosure provides a method for improving one or more clinical parameters of a SARS-CoV-2 infection, the method comprising administering a therapeutic composition to a subject with a SARS-CoV-2 infection, wherein the therapeutic composition comprises a first anti-SARS-CoV-2 spike glycoprotein antibody or antigen-binding fragment thereof comprising three heavy chain complementarity determining regions (HCDRs) and three light chain complementarity determining regions (LCDRs) contained within a heavy chain variable region (HCVR) and light chain variable region (LCVR) amino acid sequence pair comprising the amino acid sequences of SEQ ID NOs: 2/10, and a second anti-SARS-CoV-2 spike glycoprotein antibody or antigen-binding fragment thereof comprising three HCDRs and three LCDRs contained within an HCVR and an LCVR amino acid sequence pair comprising the amino acid sequences of SEQ ID NOs: 22/30, wherein said therapeutic composition reduces viral load through 7 days post-administration (Day 7) to a population of subjects as compared to the day of administration (Day 0).

In some embodiments, the time-weighted-average change from baseline nasopharyngeal (NP) viral load through Day 7 in a seronegative population of subjects is at least 0.86 log 10 copies/mL greater reduction (p<0.0001) in patients treated with 0.6 g of the first anti-SARS-CoV-2 spike glycoprotein antibody and 0.6 g of the second anti-SARS-CoV-2 spike glycoprotein antibody, as compared to a comparable population of subjects treated with a placebo.

In some embodiments, the change from baseline nasopharyngeal (NP) viral load through Day 7 in a seronegative population of subjects is at least 1.04 log 10 copies/mL greater reduction (p<0.0001) in patients treated with 1.2 g of the first anti-SARS-CoV-2 spike glycoprotein antibody and 1.2 g of the second anti-SARS-CoV-2 spike glycoprotein antibody, as compared to a comparable population of subjects treated with a placebo.

In some embodiments, the average change from baseline nasopharyngeal (NP) viral load through Day 7 in the population of subjects is at least 0.71 log 10 copies/mL greater reduction (p<0.0001) in patients treated with 0.6 g of the first anti-SARS-CoV-2 spike glycoprotein antibody and 0.6 g of the second anti-SARS-CoV-2 spike glycoprotein antibody, as compared to a comparable population of subjects treated with a placebo.

In some embodiments, the average change from baseline nasopharyngeal (NP) viral load through Day 7 in the population of subjects is a 0.86 log 10 copies/mL greater reduction (p<0.0001) in patients treated with 1.2 g of the first anti-SARS-CoV-2 spike glycoprotein antibody and 1.2 g of the second anti-SARS-CoV-2 spike glycoprotein antibody, as compared to a comparable population of subjects treated with a placebo.

In one aspect, the present disclosure provides a method for improving one or more clinical parameters of a SARS-CoV-2 infection, the method comprising administering a therapeutic composition to a subject with a SARS-CoV-2 infection, wherein the therapeutic composition comprises a first anti-SARS-CoV-2 spike glycoprotein antibody or antigen-binding fragment thereof comprising three heavy chain complementarity determining regions (HCDRs) and three light chain complementarity determining regions (LCDRs) contained within a heavy chain variable region (HCVR) and light chain variable region (LCVR) amino acid sequence pair comprising the amino acid sequences of SEQ ID NOs: 2/10, and a second anti-SARS-CoV-2 spike glycoprotein antibody or antigen-binding fragment thereof comprising three HCDRs and three LCDRs contained within an HCVR and an LCVR amino acid sequence pair comprising the amino acid sequences of SEQ ID NOs: 22/30, wherein said therapeutic composition reduces viral load in a population of subjects.

In some embodiments of the methods discussed above or herein, administration of said therapeutic composition comprises administering 0.6 g of the first anti-SARS-CoV-2 spike glycoprotein antibody and 0.6 g of the second anti-SARS-CoV-2 spike glycoprotein antibody, and wherein said administering produces a mean reduction in viral load at day 7 post-administration compared to baseline viral load measured at day 0 pre-administration of at least 3.00 log 10 copies/mL. In some cases, said reduction is at least 3.50 log 10 copies/mL. In some cases, said reduction is at least 3.90 log 10 copies/mL.

In some embodiments, administration of said therapeutic composition comprises administering 1.2 g of the first anti-SARS-CoV-2 spike glycoprotein antibody and 1.2 g of the second anti-SARS-CoV-2 spike glycoprotein antibody, and wherein said administering produces a mean reduction in viral load at day 7 post-administration compared to baseline viral load measured at day 0 pre-administration of at least 3.50 log 10 copies/mL. In some cases, said reduction is at least 3.75 log 10 copies/mL. In some cases, said reduction is at least 4.09 log 10 copies/mL.

In one aspect, the present disclosure provides a method for improving one or more clinical parameters of a SARS-CoV-2 infection, the method comprising administering a therapeutic composition to a subject with a SARS-CoV-2 infection, wherein the therapeutic composition comprises a first anti-SARS-CoV-2 spike glycoprotein antibody or antigen-binding fragment thereof comprising three heavy chain complementarity determining regions (HCDRs) and three light chain complementarity determining regions (LCDRs) contained within a heavy chain variable region (HCVR) and light chain variable region (LCVR) amino acid sequence pair comprising the amino acid sequences of SEQ ID NOs: 2/10, and a second anti-SARS-CoV-2 spike glycoprotein antibody or antigen-binding fragment thereof comprising three HCDRs and three LCDRs contained within an HCVR and an LCVR amino acid sequence pair comprising the amino acid sequences of SEQ ID NOs: 22/30, wherein said therapeutic composition reduces time to symptom alleviation (defined as symptoms becoming mild or absent) by a median of 4 days in a population of subjects treated with 0.6 g of the first anti-SARS-CoV-2 spike glycoprotein antibody and 0.6 g of the second anti-SARS-CoV-2 spike glycoprotein antibody or 1.2 g of the first anti-SARS-CoV-2 spike glycoprotein antibody and 1.2 g of the second anti-SARS-CoV-2 spike glycoprotein antibody, as compared to a comparable population of subjects treated with a placebo. In some embodiments, the subjects and/or population of subjects comprises subjects not hospitalized for COVID-19.

Any of the various methods discussed above or herein can be reformatted as (i) antigen-binding molecules or antibodies (and antigen-binding fragments) for use in a method of treating and/or preventing SARS-CoV-2 infections and/or COVID-19, and/or for treating, preventing and reducing the severity or progression of a SARS-CoV-2 infection and/or COVID-19, or symptoms thereof, or (ii) use of the antigen-binding molecules or antibodies (and antigen-binding fragments) in the manufacture of a medicament for treating and/or preventing SARS-CoV-2 infections and/or COVID-19, and/or for treating, preventing and reducing the severity or progression of a SARS-CoV-2 infection and/or COVID-19, or symptoms thereof. In particular, the present disclosure includes use of antigen-binding molecules that bind a surface protein of SARS-CoV-2, including the anti-SARS-CoV-2 spike glycoprotein antibodies or antigen-binding fragments thereof discussed herein, for preventing and treating SARS-CoV-2 infections and COVID-19 and/or for treating, preventing and reducing the severity or progression of a SARS-CoV-2 infection and/or COVID-19, or symptoms thereof. The present disclosure also includes use of antigen-binding molecules that bind a surface protein of SARS-Co-2, including the anti-SARS-CoV-2 spike glycoprotein antibodies or antigen-binding fragments thereof discussed herein, in the manufacture of a medicament for preventing and treating SARS-CoV-2 infections and COVID-19 and/or for treating, preventing and reducing the severity or progression of a SARS-CoV-2 infection and/or COVID-19. Where methods are discussed herein with reference to a combination of two anti-SARS-CoV-2 spike protein antibodies, such combinations include use of a first such antibody or antigen-binding fragment thereof in the manufacture of a medicament for use in combination with a second such antibody or antigen-binding fragment thereof (or a third or fourth, etc. such antibody or antigen-binding fragment), as well as use of the second such antibody or antigen-binding fragment thereof (or a third or fourth, etc. such antibody or antigen-binding fragment) in the manufacture of a medicament for use in combination with the first such antibody.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges are encompassed within the scope of the present disclosure.

Other embodiments will become apparent from a review of the ensuing detailed description.

BRIEF DESCRIPTION OF THE DRAWINGS

FIG. 3A and FIG. 3B illustrate the results of RNA sequence analysis of viral RNA from the study illustrated in FIGS. 2A-2D. FIG. 3A shows the frequencies of all amino acid changes identified in the spike protein across all virus sequences; each dot represents the frequency of the corresponding amino acid change in a specific virus sample, and samples are grouped based on treatment regimen: isotype control (placebo), therapeutic antibodies administered prior (prophylactic) or following (treatment) viral challenge. FIG. 3B shows detailed genomic information on all amino acid changes identified within the spike protein sequence across all samples; for each sample, the frequency of all mutations has been calculated, and these frequencies are shown as percentage of the virus population with the amino acid change in the input virus or as range of frequency percentages (lowest to highest %) in the virus populations isolated from the placebo, prophylactic and therapeutic groups.

and in groups defined according to baseline antibody status and baseline viral load. I bars in Panel C indicate the standard error. The lower limit of detection (dashed line) is 714 copies per milliliter (2.85 log 10 copies per milliliter). IV, intravenous(ly); SE, standard error.

Figure 12:
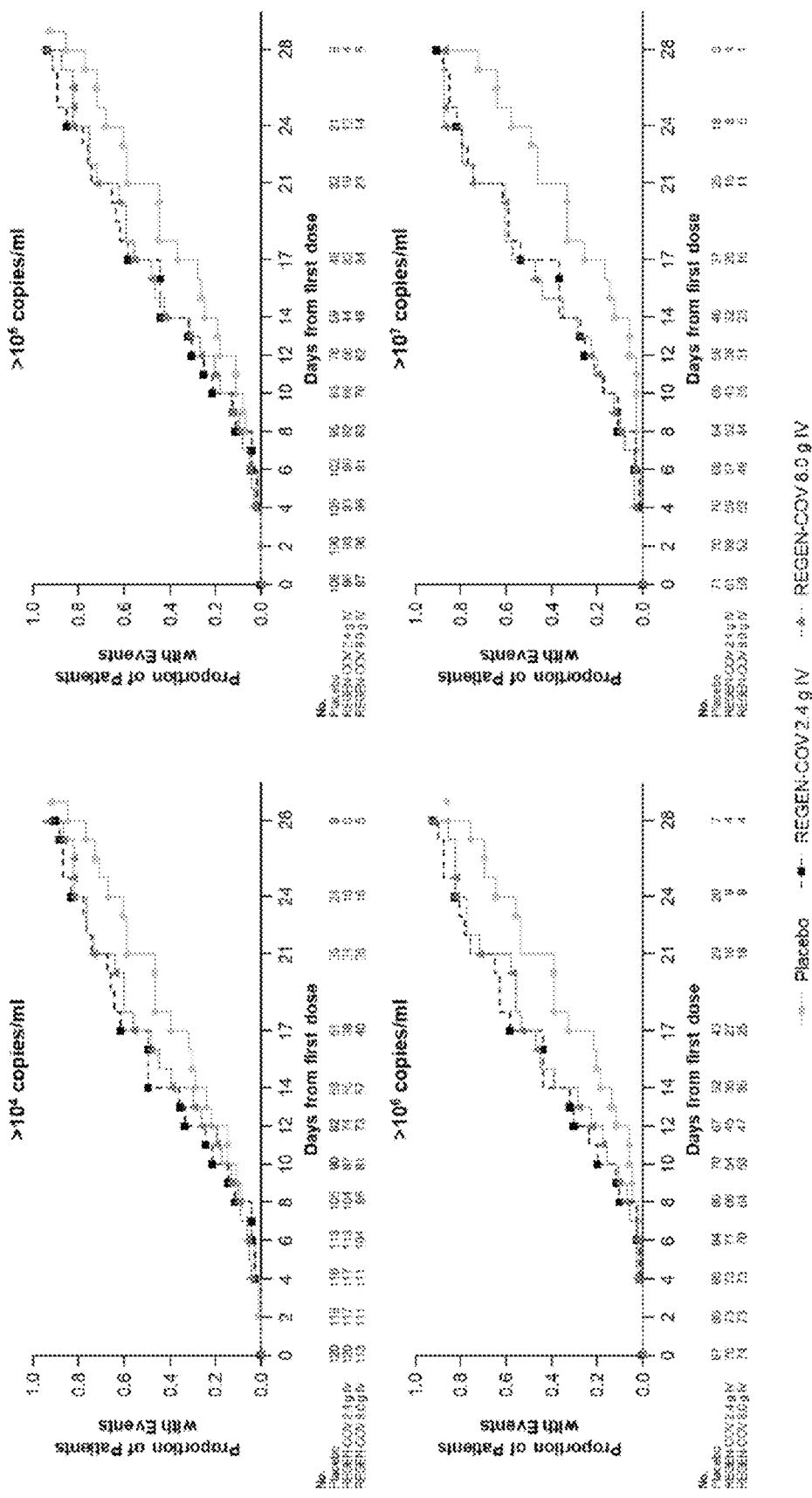

FIG. 12 illustrates time to sustained negative RT-qPCR by baseline viral load category in the study discussed in Example 2.

Figure 13:
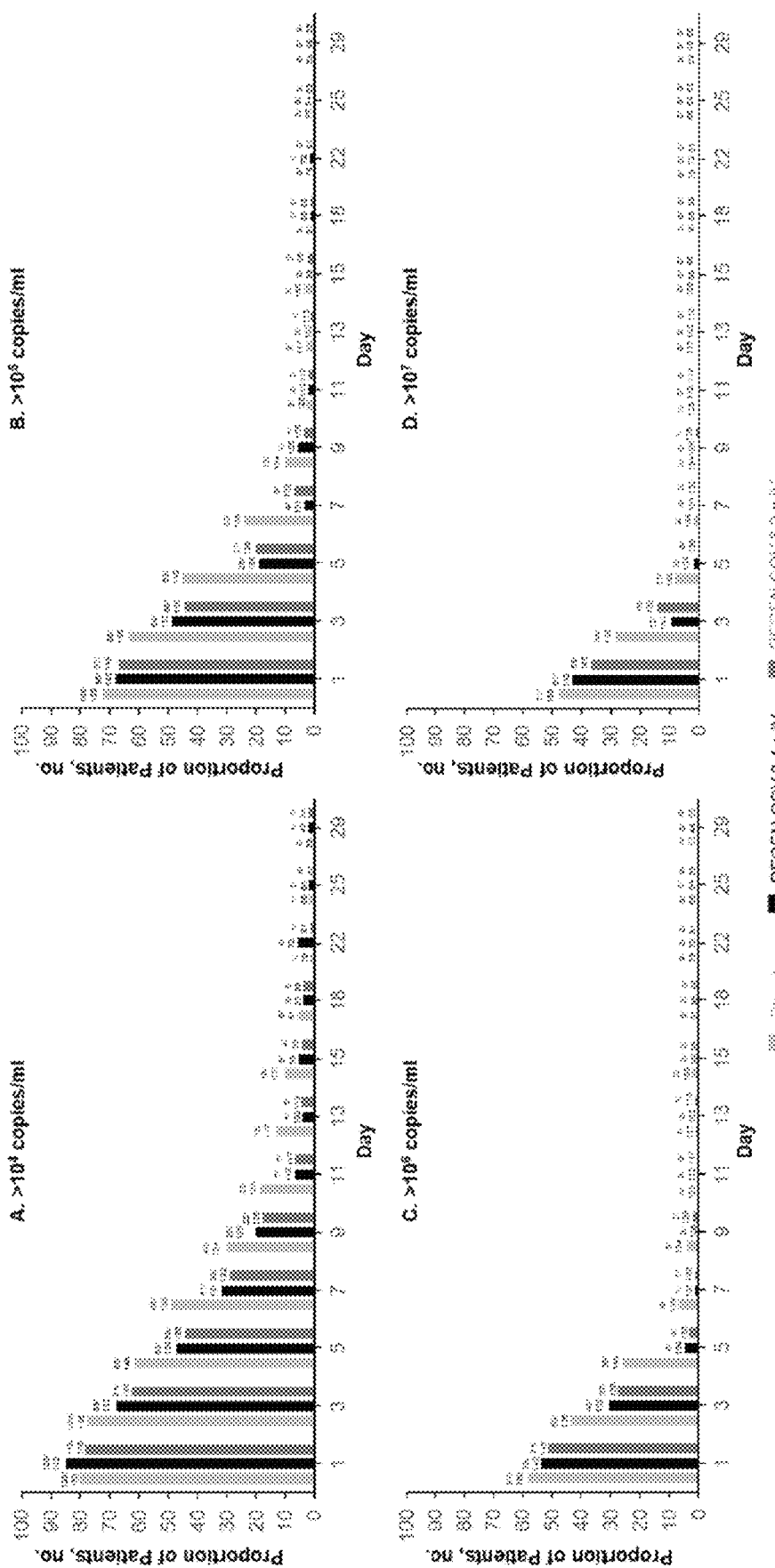

FIG. 13 illustrates the proportion of patients with high viral load at each visit in the study discussed in Example 2.

Figure 14A:
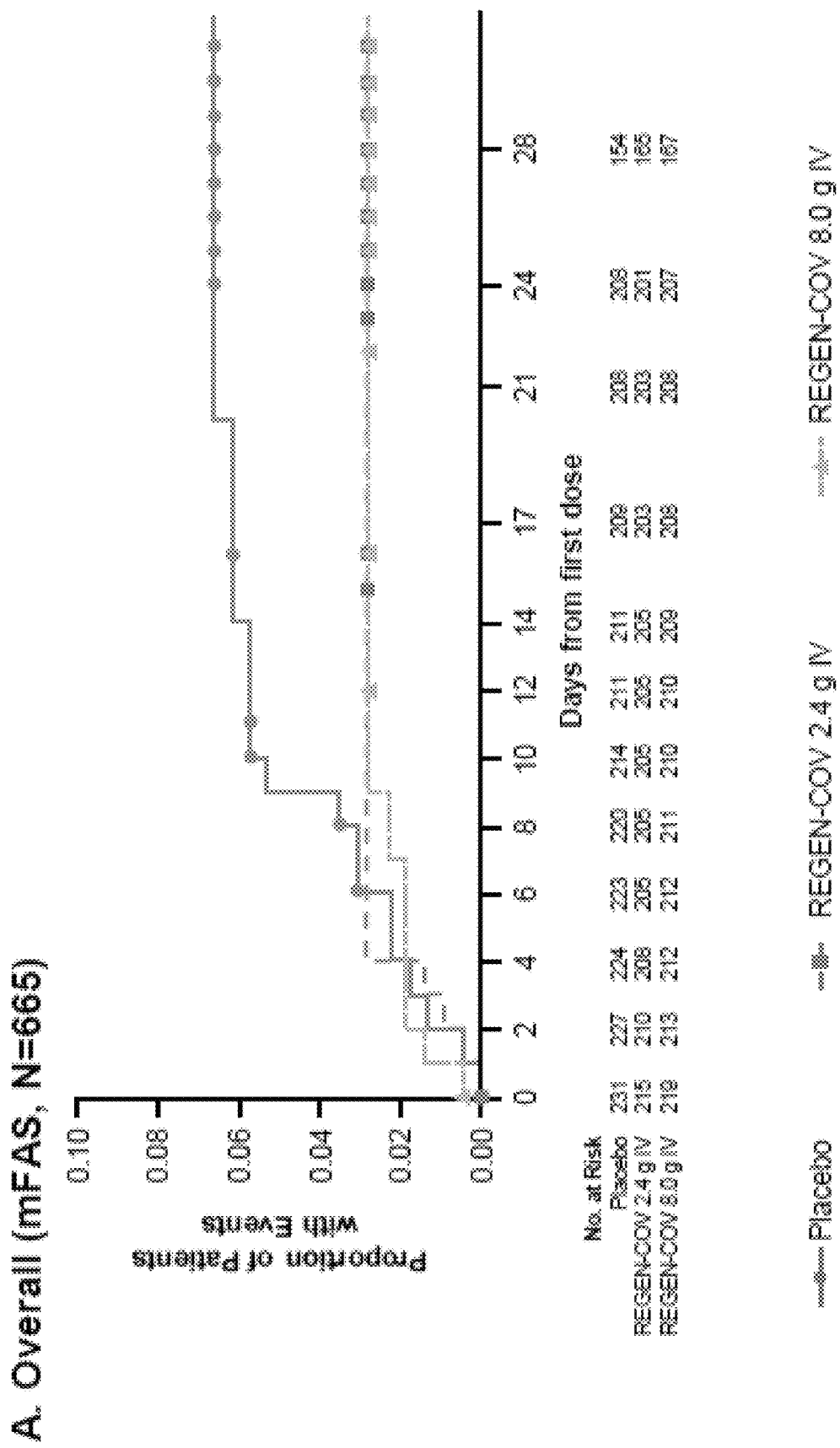
Figure 14B:
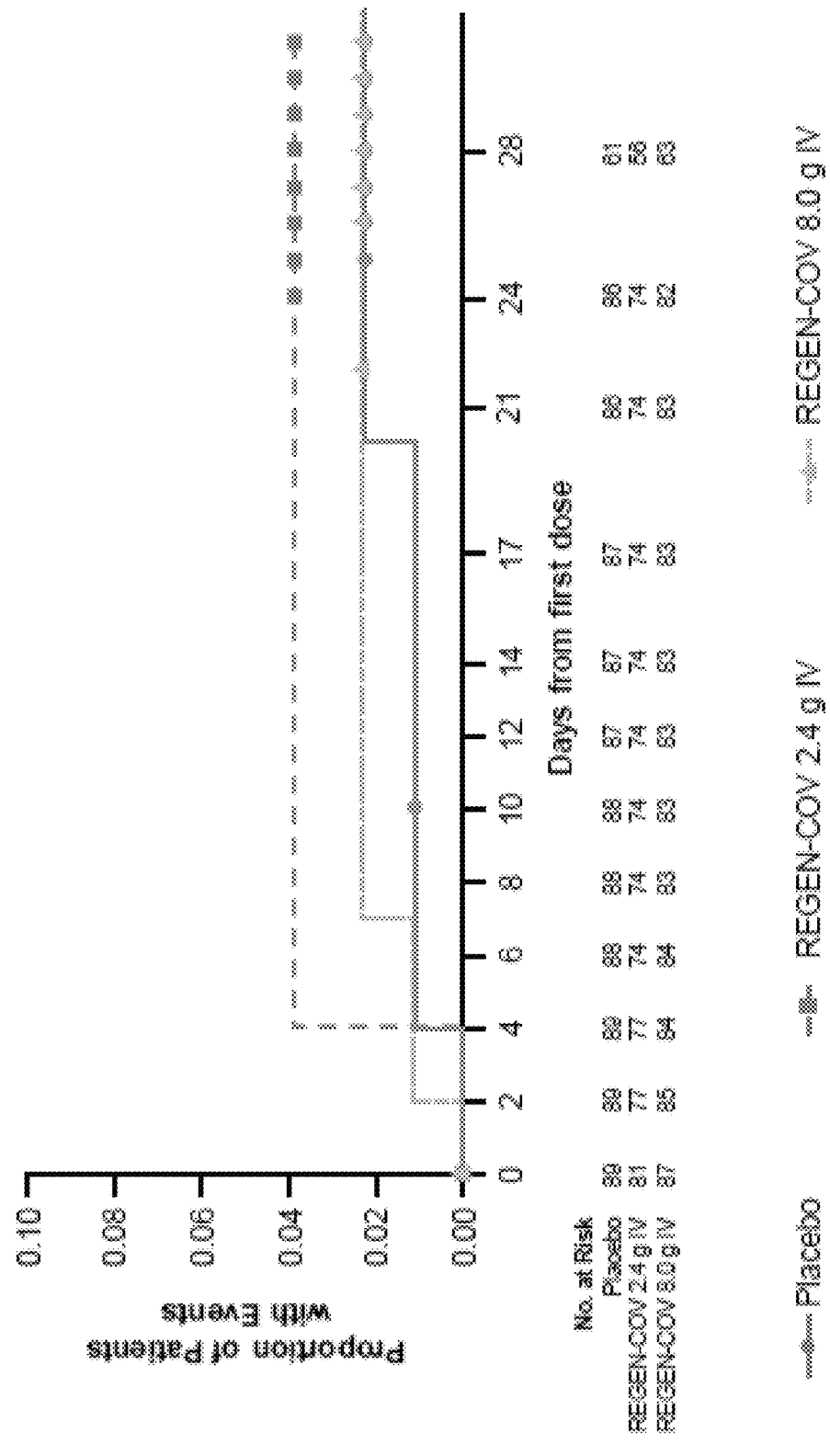
Figure 14C:
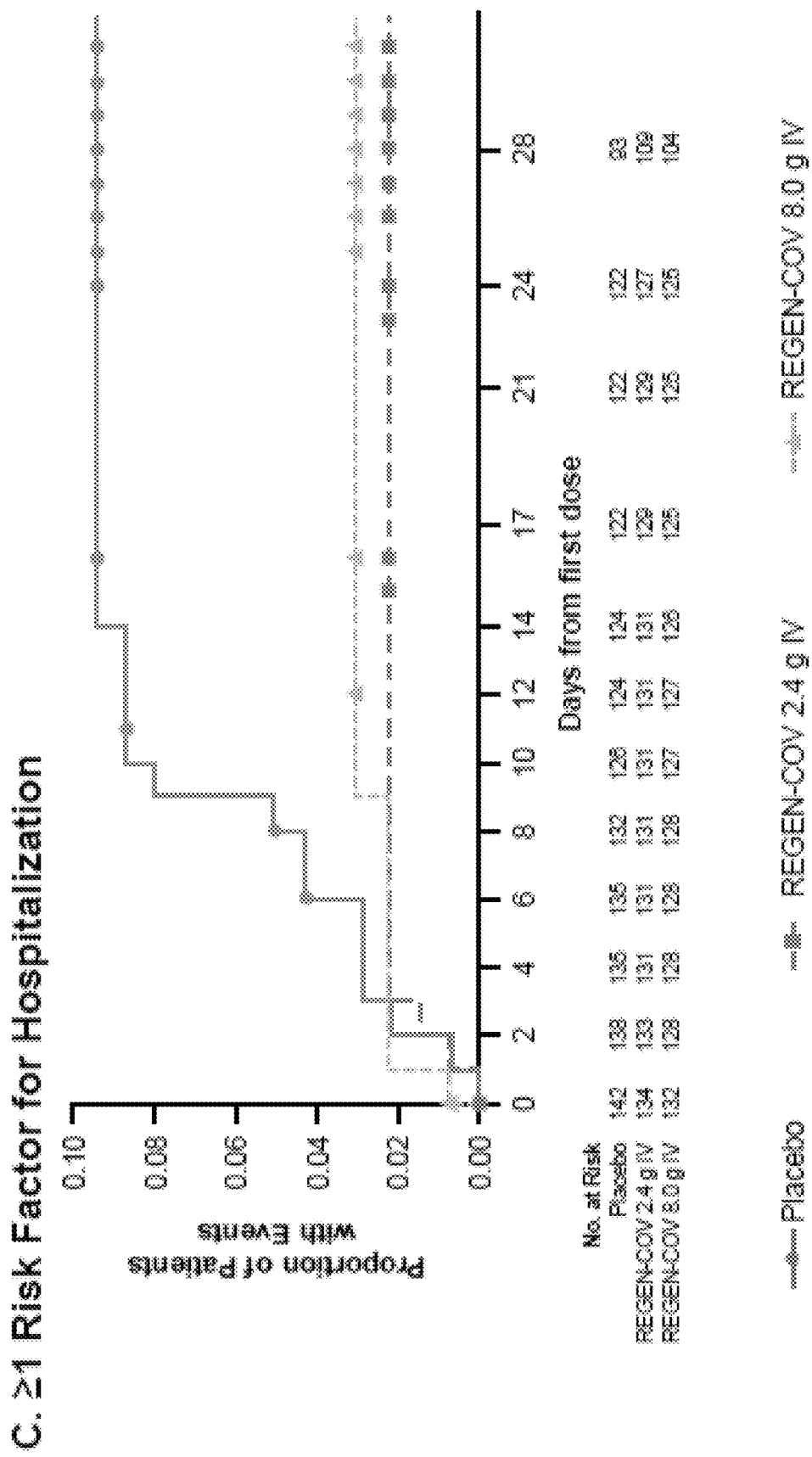

FIG. 14A, FIG. 14B, and FIG. 14C illustrate the proportion of patients with Covid-19-related MAVs in the study discussed in Example 2.

Figure 15A:
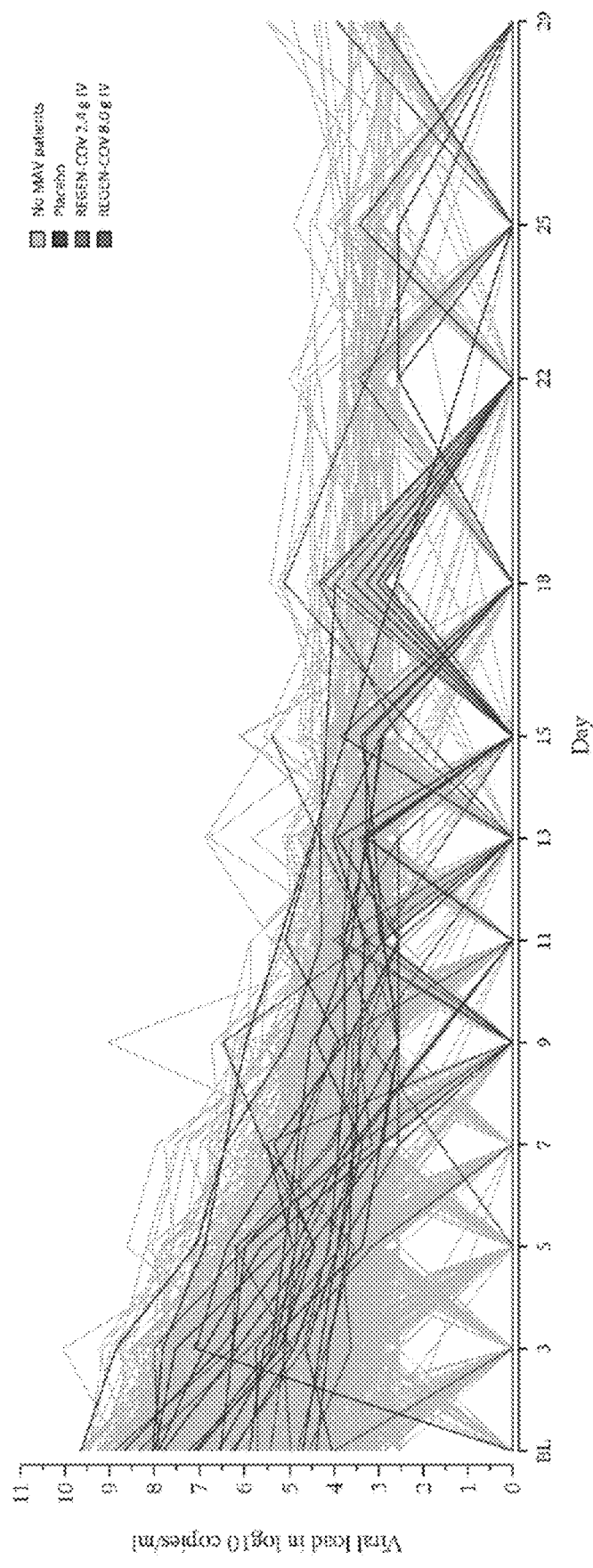
Figure 15B:
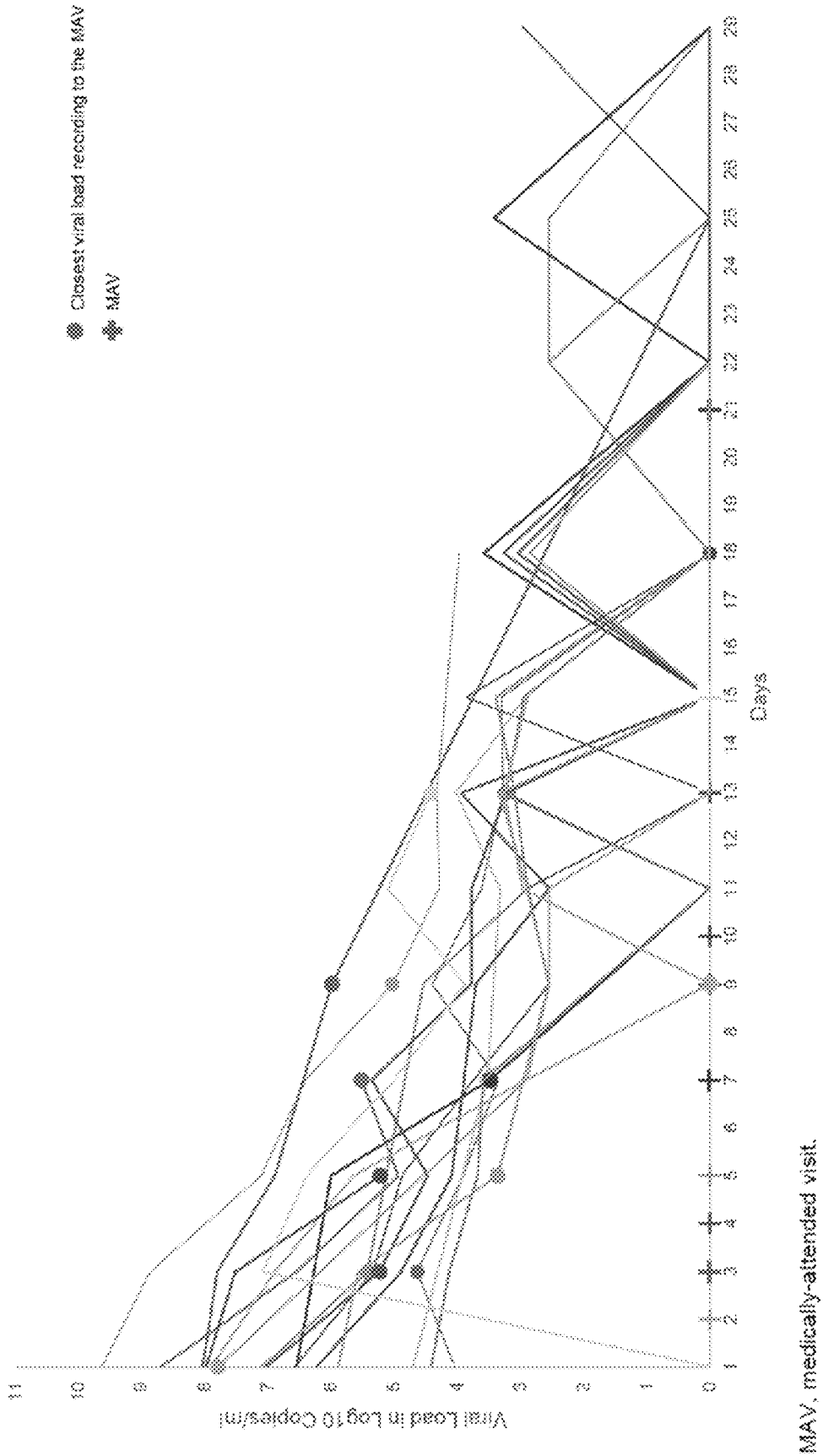
Figure 15C:
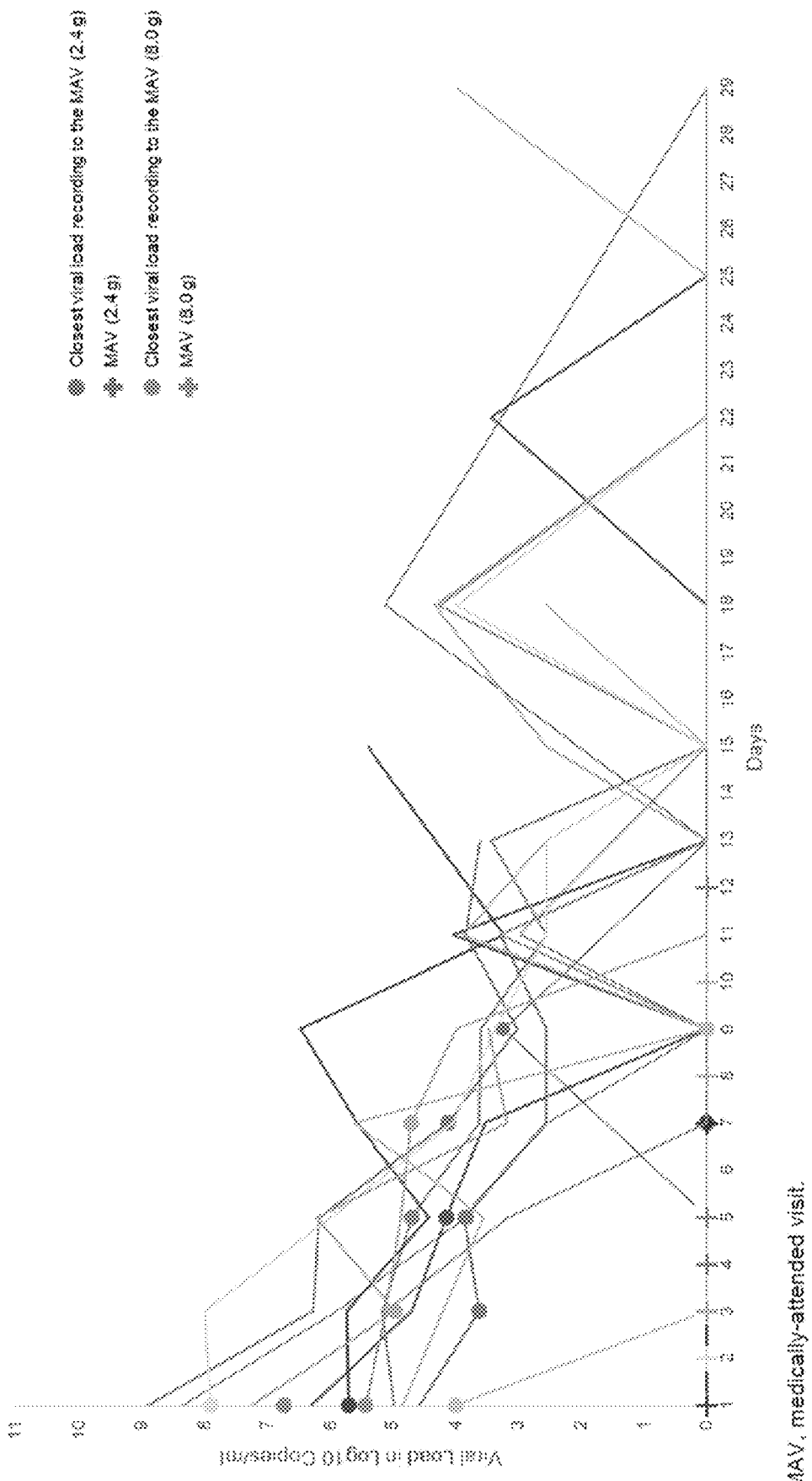

FIG. 15A, FIG. 15B and FIG. 15C illustrate the viral load through day 29 in patients with and without ≥1 Covid-19-related MAVs in the study discussed in Example 2.

FIG. 16 illustrates that seronegative patients (n=217) had much higher viral loads than those who had already developed their own antibodies (seropositive) to SARS-CoV-2 at the time of randomization.

Figure 17:
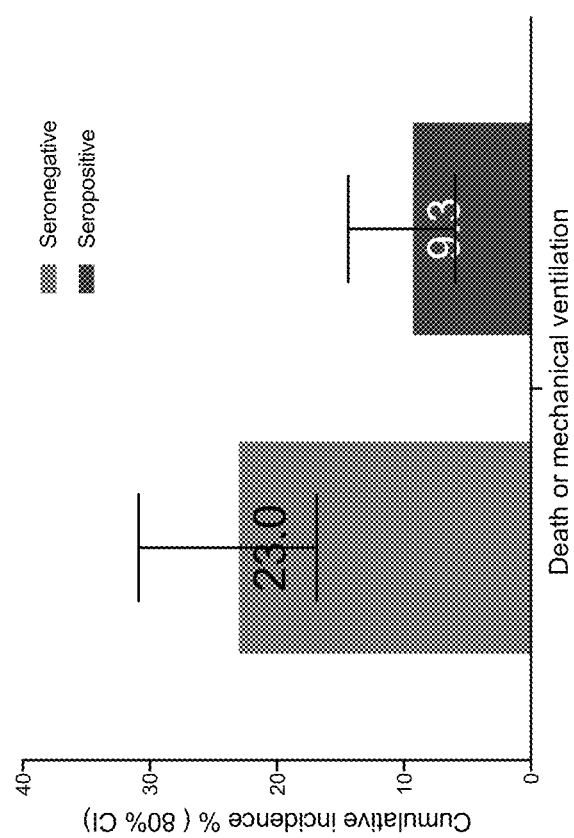

FIG. 17 illustrates that, among hospitalized patients with COVID-19 on low flow supplemental oxygen, seropositive patients had lower cumulative incidence of death or mechanical ventilation compared to seronegative patients FIG. 18 illustrates clinical outcomes in Cohort 1, by serostatus and viral load. Clinical outcomes were worse in patients who were seronegative at baseline or who had high viral load at baseline.

Figure 19:
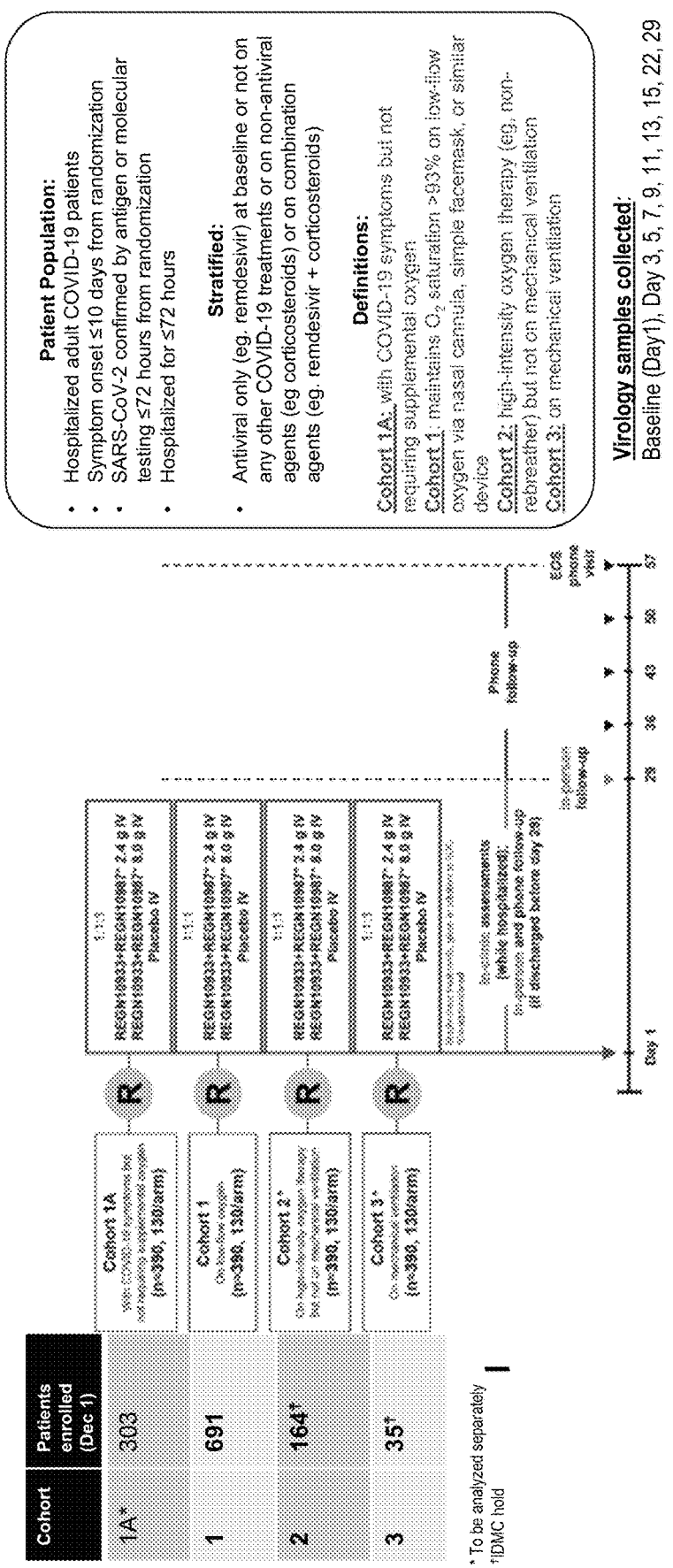

FIG. 19 illustrates a seamless phase 1/2/3 study design in hospitalized patients with COVID-19.

Figure 20:
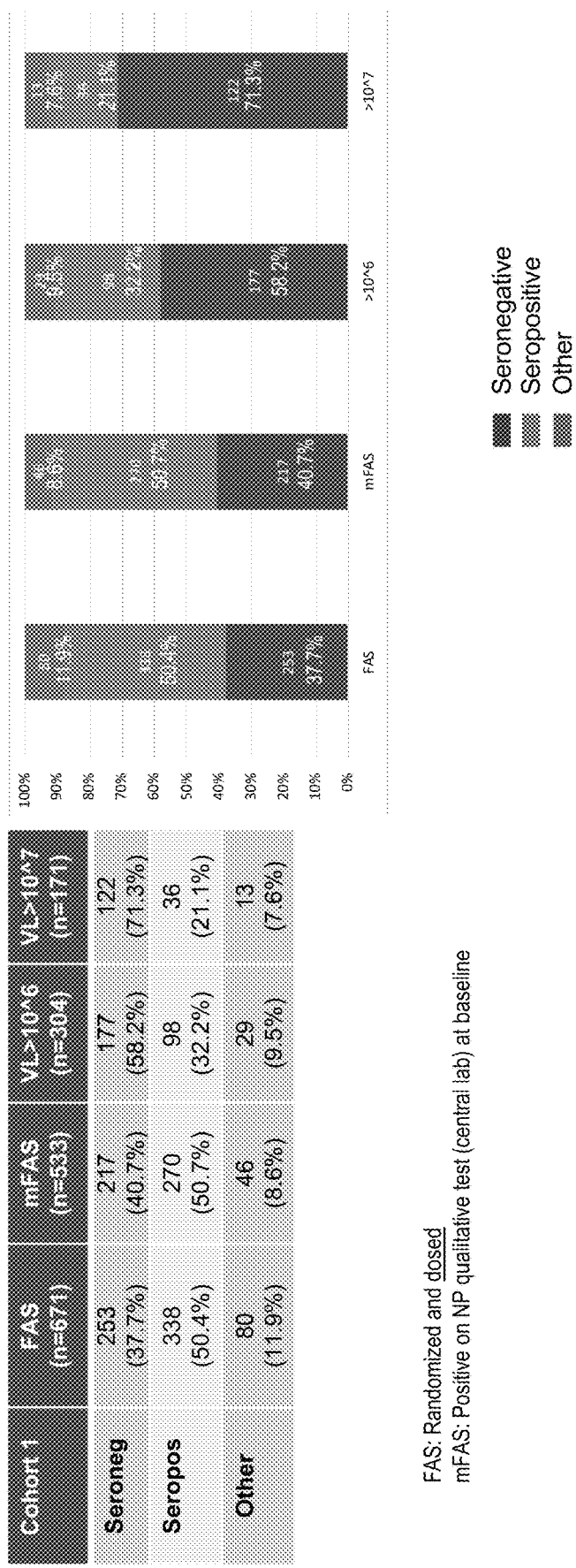

FIG. 20 illustrates the number of patients that are seronegative, seropositive, or having borderline results or missing data ("other"), in the full analysis set (FAS), modified full analysis set (mFAS), having viral loads >$10^6$, or having viral loads >$10^7$.

Figure 21:
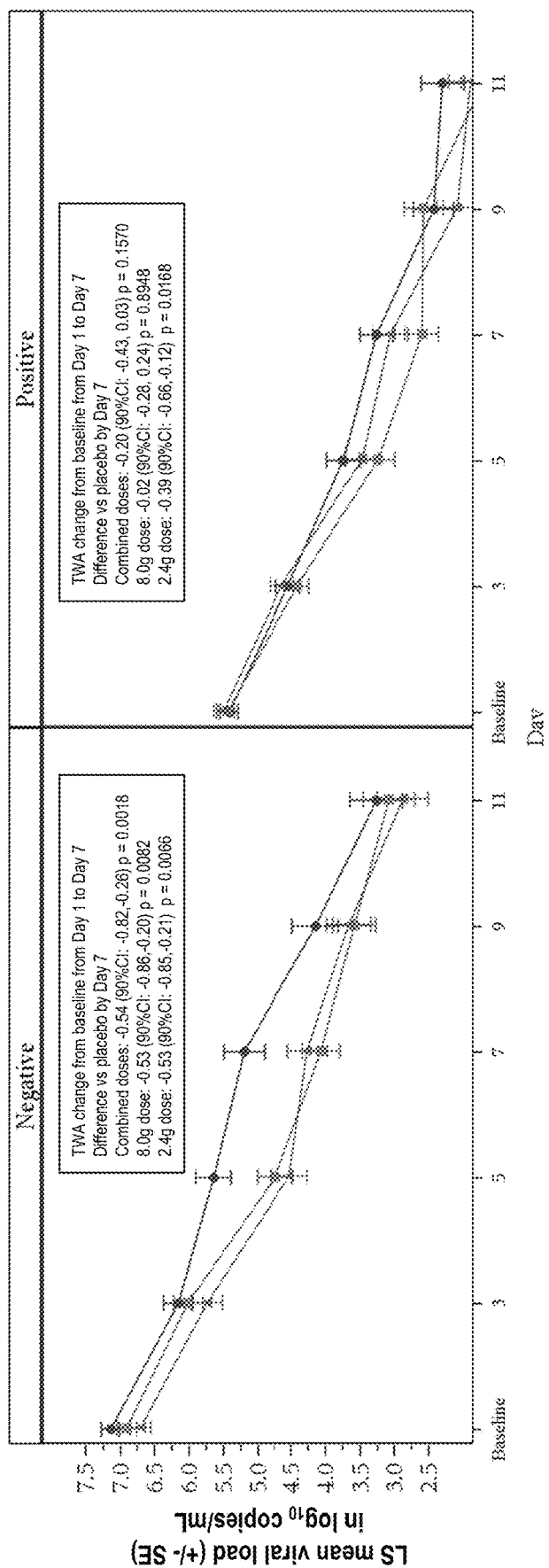

FIG. 21 illustrates the mean viral load in seronegative patients (circles), seropositive patients (squares), and other patients (borderline results or missing data; triangles). TWA, time-weighted average; CI, confidence interval.

Figure 22:
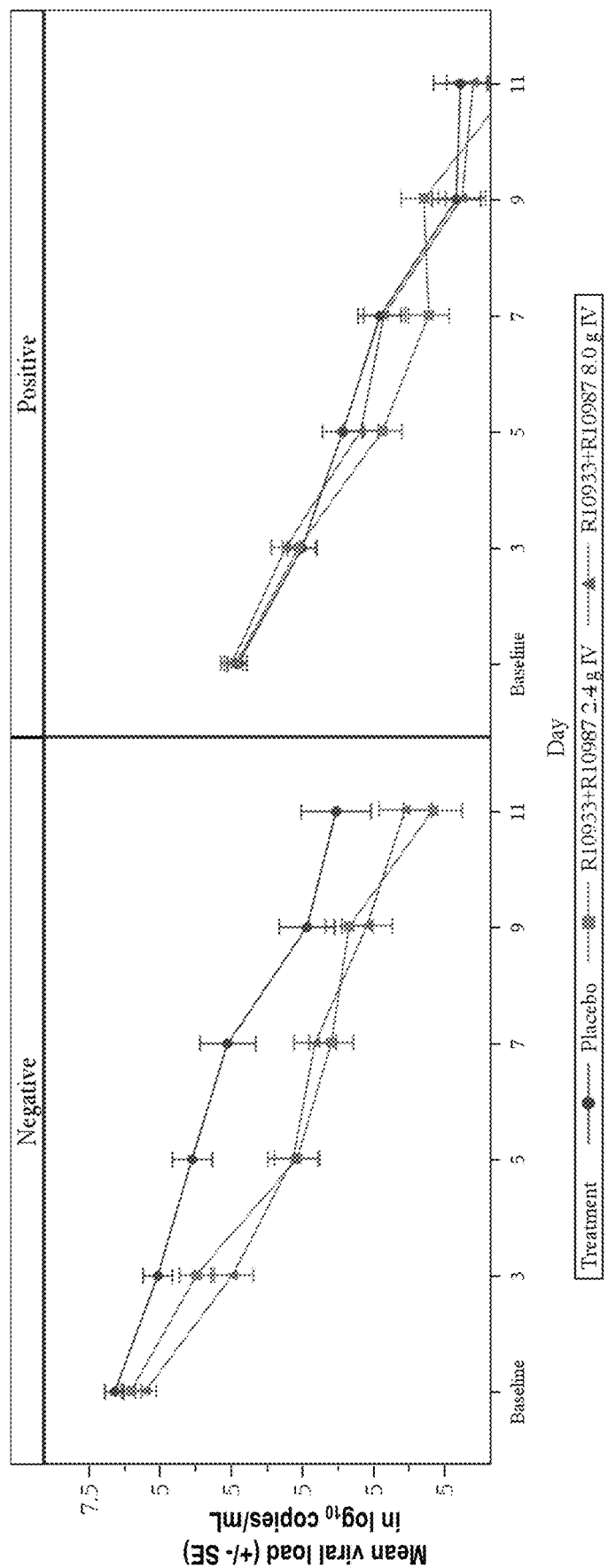

FIG. 22 illustrates the mean viral load in patients treated intravenously with placebo (circles), 1.2 g mAb10933+1.2 mAb10987 (2.4 g total; squares), or 4 g mAb10933+4 mAb10987 (8 g total; triangles).

Figure 23:
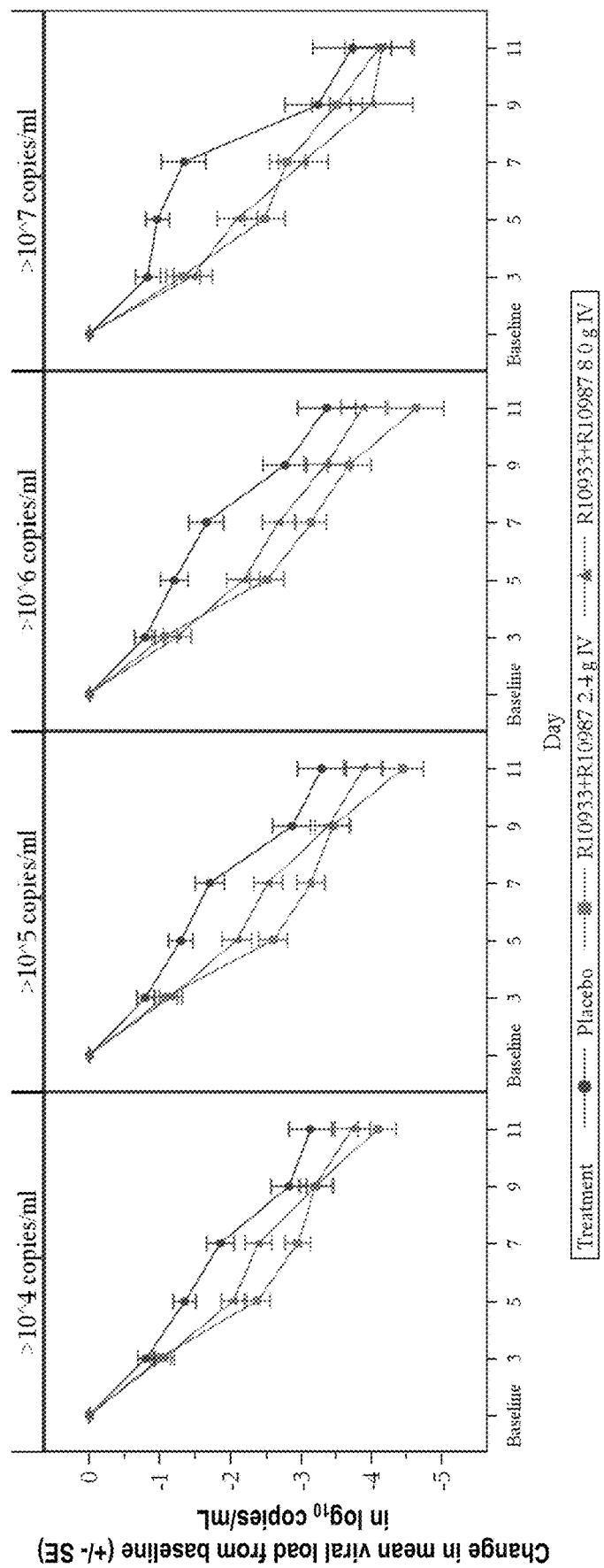

FIG. 23 illustrates change in mean viral load from baseline in patients treated intravenously with placebo (circles), 1.2 g mAb10933+1.2 mAb10987 (2.4 g total; squares), or 4 g mAb10933+4 mAb10987 (8 g total; triangles). Graphs divide patients by viral load: >$10^4$ copies/ml, >$10^5$ copies/ml, >$10^6$ copies/ml, and >$10^7$ copies/ml.

Figure 24:
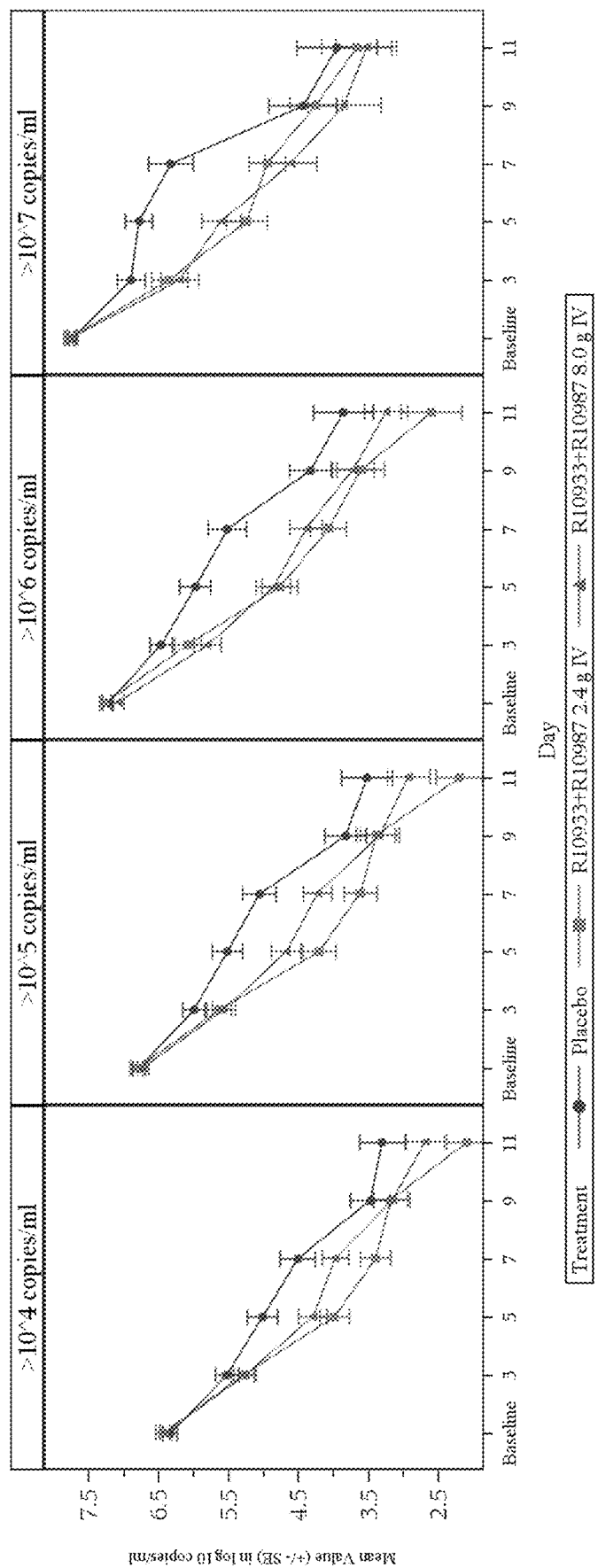

FIG. 24 illustrates mean viral load over time in patients treated intravenously with placebo (circles), 1.2 g mAb10933+1.2 mAb10987 (2.4 g total; squares), or 4 g mAb10933+4 mAb10987 (8 g total; triangles). Graphs divide patients by baseline viral load: >$10^4$ copies/ml, >$10^5$ copies/ml, >$10^6$ copies/ml, and >$10^7$ copies/ml.

Figure 25:
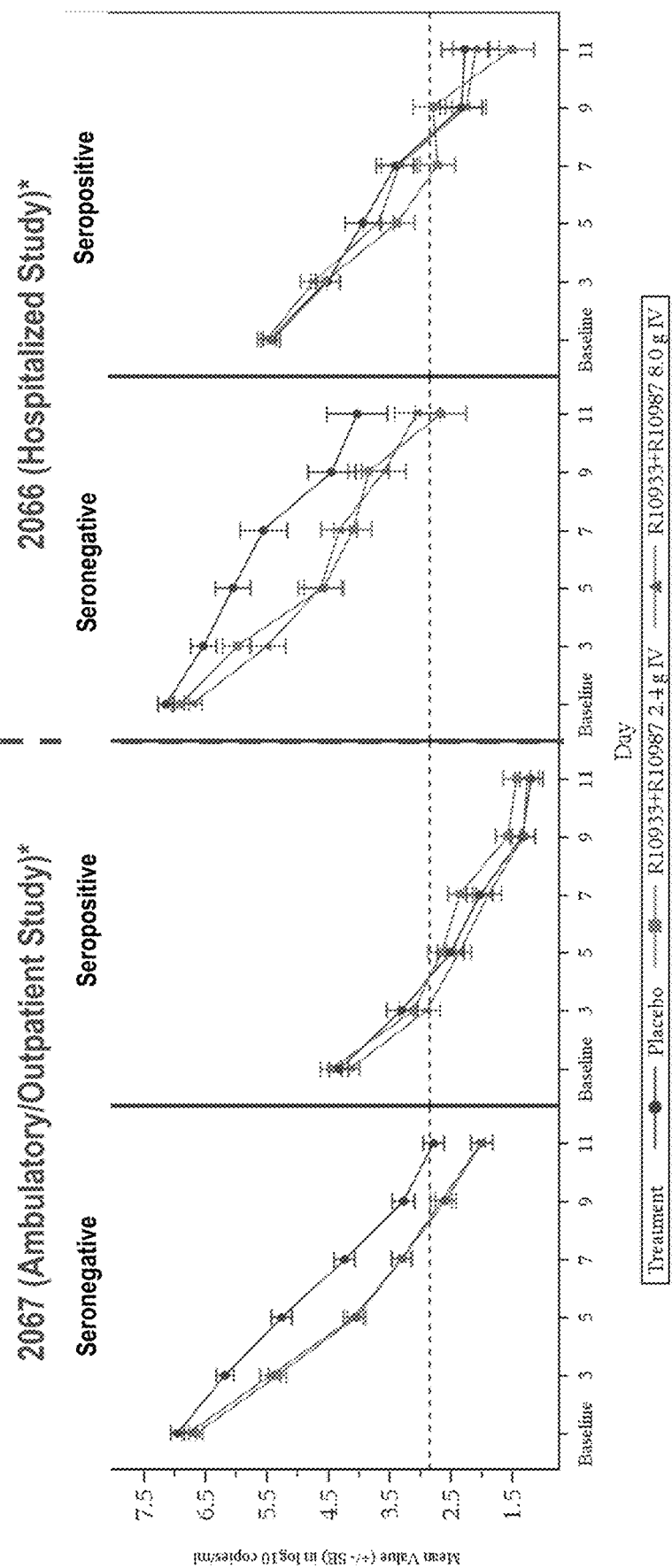

FIG. 25 illustrates mean viral load over time in seronegative or seropositive patients treated intravenously with placebo (circles), 1.2 g mAb10933+1.2 mAb10987 (2.4 g total; squares), or 4 g mAb10933+4 mAb10987 (8 g total; triangles). Graphs divide patients by serostatus and clinical trial: 2066 (hospitalized study; Example 1) and 2067 (ambulatory/outpatient study; Example 2).

Figure 26:
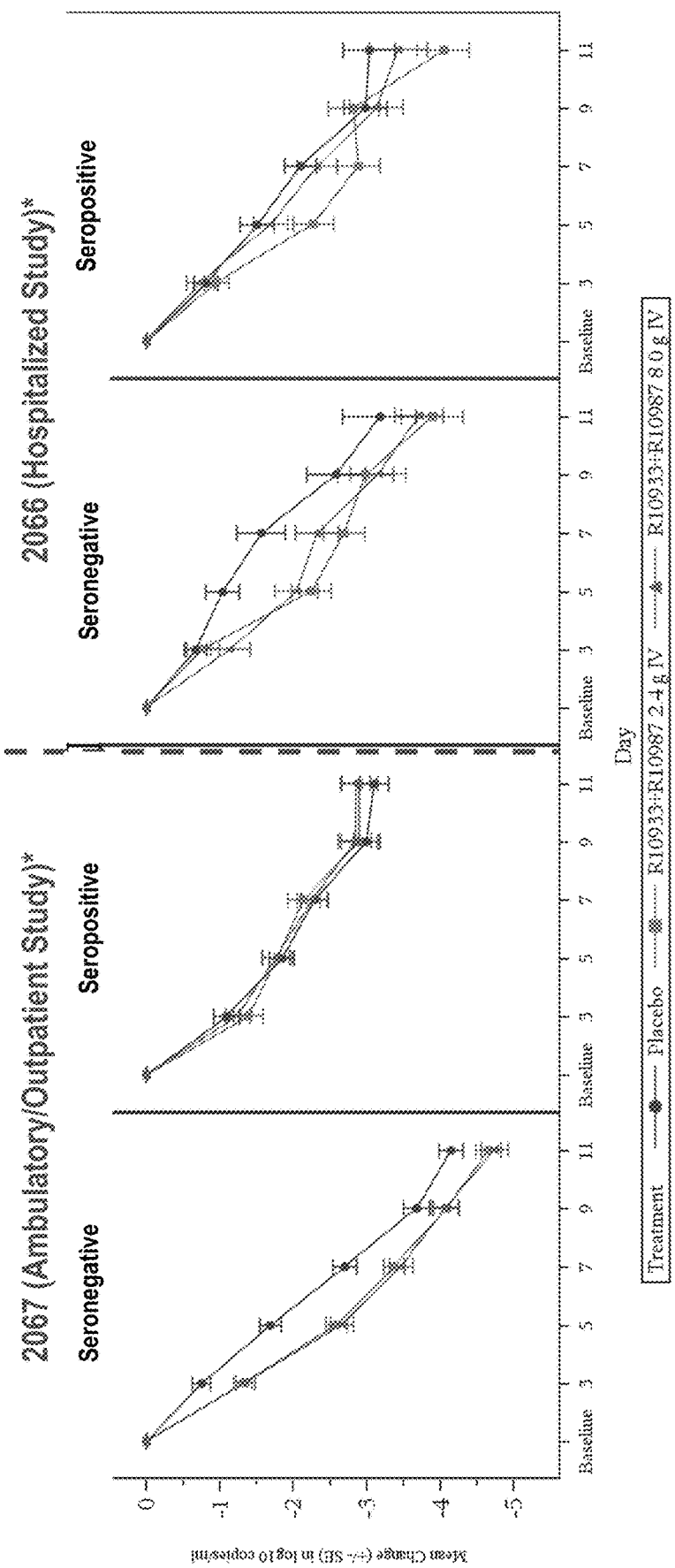

FIG. 26 illustrates change in mean viral load from baseline in patients treated intravenously with placebo (circles), 1.2 g mAb10933+1.2 mAb10987 (2.4 g total; squares), or 4 g mAb10933+4 mAb10987 (8 g total; triangles). Graphs divide patients by serostatus and clinical trial: 2066 (hospitalized study; Example 1) and 2067 (ambulatory/outpatient study; Example 2).

Figure 27:
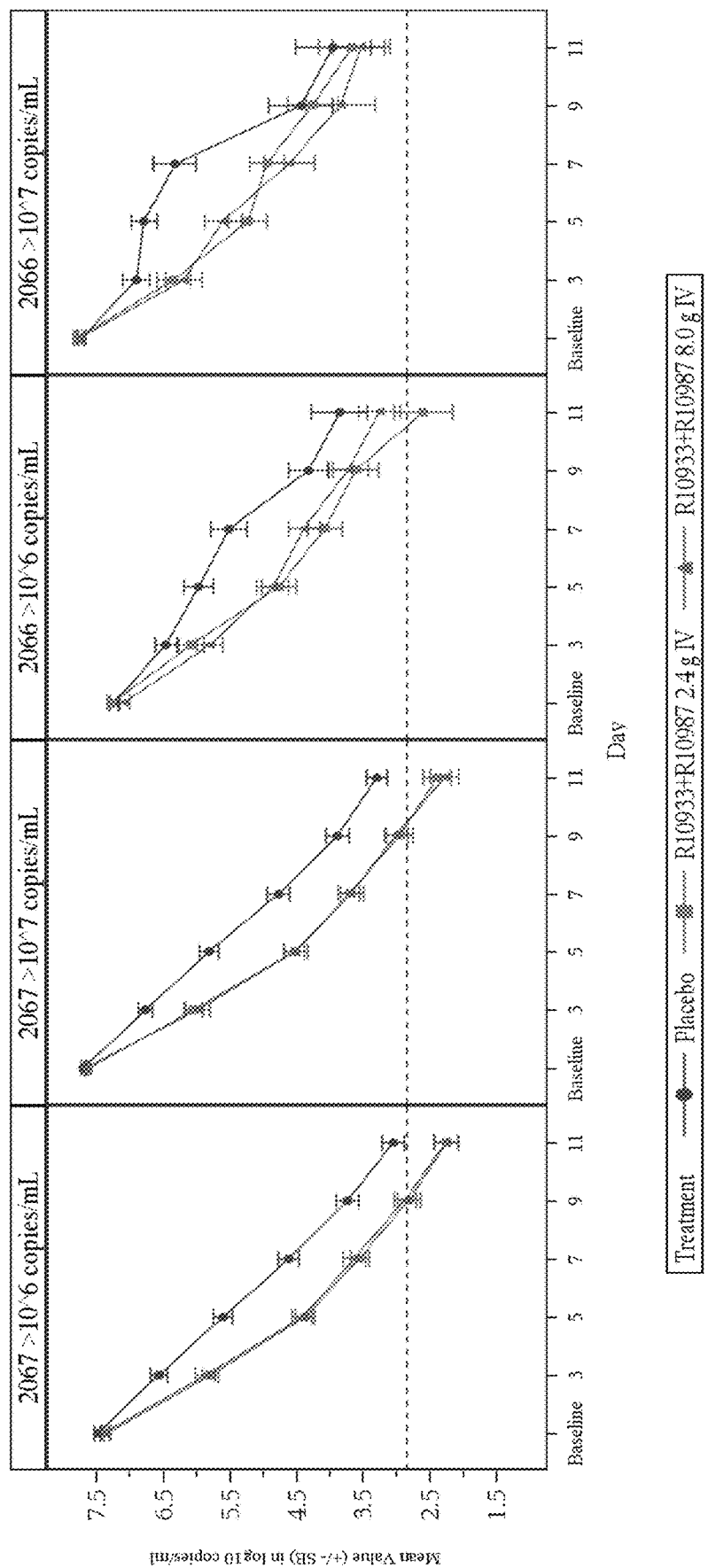

FIG. 27 illustrates mean viral load over time in patients treated intravenously with placebo (circles), 1.2 g mAb10933+1.2 mAb10987 (2.4 g total; squares), or 4 g mAb10933+4 mAb10987 (8 g total; triangles). Graphs divide patients by baseline viral load and clinical trial: 2066 (hospitalized study; Example 1) and 2067 (ambulatory/outpatient study; Example 2).

Figure 28:
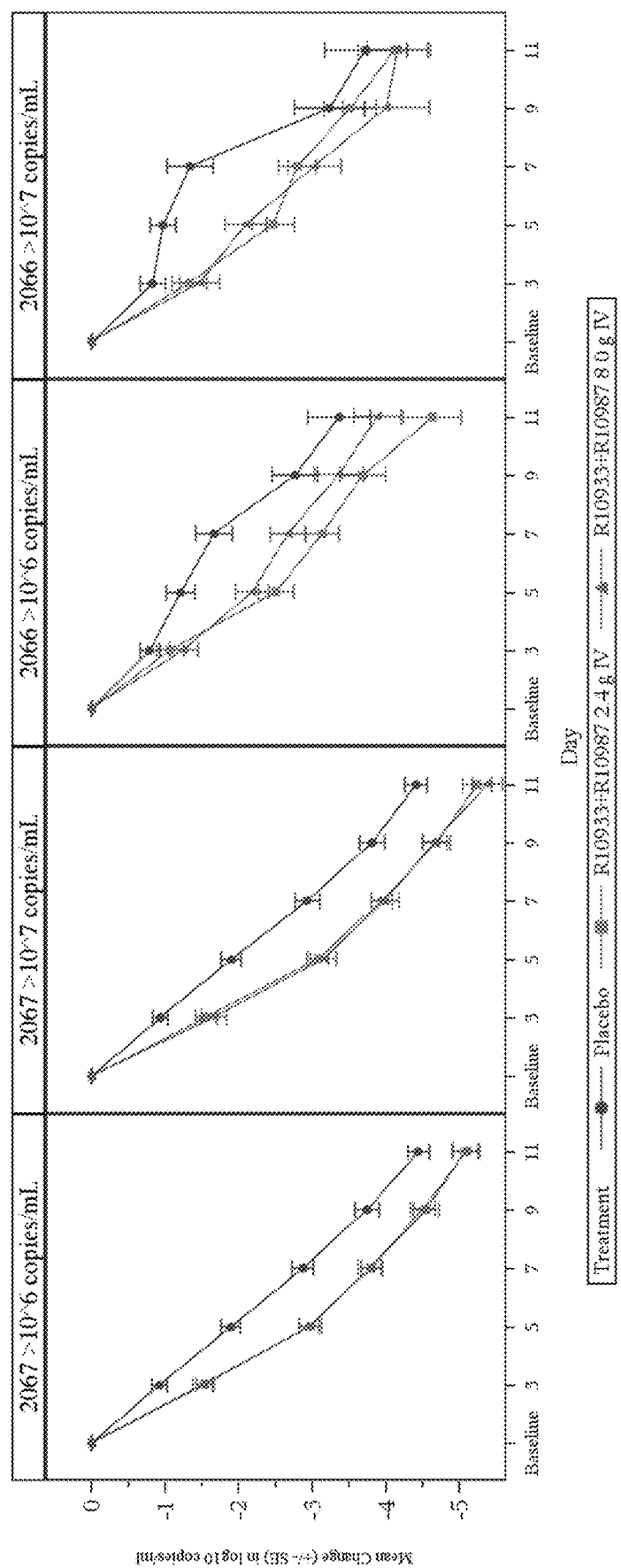

FIG. 28 illustrates change in mean viral load from baseline in patients treated intravenously with placebo (circles), 1.2 g mAb10933+1.2 mAb10987 (2.4 g total; squares), or 4 g mAb10933+4 mAb10987 (8 g total; triangles). Graphs divide patients by baseline viral load and clinical trial: 2066 (hospitalized study; Example 1) and 2067 (ambulatory/outpatient study; Example 2).

Figure 29:
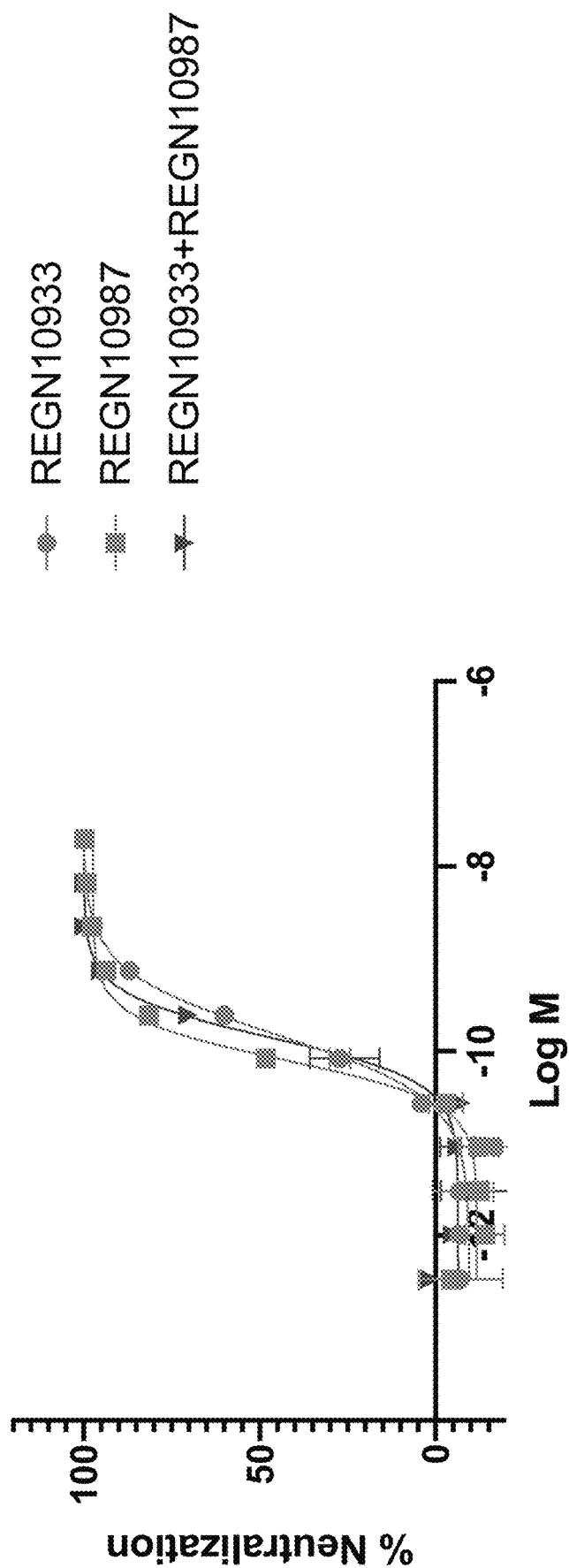

FIG. 29 illustrates % neutralization of a pseudotyped VSV expressing the B.1.1.7 SARS-CoV-2 variant (also called the "UK variant") by mAb10933 (REGN10933) alone, mAb10987 (REGN10987) alone, and the combination of mAb10933+mAb10987 (REGN10933+REGN10987). The antibodies both alone and in combination neutralize the virus.

Figure 30:
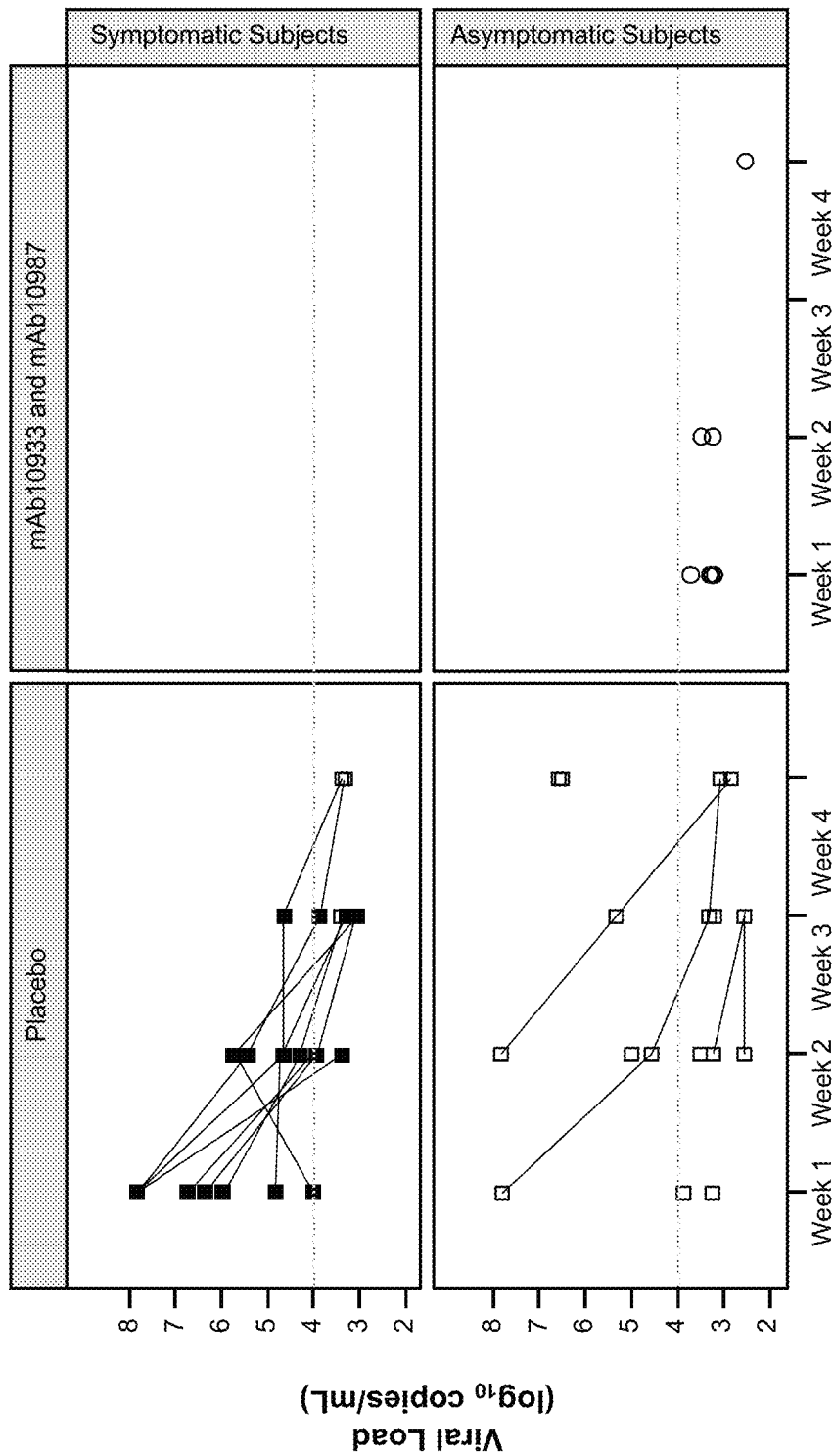

FIG. 30 illustrates the weekly viral load for individual symptomatic subjects (filled symbol) and asymptomatic subjects (open symbol) in the two treatment groups, placebo and mAb10933+mAb10987 (also collectively called REGEN-COV™). Infections in the REGEN-COV™ group lasted no more than 1 week, while approximately 40% of infections in the placebo group lasted 3-4 weeks, as assessed by measuring viral load.

Figure 31:
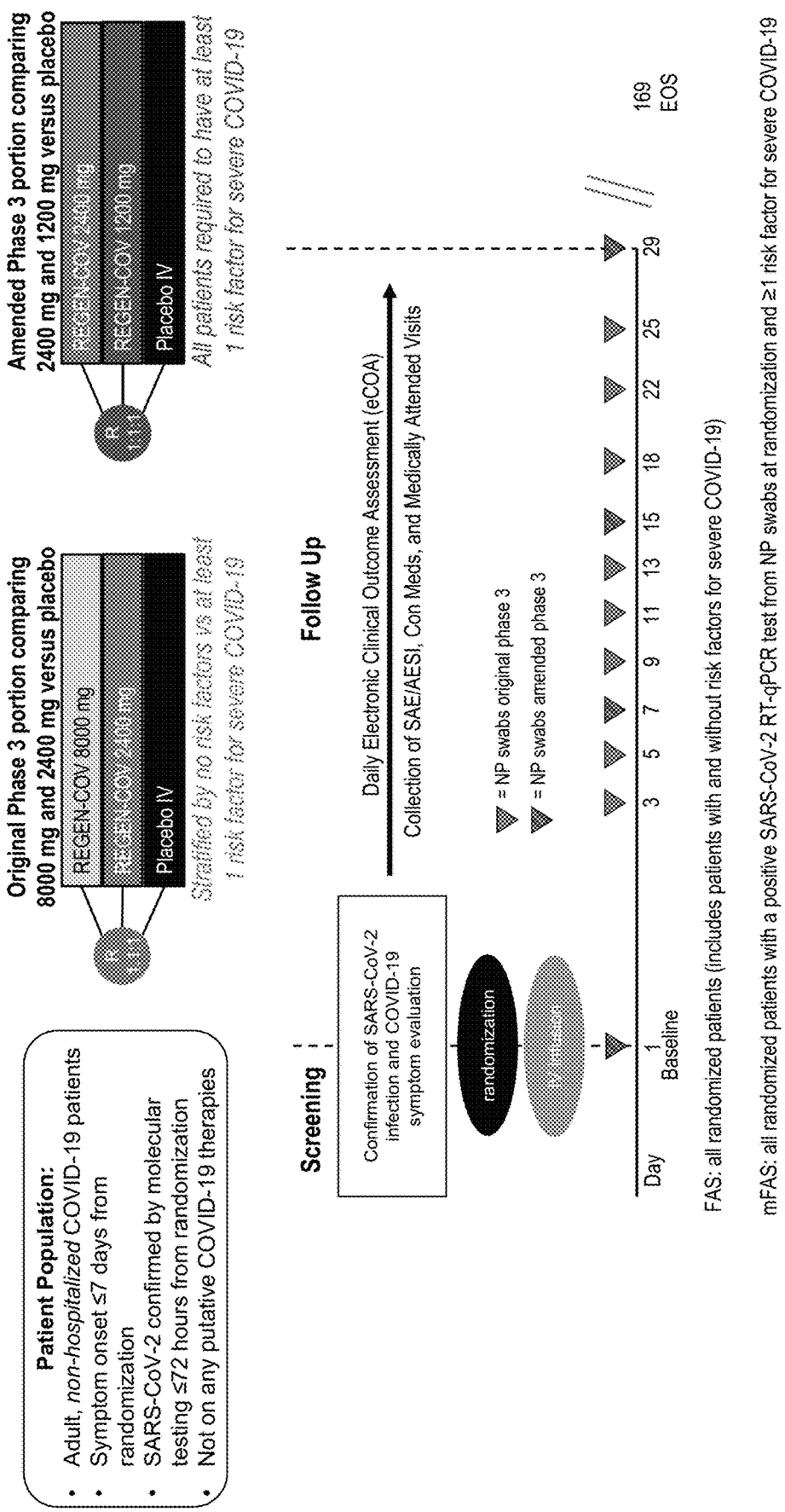

FIG. 31 illustrates the phase 3 study schematic for non-hospitalized patients treated with REGEN-COV or placebo.

Figure 32:
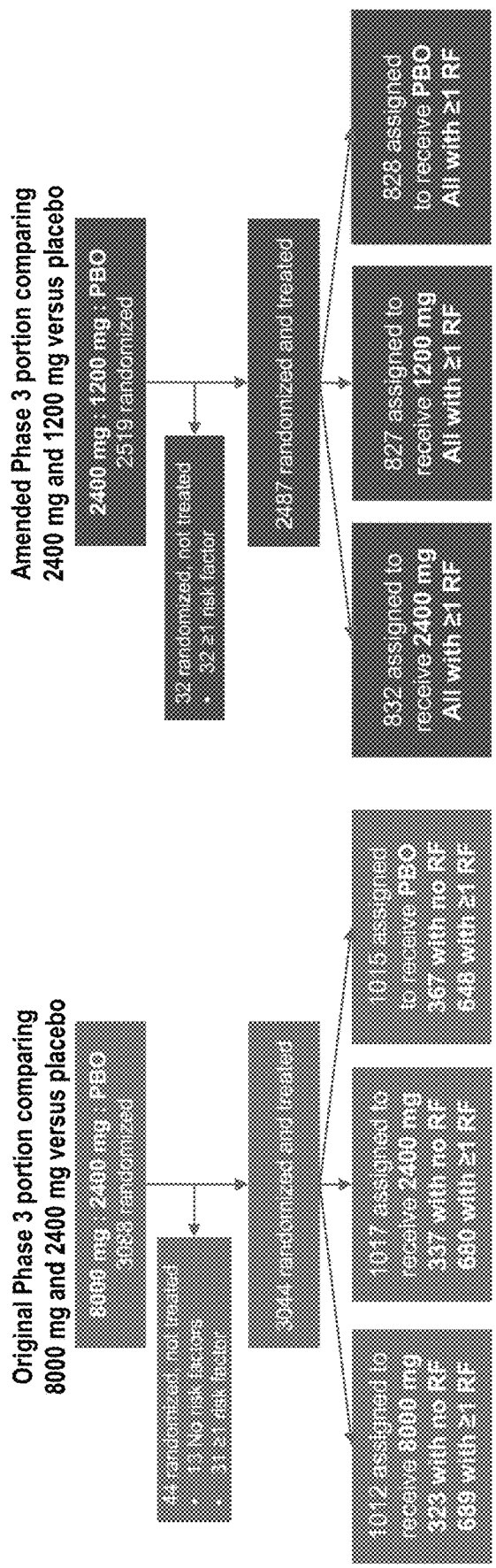

FIG. 32 illustrates an amendment to the phase 3 cohort enrollment, modifying the trial to include 2400 mg and 1200 mg doses.

FIG. 33 illustrates the clinical efficacy of REGEN-COV, comparing treatment effects in placebo, 2400 mg, and 1200 mg intravenous treatment groups. Treatment significantly reduced COVID-19-related hospitalization or all-cause death and duration of symptoms, and there was a similar treatment effect in the two dose levels (higher confidence in point estimates for 2400 mg dose due to larger event size).

FIG. 34 illustrates balanced baseline demographics in the phase 3 cohort 1 mFAS (patients 18 years who are SARS-CoV-2 PCR-positive at baseline and have ≥1 risk factor for severe covid-19) for outpatients treated with 8000 mg REGEN-COV, 2400 mg REGEN-COV, 1200 mg REGEN-COV, or placebo (PBO). Phase 3 patients had higher baseline viral load and higher baseline seronegativity than high-risk patients in phase 1/2.

Figure 35:
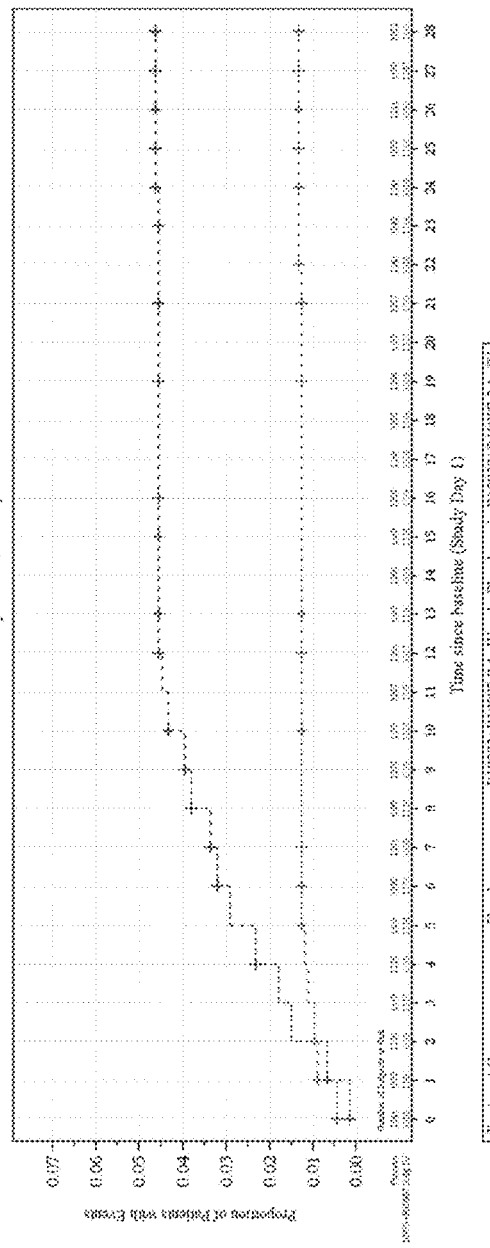

FIG. 35 illustrates a Kaplan-Meier curve for time to COVID-19 related hospitalization or all-cause death through day 29 post-administration of 1200 mg mAb10933+_1200 mg mAb10987 (intravenously) in subjects with ≥1 risk factor for severe COVID-19. The risk for COVID-19 hospitalization or all-cause death was reduced by 71% in the overall modified full analysis set (mFAS) population compared to placebo.

Figure 36:
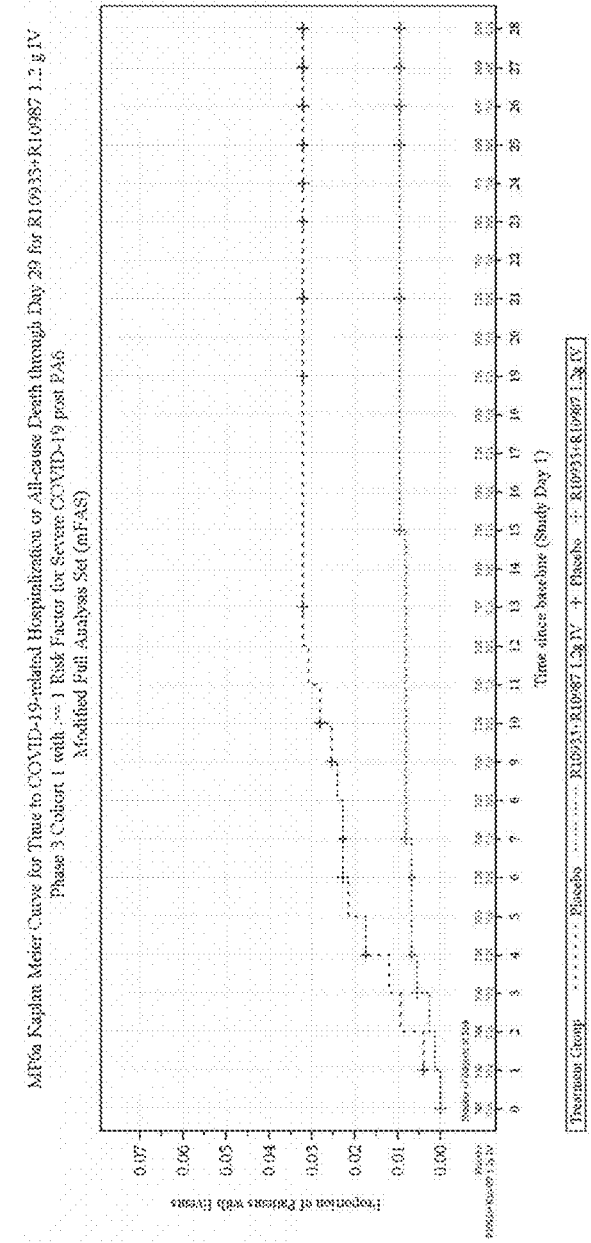

FIG. 36 illustrates a Kaplan-Meier curve for time to COVID-19 related hospitalization or all-cause death through day 29 post-administration of 600 mg mAb10933+_600 mg mAb10987 (intravenously) in subjects with ≥1 risk factor for severe COVID-19. The risk for COVID-19 hospitalization or all-cause death was reduced by 71% in the overall modified full analysis set (mFAS) population compared to placebo.

Figure 37:
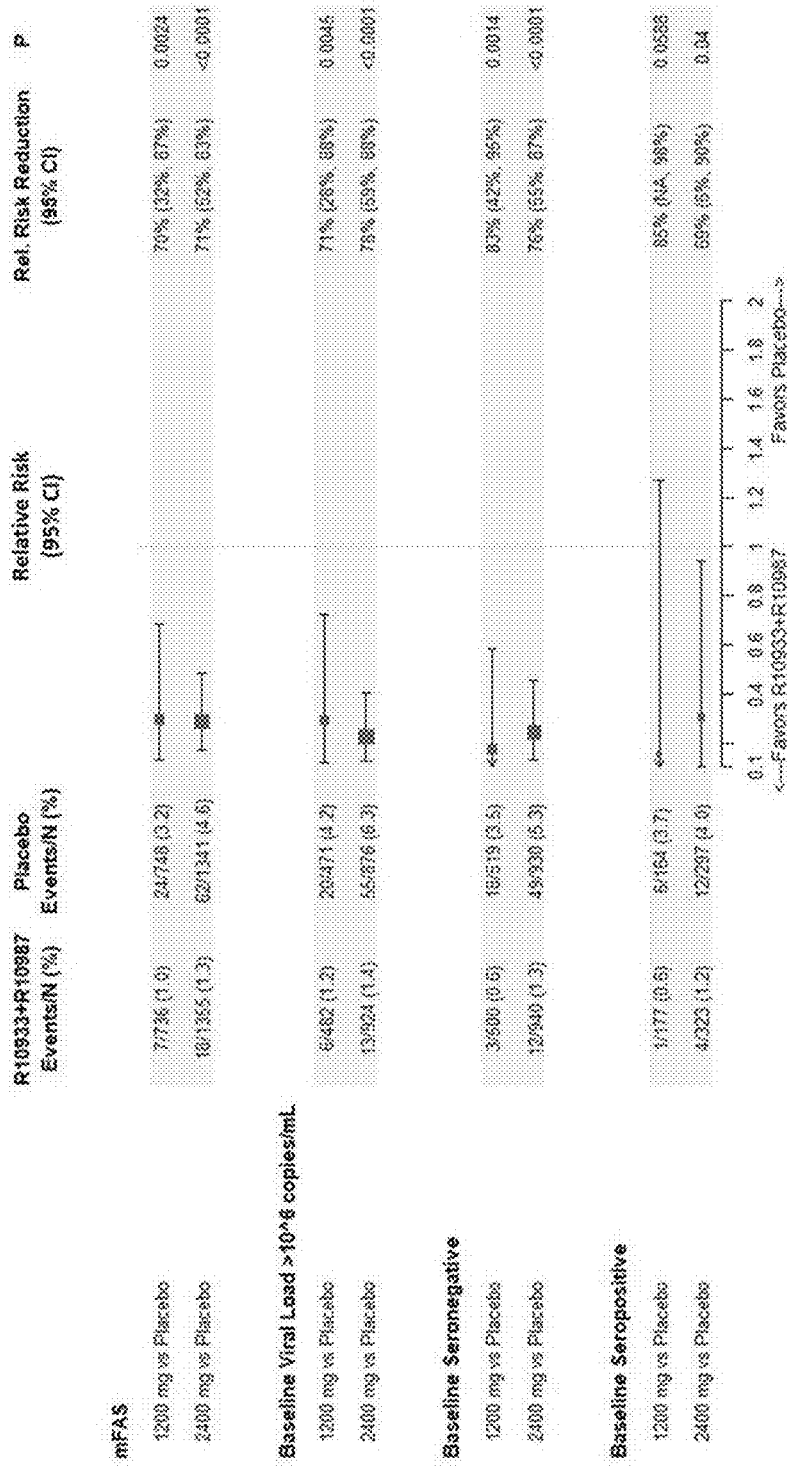

FIG. 37 illustrates the number of COVID-19 related hospitalization or all-cause death through day 29 post-administration of 1200 mg mAb10933+_1200 mg mAb10987 (intravenously) or 600 mg mAb10933+_600 mg mAb10987 (intravenously) in subjects with ≥1 risk factor for severe COVID-19. Results were consistent between the two treatment groups.

Figure 38:
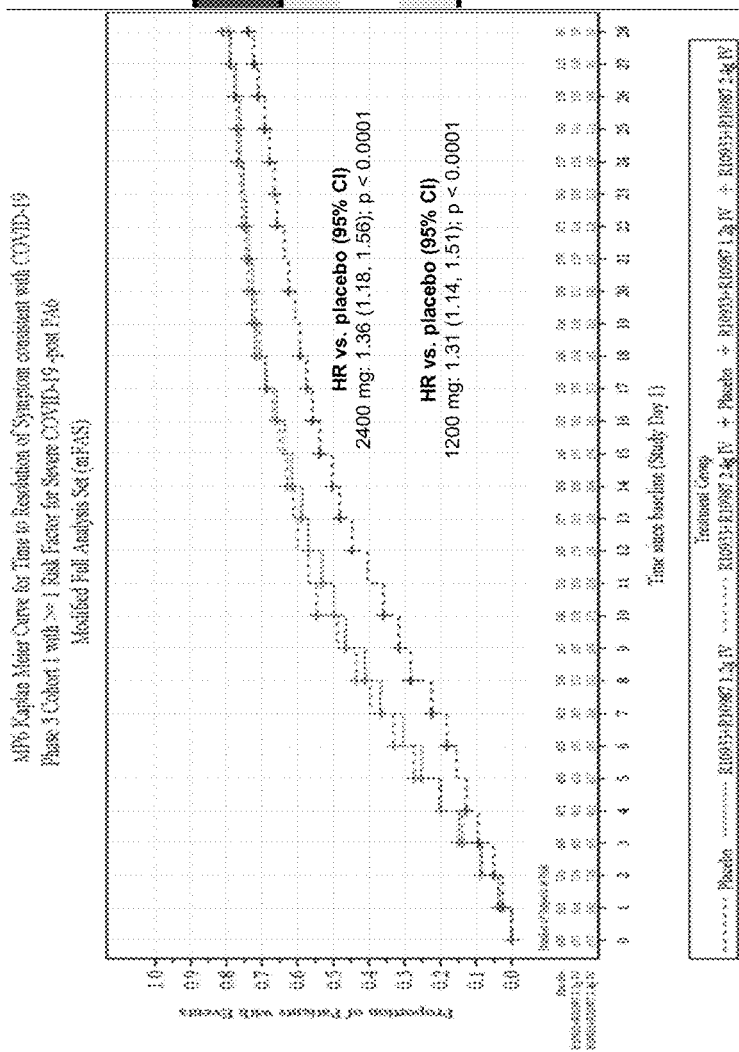

FIG. 38 illustrates a Kaplan-Meier curve for time to resolution of symptoms consistent with COVID-19 among patients with ≥1 risk factor for severe COVID-19. HR: hazard ratio. Median time to symptom resolution was 14 days in the placebo group and 10 days in each of the 1.2 g and 2.4 g treatment groups.

Figure 39:
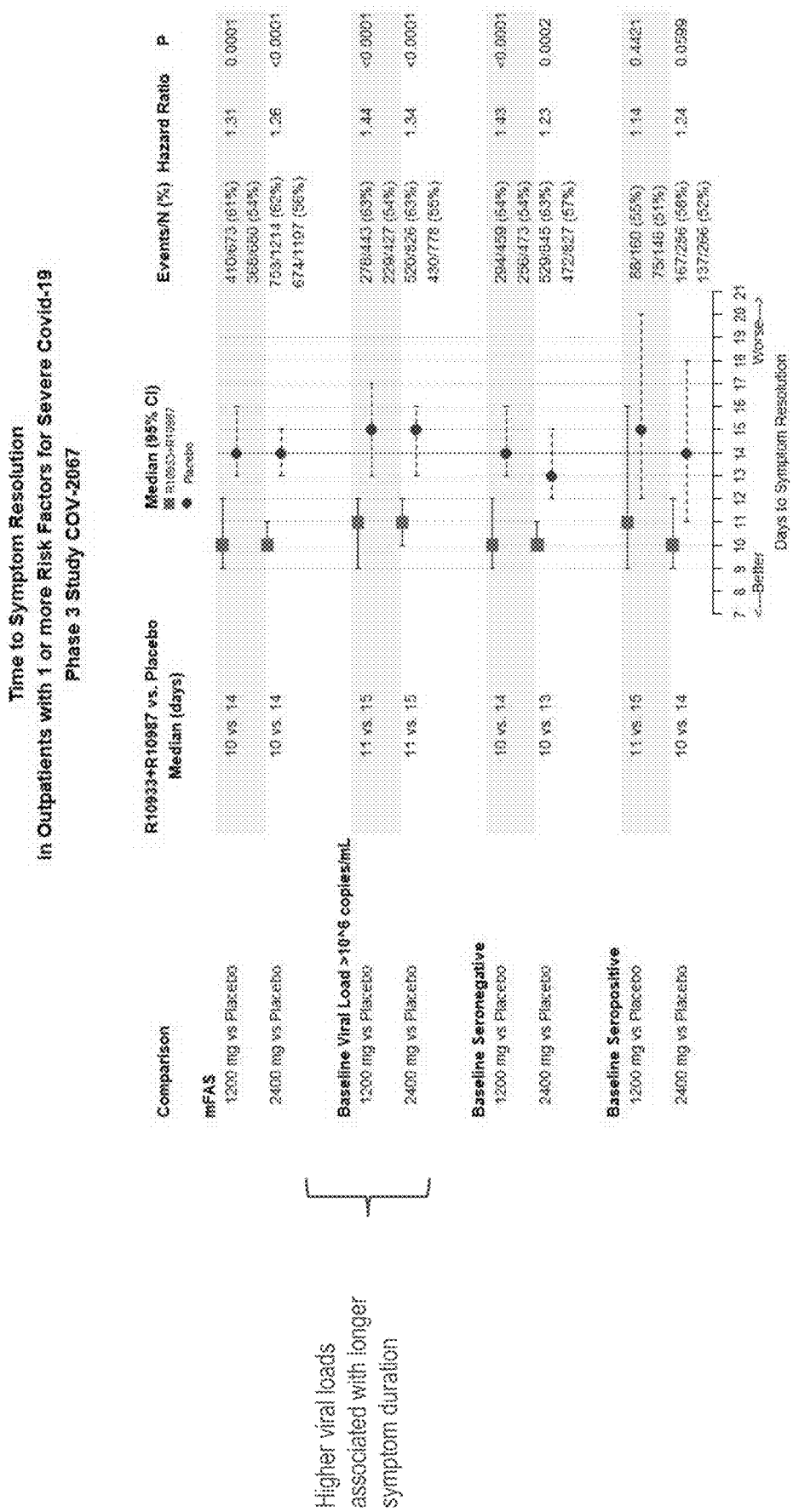

FIG. 39 illustrates time to symptom resolution in outpatients with ≥1 risk factor for severe COVID-19. Symptom resolution improvement was consistent between the modified full analysis set (mFAS) population and those with high viral load or seronegativity at baseline.

FIG. 40 illustrates serious adverse events (SAEs) and adverse events of special interest (SAEIs) in Phase 3 cohort 1 outpatients treated intravenously with 1200 mg REGEN-COV, 2400 mg REGEN-COV, 8000 mg REGEN-COV, or placebo (PBO). Safety among all treatment arms was acceptable and no serious safety concerns were identified. In particular, SAEs and AESIs occurred more frequently in the placebo group compared to any REGEN-COV treatment group, no imbalance in safety was found between the different REGEN-COV dose groups, no safety signal was observed in safety labs (chemistry, hematology), more patients had treatment-emergent adverse events (TEAEs) with fatal outcome in the placebo group as compared to any REGEN-COV treatment group, and very few patients experienced AESIs of infusion-related reactions (IRRs) and hypersensitivity reactions in REGEN-COV dose groups.

FIG. 41 illustrates serious adverse events (SAEs) in Phase 3 cohort 1 outpatients treated intravenously with 1200 mg REGEN-COV, 2400 mg REGEN-COV, 8000 mg REGEN-COV, or placebo (PBO) that occurred in >1 patient in any treatment group. SAEs occurred more frequently in the placebo group as compared to any REGEN-COV dose groups, the more frequently reported events were consistent with COVID-19 and associated complications, and a lower frequency of events in the REGEN-COV dose groups was consistent with treatment benefit.

FIG. 42 illustrates adverse events of special interest (AESIs) (e.g., infusion-related reactions or hypersensitivity reactions) in Phase 3 cohort 1 outpatients treated intravenously with 1200 mg REGEN-COV, 2400 mg REGEN-COV, 8000 mg REGEN-COV, or placebo (PBO) that occurred in >1 patient in any treatment group. There were low rates of infusion-related reactions or hypersensitivity reactions across all dose groups.

Figure 43:
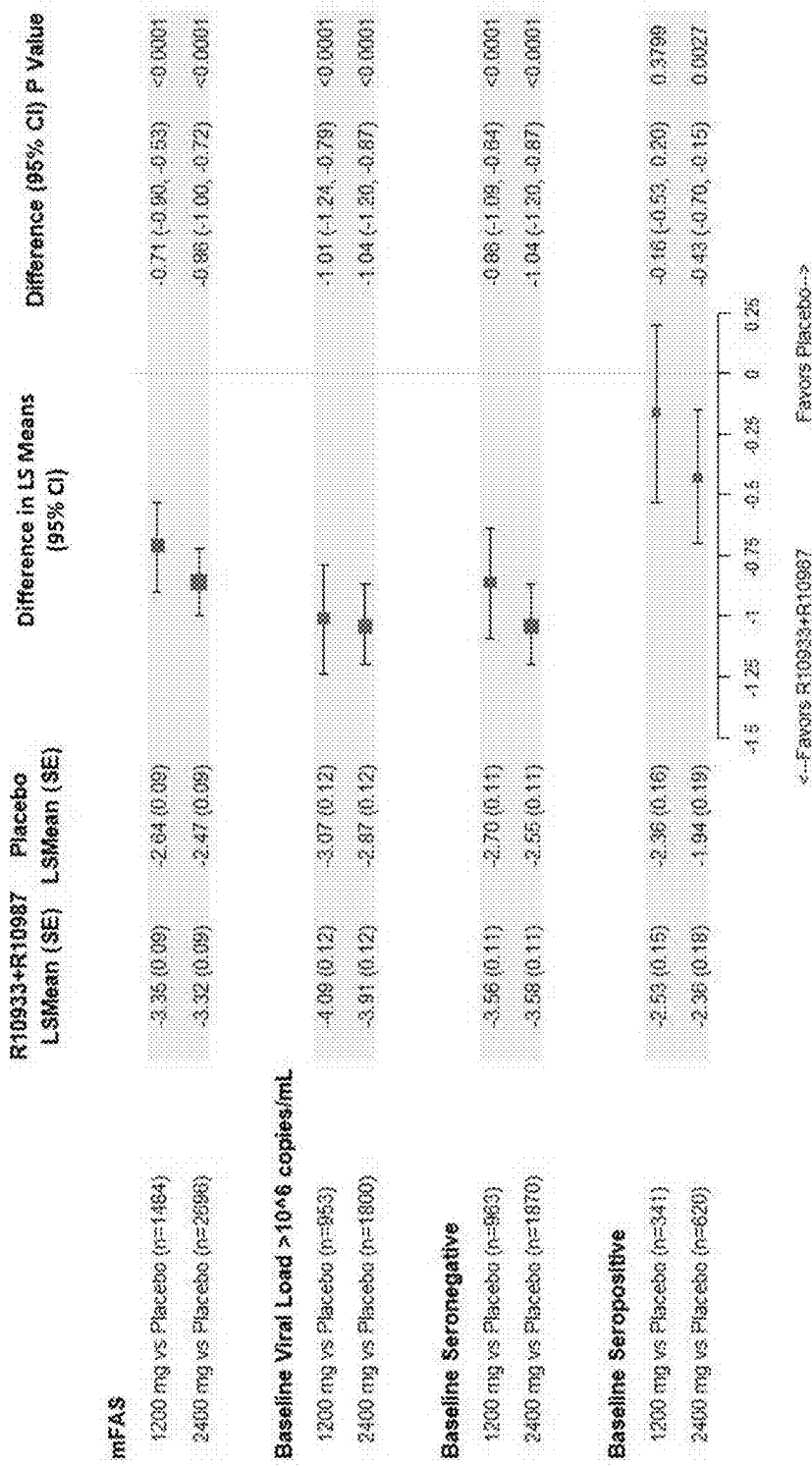

FIG. 43 illustrates the change from baseline in viral load (log 10 copies/mL) at Day 7 post-treatment with mAb10933 and mAb10987 in outpatients with 1 or more risk factors for severe COVID-19.

FIG. 44 illustrates the change from baseline in viral load (log 10 copies/mL) at Day 7 post-treatment with mAb10933 and mAb10987 in outpatients with 1 or more risk factors for severe COVID-19. N: number of subjects; SD: standard deviation; D7: day 7; mFAS: modified full analysis set; PA6: protocol amendment 6, which modified the clinical trial protocol to remove the 8 g dose and introduce the 1.2 g dose.

FIG. 45 illustrates the demographics and baseline characteristics for seronegative IV patients (seronegative mFAS). The groups were well balanced.

FIG. 46 illustrates the demographics and baseline characteristics for seronegative subcutaneous patients (seronegative mFAS). The groups were well balanced.

Figure 47:
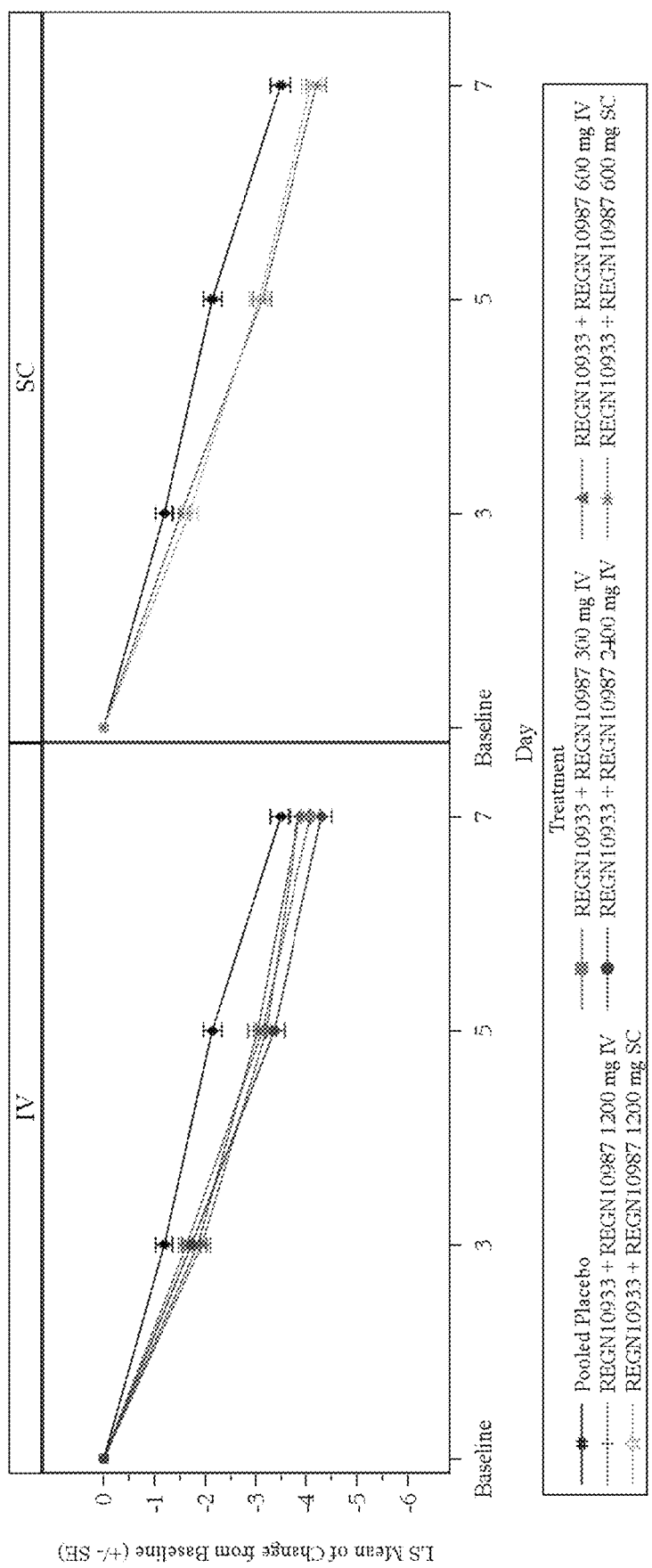

FIG. 47 illustrates the least squares mean of change from baseline viral load in patients treated with mAb10933+ mAb10987 either intravenously (IV) or subcutaneously (SC), over time.

Figure 48:
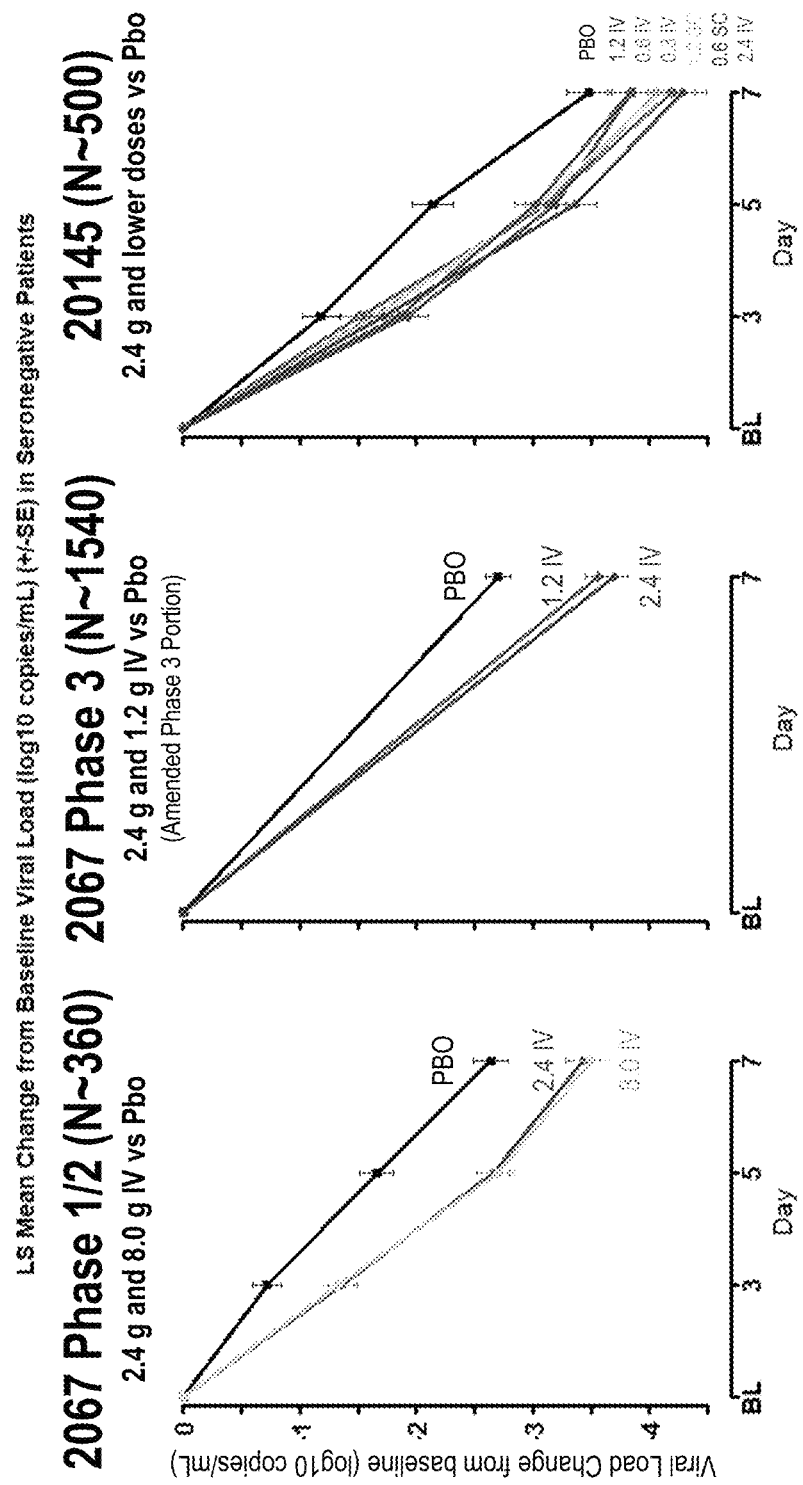

FIG. 48 illustrates the change from baseline viral load in the 2067 (Example 2; outpatient) phase 1/2 and phase 3 trials, and the 20145 (Example 7; dose range-finding) trial among seronegative patients. The change from baseline viral load was comparable between the studies.

FIG. 49 illustrates safety data for the clinical trial described in Example 7. All treatment groups were well tolerated, with no safety signal identified.

FIG. 50 illustrates the treatment emergent adverse events among the patients treated subcutaneously in the clinical trial described in Example 7. All doses were well tolerated with few treatment emergent adverse events. Among those events observed, the events were not serious.

FIG. 51 illustrates a comparison between the clinical trial described in Example 2 ("2067 analysis set") and the clinical trial described in Example 7 ("20145 analysis set"). 2067 data is presented both before and after the amendment that changed the dosage groups from 2400 mg and 8000 mg to 1200 mg and 2400 mg (original Ph3 and amended Ph3, respectively). The analysis of change from baseline to day 7 in viral load (log 10 copies/mL) showed similar viral load reduction before and after amendment change and across all doses.

Figure 52:
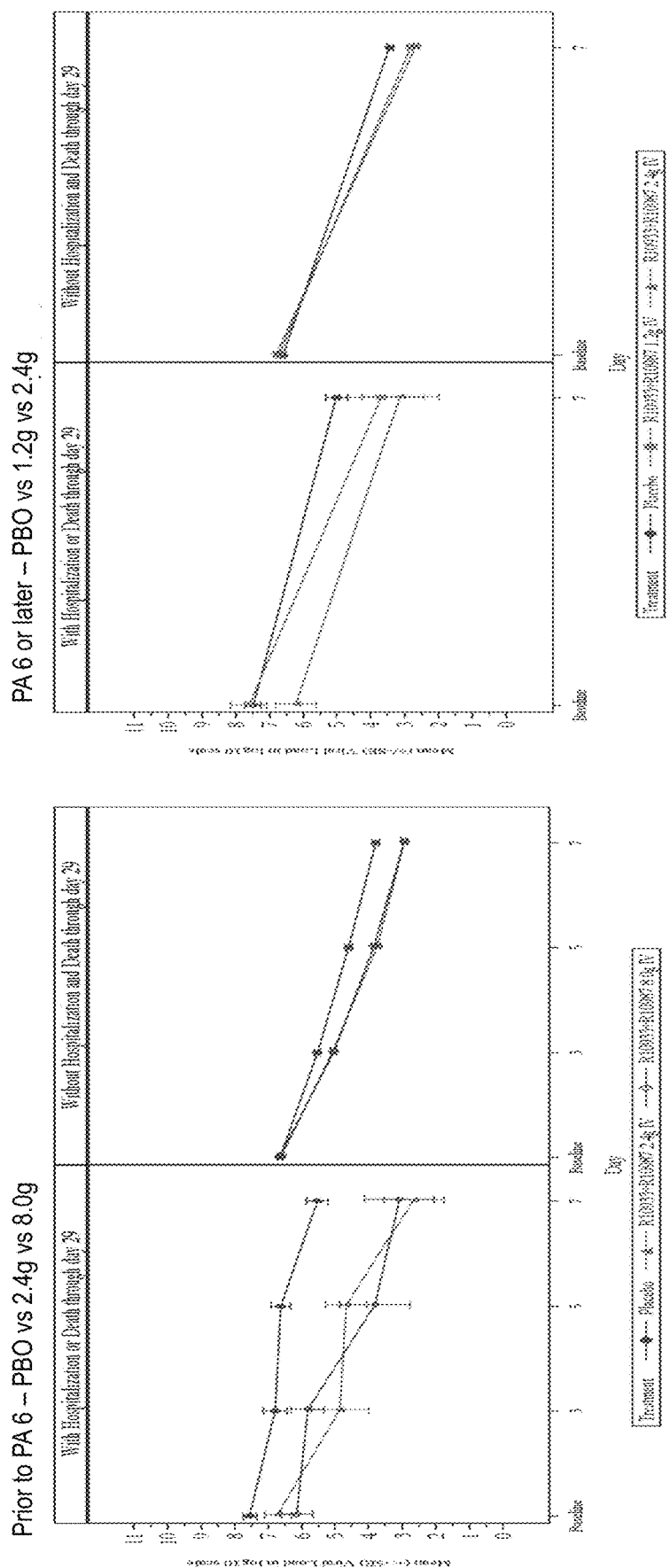

FIG. 52 illustrates the mean viral load for patients with outcomes of hospitalization/death and without outcomes of hospitalization/death. Prior to PA 6 shows viral load in patients treated with placebo (PBO), 2.4 g of REGEN-COV, or 8.0 g of REGEN-COV. PA 6 or later shows viral load in patients treated with PBO, 1.2 g of REGEN-COV, or 2.4 g of REGEN-COV.

Figure 53:
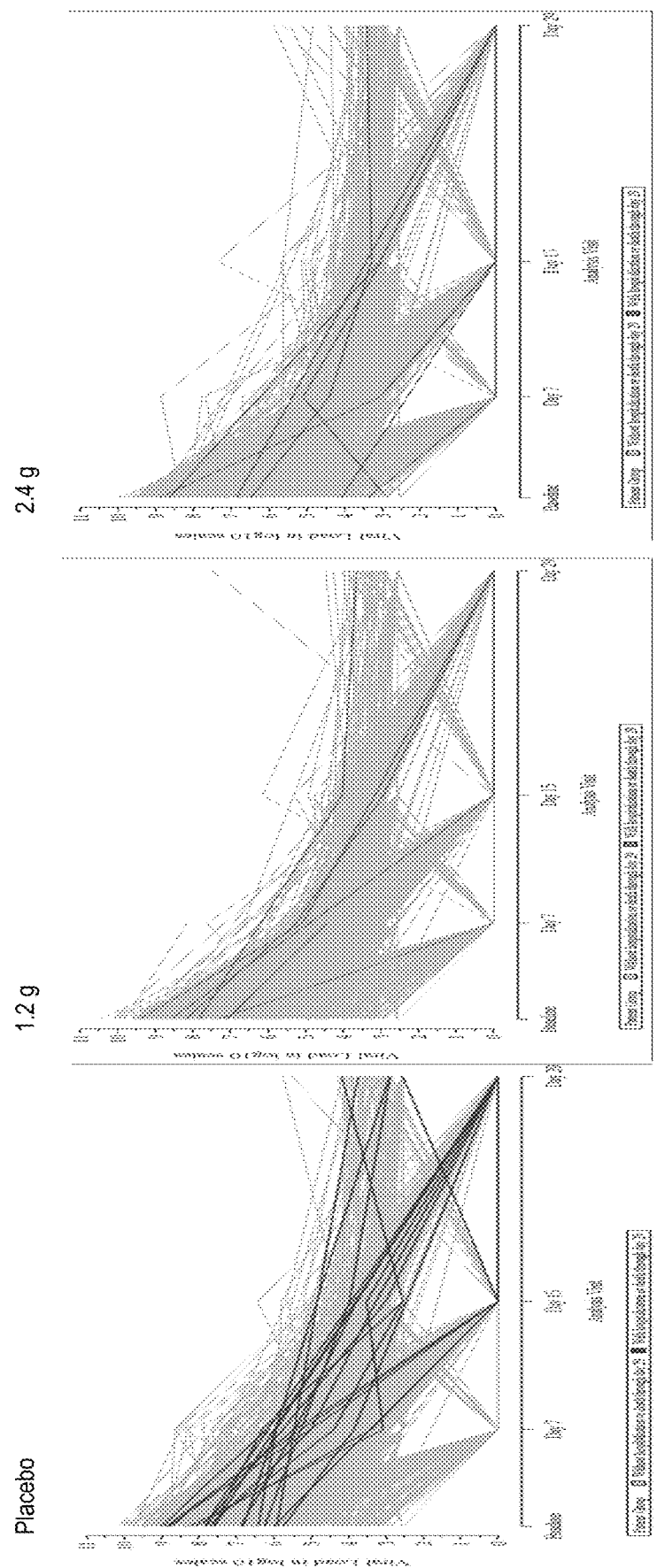

FIG. 53 illustrates spaghetti plots of viral load for individual patients with outcomes of hospitalization/death and without outcomes of hospitalization/death (placebo, 1.2 g REGEN-COV, and 2.4 g REGEN-COV).

Figure 54:
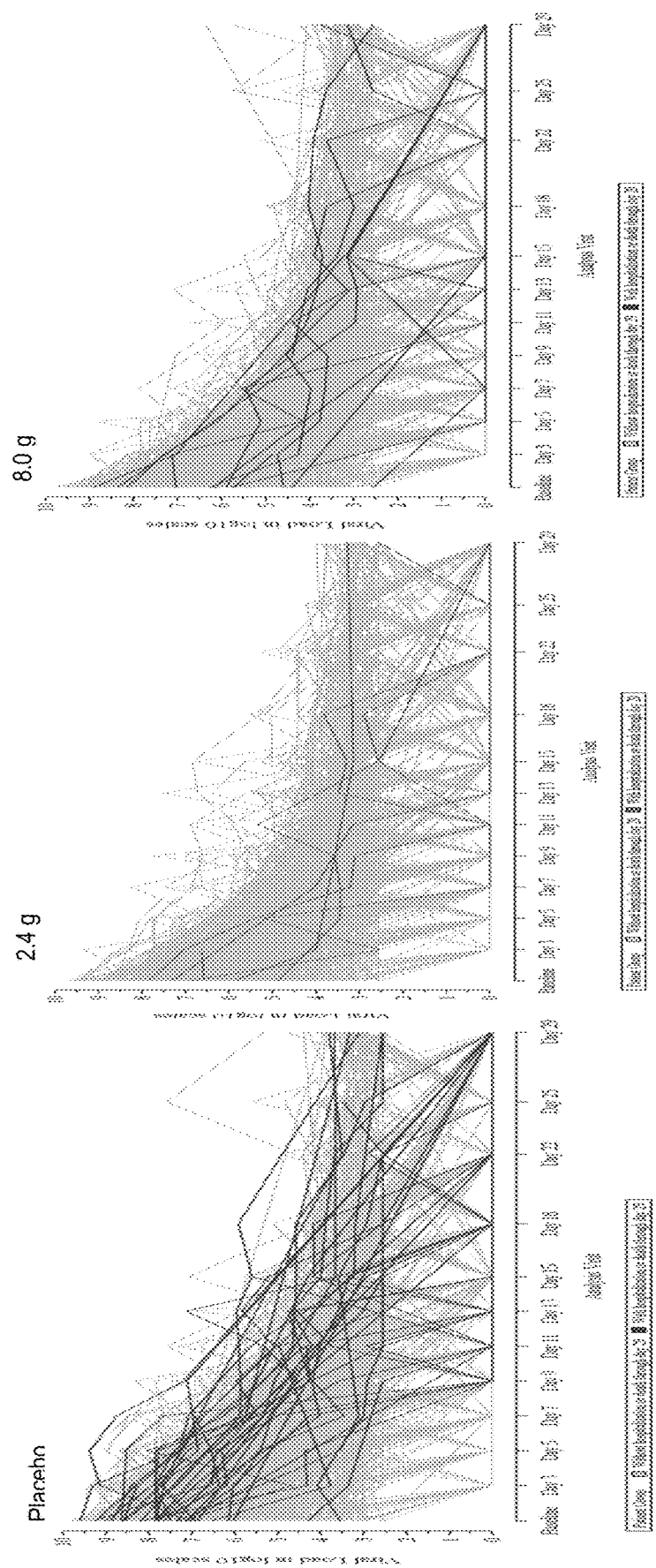

FIG. 54 illustrates spaghetti plots of viral load for individual patients with outcomes of hospitalization/death and without outcomes of hospitalization/death (placebo, 2.4 g REGEN-COV, and 8.0 g REGEN-COV).

Figure 55:
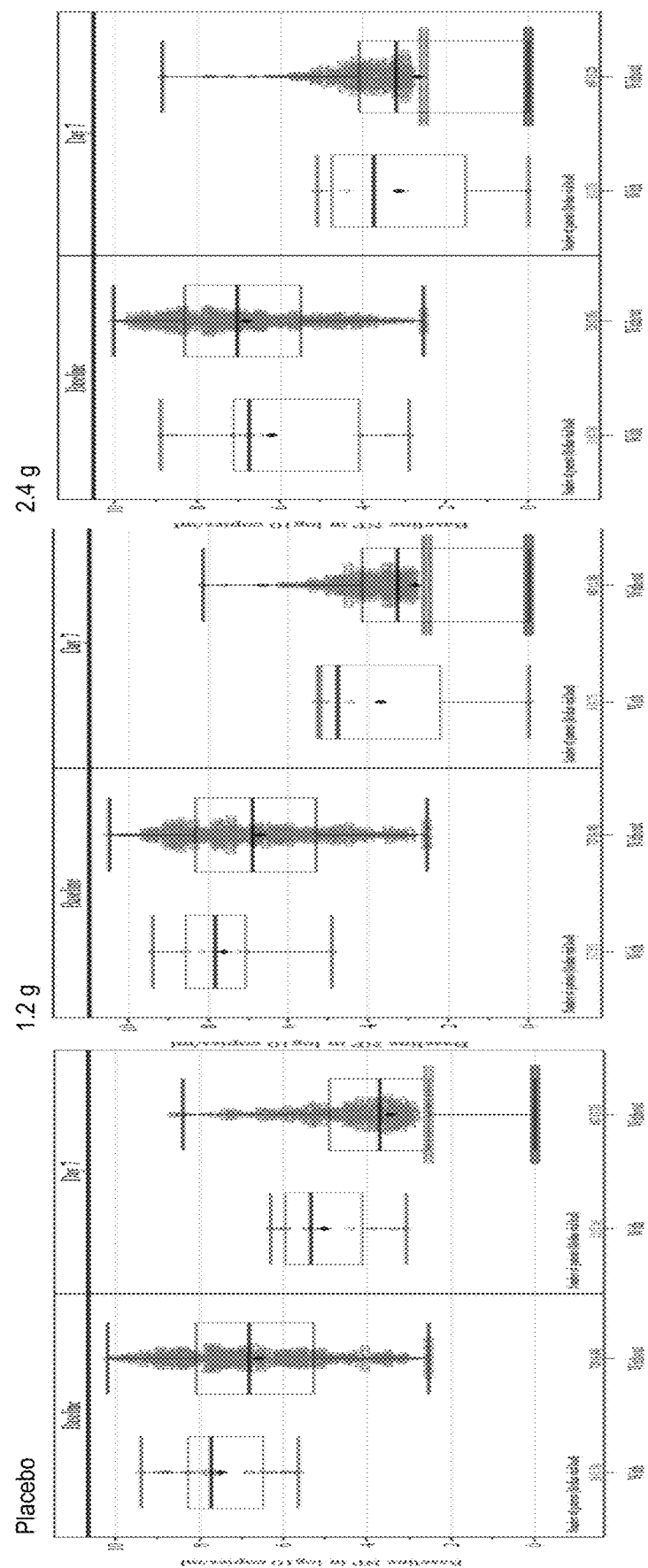

FIG. 55 illustrates boxplots of viral load at baseline and Day 7 post-treatment for patients with outcomes of hospitalization/death and without outcomes of hospitalization/death (placebo, 1.2 g REGEN-COV, and 2.4 g REGEN-COV).

Figure 56:
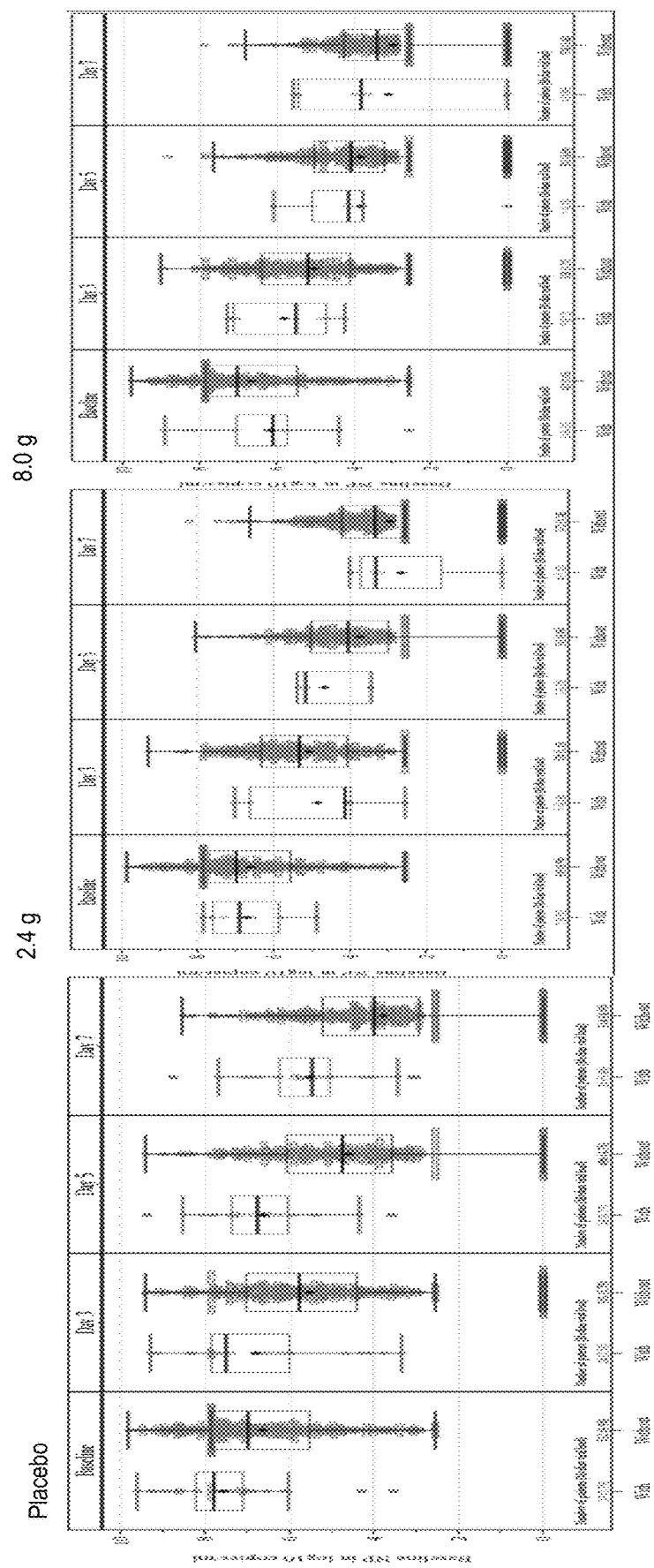

FIG. 56 illustrates boxplots of viral load at baseline and Day 7 post-treatment for patients with outcomes of hospitalization/death and without outcomes of hospitalization/death (placebo, 2.4 g REGEN-COV, and 8.0 g REGEN-COV).

Figure 57:
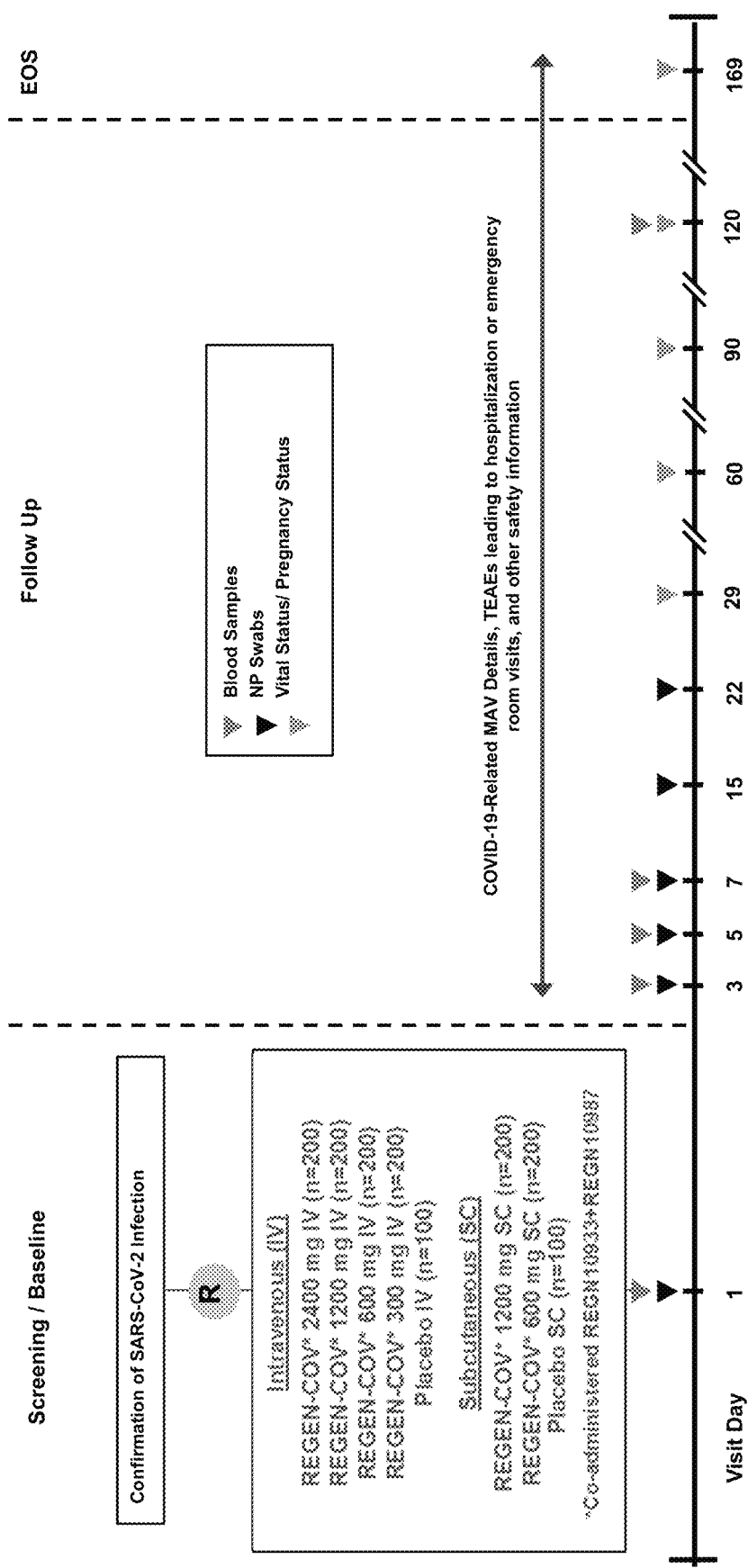

FIG. 57 illustrates an overview of the clinical trial described in Example 7.

FIG. 58 illustrates change in Day 7 post-treatment viral load in all patients, seronegative patients, and seropositive patients, divided between patients with and without COVID-19 related events. Patients on placebo with an event had higher baseline virus and cleared the virus more slowly, while seropositive patients who had events had similarly high baseline viral levels and delayed clearance, indicating that they may have had an ineffective antibody response.

FIG. 59 illustrates the hierarchy for hypothesis testing in the Phase 3 prevention trial described in Example 4, and the treatment effect for each endpoint. REGEN-COV significantly prevented infection, modified disease progression, and reduced viral burden.

FIG. 60 illustrates the symptomatic infection endpoints in the Phase 3 prevention trial described in Example 4. REGEN-COV significantly reduced symptomatic COVID-19 by all three definitions.

Figure 61:
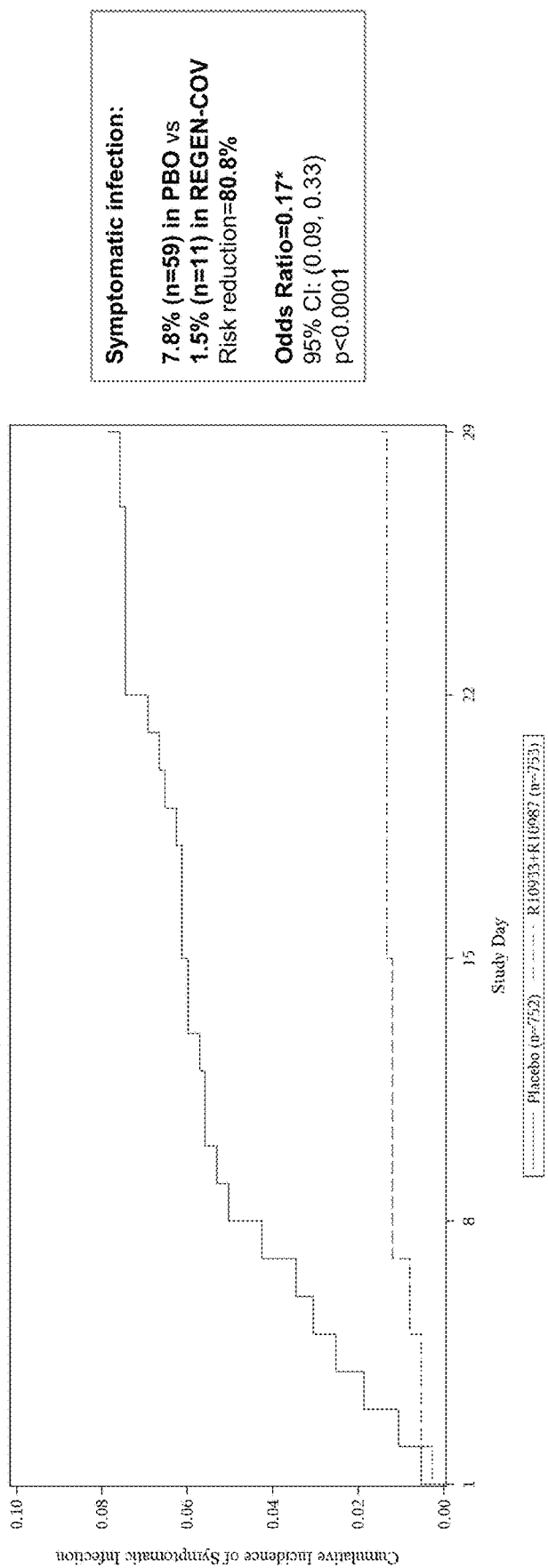

FIG. 61 illustrates the cumulative incidence of symptomatic infection in the Phase 3 prevention trial described in Example 4. REGEN-COV prevented the onset of symptomatic infection starting 1 day after dosing.

Figure 62:
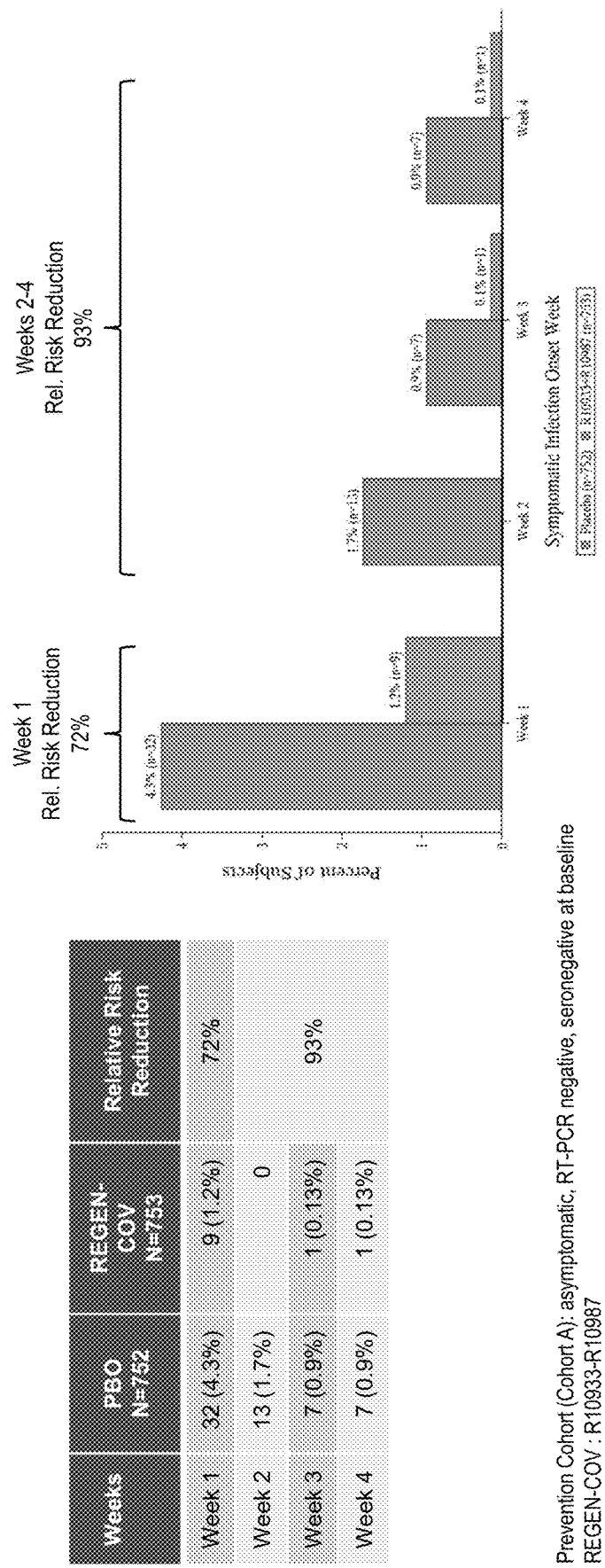

FIG. 62 illustrates the onset of symptomatic infection by week in the Phase 3 prevention trial described in Example 4. REGEN-COV reduced the risk of symptomatic infections by 81% overall, 72% in the first week, and 93% in weeks 2-4.

FIG. 63 illustrates that the number of weeks of symptomatic infection was significantly reduced by REGEN-COV in the Phase 3 prevention trial described in Example 4.

Figure 64:
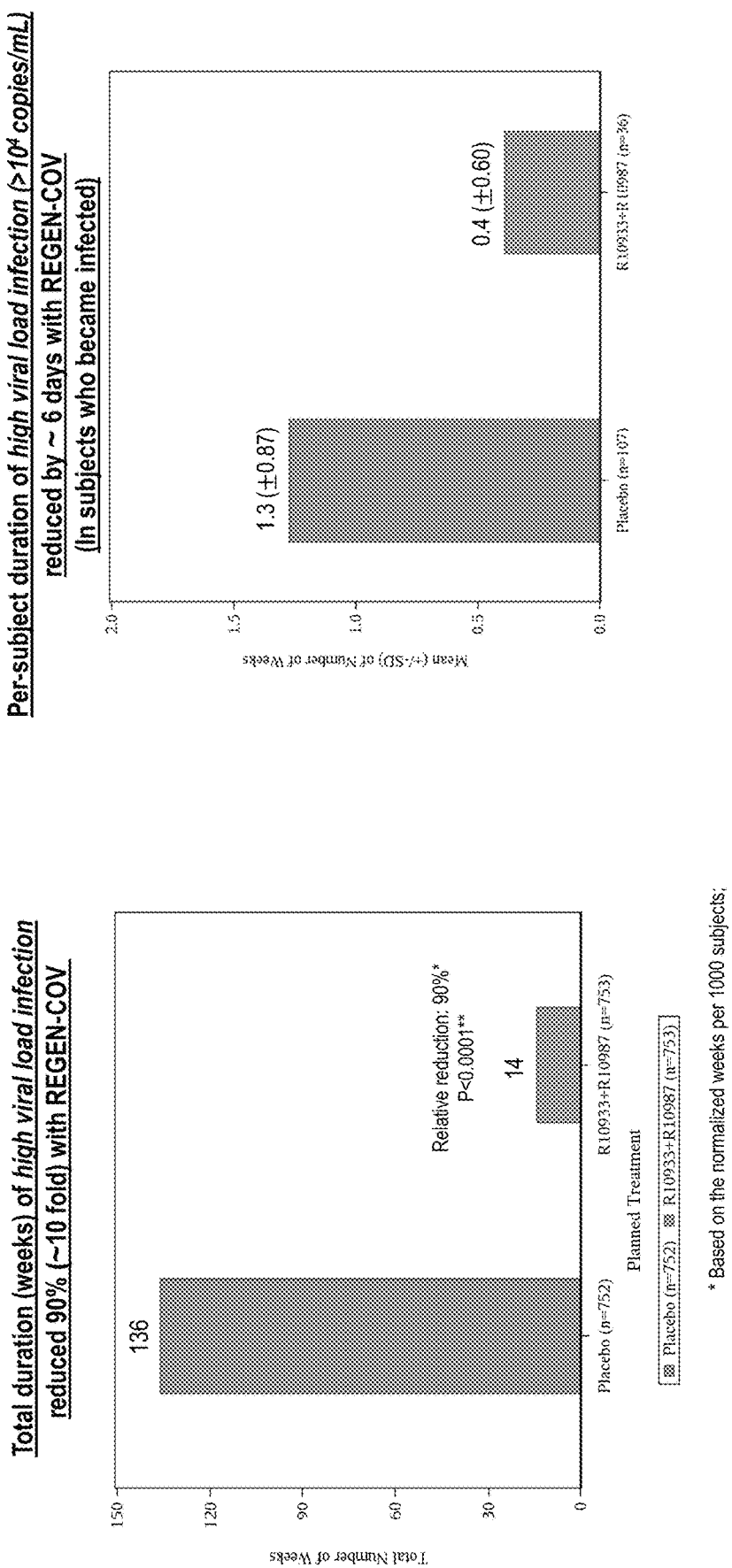

FIG. 64 illustrates that the number of weeks of symptomatic infection was significantly reduced by REGEN-COV in the Phase 3 prevention trial described in Example 4.

Figure 65:
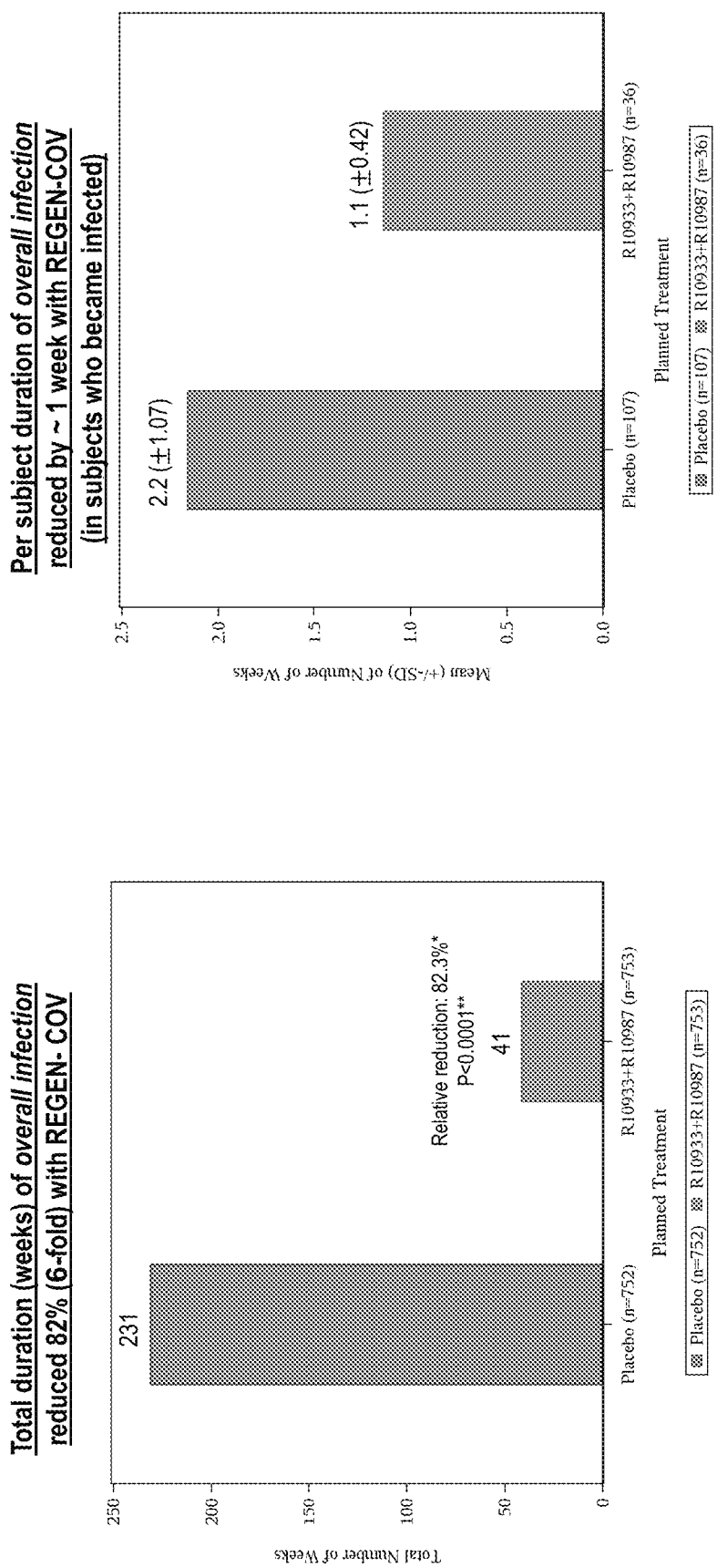

FIG. 65 illustrates that the number of weeks of overall infection was significantly reduced by REGEN-COV in the Phase 3 prevention trial described in Example 4.

FIG. 66 illustrates the hierarchy for hypothesis testing in the Phase 3 pre-emptive therapy trial described in Example 4. REGEN-COV significantly prevented the progression of asymptomatic infection to disease and reduced viral burden. The treatment effect was stronger after the first three days.

Figure 67:
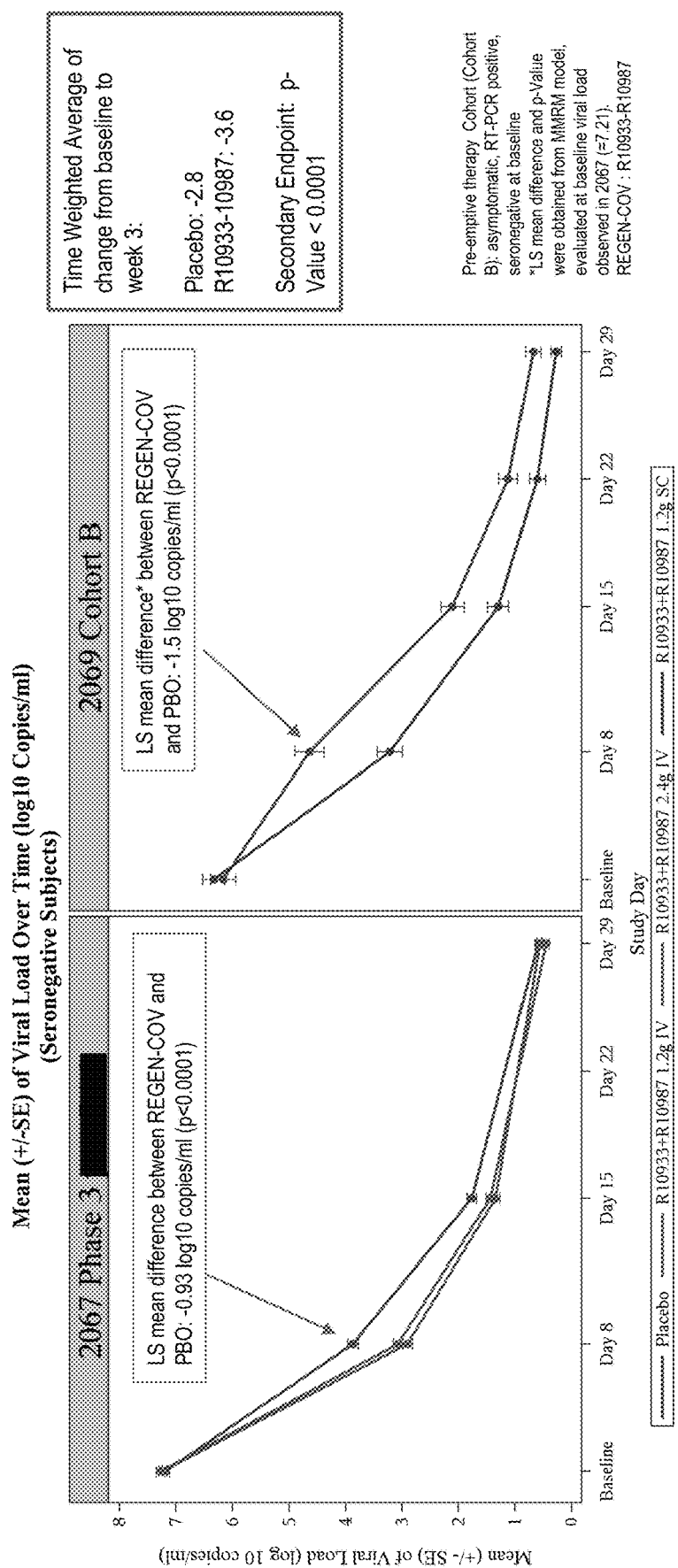

FIG. 67 illustrates the mean of viral load over time in asymptomatic patients in the Phase 3 pre-emptive therapy trial described in Example 4 (2069) as compared to symptomatic patients in the amended phase 3 trial of Example 2 (2067). Early treatment with REGEN-COV provided greater viral load reduction over time.

Figure 68:
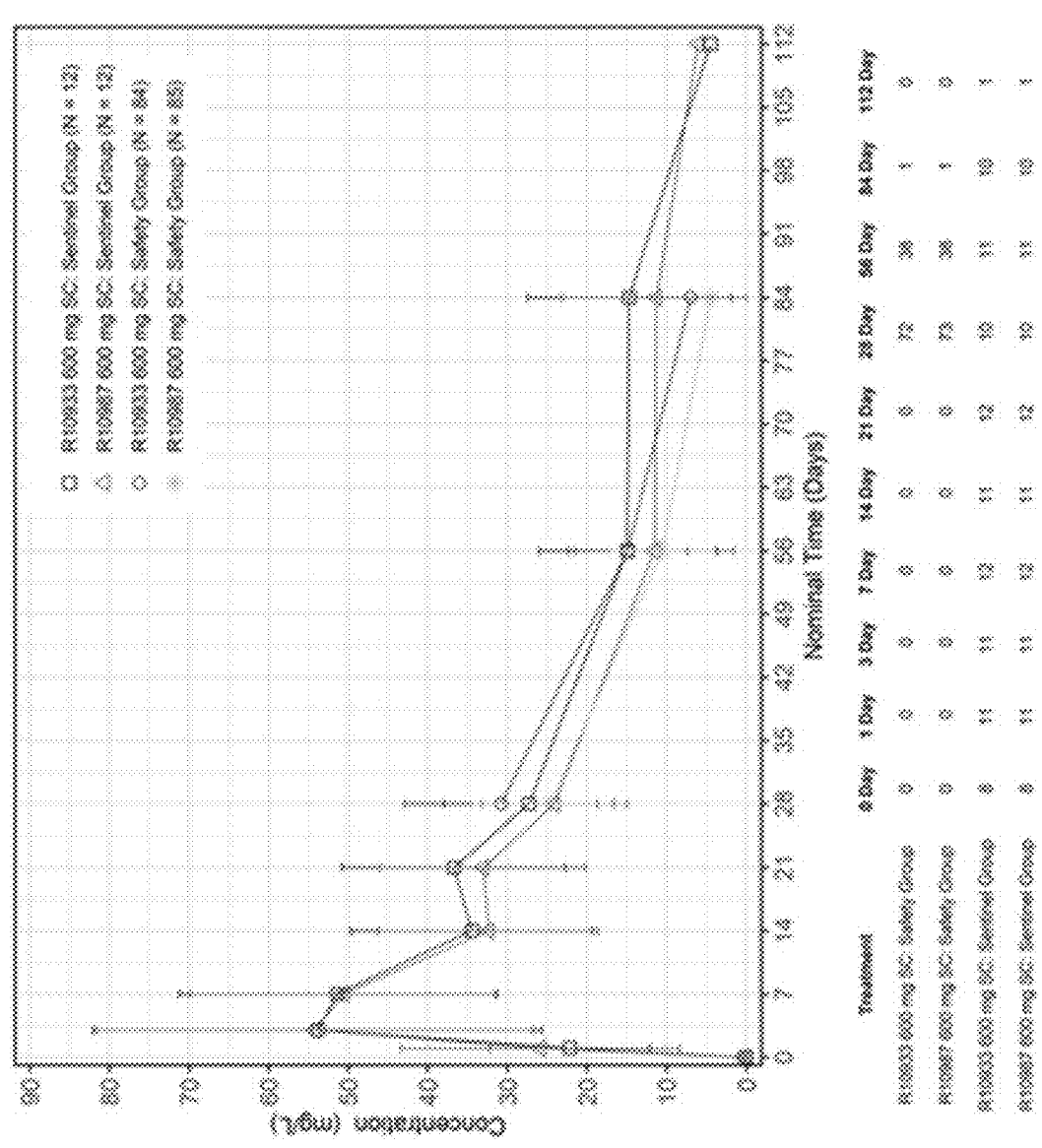

FIG. 68 illustrates the mean concentrations of mAb10933 and mAb10987 in serum over time for sentinel and safety cohorts after a single 1200 mg dose in the Phase 3 pre-emptive therapy trial described in Example 4.

FIG. 69 illustrates that REGEN-COV had an acceptable and well-tolerated safety profile with no serious or severe safety concerns in the Phase 3 trial of Example 4.

FIG. 70 illustrates the treatment emergent adverse events that occurred in ≥2% of any treatment group in the Phase 3 trial of Example 4.

FIG. 71 illustrates that serious adverse events are rare, with no COVID-related serious adverse events in REGEN-COV treated patients.

Figure 72:
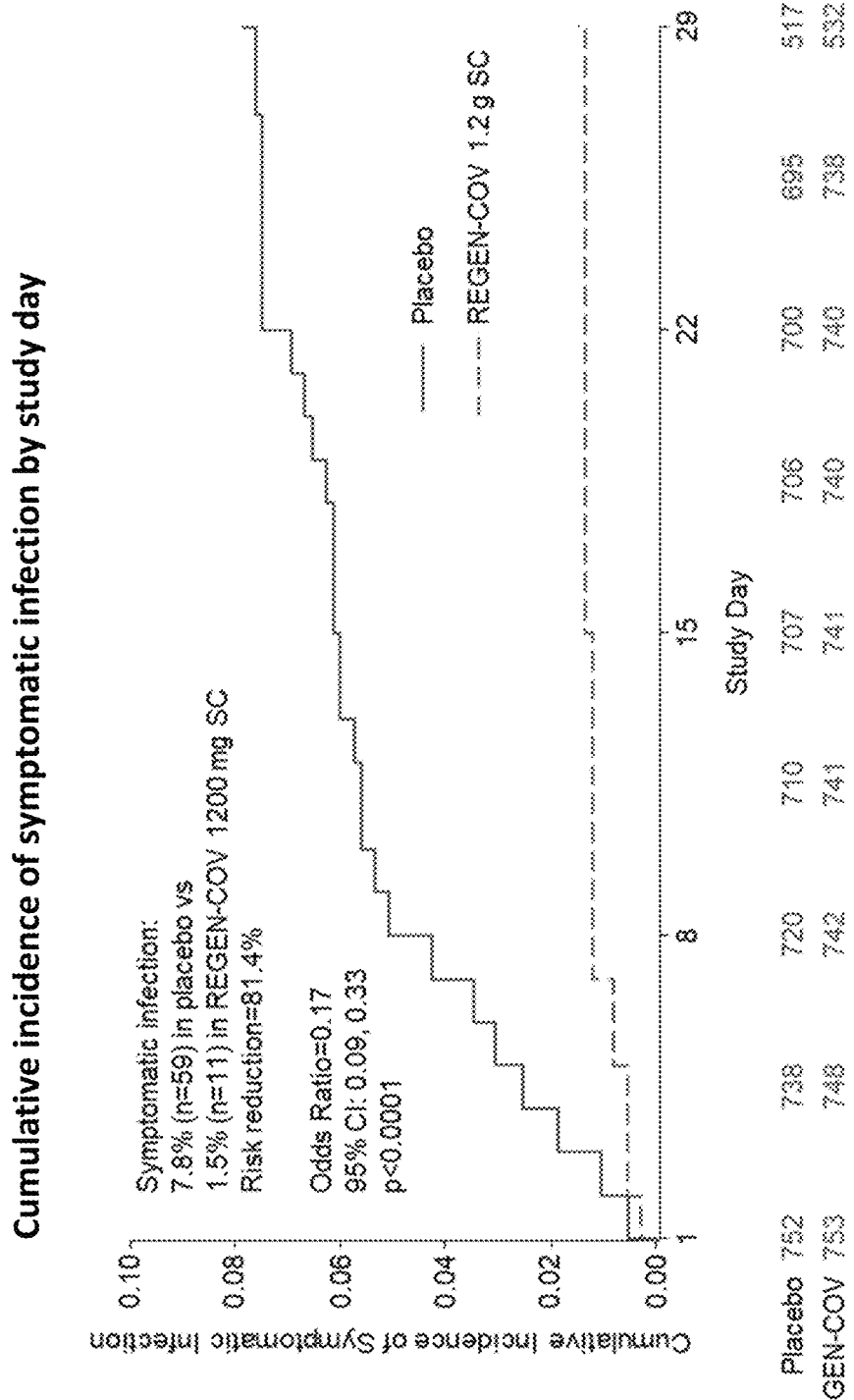

FIG. 72 illustrates the cumulative incidence of symptomatic infection by study day in a clinical trial assessing the ability of REGEN-COV to prevent COVID-19 symptoms. There was an 81.4% reduced risk of symptomatic SARS-CoV-2 infections with subcutaneous administration of REGEN-COV.

Figure 73:
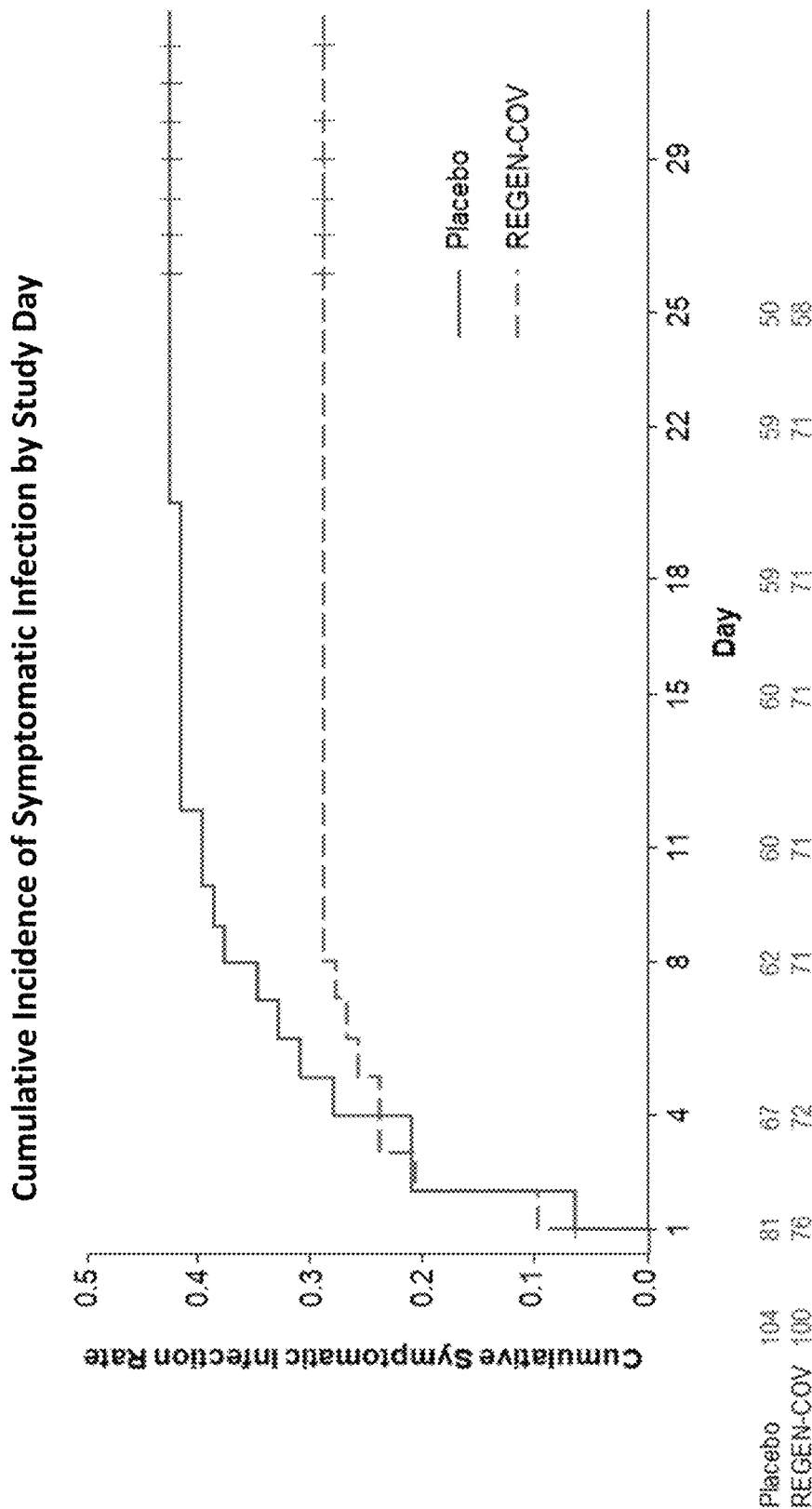

FIG. 73 illustrates the cumulative incidence of symptomatic infection by study day in a clinical trial assessing the ability of REGEN-COV to prevent COVID-19 symptoms. Treatment with REGEN-COV 1200 mg subcutaneous (SC) resulted in a 31.5% relative risk reduction in progression from asymptomatic to symptomatic infection during the efficacy assessment period (29/100 [29.0%] vs 44/104 [42.3%] for placebo; p=0.0380), with a more pronounced effect 3 days or longer following REGEN-COV administration (76.4% relative risk reduction).

Figure 74:
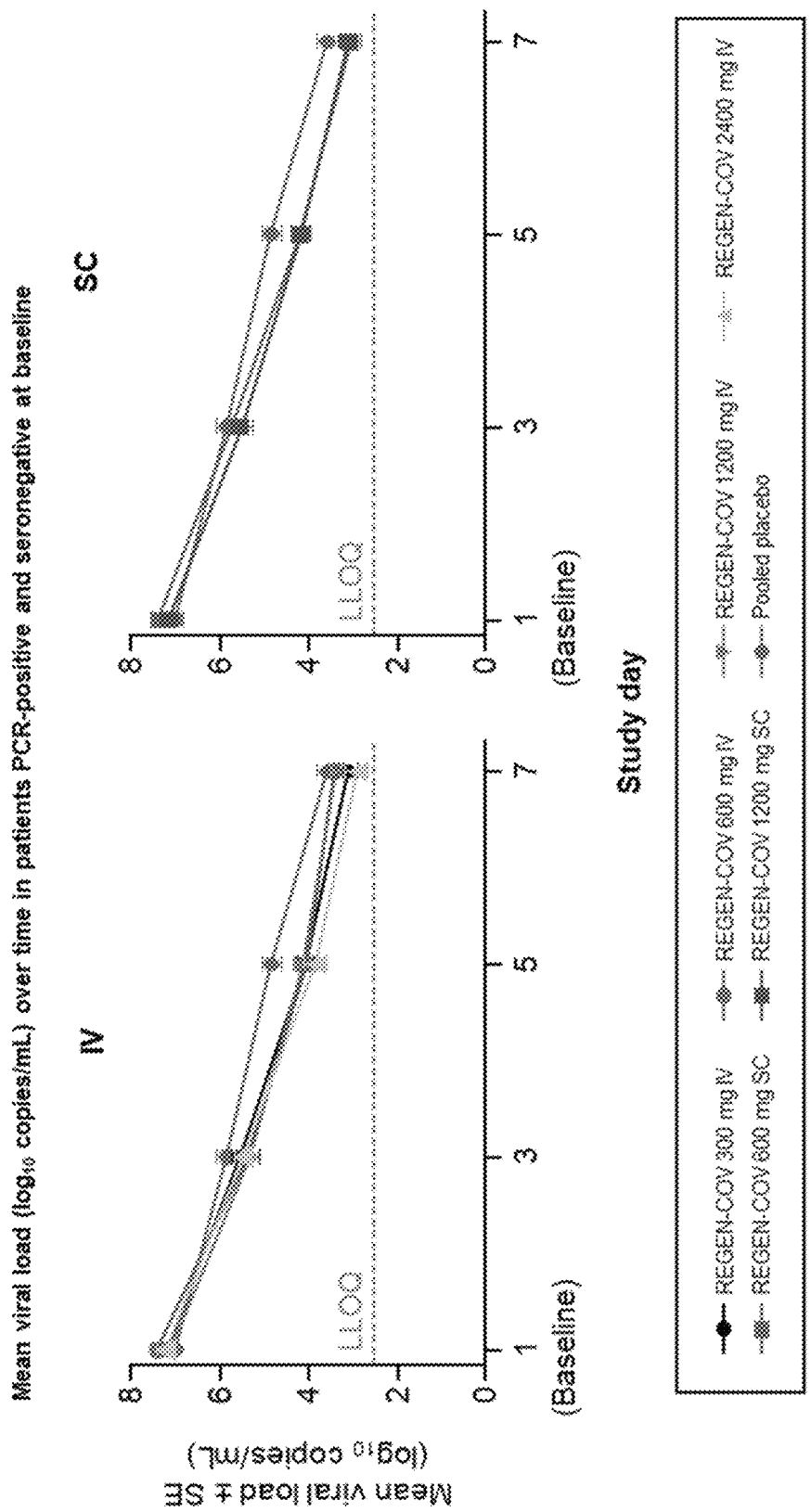

FIG. 74 illustrates the mean viral load over time in patients that were PCR-positive and seronegative at baseline in the clinical trial described in Example 7.

Figure 75:
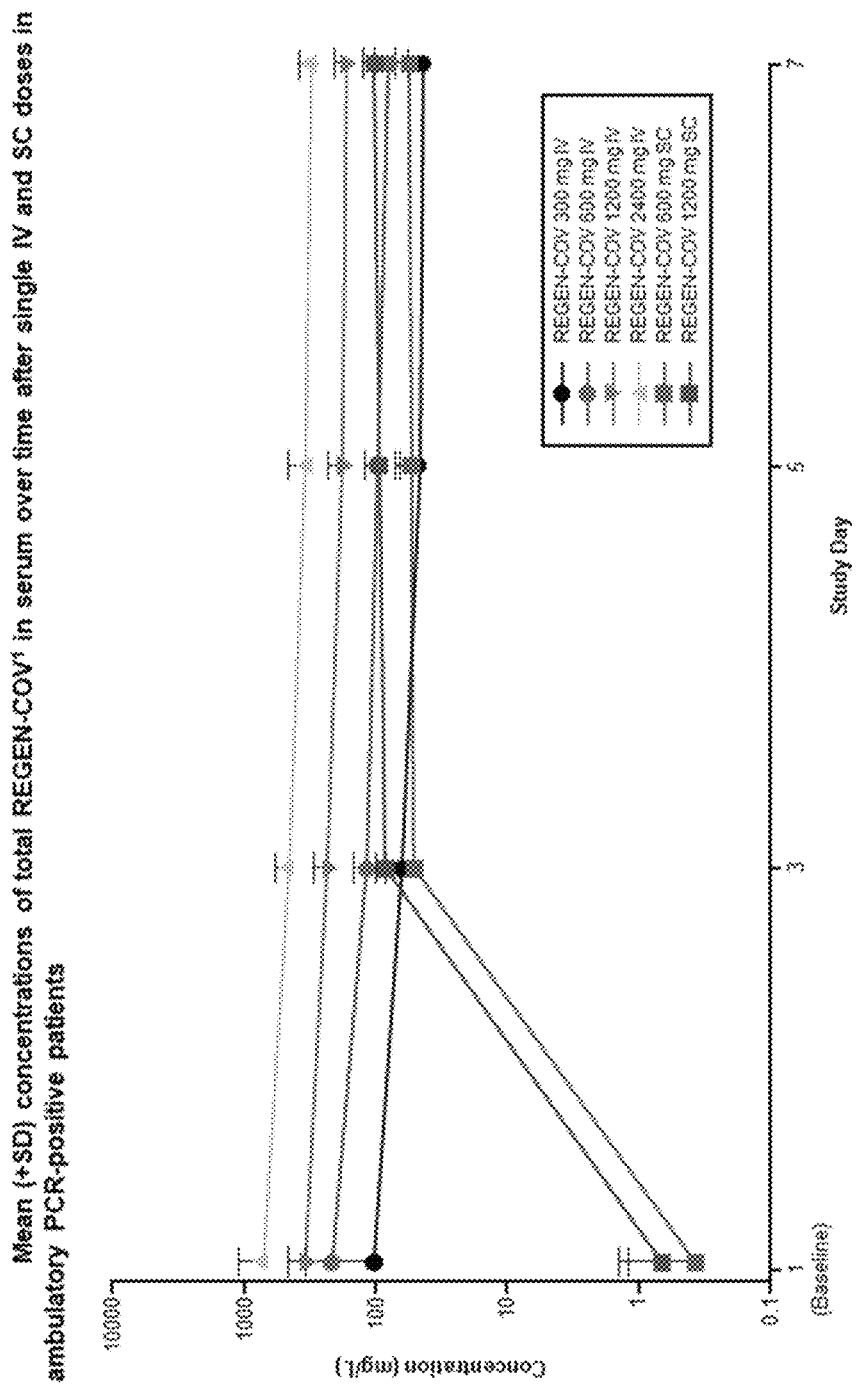

FIG. 75 illustrates the mean concentrations of total REGEN-COV in serum after single intravenous (IV) and subcutaneous (SC) in ambulatory PCR-positive patients enrolled in the clinical trial described in Example 7.

Figure 76:
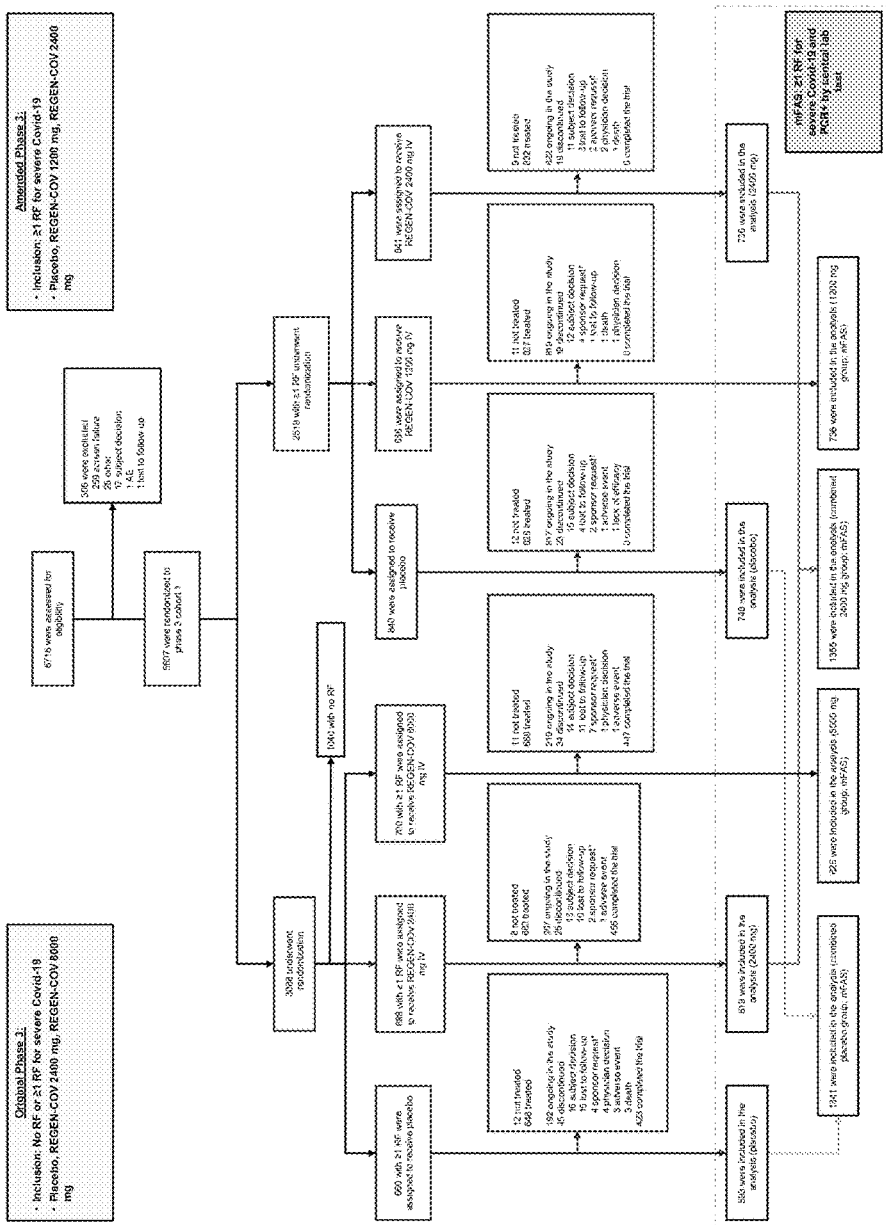

FIG. 76 illustrates the number of patients assigned to different treatment groups in a clinical trial designed to study REGEN-COV treatment in nonhospitalized patients.

Figure 77A:
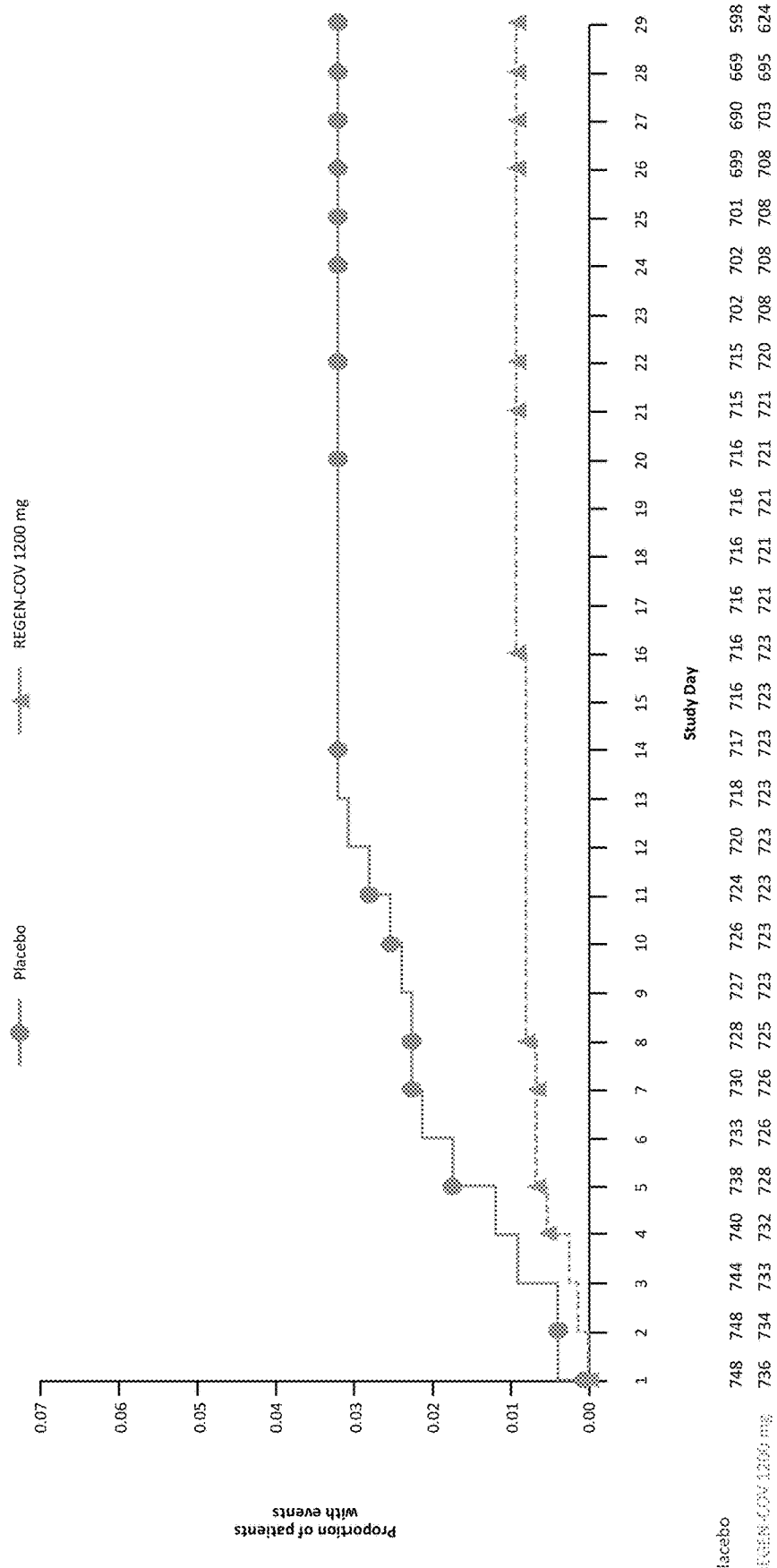
Figure 77B:
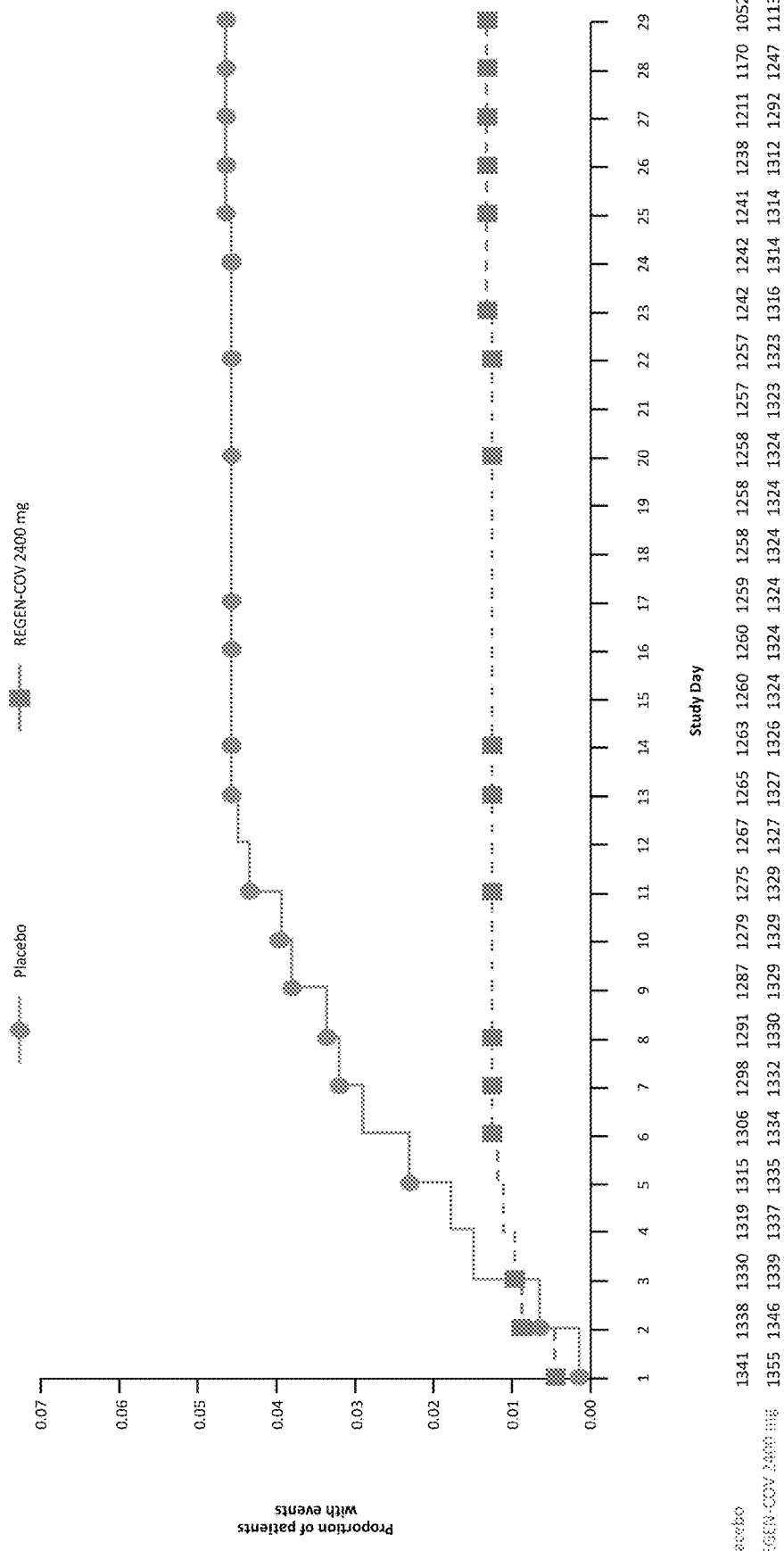
Figure 77C:
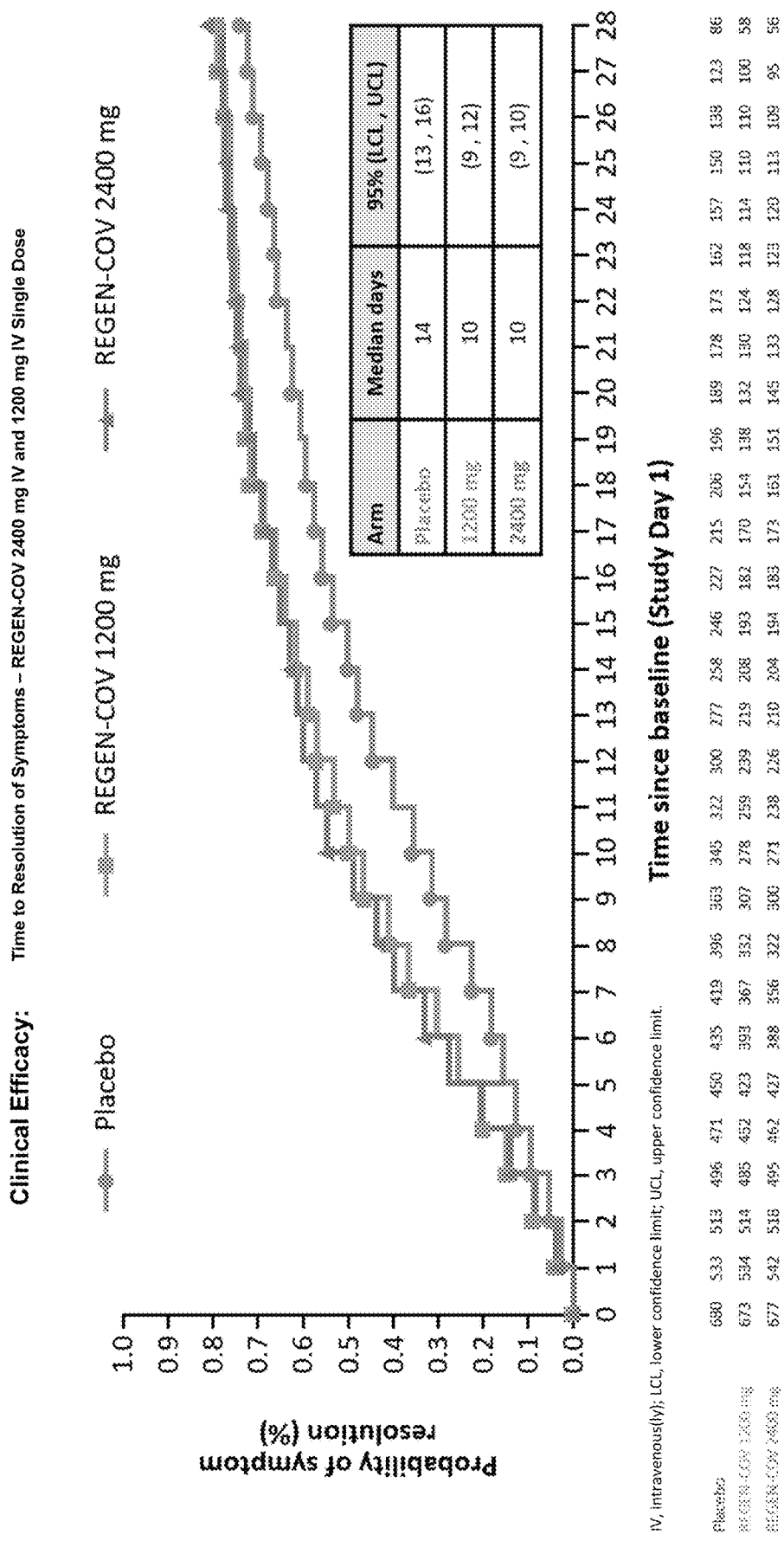

FIG. 77A, FIG. 77B, and FIG. 77C: FIG. 77A illustrates the clinical efficacy of a 1200 mg IV dose of REGEN-COV on hospitalization or all-cause death. Treatment significantly reduced hospitalization or all-cause death. FIG. 77B illustrates the clinical efficacy of a 2400 mg IV dose of REGEN-COV on hospitalization or all-cause death. Treatment significantly reduced hospitalization or all-cause death. FIG. 77C illustrates the clinical efficacy of a 1200 mg IV dose and a 2400 mg IV dose of REGEN-COV on time to resolution of symptoms. Treatment reduced the median days to symptom resolution by 4 days.

FIG. 78 illustrates the demographic and baseline medical characteristics of patients assigned to different treatment groups in a clinical trial designed to study REGEN-COV treatment in nonhospitalized patients.

FIG. 79 illustrates the effect of different treatment groups across each of the phase 3 clinical trial endpoints in nonhospitalized adult patients with COVID-19.

FIG. 80 illustrates an overview of serious adverse events and adverse events of special interest among patients treated intravenously with 1200 mg REGEN-COV, 2400 mg REGEN-COV, 8000 mg REGEN-COV, or placebo.

Figure 81:
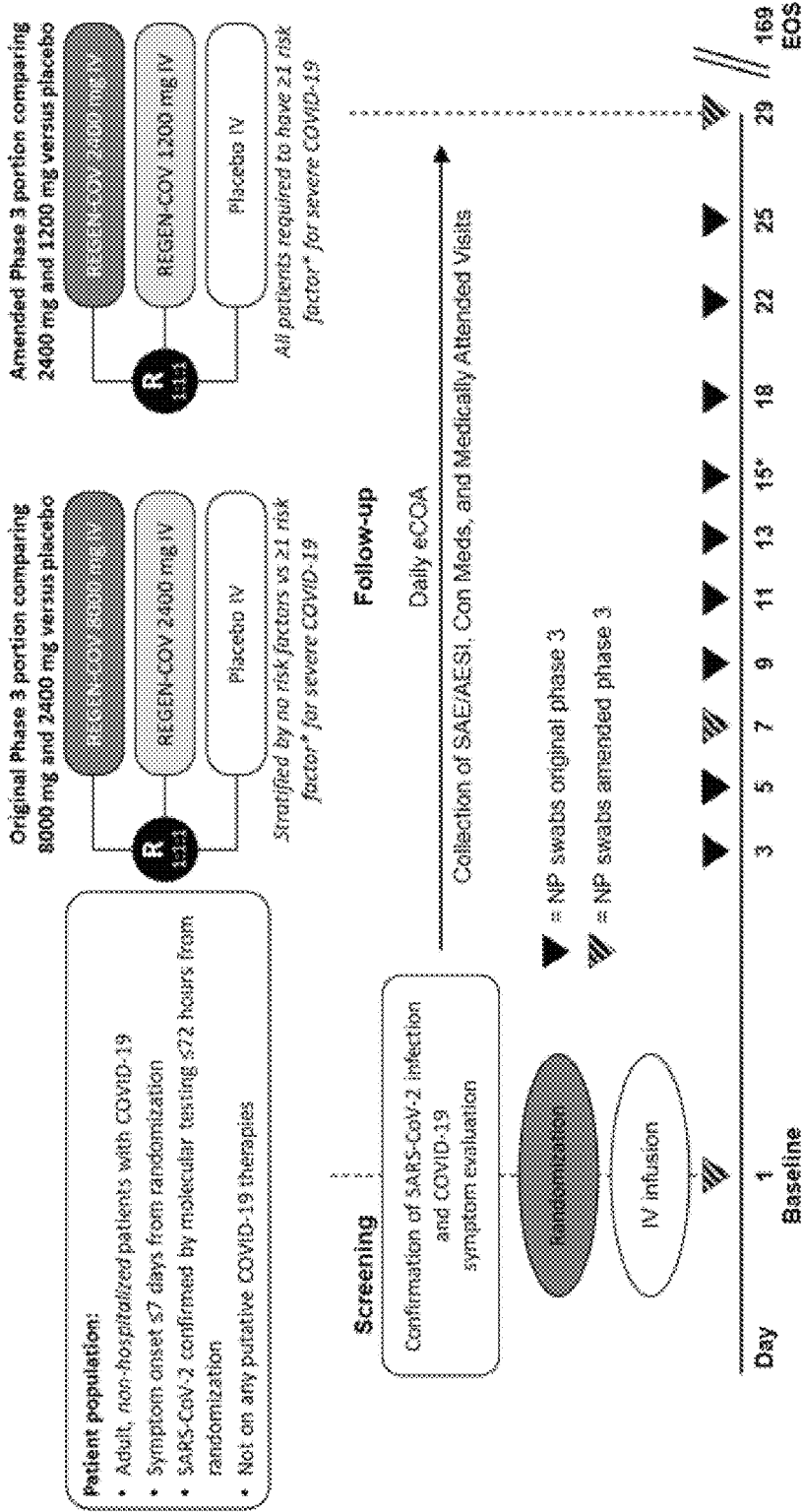

FIG. 81 illustrates a schematic overview of the study design to evaluate treatment with REGEN-COV in adult nonhospitalized patients with COVID-19.

Figure 82:
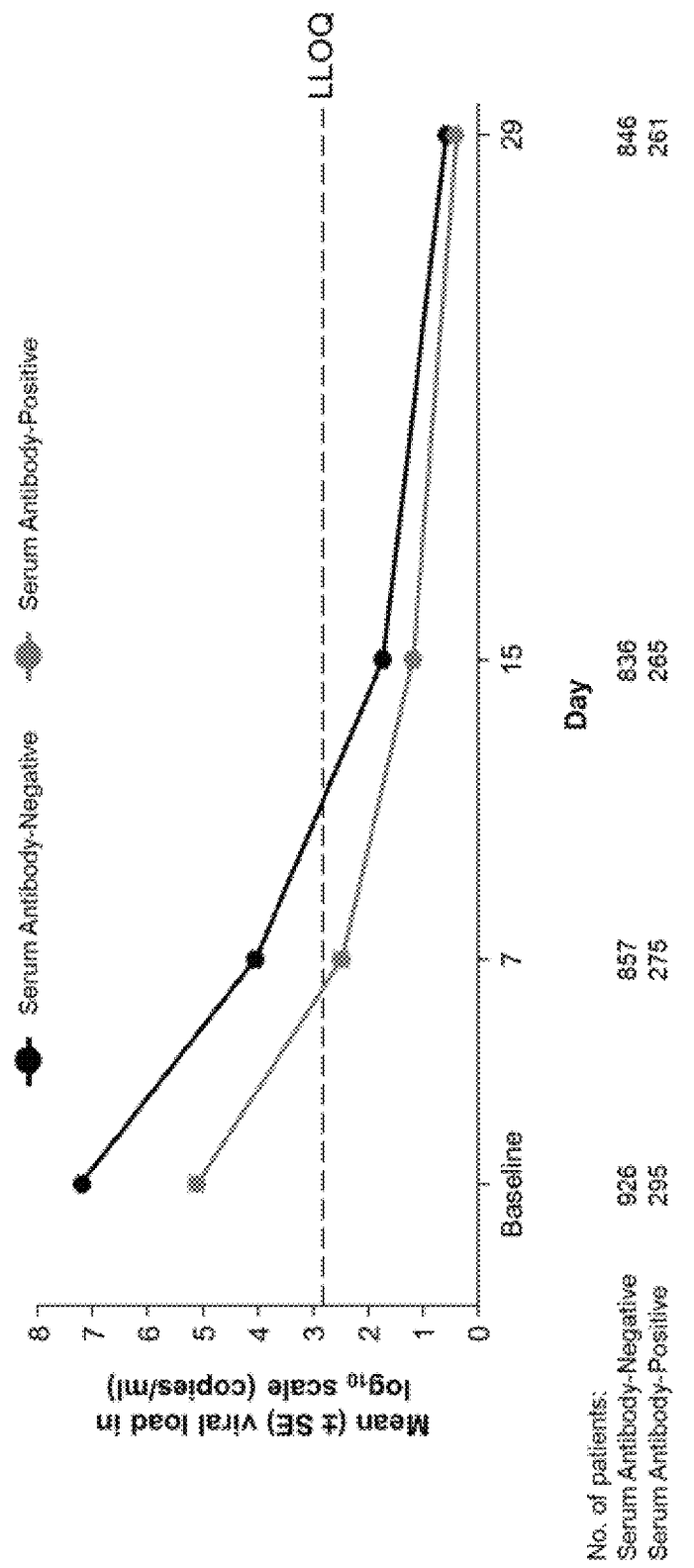

FIG. 82 illustrates viral load over time in the placebo arm by baseline serum antibody status.

Figure 83A:
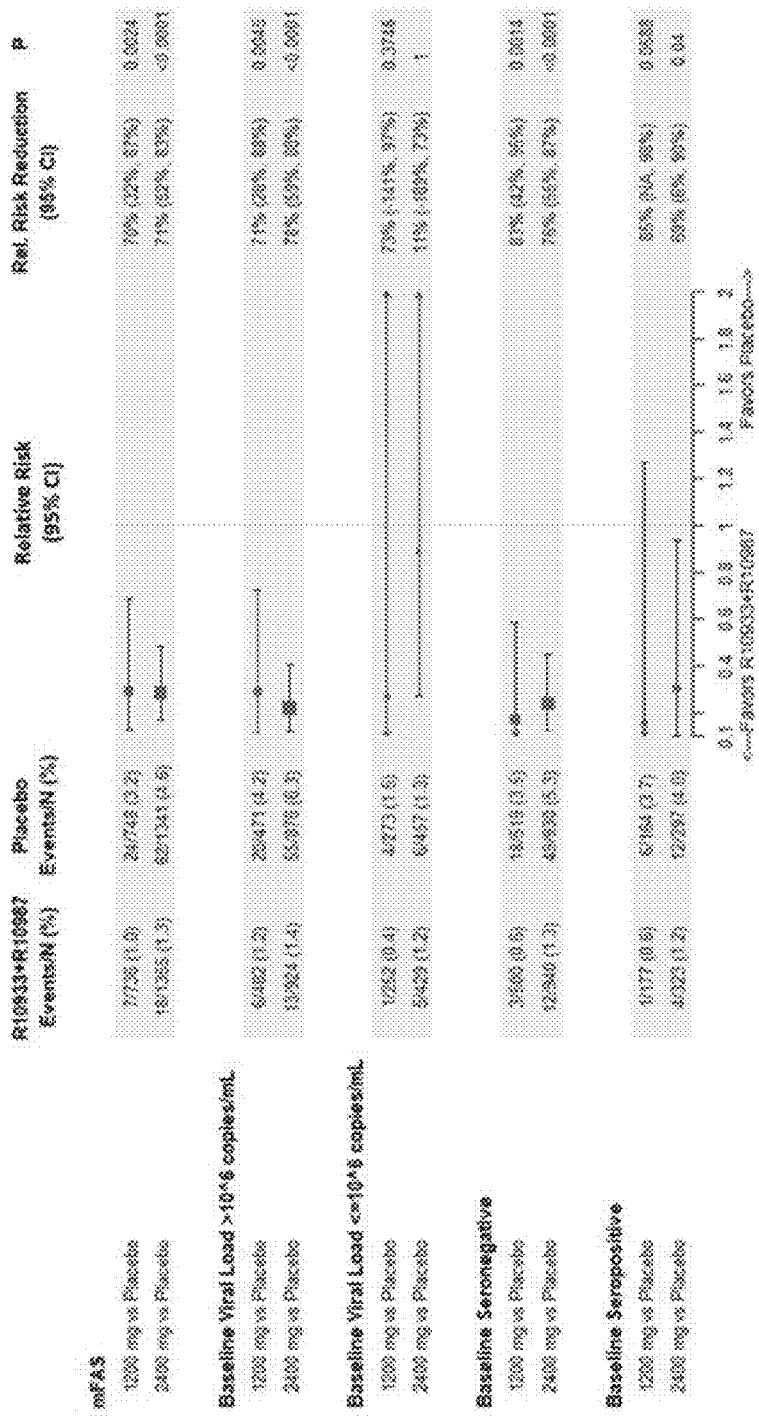
Figure 83B:
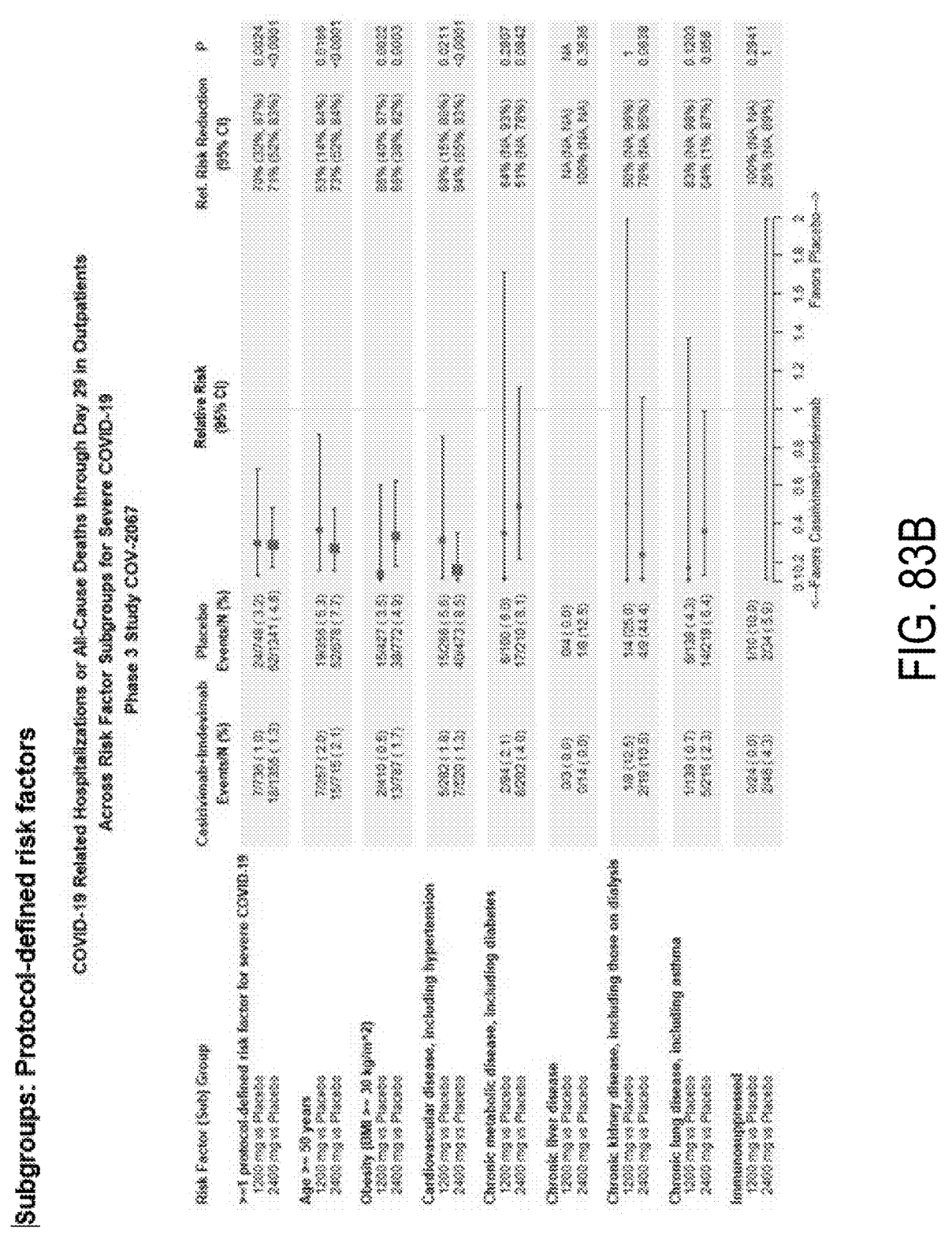
Figure 83C:
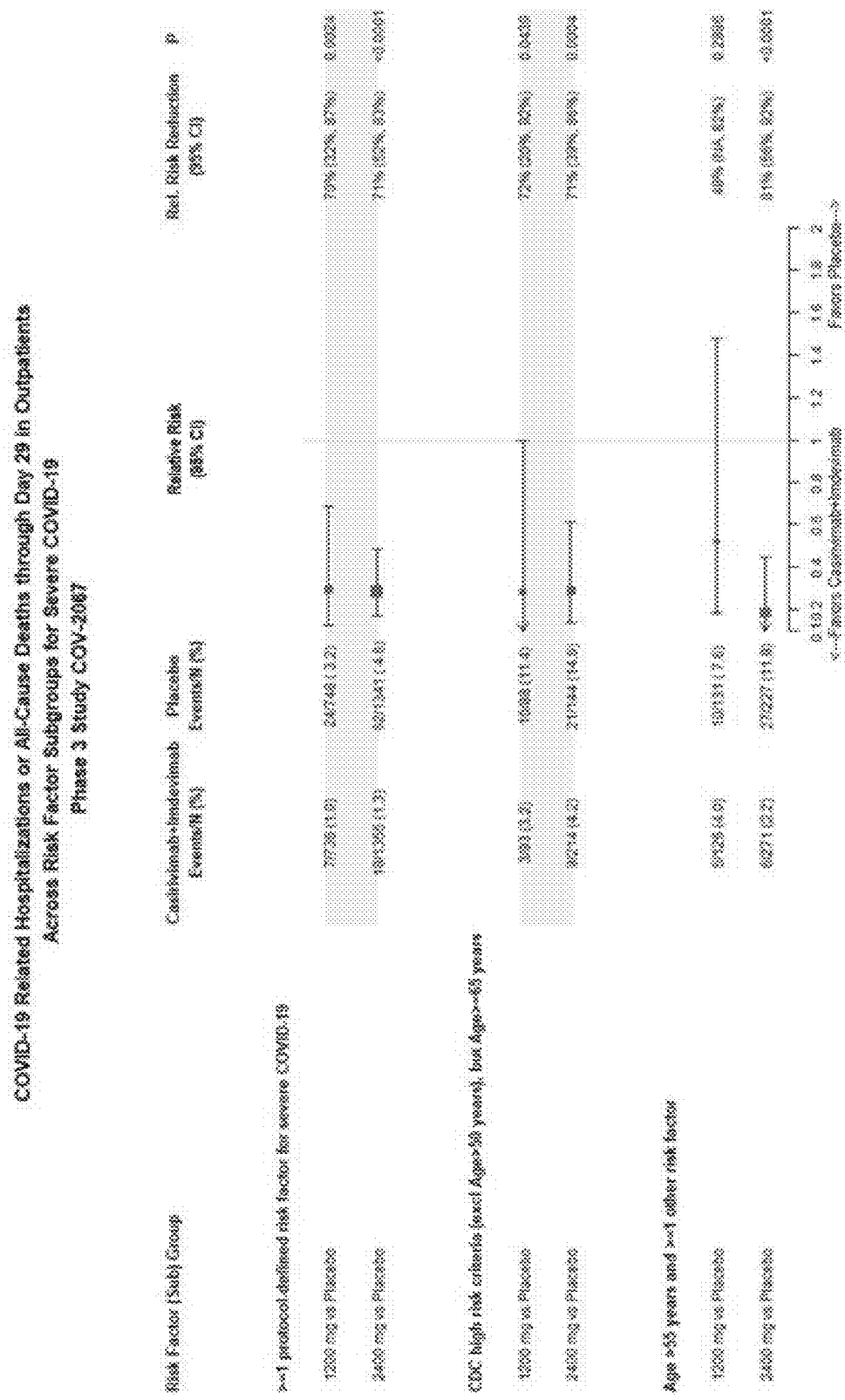

FIG. 83A, FIG. 83B and FIG. 83C: FIG. 83A illustrates a Forest Plot showing COVID-19 related hospitalization or all-cause death through Day 29 in adult nonhospitalized adults with one or more risk factors for severe COVID-19. FIG. 83B breaks down those data by protocol-defined risk factor, and FIG. 83C breaks down the data by other risk factor combinations.

Figure 84A:
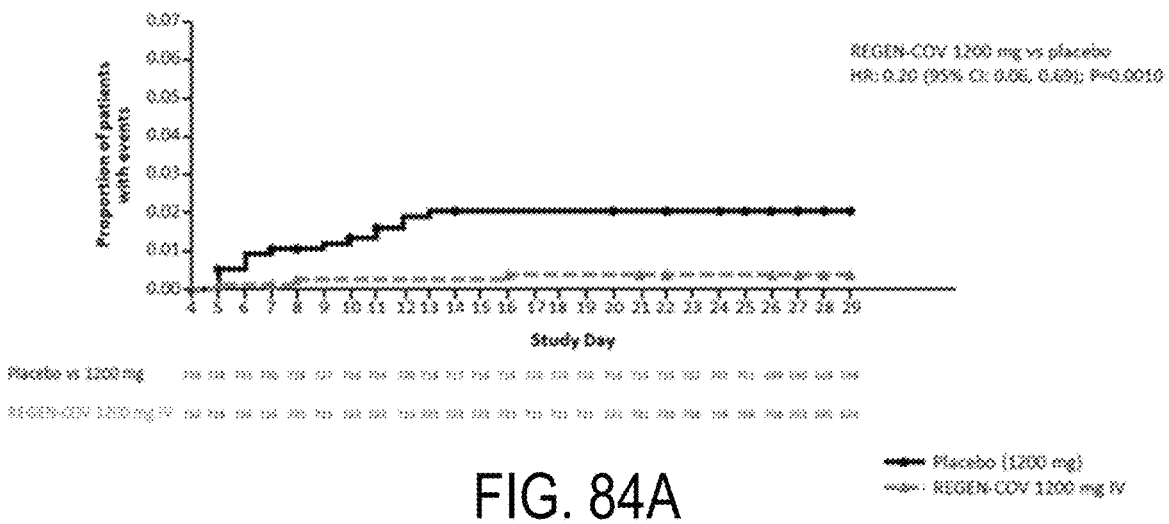
Figure 84B:
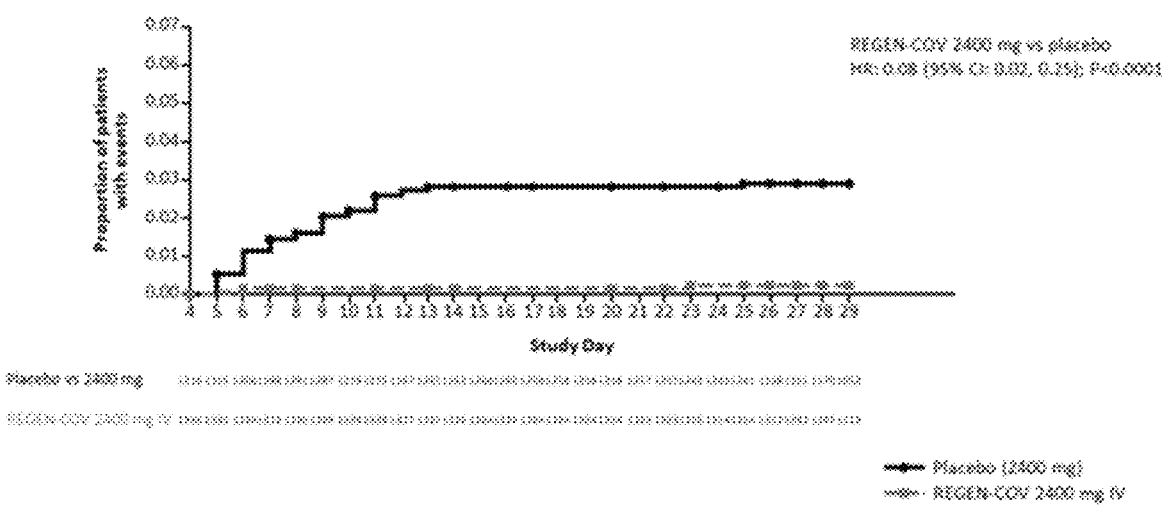

FIG. 84A and FIG. 84B: FIG. 84A illustrates the proportion of patients with COVID-19 related hospitalization or all-cause death from Day 4 to Day 29 among patients treated with a single intravenous dose of 1200 mg REGEN-COV. FIG. 84B illustrates the proportion of patients with COVID-19 related hospitalization or all-cause death from Day 4 to Day 29 among patients treated with a single intravenous dose of 2400 mg REGEN-COV.

Figure 85:
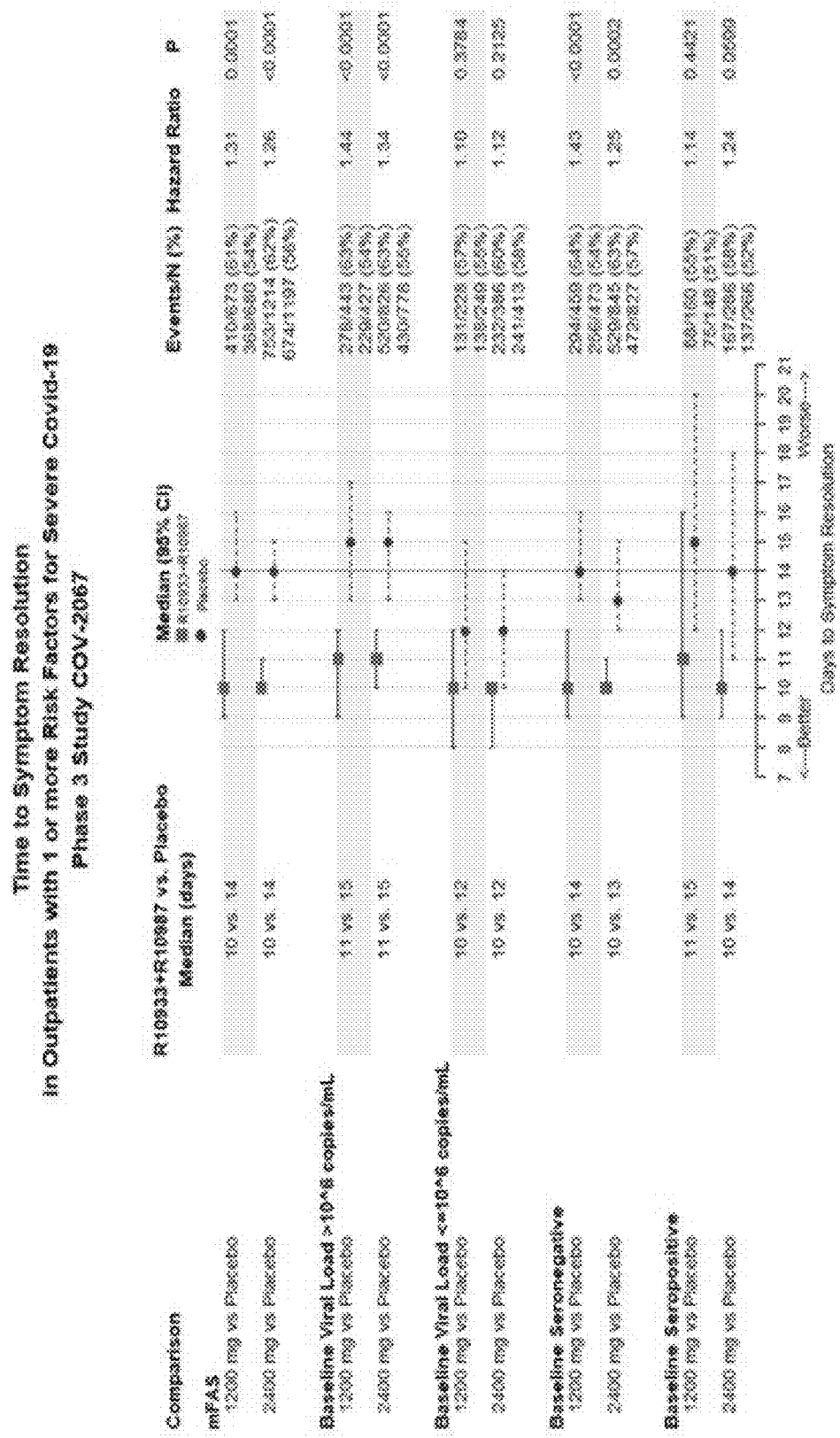

FIG. 85 illustrates the time to symptom resolution in outpatients with 1 or more risk factors for severe COVID-19 treated intravenously with 1200 mg REGEN-COV or 2400 mg REGEN-COV.

FIG. 86A, FIG. 86B, and FIG. 86C: FIG. 86A illustrates viral load over time in outpatients with 1 or more risk factors for severe COVID-19 treated intravenously with 1200 mg REGEN-COV or 2400 mg REGEN-COV. Both doses significantly reduced viral load compared to placebo. FIG. 86B illustrates viral load over time in those patients, broken down by baseline serum antibody status (seronegative vs. seropositive). FIG. 86C illustrates viral load over time in those patients, broken down by baseline viral load category ($>10^4$ copies/mL, $>10^5$ copies/mL, $>10^6$ copies/mL, and $>10^7$ copies/mL).

Figure 87:
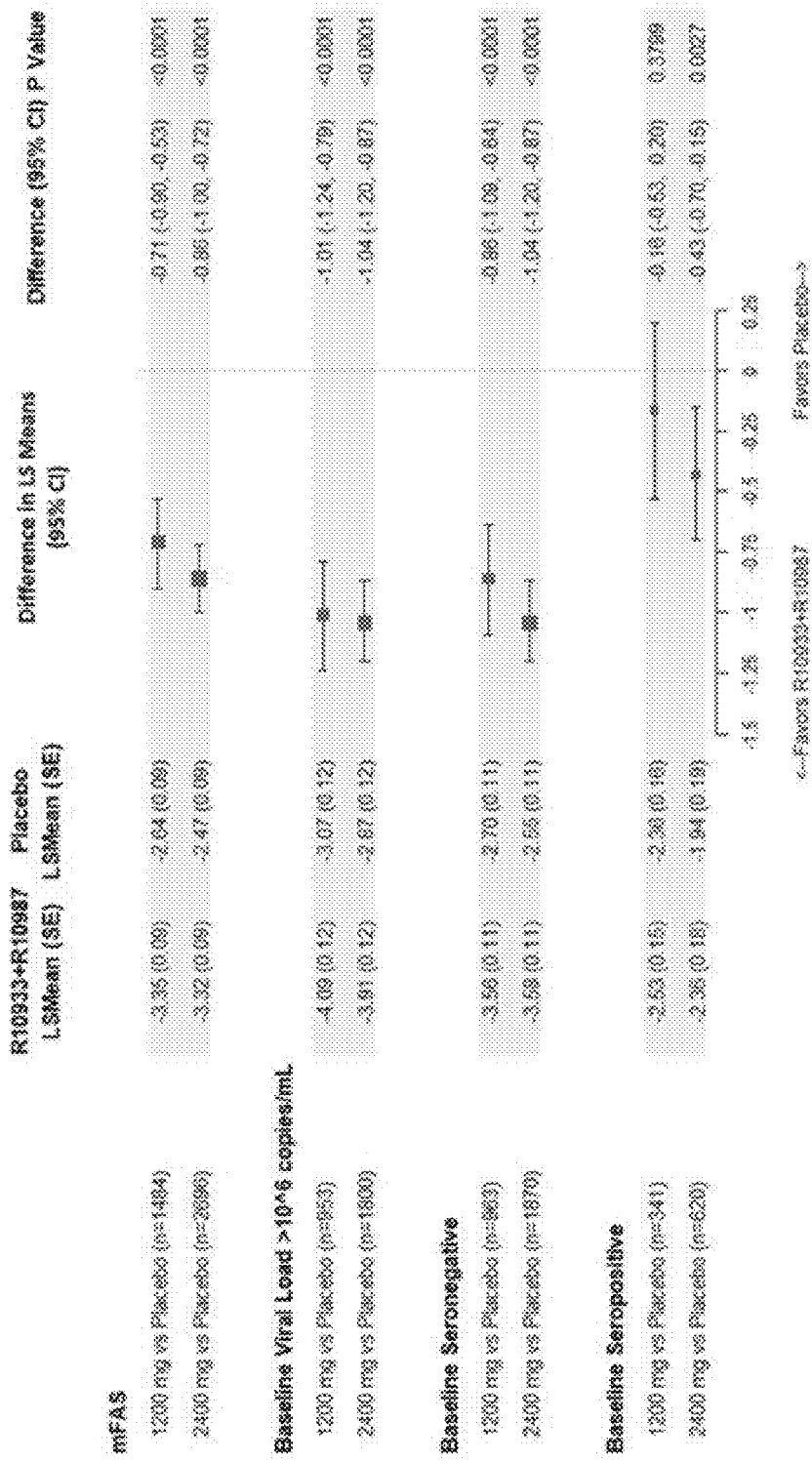

FIG. 87 illustrates change from baseline in viral load (log 10 copies/mL) at Day 7 in outpatients with 1 or more risk factors for severe COVID-19 treated intravenously with 1200 mg REGEN-COV or 2400 mg REGEN-COV.

FIG. 88A, FIG. 88B, and FIG. 88C: FIG. 88A illustrates viral load over time in outpatients with 1 or more risk factors for severe COVID-19 treated intravenously with 2400 mg REGEN-COV or 8000 mg REGEN-COV. Both doses significantly reduced viral load compared to placebo. FIG. 88B illustrates viral load over time in those patients, broken down by baseline serum antibody status (seronegative vs. seropositive). FIG. 88C illustrates viral load over time in those patients, broken down by baseline viral load category ($>10^4$ copies/mL, $>10^5$ copies/mL, $>10^6$ copies/mL, and $>10^7$ copies/mL).

FIG. 89 illustrates a primary hierarchical analysis testing order indicating in what order primary and secondary endpoints were assessed.

FIG. 90 illustrates the protocol-defined risk factors for severe COVID-19 in a clinical trial to assess REGEN-COV in nonhospitalized patients.

FIG. 91 illustrates demographic and baseline medical characteristics of patients receiving 8000 mg of REGEN-COV or placebo.

FIG. 92 illustrates the proportion of patients in the placebo arm with at least 1 COVID-19 related hospitalization or all-cause death by baseline viral load category.

FIG. 93 illustrates viral load in the placebo arm (with hospitalization/death, without hospitalization/death, and by baseline serum antibody status).

FIG. 94 illustrates the proportion of patients with one or more COVID-19 related hospitalization and/or all-cause death.

FIG. 95 illustrates the proportion of patients that had one or more medically attended visits, or all-cause death, after treatment with REGEN-COV.

FIG. 96 illustrates the outcomes for patients hospitalized during the course of the clinical trial in outpatients with 1 or more risk factors for severe COVID-19.

FIG. 97 illustrates the proportion of patients with one or more COVID-19 related hospitalization, emergency room visits, or all-cause death in patients treated with 1200 mg REGEN-COV, 2400 mg REGEN-COV, or placebo.

FIG. 98 illustrates the proportion of patients with one or more COVID-19 related hospitalization or all-cause death in patients treated with 8000 mg REGEN-COV or placebo.

FIG. 99 illustrates the proportion of patients with one or more COVID-19 related medically attended visit or all-cause death in patients treated with 8000 mg REGEN-COV or placebo.

FIG. 100 illustrates the treatment-emergent adverse events leaving to death in patients treated with 1200 mg REGEN-COV, 2400 mg REGEN-COV, 8000 mg REGEN-COV, or placebo FIG. 101 illustrates an overview of treatment-emergent serious adverse events and adverse events of special interest in patients treated with 1200 mg REGEN-COV, 2400 mg REGEN-COV, 8000 mg REGEN-COV, or placebo.

FIG. 102 illustrates adverse events of special interest in patients treated with 1200 mg REGEN-COV, 2400 mg REGEN-COV, 8000 mg REGEN-COV, or placebo, that required medical attention at a healthcare facility.

FIG. 103 illustrates the mean pharmacokinetic parameters of mAb10933 and mAb10987 in serum, in patients treated with 1200 mg REGEN-COV, 2400 mg REGEN-COV, 8000 mg REGEN-COV, or placebo.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Methods of Preventing and Treating SARS-CoV-2 Infections and COVID-19

The present invention provides methods for preventing and treating SARS-CoV-2 infections and COVID-19 in subjects in need thereof via administration of an antigen-binding molecule or molecules that bind a surface protein of SARS-CoV-2, including the anti-SARS-CoV-2 spike glycoprotein antibodies or antigen-binding fragments thereof discussed herein. In some cases, the subject is a hospitalized COVID-19 patient. In some cases, the subject is an outpatient (i.e., an ambulatory patient) that has tested positive for a SARS-CoV-2 infection. In some cases, the subject is a human patient with laboratory-confirmed SARS-CoV-2 and one or more COVID-19 symptoms, such as fever, cough, or shortness of breath. In some cases, the subject is (a) a human COVID-19 patient requiring low-flow oxygen supplementation; (b) a human COVID-19 patient requiring high-intensity oxygen therapy but not on mechanical ventilation; or (c) a human COVID-19 patient requiring mechanical ventilation. In some cases, the subject is a non-hospitalized symptomatic COVID-19 human. In some cases, the subject is an uninfected human, e.g., an uninfected human that is in a group at high risk of exposure (such as healthcare workers or first responders) or an uninfected human with close exposure to a subject that has been infected by SARS-CoV-2 (such as a housemate or family member that has contracted COVID-19. In some cases, the subject is at high risk of complications from COVID-19 or who are more likely to be infected by SARS-CoV-2, such as elderly humans, immunocompromised humans, and humans who often do not respond well to vaccines. In some embodiments, the present invention provides methods for treating, preventing and reducing the severity or progression of a SARS-CoV-2 infection and/or COVID-19.

The present invention also includes use of antigen-binding molecules that bind a surface protein of SARS-CoV-2, including the anti-SARS-CoV-2 spike glycoprotein antibodies or antigen-binding fragments thereof discussed herein, for preventing and treating SARS-CoV-2 infections and COVID-19 and/or for treating, preventing and reducing the severity or progression of a SARS-CoV-2 infection and/or COVID-19, or symptoms thereof. The present invention also includes use of antigen-binding molecules that bind a surface protein of SARS-Co-2, including the anti-SARS-CoV-2 spike glycoprotein antibodies or antigen-binding fragments thereof discussed herein, in the manufacture of a medicament for preventing and treating SARS-CoV-2 infections and COVID-19 and/or for treating, preventing and reducing the severity or progression of a SARS-CoV-2 infection and/or COVID-19. Where methods are discussed herein with reference to a combination of two anti-SARS-CoV-2 spike protein antibodies, such combinations include use of a first such antibody or antigen-binding fragment thereof in the manufacture of a medicament for use in combination with a second such antibody or antigen-binding fragment thereof, as well as use of the second such antibody or antigen-binding fragment thereof in the manufacture of a medicament for use in combination with the first such antibody.

As used herein, a therapeutic or prophylactic agent (e.g., an anti-SARS-CoV-2 spike glycoprotein antibody) that "prevents" a disorder or condition refers to a compound that, in a statistical sample, reduces the occurrence of the disorder or condition in the treated sample relative to an untreated control sample or delays the onset of the disorder or condition relative to the untreated control sample. The term "treating" as used herein includes amelioration or elimination of the condition once it has been established. In either case, prevention or treatment may be discerned in the diagnosis provided by a physician or other health care provider and the intended result of administration of the therapeutic or prophylactic agent.

In general, treatment or prevention of a disease or condition as described in the present disclosure is achieved by administering one or more anti-SARS-CoV-2 spike glycoprotein antibodies or antigen-binding fragment thereof in an effective amount. An effective amount of an agent refers to an amount effective, at dosages and for periods of time necessary, to achieve the desired therapeutic or prophylactic result. A therapeutically effective amount of an agent of the present disclosure may vary according to factors such as the disease state, age, sex, and weight of the individual, and the ability of the agent to elicit a desired response in the individual. A prophylactically effective amount refers to an amount effective, at dosages and for periods of time necessary, to achieve the desired prophylactic result.

In some embodiments, anti-SARS-CoV-2 spike glycoprotein antibodies or antigen-binding fragments thereof may be used to treat, prevent, or reduce the progression of a SARS-CoV-2 infection or COVID-19. In some cases, the anti-SARS-CoV-2 spike glycoprotein antibodies or antigen-binding fragments thereof block the spike protein receptor binding domain (RBD) interaction with angiotensin-converting enzyme 2 (ACE2), leading to decreased infectivity of host cells. Blocking viral entry results in reductions in SARS-CoV-2 RNA replication, and corresponding viral shedding in affected tissues. Thus, in some embodiments, the anti-SARS-CoV-2 spike glycoprotein antibodies or antigen-binding fragments thereof will reduce viral shedding in the upper respiratory tract. In some embodiments, viral shedding is measured in samples collected from the upper respiratory tract in patients from 7 to 29 days after the start of dosing (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or 29 days after the start of dosing). In some cases, a reduction from baseline in SARS-CoV-2 viral shedding is determined by RT-qPCR in nasopharyngeal swab samples, nasal samples, or saliva samples.

In some cases, the anti-SARS-CoV-2 spike glycoprotein antibodies or antigen-binding fragments thereof improve clinical status of a patient (e.g., a patient diagnosed with a SARS-CoV-2 infection or COVID-19). In some embodiments, an improvement in clinical status is based on a 7-point ordinal scale (rating clinical status from death [1] to not hospitalized [7]) used to assess changes in clinical status. Utilization of an ordinal scale that incorporates multiple clinical outcomes of interest (e.g., death, mechanical ventilation etc.) ordered by their clinical importance is an appropriate measure for assessing efficacy in trials of severe and/or critical patients with COVID-19. In some cases, administration of the anti-SARS-CoV-2 spike glycoprotein antibodies or antigen-binding fragments thereof improve the clinical status of a patient by at least 1-point or 2-points. In some cases, administration of the anti-SARS-CoV-2 spike glycoprotein antibodies or antigen-binding fragments thereof lead to a reduction in rates of mortality and/or use of oxygen therapy, and/or increase ventilator-free days of such patients. As discussed above, improvements in clinical status can be assessed using the following ordinal scale:

[1] Death
[2] Hospitalized, requiring invasive mechanical ventilation or ECMO
[3] Hospitalized, requiring non-invasive ventilation or high flow oxygen devices
[4] Hospitalized, requiring supplemental oxygen
[5] Hospitalized, not requiring supplemental oxygen— requiring ongoing medical care (COVID-19-related or otherwise)
[6] Hospitalized, not requiring supplemental oxygen—no longer requires ongoing medical care
[7] Not hospitalized.

In some cases, a subject, following administration of the anti-SARS-CoV-2 spike glycoprotein antibodies or antigen-binding fragments thereof, exhibits less than 5 COVID-19 related medically-attended visits, telemedicine visits, hospital admissions, and/or intensive care unit (ICU) admissions. In some cases, the less than 5 (e.g., less than 5, less than 4, less than 3, less than 2, or less than 1) COVID-19 related medically-attended visits, telemedicine visits, hospital admissions, and/or intensive care unit (ICU) admissions are exhibited by the subject within a period of from 7 to 42 (e.g., 21 to 42 days) following administration of a first dose of the anti-SARS-CoV-2 spike glycoprotein antibodies or antigen-binding fragments thereof. In some embodiments, the less than 5 COVID-19 related visits are exhibited by the subject with a period of 29 days following administration of the first dose. In some cases, the subject exhibits less than 4 COVID-19 related medically-attended visits, telemedicine visits, hospital admissions, and/or intensive care unit (ICU) admissions. In some cases, the subject exhibits less than 3 COVID-19 related medically-attended visits, telemedicine visits, hospital admissions, and/or intensive care unit (ICU) admissions. In some cases, the subject exhibits less than 2 COVID-19 related medically-attended visits, telemedicine visits, hospital admissions, and/or intensive care unit (ICU) admissions. In some cases, the subject exhibits no more than 1 COVID-19 related medically-attended visits, telemedicine visits, hospital admissions, and/or intensive care unit (ICU) admissions.

In some cases, a subject, following administration of the anti-SARS-CoV-2 spike glycoprotein antibodies or antigen-binding fragments thereof, tests negative for SARS-CoV-2 within 2 days to 3 weeks following first administration of the therapeutic composition. In some cases, the negative test for SARS-CoV-2 is determined by RT-qPCR in nasopharyngeal swab samples, nasal samples, or saliva samples.

In any of the various embodiments discussed above or herein (e.g., combination prophylactic or therapeutic administration of mAb10933 and mAb10987), the result of administration of the anti-SARS-CoV-2-spike glycoprotein antibody or antibodies may be any one or more of the following:

(a) a reduction in time-weighted average viral shedding ($\log_{10}$ copies/mL) from baseline, as measured by RT-qPCR in nasopharyngeal (NP) swabs;
(b) a reduction in time-weighted average viral shedding ($\log_{10}$ copies/mL) from baseline, as measured by RT-qPCR in nasal swabs;
(c) a reduction in time-weighted average viral shedding ($\log_{10}$ copies/mL) from baseline, as measured by RT-qPCR in saliva samples;
(d) an at least 1-point improvement in clinical status using the 7-point ordinal scale relative to baseline;
(e) a reduction in COVID-19 related medically-attended visits relative to control (a COVID-19-related medically-attended visit is defined as follows: hospitalization, emergency room (ER) visit, urgent care visit, physician's office visit, or telemedicine visit, with the primary reason for the visit being COVID-19);
(f) a reduction in time to negative RT-qPCR in NP swabs with no subsequent positive RT-qPCR relative to control;
(g) a reduction in incidence of hospitalization or days hospitalized relative to control;
(h) a reduction in incidence of admission to ICU or days in ICU relative to control;
(i) a reduction in incidence of mechanical ventilation or time on mechanical ventilation relative to control;
(j) a reduction in duration of COVID-19 symptoms relative to control;
(k) a reduction in time to negative RT-qPCR in all tested samples with no subsequent positive RT-qPCR in any tested samples (nasopharyngeal swabs, nasal swabs, saliva) relative to control;
(l) a reduction in incidence of subsequent development of signs or symptoms of SARS-CoV-2 infection (strict term or broad term);
(m) a reduction in time-weighted average daily viral load (e.g., a reduction through day 7 by 0.4 or more log 10 copies/mL, a reduction through day 7 by 0.5 or more log 10 copies/mL, or a reduction through day 7 by 0.6 or more log 10 copies/mL, a reduction through day 11 by 0.5 or more log 10 copies/mL, a reduction through day 11 by 0.6 or more log 10 copies/m, or a reduction through day 11 by 0.7 or more log 10 copies/m; and
(n) a reduction in time-weighted average viral load from baseline (log 10 copies/mL).

In some embodiments, administration of the anti-SARS-CoV-2 spike glycoprotein antibodies can have a greater effect on subjects without an effective amount of existing antibodies in their blood against SARS-CoV-2 ("seronegative" subjects) than on subjects with an effective amount of existing antibodies in their blood against SARS-CoV-2 ("seropositive" subjects). In the Examples provided herein, serostatus seronegative, seropositive, or undetermined) was determined by assessing for the presence of serum anti-SARS-CoV-2 antibodies: anti-spike [S1] IgA (Euroimmun IgA test), anti-spike [S1] IgG (Euroimmun IgG test), and anti-nucleocapsid IgG (Abbot IgG test). Study participants were grouped for analyses as seronegative (if all available tests were negative), seropositive (if any of the tests were positive), or sero-undetermined (missing or inconclusive results). A test was categorized as negative if the antibodies in the sample were below the lower limit of quantitation for the test. As described herein, the methods described herein can have a differential effect in seronegative subjects over a comparable population of seropositive subjects (e.g., a greater reduction in viral load, faster time to symptom alleviation, fewer medically-attended visits post-administration).

Antigen-Binding Molecules and Anti-SARS-Cov-2 Spike Glycoprotein Antibodies

The methods and uses of the present invention utilize antigen-binding molecules that bind a surface protein of SARS-CoV-2. In some embodiments, the antigen-binding molecules are anti-SARS-CoV-2 spike glycoprotein antibodies or antigen-binding fragments thereof.

The amino acid and nucleotide sequences of the variable regions, CDRs, and heavy chains and light chains of exemplary antibodies that bind to the SARS-CoV-2 spike protein are shown in Tables 1 and 2, below. Additional amino acid and nucleotide sequences of variable regions, CDRs, and heavy and light chains of exemplary antibodies and antigen binding fragments that bind to the SARS-CoV-2 spike protein and that are useful in the methods described herein are found in U.S. Pat. No. 10,787,501, which is hereby incorporated by reference in its entirety.

TABLE 1

| Amino Acid Sequence Identifiers | | | | | | | | | |
|---|---|---|---|---|---|---|---|---|---|
| Antibody | SEQ ID NOs | | | | | | | | |
| Designation | HCVR | HCDR1 | HCDR2 | HCDR3 | LCVR | LCDR1 | LCDR2 | LCDR3 | HC | LC |
| mAb10933 | 2 | 4 | 6 | 8 | 10 | 12 | 14 | 16 | 18 | 20 |
| mAb10987 | 22 | 24 | 26 | 28 | 30 | 32 | 34 | 36 | 38 | 40 |
| mAb10989 | 42 | 44 | 46 | 48 | 50 | 52 | 34 | 54 | 56 | 58 |
| mAb10985 | 73 | 75 | 77 | 79 | 81 | 83 | 85 | 87 | 89 | 91 |

TABLE 2

| Antibody Designation | Nucleic Acid Sequence Identifiers SEQ ID NOs | | | | | | | | | |
|---|---|---|---|---|---|---|---|---|---|---|
| | HCVR | HCDR1 | HCDR2 | HCDR3 | LCVR | LCDR1 | LCDR2 | LCDR3 | HC | LC |
| mAb10933 | 1 | 3 | 5 | 7 | 9 | 11 | 13 | 15 | 17 | 19 |
| mAb10987 | 21 | 23 | 25 | 27 | 29 | 31 | 33 | 35 | 37 | 39 |
| mAb10989 | 41 | 43 | 45 | 47 | 49 | 51 | 33 | 53 | 55 | 57 |
| mAb10985 | 72 | 74 | 76 | 78 | 80 | 82 | 84 | 86 | 88 | 90 |

In various embodiments, the anti-SARS-CoV-2 spike glycoprotein antibody or antigen-binding fragment for use in the methods or uses discussed herein is an antibody or antigen-binding fragment comprising the six CDRs (HCDR1-HCDR2-HCDR3-LCDR1-LCDR2-LCDR3) of any one or more of the antibodies listed in Table 1. In some cases, the anti-SARS-CoV-2 spike glycoprotein antibody or antigen-binding fragment comprises the CDRs of a heavy chain variable region (HCVR) and light chain variable region pair comprising the amino acid sequences selected from the group consisting of SEQ ID NOs: 2/10, 22/30, 42/50, and 73/81. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., J Mol Biol 273: 927-948 (1997); and Martin et al., PNAS (USA) 86:9268-9272 (1989). Public databases are also available for identifying CDR sequences within an antibody.

In some embodiments, the anti-SARS-CoV-2 spike glycoprotein antibody or antigen-binding fragment comprises HCDR1-HCDR2-HCDR3-LCDR1-LCDR2-LCDR3 domains comprising the amino acid sequences, respectively, selected from the group consisting of SEQ ID NOs: 4-6-8-12-14-16, 24-26-28-32-34-36, 44-46-48-52-34-54, and 75-77-79-83-85-87.

In some embodiments, the anti-SARS-CoV-2 spike glycoprotein antibody or antigen-binding fragment comprises a HCVR/LCVR amino acid sequence pair comprising the amino acid sequences selected from the group consisting of SEQ ID NOs: 2/10, 22/30, 42/50, and 73/81.

In some embodiments, the anti-SARS-CoV-2 spike glycoprotein antibody comprises a heavy chain (HC) and light chain (LC) pair comprising the amino acid sequences selected from the group consisting of SEQ ID NOs: 18/20, 38/40, 56/58, and 89/91.

In some embodiments, the anti-SARS-CoV-2 spike glycoprotein antibody binds to an epitope within the SARS-CoV-2 spike protein receptor binding domain (RBD) (amino acids 1-1273 of NCBI accession number (MN908947.3), SEQ ID NO: 59). In some cases, the antibody (e.g., mAb10989) binds to residues 467-513 (DISTEIYQAGSTPCNGVEGFNCYFPLQSYGFQPTNGVGYQPYRVVVL) (SEQ ID NO: 60) of the RBD. In some cases, the antibody (e.g., mAb10987) binds to residues 432-452 (CVIAWNSNNLDSKVGGNYNYL) (SEQ ID NO: 61) of the RBD. In some cases, the antibody (e.g., mAb10933) binds to residues 467-510 (DISTEIYQAGSTPCNGVEGFNCYFPLQSYGFQPTNGVGYQPYRV) (SEQ ID NO: 62) of the RBD.

In some embodiments, the anti-SARS-CoV-2 spike glycoprotein antibody is mAb10933. In some embodiments, the anti-SARS-CoV-2 spike glycoprotein antibody is mAb10987. In some embodiments, the anti-SARS-CoV-2 spike glycoprotein antibody is mAb10989. In various embodiments, the anti-SARS-CoV-2 spike glycoprotein antibody is an antibody comprising the CDRs, the HCVR and LCVR, or the heavy chain and light chain (e.g., the amino acid sequences shown in Table 1) of mAb10933. In various embodiments, the anti-SARS-CoV-2 spike glycoprotein antibody is an antibody comprising the CDRs, the HCVR and LCVR, or the heavy chain and light chain (e.g., the amino acid sequences shown in Table 1) of mAb10987. In various embodiments, the anti-SARS-CoV-2 spike glycoprotein antibody is an antibody comprising the CDRs, the HCVR and LCVR, or the heavy chain and light chain (e.g., the amino acid sequences shown in Table 1) of mAb10989. The antibodies provided herein can be identified as "mAb" followed by a number or "REGN" followed by a number, interchangeably. For example, mAb10933 and REGN10933 refer to the same antibody (amino acid sequences provided in Table 1 and nucleic acid sequences provided in Table 2). Similarly, mAb10987 and REGN10987 are equivalent, mAb10989 and REGN10989 are equivalent, and mAb10985 and REGN10985 are equivalent. In addition, mAb10933 can be referred to as casirivimab and mAb10987 can be referred to as imdevimab. The combination of casirivimab and imdevimab is known as REGEN-COV.

In some embodiments, the methods and uses discussed herein include a composition comprising a first antigen-binding molecule (e.g., an antibody) that binds a first epitope on a surface protein of SARS-CoV-2, and a second antigen-binding molecule (e.g., an antibody) that binds a second epitope on a surface protein of SARS-CoV-2, wherein the first epitope and the second epitope are structurally non-overlapping. In some embodiments, the methods and uses discussed herein include a combination of two or more anti-SARS-CoV-2 spike glycoprotein antibodies or antigen-binding fragments thereof. In some cases, the two antibodies or antigen-binding fragments used in combination bind to structurally non-overlapping epitopes of the RBD. In some embodiments, the combination includes mAb10987 and mAb10933. In some embodiments, the combination includes mAb10987 and mAb10989. In some embodiments, the combination includes mAb10933 and mAb10987 and mAb10985. In various embodiments, the combination includes a first anti-SARS-CoV-2 spike glycoprotein antibody that is an antibody comprising the CDRs, the HCVR and LCVR, or the heavy chain and light chain (e.g., the amino acid sequences shown in Table 1) of mAb10933, and the second anti-SARS-CoV-2 spike glycoprotein antibody that is an antibody comprising the CDRs, the HCVR and LCVR, or the heavy chain and light chain (e.g., the amino acid sequences shown in Table 1) of mAb10987, and optionally a third anti-SARS-CoV-2 spike glycoprotein antibody that is an antibody comprising the CDRs, the HCVR and LCVR, or the heavy chain and light chain (e.g., the amino acid sequences shown in Table 1) of mAb10985. In various embodiments, the combination includes a first anti-SARS-CoV-2 spike glycoprotein antibody that is an antibody comprising the CDRs, the HCVR and LCVR, or the heavy chain and light chain (e.g., the amino acid sequences shown in Table 1) of mAb10989, and the second anti-SARS-CoV-2 spike glycoprotein antibody that is an antibody comprising the CDRs, the HCVR and LCVR, or the heavy chain and light chain (e.g., the amino acid sequences shown in Table 1) of mAb10987. In some embodiments, a combination of antigen-binding molecules (e.g., antibodies such as mAb10987 and mAb10933, mAb10987 and mAb10989, or mAb10987 and mAb10933 and mAb10985) can reduce the frequency of escape mutants (e.g., SARS-CoV-2 viruses that have one or more mutations in the S protein so as to reduce the efficacy of a treatment, for example by diminishing the binding of an antibody to the S protein). Escape variants were identified following two passages in cell culture of recombinant VSV encoding SARS-CoV-2 spike protein in the presence of mAb10933 (casirivimab) or mAb10987 (imdevimab) individually, but not following two passages in the presence of casirivimab and imdevimab together. This combination of antibodies also is effective against variant SARS-CoV-2 viruses. For example, the combination of mAb10933 and mAb10987 was evaluated for its ability to neutralize pseudotyped VSV expressing a SARS-CoV-2 variant known as B.1.1.7, also called the "UK variant." This variant is rapidly expanding, and may have different effects than wild-type SARS-CoV-2, including more severe symptoms than the wild-type virus and potential resistance to vaccines and/or therapeutics. It is classified, in part, by the following mutations in the spike protein: HV 69-70 deletion, Y144 deletion, N501Y, A570D, P681H, T716I, S982A, and D1118H. Casirivimab and imdevimab, in combination, was shown to effectively neutralize the virus (FIG. 29). Indeed, casirivimab and imdevimab individually and together retained neutralization activity against pseudovirus expressing all spike protein substitutions found in the B.1.1.7 lineage (UK origin) and against pseudovirus expressing only N501Y found in B.1.1.7 and other circulating lineages. Casirivimab and imdevimab together retained neutralization activity against pseudovirus expressing all spike protein substitutions, or individual substitutions K417N, E484K or N501Y, found in the B.1.1351 lineage (South Africa origin), and against K417T+E484K, found in the P.1 lineage (Brazil origin), although casirivimab alone, but not imdevimab, had reduced activity against pseudovirus expressing K417N or E484K, as indicated above. The E484K substitution is also found in the B.1.526 lineage (New York origin).

TABLE 3A

Casivirimab and imdevimab, individually and together, retained neutralization activity against the L452R substitution found in the B.1.427/B.1.429 lineages (California origin).

| Variant | mAb10933 | mAb10987 | mAb10933 + mAb10987 |
|---|---|---|---|
| | Fold decrease in IC50 from reference SARS-CoV-2 D614G | | |
| UK B.1.1.7 | 0.98 | 0.70 | 1.04 |

TABLE 3B

Pseudovirus Neutralization Data for SARS-CoV-2 Variant Substitutions with Casirivimab and Imdevimab Together

| Lineage with Spike Protein Substitution | Key Substitutions Tested | Fold Reduction in Susceptibility |
|---|---|---|
| B.1.1.7 (UK origin) | N501Y[a] | No change[c] |
| B.1.351 (South Africa origin) | K417N, E484K, N501Y[b] | No change[c] |
| P.1 (Brazil origin) | K417T + E484K | No change[c] |
| B.1.427/B.1.429 (California origin) | L452R | No change[c] |
| B.1.526 (New York origin)[d] | E484K | No change[c] |

[a]Pseudovirus expressing the entire variant spike protein was tested. The following changes from wild-type spike protein are found in the variant: del69-70, del145, N501Y, A570D, D614G, P681H, T716I, S982A, D1118H.
[b]Pseudovirus expressing the entire variant spike protein was tested. The following changes from wild-type spike protein are found in the variant: D80Y, D215Y, del241-243, K417N, E484K, N501Y, D614G, A701V.
[c]No change: <2-fold reduction in susceptibility.
[d]Not all isolates of the New York lineage harbor the E484K substitution (as of February 2021).

Certain variants showed reduced susceptibility to casirivimab alone, including those with spike protein amino acid substitutions K417E (182-fold), K417N (7-fold), K417R (61-fold), Y453F (>438-fold), L455F (80-fold), E484K (25-fold), F486V (>438-fold) and Q493K (>438-fold). Variants which showed reduced susceptibility to imdevimab alone included substitutions K444N (>755-fold), K444Q (>548-fold), K444T (>1,033-fold), and V445A (548-fold). Casirivimab and imdevimab together showed reduced susceptibility to variants with K444T (6-fold) and V445A (5-fold) substitutions. In neutralization assays using VSV pseudotyped with 39 different spike protein variants identified in circulating SARS-CoV-2, variants with reduced susceptibility to casirivimab alone included those with Q409E (4-fold), G476S (5-fold) and S494P (5-fold) substitutions, and variants with reduced susceptibility to imdevimab alone included one with N439K (463-fold) substitution. Additional substitutions that were tested in pseudovirus assays and had reduced activity to casirivimab alone included E484Q (9-fold) and Q493E (446-fold). Casirivimab and imdevimab together retained activity against all variants tested. In some embodiments, the present disclosure provides a method for treating SARS-CoV-2 infection comprising administering mAb10933 and mAb10987, wherein the SARS-CoV-2 is a variant SARS-CoV-2, e.g., comprising a HV 69-70 deletion, Y144 deletion, Q409E, K417E, K417N, K417R, N439K, Y453F, L455F, G476S, E484K, E484Q, F486V, Q493K, Q493E, S494P, N501Y, A570D, P681H, T716I, S982A, or D1118H, or any combination thereof. In the clinical trial of Example 2, interim data indicated only one variant (G446V) occurring at an allele fraction ≥15%, which was detected in 3/66 subjects who had nucleotide sequencing data, each at a single time point (two at baseline in subjects from placebo and 2,400 mg casirivimab and imdevimab groups, and one at Day 25 in a subject from the 8,000 mg casirivimab and imdevimab group). The G446V variant had reduced susceptibility to imdevimab of 135-fold compared to wild-type in a VSV pseudoparticle neutralization assay but retained susceptibility to casirivimab alone and casirivimab and imdevimab together.

In some embodiments, the methods and uses discussed herein include a composition comprising a first antigen-binding molecule (e.g., an antibody) that binds a first epitope on a surface protein of SARS-CoV-2, and a second antigen-binding molecule (e.g., an antibody) that binds a second epitope on a surface protein of SARS-CoV-2, wherein the first antigen-binding molecule and the second antigen-binding molecule are capable of simultaneously binding the surface protein of SARS-CoV-2.

In certain embodiments, one, two, three, four, or more antibodies, or antigen-binding fragments thereof can be administered in combination (e.g., concurrently or sequentially). Exemplary combinations include mAb10933 and mAb10987, mAb10989 and mAb10987, mAb10933 and mAb10989, mAb10933 and mAb10987 and mAb10985.

As used herein, "an antibody that binds SARS-CoV-2 spike protein" or an "anti-SARS-CoV-2 spike glycoprotein antibody" or an "anti-SARS-CoV-2 spike protein antibody" includes antibodies, and antigen-binding fragments thereof, that bind a soluble fragment of the SARS-CoV-2 spike protein and may also bind an epitope within the receptor binding domain (RBD) of the spike protein. Other antibodies that can be used alone or in combination with one another or with one or more of the antibodies disclosed herein for use in the context of the methods of the present disclosure include, e.g., LY-CoV555 (Eli Lilly); 47D11 (Wang et al Nature Communications Article No. 2251); B38, H4, B5 and/or H2 (Wu et al., 10.1126/science.abc2241 (2020); STI-1499 (Sorrento Therapeutics); VIR-7831 and VIR-7832 (Vir Biotherapeutics).

The term "antibody" means any antigen-binding molecule or molecular complex comprising at least one complementarity determining region (CDR) that specifically binds to or interacts with a particular antigen (e.g., SARS-CoV-2 spike protein). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-SARS-CoV-2 spike protein antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$—$V_L$ or $V_L$—$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$—$C_H1$; (ii) $V_H$—$C_H2$; (iii) $V_H$—$C_H3$; (iv) $V_H$—$C_H1$-$C_H2$; (v) $V_H$—$C_H1$-$C_H2$-$C_H3$; (vi) $V_H$—$C_H2$-$C_H3$; (vii) $V_H$—$C_L$; (viii) $V_L$—$C_H1$; (ix) $V_L$—$C_H2$; (x) $V_L$—$C_H3$; (xi) $V_L$—$C_H1$-$C_H2$; (xii) $V_L$—$C_H1$-$C_H2$-$C_H3$; (xiii) $V_L$—$C_H2$-$C_H3$; and (xiv) $V_L$—$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

In certain embodiments of the invention, the anti-SARS-CoV-2 spike protein antibodies of the invention are human antibodies. The term "human antibody," as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al., Nucl Acids Res 20:6287-6295 (1992)) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. Molecular Immunology 30:105 1993)) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention includes neutralizing and/or blocking anti-SARS-CoV-2 spike protein antibodies. A "neutralizing" or "blocking" antibody, as used herein, is intended to refer to an antibody whose binding to SARS-CoV-2 spike protein: (i) inhibits an activity of SARS-CoV-2 spike protein to any detectable degree, e.g., inhibits the ability of SARS-CoV-S to bind to a receptor such as ACE2, to be cleaved by a protease such as TMPRSS2, or to mediate viral entry into a host cell or viral reproduction in a host cell.

The anti-SARS-CoV-2 spike protein antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-SARS-CoV-2 spike protein antibodies comprising variants of any of the HCVR, LCVR, and/or CDR amino acid sequences disclosed herein having one or more conservative substitutions. For example, the present invention includes anti-SARS-CoV-2 spike protein antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, W. R., Methods Mol Biol 24: 307-331 (1994), herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al., Science 256: 1443-1445 (1992), herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (see, e.g., Pearson, W. R., Methods Mol Biol 132: 185-219 (2000), herein incorporated by reference). Another preferred algorithm when comparing a sequence of the invention to a database containing a large number of sequences from different organisms is the computer program BLAST, especially BLASTP or TBLASTN, using default parameters. See, e.g., Altschul et al., J Mol Biol 215:403-410 (1990) and Altschul et al., Nucleic Acids Res 25:3389-402 (1997), each herein incorporated by reference.

Specific Binding

The term "specifically binds" or the like, as used herein, means that an antigen-specific binding protein, or an antigen-specific binding domain, forms a complex with a particular antigen characterized by a dissociation constant ($K_D$) of 50 nM or less, and does not bind other unrelated antigens under ordinary test conditions. "Unrelated antigens" are proteins, peptides or polypeptides that have less than 95% amino acid identity to one another. Methods for determining whether two molecules specifically bind one another are well known in the art and include, for example, equilibrium dialysis, surface plasmon resonance, and the like. For example, an antigen-specific binding protein or an antigen-specific binding domain, as used in the context of the present invention, includes molecules that bind a particular antigen (e.g., SARS-CoV-2 spike protein, SARS-CoV-2 spike protein RBD, or a specific epitope of the SARS-CoV-2 spike protein RBD) or a portion thereof with a $K_D$ of less than about 50 nM, less than about 40 nM, less than about 30 nM, less than about 20 nM, less than about 10 nM, less than about 5 nM, less than about 4 nM, less than about 3 nM, less than about 2 nM, or less than about 1 nM, as measured in a surface plasmon resonance assay.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, NJ).

The term "$K_D$", as used herein, means the equilibrium dissociation constant of a particular protein-protein interaction (e.g., antibody-antigen interaction). Unless indicated otherwise, the $K_D$ values disclosed herein refer to $K_D$ values determined by surface plasmon resonance assay at 25° C.

Antibodies Comprising Heavy Chain Constant Region Variants

According to certain embodiments of the present invention, anti-SARS-CoV-2 spike protein antibodies are provided comprising an Fc domain comprising one or more mutations which enhance or diminish antibody binding to the FcRn receptor, e.g., at acidic pH as compared to neutral pH. For example, the present invention includes anti-SARS-CoV-2 spike protein antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-SARS-CoV-2 spike protein antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations, and other mutations within the antibody variable domains disclosed herein, are contemplated within the scope of the present invention.

In various embodiments, the anti-SARS-CoV-2 spike protein antibodies comprise a heavy chain constant region combining sequences derived from more than one immunoglobulin isotype. For example, a chimeric heavy chain constant region can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric heavy chain constant region can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric heavy chain constant region that can be included in any of the antibodies set forth herein comprises, from N- to C-terminus: [IgG4 $C_H1$]-[IgG4 upper hinge]-[IgG2 lower hinge]-[IgG4 CH2]-[IgG4 CH3]. Another example of a chimeric heavy chain constant region that can be included in any of the antibodies set forth herein comprises, from N- to C-terminus: [IgG1 $C_H1$]-[IgG1 upper hinge]-[IgG2 lower hinge]-[IgG4 CH2]-[IgG1 CH3]. These and other examples of chimeric heavy chain constant regions that can be included in any of the antibodies of the present invention are described in WO 2014/121087 (8550-WO). Chimeric heavy chain constant regions having these general structural arrangements, and variants thereof, can have altered Fc receptor binding, which in turn affects Fc effector function.

In various embodiments, the anti-SARS-CoV-2 spike protein antibodies comprise a heavy chain constant region including a hinge domain in which positions 233-236 within the hinge domain may be G, G, G and unoccupied; G, G, unoccupied, and unoccupied; G, unoccupied, unoccupied, and unoccupied; or all unoccupied, with positions numbered by EU numbering. Optionally, the heavy chain constant region comprises from N-terminal to C-terminal the hinge domain, a CH2 domain and a CH3 domain. Optionally, the heavy chain constant region comprises from N-terminal to C-terminal a CH1 domain, the hinge domain, a CH2 domain and a CH3 domain. Optionally, the CH1 region, if present, remainder of the hinge region, if any, CH2 region and CH3 region are the same human isotype. Optionally, the CH1 region, if present, remainder of the hinge region, if any, CH2 region and CH3 region are human IgG1. Optionally, the CH1 region, if present, remainder of the hinge region, if any, CH2 region and CH3 region are human IgG2. Optionally, the CH1 region if present, remainder of the hinge region, if any, CH2 region and CH3 region are human IgG4. Optionally, the constant region has a CH3 domain modified to reduce binding to protein A. These and other examples of modified heavy chain constant regions that can be included in any of the antibodies of the present invention are described in WO 2016/161010 (10140WO01).

Epitope Mapping and Related Technologies

The present invention includes anti-SARS-CoV-2 spike protein antibodies which interact with one or more amino acids found within the SARS-CoV-2 spike protein (e.g., within the spike protein RBD). The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within the spike protein RBD. Alternatively, the epitope may consist of a plurality of non-contiguous amino acids (or amino acid sequences) located within the spike protein RBD.

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., NY), alanine scanning mutational analysis, peptide blots analysis (Reineke, Methods Mol Biol 248:443-463 (2004)), and peptide cleavage analysis. In addition, methods such as epitope excision, epitope extraction and chemical modification of antigens can be employed (Tomer, Protein Science 9:487-496 (2000)). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring, Analytical Biochemistry 267(2):252-259 (1999); Engen and Smith, Anal. Chem. 73:256A-265A (2001).

The present invention further includes anti-SARS-CoV-2 spike protein antibodies that bind to the same epitope as any of the exemplary antibodies mentioned above (e.g., mAb10933, mAb10987, or mAb10989). Likewise, the present invention also includes anti-SARS-CoV-2 spike protein antibodies that compete for binding to the SARS-CoV-2 spike protein with any of the specific exemplary antibodies described herein (e.g., mAb10933, mAb10987, or mAb10989).

One can easily determine whether an antibody binds to the same epitope as, or competes for binding with, a reference anti-SARS-CoV-2 spike protein antibody by using routine methods known in the art and exemplified herein. For example, to determine if a test antibody binds to the same epitope as a reference anti-SARS-CoV-2 spike protein antibody discussed herein, the reference antibody is allowed to bind to SARS-CoV-2 spike protein. Next, the ability of a test antibody to bind to SARS-CoV-2 spike protein is assessed. If the test antibody is able to bind to SARS-CoV-2 spike protein following saturation binding with the reference anti-SARS-CoV-2 spike protein antibody, it can be concluded that the test antibody binds to a different epitope than the reference anti-SARS-CoV-2 spike protein antibody. On the other hand, if the test antibody is not able to bind to SARS-CoV-2 spike protein following saturation binding with the reference anti-SARS-CoV-2 spike protein antibody, then the test antibody may bind to the same epitope as the epitope bound by the reference anti-SARS-CoV-2 spike protein antibody discussed herein. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 50:1495-1502 (1990)). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

Preparation of Human Antibodies

Methods for generating monoclonal antibodies, including fully human monoclonal antibodies are known in the art. Any such known methods can be used in the context of the present invention to make human antibodies that specifically bind to SARS-CoV-2 spike protein.

Using VELOCIMMUNE™ technology, for example, or any other known method for generating fully human monoclonal antibodies, high affinity chimeric antibodies to SARS-CoV-2 spike protein are initially isolated having a human variable region and a mouse constant region. The antibodies are characterized and selected for desirable characteristics, including affinity, selectivity, epitope, etc. If necessary, mouse constant regions are replaced with a desired human constant region, for example wild-type or modified IgG1 or IgG4, to generate a fully human anti-SARS-CoV-2 spike protein antibody. While the constant region selected may vary according to specific use, high affinity antigen-binding and target specificity characteristics reside in the variable region. In certain instances, fully human anti-SARS-CoV-2 spike protein antibodies are isolated directly from antigen-positive B cells.

Bioequivalents

The anti-SARS-CoV-2 spike protein antibodies and antibody fragments of the present invention encompass proteins having amino acid sequences that vary from those of the described antibodies but that retain the ability to bind SARS-CoV-2 spike protein. Such variant antibodies and antibody fragments comprise one or more additions, deletions, or substitutions of amino acids when compared to parent sequence, but exhibit biological activity that is essentially equivalent to that of the described antibodies. Likewise, the anti-SARS-CoV-2 spike protein antibody-encoding DNA sequences of the present invention encompass sequences that comprise one or more additions, deletions, or substitutions of nucleotides when compared to the disclosed sequence, but that encode an anti-SARS-CoV-2 spike protein antibody or antibody fragment that is essentially bioequivalent to an anti-SARS-CoV-2 spike protein antibody or antibody fragment of the invention.

Two antibodies are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antibodies are bioequivalent if there are no clinically meaningful differences in their safety, purity, and potency.

In one embodiment, two antibodies are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antibodies are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-SARS-CoV-2 spike protein antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-SARS-CoV-2 spike protein antibody variants comprising amino acid changes which modify the glycosylation characteristics of the antibodies, e.g., mutations which eliminate or remove glycosylation.

In some embodiments, the antibodies disclosed herein lack fucose in its constant region glycosylation. Methods of measuring fucose in an antibody composition have been described in the art, e.g., U.S. Pat. No. 8,409,838 (Regeneron Pharmaceuticals), incorporated herein by reference. In some embodiments, fucose is undetectable in a composition comprising a population of antibody molecules. In some embodiments, an antibody lacking fucose has enhanced ADCC activity.

In some embodiments, antibodies that lack fucose can be produced using cell lines that are deficient in their ability to fucosylate proteins, i.e., the ability to fucosylate proteins is reduced or eliminated. Fucosylation of glycans requires synthesis of GDP-fucose via the de novo pathway or the salvage pathway, both of which involve sequential function of several enzymes, leading to addition of a fucose molecule to the first N-acetylglucosamine (GlcNAc) moiety of the reducing end of a glycan. The two key enzymes of the de novo pathway responsible for production of GDP-fucose are GDP-D-mannose-4,6-dehydratase (GMD) and GDP-keto-6-deoxymannose-3,5-epimerase,4-reductase (FX). In the absence of fucose, these two de novo pathway enzymes (GMD and FX) convert mannose and/or glucose to GDP-fucose which is then transported into the Golgi complex where nine fucosyl-transferases (FUT1-9) act in concert to fucosylate the first GlcNAc molecule of a glycan. In the presence of fucose, however, the salvage pathway enzymes, fucose-kinase and GDP-fucose pyrophosphorylase, convert fucose into GDP-fucose.

Cell lines that are deficient in their ability to fucosylate proteins have been described in the art. In some embodiments, a cell line deficient in its ability to fucosylate proteins is a mammalian cell line (e.g., CHO cell lines, such as CHO K1, DXB-11 CHO, Veggie-CHO) comprising a mutation or genetic modification in one or more of endogenous FUT1 to 9 genes resulting in a lack of one or more functional fucosyl-transferases. In some embodiments, the mammalian cell line comprises a mutation in an endogenous FUT8 gene (e.g., a FUT8 knock-out cell line in which the FUT8 gene has been disrupted resulting in a lack of a functional α1,6-fucosyltransferase in the cell line, as described in U.S. Pat. No. 7,214,775 (Kyowa Hakko Kogyo Co., Ltd.) and U.S. Pat. No. 7,737,725 (Kyowa Hakko Kirin Co., Ltd), incorporated herein by reference. In some embodiments, the mammalian cell line comprises a mutation or genetic modification in an endogenous GMD gene resulting in a lack of a functional GMD in the cell line, e.g., a GMD knock-out cell line in which the GMD gene has been disrupted, described in e.g., U.S. Pat. No. 7,737,725 (Kyowa Hakko Kirin Co., Ltd), incorporated herein by reference. In some embodiments, the mammalian cell line comprises a mutation or genetic modification in an endogenous Fx gene resulting in a lack of a functional Fx protein. In some embodiments, the mammalian cell line is an Fx knock-out cell line in which the endogenous Fx gene has been disrupted (see, e.g., U.S. Pat. No. 7,737,725 (Kyowa Hakko Kirin Co., Ltd), incorporated herein by reference). In some embodiments, the mammalian cell line comprises a mutation in an endogenous Fx mutation that confers temperature sensitive phenotypes (as described in, e.g., U.S. Pat. No. 8,409,838 (Regeneron Pharmaceuticals), incorporated herein by reference). In some embodiments, the mammalian cell line deficient in its ability to fucosylate proteins is a cell line that has been selected based on resistance to certain lectins, e.g., the Lens culinaris lectin. See, e.g., U.S. Pat. No. 8,409,838 (Regeneron Pharmaceuticals), incorporated herein by reference.

Therapeutic Formulation and Administration

The anti-SARS-CoV-2 spike protein antibodies or antigen-binding fragments used in the methods and uses of the present invention may be formulated for administration in pharmaceutical compositions with one or more pharmaceutically acceptable carriers, excipients or diluents. The pharmaceutical compositions are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN™, Life Technologies, Carlsbad, Ca.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA, J Pharm Sci Technol 52:238-311 (1998).

mAb10933 and mAb10987 are human IgG1 mAbs that bind simultaneously to different, non-overlapping epitopes on severe acute respiratory syndrome coronavirus 2 (SARS-CoV-2) Spike (S) glycoprotein. mAb10933 and mAb10987, the combination of which can be found in the antibody cocktail named REGN-COV2 or REGEN-COV, can be produced by recombinant DNA technology in Chinese hamster ovary (CHO) cell suspension culture and have approximate molecular weights of 145.23 kDa and 144.14 kDa, respectively. The antibodies described herein (e.g., mAb10933 and mAb10987) can be formulated individually or co-formulated. For example, a co-formulated composition can be used to streamline administration (e.g., intravenously or subcutaneously), while individual formulations provide more flexibility in dosing. In particular embodiments, the two antibodies in the composition referred to as REGEN-COV (mAb10933 and mAb10987) can be co-formulated, or the two antibodies can be individually formulated and combined prior to administration.

In some embodiments, the mAb10933 and mAb10987 injection is a sterile, preservative-free, clear to slightly opalescent and colorless to pale yellow solution with a pH of 6.0. In some embodiments, each of mAb10933 and mAb10987 can be formulated as: 120 mg/mL of antibody, 10 mM histidine, 8% (w/v) sucrose, and 0.1% (w/v) polysorbate 80, pH 6.0. Two strengths are available for each antibody: 300 mg in 2.5 mL, and 1332 mg in 11.1 mL. In some embodiments, mAb10933 and mAb10987 are each available as vials with 300 mg antibody (e.g., in a 2.5 mL solution) vial or 1332 mg antibody (e.g., in an 11.1 mL solution). Exemplary contents for each vial are shown below:

300 mg Vial
  mAb10933: Each 2.5 mL of solution contains 300 mg of mAb10933, L-histidine (1.9 mg), L-histidine monohydrochloride monohydrate (2.7 mg), polysorbate 80 (2.5 mg), sucrose (200 mg), and Water for Injection, USP. The pH is 6.0.
  mAb10987: Each 2.5 mL of solution contains 300 mg of mAb10987, L-histidine (1.9 mg), L-histidine monohydrochloride monohydrate (2.7 mg), polysorbate 80 (2.5 mg), sucrose (200 mg), and Water for Injection, USP. The pH is 6.0.

1332 mg Vial
  mAb10933: Each 11.1 mL of solution contains 1332 mg of mAb10933, L-histidine (8.3 mg), L-histidine monohydrochloride monohydrate (12.1 mg), polysorbate 80 (11.1 mg), sucrose (888 mg), and Water for Injection, USP. The pH is 6.0.
  mAb10987: Each 11.1 mL of solution contains 1332 mg of mAb10987, L-histidine (8.3 mg), L-histidine monohydrochloride monohydrate (12.1 mg), polysorbate 80 (11.1 mg), sucrose (888 mg), and Water for Injection, USP. The pH is 6.0.

The dose of antibody administered to a patient may vary depending upon the age and the size of the patient, conditions, route of administration, and the like. The preferred dose is typically calculated according to body weight or body surface area. When an antibody of the present invention is used for treating an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-SARS-CoV-2 spike protein antibodies may be determined empirically; for example, patient progress can be monitored by periodic assessment, and the dose adjusted accordingly. Moreover, interspecies scaling of dosages can be performed using well-known methods in the art (e.g., Mordenti et al., Pharmaceut Res 8:1351 (1991)).

Various delivery systems are known and can be used to administer the pharmaceutical composition of the invention, e.g., encapsulation in liposomes, microparticles, microcapsules, recombinant cells capable of expressing an antibody or other therapeutic protein of the invention, receptor mediated endocytosis (see, e.g., Wu et al., J Biol Chem 262:4429-4432 (1987)). The antibodies and other therapeutically active components of the present invention may also be delivered by gene therapy techniques. Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition as discussed herein. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L.P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, CRC Crit. Ref. Biomed. Eng. 14:201 (1987)). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, Science 249:1527-1533 (1990).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents.

Combination Therapies

In some cases, the anti-SARS-CoV-2 spike protein antibodies can be administered with a further therapeutic agent. In some embodiments, the further therapeutic agent is an anti-viral drug or a vaccine. In some embodiments, the further therapeutic agent is selected from the group consisting of: an anti-inflammatory agent, an antimalarial agent, an antibody or antigen-binding fragment thereof that specifically binds TMPRSS2, and an antibody or antigen-binding fragment thereof that specifically binds to SARS-CoV-2 spike protein. In some cases, the antimalarial agent is chloroquine or hydroxychloroquine. In some cases, the anti-inflammatory agent is an antibody, such as sarilumab, tocilizumab, or gimsilumab. In some embodiments, the further therapeutic agent is a second antibody or antigen-binding fragment comprising HCDR1, HCDR2, HCDR3, LCDR1, LCDR2, and LCDR3 sequences of Table 1.

The further therapeutic agents may be administered to a subject or used prior to administration of an anti-SARS-CoV-2 spike protein antibody of the present invention. For example, a first component may be deemed to be administered/used "prior to" a second component if the first component is administered/used 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration/use of the second component. In other embodiments, the further therapeutic agents may be administered to a subject or used after administration of an anti-SARS-CoV-2 spike protein antibody of the present invention. For example, a first component may be deemed to be administered/used "after" a second component if the first component is administered/used 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration/use of the second component. In yet other embodiments, the further therapeutic agents may be administered to a subject or used concurrent with administration of an anti-SARS-CoV-2 spike protein antibody of the present invention. "Concurrent" administration, for purposes of the present invention, includes, e.g., administration of an anti-SARS-CoV-2 spike protein antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-SARS-CoV-2 spike protein and the additional therapeutically active component may be administered intravenously, subcutaneously, etc.). In any event, administering the components in a single dosage form, in separate dosage forms by the same route, or in separate dosage forms by different routes are all considered "concurrent administration," for purposes of the present disclosure. For purposes of the present disclosure, administration of an anti-SARS-CoV-2 spike protein antibody "prior to", "concurrent with," or "after" (as those terms are defined herein above) administration of a further therapeutic agent is considered administration of an anti-SARS-CoV-2 spike protein antibody "in combination with" the further therapeutic agent.

Dosage

The amount of active ingredient (e.g., anti-SARS-CoV-2 spike protein antibodies, or other therapeutic agents given in combination with anti-SARS-CoV-2 spike protein antibodies) that can be administered to a subject is, generally, a therapeutically effective amount, as discussed elsewhere herein.

In some embodiments, a therapeutically effective amount can be from about 0.05 mg to about 20 g; e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, about 1 g, about 1.1 g, about 1.2 g, about 1.3 g, about 1.4 g, 1.5 g, about 1.6 g, about 1.7 g, about 1.8 g, about 1.9 g, about 2 g, about 2.1 g, about 2.2 g, about 2.3 g, about 2.4 g, about 2.5 g, about 2.6 g, about 2.7 g, about 2.8 g, about 2.9 g, about 3 g, about 3.1 g, about 3.2 g, about 3.3 g, about 3.4 g, about 3.5 g, about 3.6 g, about 3.7 g, about 3.8 g, about 3.9 g, about 4 g, about 4.1 g, about 4.2 g, about 4.3 g, about 4.4 g, about 4.5 g, about 4.6 g, about 4.7 g, about 4.8 g, about 4.9 g, about 5 g, about 5.1 g, about 5.2 g, about 5.3 g, about 5.4 g, about 5.5 g, about 5.6 g, about 5.7 g, about 5.8 g, about 5.9 g, about 6 g, about 6.1 g, about 6.2 g, about 6.3 g, about 6.4 g, about 6.5 g, about 6.6 g, about 6.7 g, about 6.8 g, about 6.9 g, about 7 g, about 7.1 g, about 7.2 g, about 7.3 g, about 7.4 g, about 7.5 g, about 7.6 g, about 7.7 g, about 7.8 g, about 7.9 g, about 8 g, about 8.1 g, about 8.2 g, about 8.3 g, about 8.4 g, about 8.5 g, about 8.6 g, about 8.7 g, about 8.8 g, about 8.9 g, about 9 g, about 9.1 g, about 9.2 g, about 9.3 g, about 9.4 g, about 9.5 g, about 9.6 g, about 9.7 g, about 9.8 g, about 9.9 g, about 10 g, about 11 g, about 12 g, about 13 g, about 14 g, about 15 g, about 16 g, about 17 g, about 18 g, about 19 g, or about 20 g of the respective antibody. In some cases, the therapeutically effective amount is from 0.1 g to 3.5 g. In some cases, the therapeutically effective amount is from 0.5 g to 2 g. In some cases, the therapeutically effective amount is from 0.8 g to 1.6 g. In some cases, the therapeutically effective amount is from 1.0 g to 1.4 g. In some cases, the therapeutically effective amount is from 1 g to 7 g. In some cases, the therapeutically effective amount is from 3 g to 5 g. In some cases, the therapeutically effective amount is from 3.5 g to 4.5 g. In any of these embodiments, discussed above, the dose may represent the dose of a single antibody or, alternatively, the total dose of a combination of antibodies. For example, two different anti-SARS-CoV-2-spike glycoprotein antibodies may be co-administered, in which the dose of each antibody represents one-half of the total dose administered.

In some embodiments, a combination of mAb10933 and mAb10987 are co-administered intravenously or subcutaneously at a total dose of from 300 mg to 2400 mg. In some cases, the total dose is from 100 mg to 5000 mg. In some embodiments, the total dose is from 200 mg to 400 mg, from 500 mg to 700 mg, from 1000 mg to 1400 mg, or from 2000 mg to 2800 mg. In some embodiments, the total dose is from 250 mg to 350 mg, from 550 mg to 650 mg, from 1150 mg to 1250 mg, or from 2300 mg to 2500 mg. In some cases, the total dose is 300 mg, 600 mg, 1200 mg or 2400 mg. In some cases, the total dose is 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1000 mg, 1050 mg, 1100 mg, 1150 mg, 1200 mg 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, or 3000 mg. In some embodiments, the total dose is 2400 mg, and each of mAb10933 and mAb10987 is administered at a dose of 1200 mg intravenously. In some embodiments, the total dose is 1200 mg, and each of mAb10933 and mAb10987 is administered at a dose of 600 mg intravenously. In some embodiments, the total dose is 600 mg, and each of mAb10933 and mAb10987 is administered at a dose of 300 mg intravenously. In some embodiments, the total dose is 300 mg, and each of mAb10933 and mAb10987 is administered at a dose of 150 mg intravenously. In some embodiments, the total dose is 1200 mg, and each of mAb10933 and mAb10987 is administered at a dose of 600 mg subcutaneously. In some embodiments, the total dose is 600 mg, and each of mAb10933 and mAb10987 is administered at a dose of 300 mg subcutaneously. In some embodiments, each individual antibody is administered at a dose of from 100 mg to 200 mg, from 200 mg to 400 mg, from 500 mg to 700 mg, or from 2300 mg to 2500 mg. In some cases, each individual antibody is administered at a dose of from 124 mg to 175 mg, from 250 mg to 350 mg, from 550 mg to 650 mg, or from 1150 mg to 1250 mg.

The amount of anti-SARS-CoV-2 spike protein antibody or other therapeutic agent contained within the individual doses may be expressed in terms of milligrams of antibody per kilogram of patient body weight (i.e., mg/kg). For example, the anti-SARS-CoV-2 spike protein antibodies may be administered to a patient at a dose of about 0.0001 to about 200 mg/kg of patient body weight (e.g. 0.1 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 10.5 mg/kg, 11.0 mg/kg, 11.5 mg/kg, 12.0 mg/kg, 12.5 mg/kg, 13.0 mg/kg, 13.5 mg/kg, 14.0 mg/kg, 14.5 mg/kg, 15.0 mg/kg, 15.5 mg/kg, 16.0 mg/kg, 16.5 mg/kg, 17.0 mg/kg, 17.5 mg/kg, 18.0 mg/kg, 18.5 mg/kg, 19.0 mg/kg, 19.5 mg/kg, 20.0 mg/kg, 20.5 mg/kg, 21.0 mg/kg, 21.5 mg/kg, 22.0 mg/kg, 22.5 mg/kg, 23.0 mg/kg, 23.5 mg/kg, 24.0 mg/kg, 24.5 mg/kg, 25.0 mg/kg, 25.5 mg/kg, 26.0 mg/kg, 26.5 mg/kg, 27.0 mg/kg, 27.5 mg/kg, 28.0 mg/kg, 28.5 mg/kg, 29.0 mg/kg, 29.5 mg/kg, 30.0 mg/kg, 30.5 mg/kg, 31.0 mg/kg, 31.5 mg/kg, 32.0 mg/kg, 32.5 mg/kg, 33.0 mg/kg, 33.5 mg/kg, 34.0 mg/kg, 34.5 mg/kg, 35.0 mg/kg, 35.5 mg/kg, 36.0 mg/kg, 36.5 mg/kg, 37.0 mg/kg, 37.5 mg/kg, 38.0 mg/kg, 38.5 mg/kg, 39.0 mg/kg, 39.5 mg/kg, 40.0 mg/kg, 40.5 mg/kg, 41.0 mg/kg, 41.5 mg/kg, 42.0 mg/kg, 42.5 mg/kg, 43.0 mg/kg, 43.5 mg/kg, 44.0 mg/kg, 44.5 mg/kg, 45.0 mg/kg, 45.5 mg/kg, 46.0 mg/kg, 46.5 mg/kg, 47.0 mg/kg, 47.5 mg/kg, 48.0 mg/kg, 48.5 mg/kg, 49.0 mg/kg, 49.5 mg/kg, 50.0 mg/kg, 50.5 mg/kg, 51.0 mg/kg, 51.5 mg/kg, 52.0 mg/kg, 52.5 mg/kg, 53.0 mg/kg, 53.5 mg/kg, 54.0 mg/kg, 54.5 mg/kg, 55.0 mg/kg, 55.5 mg/kg, 56.0 mg/kg, 56.5 mg/kg, 57.0 mg/kg, 57.5 mg/kg, 58.0 mg/kg, 58.5 mg/kg, 59.0 mg/kg, 59.5 mg/kg, 60.0 mg/kg, 60.5 mg/kg, 61.0 mg/kg, 61.5 mg/kg, 62.0 mg/kg, 62.5 mg/kg, 63.0 mg/kg, 63.5 mg/kg, 64.0 mg/kg, 64.5 mg/kg, 65.0 mg/kg, 65.5 mg/kg, 66.0 mg/kg, 66.5 mg/kg, 67.0 mg/kg, 67.5 mg/kg, 68.0 mg/kg, 68.5 mg/kg, 69.0 mg/kg, 69.5 mg/kg, 70.0 mg/kg, 70.5 mg/kg, 71.0 mg/kg, 71.5 mg/kg, 72.0 mg/kg, 72.5 mg/kg, 73.0 mg/kg, 73.5 mg/kg, 74.0 mg/kg, 74.5 mg/kg, 75.0 mg/kg, 75.5 mg/kg, 76.0 mg/kg, 76.5 mg/kg, 77.0 mg/kg, 77.5 mg/kg, 78.0 mg/kg, 78.5 mg/kg, 79.0 mg/kg, 79.5 mg/kg, 80.0 mg/kg, 80.5 mg/kg, 81.0 mg/kg, 81.5 mg/kg, 82.0 mg/kg, 82.5 mg/kg, 83.0 mg/kg, 83.5 mg/kg, 84.0 mg/kg, 84.5 mg/kg, 85.0 mg/kg, 85.5 mg/kg, 86.0 mg/kg, 86.5 mg/kg, 87.0 mg/kg, 87.5 mg/kg, 88.0 mg/kg, 88.5 mg/kg, 89.0 mg/kg, 89.5 mg/kg, 90.0 mg/kg, 90.5 mg/kg, 91.0 mg/kg, 91.5 mg/kg, 92.0 mg/kg, 92.5 mg/kg, 93.0 mg/kg, 93.5 mg/kg, 94.0 mg/kg, 94.5 mg/kg, 95.0 mg/kg, 95.5 mg/kg, 96.0 mg/kg, 96.5 mg/kg, 97.0 mg/kg, 97.5 mg/kg, 98.0 mg/kg, 98.5 mg/kg, 99.0 mg/kg, 99.5 mg/kg, 100.0 mg/kg, 100.5 mg/kg, 101.0 mg/kg, 101.5 mg/kg, 102.0 mg/kg, 102.5 mg/kg, 103.0 mg/kg, 103.5 mg/kg, 104.0 mg/kg, 104.5 mg/kg, 105.0 mg/kg, 105.5 mg/kg, 106.0 mg/kg, 106.5 mg/kg, 107.0 mg/kg, 107.5 mg/kg, 108.0 mg/kg, 108.5 mg/kg, 109.0 mg/kg, 109.5 mg/kg, 110.0 mg/kg, 110.5 mg/kg, 111.0 mg/kg, 111.5 mg/kg, 112.0 mg/kg, 112.5 mg/kg, 113.0 mg/kg, 113.5 mg/kg, 114.0 mg/kg, 114.5 mg/kg, 115.0 mg/kg, 115.5 mg/kg, 116.0 mg/kg, 116.5 mg/kg, 117.0 mg/kg, 117.5 mg/kg, 118.0 mg/kg, 118.5 mg/kg, 119.0 mg/kg, 119.5 mg/kg, 120.0 mg/kg, 120.5 mg/kg, 121.0 mg/kg, 121.5 mg/kg, 122.0 mg/kg, 122.5 mg/kg, 123.0 mg/kg, 123.5 mg/kg, 124.0 mg/kg, 124.5 mg/kg, 125.0 mg/kg, 125.5 mg/kg, 126.0 mg/kg, 126.5 mg/kg, 127.0 mg/kg, 127.5 mg/kg, 128.0 mg/kg, 128.5 mg/kg, 129.0 mg/kg, 129.5 mg/kg, 130.0 mg/kg, 130.5 mg/kg, 131.0 mg/kg, 131.5 mg/kg, 132.0 mg/kg, 132.5 mg/kg, 133.0 mg/kg, 133.5 mg/kg, 134.0 mg/kg, 134.5 mg/kg, 135.0 mg/kg, 135.5 mg/kg, 136.0 mg/kg, 136.5 mg/kg, 137.0 mg/kg, 137.5 mg/kg, 138.0 mg/kg, 138.5 mg/kg, 139.0 mg/kg, 139.5 mg/kg, 140.0 mg/kg, 140.5 mg/kg, 141.0 mg/kg, 141.5 mg/kg, 142.0 mg/kg, 142.5 mg/kg, 143.0 mg/kg, 143.5 mg/kg, 144.0 mg/kg, 144.5 mg/kg, 145.0 mg/kg, 145.5 mg/kg, 146.0 mg/kg, 146.5 mg/kg, 147.0 mg/kg, 147.5 mg/kg, 148.0 mg/kg, 148.5 mg/kg, 149.0 mg/kg, 149.5 mg/kg, 150.0 mg/kg, 150.5 mg/kg, 151.0 mg/kg, 151.5 mg/kg, 152.0 mg/kg, 152.5 mg/kg, 153.0 mg/kg, 153.5 mg/kg, 154.0 mg/kg, 154.5 mg/kg, 155.0 mg/kg, 155.5 mg/kg, 156.0 mg/kg, 156.5 mg/kg, 157.0 mg/kg, 157.5 mg/kg, 158.0 mg/kg, 158.5 mg/kg, 159.0 mg/kg, 159.5 mg/kg, 160.0 mg/kg, 160.5 mg/kg, 161.0 mg/kg, 161.5 mg/kg, 162.0 mg/kg, 162.5 mg/kg, 163.0 mg/kg, 163.5 mg/kg, 164.0 mg/kg, 164.5 mg/kg, 165.0 mg/kg, 165.5 mg/kg, 166.0 mg/kg, 166.5 mg/kg, 167.0 mg/kg, 167.5 mg/kg, 168.0 mg/kg, 168.5 mg/kg, 169.0 mg/kg, 169.5 mg/kg, 170.0 mg/kg, 170.5 mg/kg, 171.0 mg/kg, 171.5 mg/kg, 172.0 mg/kg, 172.5 mg/kg, 173.0 mg/kg, 173.5 mg/kg, 174.0 mg/kg, 174.5 mg/kg, 175.0 mg/kg, 175.5 mg/kg, 176.0 mg/kg, 176.5 mg/kg, 177.0 mg/kg, 177.5 mg/kg, 178.0 mg/kg, 178.5 mg/kg, 179.0 mg/kg, 179.5 mg/kg, 180.0 mg/kg, 180.5 mg/kg, 181.0 mg/kg, 181.5 mg/kg, 182.0 mg/kg, 182.5 mg/kg, 183.0 mg/kg, 183.5 mg/kg, 184.0 mg/kg, 184.5 mg/kg, 185.0 mg/kg, 185.5 mg/kg, 186.0 mg/kg, 186.5 mg/kg, 187.0 mg/kg, 187.5 mg/kg, 188.0 mg/kg, 188.5 mg/kg, 189.0 mg/kg, 189.5 mg/kg, 190.0 mg/kg, 190.5 mg/kg, 191.0 mg/kg, 191.5 mg/kg, 192.0 mg/kg, 192.5 mg/kg, 193.0 mg/kg, 193.5 mg/kg, 194.0 mg/kg, 194.5 mg/kg, 195.0 mg/kg, 195.5 mg/kg, 196.0 mg/kg, 196.5 mg/kg, 197.0 mg/kg, 197.5 mg/kg, 198.0 mg/kg, 198.5 mg/kg, 199.0 mg/kg, 199.5 mg/kg, or 200.0 mg/kg).

Administration Regimens

According to certain embodiments of the present invention, multiple doses of an active ingredient (e.g., an anti-SARS-CoV-2 spike protein antibody) may be administered to a subject over a defined time course. The methods according to this aspect of the invention comprise sequentially administering to a subject multiple doses of an active ingredient of the invention. As used herein, "sequentially administering" means that each dose of an active ingredient is administered to the subject at a different point in time, e.g., on different days separated by a predetermined interval (e.g., hours, days, weeks or months). The present invention includes methods which comprise sequentially administering to the patient a single initial dose of an active ingredient, followed by one or more secondary doses of the active ingredient, and optionally followed by one or more tertiary doses of the active ingredient.

The terms "initial dose," "secondary doses," and "tertiary doses," refer to the temporal sequence of administration of the active ingredient, e.g., anti-SARS-CoV-2 spike protein antibody of the invention or of a combination therapy of the invention, e.g., two different anti-SARS-CoV-2 spike protein antibodies. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the active ingredient, e.g., anti-SARS-CoV-2 spike protein antibody, but generally may differ from one another in terms of frequency of administration. In certain embodiments, however, the amount of the active ingredient, e.g., anti-SARS-CoV-2 spike protein antibody, contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of the active ingredient, e.g., an anti-SARS-CoV-2 spike protein antibody, which is administered to a patient prior to the administration of the very next dose in the sequence with no intervening doses.

The methods according to this aspect of the invention may comprise administering to a patient any number of secondary and/or tertiary doses of an active ingredient of the invention, e.g., an anti-SARS-CoV-2 spike protein antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens in which 2 to 6 loading doses are administered to a patient a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of once a month, then the maintenance doses may be administered to the patient once every six weeks, once every two months, once every three months, etc.). In certain embodiments, a single dose is administered to the subject as part of a prophylactic or therapeutic course of treatment. In some embodiments, the dose or doses are administered to treat a high-risk adult or pediatric patient with diagnosed mild-to-moderate coronavirus disease (COVID-19).

In some embodiments, dosage in adults and in pediatric patients (12 years of age and older weighing at least 40 kg) is:

600 mg of mAb10933 (casirivimab) and 600 mg of mAb10987 (imdevimab) administered together as a single intravenous infusion via pump or gravity (see Table 4A), or as a single subcutaneous injection, or as two subcutaneous injections; or 1,200 mg of casirivimab and 1,200 mg of imdevimab administered together as a single intravenous infusion via pump or gravity (see Table 4B). Exemplary preparation instructions for mAb10933+mAb10987 (casirivimab and imdevimab, respectively) are as follows:
1. Remove the casirivimab and imdevimab vials from refrigerated storage and allow to equilibrate to room temperature for approximately 20 minutes before preparation. Do not expose to direct heat. Do not shake the vials.
2. Inspect casirivimab and imdevimab vials visually for particulate matter and discoloration prior to administration. Should either be observed, the solution must be discarded, and fresh solution prepared. The solution for each vial should be clear to slightly opalescent, colorless to pale yellow.
3. Obtain a prefilled IV infusion bag containing either 50 mL, 100 mL, 150 mL, or 250 mL of 0.9% Sodium Chloride Injection.
4. If administering the 600 mg/600 mg dose:
   Withdraw 5 mL of casirivimab and 5 mL of imdevimab from each respective vial using two separate syringes (see Table 4A) and inject all 10 mL into a prefilled infusion bag containing 0.9% Sodium Chloride Injection (see Table 4A). Discard any product remaining in the vial.
OR
   If administering the alternative 1,200 mg/1,200 mg dose:
   Withdraw 10 mL of casirivimab and 10 mL of imdevimab from each respective vial using two separate syringes (see Table 4B) and inject all 20 mL into a prefilled infusion bag containing 0.9% Sodium Chloride Injection (see Table 4B). Discard any product remaining in the vial.
5. Gently invert infusion bag by hand approximately 10 times. Do not shake.
6. This product is preservative-free and therefore, the diluted infusion solution should be administered immediately.
If immediate administration is not possible, store the diluted casirivimab with imdevimab infusion solution in the refrigerator between 2° C. to 8° C. (36° F. to 46° F.) for no more than 36 hours or at room temperature up to 25° C. (77° F.) for no more than 4 hours. If refrigerated, allow the infusion solution to equilibrate to room temperature for approximately 30 minutes prior to administration.
Exemplary administration instructions are as follows:
1. Gather the recommended materials for infusion:
   a. Polyvinyl chloride (PVC), Polyethylene (PE)-lined PVC, or Polyurethane (PU) infusion set
   b. In-line or add-on 0.2 micron polyethersulfone (PES) filter
2. Attach the infusion set to the IV bag.
3. Prime the infusion set.
4. Administer as an IV infusion via pump or gravity over at least 60 minutes through an intravenous line containing a sterile, in-line or add-on 0.2-micron polyethersulfone (PES) filter (see Table 4A or Table 4B).
5. The prepared infusion solution should not be administered simultaneously with any other medication. The compatibility of mAb10933 and mAb10987 injection with IV solutions and medications other than 0.9% Sodium Chloride Injection is not known.
6. After infusion is complete, flush with 0.9% Sodium Chloride Injection.
7. Discard unused product.
8. Clinically monitor patients during administration and observe patients for at least 1 hour after infusion is complete.

TABLE 4A

Recommended Dosing, Dilution and Administration Instructions for 600 mg Casirivimab with 600 mg Imdevimab for IV Infusion
Casirivimab with Imdevimab 1,200 mg Dose[a] Add:
5 mL of casirivimab (use 1 vial of 11.1 mL OR 2 vials of 2.5 mL) and
5 mL of imdevimab (use 1 vial of 11.1 mL OR 2 vials of 2.5 mL)
for a total of 10 mL into a prefilled 0.9% sodium chloride infusion bag and administer as instructed below[b]

| Size of Prefilled 0.9% Sodium Chloride Infusion Bag | Maximum Infusion Rate | Minimum Infusion Time |
|---|---|---|
| 50 mL[c] | 180 mL/hr | 20 minutes |
| 100 mL | 310 mL/hr | 21 minutes |
| 150 mL | 310 mL/hr | 31 minutes |
| 250 mL | 310 mL/hr | 50 minutes |

[a]600 mg casirivimab and 600 mg imdevimab are added to the same infusion bag and administered together as a single intravenous infusion.
[b]After infusion is complete, flush with 0.9% Sodium Chloride Injection
[c]The minimum infusion time for patients administered casirivimab with imdevimab together using the 50 mL prefilled 0.9% Sodium Chloride infusion bag must be at least 20 minutes to ensure safe use.

TABLE 4B

Recommended Dosing, Dilution and Administration Instructions for 1,200 mg Casirivimab with 1,200 mg Imdevimab for IV Infusion
Casirivimab with Imdevimab 2,400 mg Dose[a]. Add:
10 mL of casirivimab (use 1 vial of 11.1 mL OR 4 vials of 2.5 mL) and
10 mL of imdevimab (use 1 vial of 11.1 mL OR 4 vials of 2.5 mL)
for a total of 20 mL into a prefilled 0.9% sodium chloride infusion bag and administer as indicated below[b].

| Size of prefilled 0.9% sodium chloride infusion bag | Maximum infusion rate | Minimum infusion time |
|---|---|---|
| 50 mL[c] | 210 mL/hr | 20 minutes |
| 100 mL | 310 mL/hr | 23 minutes |
| 150 mL | 310 mL/hr | 33 minutes |
| 250 mL | 310 mL/hr | 52 minutes |

[a]1,200 mg casirivimab and 1,200 mg imdevimab are added to the same infusion bag and administered together as a single intravenous infusion.
[b]After infusion is complete, flush with 0.9% Sodium Chloride Injection.
[c]The minimum infusion time for patients administered casirivimab with imdevimab together using the 50 mL prefilled 0.9% Sodium Chloride infusion bag should be at least 20 minutes to ensure safe use.

Kits

The present invention further provides an article of manufacturing or kit, comprising a packaging material, container and a pharmaceutical agent contained within the container, wherein the pharmaceutical agent comprises at least one anti-SARS-CoV-2 spike glycoprotein antibody, and wherein the packaging material comprises a label or package insert showing indications and directions for use. In one embodiment, the kit may include two anti-SARS-CoV-2 spike glycoprotein antibodies, and the two antibodies may be contained in separate containers.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight,

Example 1. Clinical Evaluation of Anti-SARS-CoV-2 Spike Glycoprotein Antibodies in Hospitalized Adult Patients with COVID-19

The below-described clinical study is an adaptive, phase 1/2/3, randomized, double-blinded, placebo-controlled master protocol to evaluate the efficacy, safety, and tolerability of mAb10933+mAb10987 in hospitalized adult patients with COVID-19. The safety, tolerability, and efficacy of mAb10989 will also be evaluated in the phase 1 portion of the study to enable further investigation in other clinical settings.

Study Objectives: The primary and secondary objectives of each phase of the study are set forth below.

Primary Objectives:
Phase 1
Part A
 To evaluate the safety and tolerability of mAb10933+mAb10987 compared to placebo
 To evaluate the virologic efficacy of mAb10933+mAb10987 compared to placebo in reducing viral shedding of SARS-CoV-2
Part B
 To evaluate the safety and tolerability of mAb10989 compared to placebo
 To evaluate the virologic efficacy of mAb10989 compared to placebo in reducing viral shedding of SARS-CoV-2
Phase 2
 To evaluate the virologic efficacy of mAb10933+mAb10987 compared to placebo in reducing viral shedding of SARS-CoV-2
 To evaluate the clinical efficacy of mAb10933+mAb10987 compared to placebo in improving clinical status
Phase 3
The primary objective of phase 3 is to evaluate and confirm the clinical efficacy of mAb10933+mAb10987 compared to placebo in improving clinical status.

Secondary Objectives:
Phase 1
Part A
 To evaluate additional indicators of virologic efficacy of mAb10933+mAb10987 compared to placebo
 To evaluate the clinical efficacy of mAb10933+mAb10987 compared to placebo in improving clinical outcomes
 To characterize the pharmacokinetic (PK) profiles of mAb10933 and mAb10987 in serum
 To assess the immunogenicity of mAb10933 and mAb10987
Part B
 To evaluate additional indicators of virologic efficacy of mAb10989 compared to placebo
 To evaluate the clinical efficacy of mAb10989 compared to placebo in improving clinical outcomes
 To compare quantitative reverse transcription polymerase chain reaction (RT-qPCR) results acquired with different sample types (nasopharyngeal, nasal, and saliva)
 To characterize the PK profile of mAb10989 in serum
 To assess the immunogenicity of mAb10989
Phase 2
 To evaluate additional indicators of virologic efficacy of mAb10933+mAb10987 compared to placebo
 To evaluate additional indicators of clinical efficacy of mAb10933+mAb10987 compared to placebo
 To evaluate the safety and tolerability of mAb10933+mAb10987 compared to placebo
 To characterize the concentrations of mAb10933 and mAb10987 in serum over time
 To assess the immunogenicity of mAb10933 and mAb10987
Phase 3
 To evaluate the clinical efficacy of mAb10933+mAb10987 compared to placebo
 To evaluate the safety and tolerability of mAb10933+mAb10987 compared to placebo
 To characterize the concentrations of mAb10933 and mAb10987 in serum over time
 To assess the immunogenicity of mAb10933 and mAb10987

Study Design: This study was an adaptive, phase 1/2/3, randomized, double-blinded, placebo-controlled master protocol to evaluate the efficacy, safety, and tolerability of mAb10933+mAb10987 in hospitalized adult patients with COVID-19. The safety, tolerability, and efficacy of mAb10989 was evaluated in the phase 1 portion of the study to enable further investigation in other clinical settings. Eligible patients who were hospitalized for ≤72 hours at screening were enrolled in 1 of 4 cohorts based on disease severity at randomization. Phase 2 was initiated following independent data monitoring committee (IDMC) clearance of a phase 1 sentinel safety group, and after initiation, enrolled concurrently with phase 1. Once phase 2 was active, phase 1 continued to enroll to completion, but phase 2 enrollment did not require the completion of phase 1 enrollment.

Study Duration: The phase 1 portion of the study lasted up to 170 days. The phase 2 portion of the study lasted up to 58 days. The phase 3 portion of the study lasted up to 58 days.

Study Population: In order to evaluate potential differential treatment effects across the spectrum of hospitalized COVID-19 patients, the study was conducted and analyzed in four cohorts of hospitalized adult patients with COVID-19: Cohort 1A (Patients with COVID-19 symptoms but not requiring supplemental oxygen); Cohort 1 (Patients on low-flow oxygen supplementation); Cohort 2 (Patients requiring high-intensity oxygen therapy but not on mechanical ventilation); and Cohort 3 (Patients requiring mechanical ventilation).

Cohorts—Eligible patients were enrolled in 1 of 4 cohorts based on disease severity at randomization: Cohort 1A (Patients with COVID-19 symptoms but not requiring supplemental oxygen); Cohort 1 (O2 saturation >93% on low-flow oxygen via nasal cannula, simple face mask, or other similar device); Cohort 2 (On high-intensity oxygen therapy* but not on mechanical ventilation—* High-intensity oxygen therapy is defined as the use of non-rebreather mask with an oxygen flow rate of at least 10 L/min; use of a high flow device with at least 50% FiO2, or use of non-invasive ventilation to treat hypoxemia); and Cohort 3 (On mechanical ventilation).

Sample Size—The phase 1 portion of the study included up to 100 patients from cohort 1 only: Part A for mAb10933+mAb10987: Approximately 20 patients per arm for a total of 60 patients across 3 treatment arms; and Part B for mAb10989: Approximately 20 patients per arm for a total of 40 patients across 2 treatment arms. The phase 2 portion of the study included approximately 1560 patients: Cohort 1A: Approximately 130 patients per arm for a total of 390 patients across 3 treatment arms; Cohort 1: Approximately 130 patients per arm for a total of 390 patients across 3 treatment arms; Cohort 2: Approximately 130 patients per arm for a total of 390 patients across 3 treatment arms; and Cohort 3: Approximately 130 patients per arm for a total of 390 patients across 3 treatment arms. Sample size for phase 3 is estimated to be approximately 1350 (150 patients per arm across 3 treatment arms in each of the 3 cohorts). Finalization of the sample size and patient population for phase 3 is subject to change and will be determined after a full review of phase 2 data.

Inclusion Criteria: A patient must have met the following criteria to be eligible for inclusion in the study:

1. Has provided informed consent (signed by study patient or legally acceptable representative);
2. Male or female adult ≥18 years of age (or country's legal age of adulthood) at randomization;
3. Has SARS-CoV-2-positive molecular diagnostic test (by validated SARS-CoV-2 RT-PCR or other molecular diagnostic assay, using an appropriate sample such as NP, nasal, oropharyngeal [OP], or saliva) ≤72 hours prior to randomization and no alternative explanation for current clinical condition. A historical record of positive result from test conducted ≤72 hours prior to randomization is acceptable;
4. Has symptoms consistent with COVID-19, with onset ≤10 days before randomization; and
5. Hospitalized for COVID-19 illness for <72 hours with at least 1 of the following at randomization—patients meeting more than one criterion will be categorized in the most severely affected category:
   a. Cohort 1A: With COVID-19 symptoms but not requiring supplemental oxygen
   b. Cohort 1: Maintains O2 saturation >93% on low-flow oxygen via nasal cannula, simple face mask, or other similar device
   c. Cohort 2: High-intensity oxygen therapy without mechanical ventilation, where high-intensity is defined as receiving supplemental oxygen delivered by 1 of the following devices:
      Non-rebreather mask (with an SpO2 ≤96% while receiving an oxygen flow rate of at least 10 L/min)
      High-flow device (e.g., AIRVO™ or Optiflow™) with at least 50% FiO2
      Non-invasive ventilator, including continuous positive airway pressure (CPAP), to treat hypoxemia (excluding isolated use for sleep-disordered breathing)
   d. Cohort 3: On mechanical ventilation.

Exclusion Criteria: A patient who met any of the following criteria was excluded from the study:

1. Phase 1 only: Patients maintaining O2 saturation >94% on room air;
2. In the opinion of the investigator, unlikely to survive for >48 hours from screening;
3. Receiving extracorporeal membrane oxygenation (ECMO);
4. Has new-onset stroke or seizure disorder during hospitalization;
5. Initiated on renal replacement therapy due to COVID-19;
6. Has circulatory shock requiring vasopressors at randomization (Patients who require vasopressors for sedation-related hypotension or reasons other than circulatory shock may be eligible in this study);
7. Patients who have received convalescent plasma or IVIG in the past 5 months or plan to receive during the study period for any indication;
8. Participation in a clinical research study, including any double-blind study, evaluating an investigational product within 30 days and less than 5 half-lives of the investigational product prior to the screening visit (The use of remdesivir, hydroxychloroquine, or other treatments (except for COVID-19 convalescent plasma or IVIG) being used for COVID-19 treatments in the context of the local standard-of-care or an open-label study or compassionate use protocol is permitted);
9. Any physical examination findings, history of illness, and/or concomitant medications that, in the opinion of the study investigator, might confound the results of the study or pose an additional risk to the patient by their participation in the study;
10. Known allergy or hypersensitivity to components of study drug;
11. Pregnant or breastfeeding women; or
12. Continued sexual activity in women of childbearing potential (WOCBP)* or sexually active men who are unwilling to practice highly effective contraception prior to the initial dose/start of the first treatment, during the study, and for at least 6 months after the last dose.

Highly effective contraceptive measures in women include:
  Stable use of combined (estrogen and progestogen containing) hormonal contraception (oral, intravaginal, transdermal) or progestogen-only hormonal contraception (oral, injectable, implantable) associated with inhibition of ovulation initiated 2 or more menstrual cycles prior to screening
  Intrauterine device (IUD)
  Intrauterine hormone-releasing system (IUS)
  Bilateral tubal ligation
  Vasectomized partner,† and/or
  Sexual abstinence‡,§

Male study participants with WOCBP partners were required to use condoms unless they were vasectomized† or practice sexual abstinence.‡,§

\* WOCBP defined as women who are fertile following menarche until becoming postmenopausal, unless permanently sterile. A postmenopausal state is defined as no menses for 12 months without an alternative medical cause. A high follicle stimulating hormone (FSH) level in the postmenopausal range may be used to confirm a postmenopausal state in women not using hormonal contraception or hormonal replacement therapy. However, in the absence of 12 months of amenorrhea, a single FSH measurement is insufficient to determine the occurrence of a postmenopausal state. The above definitions are according to Clinical Trial Facilitation Group (CTFG) guidance. Pregnancy testing and contraception are not required for women with documented hysterectomy or tubal ligation. Permanent sterilization methods include hysterectomy, bilateral salpingectomy, and bilateral oophorectomy.

† Vasectomized partner or vasectomized study participant must have received medical assessment of the surgical success.

‡ Sexual abstinence is considered a highly effective method only if defined as refraining from heterosexual intercourse during the entire period of risk associated with the study drugs. The reliability of sexual abstinence needs to be evaluated in relation to the duration of the clinical trial and the preferred and usual lifestyle of the patient.

§ Periodic abstinence (calendar, symptothermal, post-ovulation methods), withdrawal (coitus interruptus), spermicides only, and lactational amenorrhea method (LAM) are not acceptable methods of contraception. Female condom and male condom should not be used together.

Study Treatments: In phase 1, part A, patients received co-administered mAb10933+mAb10987 combination therapy 2.4 g (1.2 g of mAb10933 plus 1.2 g of mAb10987) intravenously (IV) single dose, co-administered mAb10933+mAb10987 combination therapy 8.0 g (4.0 g of mAb10933 plus 4.0 g of mAb10987) IV single dose, or placebo IV single dose. In phase I, part B, patients received mAb10989 monotherapy 1.2 g IV single dose, or placebo IV single dose. In phase 2, patients received co-administered mAb10933+mAb10987 combination therapy 2.4 g (1.2 g of mAb10933 plus 1.2 g of mAb10987) IV single dose, co-administered mAb10933+mAb10987 combination therapy 8.0 g (4.0 g of mAb10933 plus 4.0 g of mAb10987) IV single dose, or placebo IV single dose. Treatment arms for phase 3 are determined after review of phase 2 data.

Endpoints: Primary, secondary, and exploratory endpoints are specified for each phase, as defined below.

Primary Endpoints

Phase 1 (Cohort 1 Only)

The primary endpoints for phase 1 (Part A and Part B) were:
  Proportion of patients with treatment-emergent serious adverse events (SAEs) through day 169
  Proportion of patients with infusion-related reactions (grade ≥2) through day 4
  Proportion of patients with hypersensitivity reactions (grade ≥2) through day 29
  Time-weighted average change from baseline viral shedding ($\log_{10}$ copies/mL) from day 1 to day 22, as measured by quantitative reverse transcription polymerase chain reaction (RT-qPCR) in nasopharyngeal (NP) swab samples (time-weighted average of change from baseline viral shedding from day 1 to day 22 will be calculated for each patient using the trapezoidal rule as the area under the curve for change from baseline at each time point divided by the time interval for the observation period).

Phase 2

The primary endpoints for phase 2 in each cohort were:
Cohort 1A and Cohort 1
  Time-weighted average change from baseline viral shedding ($\log_{10}$ copies/mL) from day 1 to day 22, as measured by RT-qPCR in nasopharyngeal (NP) swabs
  Proportion of patients with at least 1-point improvement in clinical status from day 1 (time of randomization) to day 8 using the 7-point ordinal scale
Cohort 2 and Cohort 3
  Time-weighted average change from baseline viral shedding ($\log_{10}$ copies/mL) from day 1 to day 22, as measured by RT-qPCR in NP swabs
  Proportion of patients with at least 1-point improvement in clinical status from day 1 (time of randomization) to day 22 using the 7-point ordinal scale Phase 3

The primary endpoint for phase 3 in each cohort is:
Cohort 1A and Cohort 1
  Proportion of patients with at least 1-point improvement in clinical status from day 1 (time of randomization) to day 8 using the 7-point ordinal scale
Cohort 2 and Cohort 3
  Proportion of patients with at least 1-point improvement in clinical status from day 1 (time of randomization) to day 22 using the 7-point ordinal scale The patient population (cohort 1A, cohort 1, cohort 2, and/or cohort 3) and the primary clinical efficacy endpoint(s) for phase 3 will be finalized after review of phase 2 data.

Secondary Endpoints

Phase 1 (Cohort 1 Only)

The secondary endpoints for phase 1 were:
  Time-weighted average change from baseline viral shedding ($\log_{10}$ copies/mL) from day 1 to day 22, as measured by RT-qPCR in saliva samples
  Time-weighted average change from baseline viral shedding ($\log_{10}$ copies/mL) from day 1 to day 22, as measured by RT-qPCR in nasal samples
  Time to negative RT-qPCR in all tested samples with no subsequent positive RT-qPCR in any tested samples (NP swabs, saliva, or nasal swabs)
  Change from baseline in SARS-CoV-2 viral shedding at each visit through day 29, as measured by RT-qPCR in NP swabs
  Change from baseline in SARS-CoV-2 viral shedding at each visit through day 29, as measured by RT-qPCR in saliva samples
  Change from baseline in SARS-CoV-2 viral shedding at each visit through day 29, as measured by RT-qPCR in nasal swabs
  Correlation and concordance with respect to RT-qPCR results over time between different sample types (NP, nasal, and saliva)
  Time-weighted average change from baseline in viral shedding (log 10 copies/mL) from day 1 to post-baseline study days (eg, day 5, 7, 15, and 29)Proportion of patients with at least 1-point improvement in clinical status from day 1 (time of randomization) to day 8 using the 7-point ordinal scale
  Proportion of patients with at least 2-point improvement in clinical status from day 1 (time of randomization) to day 8 using the 7-point ordinal scale
  Proportion of patients with at least 1-point improvement in clinical status from day 1 (time of randomization) to day 29 or discharge using the 7-point ordinal scale
  Proportion of patients with at least 2-point improvement in clinical status from day 1 (time of randomization) to day 29 or discharge using the 7-point ordinal scale
  Time to no longer requiring oxygen supplementation by day 29
  Days of supplemental oxygen use up to day 29
  Proportion of patients initiating high-intensity oxygen therapy up to day 29 or discharge
  Days of high-intensity oxygen therapy up to day 29
  Proportion of patients initiating mechanical ventilation up to day 29 or discharge
  Days of mechanical ventilation up to day 29
  Ventilator-free days up to day 29
  Days of hospitalization up to day 29
  Proportion of patients re-admitted to hospital after discharge through the end of study
  Proportion of patients admitted into an intensive care unit (ICU) up to day 29
  Days of ICU stay up to day 29
  All-cause mortality up to day 29
  All-cause mortality through the end of study
  Overall survival
  Proportion of patients with treatment-emergent SAEs through day 29

Concentrations of mAb10987, mAb10933, and mAb10989 in serum and corresponding PK parameters Immunogenicity, as measured by anti-drug antibodies (ADAs) to mAb10933, mAb10987, and mAb10989

Phase 2

The secondary endpoints for phase 2 were:

Cohort 1A and Cohort 1 only

Proportion of patients with at least 2-point improvement in clinical status from day 1 (time of randomization) to day 8 using the 7-point ordinal scale Cohort 2 and Cohort 3 only Proportion of patients with at least 2-point improvement in clinical status from day 1 (time of randomization) to day 22 using the 7-point ordinal scale Cohort 1A, Cohort 1, Cohort 2, and Cohort 3

Time to negative RT-qPCR in NP swabs with no subsequent positive RT-qPCR

Change from baseline in viral shedding at each visit through day 29, as measured by RT-qPCR in NP swabs Time-weighted average change from baseline in viral shedding ($\log_{10}$ copies/mL) from day 1 to post-baseline study days (e.g., day 5, 7, 15, and 29)

Proportion of patients with at least 1-point improvement in clinical status from day 1 (time of randomization) to day 29 or discharge using the 7-point ordinal scale Proportion of patients with at least 2-point improvement in clinical status from day 1 (time of randomization) to day 29 or discharge using the 7-point ordinal scale Time to no longer requiring oxygen supplementation by day 29 (only cohort 1, cohort 2, and cohort 3)

Days of supplemental oxygen use up to day 29

Proportion of patients initiating high-intensity oxygen therapy up to day 29

Days of high-intensity oxygen therapy up to day 29

Proportion of patients initiating mechanical ventilation up to day 29 or discharge Days of mechanical ventilation up to day 29

Ventilator-free days up to day 29

Days of hospitalization up to day 29

Proportion of patients re-admitted to hospital after discharge through the end of study Proportion of patients admitted into an ICU up to day 29

Days of ICU stay up to day 29

All-cause mortality up to day 29

All-cause mortality through the end of study

Overall survival

Proportion of patients with treatment-emergent SAEs through day 29

Proportion of patients with treatment-emergent SAEs through day 57

Proportion of patients with infusion-related reactions (grade ≥2) through day 4

Proportion of patients with hypersensitivity reactions (grade ≥2) through day 29

Concentrations of mAb10933 and mAb10987 in serum over time

Immunogenicity, as measured by ADAs to mAb10933 and mAb10987

Phase 3

The patient population (cohort 1A, cohort 1, cohort 2, and/or cohort 3) and the secondary clinical efficacy endpoint(s) for phase 3 are finalized after review of complete phase 2 data.

Other possible secondary endpoints for phase 3 included:

Proportion of patients with treatment-emergent SAEs through day 57

Proportion of patients with infusion-related reactions (grade ≥2) through day 4

Proportion of patients with hypersensitivity reactions (grade ≥2) through day 29

Concentrations of mAb10933 and mAb10987 in serum over time

Immunogenicity, as measured by ADAs to mAb10933 and mAb10987

Exploratory Endpoints

The exploratory endpoints included:

Proportion of patients with treatment failure having mutations in the gene encoding the SARS-CoV-2 S protein through day 29

Change and percentage change in neutrophil-lymphocyte ratio (NLR) at each visit through day 29

Change and percentage change in D-dimer at each visit through day 29

Change and percentage change in ferritin at each visit through day 29

Change and percentage change in C-reactive protein (CRP) at each visit through day 29

Change and percentage change in lactate dehydrogenase (LDH) at each visit through day 29

Procedures and Assessments: Efficacy—nasopharyngeal (all phases), saliva (phase 1 only), and/or nasal swabs (phase 1 only) for SARS-CoV-2 RT-PCR, and clinical and oxygen status; Safety—recorded serious adverse events and adverse events of special interest. Nasal swab, saliva sample, and (in phase 1) nasopharyngeal samples were used to collect secretions from patients to determine presence or absence of SARS-CoV-2 virus and to measure viral shedding. Samples were used for RT-qPCR analysis. Samples may additionally be used for exploratory viral RNA sequencing (nasopharyngeal, nasal swab, saliva) and/or viral culture (nasopharyngeal, nasal swab).

Statistical Plan:

Phase 1—The sample size is a total of 60 patients for phase 1 part A and 40 for part B. The sample size allows preliminary estimation of the incidences of SAE, AESIs, and grade 3 or 4 TEAEs in treatment arms relative to placebo.

The primary efficacy endpoint in phase 1 was the time-weighted average change from baseline in viral shedding ($\log_{10}$ copies/mL) in NP swab samples from day 1 to day 22. Assuming a standard deviation of 2.1 $\log_{10}$ copies/mL, a sample size of 20 patients per arm in phase 1 should have at least 80% power to detect a difference of 1.91 $\log_{10}$ copies/mL between the treatment arm and placebo group, using a two-sample t-test at a 2-sided significance of $\alpha=0.05$.

Phase 2—The sample size for phase 2 was based on the time-weighted average change from baseline in viral shedding ($\log_{10}$ copies/mL) in NP swab samples from day 1 to day 22. Assuming a ~23% dropout rate (including missing data at baseline) and standard deviation of 2.1 $\log_{10}$ copies/mL, a sample size of 130 patients per arm (ie, 100 patients per arm with available data) across 3 treatment arms within each of the 3 cohorts should have 80% power to detect a difference of 0.84 $\log_{10}$ copies/mL between each treatment arm and placebo in a cohort, using a 2-sample t-test at a 2-sided significance of $\alpha=0.05$. If a standard deviation of 3.8 $\log_{10}$ copies/mL is assumed, the detectable difference at 80% power would be 1.51 $\log_{10}$ copies/mL For the clinical endpoint of proportion of patients with at least 1-point improvement in clinical status from baseline to day 22, the minimum detectable difference (MDD) between treatment arm and placebo—based on a chi-square test of equal proportions—for a sample size of 100 per arm (130 per arm assuming ~23% dropout rate) will be as follows:

In cohorts 1A and 1, the MDD will be 13.7% assuming the response rate in the placebo group is 51% (ie, 64.7% in anti-SARS-CoV-2 S protein mAb versus 51% in placebo). The assumed response rate in the placebo group is similar to the rate observed for remdesivir.

In cohorts 2 and 3, the MDD will be 13.3% assuming the response rate in placebo group is 57.1% (ie, 70.4% in anti-SARS-CoV-2 S protein mAb versus 57.1% in placebo). The assumed response rate in the placebo group is similar to the rate observed in sarilumab COVID-19 phase 2/3 study (6R88-COV-2040) with an advanced population similar to cohorts 2 and 3 in this study.

Phase 3—The study will continue to enroll additional patients seamlessly into the phase 3 portion of the study, until an adaptation decision on the primary endpoint and final sample size for phase 3 is made based on the complete phase 2 data analysis. An initial sample size of total 1350 patients is estimated for the phase 3 portion of the study (150 per arm across 3 treatment arms in 3 cohorts). For example, for cohort 3, a sample size of 450 patients (150 patients per arm) will provide 90% power using a chi-square test to detect a treatment difference of 15.9% in the proportion of patients alive and off mechanical ventilation at day 22, assuming a 68.2% rate in the placebo group.

Results—Analysis of Phase 1/2/3 clinical trial (see FIG. 19) of the antibody cocktail, casirivimab and imdevimab (mAb10933 and mAb10987, respectively), in hospitalized COVID-19 patients requiring low-flow oxygen was prospectively designed to focus on patients who had not yet mounted their own immune response to SARS-CoV-2 (i.e., did not have antibodies at baseline: seronegative), as evidence (see Example 2) suggested these patients were at greater risk. In addition, among subjects treated with placebo, patients who had mounted an immune response at baseline (seropositive patients) had much lower viral levels at baseline compared to patients who had not mounted an immune response at baseline (seronegative patients) and achieved viral loads below the lower level of quantitation ("LLQ") sooner even without treatment. See FIG. 16. In addition, among hospitalized patients with COVID-19 on low flow supplemental oxygen, seropositive patients had lower cumulative incidence of death or mechanical ventilation compared to seronegative patients. See FIG. 17. Clinical outcomes in Cohort 1 were worse in patients who were seronegative at baseline or who had high viral load at baseline. See FIG. 18. The primary clinical objective of this initial analysis was to determine if there was sufficient efficacy in these patients to warrant continuing the trial (i.e., futility analysis). The results passed the futility analysis (p<0.3 single-sided), as seronegative patients treated with the antibody cocktail had a lower risk of death or receiving mechanical ventilation (hazard ratio (HR): 0.78; 80% CI: 0.51-1.2). The benefit was driven by results starting one week post-treatment, when the risk of dying or receiving mechanical ventilation was reduced by approximately half with antibody cocktail treatment, based on a post-hoc analysis.

Cohort 1 was analyzed for prevalence of seronegativity in both the full analysis set (FAS; randomized and dosed patients) and the modified full analysis set (mFAS; patients testing positive for SARS-CoV-2 via a nasopharyngeal qualitative test at baseline), and seronegative prevalence was similar in both the FAS and the mFAS groups. See FIG. 20. Seronegative patients (n=217) had much higher viral loads than those who had already developed their own antibodies (seropositive) to SARS-CoV-2 at the time of randomization. See FIG. 16. As hypothesized, there as a stronger anti-viral effect with the antibody cocktail compared to placebo in patients who had not mounted their own immune response (seronegative at baseline), patients treated with the antibody cocktail had more brisk viral reductions compared to placebo, and the cocktail reduced viral load faster compared to placebo at all baseline viral load thresholds. See FIGS. 21-24. In seronegative patients, the antibody cocktail reduced the time-weighted average daily viral load through day 7 by −0.54 log 10 copies/mL, and through day 11 by −0.63 log 10 copies/mL (nominal p=0.002 for combined doses). At day 5, the relative reduction compared to placebo was −1.1 log 10 copies (nominal p=0.002 for combined doses). In seropositive patients (n=270) the clinical and virologic benefit of the antibody cocktail was limited (clinical endpoint HR: 0.98; time-weighted-average viral load reduction by day 7 of −0.20 log 10 copies/mL for combined doses). Treatment with the cocktail resulted in similar viral load reductions in hospitalized patients and outpatients, and the most pronounced difference was observed between patients treated with the cocktail and those receiving placebo in seronegative patients, which is consistent with the data of Example 2 (FIGS. 25-28).

The clinical and virological analyses include data from hospitalized patients who were on low-flow oxygen (defined as maintaining oxygen saturation of >93% via nasal cannula, simple facemask, or similar device), including 217 who were seronegative when they entered the trial and 270 who were seropositive; although seronegative patients comprised less than half of the trial population, based on placebo rates they account for approximately two-thirds of the deaths in the absence of antibody cocktail treatment. Patients were randomized to receive the antibody cocktail (either 8,000 mg high dose or 2,400 mg low dose) or placebo, in addition to standard-of-care therapies, with 67% receiving remdesivir and 74% receiving systemic corticosteroids. Similar clinical and virologic efficacy was observed for the high and low doses of the antibody cocktail.

Both antibody cocktail doses were well-tolerated. In the overall trial population, the incidence of serious adverse events was 21% for high dose, 20% for low dose and 24% for placebo. Infusion reactions were more common with the high dose of the antibody cocktail (2.7% high dose, 0.9% low dose, 1.4% placebo) and there were two discontinuations due to infusion-related reactions, both of which occurred in the high dose group.

Example 2. Clinical Evaluation of
Anti-SARS-CoV-2 Spike Glycoprotein Antibodies
in Ambulatory Patients with COVID-19

The below-described clinical study is an adaptive, phase 1/2/3, randomized, double-blinded, placebo-controlled master protocol to evaluate the efficacy, safety, and tolerability of mAb10933+mAb10987 combination therapy (which together, can be referred to as REGN-COV2 or REGEN-COV), or alternatively mAb10989 monotherapy in adult outpatients (i.e., ambulatory patients) with COVID-19 or asymptomatic SARS-CoV-2 infection.

Study Objectives: The primary and secondary objectives of each phase of the study are set forth below.

Exemplary Use: An exemplary use that could be authorized based on the results (including interim results) from this Example is as follows:

This exemplary use applies to intravenous infusion of REGEN-COV, wherein mAb10933 and mAb10987 are administered together. REGEN-COV should be administered as soon as possible after positive viral test for SARS- CoV-2 and within 7 days of symptom onset in adults and pediatric patients 12 years of age and older weighing at least 40 kg who are at high risk for progressing to severe COVID-19 and/or hospitalization. COVID-19 illnesses can range from very mild (including some with no reported symptoms) to severe, including illness resulting in death. While information so far suggests that most COVID-19 illness is mild, serious illness can happen and may cause some of your other medical conditions to become worse. People of all ages with severe, long-lasting (chronic) medical conditions like heart disease, lung disease, and diabetes, for example, and other conditions including obesity, seem to be at higher risk of being hospitalized for COVID-19. Older age, with or without other conditions, also places people at higher risk of being hospitalized for COVID-19.

This exemplary authorization is for the use of REGEN-COV for the treatment of mild to moderate coronavirus disease 2019 (COVID-19) in adults and pediatric patients with positive results of direct SARS-CoV-2 viral testing who are 12 years of age and older weighing at least 40 kg, and who are at high risk for progressing to severe COVID-19 and/or hospitalization.

The following medical conditions or other factors may place adults and pediatric patients (age 12-17 years and weighing at least 40 kg) at higher risk for progression to severe COVID-19:

Older age (for example age ≥65 years of age)

Obesity or being overweight (for example, adults with BMI >25 kg/m², or if age 12-17, have BMI ≥85th percentile for their age and gender based on CDC growth charts, https://www.cdc.gov/growthcharts/clinical_charts.htm)

Pregnancy

Chronic kidney disease

Diabetes

Immunosuppressive disease or immunosuppressive treatment

Cardiovascular disease (including congenital heart disease) or hypertension

Chronic lung diseases (for example, chronic obstructive pulmonary disease, asthma [moderate-to-severe], interstitial lung disease, cystic fibrosis and pulmonary hypertension)

Sickle cell disease

Neurodevelopmental disorders (for example, cerebral palsy) or other conditions that confer medical complexity (for example, genetic or metabolic syndromes and severe congenital anomalies)

Having a medical-related technological dependence (for example, tracheostomy, gastrostomy, or positive pressure ventilation (not related to COVID-19))

Other medical conditions or factors (for example, race or ethnicity) may also place individual patients at high risk for progression to severe COVID-19 and authorization of REGEN-COV under the EUA is not limited to the conditions listed above. For additional information on medical conditions and factors associated with increased risk for progression to severe COVID-19, see the CDC website: www.cdc.gov/coronavirus/2019-ncov/need-extra-precautions/people-with-medical-conditions.html. Healthcare providers should consider the benefit-risk for an individual patient.

Limitations of an Authorized Use:
In this exemplary use, REGEN-COV should not be used in patients:
who are hospitalized due to COVID-19, OR
who require oxygen therapy due to COVID-19, OR
who require an increase in baseline oxygen flow rate due to COVID-19 in those on chronic oxygen therapy due to underlying non-COVID-19 related comorbidity.

However, alternative authorized uses contemplate the use of REGEN-COV in patients who can be hospitalized due to COVID-19, and/or who require oxygen therapy due to COVID-19, and/or who require an increase in baseline oxygen flow rate due to COVID-19 in those on chronic oxygen therapy due to underlying non-COVID-19 related comorbidity.

Primary Objectives:
Phase 1
Part A
To evaluate the safety and tolerability of mAb10933+mAb10987 compared to placebo
To evaluate the virologic efficacy of mAb10933+mAb10987 compared to placebo in reducing viral shedding of SARS-CoV-2
Part B
To evaluate the safety and tolerability of mAb10989 compared to placebo
To evaluate the virologic efficacy of mAb10989 compared to placebo in reducing viral shedding of SARS-CoV-2
Phase 2
To evaluate the virologic efficacy of mAb10933+mAb10987 and mAb10989 compared to placebo in reducing viral shedding of SARS-CoV-2.
Phase 3
To evaluate the clinical efficacy of mAb10933+mAb10987 and mAb10989 compared to placebo.

Secondary Objectives:
Phase 1
Part A
To evaluate additional indicators of virologic efficacy of mAb10933+mAb10987 compared to placebo
To evaluate the clinical efficacy of mAb10933+mAb10987 compared to placebo
To compare quantitative reverse transcription polymerase chain reaction (RT-qPCR) results acquired with different sample types (nasopharyngeal [NP], nasal, and saliva)
To characterize the pharmacokinetic (PK) profiles of mAb10933 and mAb10987 in serum
To assess the immunogenicity of mAb10933 and mAb10987
Part B
To evaluate additional indicators of virologic efficacy of mAb10933+mAb10987 compared to placebo
To evaluate the clinical efficacy of mAb10989 compared to placebo
To compare RT-qPCR results acquired with different sample types (NP, nasal, and saliva)
To characterize the PK profile of mAb10989 in serum
To assess the immunogenicity of mAb10989
Phase 2
To evaluate additional indicators of virologic efficacy of mAb10933+mAb10987 compared to placebo
To evaluate the clinical efficacy of mAb10933+mAb10987 and mAb10989 compared to placebo
To evaluate the safety and tolerability of mAb10933+mAb10987 and mAb10989 compared to placebo
To characterize the concentrations of mAb10933, mAb10987, and mAb10989 in serum
To assess the immunogenicity of mAb10933, mAb10987, and mAb10989

Phase 3
  To evaluate the virologic efficacy of mAb10933+mAb10987 and mAb10989 compared to placebo in reducing viral shedding of SARS-CoV-2
  To evaluate the safety and tolerability of mAb10933+mAb10987 and mAb10989 compared to placebo
  To characterize the concentrations of mAb10933, mAb10987, and mAb10989 in serum
  To assess the immunogenicity of mAb10933, mAb10987, and mAb10989

Study Design: This is an adaptive, phase 1/2/3, randomized, double-blinded, placebo-controlled master protocol to evaluate the efficacy, safety, and tolerability of mAb10933+mAb10987 combination therapy and mAb10989 monotherapy in adult outpatients (i.e., ambulatory patients) with COVID-19 or asymptomatic SARS-CoV-2 infection. To have been eligible, adult patients must have had laboratory-confirmed SARS-CoV-2 and COVID-19 symptoms but must not have been previously hospitalized or currently hospitalized. In phase 1, only patients with COVID-19 were enrolled. In phase 2, symptomatic patients and asymptomatic patients were enrolled into separate cohorts.

Phase 1

In phase 1 part A, randomization was limited to mAb10933+mAb10987 low dose, mAb10933+mAb10987 high dose, and placebo. In part B, randomization was limited to mAb10989, and placebo. On day 1, eligible patients in part A were randomized to a single intravenous (IV) administration of mAb10933+mAb10987 (low dose), mAb10933+mAb10987 (high dose), mAb10989, or placebo.

Patients were then be sequestered for the first 48 hours after dosing, during which time they were closely monitored for serious adverse events (SAEs) and adverse events of special interest (AESIs). On day 3, patients could return home, if medically appropriate, after completing the day's assessments. After completing assessments on day 7, all patients were sent home, if medically appropriate. Throughout the study, safety information (SAEs and AESIs) were collected, as was information about any medically-attended visits related to COVID-19. Nasopharyngeal (NP swab), nasal swab, and saliva samples were collected to assess viral shedding. The study ended on day 29, when patients had final assessments conducted in person including NP swab, nasal swab, and/or saliva sample collection (as feasible) and blood draws for PK, anti-drug antibody (ADA), and exploratory analyses.

Phase 2

On day 1, eligible patients were randomized 1:1:1:1 to a single dose of mAb10933+mAb10987 (low dose), mAb10933+mAb10987 (high dose), mAb10989, or placebo. After infusion of study drug, patients were observed for 2 hours and, if no SAEs or AESIs were observed, were sent home. Nasopharyngeal swabs were collected every other day for the first 2 weeks and then twice weekly thereafter. Blood samples were collected periodically. Information regarding treatment-emergent SAEs, AESIs, and medically-attended related to COVID-19 were recorded throughout the study.

On day 29, patients had final assessments, including nasopharyngeal swab collection and blood draws for PK, ADA, and exploratory analysis.

Study Duration: The duration of the study was 30 days for each patient.

Study Population: This study enrolled adult, non-hospitalized patients who had a positive diagnostic test for SARS-CoV-2.

Sample Size—Phase 1 enrolled until up to 100 patients are randomized. Phase 2 enrolled until approximately 1300 patients are randomized. It was estimated that 704 patients (176 patients per arm) would be required for phase 3.

Inclusion Criteria: A patient must have met the following criteria to be eligible for inclusion in the study:
1. Is male or female ≥18 years of age (or country's legal age of adulthood) at randomization;
2. Has SARS-CoV-2-positive molecular diagnostic test (by validated SARS-CoV-2 RT-PCR or other molecular diagnostic assay, using an appropriate sample such as NP, nasal, oropharyngeal [OP], or saliva) ≤72 hours prior to randomization. A historical record of positive result from test conducted ≤72 hours prior to randomization is acceptable;
3. Meets one of the following two criteria:
   a. Symptomatic Cohort (All Phases): Has symptoms consistent with COVID-19 as determined by the investigator with onset ≤7 days before randomization
   Or
   b. Asymptomatic Cohort (Phase 2): Meets all of the following:
      Has no symptoms consistent with COVID-19 (as determined by the investigator) occurring at any time <2 months prior to randomization
      Has no positive SARS-CoV-2 test results from a sample collected >7 days prior to randomization
      Has no known contact (of any duration) with an individual who has confirmed COVID-19 or confirmed positive SARS-COV-2 test >14 days prior to randomization
4. Maintains $O_2$ saturation ≥93% on room air;
5. Is willing and able to provide informed consent signed by study patient or legally acceptable representative; and
6. Is willing and able to comply with study procedures, including providing samples for viral shedding testing after discharge.

Exclusion Criteria: A patient who met any of the following criteria was excluded from the study:
1. Has been admitted to a hospital prior to randomization, or is hospitalized (inpatient) at randomization, due to COVID-19;
2. Has participated, or is participating, in a clinical research study evaluating COVID-19 convalescent plasma, monoclonal antibodies against SARS-CoV-2, or intravenous immunoglobulin (IVIG) within 3 months or less than 5 half-lives of the investigational product (whichever is longer) prior to the screening visit;
3. Prior, current, or planned future use of COVID-19 convalescent plasma, mAbs against SARS CoV 2, intravenous immunoglobulin (IVIG) (any indication), systemic corticosteroids (any indication), or any Emergency Use Authorization (EUA)-approved treatments in the past 30 days or less than 5 half-lives of the investigational product (whichever is longer) prior to the screening visit;
4. Has known allergy or hypersensitivity to components of study drug;
5. Has been discharged, or is planned to be discharged, to a quarantine center;
6. Pregnant or breastfeeding women; or
7. Continued sexual activity in women of childbearing potential (WOCBP)* or sexually active men who are unwilling to practice highly effective contraception prior to the initial dose/start of the first treatment, during the study, and for at least 6 months after the last dose.

Signs and symptoms of hypersensitivity including infusion related reactions may include: fever, chills, nausea, headache, bronchospasm, hypotension, angioedema, throat irritation, rash including urticaria, pruritus, myalgia, and dizziness.

Highly effective contraceptive measures in women include:

Stable use of combined (estrogen and progestogen containing) hormonal contraception (oral, intravaginal, transdermal) or progestogen-only hormonal contraception (oral, injectable, implantable) associated with inhibition of ovulation initiated 2 or more menstrual cycles prior to screening, Intrauterine device (IUD), Intrauterine hormone-releasing system (IUS), Bilateral tubal ligation, Vasectomized partner,† and/or Sexual abstinence.‡,§

Male study participants with WOCBP partners are required to use condoms unless they are vasectomized† or practice sexual abstinence.‡,§

* WOCBP are defined as women who are fertile following menarche until becoming postmenopausal, unless permanently sterile. A postmenopausal state is defined as no menses for 12 months without an alternative medical cause. A high follicle stimulating hormone (FSH) level in the postmenopausal range may be used to confirm a postmenopausal state in women not using hormonal contraception or hormonal replacement therapy. However, in the absence of 12 months of amenorrhea, a single FSH measurement is insufficient to determine the occurrence of a postmenopausal state. The above definitions are according to Clinical Trial Facilitation Group (CTFG) guidance. Pregnancy testing and contraception are not required for women with documented hysterectomy or tubal ligation.

Permanent sterilization methods include hysterectomy, bilateral salpingectomy, and bilateral oophorectomy.

† Vasectomized partner or vasectomized study participant must have received medical assessment of the surgical success.

‡ Sexual abstinence is considered a highly effective method only if defined as refraining from heterosexual intercourse during the entire period of risk associated with the study drugs. The reliability of sexual abstinence needs to be evaluated in relation to the duration of the clinical trial and the preferred and usual lifestyle of the patient.

Study Treatments: Co-administered mAb10933+mAb10987 combination therapy, 2.4 g (1.2 g each of mAb10933 and mAb10987) IV single dose, Co-administered mAb10933+mAb10987 combination therapy, 8.0 g (4.0 g each of mAb10933 and mAb10987) IV single dose, mAb10989 monotherapy, 1.2 g IV single dose, or placebo IV single dose.

Endpoints: Primary, secondary, and exploratory endpoints were specified for each phase, as defined below.

Primary Endpoints

Phase 1

The primary endpoints for phase 1 were:

Part A and B

Proportion of patients with treatment-emergent serious adverse events (SAEs) through day 29

Proportion of patients with infusion-related reactions (grade ≥2) through day 4

Proportion of patients with hypersensitivity reactions (grade ≥2) through day 29

Time-weighted average change from baseline in viral shedding ($\log_{10}$ copies/mL) from day 1 to day 22, as measured by quantitative reverse transcription quantitative polymerase chain reaction (RT-qPCR) in nasopharyngeal (NP) swab samples.

Phase 2

The primary endpoint for phase 2 was time-weighted average change from baseline in viral shedding ($\log_{10}$ copies/mL) from day 1 to day 22, as measured by RT-qPCR in NP swab samples.

Phase 3

The primary endpoint for phase 3 was proportion of patients with ≥1 COVID-19 related medically-attended visit through day 29.

Secondary Endpoints

Phase 1

Virologic

Time-weighted average change from baseline in viral shedding ($\log_{10}$ copies/mL) from day 1 to day 22, as measured by RT-qPCR in saliva samples Time-weighted average change from baseline in viral shedding ($\log_{10}$ copies/mL) from day 1 to day 22, as measured by RT-qPCR in nasal swab samples Time to negative RT-qPCR in all tested samples with no subsequent positive RT-qPCR in any tested samples (NP swabs, saliva, or nasal swabs)

Change from baseline in SARS-CoV-2 viral shedding at each visit through day 29, as measured by RT-qPCR in NP swabs Change from baseline in SARS-CoV-2 viral shedding at each visit through day 29, as measured by RT-qPCR in saliva samples Change from baseline in SARS-CoV-2 viral shedding at each visit through day 29, as measured by RT-qPCR in nasal swabs Correlation and concordance of RT-qPCR results across different sample types (NP, nasal, and saliva)

Time-weighted average change from baseline in viral shedding ($\log_{10}$ copies/mL) from day 1 to post-baseline study days (e.g., day 5, 7, 15, and 29)

Clinical

Proportion of patients with ≥1 COVID-19 related medically-attended visit through day 29; COVID-19 related medically-attended visit will be defined as: hospitalization with the primary reason for hospitalization being COVID-19, or an outpatient visit (including a visit to the ER, UCC, doctor's office, or telemedicine visit) with the primary reason for the visit being COVID-19

Proportion of patients with ≥2 COVID-19 related medically-attended visits through day 29

Total number of COVID-19 related medically-attended visits through day 29

Proportion of patients admitted to a hospital due to COVID-19 by day 29

Proportion of patients with ≥1 outpatient or telemedicine visit due to COVID-19 by day 29

PK/ADA

Concentrations of mAb10933, mAb10987, and mAb10989 in serum and corresponding PK parameters Immunogenicity as measured by anti-drug antibodies (ADA) to mAb10933, mAb10987, and mAb10989

Phase 2
The secondary endpoints for phase 2 were:
Virologic
  Time to negative RT-qPCR in NP swabs with no subsequent positive RT-qPCR
  Change from baseline in viral shedding at each visit through day 29, as measured by RT-qPCR in NP samples
  Time-weighted average change from baseline in viral shedding ($\log_{10}$ copies/mL) from day 1 to post-baseline study days (eg, day 5, 7, 15, and 29)
Clinical
  Proportion of patients with ≥1 COVID-19 related medically-attended visit through day 29
  Proportion of patients with ≥2 COVID-19 related medically-attended visits through day 29
  Total number of COVID-19 related medically-attended visits through day 29
  Proportion of patients admitted to a hospital due to COVID-19 by day 29
  Proportion of patients admitted to an ICU due to COVID-19 by day 29
  Proportion of patients with ≥1 outpatient or telemedicine visit due to COVID-19 by day 29
  Proportion of patients requiring mechanical ventilation due to COVID-19 by day 29
  Days of hospitalization due to COVID-19
  Proportion of patients with all-cause mortality by day 29
  Proportion of patients with treatment-emergent SAEs through day 29
  Proportion of patients with infusion-related reactions (grade ≥2) through day 4
  Proportion of patients with hypersensitivity reactions (grade ≥2) through day 29
  Time to first onset of any symptom of COVID-19
  Duration of symptoms consistent with COVID-19
PK/ADA
  Concentrations of mAb10933, mAb10987, and mAb10989 in serum
  Immunogenicity as measured by anti-drug antibodies (ADA) to mAb10933, mAb10987, and mAb10989
Phase 3
The secondary endpoints for phase 3 were:
Virologic
  Time-weighted average change from baseline in viral shedding ($\log_{10}$ copies/mL) from day 1 to day 22, as measured by RT-qPCR in NP swabs
  Time to negative RT-qPCR in NP swabs with no subsequent positive RT-qPCR
  Change from baseline in SARS-CoV-2 viral shedding at each visit through day 29, as measured by RT-qPCR in NP swabs
  Time-weighted average change from baseline in viral shedding ($\log_{10}$ copies/mL) from day 1 to post-baseline study days (eg, day 5, 7, 15, and 29)
Clinical
  Proportion of patients with ≥2 COVID-19 related medically-attended visits through day 29
  Total number of COVID-19 related medically-attended visits through day 29
  Proportion of patients with ≥1 outpatient or telemedicine visit due to COVID-19 by day 29
  Proportion of patients admitted to a hospital due to COVID-19 by day 29
  Proportion of patients admitted to an ICU due to COVID-19 by day 29
  Proportion of patients requiring mechanical ventilation due to COVID-19 by day 29
  Days of hospitalization due to COVID-19
  Proportion of patients with all-cause mortality by day 29
  Proportion of patients with treatment-emergent SAEs through day 29
  Proportion of patients with infusion-related reactions (grade ≥2) through day 4
  Proportion of patients with hypersensitivity reactions (grade ≥2) through day 29
PK/ADA
  Concentrations of mAb10933, mAb10987, and mAb10989 in serum
  Immunogenicity as measured by anti-drug antibodies to mAb10933, mAb10987, and mAb10989
Exploratory Endpoints
The exploratory endpoints for phase 1 and phase 2 were:
  Proportion of patients with treatment failure having mutations in the gene encoding the SARS-CoV-2 S protein through day 29
  Change and percentage change in neutrophil-lymphocyte ratio (NLR) at each visit through day 29
  Change and percentage change in D-dimer at each visit through day 29
  Change and percentage change in ferritin at each visit through day 29
  Change and percentage change in C-reactive protein (CRP) at each visit through day 29
  Change and percentage change in lactate dehydrogenase (LDH) at each visit through day 29
  Change in SE-C19 item scores over time
  Change in PGIS score over time
  PGIC score at day 29
  Proportion of patients admitted to an ICU due to COVID-19 by day 29 (phase 1 only)
  Proportion of patients requiring mechanical ventilation due to COVID-19 by day 29
  Procedures and Assessments: Efficacy—nasopharyngeal swabs (all phases), nasal swabs (phase 1 only), and saliva samples (phase 1 only) for SARS-CoV-2 RT-qPCR, and medically-attended COVID-19 visit details; Safety—record serious adverse events and adverse events of special interest, blood collection for safety labs, and vital signs. Nasal swab and saliva samples were used to collect secretions from patients to determine presence or absence of SARS-CoV-2 virus and to measure viral shedding.
Statistical Plan:
  Primary Efficacy Analysis—The primary efficacy variable for phase 1 and phase 2 was time-weighted average change from baseline in viral shedding from day 1 to day 22, as measured by RT-qPCR in NP swab samples. The estimant for the primary hypothesis was the difference in means between each of the anti-S SARS-CoV-2 mAb treatments and placebo in the primary efficacy variable in the FAS. The primary efficacy variable was calculated using trapezoidal rule based on observed data and was analyzed using an Analysis of Covariance (ANCOVA) model with treatment group and randomization strata as fixed effects and baseline viral shedding as covariate. For phase 2, analysis was performed for each cohort separately (symptomatic and asymptomatic) and for both cohorts combined. The least squares means estimates for the time-weighted average mean change from baseline in viral shedding for each treatment group, as well as the difference between each anti-spike mAb treatment arm and placebo (in phase 2, for each cohort separately and for both cohorts combined), was presented along with the corresponding p-value, standard error, and associated 95% confidence interval. The phase 3 primary efficacy variable was the proportion of patients with medically attended visits due to worsening COVID-19 symptoms and signs and was compared between groups using stratified Cochran-Mantel-Haenszel test at two-sided 0.05 level. P-values and 95% confidence intervals for the treatment difference are presented below.

Safety Analysis—Safety data including serious adverse events and adverse events of special interest, vital signs, and laboratory tests are listed and summarized by treatment group.

Results—The seamless Phase 1/2/3 trial described above showed a significantly reduced SARS-CoV-2 viral load and time to alleviate symptoms in non-hospitalized patients with COVID-19, when treated with a combination of mAb10933 and mAb10987 (REGN-COV-2). REGEN-COV also significantly reduced COVID-19-related medically-attended visits. The randomized, double-blind trial measured the effect of adding REGEN-COV to usual standard-of-care, compared to adding placebo to standard-of-care.

The final analysis of the phase 1/2 portion included 799 patients: 275 (group-1) and 524 (group-2). Patients were randomized (1:1:1) to placebo, 2.4 g of the mAb10933+ mAb10987 antibody cocktail (also referred to as REGEN-COV), or 8.0 g REGEN-COV, and characterized at baseline for endogenous immune response against SARS-CoV-2 (serum antibody-positive/negative). Efficacy was assessed in patients with a positive baseline RT-qPCR result; safety was assessed in all patients. Prespecified hierarchical analyses of virologic endpoints in group-2 were performed to confirm previously reported descriptive analyses from group-1. The proportion of patients with ≥1 Covid-19-related medically-attended visit (MAV) through day 29 was assessed in group-1+2.

Time-weighted average reduction in viral load (log 10 copies/mL) through day 7 was significantly greater with REGEN-COV (combined 2.4 g+8.0 g dose groups) vs placebo in patients with baseline viral load >$10^7$ copies/mL (prespecified primary endpoint): −0.68 (95% CI, −0.94 to −0.41; P<0.0001). Across all baseline viral loads, this change was −0.73 (P<0.0001) in serum antibody-negative patients and −0.36 (P=0.0003) in the overall population. Proportions of patients with ≥1 Covid-19-related MAV were 2.8% (12/434) with REGEN-COV vs 6.5% (15/231) with placebo (P=0.024; relative risk reduction=57%), with greater relative risk reductions in MAVs in patients with ≥1 risk factor for hospitalization (72%) or who were serum antibody-negative (65%). Adverse events were similar across groups.

Figure 5:
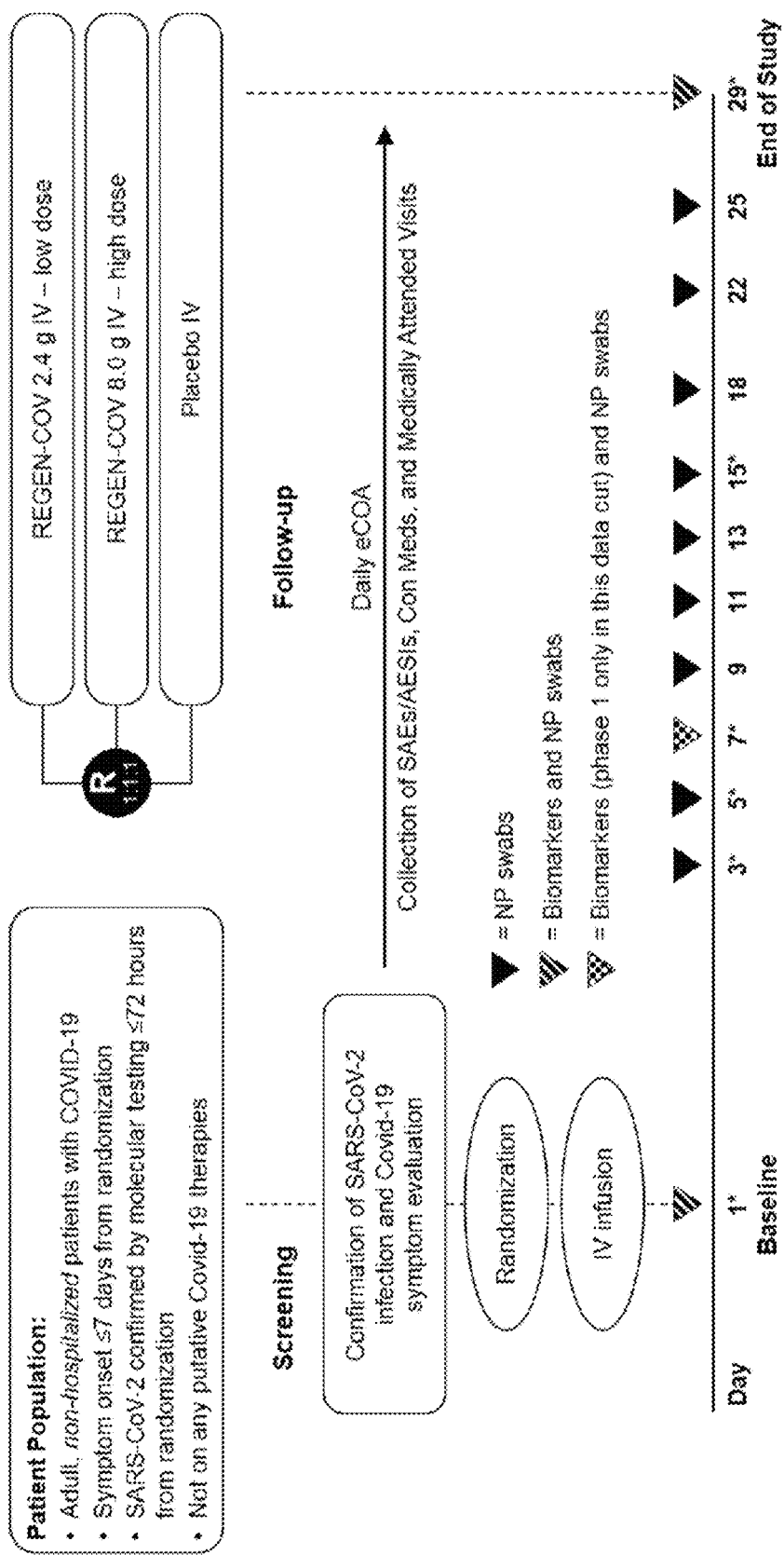
FIG. 5 is a schematic overview of the study design discussed in Example 2.

Trial Design Summary: Patients were randomly assigned (1:1:1) to receive placebo, 2.4 g REGEN-COV (1.2 g each of casirivimab and imdevimab), or 8.0 g REGEN-COV (4.0 g each of casirivimab and imdevimab) (FIG. 5). The 29-day phase 2 trial included a screening/baseline period (days −1 to 1), a follow-up period (days 2 to 25), and an end-of-study visit (day 29). The phase 1 and phase 2 portions of the trial were identical, except for additional pharmacokinetic analyses in phase 1.

Patients: Eligible patients were ≥18 years of age and non-hospitalized, with a confirmed SARS-CoV-2-positive nasopharyngeal (NP) PCR test result ≤72 hours and symptom onset ≤7 days before randomization. Randomization was stratified by country and by the presence or absence of ≥1 risk factor for severe Covid-19: age >50 years, obesity (BMI >30), immunosuppression, and chronic cardiovascular, metabolic, liver, kidney, or lung disease. All patients were assessed for the presence or absence of anti-SARS-CoV-2 antibodies: anti-spike [S1] IgA, anti-spike [S1] IgG, and anti-nucleocapsid IgG. Because these results were not available at randomization, patients underwent randomization regardless of their baseline serum antibody status and were then subsequently grouped for analyses as serum antibody-negative (if all available tests are negative), serum antibody-positive (if any of the tests are positive), or unknown status (missing or inconclusive results). The demographic and baseline medical characteristics of the patients are shown in Table 5A, below.

TABLE 5A

Demographic and Baseline Medical Characteristics* (N = 799; Full Analysis Set)

| Characteristic | Total (N = 799) | Placebo (N = 266) | REGEN-COV 2.4 g (N = 266) | REGEN-COV 8.0 g (N = 267) | REGEN-COV Combined (N = 533) |
|---|---|---|---|---|---|
| Demographics | | | | | |
| Median age (IQR)—yr | 42.0 (31.0-52.0) | 42.0 (32.0-53.0) | 42.0 (31.0-52.0) | 42.0 (30.0-52.0) | 42.0 (30.0-52.0) |
| Male sex—no. (%) | 376 (47.1) | 134 (50.4) | 122 (45.9) | 120 (44.9) | 242 (45.4) |
| Hispanic or Latino ethnic group—no. (%)† | 403 (50.4) | 137 (51.5) | 132 (49.6) | 134 (50.2) | 266 (49.9) |
| Race—no. (%)† | | | | | |
| White | 681 (85.2) | 227 (85.3) | 224 (84.2) | 230 (86.1) | 454 (85.2) |
| Black or African American | 74 (9.3) | 24 (9.0) | 27 (10.2) | 23 (8.6) | 50 (9.4) |
| Asian | 14 (1.8) | 4 (1.5) | 6 (2.3) | 4 (1.5) | 10 (1.9) |
| American Indian or Alaska Native | 5 (0.6) | 3 (1.1) | 1 (0.4) | 1 (0.4) | 2 (0.4) |
| Unknown | 7 (0.9) | 3 (1.1) | 1 (0.4) | 3 (1.1) | 4 (0.8) |
| Not Reported | 18 (2.3) | 5 (1.9) | 7 (2.6) | 6 (2.2) | 13 (2.4) |
| Median weight (IQR)—kg | 81.60 (69.90-95.30) | 81.80 (70.80-94.30) | 81.60 (69.90-94.50) | 81.20 (68.00-97.10) | 81.60 (69.30-95.30) |

TABLE 5A-continued

Demographic and Baseline Medical Characteristics* (N = 799; Full Analysis Set)

| Characteristic | Total (N = 799) | Placebo (N = 266) | REGEN-COV 2.4 g (N = 266) | REGEN-COV 8.0 g (N = 267) | REGEN-COV Combined (N = 533) |
|---|---|---|---|---|---|
| Body-mass index‡ | 29.67 ± 8.228 | 29.96 ± 10.460 | 29.51 ± 6.413 | 29.57 ± 7.355 | 29.54 ± 6.890 |
| Obesity—no. (%)§ | 298 (37.3) | 93 (35.0) | 101 (38.0) | 104 (39.0) | 205 (38.5) |
| *Baseline viral load in nasopharyngeal swab Raw values* | | | | | |
| No. of patients | 752 | 259 | 243 | 250 | 493 |
| Mean viral load (range)—copies/ml | 18719108.2 ± 28449769.31 | 20949819.7 ± 30172071.11 | 17403960.8 ± 027210806.40 | 17686414.3 ± 27755446.26 | 7547192.8 ± 127460771.64 |
| Median viral load (range)—copies/ml | 304500.0 (1-71000000) | 437000.0 (1-71000000) | 295000.0 (1-71000000) | 262500.0 (1-71000000) | 270000.0 (1-71000000) |
| *Baseline viral load in nasopharyngeal swab ($\log_{10}$ scale)* | | | | | |
| No. of patients | 752 | 259 | 243 | 250 | 493 |
| Mean viral load—log10 copies/ml | 5.16 ± 2.500 | 5.21 ± 2.511 | 5.23 ± 2.449 | 5.05 ± 2.544 | 5.14 ± 2.497 |
| Median viral load (range)—$\log_{10}$ copies/ml | 5.48 (0.0-7.9) | 5.64 (0.0-7.9) | 5.47 (0.0-7.9) | 5.42 (0.0-7.9) | 5.43 (0.0-7.9) |
| *Baseline viral load in nasopharyngeal swab category—no. (%)* | | | | | |
| $>10^4$ | 523 (65.5) | 176 (66.2) | 180 (67.7) | 167 (62.5) | 347 (65.1) |
| $>10^5$ | 439 (54.9) | 149 (56.0) | 148 (55.6) | 142 (53.2) | 290 (54.4) |
| $>10^6$ | 332 (41.6) | 114 (42.9) | 110 (41.4) | 108 (40.4) | 218 (40.9) |
| $>10^7$ | 256 (32.0) | 93 (35.0) | 82 (30.8) | 81 (30.3) | 163 (30.6) |
| Positive baseline qualitative RT-PCR—no. (%) | 665 (83.2) | 231 (86.8) | 215 (80.8) | 219 (82.0) | 434 (81.4) |
| *Baseline Serum C-reactive protein level* | | | | | |
| No. of patients | 600 | 203 | 200 | 197 | 397 |
| Mean level—mg/liter | 13.930 ± 28.8461 | 19.449 ± 037.5595 | 10.991 ± 24.1638 | 11.227 ± 21.1793 | 11.108 ± 22.7035 |
| Median level (range)—mg/liter | 3.750 (0.10–239.67) | 4.860 (0.10–232.04) | 3.240 (0.12–239.67) | 3.420 (0.14–157.96) | 3.320 (0.12–239.67) |
| *Baseline serum antibody status—no. (%)* | | | | | |
| Negative | 408 (51.1) | 134 (50.4) | 140 (52.6) | 134 (50.2) | 274 (51.4) |
| Positive | 304 (38.0) | 106 (39.8) | 96 (36.1) | 102 (38.2) | 198 (37.1) |
| Unknown | 87 (10.9) | 26 (9.8) | 30 (11.3) | 31 (11.6) | 61 (11.4) |
| *Symptom onset to randomization* | | | | | |
| No. of Patients | 698 | 240 | 222 | 236 | 458 |
| Median time from symptom onset to randomization (IQR)—days | 3.0 (2-5) | 3.0 (2-5) | 3.0 (2-5) | 3.0 (2-5) | 3.0 (2-5) |
| At least one risk factor for hospitalization—no. (%)¶ | 483 (60.5) | 158 (59.4) | 165 (62.0) | 160 (59.9) | 325 (61.0) |

SD standard deviation.

*Plus-minus values are means ± SD. Percentages may not total 100 because of rounding. IQR denotes interquartile range, and RT-PCR reverse-transcriptase polymerase chain reaction.

†Race and ethnic group were reported by the patients

‡The body-mass index is the weight in kilograms divided by the square of the heights in meters.

§Obesity is defined as a body-mass index of greater than 30.

¶Risk Factors for hospitalization include an age of more than 50 years, obesity, cardiovascular disease (including hypertension), chronic lung disease (including asthma), chronic metabolic disease (including diabetes), chronic kidney disease (including receipt of dialysis), chronic liver disease, and immunocompromised (immunosuppression or receipt of immunosuppressants).

Intervention: At baseline (day 1), mAb10933 (casirivimab) and mAb10987 (imdevimab) (diluted in a 250-ml normal saline solution for co-administration) or saline placebo was administered intravenously over a period of 1 hour.

Endpoints

The primary virologic endpoint and two key secondary clinical endpoints were prespecified in this phase 1+phase 2 (collectively referred to as phase 1/2) analysis and tested hierarchically as described in Table 5B. The primary virologic endpoint was defined as the time-weighted mean change in viral load (log 10 copies per milliliter) from baseline (day 1) through day 7. The key secondary clinical endpoints were the proportion of patients with at least one Covid-19-related medically-attended visit (MAV) through day 29 and the proportion of patients with at least one Covid-19-related MAV consisting of only hospitalization or emergency room (ER) visit or urgent care visit. A MAV was defined as a hospitalization or ER, urgent care, or physician office/telemedicine visit that was confirmed by the investigator to be related to Covid-19.

underwent randomization. Patients with a positive SARS-CoV-2 nasopharyngeal (NP) PCR test ≤72 hr of randomization (baseline) but who tested negative by the central lab qualitative PCR at baseline (limit of detection, 714 copies per milliliter) were excluded from analyses of virologic and clinical endpoints in a modified full analysis set (mFAS). Subgroup analyses by serology status and baseline viral load were prespecified in the statistical analysis plan. Safety was assessed in patients in the FAS who received study drug (active or placebo).

To confirm the virologic efficacy seen in analysis group 1 (patients 1 through 275), analyses of virologic endpoints were conducted using data from patients 276 through 799, inclusive (524 patients; analysis group 2). Analyses of clinical endpoints and safety, however, utilized data from all available patients, inclusive of the first 275 patients (patients 1 through 799; analysis group 1+2).

The virologic efficacy endpoint was calculated as discussed below. The key secondary clinical endpoints were analyzed using Fisher's exact test. Analyses of virologic and

TABLE 5B

Phase 2 Primary Analysis of Virologic and Clinical Endpoints

| Endpoint Number | Description |
|---|---|
| 1 | Time-weighted average daily change from baseline in viral load (log10 copies/mL) from day 1 through day 7 in the mFAS patients with baseline viral load >$10^7$ copies/mL for REGEN-COV 2.4 g and 8.0 g combined group versus placebo (patients 276 through 799) |
| 2 | Time-weighted average daily change from baseline in viral load (log10 copies/mL) from day 1 through day 7 in the mFAS patients with baseline viral load >$10^6$ copies/mL for REGEN-COV 2.4 g and 8.0 g combined versus placebo (patients 276 through 799) |
| 3 | Time-weighted average daily change from baseline in viral load (log10 copies/mL) from day 1 through day 7 in the serum antibody-negative (seronegative) mFAS for REGEN-COV 2.4 g and 8.0 g combined group versus placebo (patients 276 through 799) |
| 4 | Time-weighted average daily change from baseline in viral load (log10 copies/mL) from day 1 through day 7 in the mFAS for REGEN-COV 2.4 g and 8.0 g combined group versus placebo (patients 276 through 799) |
| 5 | Time-weighted average daily change from baseline in viral load (log10 copies/mL) from day 1 through day 7 in the mFAS patients with baseline viral load >$10^7$ copies/mL for REGEN-COV 8.0 g group versus placebo (patients 276 through 799) |
| 6 | Time-weighted average daily change from baseline in viral load (log10 copies/mL) from day 1 through day 7 in the mFAS patients with baseline viral load >$10^7$ copies/mL for REGEN-COV 2.4 g group versus placebo (patients 276 through 799) |
| 7 | Time-weighted average daily change from baseline in viral load (log10 copies/mL) from day 1 through day 7 in the mFAS patients with baseline viral load >$10^6$ copies/mL for REGEN-COV 8.0 g group versus placebo (patients 276 through 799) |
| 8 | Time-weighted average daily change from baseline in viral load (log10 copies/mL) from day 1 through day 7 in the mFAS patients with baseline viral load >$10^6$ copies/mL for REGEN-COV 2.4 g versus placebo (patients 276 through 799) |
| 9 | Proportion of patients with MAVs through day 29 in the mFAS for REGEN-COV 2.4 g and 8.0 g combined group versus placebo (patients |
| 10 | Proportion of patients with subset of MAVs consisting only of hospitalization or emergency room visit or urgent care visit through day 29 in the mFAS for REGEN-COV 2.4 g and 8.0 g combined group versus placebo (patients 1 through 799) | mFAS modified full analysis set;
MAV medically attended visit

Safety endpoints for the phase 1/2 portion of the trial included adverse events that occurred or worsened during the observation period (only in phase 1; grade 3 and 4 only), serious adverse events (SAEs), and adverse events of special interest (AESIs): grade ≥2 hypersensitivity or infusion-related reactions.

Statistical Analysis

The statistical analysis plan for the presented analysis was finalized prior to database lock and unblinding of the additional 524-patient phase 2 dataset. The full analysis set (FAS) included patients with Covid-19 symptoms who clinical endpoints were conducted at a two-sided α=0.05 utilizing a hierarchical testing strategy to control for type I error. Statistical analyses were performed with SAS software, version 9.4 or higher (SAS Institute).

Figure 6:
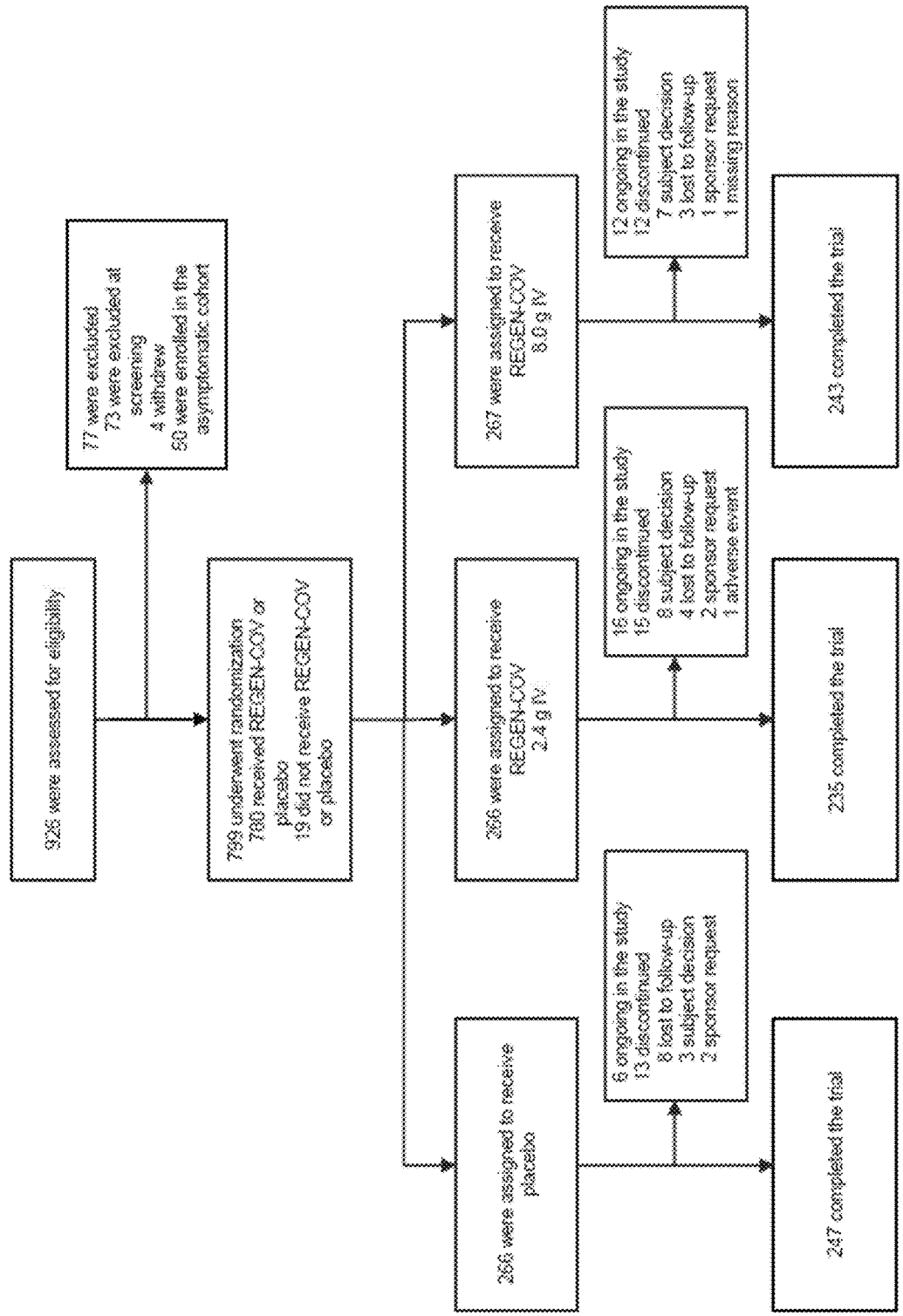
FIG. 6 illustrates a CONSORT diagram showing the screening, randomization and treatment of subjects in the study discussed in Example 2.

Baseline Characteristics 799 patients underwent randomization in the phase 1/2 portion of the trial. In the pooled 799-patient group, 266, 267, and 266 patients were assigned to receive low-dose REGEN-COV, high-dose REGEN-COV, or placebo, respectively (FIG. 6). Among the 799 patients (analysis group 1+2), 87 (10.9%) tested negative in the central lab SARS- CoV-2 NP RT-qPCR assay at baseline and 47 (5.9%) were without central lab baseline viral load data; consequently, the modified full analysis (mFAS) set comprised 665 patients. Similarly, among the 524 patients in analysis group 2 (primary virologic efficacy analysis), the mFAS set comprised 437 patients.

Of the 799 randomized patients, the median age was 42.0 years, 47% were male, 9% identified as Black or African American, 50% identified as Hispanic or Latino (Table 5A). 483 (60.5%) patients had ≥1 risk factor for hospitalization due to Covid-19, including obesity (37.3%), age >50 years (29.3%), cardiovascular disease (20.5%), or chronic metabolic disease (13.1%). Baseline characteristics were similar between the 275-patient analysis group 1 and 524-patient analysis group 2 (Table 5C).

TABLE 5C

Phase 1/2 Demographic and Baseline Medical Characteristics* (N = 524; Full Analysis Set)

| Characteristic | Total (N = 524) | Placebo (N = 173) | REGEN-COV 2.4 g (N = 174) | REGEN-COV 8.0 g (N = 177) | REGEN-COV combined (N = 351) |
|---|---|---|---|---|---|
| Median age (IQR)—yr | 41.0 (28.0-52.0) | 40.0 (28.0-53.0) | 42.0 (29.0-53.0) | 39.0 (28.0-51.0) | 41.0 (28.0-52.0) |
| Male sex—no. (%) | 242 (46.2) | 84 (48.6) | 76 (43.7) | 82 (46.3) | 158 (45.0) |
| Hispanic or Latino ethnic group—no. (%)† | 250 (47.7) | 91 (52.6) | 80 (46.0) | 79 (44.6) | 159 (45.3) |
| Race—no. (%)† | | | | | |
| White | 457 (87.2) | 155 (89.6) | 150 (86.2) | 152 (85.9) | 302 (86.0) |
| Black or African American | 39 (7.4) | 10 (5.8) | 12 (6.9) | 17 (9.6) | 29 (8.3) |
| Asian | 11 (2.1) | 2 (1.2) | 6 (3.4) | 3 (1.7) | 9 (2.6) |
| American Indian or Alaska Native | 3 (0.6) | 1 (0.6) | 1 (0.6) | 1 (0.6) | 2 (0.6) |
| Unknown | 4 (0.8) | 1 (0.6) | 1 (0.6) | 2 (1.1) | 3 (0.9) |
| Not Reported | 10 (1.9) | 4 (2.3) | 4 (2.3) | 2 (1.1) | 6 (1.7) |
| Median weight (IQR)—kg | 79.80 (68.00-93.00) | 81.00 (69.40-91.00) | 79.30 (68.35-91.40) | 79.40 (67.60-95.70) | 79.40 (68.00-94.00) |
| Body-mass index‡ | 29.38 ± 8.800 | 30.0 ± 11.828 | 29.03 ± 6.291 | 29.04 ± 7.386 | 29.04 ± 6.855 |
| Obesity—no. (%)§ | 183 (34.9) | 59 (34.1) | 62 (35.6) | 62 (35.0) | 124 (35.3) |
| Baseline viral load in nasopharyngeal swab Raw values | | | | | |
| No. of patients | 494 | 168 | 159 | 167 | 326 |
| Mean viral load—copies/ml | 20153955.3 ± 28853829.01 | 25281106.2 ± 31606803.98 | 18101836.4 ± 26953942.48 | 16949916.6 ± 27112316.53 | 17511742.5 ± 26999735.08 |
| Median viral load (range)—copies/ml | 630500.0 (1-71000000) | 1660000.0 (1-71000000) | 301000.0 (1-71000000) | 369000.0 (1-71000000) | 342500.0 (1-71000000) |
| Baseline viral load in nasopharyngeal swab ($\log_{10}$ scale) | | | | | |
| No. of patients | 494 | 168 | 159 | 167 | 326 |
| Mean viral load—$\log_{10}$ copies/ml | 5.30 ± 2.514 | 5.50 ± 2.546 | 5.34 ± 2.426 | 5.08 ± 2.560 | 5.20 ± 2.495 |
| Median viral load (range)—$\log_{10}$ copies/ml | 5.80 (0.0-7.9) | 6.22 (0.0-7.9) | 5.48 (0.0-7.9) | 5.57 (0.0-7.9) | 5.53 (0.0-7.9) |
| Baseline viral load in nasopharyngeal swab category—no. (%) | | | | | |
| >$10^4$ | 353 (67.4) | 120 (69.4) | 120 (69.0) | 113 (63.8) | 233 (66.4) |
| >$10^5$ | 301 (57.4) | 108 (62.4) | 96 (55.2) | 97 (54.8) | 193 (55.0) |
| >$10^6$ | 237 (45.2) | 87 (50.3) | 76 (43.7) | 74 (41.8) | 150 (42.7) |
| >$10^7$ | 185 (35.3) | 71 (41.0) | 61 (35.1) | 53 (29.9) | 114 (32.5) |
| Positive baseline qualitative RT-PCR—no. (%) | 437 (83.4) | 150 (86.7) | 142 (81.6) | 145 (81.9) | 287 (81.8) |
| Baseline serum C-reactive protein level | | | | | |
| No. of Patients | 333 | 111 | 112 | 110 | 222 |
| Mean level—mg/liter | 13.066 (25.5848) | 17.722 (31.9234) | 10.931 (20.8046) | 10.540 (22.1667) | 10.738 (21.4425) |
| Median level (range)—mg/liter | 3.570 (0.10-157.96) | 5.020 (0.10-153.80) | 3.640 (0.12-135.36) | 2.475 (0.18-157.96) | 3.145 (0.12-157.96) |

TABLE 5C-continued

Phase 1/2 Demographic and Baseline Medical Characteristics* (N = 524; Full Analysis Set)

| Characteristic | Total (N = 524) | Placebo (N = 173) | REGEN-COV 2.4 g (N = 174) | REGEN-COV 8.0 g (N = 177) | REGEN-COV combined (N = 351) |
|---|---|---|---|---|---|
| Baseline Serum antibody status—no. (%) | | | | | |
| Negative | 292 (55.7) | 101 (58.4) | 96 (55.2) | 95 (53.7) | 191 (54.4) |
| Positive | 176 (33.6) | 56 (32.4) | 58 (33.3) | 62 (35.0) | 120 (34.2) |
| Unknown | 56 (10.7) | 16 (9.2) | 20 (11.5) | 20 (11.3) | 40 (11.4) |
| Median time from symptom onset to randomization (IQR)—days | 3.0 (2-5) | 3.0 (2-5) | 3.0 (2-5) | 3.0 (2-5) | 3.0 (2-5) |
| At least one risk factor for hospitalization—no. (%)¶ | 307 (58.6) | 100 (57.8) | 108 (62.1) | 99 (55.9) | 207 (59.0) |

SD, standard deviation.
*Plus-minus values are means ± SD. Percentages may not total 100 because of rounding. IQR denotes interquartile range, and RT-PCR reverse-transcriptase polymerase chain reaction.
†Race and ethnic group were reported by the patients
‡The body-mass index is the weight in kilograms divided by the square of the heights in meters.
§Obesity is defined as a body-mass index of greater than 30.
¶Risk Factors for hospitalization include an age of more than 50 years, obesity, cardiovascular disease (including hypertension), chronic lung disease (including asthma), chronic metabolic disease (including diabetes), chronic kidney disease (including receipt of dialysis), chronic liver disease, and immunocompromised (immunosuppression or receipt of immunosuppressants).

At randomization, 408 (51.1%) patients were serum antibody-negative, 304 (38.0%) were serum antibody-positive, and 87 (10.9%) were serum antibody-unknown. Median baseline viral load was 5.48 log 10 copies/mL (47 of 799 with missing baseline data); 256 (32.0%) patients had baseline viral load >107 copies/mL. The mean time from symptom onset to randomization was 3.4 days in the overall trial population: 3.2 days in serum antibody-negative patients; 3.6 days in serum antibody-positive patients; 2.9 days patients with viral load >107 copies/mL; and 3.8 days in patients with viral load ≤107 copies/mL. Among 408 patients with ≥1 risk factor for hospitalization, 336 (82.3%) were serum antibody-negative or had viral load >104 copies/mL.

Natural History

Figure 7:
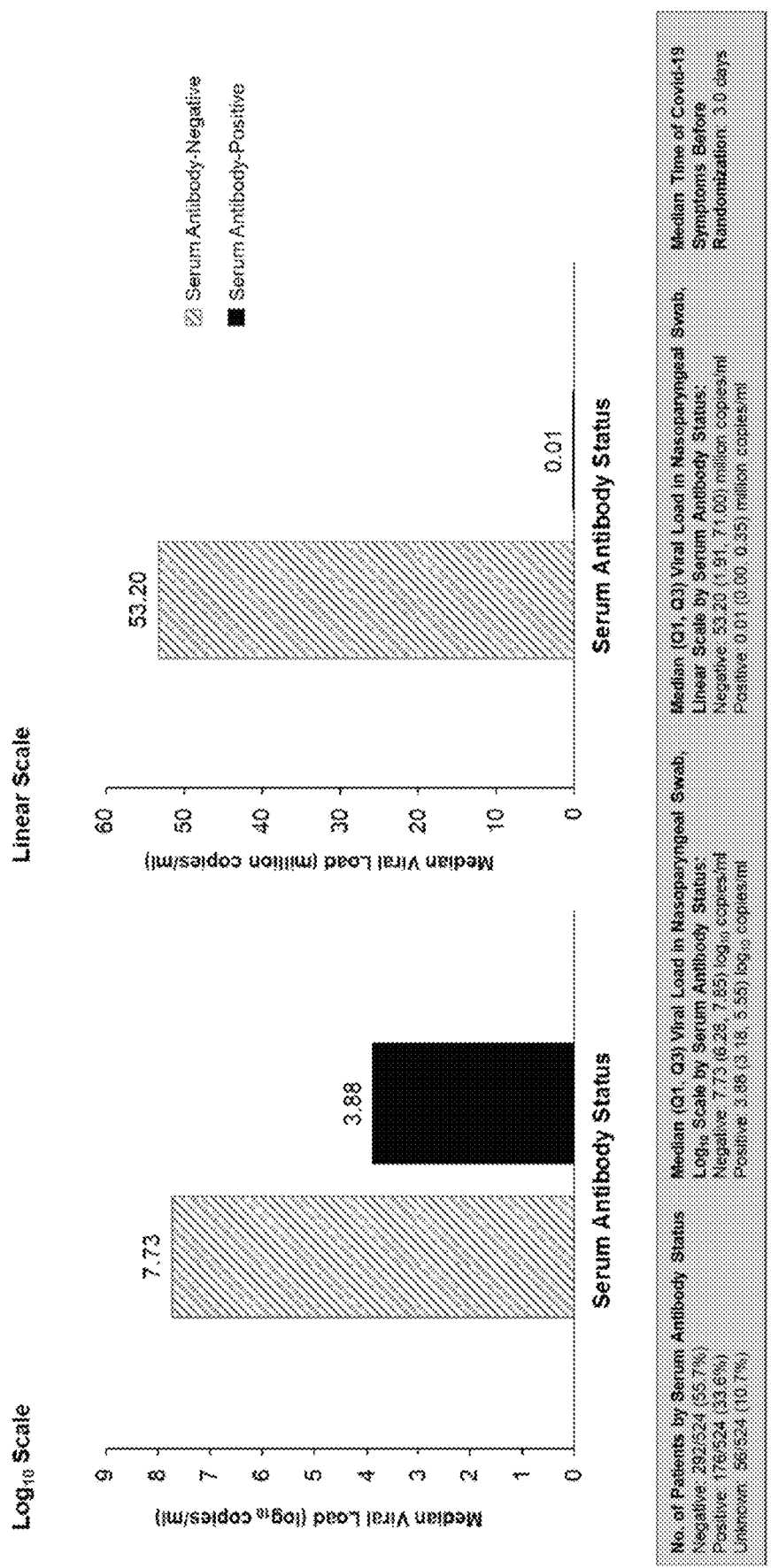
FIG. 7 illustrates the relationship between baseline serum antibody status and baseline viral load in the placebo arm of the study discussed in Example 2.
Figure 8:
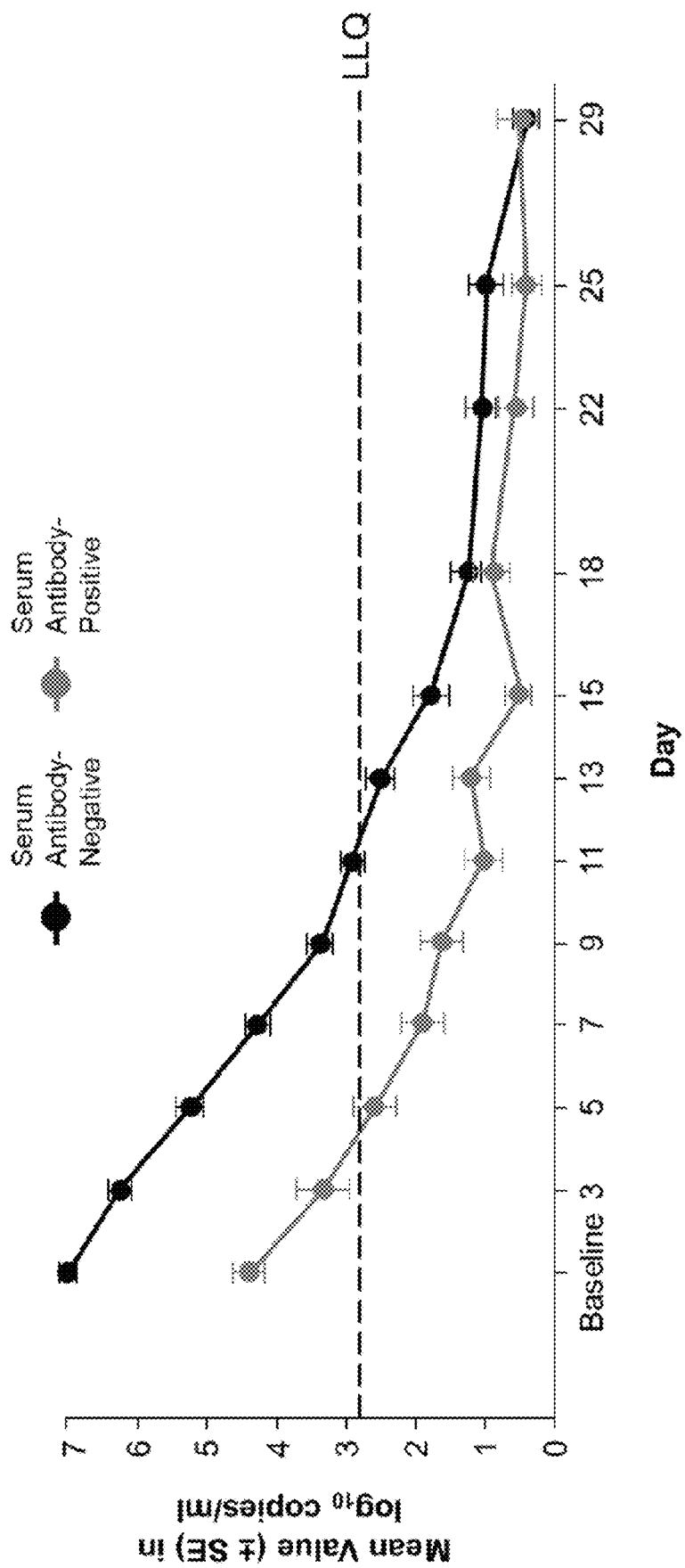
FIG. 8 illustrates viral load over time in the placebo arm by baseline serum antibody status in the study discussed in Example 2.
Figure 9:
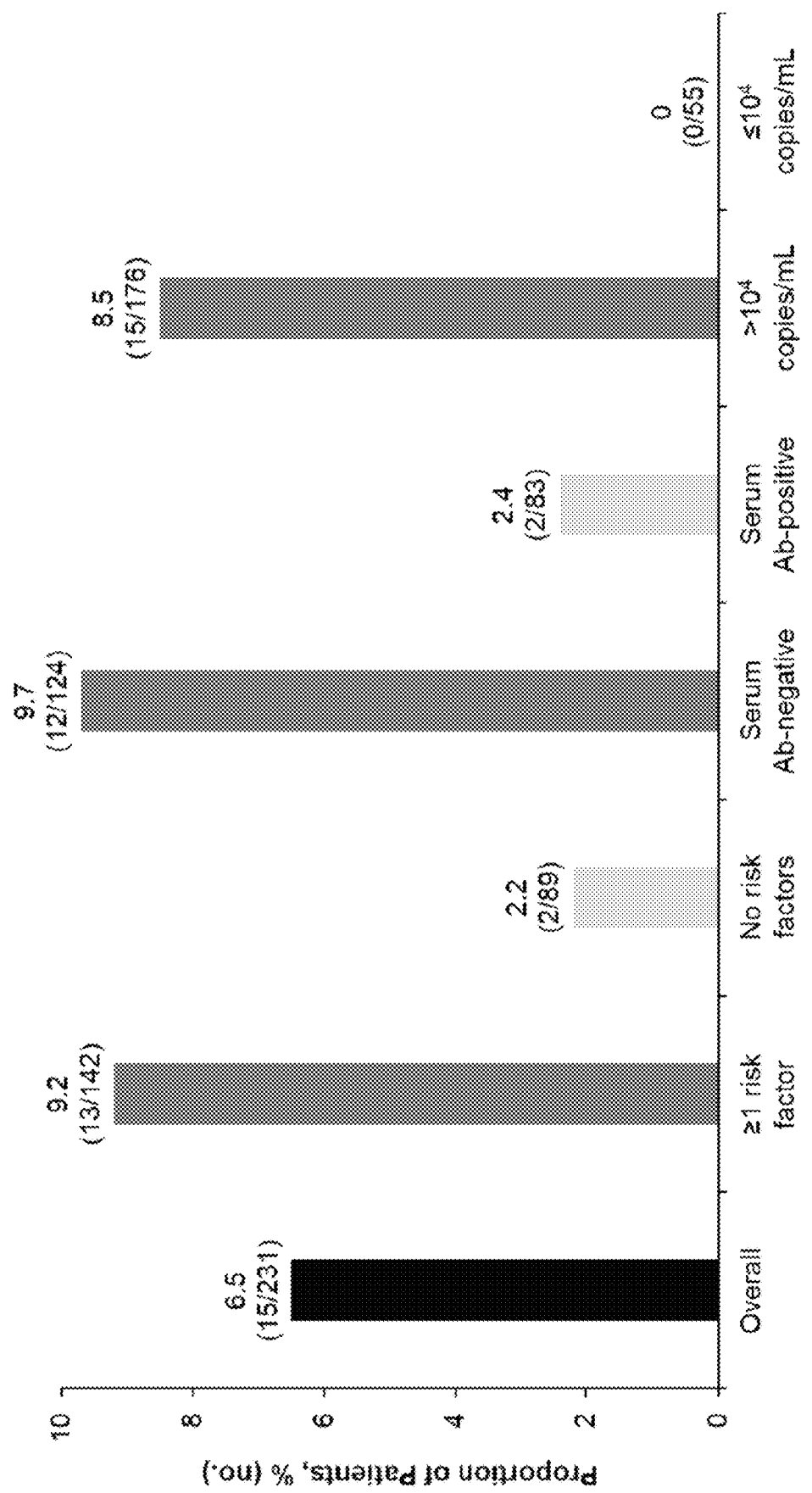
FIG. 9 illustrates the proportion of patients in the placebo arm with ≥1 Covid-19-related medically-attended visit (MAV) through day 29 in the study discussed in Example 2.

The natural history of Covid-19 among placebo-treated patients in this analysis confirmed that the presence of endogenous antibodies against SARS-CoV-2 at baseline is an important indicator of viral and clinical outcomes. Patients in the placebo arm who were serum antibody-negative at baseline had higher median viral loads at baseline compared to those who were serum antibody-positive (7.73 log 10 copies/ml vs 3.88 log 10 copies/ml), and they took substantially longer to bring their viral levels to LLQ or to undetectable (FIGS. 7 and 8). Similarly, for clinical outcomes, placebo patients who were serum antibody-negative at baseline had substantially higher rates of Covid-19-related MAVs (9.7%; 12/124) than placebo patients who were serum antibody-positive at baseline (2.4%; 2/83). As the endogenous immune response was associated with baseline viral titers, there was the expected association of Covid-19-related MAV risk with baseline viral load as well as with presence of risk factors: MAVs occurred in 0% (0/55) of patients with baseline viral load ≤104 copies/mL vs 8.5% (15/176) with baseline viral load >104 copies/mL and MAVs occurred in 2.2% (2/89) of patients with no risk factors vs 9.2% (13/142) with ≥1 risk factor (FIG. 9).

Virologic Efficacy

Figure 10A:
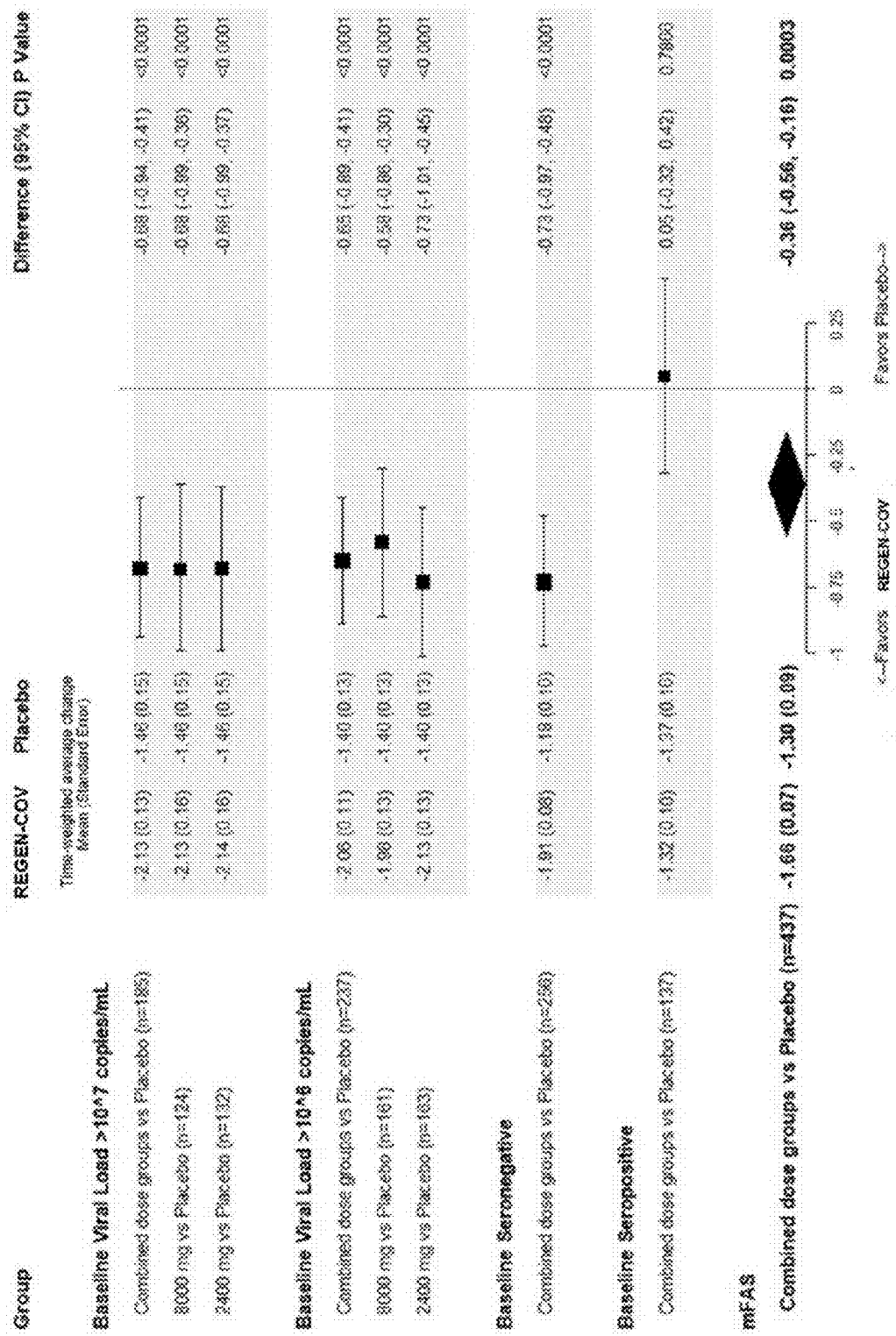
FIG. 10A and FIG. 10B illustrate time-weighted-average (TWA) daily change from baseline in viral load ($\log_{10}$ copies/mL) with REGEN-COV treatment (forest plots) in the study discussed in Example 2.
Figure 10B:
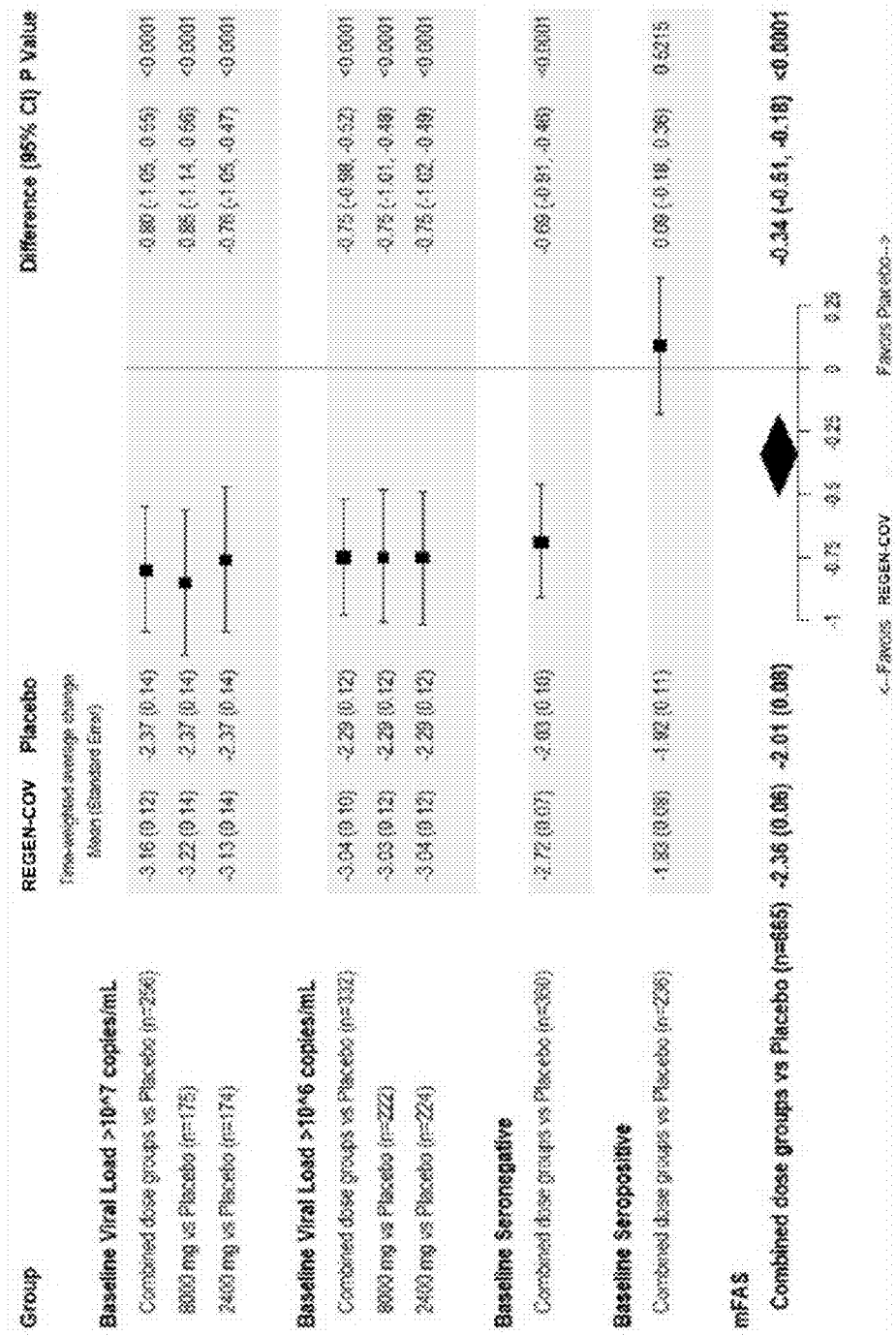
Figure 11:
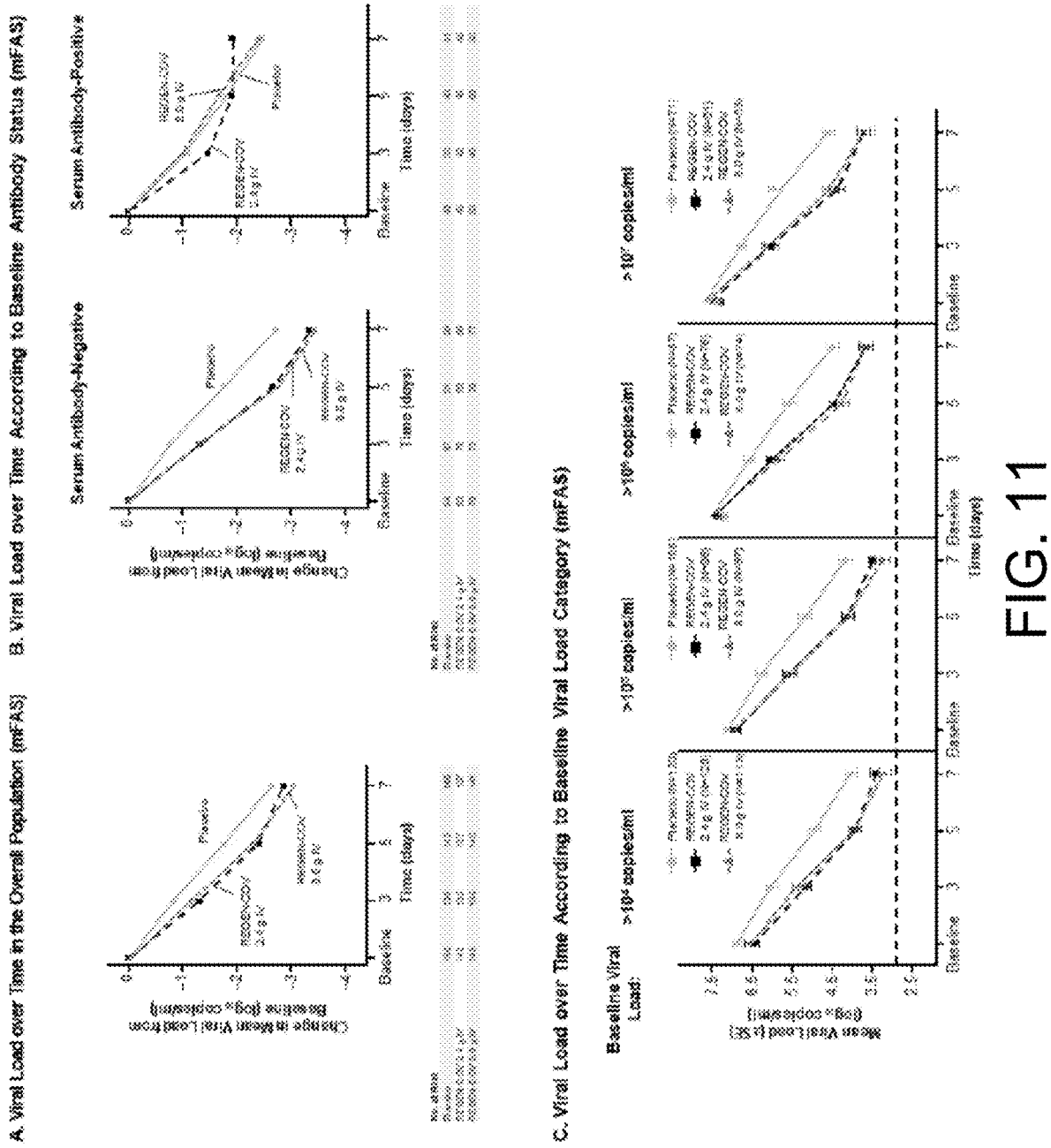
FIG. 11 illustrates TWA daily change from baseline in viral load ($\log_{10}$ copies/mL) with REGEN-COV treatment (graphs) in the study discussed in Example 2. Shown is the change in mean viral load (in log 10 copies per milliliter) from baseline at each visit through day 7 in the overall population (modified full analysis set, which excluded patients who tested negative for severe acute respiratory syndrome coronavirus 2 (SARS-CoV-2) by qualitative reverse-transcriptase polymerase chain reaction at baseline)

Prespecified comparisons for the virologic efficacy endpoint were assessed hierarchically in the 524-patient analysis group 2 who were confirmed SARS-CoV-2-positive by NP RT-qPCR at baseline (mFAS; n=437) (Tables 5B and 5D). REGEN-COV treatment significantly reduced viral load through day 7 vs placebo in all the prespecified virologic efficacy comparisons (Table 5D; FIG. 10A, FIG. 10B, and FIG. 11). In the first comparison, among patients with baseline viral load >$10^7$ copies/mL, the least-squares mean difference between REGEN-COV treatment (combined 2.4 g and 8.0 g doses) versus placebo in the time-weighted average (TWA) daily change in viral load through day 7 was −0.68 log 10 copies/mL (95% CI, −0.94 to −0.41; P<0.0001) (Table 5D). Similarly, the least-squares mean difference in TWA daily change from baseline with REGEN-COV treatment vs placebo was −0.73 log 10 copies/mL (95% CI, −0.97 to −0.48; P<0.0001) in patients who were serum antibody-negative at baseline (n=256), while it was −0.36 log 10 copies/mL (95% CI, −0.56 to −0.16; P=0.0003) in the overall modified full analysis set (n=437). These data indicate that reductions in viral load observed with the antibody cocktail treatment were primarily driven by effects in serum antibody-negative patients, as previously observed (Table 5D; FIG. 10A, FIG. 10B, and FIG. 11). Treatment effects were similar with the low-dose and high-dose antibody cocktail across all the virologic efficacy endpoint comparisons (Table 5D). Results from additional key virologic endpoints are provided in Table 5E, FIG. 12, and FIG. 13.

TABLE 5D

Key Virologic and Clinical End Points

| End Point | Placebo | REGEN-COV 2.4 g | REGEN-COV 8.0 g | REGEN-COV combined |
|---|---|---|---|---|
| Time-weighted average change from baseline in viral load* ($\log_{10}$ copies/mL) from day 1 through day 7 (analysis group 2) | | | | |
| Baseline viral load >$10^7$ copies/mL (mFAS) | | | | |
| No. of patients | 70 | 58 | 52 | 110 |

TABLE 5D-continued

Key Virologic and Clinical End Points

| End Point | Placebo | REGEN-COV 2.4 g | REGEN-COV 8.0 g | REGEN-COV combined |
|---|---|---|---|---|
| Least-squares mean change (SE)—$\log_{10}$ copies/ml | −1.46 (0.15) | −2.14 (0.16) | −2.13 (0.16) | −2.13 (0.13) |
| 95% CI | −1.75, −1.16 | −2.44, −1.83 | −2.44, −1.82 | −2.39, −1.87 |
| Difference vs. placebo at day 7—$\log_{10}$ copies/ml | | | | |
| Least-squares mean (SE) | | −0.68 (0.16) | −0.68 (0.16) | −0.68 (0.14) |
| 95% CI† (P value) | | −0.99, −0.37 (<0.0001) | −0.99, −0.36 (<0.0001) | −0.94, −0.41 (<0.0001) |
| Baseline Viral Load >$10^8$ copies/mL (mFAS) | | | | |
| No. of patients | 86 | 72 | 73 | 145 |
| Least-squares mean change (SE)—$\log_{10}$ copies/ml | −1.40 (0.13) | −2.13 (0.13) | −1.98 (0.13) | −2.06 (0.11) |
| 95% CI | −1.65, −1.14 | −2.38, −1.88 | −2.24, −1.72 | −2.27, −1.85 |
| Difference vs. placebo at day 7—$\log_{10}$ copies/ml | | | | |
| Least squares mean (SE) | | −0.73 (0.14) | −0.58 (0.14) | −0.65 (0.12) |
| 95% CI† (P value) | | −1.01, −0.45 (<0.0001) | −0.86, −0.30 (<0.0001) | −0.89, −0.41 (<0.0001) |
| Baseline Serum antibody status: negative (mFAS) | | | | |
| No. of patients | 93 | 80 | 77 | 157 |
| Least-squares mean change (SE)—$\log_{10}$ copies/ml | −1.18 (0.10) | −1.92 (0.11) | −1.90 (0.11) | −1.91 (0.08) |
| 95% CI | −1.38, −0.99 | −2.13, −1.71 | −2.11, −1.69 | −2.06, −1.76 |
| Difference vs. placebo at day 7—$\log_{10}$ copies/ml | | | | |
| Least-squares mean (SE) | | −0.74 (0.14) | −0.71 (0.14) | −0.73 (0.12) |
| 95% CI† (P value) | | −1.02, −0.45 (<0.0001) | −1.00, −0.43 (<0.0001) | −0.97, −0.48 (<0.0001) |
| mFAS | | | | |
| No. of Patients | 146 | 137 | 141 | 278 |
| Least-squares mean change (SE)—$\log_{10}$ copies/ml | −1.30 (0.09) | −1.69 (0.09) | −1.64 (0.09) | −1.66 (0.07) |
| 95% CI | −1.49, −1.12 | −1.87, −1.50 | −1.82, −1.46 | −1.81, −1.52 |
| Difference vs. placebo at day 7—$\log_{10}$ copies/ml | | | | |
| Least-squares mean (SE) | | −0.38 (0.12) | −0.34 (0.12) | −0.36 (0.10) |
| 95% CI† (P value) | | −0.61, −0.15 (0.0011) | −0.57, −0.11 (0.0035) | −0.56, −0.16 (0.0003) |
| Proportions of patients with Covid-19-related MAVs through day 29 (analysis group 1 + 2) | | | | |
| mFAS | | | | |
| No. of Patients | 231 | 215 | 219 | 434 |
| Patients with ≥1 visit within 29 days—no. (%) | 15 (6.5) | 6 (2.8) | 6 (2.7) | 12 (2.8) |
| Difference vs. placebo—percentage points | | −3.7 | −3.8 | −3.7 |
| 95% CI† (P value) | | −12.9, 5.6 (0.0754) | −13.0, 5.5 (0.0737) | −11.7, 4.3 (0.0240) |
| Proportion of patients with subset of Covid-19-related MAVs consisting only of hospitalization or ER visit or urgent care visit through day 29 (analysis group 1 + 2) | | | | |
| mFAS | | | | |
| No. of Patients | 231 | 215 | 219 | 434 |
| Patients with ≥1 visit within 29 days—no. (%) | 10 (4.3) | 5 (2.3) | 5 (2.3) | 10 (2.3) |
| Difference vs. placebo—percentage points | | −2.0 | −2.0 | −2.0 |
| 95% CI† (P value) | | −11.2, 7.3 (0.2983) | −11.3, 7.2 (0.2962) | −10.0, 6.0 (0.1575) |

*The time-weighted mean change in viral load was based on an analysis of covariance model with treatment group, risk factor, and baseline antibody status as fixed effects and baseline viral load and treatment group-by-baseline viral load as covariates. Confidence intervals were not adjusted for multiplicity.

†Confidence intervals for the difference (REGEN-COV minus placebo) were based on the exact method and were not adjusted for multiplicity.

TABLE 5E

Change from Baseline in Viral Load ($\log_{10}$ copies/mL) at Each Visit in Patients With No or ≥1 Risk Factors for Hospitalization

| End Point | Placebo | REGEN-COV 2.4g | REGEN-COV 8.0 g | REGEN-COV combined |
|---|---|---|---|---|
| Change from baseline in viral load ($\log_{10}$ copies/mL) to day 7 (analysis group 2) | | | | |
| No risk factors for hospitalization due to COVID-19 (mFAS) | | | | |
| No. of Patients | 55 | 48 | 58 | 106 |
| Least-squares mean change (SE)—$\log_{10}$ copies/ml† | −2.50 (0.21) | −2.90 (0.23) | −3.02 (0.21) | −2.97 (0.16) |
| 95% CI | −2.92, −2.08 | −3.34, −2.45 | −3.44, −2.60 | −3.28, −2.65 |
| Difference vs. placebo at day 7—$\log_{10}$ copies/ml | | | | |
| Least-squares mean (SE) | | −0.39 (0.30) | −0.51 (0.29) | −0.47 (0.25) |
| 95% CI (P value) | | −0.99, 0.20 (0.1933) | −1.08, 0.05 (0.0757) | −0.97, 0.03 (0.0677) |
| ≥1 risk factor for hospitalization due to COVID-19 (mFAS) | | | | |
| No. of Patients | 84 | 83 | 74 | 157 |
| Least-squares mean change (SE)—$\log_{10}$ copies/ml† | −2.56 (0.17) | −2.74 (0.17) | −3.08 (0.17) | −2.90 (0.13) |
| 95% CI | −2.90, −2.23 | −3.08, −2.41 | −3.42, −2.73 | −3.14, −2.65 |

TABLE 5E-continued

Change from Baseline in Viral Load (log$_{10}$ copies/mL) at Each Visit in Patients With No or ≥1 Risk Factors for Hospitalization

| End Point | Placebo | REGEN-COV 2.4g | REGEN-COV 8.0 g | REGEN-COV combined |
|---|---|---|---|---|
| Difference vs. placebo at day 7—log$_{10}$ copies/ml | | | | |
| Least-squares mean (SE) | | −0.18 (0.23) | −0.51 (0.24) | −0.34 (0.20) |
| 95% CI | | −0.63, 0.27 | −0.98, −0.05 | −0.73, 0.06 |
| (P value)* | | (0.4310) | (0.0302) | (0.0951) |

*P-values are based on MMRM model with terms for baseline, baseline serology status, country, treatment, visit, treatment-by-visit, treatment-by-base, and base-by-visit interaction as fixed effect and subject as random effect.
CI confidence interval;
LS least squares;
SE standard error.

The virologic efficacy endpoint of time-weighted average (TWA) daily change from baseline (day 1) through day 7 was calculated for each patient as the area under the concentration-time curve with the use of the linear trapezoidal rule (area under the curve for change from baseline divided by the time interval of the observation period), and analyzed using an analysis of covariance model with treatment group, country, and risk factor (no risk factor versus at least one risk factor) as fixed effects and baseline viral load and treatment by baseline interaction as covariates.

Clinical Efficacy

There were two clinical efficacy endpoints prespecified for hierarchical testing: the proportion of patients with at least one Covid-19-related medically-attended visits (MAV) and the proportion of patients with at least one Covid-19-related MAV consisting of only hospitalization or ER or urgent care visits (Tables 5B and 5D). Both endpoints were assessed through day 29 in the pooled 799-patient group (analysis group 1+2) who were confirmed SARS-CoV-2-positive by NP RT-qPCR at baseline (mFAS; n=665). Overall, 67% of the Covid-19-related MAVs were hospitalizations or emergency room (ER) visits (30% and 37%, respectively), 26% physician office visits/telemedicine, and 7% urgent care visits. Descriptions of Covid-19 related MAVs are included in Table 5F.

TABLE 5F

Description of Covid-19-related MAVs*

| | Pt | Age | Sex | Ethnicity | Race | Risk Factor(s) (Y/N) | Symptom duration prior to randomization | Baseline viral load (log10 copies/ml) | Treatment Arm |
|---|---|---|---|---|---|---|---|---|---|
| 1 | 23 | 42 | M | Not Hispanic or Latino | White | Y | 7 days | 7.08 | Placebo |
| 2 | 13 | 77 | F | Hispanic or Latino | Not Reported | Y | 6 days | 4.04 | Placebo |
| 3 | 12 | 40 | M | Hispanic or Latino | White | Y | 2 days | 7.85 | Placebo |
| 4 | 28 | 89 | F | Hispanic or Latino | White | Y | 3 days | 7.85 | Placebo |
| 5 | 30 | 50 | F | Hispanic or Latino | White | Y | 1 day | 7.85 | Placebo |
| 6 | 10 | 48 | F | Not Hispanic or Latino | White | Y | 4 days | 7.09 | Placebo |
| 7 | 19 | 62 | F | Not Hispanic or Latino | White | Y | Pending | 7.85 | Placebo |
| 8 | 9 | 27 | F | Not Hispanic or Latino | Asian American | Y | 5 days | 4.41 | Placebo |
| 9 | 21 | 37 | F | Not Hispanic or Latino | White | Y | 6 days | 6.23 | Placebo |
| 10 | 4 | 31 | F | Not Hispanic or Latino | White | N | 1 day | 6.59 | Placebo |
| 11 | 26 | 66 | M | Not Hispanic or Latino | White | Y | 2 days | 7.03 | Placebo |
| 12 | 31 | 26 | M | Not Hispanic or Latino | White | N | 6 days | 5.88 | Placebo |

TABLE 5F-continued

Description of Covid-19-related MAVs*

| | Pt | | | | | | | | |
|---|---|---|---|---|---|---|---|---|---|
| 13 | 5 | 43 | M | Hispanic or Latino | White | Y | 4 days | 6.55 | Placebo |
| 14 | 6 | 53 | F | Hispanic or Latino | White | Y | 3 days | 4.7 | Placebo |
| 15 | 29 | 63 | F | Hispanic or Latino | White | Y | pending | 7.85 | Placebo |
| 16 | 16 | 28 | F | Not Hispanic or Latino | White | Y | 7 days | 3.99 | Low Dose |
| 17 | 25 | 82 | F | Hispanic or Latino | White | Y | 2 days | 6.73 | Low Dose |
| 18 | 7 | 25 | M | Not Hispanic or Latino | White | N | 7 days | 6.29 | Low Dose |
| 19 | 20 | 19 | F | Not Hispanic or Latino | White | N | 2 days | 7.85 | Low Dose |
| 20 | 27 | 58 | F | Hispanic or Latino | White | Y | 6 days | 4.57 | Low Dose |
| 21 | 22 | 44 | M | Not Hispanic or Latino | Vietnamese | N | 5 days | 4.97 | Low Dose |
| 22 | 24 | 20 | F | Not Hispanic or Latino | White | N | 4 days | 7.24 | High Dose† |
| 23 | 14 | 20 | M | Hispanic or Latino | White | Y | pending | 5.71 | High Dose |
| 24 | 2 | 37 | F | Not Hispanic or Latino | White, American Indian or Alaska Native | Y | 2 days | 5.45 | High Dose |
| 25 | 8 | 49 | M | Not Hispanic or Latino | White | Y | 3 days | 7.85 | High Dose |
| 26 | 17 | 36 | F | Not Hispanic or Latino | White | N | 1 day | 7.85 | High Dose |
| 27 | 15 | 55 | F | Not Hispanic or Latino | White | Y | 6 days | 4.84 | High Dose |

| Pt | Type of MAV | Study Day | Viral load at or around the time of MAV (log10 copies/ml) (day) | Reason for MAV | Details |
|---|---|---|---|---|---|
| 1 | 23 Hospitalization | 2 | 7.80 (1) | Pneumonia | 6-day hospitalization, did not require supplemental oxygen, ICU care, or mechanical ventilation |
| 2 | 13 Hospitalization | 3 | 4.64 (3) | Hypoxemia | 5-day hospitalization, received supplemental oxygen. No ICU care or mechanical ventilation required |

TABLE 5F-continued

| | | | | | | |
|---|---|---|---|---|---|---|
| | | | | Description of Covid-19-related MAVs* | | |
| 3 | 12 | Hospitalization | 9 | 5.97 (9) | Respiratory Failure | 6-day hospitalization, treated with albuterol and supplemental oxygen. Did not require ICU care or mechanical ventilation. |
| 4 | 28 | Hospitalization | 10 | 5.51 (7) | Worsening of COVID-19/Acute respiratory failure | 15-day hospitalization, treated with steroids and antibiotics, received supplemental oxygen. No ICU care or mechanical ventilation required. |
| 5 | 30 | Hospitalization | 10 | 5.22 (5) | Pneumonia | No additional details at this time. |
| 6 | 10 | ER Visit | 5 | 5.42 (3) | Vomiting/Abdominal Pain | No additional details at this time. |
| 7 | 19 | ER Visit | 10 | 5.02 (9) | Fever/Shortness of breath | No additional details at this time. |
| 8 | 9 | ER Visit | 13 | 3.24 (13) | Tachycardia | Prescribed ibuprofen and given IV normal saline |
| 9 | 21 | ER Visit | 15 | 0 (15) | Shortness of breath | Prescribed fluticasone and albuterol |
| 10 | 4 | ER Visit | 21 | 0 (18) | Prolonged COVID-19 symptoms/fever/intermittent chest pain | Prescribed doxycycline and albuterol |
| 11 | 26 | Phys Office/Tele med | 4 | 5.23 (3) | Cough | Prescribed benzonatate, ibuprofen |
| 12 | 31 | Phys Office/Tele med | 5 | 3.36 (5) | Persistent cough | Prescribed azithromycin and acetaminophen |
| 13 | 5 | Phys Office/Tele med | 7 | 3.49 (7) | Worsening cough | Prescribed ceftriaxone, azithromycin, and ambroxol |
| 14 | 6 | Phys Office/Tele med | 7 | 3.53 (7) | Worsening cough | Prescribed ceftriaxone, azithromycin, and ambroxol |
| 15 | 29 | Phys Office/Tele med | 10 | 0 (9) | Worsening of COVID-19 | Prescribed promethazine |
| 16 | 16 | Hospitalization | 2 | 3.99 (1) | Shortness of breath/Pneumonia | 2-day hospitalization, treated with antibiotics, remdesivir, tocilizumab, and steroids. Did not require supplemental oxygen, ICU care, or mechanical ventilation |
| 17 | 25 | Hospitalization | 3 | 6.73 (1) | Pneumonia | 7-day hospitalization, received supplemental oxygen. No ICU care or mechanical ventilation required. |
| 18 | 7 | ER Visit | 5 | 4.14 (5) | Pneumonia | No additional details at this time. |
| 19 | 20 | ER Visit | 5 | 3.83 (5) | Shortness of breath | No additional details at this time. |

TABLE 5F-continued

| | | | | | | |
|---|---|---|---|---|---|---|
| | | | Description of Covid-19-related MAVs* | | | |
| 20 | 27 | Phys Office/ Tele med | 4 | 3.61 (3) | Cough/Shortness of Breath | Prescribed budesonide, salbutamol, promethazine. |
| 21 | 22 | Urgent Care Clinic | 5 | 4.70 (5) | Shortness of breath/dropping oxygen saturation | Prescribed cefdinir, azithromycin, and combivent |
| 22 | 24 | ER Visit | 3 | 4.95 (3) | Dyspnea | No additional details at this time. |
| 23 | 14 | Hospitalization | 1 | 5.71 (1) | Shortness of Breath/worsening of COVID-19 Infection | 7-day hospitalization, required supplemental oxygen and ICU care. Did not require mechanical Ventilation. |
| 24 | 2 | ER Visit | 2 | 5.45 (1) | Shortness of Breath | Prescribed ketorolac, dexamethasone, ondansetron |
| 25 | 8 | ER Visit | 2 | 7.90 (1) | Chest Pain | No additional details at this time. |
| 26 | 17 | Phys Office/ Tele med | 8 | 4.11 (7) | Pleurisy | Prescribed prednisone |
| 27 | 15 | Urgent Care Clinic | 10 | 0 (9) | Covid-19 symptoms | Prescribed azithromycin and prednisone |

*Analysis group 1 + 2; modified Full Analysis Set.
†Only received 12.7 mLs of infusion, stopped due to possible infusion-related reaction.
ER, emergency room;
ICU, intensive care unit;
MAV, medically-attended visit.

The proportion of patients in the REGEN-COV treatment group (combined 2.4 g and 8.0 g doses) with ≥1 Covid-19-related MAV was 2.8% (12 of 434) compared to 6.5% (15 of 231) in the placebo group, which represents a relative reduction of 57% (absolute difference vs. placebo, −3.7 percentage points; 95% CI, −7.9% to −0.3%; P=0.024) (Table 5D). Treatment effects observed with REGEN-COV were more pronounced in baseline serum antibody-negative patients (3.4% vs 9.7% placebo; 65% relative reduction) (Table 5G). For the final hierarchical endpoint, the proportion of patients with Covid-19-related hospitalization or ER or urgent care visits was numerically lower in the REGEN-COV group (vs placebo) but the difference did not reach statistical significance (Table 5D). Post-hoc analyses demonstrated a reduction in the proportion of antibody cocktail treated patients (combined dose group) who were hospitalized or died (0.7% [3 of 434] vs 2.2% [5 of 231]; relative reduction of 68%) and in those who were hospitalized or had an ER visit (1.8% [8 of 434] vs 4.3% [10 of 231]; relative reduction of 58%) (Table 5H).

TABLE 5G

Proportion of Patients with ≥1 Covid-19-related MAVs by Baseline Serum Antibody Status

| End Point | Placebo | REGEN-COV 2.4 g | REGEN-COV 8.0 g | REGEN-COV combined |
|---|---|---|---|---|
| Proportion of patients with MAVs* through day 29 (analysis group 1 + 2) Baseline serum antibody status: negative (mFAS) | | | | |
| No. of patients | 124 | 121 | 115 | 236 |
| Patients with ≥1 visit within 29 days—no. (%) | 12 (9.7) | 4 (3.3) | 4 (3.5) | 8 (3.4) |
| Difference vs. placebo—percentage points | | −6.4 | −6.2 | −6.3 |
| 95% CI (P value)† | | −18.9, 6.0 (0.0677) | −18.7, 6.6 (0.0704) | −17.1, 4.6 (0.0264) |
| Baseline serum antibody status: positive (mFAS) | | | | |
| No. of patients | 83 | 73 | 80 | 153 |
| Patients with ≥1 visit within 29 days—no. (%) | 2 (2.4) | 2 (2.7) | 1 (1.3) | 3 (2.0) |
| Difference vs. placebo—percentage points | | 0.3 | −1.2 | −0.4 |
| 95% CI (P value)† | | −15.3, 16.0 (1.0000) | −16.5, 14.1 (1.0000) | −13.7, 12.9 (1.0000) |
| Baseline serum antibody status: unknown (mFAS) | | | | |
| No. of patients | 24 | 21 | 24 | 45 |
| Patients with ≥1 visit within 29 days—no. (%) | 1 (4.2) | 0 | 1 (4.2) | 1 (2.2) |
| Difference vs. placebo—percentage points | | −4.2 | 0 | −1.9 |

TABLE 5G-continued

Proportion of Patients with ≥1 Covid-19-related MAVs by Baseline Serum Antibody Status

| End Point | Placebo | REGEN-COV 2.4 g | REGEN-COV 8.0 g | REGEN-COV combined |
|---|---|---|---|---|
| 95% CI (P value)† | | −32.9, 24.8 (1.0000) | −29.5, 29.5 (1.0000) | −26.7, 22.8 (1.0000) |

*COVID-19-related MAV included hospitalizations, ER visits, urgent care clinic visits, and outpatient/physician office/telemedicine visits.
†95% CI and P-value are based on exact method.
CI confidence interval;
ER emergency room;
MAV medically-attended visit.

TABLE 5H

Proportion of Patients Who Were Hospitalized, Visited the ER, and/or Died

| End Point | Placebo | REGEN-COV 2.4 g | REGEN-COV 8.0 g | REGEN-COV combined |
|---|---|---|---|---|
| Proportion of patients who were hospitalized or visited the ER through day 29 (analysis group 1 + 2) | | | | |
| mFAS | | | | |
| No. of patients | 231 | 215 | 219 | 434 |
| Patients with event within 29 days—no. (%) | 10 (4.3) | 4 (1.9) | 4 (1.8) | 8 (1.8) |
| Difference vs. placebo—percentage points | | −2.5 | −2.5 | −2.5 |
| 95% CI (P value)* | | −11.7, 6.8 (0.1766) | −11.7, 6.8 (0.1749) | −10.4, 5.5 (0.0778) |
| Proportion of patients who were hospitalized or died through day 29 (analysis group 1 + 2) | | | | |
| mFAS | | | | |
| No. of patients | 231 | 215 | 219 | 434 |
| Patients with event within 29 days—no. (%) | 5 (2.2) | 2 (0.9) | 1 (0.5) | 3 (0.7) |
| Difference vs. placebo—percentage points | | −1.2 | −1.7 | −1.5 |
| 95% CI (P value)* | | −10.5, 8.0 (0.4516) | −10.9, 7.6 (0.2166) | −9.4, 6.5 (0.1339) |
| Proportion of patients who were hospitalized through day 29 (analysis group 1 + 2) | | | | |
| mFAS | | | | |
| No. of patients | 231 | 215 | 219 | 434 |
| Patients with event within 29 days—no. (%) | 5 (2.2) | 2 (0.9) | 1 (0.5) | 3 (0.7) |
| Difference vs. placebo—percentage points | | −1.2 | −1.7 | −1.5 |
| 95% CI (P value)* | | −10.5, 8.0 (0.4516) | −10.9, 7.6 (0.2166) | −9.4, 6.5 (0.1339) |

*95% CI and p-value are based on exact method.
CI confidence interval.

Additional post hoc analyses investigated the effects of the antibody cocktail treatment on MAVs in various high-risk subgroups. The proportion of patients with ≥1 risk factors for hospitalization (n=408) who had Covid-19-related MAVs in the REGEN-COV group (combined dose) vs the placebo group was: 2.6% vs 9.2% (absolute difference vs. placebo, −6.5 percentage points; 95% CI, −17 to 4; 72% relative reduction) (FIG. 14A, FIG. 14B, and FIG. 14C; Table 5I). The proportion of patients with ≥1 risk factor who were baseline serum antibody-negative and had a viral load >10⁴ copies/mL (n=217) who had Covid-19-related MAVs in the REGEN-COV group (combined doses) vs the placebo group was: 2.1% vs 13.2% (absolute difference vs. placebo, −11.0 percentage points; 95% CI, −21 to −3; 84% relative reduction) (Table 5J). The majority (59%) of patients who experienced a MAV had a viral load of ≥4 log 10 copies/ml around the time of the medically-attended visit (Table 5F; FIG. 15A, FIG. 15B, and FIG. 15C). As with virologic endpoints, no meaningful differences in clinical outcomes were observed between low dose and high dose treatments.

TABLE 5I

Proportion of Patients with ≥Covid-19-related MAVs in Those With No or Risk Factors for Hospitalization

| End Point | Placebo | REGEN-COV 2.4 g | REGEN-COV 8.0 g | REGEN-COV combined |
|---|---|---|---|---|
| Proportion of patients with Covid-19-related MAVs* through day 29 (analysis group 1 + 2) | | | | |
| No risk factors for hospitalization due to Covid-19 (mFAS) | | | | |
| No. of patients | 89 | 81 | 87 | 168 |
| Patients with ≥1 visit within 29 days—no. (%) | 2 (2.2) | 3 (3.7) | 2 (2.3) | 5 (3.0) |
| Difference vs. placebo—percentage points | | 1.5 | 0.1 | 0.7 |
| 95% CI (P value)† | | −13.5, 16.4 (0.6700) | −14.8, 15.1 (1.0000) | −12.1, 13.5 (1.0000) |
| ≥1 risk factor for hospitalization due to Covid-19 (mFAS) | | | | |
| No. of patients | 142 | 134 | 132 | 266 |
| Patients with ≥1 visit within 29 days—no. (%) | 13 (9.2) | 3 (2.2) | 4 (3.0) | 7 (2.6) |
| Difference vs. placebo—percentage points | | −6.9 | −6.1 | −6.5 |
| 95% CI (P value)† | | −18.6, 5.0 (0.0185) | −17.9, 5.8 (0.0447) | −16.6, 3.7 (0.0065) |

*COVID-19-related MAV included hospitalizations, ER visits, urgent care clinic visits, and outpatient/physician office/telemedicine visits.
†95% CI and p-value are based on exact method.
CI confidence interval;
ER emergency room;
MAV medically-attended visit.

TABLE 5J

Proportion of Patients with ≥1 Covid-19-related MAVs in Those Who Are Serum Antibody-Negative & High-Risk & Have a Viral Load >10$^4$

| End Point | Placebo | REGEN-COV 2.4 g | REGEN-COV 8.0 g | REGEN-COV combined |
|---|---|---|---|---|
| Proportion of patients with Covid-19-related MAVs* through day 29 (analysis group 1 + 2) | | | | |
| Seronegative and Viral Load >10$^4$ copies/ml and High Risk | | | | |
| No. of patients | 76 | 79 | 62 | 141 |
| Patients with ≥1 visit within 29 days - no. (%) | 10 (13.2) | 1 (1.3) | 2 (3.2) | 3 (2.1) |
| Difference vs. placebo - percentage points | | −11.9% | −9.9% | −11.0% |
| 95% CI (P value) | | −22.0, −4.0 (0.0042) | −20.0, −0.1 (0.0651) | −20.8, −2.9 (0.0019) |

*COVID-19-related MAV included hospitalizations, ER visits, urgent care clinic visits, and outpatient/physician office/telemedicine visits.
†95% CI and p-value are based on exact method.
CI, confidence interval;
ER, emergency room;
MAV, medically-attended visit.

The proportions of patients with medically attended visits due to worsening Covid-19 was compared between the REGEN-COV combined dose group and placebo as well as between each REGEN-COV treatment arm and placebo using Fisher's exact test at a two-sided alpha level of 0.05. A similar analysis was performed for the proportion of patients with Covid-19-related hospitalization or emergency room or urgent care visits as well as proportions of patients with each type of medically attended visit.

Safety

Serious Adverse Events (SAEs) were experienced by 4 of 258 patients (1.6%) in the REGEN-COV 2.4 g group, 2 of 260 patients (0.8%) in the REGEN-COV 8.0 g group, and a higher number of patients (i.e., 6 of 262 patients [2.3%]) in the placebo group (Tables 5K and 5L). All serious adverse events were considered to be due to advanced or progressive Covid-19 disease and/or associated concomitant clinical conditions and were not evaluated to be related to the study drug treatment.

Adverse Events of Special Interest (AESIs)—grade ≥2 infusion-related reactions and hypersensitivity reactions—that occurred or worsened during the safety observation period were reported in no patients in the 2.4 g group, 4 (1.5%) patients in the 8.0 g group, and 2 (0.8%) patients in the placebo group, (Tables 5K and 5L).

TABLE 5K

Overview of Serious Adverse Events and Adverse Events of Special Interest in the Safety Population

| Event | Placebo (N = 262) | REGEN-COV 2.4 g IV (N = 258) | REGEN-COV 8.0 g IV (N = 260) | REGEN-COV combined (N = 518) |
|---|---|---|---|---|
| | number of patients (percent) | | | |
| Any serious adverse event | 6 (2.3) | 4 (1.6) | 2 (0.8) | 6 (1.2) |
| Any adverse event of special interest* | 2 (0.8) | 0 | 4 (1.5) | 4 (0.8) |
| Any serious adverse event of special interest* | 0 | 0 | 0 | 0 |
| Grade ≥2 infusion-related reaction within 4 days | 1 (0.4) | 0 | 4 (1.5) | 4 (0.8) |
| Grade ≥2 hypersensitivity reaction within 29 days | 2 (0.8) | 0 | 0 | 0 |
| Patients with adverse events that occurred or worsened during the observation period† | | | | |
| Patients with Grade 3 or 4 event | 4 (1.5) | 3 (1.2) | 2 (0.8) | 5 (1.0) |

TABLE 5K-continued

Overview of Serious Adverse Events and Adverse Events of Special Interest in the Safety Population

| Event | Placebo (N = 262) | REGEN-COV 2.4 g IV (N = 258) | REGEN-COV 8.0 g IV (N = 260) | REGEN-COV combined (N = 518) |
|---|---|---|---|---|
| Patients with adverse event that led to death | 0 | 0 | 0 | 0 |
| Patients with adverse event that led to withdrawal from the trial | 0 | 0 | 1 (0.4) | 1 (0.2) |
| Patients with adverse event that led to infusion interruption* | 1 (0.4) | 0 | 1 (0.4) | 1 (0.2) |

*Events were grade 2 or higher hypersensitivity reactions or infusion-related reactions.
†Events listed here were not present at baseline or were an exacerbation of a preexisting condition that occurred during the observation period, which is defined as the time from administration of REGEN-COV or placebo to the final follow-up visit.

TABLE 5L

Treatment-Emergent Serious Adverse Events and Adverse Events of Special Interest Reported in Subjects Receiving REGEN-COV

| System Organ Class Preferred Term | Placebo Group (N = 262) | REGEN-COV 2.4 g IV (N = 258) | REGEN-COV 8.0 g IV (N = 260) | REGEN-COV combined (N = 518) |
|---|---|---|---|---|
| | | number of patients (percent) | | |
| | | Serious adverse events* | | |
| | | Gastrointestinal disorders | | |
| Vomiting | 0 | 1 (0.4) | 0 | 1 (0.2) |
| Intestinal obstruction | 0 | 0 | 1 (0.4) | 1 (0.2) |
| Nausea | 0 | 1 (0.4) | 0 | 1 (0.2) |
| | | Vascular disorders | | |
| Hypertension | 1 (0.4) | 0 | 0 | 0 |
| | | Respiratory, thoracic and mediastinal disorders | | |
| Hypoxia | 2 (0.8) | 0 | 0 | 0 |
| Dyspnea | 0 | 0 | 1 (0.4) | 1 (0.2) |
| | | Metabolic and nutrition disorders | | |
| Hyperglycemia | 0 | 1 (0.4) | 0 | 1 (0.2) |
| | | Infections & infestations | | |
| Pneumonia | 2 (0.8) | 1 (0.4) | 0 | 1 (0.2) |
| Covid-19 | 1 (0.4) | 0 | 0 | 0 |
| Covid-19 pneumonia | 0 | 1 (0.4) | 0 | 1 (0.2) |
| | | Adverse events of special interest* | | |
| | | Gastrointestinal disorders | | |
| Abdominal pain | 0 | 0 | 1 (0.4) | 1 (0.2) |
| Vomiting | 1 (0.4) | 0 | 0 | 0 |
| Nausea | 1 (0.4) | 0 | 0 | 0 |
| | | Skin and subcutaneous tissue disorders | | |
| Pruritus | 0 | 0 | 1 (0.4) | 1 (0.2) |
| Urticaria | 0 | 0 | 1 (0.4) | 1 (0.2) |
| Rash | 1 (0.4) | 0 | 0 | 0 |
| | | General disorders and administration site conditions | | |
| Chills | 0 | 0 | 1 (0.4) | 1 (0.2) |
| Pyrexia | 0 | 0 | 1 (0.4) | 1 (0.2) |
| | | Vascular disorders | | |
| Flushing | 0 | 0 | 1 (0.4) | 1 (0.2) |
| | | Nervous system disorders | | |
| Dizziness | 1 (0.4) | 0 | 0 | 0 |
| Headache | 1 (0.4) | 0 | 0 | 0 |

TABLE 5L-continued

Treatment-Emergent Serious Adverse Events and Adverse Events of
Special Interest Reported in Subjects Receiving REGEN-COV

| System Organ Class Preferred Term | Placebo Group (N = 262) | REGEN-COV 2.4 g IV (N = 258) | REGEN-COV 8.0 g IV (N = 260) | REGEN-COV combined (N = 518) |
|---|---|---|---|---|
| Injury, poisoning and procedural complications | | | | |
| Infusion-related reaction | 0 | 0 | 1 (0.4) | 1 (0.2) |

*Only serious adverse events and adverse events of special interest (grade 2 or higher infusion-related reactions and hypersensitivity reactions) were collected.
IV, intravenous(ly).

Pharmacokinetics: The mean concentrations for casirivimab and imdevimab increased in a dose-proportional manner and were consistent with linear pharmacokinetics for single intravenous doses (Table 5M). The mean±SD day 29 concentrations of casirivimab and imdevimab in serum were 79.7±34.6 mg per liter and 65.2±28.1 mg/L, respectively, for the low (1.2 g) doses and 250±97.4 and 205±82.7 mg/L, respectively, for the high (4.0 g) doses (Table 5M).

TABLE 5M

Mean Concentrations of REGN10933 and REGN10987 in Serum

| Nominal Sampling Time | REGN10933 (casirivimab)* | | REGN10987 (imdevimab)* | |
|---|---|---|---|---|
| | 1.2 g | 4.0 g | 1.2 g | 4.0 g |
| Predose | 0.0578 (0.594) [202] | 0.0421 (0.611) [210] | 0.0640 (0.603) [186] | 0 (0) [195] |
| End of Infusion† | 333 (86.8) [135] | 1022 (341) [126] | 336 (106) [136] | 1037 (332) [125] |
| Day 29§ | 79.7 (34.6) [210] | 250 (97.4) [223] | 65.2 (28.1) [212] | 205 (82.7) [222] |

*Mean (SD) [N], where N is the number of observations
†Infusion duration was 1 hour
§Observed concentration 28 days after dosing, i.e. on day 29

Serum for drug concentration analysis was collected from all patients at pre-dose (at the screening or baseline visit), day 1 at the end of the infusion, and day 29. Additional serum collections were on days 3, 5, 7, and 15 for Phase 1 patients only. The human serum concentrations of REGN10933 (casirivimab) and REGN10987 (imdevimab) were measured using validated immunoassays which employ streptavidin microplates from Meso Scale Discovery (MSD, Gaithersburg, MD, USA). The methods utilized two anti-idiotypic monoclonal antibodies, each specific for either mAb10933 or mAb10987, as the capture antibodies. Captured mAb10933 and mAb10987 were detected using two different, non-competing anti-idiotypic monoclonal antibodies, each also specific for either mAb10933 or mAb10987. The bioanalytical methods specifically quantitated the levels of each anti-SARS-CoV-2 spike mAb separately, with no interference from the other antibody. The assay had a lower limit of quantitation (LLOQ) of 0.156 µg/mL for each analyte in the undiluted serum sample.

Discussion

The findings from this final phase 1/2 analysis of REGEN-COV antibody cocktail for the treatment of outpatients with Covid-19 confirmed and extended the findings from the first 275 patients. To better understand the natural history of Covid-19 in outpatients, data from placebo patients in this trial were described. These data confirms previous findings that patients who had not yet mounted their own immune response at baseline (i.e., were serum antibody-negative at baseline) had median viral loads at baseline that were almost 3 log copies/mL higher compared to patients who were serum antibody-positive, and took longer to reach low or undetectable levels. Similar to other viral infections, such as HIV, ebola virus disease, and influenza, high viral load appears to be a predictor of disease progression in Covid-19, as evidenced by the fact that Covid-19-related MAVs were enriched in placebo patients with baseline viral loads >$10^4$ copies/ml. The data also indicate that risk factors for severe disease, such as older age and obesity, may help to predict outpatients who are most likely to have a subsequent Covid-19-related MAV. For example, 9.2% (13/142) of placebo patients with ≥1 risk factors had a MAV compared to 2.2% (2/89) of placebo patients without any risk factors. In this trial, >80% of patients with risk factors were serum antibody-negative or had a viral load >$10^4$ copies/mL. In the absence of a rapid serology test or quantitative PCR assay to identify at-risk patients, identifying patients with risk factors for hospitalization may help identify outpatients most likely to benefit from early treatment with the antibody cocktail.

The prespecified hierarchical analysis described herein prospectively and with high statistical significance confirmed the virologic efficacy of REGEN-COV, and revealed similar virologic efficacy with both the 2.4 g and 8.0 g doses of the antibody cocktail. The reduction in viral load was greatest in the first 5 days after treatment, in patients who were serum antibody-negative or had high viral load at baseline. Treatment had no apparent additional virologic benefit in patients who had already mounted an effective endogenous antibody response to the infection (serum antibody-positive). The reduction in the viral load after treatment with either dose of REGEN-COV was accompanied by a significant reduction in the proportion of patients requiring a subsequent Covid-19-related medically-attended visits, the majority (67%) of which were hospitalizations or ER visits. REGEN-COV antibody cocktail led to a relative reduction in MAVs by 57% (6.5% in placebo vs 2.8% in the combined dose group; P=0.0240). Interestingly, the reduction in the proportion of patients with MAVs treated with REGEN-COV compared to placebo occurs only after the first week of treatment. One possible explanation for this finding is that medical visits occurring in the first week are not modifiable despite accelerated clearance of the virus. For example, among patients treated with the antibody cocktail, all three hospitalizations occurred in the first three days after treatment when viral loads were still ≥4 log 10 copies/mL but no hospitalizations occurred after day 7 (Table 5F; FIG. 15A, FIG. 15B, and FIG. 15C). In contrast, among patients treated with placebo, 3 of the 5 hospitalizations occurred after Day 7, when viral loads continued to be high (≥4 log 10 copies/ mL). These data support early identification and rapid treatment of outpatients with Covid-19 in order to optimize the efficacy of REGEN-COV treatment.

A low incidence of serious adverse events, infusion-related reactions, and hypersensitivity reactions was observed. Similar to the results reported previously, concentrations of each antibody in serum at day 29 were well above the predicted neutralization target concentration based on in vitro and preclinical data.

The clinical evidence from this trial suggests that treatment had the greatest benefit when given to high-risk patients who present early after diagnosis when they were most likely to have high viral load and may not have yet mounted their own immune response. Moreover, there were no adverse findings observed in patients who were serum antibody-positive at baseline. Early treatment of Covid-19 outpatients is crucial and, if unable to rapidly determine viral load or serum antibody status, the risk-benefit assessment supports treatment to prevent MAVs in high-risk patients.

Phase 3 Trial Plan

Patient population for Cohort 1—the patient population for Cohort 1 of the Phase 3 portion of the study was adult (≥18 years old) male and female patients with:

SARS-CoV-2-positive antigen or molecular diagnostic test (by validated SARS CoV-2 antigen, RT-PCR, or other molecular diagnostic assay) ≤72 hours prior to randomization. and symptoms consistent with COVID-19, as determined by the investigator, with onset ≤7 days before randomization and ≥1 risk factor for severe COVID-19

Risk factors are defined as follows:
a. Age >50 years
b. Obesity, defined as body mass index (BMI) >30 kg/m2
c. Cardiovascular disease, including hypertension
d. Chronic lung disease, including asthma
e. Type 1 or type 2 diabetes mellitus
f. Chronic kidney disease, including those on dialysis
g. Chronic liver disease
h. Pregnancy
i. Immunosuppressed (examples include cancer treatment, bone marrow or organ transplantation, immune deficiencies, HIV (if poorly controlled or evidence of AIDS), sickle cell anaemia, thalassemia, and prolonged use of immune-weakening medications).

Primary and key secondary endpoint for Cohort 1:

For cohort 1, the primary endpoint was COVID-19-related medically-attended visits (MAVs) through day 29. A COVID-19-related medically-attended visit was defined as follows: hospitalization, emergency room (ER) visit, urgent care visit, physician's office visit, or telemedicine visit, with the primary reason for the visit being COVID-19. A patient with multiple medically-attended visits was counted as having 1 event.

The key pre-specified secondary endpoint was the cumulative incidence of COVID-19-related hospitalizations or emergency room visits through day 29.

Other key pre-specified secondary endpoints included various types of COVID-19-related MAVs, and related outcomes.

The virologic data collectively provide definitive evidence that mAb10933+mAb10987 markedly enhances SARS-CoV-2 viral clearance. Moreover, data from a pooled phase 1/2 analysis indicated that the viral load reduction translated into clinical benefit by significantly reducing COVID-19-related MAVs, defined as hospitalizations, ER visits, urgent care visits, or physician office or telemedicine visits for COVID-19. Specifically, a prespecified and multiplicity-controlled analysis of pooled phase 1/2 data (n=799) showed a statistically significant reduction in MAVs in the mAb10933+mAb10987 treated groups compared to placebo (2.8% combined dose groups vs 6.5% placebo; p=0.0240). Most of the MAVs occurred in patients who were higher risk, defined as seronegative at baseline, had higher baseline viral load, or had at least 1 pre-existing risk factor for severe COVID-19 (eg, age >50 years old, obesity, co-morbid conditions). In exploratory analyses, treatment with mAb10933+mAb10987 showed the greatest benefit in these high-risk groups, with reductions in the proportion of patients with MAVs compared to placebo of 62% (3.2% combined treatment vs 8.5% placebo) for those with baseline viral loads >104 copies/mL, 65% (3.4% combined treatment vs 9.7% placebo) for those who were seronegative at baseline, and 72% (2.6% combined treatment vs 9.2% placebo) for those who had at least 1 risk factor for severe COVID-19. Considering the clinical benefits observed in phase 2, phase 3 will focus on confirming the clinical benefit of mAb10933+mAb10987 in reducing MAVs for high-risk patients, thereby demonstrating the clinical benefit of reducing viral burden.

The sample size of the phase 3 Cohort 1 was estimated to be approximately 5400 patients. Cohort 1 continued until at least 80 patients with hospitalizations or ER visits were observed in patients enrolled into the primary analysis population (patients in mFAS with at least 1 risk factor) and the total number of patients with hospitalizations or ER visits during the study in the primary analysis population is more than 120.

The primary efficacy endpoint for phase 3 cohort 1 was the cumulative incidence of COVID 19 related MAVs through day 29 in the mFAS (randomized and treated PCR-positive patients with at least 1 risk factor at baseline).

Analyses were performed for the phase 3 cohort 1 key secondary endpoint, cumulative incidence of COVID-19-related hospitalization/ER visit through day 29, based on the time to first hospitalization/ER visit.

For phase 3, planned virologic analyses were descriptive. The time-weighted average change from baseline in viral load (log 10 copies/mL) from day 1 to post-baseline visit timepoints was analyzed using the same method as the phase 2 primary virologic endpoint based on mFAS for seronegative patients and seropositive patients separately for patients that underwent an intensive sampling schedule. Proportion endpoints based on observed virologic data were compared between groups using similar method as the proportion clinical endpoints. The analyses were performed for seronegative mFAS as well as for mFAS.

To assess the time course of treatment effect in viral load, the change from baseline in viral load (log 10 copies/mL) at each visit for seronegative mFAS and mFAS was analysed using a mixed effect model for repeated measures (MMRM) with terms for baseline, randomization strata, treatment, visit, treatment by baseline interaction, baseline by visit interaction, and treatment by visit interaction.

The phase 3 portion of the study assessed 2 dose levels of mAb10933+mAb10987, 1200 mg and 2400 mg, in a 1:1 ratio (600 mg and 1200 mg per mAb, respectively). In the phase 1 and 2 results, the 2400 mg and 8000 mg doses of mAb10933+mAb10987 demonstrated similar virologic and clinical efficacy as assessed by MAVs, and both doses had similar and acceptable safety profiles. Given the similarities between the 2400 mg and 8000 mg doses, the 2400 mg dose was studied in this phase 3 study as the highest dose, along with lower doses.

Pediatric patients aged 0 to <18 years can be included in the phase 3 portion of the study as a separate cohort (cohort 2) to assess the safety, PK, immunogenicity, and efficacy of mAb10933+mAb10987. Both patients that are symptomatic with COVID-19 or asymptomatic patients that are SARS-CoV-2 positive at baseline can be included in this cohort. Pediatric patients that have a risk factor for severe COVID-19 can be included in cohort 2.

Pediatric patients in cohort 2 can be randomized in a 1:1:1 allocation ratio to receive a single intravenous (IV) dose of mAb10933+mAb10987 combination therapy at a low dose, a high dose, or placebo. However, the mAb10933+mAb10987 treatment arms can be tiered according to body weight, as defined in Table 6, below.

Dose selection in the pediatric population (<18 years of age) can utilize a body weight-tiered flat dose approach for both the high and low doses. For each weight-tiered dose targeting the higher dose in adults (2400 mg), the goal is to select doses that are predicted by population PK modelling to ensure that the fifth percentile of concentration in serum 28 days after dosing (C28) is similar to, or greater than, the observed fifth percentile of C28 in adults for the 2400 mg dose. An additional consideration is to ensure that predicted Cmax and AUC0-28 for each weight-tiered dose do not exceed values previously achieved in adults. Both mAb10933 and mAb10987 have demonstrated linear PK, and as such, the same 50% reduction employed in selecting the lower adult dose in phase 3 (2400 mg to 1200 mg) was applied to each of the pediatric body weight tiered flat doses targeting the 1200 mg adult dose (Table 6).

Up to approximately 180 pediatric patients in cohort 2 (60 per treatment arm) would allow 45 patients to be randomized to each PK-ADA sampling schedule.

Phase 3 Adult Data: Summary

An objective of the confirmatory Phase 3 trial (FIG. 31 and FIG. 32) was to prospectively demonstrate clinically significant effect on risk of COVID-19 hospitalization or all-cause death in high-risk outpatients and confirm safety. This trial also prospectively evaluated potential benefit on symptom duration. The seamless design began comparing 8000 mg and 2400 mg versus placebo, and was amended to evaluate 2400 mg and 1200 mg versus placebo based on the final analysis of the phase 1/2 portion, which showed that the 8000 mg and 2400 mg doses were indistinguishable based on antiviral and clinical endpoints (and that clinical events were largely occurring in high-risk patients). Data comparing 8000 mg to placebo was converted to descriptive analysis. A formal hierarchical analysis first evaluated the 2400 mg dose versus concurrent placebo (in patients with ≥1 risk factor from original and amended portions, n=~2700) and then evaluated 1200 mg dose versus concurrent placebo (in patients with ≥1 risk factor, n=~1500. A companion dose ranging virology study in outpatients further evaluated REGEN-COV doses from 2400 mg to 300 mg IV (and 1200 mg to 600 mg subcutaneous) for anti-viral efficacy (Example 7). Key results are shown below.

TABLE 6 mAb10933 + mAb10987 IV Doses for Each Weight Group,
Phase 3 Cohort 2 (Ages 0 to <18 Years)

| Body Weight Group | Phase 3 Cohort 2 Dose Equivalent for mAb10933 + mAb10987 1200 mg IV Dose (600 mg per mAb)[1] | Phase 3 Cohort 2 Dose Equivalent for mAb10933 + mAb10987 2400 mg IV Dose (1200 mg per mAb)[1] |
|---|---|---|
| ≥40 kg | 1200 mg (600 mg per mAb) | 2400 mg (1200 mg per mAb) |
| ≥20 kg to <40 kg | 450 mg (225 mg per mAb) | 900 mg (450 mg per mAb) |
| ≥10 kg to <20 kg | 224 mg (112 mg per mAb) | 450 mg (225 mg per mAb) |
| ≥5 kg to <10 kg | 120 mg (60 mg per mAb) | 240 mg (120 mg per mAb) |
| ≥2.5 kg to <5 kg | 60 mg (30 mg per mAb) | 120 mg (60 mg per mAb) |
| <2.5 kg | 30 mg (15 mg per mAb) | 60 mg (30 mg per mAb) |

[1]Dose values represent total amount of co-administered mAb10933 + mAb10987 combination therapy, IV single dose.

The primary objective for the patients in cohort 2 is safety, with MAVs as a descriptive secondary objective.

The primary endpoints for cohort 2 is safety/tolerability and drug concentrations in serum over time:

Proportion of patients with treatment-emergent serious adverse events (SAEs) through day 29

Proportion of patients with infusion-related reactions (grade ≥2) through day 4

Proportion of patients with hypersensitivity reactions (grade ≥2) through day 29

Concentrations of mAb10933 and mAb10987 in serum over time

Immunogenicity, as measured by antidrug antibody (ADA) and neutralising antibodies (NAbs) to mAb10933 and mAb10987

TABLE 7

Key Results from Phase 3 Outpatient Trial[1-3]

| | 1,200 mg IV n = 736 | Placebo n = 748 | 2,400 mg IV n = 1,355 | Placebo n = 1,341 |
|---|---|---|---|---|
| Patients with ≥1 COVID-19-related hospitalization or death through day 29 | | | | |
| Risk reduction | 70% ($p = 0.0024$) | | 71% ($p < 0.0001$) | |
| # of patients with | 7 (1.0%) | 24 (3.2%) | 18 (1.3%) | 62 (4.6%) |

TABLE 7-continued

Key Results from Phase 3 Outpatient Trial[1-3]

| | 1,200 mg IV n = 736 | Placebo n = 748 | 2,400 mg IV n = 1,355 | Placebo n = 1,341 |
|---|---|---|---|---|
| events | | | | |
| Time to COVID-19 symptom resolution | | | | |
| Median reduction (days) | 4 (p <0.0001) | | 4 (p <0.0001) | |
| Median (days) | 10 | 14 | 10 | 14 |

[1]Based on the modified full analysis set (mFAS) population, which includes all randomized patients with a positive SARS-CoV-2 RT-qPCR test from nasopharyngeal swabs at randomization and ≥1 risk factor for severe COVID-19.
[2]The formal hierarchical analysis first evaluated 2,400 mg dose vs. concurrent placebo and then evaluated 1,200 mg dose vs. concurrent placebo.
[3]Based on Phase 1/2 analyses showing that the 8,000 mg and 2,400 mg doses were indistinguishable, the Phase 3 protocol was amended to compare 2,400 mg and 1,200 mg vs. placebo, and 8,000 mg data were converted to a descriptive analysis.

In the Phase 3 trial in 4567 high-risk patients, mAb10933+mAb10987 (REGEN-COV) significantly reduced COVID-19 hospitalization or all-cause death, and shortened time to symptoms resolution by 4 days, confirming the clinical benefits seen in Phase 1/2. Additionally, REGEN-COV administered as a 1200 mg or 2400 mg single IV infusion significantly reduced the proportion of patients with COVID-19-related hospitalization or all-cause death in those who were SARS-CoV-2 PCR+ at baseline and had ≥1 risk factor for severe COVID-19. There was a similar treatment effect with the two dose levels: 2400 mg vs placebo (PBO), 71.3% reduction (1.3% vs 4.6%; p<0.0001); 1200 mg vs PBO, 70.4% reduction (1.0% vs 3.2%; p=0.0024). There was a greater reduction in COVID-19 hospitalization or all-cause death after study day 3 (89.2%, 2400 mg vs PBO, p<0.0001; 71.7%, 1200 mg vs PBO, p=0.0101); with early events less modifiable. See FIG. 35, FIG. 36, and FIG. 37. Effects were more pronounced in patients with high viral loads and/or seronegativity at baseline, but meaningful risk reductions were seen in seropositive patients. There was also a significant reduction in viral load at day 7 across subgroups, with consistency between 2400 mg and 1200 mg doses (FIG. 43, FIG. 44, FIG. 52, FIG. 53, FIG. 54, FIG. 55, FIG. 56, and FIG. 58). Administration of REGEN-COV resulted in faster symptom resolution at both doses: 2400 mg vs PBO, median 10 vs 14 days; p<0.0001; 1200 mg vs PBO, median 10 vs 14 days; p<0.0001 (FIG. 38, FIG. 39). A summary of these data are shown in FIG. 33. Moreover, serious adverse events (including fatal events) were more frequent in the placebo (PBO) group compared to REGEN-COV dose groups (4.0% PBO vs 1.4% combined REGEN-COV groups) (FIG. 40, FIG. 41, FIG. 42). Demographics for this study are shown in FIG. 34.

Phase 3 Adult Data: Full Results and Discussion

In the phase 1/2 portion of this adaptive phase 1-3 randomized, placebo-controlled master protocol, REGEN-COV demonstrated efficacy in outpatients, where it was shown to rapidly reduce viral load and the need for medical attention related to Covid-19. In fact, on Feb. 19, 2021, an independent data monitoring committee (IDMC) recommended stopping enrollment of patients into the placebo group of the phase 3 portion of this master protocol because of clear efficacy of REGEN-COV.

The phase 3 portion of this adaptive, randomized, master protocol, included 4,057 COVID-19 outpatients with one or more risk factors for severe disease. Patients were randomized to a single treatment of intravenous placebo, or various doses of REGEN-COV and followed for 29 days. The prespecified hierarchical analysis compared the REGEN-COV 2400 mg dose versus concurrent placebo, followed by the 1200 mg dose versus concurrent placebo, for endpoints assessing risk of hospitalization or death, and time to symptom resolution. Safety was evaluated in all treated patients.

Both REGEN-COV 2400 mg and 1200 mg significantly reduced Covid-19-related hospitalization or all-cause death compared to placebo (71% reduction, 1.0% vs 3.2%, p<0.0024; 70% reduction,1.3% vs 4.6%, respectively; p<0.0001). The median time to resolution of Covid-19 symptoms was 4 days shorter in both dose arms vs placebo (10 vs 14 days; p<0.0001). Efficacy of REGEN-COV was consistent across subgroups, including serum antibody-positive patients. REGEN-COV more rapidly reduced viral load than placebo. Serious adverse events occurred more frequently in the placebo group (4.0% vs 1.1% and 1.3% in the 1200 mg and 2400 mg groups, respectively) and infusion-related reactions were infrequent (<2 patients in all groups).

Treatment with REGEN-COV was well-tolerated and significantly reduced Covid-19-related hospitalization or all-cause death, rapidly resolved symptoms, and reduced viral load.

Trial Design—This was an adaptive, multicenter, randomized, double-blind, placebo-controlled, phase 1/2/3 master protocol in Covid-19 outpatients (NCT04425629). The phase 3 portion comprised 3 cohorts: Cohort 1 (≥18 years), Cohort 2 (<18 years), and Cohort 3 (pregnant at randomization). Initially, phase 3 patients were randomized 1:1:1 to receive placebo, REGEN-COV 2400 mg (1200 mg each of casirivimab and imdevimab) IV, or REGEN-COV 8000 mg (4000 mg each antibody) IV (FIG. 81). Based upon phase 1/2 results that showed the 8000 mg and 2400 mg doses had similar antiviral and clinical efficacy and that most clinical events occurred in high-risk patients, the trial was subsequently amended on Nov. 14, 2020 to revise the population and the doses. As a result of the amendment, subsequent patients enrolled had ≥1 risk factor for severe Covid-19 and were randomized 1:1:1 to receive placebo, REGEN-COV 1200 mg (600 mg each antibody) IV, or REGEN-COV 2400 mg (1200 mg each antibody) IV. On Feb. 19, 2021, per IDMC recommendation, patients were no longer randomized to receive placebo. The phase 3 analysis presented here is comprised of Cohort 1 patients (≥18 years) randomized to REGEN-COV 2400 mg or 1200 mg with their concurrent placebo groups serving as a control.

Eligible patients (Cohort 1) were ≥18 years of age and non-hospitalized, with a confirmed local SARS-CoV-2-positive diagnostic test result ≤72 hours and onset of any Covid-19 symptom ≤7 days before randomization. Randomization into the initial phase 3 portion was stratified by country and presence of risk factors for severe Covid-19. In the amended phase 3 portion, only patients with ≥1 risk factor for severe Covid-19 were eligible. All patients were assessed at baseline for anti-SARS-CoV-2 antibodies: anti-spike [S1] IgA, anti-spike [S1] IgG, and anti-nucleocapsid IgG. Because assay results were not available at randomization, patients were subsequently grouped for the purposes of virologic and subgroup analyses as serum antibody-negative (if all available tests were negative), serum antibody-positive (if any available test was positive), or other (inconclusive/unknown results).

At baseline (day 1), REGEN-COV (diluted in normal saline solution for co-administration) or saline placebo was administered intravenously. Hospitalizations were assessed to be related to Covid-19 by the investigator. The Symptoms Evolution of COVID-19 (SE-C19) instrument, an electronic diary, assessed 23 Covid-19 symptoms daily. Quantitative virologic analysis of nasopharyngeal (NP) swab samples and serum antibody testing were conducted in a central laboratory and were previously described.

The prespecified primary and two key secondary endpoints were tested hierarchically (FIG. 89). The primary endpoint was the proportion of patients with ≥1 Covid-19-related hospitalization or all-cause death through day 29. The two key secondary clinical endpoints were (1) the proportion of patients with ≥1 Covid-19-related hospitalization or all-cause death from day 4 through day 29 and (2) the time to Covid-19 symptoms resolution. Time to Covid-19 symptoms resolution was defined as time from randomization to the first day during which the subject scored "no symptom' (score of 0) on all of the symptoms except cough, fatigue, and headache, which could have been "mild/moderate symptom" (score of 1) or "no symptom" (score of 0). Safety endpoints for the phase 3 portion of the trial included serious adverse events (SAEs) that occurred or worsened during the observation period and adverse events of special interest (AESIs): grade ≥2 hypersensitivity reactions and infusion-related reactions and treatment-emergent adverse events requiring medical attention at a healthcare facility.

The statistical analysis plan for the presented analysis was finalized prior to database lock and unblinding of phase 3 Cohort 1; the primary analysis did not include patients from the previously reported phase 1/2 portion of the trial. The full analysis set (FAS) included all randomized symptomatic patients. Efficacy analyses were performed based on a modified FAS (mFAS) defined as all randomized patients with a positive SARS-CoV-2 central lab-determined RT-qPCR test at baseline and with ≥1 risk factor for severe Covid-19. Safety was assessed in treated patients in the FAS. The proportion of patients with ≥1 Covid-19-related hospitalization or all-cause death was compared between each dose group and placebo using the stratified Cochran-Mantel-Haenszel (CMH) test with country as a stratification factor. P-values from the stratified CMH test and 95% confidence intervals (CIs) for the relative risk reduction using the Farrington-Manning method are presented. Time to Covid-19 symptoms resolution was assessed in patients with a baseline total severity score >3 and analyzed using the stratified log-rank test with country as a stratification factor. Median times and associated 95% CIs were derived from the Kaplan-Meier method. The hazard ratio and 95% CI were estimated by the Cox regression model. Analyses of the primary and key clinical endpoints were conducted at a two-sided α=0.05 utilizing a hierarchical testing strategy to control for type I error (FIG. 89). Statistical analyses were performed with SAS software, version 9.4 or higher (SAS Institute).

Results (Trial Population)

Phase 3 patients were enrolled between Sep. 24, 2020 and Jan. 17, 2021. Initially, in the original phase 3 portion, a total of 3088 patients, with or without risk factors for severe Covid-19, underwent randomization to receive a single dose of either placebo, REGEN-COV 8000 mg or REGEN-COV 2400 mg. Subsequently, in the amended phase 3 portion, an additional 2519 patients with ≥1 risk factor were randomized to receive a single dose of either placebo, REGEN-COV 2400 mg or REGEN-COV 1200 mg (FIG. 76). Patients had a median follow-up duration of 45 days, with 96.6% of patients having >28 days follow-up.

The primary efficacy population included those with ≥1 risk factors for severe Covid-19 and baseline central laboratory test positive for SARS-CoV-2 (mFAS) (FIG. 76). Among the mFAS population (n=4057), demographic and baseline medical characteristics were balanced between the placebo and REGEN-COV groups (FIG. 78). The median age was 50 years (interquartile range [IQR, 38-59]), 52% male, 14% ≥65 years, 28% Hispanic, and 61% obese. The most common risk factor were obesity (58%), age ≥50 years (52%), and cardiovascular disease (36%); 3% of patients were immunosuppressed or on immunosuppressive medications (FIG. 90). Similar demographic and baseline medical characteristics were observed in the overall full analysis set (n=5607) and in the REGEN-COV 8000 mg group (FIG. 91).

The median NP viral load was 6.98 $\log_{10}$ copies/mL (IQR 5.45-7.85) and the majority of patients (69%) were SARS-CoV-2 serum antibody negative at baseline (FIG. 78); these high viral loads and lack of endogenous immune response at baseline indicated that the enrolled individuals were early in the course of their infection. NP viral load and serum antibody-negative status were similar across treatment groups. Patients had a median of 3 days (IQR 2-5) of Covid-19 symptoms at randomization and this was well-balanced across treatment groups.

Results (Natural History)

There was an association between Covid-19-related hospitalization or all-cause death risk with baseline viral load: hospitalization/deaths occurred in a greater proportion of patients with high viral load compared to those with lower viral load at baseline (baseline viral load >$10^6$ copies/mL: 6.3% [55/876] and 4.2% [20/471] in the concurrent placebo groups for 2400 mg and 1200 mg, respectively; baseline viral load ≤$10^6$ copies/mL: 1.3% [6/457] and 1.5% [4/273] of patients in the concurrent placebo groups for 2400 mg and 1200 mg, respectively) (FIG. 92).

Patients in the placebo group who were serum antibody-negative at baseline had higher median viral loads at baseline compared to those who were serum antibody-positive (7.45 $\log_{10}$ copies/ml vs 4.96 $\log_{10}$ copies/ml) and they took longer to bring their viral levels to below the lower limit of quantification (LLQ) (FIG. 82).

Baseline serum antibody status of placebo patients was not predictive of subsequent Covid-19-related hospitalizations or all-cause death, as these rates were similar in patients who were serum antibody-negative and antibody-positive (antibody negative: 5.3% [49/930] and 3.5% [18/519] of patients in the concurrent placebo groups for 2400 mg and 1200 mg, respectively; antibody-positive: 4.0% [12/297] and 3.7% [6/164] in the concurrent placebo groups for 2400 and 1200 mg, respectively). However, placebo patients who were serum antibody-positive and subsequently required hospitalization or died had high viral loads at baseline and day 7, similar to patients who were serum antibody-negative who required hospitalization or died, arguing that some serum antibody-positive patients may have an ineffective innate antibody response (FIG. 93).

Efficacy (Primary Endpoint)

REGEN-COV 2400 mg and 1200 mg similarly reduced Covid-19-related hospitalization or all-cause death by 71.3% (1.3% vs 4.6% placebo; 95% CI: 51.7%, 82.9%; p<0.0001) and 70.4% (1.0% vs 3.2% placebo; 95% CI: 31.6%, 87.1%; p<0.0024), respectively (FIG. 79, FIG. 77A, FIG. 77B, FIG. 94). Similar reductions in Covid-19-related hospitalizations or all-cause deaths were observed across subgroups, including in patients who were serum antibody-positive at baseline (FIG. 79, FIG. 83A, FIG. 83B, and FIG. 83C).

Efficacy (Key Secondary Endpoints)

The reduction in the proportion of patients with Covid-19-related hospitalization or death was observed starting approximately 1 to 3 days after treatment with REGEN-COV (FIG. 77A, FIG. 77B, FIG. 79). After these first 1 to 3 days, patients in the placebo group continued to experience Covid-19-related hospitalization or death events during the study period (46/1340 [3.4%]), while very few events occurred in the 2400 mg or 1200 mg REGEN-COV treatment groups (5/1351 [0.4%] and 5/735 [0.7%], respectively) (FIG. 79, FIG. 84A, FIG. 84B).

The median time to resolution of Covid-19 symptoms was 4 days sooner than placebo in both REGEN-COV dose groups (10 days vs 14 days; p<0.0001 each for 2400 mg and 1200 mg) (FIG. 79 and FIG. 77C). The more rapid resolution of Covid-19 symptoms with either dose of REGEN-COV was evident by day 3. Both REGEN-COV doses were associated with similar improvements in symptoms resolution across subgroups (FIG. 85).

All REGEN-COV dose levels (1200 mg, 2400 mg, and 8000 mg) led to similar and rapid declines in viral load compared to placebo (FIG. 86A, FIG. 86B. FIG. 86C, FIG. 87, FIG. 88A, FIG. 88B, and FIG. 88C).

Efficacy (Other Secondary Endpoints)

REGEN-COV treatment was associated with a lower proportion of patients with Covid-19-related hospitalization (FIG. 95). Among patients that were hospitalized due to Covid-19, those in the REGEN-COV group had shorter hospital stays and a lower rate of admission to an intensive care unit (FIG. 96).

REGEN-COV treatment was associated with a lower proportion of patients with Covid-19-related hospitalization, emergency room visits, or all-cause death through Day 29 (FIG. 97) and a lower proportion requiring any medically-attended visit for worsening Covid-19 (hospitalization, emergency room visit, urgent care visit or physician office/telemedicine visit) or all-cause death (FIG. 95, FIG. 98, and FIG. 99).

Safety

Serious adverse events (SAEs) were experienced by more patients in the placebo group (4.0%) compared to the REGEN COV dose groups: 1.1% 1200 mg, 1.3% 2400 mg and 1.7% 8000 mg (FIG. 80). More patients experienced treatment emergent adverse events (TEAEs) that resulted in death in the placebo group (5 patients, 0.3%) compared to the REGEN-COV dose groups: 1 (0.1%) in 1200 mg, 1 (<0.1%) in 2400 mg, and 0 in 8000 mg (FIG. 80 and FIG. 100). Most adverse events were consistent with complications of Covid-19 (FIG. 101 and FIG. 102) and the majority were not considered to be related to study drug. Few patients experienced infusion-related reactions (0 in placebo; 2, 1, and 3 patients in 1200 mg, 2400 mg, and 8000 mg) and hypersensitivity reactions (1 in placebo and 1 in 2400 mg) (FIG. 91). A similar safety profile was observed between REGEN-COV doses, with no discernable imbalance in safety events. No safety signals were observed in safety laboratory parameters collected through day 29.

Pharmacokinetics

The mean concentrations of casirivimab and imdevimab in serum on day 29 increased in a dose-proportional manner and were consistent with linear pharmacokinetics (FIG. 103). The mean day 29 concentrations of casirivimab and imdevimab in serum were 46.4±SD22.5 and 38.3±SD19.6 mg/L, respectively, for the 1200 mg dose and 73.2±SD27.2 and 60.0±SD22.9 mg/L, respectively, for the 2400 mg dose; the mean estimated half-life was 28.8 days for casirivimab and 25.5 for imdevimab (FIG. 103).

Discussion

Previous Phase 1/2 data showed that, in outpatients with Covid-19, REGEN-COV robustly lowered viral load, reduced the need for medical attention, and despite a small number of events, was highly suggestive of a reduced risk for hospitalization. These clinical outcomes data now definitively prove that early treatment with REGEN-COV in outpatients with risk factors for severe Covid-19 can dramatically lower the risk of hospitalization or all-cause death. Both 1200 mg IV and 2400 mg IV doses of REGEN-COV led to ~70% reduction (vs placebo) in Covid-19 hospitalization or all-cause death over 28 days after treatment. In those who were hospitalized, REGEN-COV treatment also led to shorter duration of hospitalization and a lower proportion of patients requiring intensive care. In addition, REGEN-COV, at both doses, resulted in more rapid resolution of Covid-19 symptoms by a median of 4 days. Therefore, a single dose of REGEN-COV in outpatients with Covid-19 has the potential to improve patient outcomes and substantially reduce the health care burden experienced during this pandemic by reducing morbidity and mortality, including hospitalizations and intensive care. Furthermore, REGEN-COV can substantially speed recovery from Covid-19, which represents an additional benefit for patients, as there is a growing body of evidence that suggests that some patients, including those with mild symptoms, will have a variably prolonged course of recovery.

Without wishing to be bound by theory, we previously hypothesized that, while host factors play a role in the disease course, the morbidity and mortality of SARS-CoV-2 result from high viral burden and early treatment with an anti-spike monoclonal antibody cocktail could markedly ameliorate this risk. In the placebo group, we found that patients with hospitalizations or all-cause death had markedly higher viral loads at baseline and were slower to clear virus, independent of baseline serological status. Patients in the placebo group who had mounted their own endogenous antibody response to SARS-CoV-2 (serum antibody-positive) had similar rates of hospitalizations or death compared to patients who were serum antibody-negative, suggesting that some serum antibody-positive patients had an ineffective immune response. Furthermore, placebo patients who were serum antibody-positive and had a Covid-19-related hospitalization or who died, also had high baseline viral load levels similar to patients who were serum antibody-negative who also had these events, supporting high viral load as a key driver of severe Covid-19. Moreover, this study also demonstrated that there is clinical benefit of REGEN-COV, regardless of baseline serum antibody status, making serological testing at the time of Covid-19 diagnosis less critical for clinical treatment decisions. This is important given the prevalence of vaccine utilization, which will result in baseline serum antibody-positive status that may not effectively prevent severe infection in some patients (as appears to be the case for certain patients with ineffective natural immunity in this trial) or due to emerging variants of concern (VOCs).

Both 1200 mg and 2400 mg doses of REGEN-COV had similar antiviral and clinical efficacy, suggesting that we are well above the minimally effective dose. Both doses rapidly reduced viral loads with faster time to viral clearance compared to placebo. In addition to providing clinical benefit to the individual patient receiving REGEN-COV, the rapid anti-viral effect is likely to be associated with a public health benefit through reduced risk of viral transmission and containment of SARS-CoV-2 VOCs.

A low incidence of serious adverse events and hypersensitivity and infusion-related reactions was observed. Concentrations of each antibody in serum at day 29 were well above the predicted neutralization target concentration based on in vitro and preclinical data.

The emergence of resistant variants of SARS-CoV-2 during treatment with an antiviral agent(s) or via circulation within the global community will continue to be a challenge for the success of Covid-19 therapeutics and vaccines. Although in vitro studies or in vivo animal studies using recombinant viruses demonstrate that combinations of non-competing antibodies, such as REGEN-COV, are able to suppress the emergence of resistant variants, questions remain about the relevance of those studies to natural human infection. We therefore recently investigated and reported the genetic diversity of the entire spike protein across samples from 1,000 outpatients enrolled into either the outpatient REGEN-COV trial described in this Example or a separate, hospitalized Covid-19 REGEN-COV trial (described in Example 1). The analysis of 4,882 samples from these 1,000 patients treated with REGEN-COV or placebo demonstrated that REGEN-COV protects against the selection of resistant variants, as evidenced by a similar number of receptor binding domain (RBD) variants found in placebo-treated patients compared to those treated with 1200 mg and 2400 mg doses of REGEN-COV (15 RBD variants in placebo versus 12 in 1200 mg and 12 in 2400 mg dose in REGN-COV treated group). Three of these RBD variants were found in only the REGEN-COV-treated groups but were identified at baseline or soon after treatment (<5 days) and did not increase in frequency over time, suggesting the occurrence of these variants was not due to treatment pressure.

REGEN-COV antibody cocktail at the 2400 mg dose received Emergency Use Authorization (EUA) from the US FDA in November 2020 for the treatment of mild-to-moderate Covid-19. On Apr. 8, 2021, the NIH treatment guidelines recommended the use of 2400 mg REGEN-COV for the treatment of high-risk outpatients with Covid-19, with preferential use of REGEN-COV in areas where VOCs are common. The clinical evidence from this clinical outcomes trial, the largest randomized, controlled phase 3 Covid-19 outpatient treatment trial to date, indicates that 1200 mg of REGEN-COV is well-tolerated, can significantly reduce Covid-19-related hospitalizations or death, can speed time to recovery, and is unlikely to promote the emergence of treatment-resistant SARS-CoV-2 variants. With this definitive phase 3 data demonstrating a profound reduction in the risk of hospitalization or all-cause death, together with an acceptable safety profile, physicians should consider treating every high risk, SARS-CoV-2 positive individual.

Supplement Details

The Symptoms Evolution of COVID-19 (SE-C19) instrument was an electronic diary that was completed daily from Day 1 to Day 29. The SE-C19 was initially developed based on the CDC symptom list and available published literature specific to patients with COVID-19. It included a list of 23 symptoms feverish, chills, sore throat, cough, shortness of breath or difficulty breathing, nausea, vomiting, diarrhea, headache, red or watery eyes, body aches, loss of taste or smell, fatigue, loss of appetite, confusion, dizziness, pressure or tight chest, chest pain, stomachache, rash, sneezing, sputum or phlegm, runny nose). Patients indicated which of the 23 symptoms they experienced in the last 24 hours and then rated each symptom selected at its worst moment in that period on a scale of mild, moderate or severe. In parallel to the main clinical trial, patient and clinician interviews were performed to confirm the content validity of the newly developed SE-C19 and psychometric validation was conducted using blinded phase 1/2 data to explore the reliability and validity of the measure and refine a symptom endpoint.

The results indicated 19 of the original 23 items being most valid, reliable and relevant to outpatients with COVID-19 (i.e., sneezing, rash, vomiting and confusion were excluded) and refinement of the response options to three-categories (0—none, 1—mild/moderate, 2—severe). The detailed, rigorous scientific methods implemented and results of these additional studies will be published independently.

Missing data for virology endpoints was handled as follows: Analysis-positive polymerase chain reaction (PCR) results below the lower limit of quantification (LLOQ) of 714 copies/ml (2.85 log 10 copies/ml) were imputed as half the LLOQ (357 copies/ml) and negative PCR results were imputed as 0 $\log_{10}$ copies/ml (1 copy/ml). Patients with missing baseline symptom assessment were not included in the analysis of the symptom resolution endpoint. Patients who do not experience resolution of symptoms will be censored at the last observation time point. Patients who died or had COVID-19-related hospitalization prior to day 29 were censored at day 29.

Prior to protocol amendment 6, serum for drug concentration analysis was collected from all patients randomized to 2.4 g IV, 8.0 g IV, or placebo at pre-dose (at the screening or baseline visit), day 1 at the end of the infusion, and day 29. After protocol amendment 6, serum for drug concentration analysis was collected from patients randomized to 1.2 g IV, 2.4 g IV, or placebo in a PK sub-study at pre-dose (at the screening or baseline visit), day 29, and day 120. The human serum concentrations of REGN10933 (casirivimab) and REGN10987 (imdevimab) were measured using validated immunoassays which employ streptavidin microplates from Meso Scale Discovery (MSD, Gaithersburg, MD, USA). The methods utilized two anti-idiotypic monoclonal antibodies, each specific for either REGN10933 or REGN10987, as the capture antibodies. Captured REGN10933 and REGN10987 were detected using two different, non-competing anti-idiotypic monoclonal antibodies, each also specific for either REGN10933 or REGN10987. The bioanalytical methods specifically quantitated the levels of each anti-SARS-CoV-2 spike monoclonal antibody separately, with no interference from the other antibody. The assay has an LLOQ of 0.156 µg/ml for each analyte in the undiluted serum sample.

Example 3. Clinical Evaluation of Anti-SARS-CoV-2 Spike Glycoprotein Antibodies for Prevention of SARS-CoV-2 Infection and COVID-19 in At-Risk Subjects The below-described clinical study is a randomized, double-blind, placebo-controlled phase 3 study to assess the safety, and efficacy of anti-Spike SARS-CoV-2 monoclonal antibodies in first responders, healthcare workers, and other adult individuals at risk of exposure to SARS-CoV-2 in geographic areas of ongoing COVID-19 outbreaks.

Study Objectives: For analysis of endpoints, there are 2 defined cohorts based on the subjects' SARS-CoV-2 infection status at baseline, as measured by central lab SARS-CoV-2 RT-qPCR (quantitative reverse transcription polymerase chain reaction): negative (cohort A) or positive (cohort B).

A strict definition of COVID-19 signs and symptoms (i.e., strict-term) is utilized for the primary endpoint, which include: fever ($\geq 38°$ C.) PLUS $\geq 1$ respiratory symptoms (sore throat, cough, shortness of breath), OR $\geq 2$ respiratory symptoms, OR 1 respiratory symptom PLUS $\geq 2$ non-respiratory symptoms (chills, nausea, vomiting, diarrhea, headache, conjunctivitis, myalgia, arthralgia, loss of taste or smell, fatigue or general malaise). A broader definition (i.e., broad-term) including the signs/symptoms in the strict definition and additional non-specific symptoms (feverish, sore throat, cough, shortness of breath, chills, nausea, vomiting, diarrhea, headache, red or watery eyes, body aches, loss of taste/smell, fatigue, loss of appetite, confusion, dizziness, pressure/tightness in chest, chest pain, stomach ache, rash, sneezing, runny nose, or sputum/phlegm) is used for secondary endpoints.

Objectives are for subjects who are seronegative at baseline unless noted otherwise.

Cohort A: SARS-CoV-2 RT-qPCR Negative at Baseline
Cohort A Primary Efficacy Objectives
  To evaluate the efficacy of mAb10933)+mAb10987 compared to placebo in preventing symptomatic SARS-CoV-2 infection (strict-term) confirmed by RT-qPCR
  To evaluate the efficacy of mAb10933+mAb10987 compared to placebo in preventing symptomatic (strict-term or broad-term) and asymptomatic SARS-CoV-2 infection confirmed by RT qPCR
Cohort A Primary Safety Objective
  To evaluate the safety and tolerability of mAb10933+mAb10987 following subcutaneous (SC) administration compared to placebo
Cohort A Secondary Objectives
  To evaluate the efficacy of mAb10933+mAb10987 compared to placebo in preventing symptomatic SARS-CoV-2 infection (broad-term) confirmed by RT qPCR
  To evaluate the efficacy of mAb10933+mAb10987 compared to placebo in preventing asymptomatic SARS-CoV-2 infection confirmed by RT-qPCR
  To evaluate the impact of mAb10933+mAb10987 compared to placebo on the duration of signs and symptoms in subjects with symptomatic SARS CoV-2 infection confirmed by RT-qPCR
  To evaluate the impact of mAb10933+mAb10987 compared to placebo on SARS CoV-2 RT-qPCR test results
  To evaluate the impact of mAb10933+mAb10987 compared to placebo on SARS CoV-2 infection:
    On health care utilization
    On absenteeism from daily responsibilities
  To characterize the drug concentration-time profiles of mAb10933 and mAb10987 in serum and selected pharmacokinetic (PK) parameters
  To assess the immunogenicity of mAb10933 and mAb10987
  To evaluate the safety and tolerability of mAb10933+mAb10987 following SC administration in seropositive subjects
  To estimate the incidence and severity of symptomatic SARS-CoV-2 infection over time, including the period following study drug treatment, in mAb10933+mAb10987 treated seronegative and seropositive subjects compared to placebo treated subjects
Cohort B: SARS-CoV-2 RT-qPCR Positive at Baseline
Cohort B Secondary Objectives
  To evaluate the efficacy of mAb10933+mAb10987 compared to placebo in preventing development of:
    Symptomatic SARS-CoV-2 infection (strict-term)
    Symptomatic SARS-CoV-2 infection (broad-term)
  To evaluate the impact of mAb10933+mAb10987 compared to placebo on the duration of signs and symptoms in subjects with symptomatic SARS CoV-2 infection confirmed by RT-qPCR
  To evaluate the impact of mAb10933+mAb10987 compared to placebo on SARS CoV-2 RT-qPCR test results
  To evaluate the impact of mAb10933+mAb10987 compared to placebo in SARS CoV-2 infection:
    On health care utilization
    On absenteeism from daily responsibilities
  To characterize the concentration-time profiles of mAb10933 and mAb10987 in serum and selected PK parameters
  To assess the immunogenicity of mAb10933 and mAb10987
  To evaluate the safety and tolerability of mAb10933+mAb10987 following SC administration in both seronegative and seropositive subjects
  To estimate the incidence and severity of symptomatic SARS-CoV-2 infection over time, including the period following study drug treatment, in mAb10933+mAb10987 treated seronegative and seropositive subjects compared to placebo-treated subjects Study Design: This is a phase 3 randomized, double-blind, placebo-controlled study in first responders, healthcare workers, and other adult individuals at risk of exposure to SARS-CoV-2 in geographic areas of ongoing COVID-19 outbreaks. Approximately 6000 subjects are enrolled. Subjects are randomized in a 1:1:1 ratio into 1 of the 3 treatment groups. Randomization is performed by site and stratified by local molecular diagnostic assay for SARS-CoV-2 from respiratory sample (negative, positive, or undetermined), on-site LFIA serology test for SARS-CoV-2 (seropositive, seronegative, or undetermined), and age ≥50 year (yes vs no).

Cohort allocation is based on central lab baseline SARS-CoV-2 RT-qPCR for data analysis: cohort A (negative) and cohort B (positive). Approximately 5000 subjects are enrolled in cohort A and cohort B is capped to 1000 subjects. For the purpose of the study analysis, cohort A and cohort B are independent. Since this is an event driven study, the sponsor may decide to close enrollment of cohort B once cohort A is fully enrolled and/or the necessary number of events are accrued in cohort A for the primary efficacy analysis.

Enrollment in this study is carried out in 2 phases:
1. Sentinel group of approximately 30 subjects, irrespective of allocation to cohort A or cohort B: Subjects will be monitored for safety on-site for a minimum of 4 hours after administration of the first dose of study drug and then daily via visits to the study site or phone calls for the first 4 days (96 hours). Because mAb10933+mAb10987 already have cleared a sentinel safety group at higher doses administered IV, the sentinel group in this study will focus on safety evaluation for injection site reactions and hypersensitivity reactions. Blinded safety data up to day 4 assessments from a pooled ~30 subjects enrolled in the SC administered mAb10933+mAB10987 prophylaxis program (from either this study or pooled with an accompanying post-exposure prophylaxis study in household contacts (Example 4), which comprise a sentinel safety cohort) are reviewed before progressing with enrollment of additional study subjects.
2. Following a conclusion of the blinded safety data review that the study may proceed, the study resumes enrollment.

Study Duration: For each subject, the study comprises 3 periods: an up to 3-day screening/baseline period, a 4-month efficacy enhancement period (EAP), and a 7-month follow-up period after the end of the EAP.

Study Population: The study population comprises asymptomatic, healthy adult first responders, healthcare workers, and other individuals at risk of exposure to SARS-CoV-2. Enrollment of "other individuals" at risk of SARS CoV-2 infection should occur only in geographic areas where there is widespread COVID-19 and high attack rates. The decision to include such subject population(s) in the study will be based on review of epidemiologic data.

Cohorts and Sample Size—Cohort A: Approximately 5000 subjects with negative baseline rapid SARS-CoV-2 RT-PCR; Cohort B: Up to 1000 subjects with positive baseline rapid SARS CoV-2 RT-PCR.

Inclusion Criteria: A subject must meet the following criteria to be eligible for inclusion in the study:

1. 18 years of age and above at the signing of informed consent;
2. In a population at high risk for exposure to SARS-CoV-2, including but not limited to the following:
   a. Active first responders and/or healthcare workers including but not limited to physicians, nurses, nurses' aides, respiratory therapists, and members of law enforcement, firefighter, emergency medical technician or paramedic at risk of exposure to the SARS-CoV-2;
   OR
   b. Other individuals deemed to be at risk for SARS-CoV-2 infection (including but not limited to industry workers; meat packers; nursing home residents and workers; people congregating in places of worship; college students, teachers and workers) in geographic areas with an active COVID-19 outbreak. The decision to include such subject population(s) in the study will be based on review of epidemiologic data by the Sponsor and other collaborating parties;
3. Is judged by the investigator to be in good health based on medical history and physical examination at screening/baseline;
4. Willing and able to comply with study visits and study-related procedures;
5. Provides signed informed consent.

Exclusion Criteria: A subject who meets any of the following criteria will be excluded from the study:

1. Subject reported history of prior positive SARS-CoV-2 RT-PCR test or positive SARS-CoV-2 serology test at any time before the screening visit;
2. Active respiratory or non-respiratory symptoms suggestive or consistent with COVID-19;
3. History of respiratory illness with signs/symptoms of COVID-19, in the opinion of the investigator, within the prior month to screening;
4. History of clinically significant illness or presenting any concern, as assessed by the investigator that may confound the results of the study or poses an additional risk to the subject by their participation in the study;
5. Hospitalization (i.e., >24 hours) for any reason within 30 days of the screening visit;
6. Cancer requiring treatment currently or in the past 1 year, except for non-melanoma skin cancer or cervical/anus in-situ;
7. Has a history of significant multiple and/or severe allergies (e.g., latex gloves), or has had an anaphylactic reaction to prescription or non-prescription drugs or food. This is to avoid potential confounding of the safety data and not due to a particular safety risk;
8. Treatment with another investigational drug in the last 30 days or within 5 half-lives of the investigational drug, whichever is longer, prior to the screening visit;
9. Received investigational or approved SARS-CoV-2 vaccine;
10. Received investigational or approved passive antibodies for SARS-CoV-2 infection prophylaxis (e.g., convalescent plasma or sera, monoclonal antibodies, hyperimmune globulin);
11. Use of hydroxychloroquine/chloroquine, remdesivir, intravenous immunoglobulin (IVIG) or other anti-SARS viral agents within 2 months prior to screening;
12. Member of the clinical site study team and/or immediate family;
13. Pregnant or breastfeeding women;
14. Women of childbearing potential (WOCBP)* who are unwilling to practice highly effective contraception prior to the initial dose/start of the first treatment, during the study, and for at least 8 months after the last dose. Highly effective contraceptive measures include:
    a. stable use of combined (estrogen and progestogen containing) hormonal contraception (oral, intravaginal, transdermal) or progestogen-only hormonal contraception (oral, injectable, implantable) associated with inhibition of ovulation initiated 2 or more menstrual cycles prior to screening;
    b. intrauterine device (IUD); intrauterine hormone-releasing system (IUS);
    c. bilateral tubal ligation;
       *WOCBP are defined as women who are fertile following menarche until becoming postmenopausal, unless permanently sterile. Permanent sterilization methods include hysterectomy, bilateral salpingectomy, and bilateral oophorectomy.
       A postmenopausal state is defined as no menses for 12 months without an alternative medical cause. A high follicle stimulating hormone (FSH) level in the postmenopausal range may be used to confirm a postmenopausal state in women not using hormonal contraception or hormonal replacement therapy. However, in the absence of 12 months of amenorrhea, a single FSH measurement is insufficient to determine the occurrence of a postmenopausal state. The above definitions are according to the Clinical Trial Facilitation Group (CTFG) guidance. Pregnancy testing and contraception are not required for women with documented hysterectomy or tubal ligation.
15. Sexually active men who are unwilling to use the following forms of medically acceptable birth control during the study drug follow-up period and for 6 months after the last dose of study drug: vasectomy with medical assessment of surgical success OR consistent use of a condom. Sperm donation is prohibited during the study and for up to 6 months after the last dose of study drug.

Study Treatments: Patients receive mAb10933+mAb10987 600 mg (300 mg+300 mg)/subcutaneous (SC)/once every 4 weeks (Q4W) on day 1, 29, 57, and 85, mAb10933+mAb10987 1200 mg (600 mg+600 mg) loading dose/SC/on day 1, then 600 mg (300 mg+300 mg)/SC/Q4W on day 29, 57, and 85, or matching placebo SC/Q4W on day 1, 29, 57, and 85.

Endpoints: Primary and secondary endpoints are specified for each cohort, as defined below.

Primary Endpoints

Cohort A: SARS-CoV-2 RT-qPCR Negative at Baseline

Primary Efficacy Endpoints:

Incidence of symptomatic RT-qPCR confirmed SARS-CoV-2 infection (strict term) during the EAP Incidence of RT-qPCR confirmed SARS-CoV-2 infection (either symptomatic or asymptomatic) during the EAP Primary Safety Endpoint:
Incidence and severity of treatment-emergent adverse events (TEAEs)

Secondary Endpoints

Cohort A: SARS-CoV-2 RT-qPCR Negative at Baseline

Cohort A Secondary Efficacy Endpoints:
Incidence of symptomatic RT-qPCR confirmed SARS-CoV-2 infection (broad term) during the EAP Incidence of positive SARS-CoV-2 RT-qPCR and absence of signs and symptoms (strict term) during the EAP Incidence of positive SARS-CoV-2 RT-qPCR and absence of signs and symptoms (broad term) during the EAP Number of days of symptomatic SARS-CoV-2 infection (strict-term) from the first day of the first sign or symptom until the last day of the last sign or symptom associated with the first positive SARS-CoV-2 RT-qPCR that occurs during the EAP Number of days of symptomatic SARS CoV-2 infection (broad-term) from the first day of the first sign or symptom until the last day of the last sign or symptom associated with the first positive SARS CoV-2 RT-qPCR that occurs during the EAP Time-weighted average of viral shedding (log 10 copies/mL) from the first positive SARS CoV-2 RT-qPCR nasal swab sample (that has an onset during the EAP) until 22 days after the positive test Time-weighted average of viral shedding (log 10 copies/mL) from the first positive SARS CoV-2 RT-qPCR saliva sample (that has an onset during the EAP) until 22 days after the positive test Maximum SARS-CoV-2 RT-qPCR log 10 viral copies/mL in nasal swab samples among individuals with ≥1 RT-qPCR positive result that has an onset during the EAP Maximum SARS-CoV-2 RT-qPCR log 10 viral copies/mL in saliva samples among individuals with ≥1 RT-qPCR positive result that has an onset during the EAP Area under the curve (AUC) in viral shedding (log 10 copies/mL) from the first positive SARS-CoV-2 RT-qPCR in nasal swab sample until the first confirmed negative test, that has an onset during the EAP Area under the curve (AUC) in viral shedding (log 10 copies/mL) from the first positive SARS CoV-2 RT-qPCR in saliva sample until the first confirmed negative test, that has an onset during the EAP Number of medically attended visits in emergency rooms or urgent care centers related to a RT qPCR confirmed SARS-CoV-2 infection that has an onset during the EAP Proportion of subjects requiring medically attended visits in emergency rooms or urgent care centers related to a RT-qPCR confirmed SARS CoV-2 infection that has an onset during the EAP Proportion of subjects hospitalized related to a RT-qPCR confirmed SARS-CoV-2 infection that has an onset during the EAP Number of days of hospital and ICU stay in subjects hospitalized for a RT qPCR confirmed SARS CoV-2 infection that has an onset during the EAP Number of days missed for daily responsibilities, including work (employed adults) or school (matriculating students), or family obligations/responsibilities (childcare or eldercare) due to a RT-qPCR confirmed SARS-CoV-2 infection that has an onset during the EAP Cohort A Pharmacokinetic and Immunogenicity Secondary Endpoints:
Concentrations of mAb10933 and mAb10987 in serum over time and selected PK parameters in both seronegative and seropositive subjects (based on central lab test)

Immunogenicity as measured by anti-drug antibodies (ADA) to mAb10933 and mAb10987 over time in both seronegative and seropositive subjects (based on central lab test)

Cohort A Safety Secondary Endpoints:
Incidence and severity of TEAEs in baseline seropositive subjects (based on central lab test)

Incidence and severity of symptomatic SARS-CoV-2 infection in seronegative and seropositive subjects (based on central lab test) in both the EAP and follow up period Cohort B: SARS-CoV-2 RT-qPCR Positive at Baseline Cohort B Secondary Efficacy Endpoints:
Proportion of subjects who subsequently develop signs and symptoms (strict-term) of symptomatic SARS-CoV-2 infection within 14 and 28 days of a positive RT-qPCR Proportion of subjects who subsequently develop signs and symptoms (broad-term) of symptomatic SARS-CoV-2 infection within 14 and 28 days of a positive RT-qPCR Number of days of symptomatic SARS CoV-2 infection (strict-term)

Number of days of symptomatic SARS CoV-2 infection (broad-term)

Time-weighted average change from baseline in viral shedding (log 10 copies/mL) in nasal swab samples until day 23.

Time-weighted average change from baseline in viral shedding (log 10 copies/mL) in saliva samples until day 23

Area under the curve (AUC) in viral shedding (log 10 copies/mL) in nasal swab samples until the first confirmed negative test Area under the curve (AUC) in viral shedding (log 10 copies/mL) in saliva samples until the first confirmed negative test Maximum SARS-CoV-2 RT-qPCR log 10 viral copies/mL in nasal swab samples Maximum SARS-CoV-2 RT-qPCR log 10 viral copies/mL in saliva samples Number of medically attended visits in emergency rooms or urgent care centers related to a RT-qPCR confirmed SARS-CoV-2 infection Proportion of subjects requiring medically attended visits in emergency rooms or urgent care centers related to a RT-qPCR confirmed SARS-CoV-2 infection Proportion of subjects hospitalized related to a RT-qPCR confirmed SARS-CoV-2 infection Number of days of hospital and ICU stay in subjects hospitalized for a RT-qPCR confirmed SARS CoV-2 infection Number of days missed for daily responsibilities, including work (employed adults) or school (matriculating students), or family obligations/responsibilities (childcare or eldercare) due to a RT-qPCR confirmed SARS-CoV-2 infection Cohort B Pharmacokinetic and Immunogenicity Secondary Endpoints:
Concentrations of mAb10933 and mAb10987 in serum over time and selected PK parameters in both seronegative and seropositive subjects (based on central lab test)
Immunogenicity as measured by ADA to mAb10933 and mAb10987 over time in both seronegative and seropositive subjects (based on central lab test)

Cohort B Safety Secondary Endpoints:
Incidence and severity of TEAEs in both seronegative and seropositive subjects (based on central lab test)
Incidence and severity of symptomatic SARS-CoV-2 infection in seronegative and seropositive subjects (based on central lab test) in both the EAP and follow up period Procedures and Assessments: Efficacy procedures and assessment include the following:
Nasal swab and saliva SARS-CoV-2 RT-qPCR Tests (central lab)
COVID-19 Symptomology (Broad Terms and Strict Terms):
During each scheduled or unscheduled visit/contact, the investigator or sub-PI investigator, or designee (i.e., nurse practitioner in countries where allowed by local law) queries the subject about adverse events the subject is experiencing or has experienced since the last visit/contact (e.g., within the prior week if it's a weekly scheduled visit) and asks about all of the signs and symptoms associated with these adverse events including the start date, end date and severity of each. The investigator should avoid querying the subject by running a check-list of signs and symptoms, but rather allow the subject to spontaneously report everything that they presented.
All signs and symptoms related to the AEs, along with the corresponding start date, end date and severity are documented in the subject's medical records (source document). As signs and symptoms may appear and resolve on different days and may precede or occur after the collection of nasal swab and saliva samples for the SARS-CoV-2 RT-qPCR test, it is important that this detailed information be captured in the source document.
Independent of the results (positive or negative) of the SARS-CoV-2 RT-qPCR tests performed on samples collected from study subjects during the weekly or unscheduled visits, all adverse events must be documented in the AE CRF. Signs and symptoms related to the adverse events reported in the AE CRF and confirmed to be temporally related to a positive SARS-CoV-2 RT qPCR test collected from the subject's nasal swab and/or saliva sample are reported on a separate CRF (individual sign or symptom with start date and end date, and associated severity).
Strict-term COVID-19 signs and symptoms, defined as:
fever ($\geq 38°$ C.) PLUS $\geq 1$ respiratory symptom (sore throat, cough, shortness of breath);
OR
$\geq 2$ respiratory symptoms (sore throat, cough, shortness of breath);
OR
1 respiratory symptom (sore throat, cough, shortness of breath) PLUS $\geq 2$ non respiratory symptoms (chills, nausea, vomiting, diarrhea, headache, conjunctivitis, myalgia, arthralgia, loss of taste or smell, fatigue or general malaise).
Broad-term COVID-19 signs and symptoms: defined as any of the 23 symptoms listed below in the protocol or fever ($\geq 38°$ C.).
Medically Attended Visits: SARS-CoV-2 infection-related medically attended visits to the emergency department (ED), urgent care center (UCC), or hospitalization starting from the timepoint of SARS-CoV-2 RT-qPCR positive and through the end of the EAP. Data collected include nature of the visit (ED, UCC, hospital stay), date of visit, length of hospital stay, and primary reason for the visit
Absenteeism from responsibilities: Data include absenteeism, defined as number of days missed from daily responsibilities, including work (employed adults) or school (matriculating students), or family obligations/responsibilities (childcare or eldercare) due to a RT-qPCR confirmed SARS-CoV-2.
Assays for Endogenous anti-SARS-CoV-2 Antibodies (central lab)

Safety Procedures and assessments include vital signs, targeted physical examination, clinical laboratory tests, ADA assessment, and clinical evaluations. Subjects will be asked to report all adverse events (AEs) experienced from the time of informed consent until their last study visit.

Pharmacokinetics: Serum samples will be collected at specified time points for assay of concentration of mAb10933 and mAb10987.

Statistical Plan:
Primary Efficacy Analysis (Cohort A)—The primary database lock occurs when 157 total positive SARS-CoV-2 RT-qPCR symptomatic infections are observed in cohort A.

The stratified log-rank test will be used with age ($<50$, $\geq 50$ years) as the stratification factor to compare each dose of mAb10933+mAB10987 and placebo. The Kaplan-Meier approach is used to estimate the cumulative probability of laboratory-confirmed symptomatic SARS-CoV-2 infection and associated 95% CIs will be reported for each treatment arm. A Cox proportional hazards model is used to estimate the hazard ratio and its 95% CI. The model includes treatment groups and age as the stratification factor specified earlier.

Subjects who complete the EAP and do not have an event during the EAP are censored at the last date of their EAP completion. Subjects who have not completed the EAP and do not have an event are censored at the data cutoff date. Data for subjects with no post-baseline information will be censored at the date of randomization plus 1 day. Data for subjects who are lost to follow-up in the EAP prior to positive SARS-CoV-2 RT-qPCR are censored at their last available SARS CoV-2 RT-qPCR assessment. Additional details of the analysis, as well as sensitivity analyses, are provided in the Statistical Analysis Plan (SAP).

Similar analytical methods are implemented to compare mAb10933+mAb10987 and placebo for the incidence of positive SARS-CoV-2 RT-qPCR, regardless of symptoms.

As a sensitivity analysis, subjects who develop asymptomatic or symptomatic SARS-CoV-2 infection within 72 hours of the first dose of study drug are excluded. Additional sensitivity and supportive analyses are described in the SAP.

Secondary Efficacy Analysis (Cohort A)—Analysis methods for the secondary efficacy endpoints are described below. For the comprehensive evaluation of efficacy, nominal p-values may be reported even if analyses of some secondary endpoints entail non-randomized comparison. The following secondary endpoints are analyzed using the analysis method as specified for the primary efficacy analysis.

Incidence of symptomatic RT-qPCR confirmed SARS-CoV-2 infection (broad-term) during the EAP Incidence of positive SARS-CoV-2 RT-qPCR and absence of signs and symptoms (strict-term) during the EAP Incidence of positive SARS-CoV-2 RT-qPCR and absence of signs and symptoms (broad-term) during the EAP Analyses for Other Secondary Endpoints—Continuous or count endpoints (e.g., time-weighted average of viral shedding, number of days of symptoms, number of medically attended visits) are summarized using descriptive statistics (mean, median, standard deviation and quartiles). Analysis methods either use non parametric Van-Elteren test stratified by age (<50, ≥50 years) or ANOVA with treatment and age (<50, ≥50 years) in the model.

The binary endpoints such as proportion of subjects hospitalized related to a RT-qPCR confirmed SARS-CoV-2 infection will be summarized using frequency, percentages, absolute difference or odd-ratio and are analyzed using Cochran-Mantel-Haenszel (CMH) test adjusted by stratification factor of age (<50, ≥50 years) or Fisher's exact test.

Secondary Efficacy Analysis (Cohort B)—The Cochran-Mantel-Haenszel (CMH) test adjusted by the stratification factor of age (<50, ≥50 years) will be used to analyze the proportion of subjects who develop signs and symptoms (strict term) of symptomatic SARS-CoV-2 infection during the efficacy assessment period. Subjects who remain asymptomatic but do not have confirmed negative SARS-CoV-2 RT-qPCR at the time of the final analyses are imputed as having become symptomatic.

Results—This study demonstrates prevention of symptomatic and asymptomatic SARS-CoV-2 infection in adults at high risk for exposure evaluated by SARS-CoV-2 RT-qPCR test results from weekly nasal swabs and saliva samples, and prevention of symptomatic SARS-CoV-2 infection evaluated through daily collection of commonly reported clinical signs/symptoms related to COVID-19.

Example 4. Clinical Evaluation of Anti-SARS-CoV-2 Spike Glycoprotein Antibodies for Prevention of SARS-CoV-2 Infection in Household Contacts of Individuals Infected with SARS-CoV-2

The below-described clinical study is a phase 3, randomized, double-blind, placebo-controlled study assessing the efficacy and safety of anti-Spike SARS-CoV-2 monoclonal antibodies in preventing SARS-CoV-2 infection in household contacts of individuals infected with SARS-CoV-2.

Study Objectives: For analysis of endpoints, there are 4 defined cohorts based on the subjects' age and SARS-CoV-2 infection status at baseline, as measured by central lab SARS CoV-2 RT-qPCR (quantitative reverse transcription polymerase chain reaction): negative (cohort A [adult and adolescent subjects ≥12 years] and cohort A1 [pediatric subjects <12 years]) or positive (cohort B [adult and adolescent subjects ≥12 years] and cohort B1 [pediatric subjects <12 years]). A strict definition of COVID-19 signs and symptoms was utilized for the secondary endpoint, which include: fever (≥38° C.) PLUS ≥1 respiratory symptoms (sore throat, cough, shortness of breath), OR 2 respiratory symptoms, OR 1 respiratory symptom PLUS ≥2 non-respiratory symptoms (chills, nausea, vomiting, diarrhea, headache, conjunctivitis, myalgia, arthralgia, loss of taste or smell, fatigue or general malaise). A broader definition including the signs/symptoms in the strict definition and additional symptoms was used for additional secondary endpoints (24 terms: Feverish, Sore throat, Cough, Shortness of breath/difficulty breathing [nasal flaring in pediatric subjects], Chills, Nausea, Vomiting, Diarrhea, Headache, Red or watery eyes, Body aches such as muscle pain or joint pain, Loss of taste/smell, Fatigue [fatigue or general malaise or lethargy in pediatric subjects], Loss of appetite or poor eating/feeding, Confusion, Dizziness, Pressure/tightness in chest, Chest pain, Abdominal pain, Stomach ache, Rash, Sneezing, Runny nose, Sputum/phlegm). Objectives are for subjects who are seronegative at baseline (by central lab test) unless noted.

Cohort A: SARS-CoV-2 RT-qPCR Negative at Baseline

Cohort A Primary Efficacy Objective

To evaluate the efficacy of mAb10933+mAb10987 compared to placebo in preventing asymptomatic or symptomatic SARS-CoV-2 infection confirmed by RT-qPCR Cohort A and Cohort A1 Primary Safety Objective To evaluate the safety and tolerability of mAb10933+mAb10987 following subcutaneous (SC) administration compared to placebo Cohort A and Cohort A1 Secondary Objectives To evaluate the efficacy of mAb10933+mAb10987 compared to placebo in preventing symptomatic SARS-CoV-2 infection (broad-term) confirmed by RT-qPCR To evaluate the efficacy of mAb10933+mAb10987 compared to placebo in preventing asymptomatic SARS-CoV-2 infection confirmed by RT-qPCR To evaluate the efficacy of mAb10933+mAb10987 compared to placebo in preventing symptomatic SARS-CoV-2 infection (strict-term) confirmed by RT-qPCR To evaluate the impact of mAb10933+mAb10987 compared to placebo on the duration of signs and symptoms in subjects with symptomatic SARS-CoV-2 infection confirmed by RT-qPCR To evaluate the impact of mAb10933+mAb10987 compared to placebo on SARS-CoV-2 RT-qPCR test results To evaluate the impact of mAb10933+mAb10987 compared to placebo On health care utilization On absenteeism from daily responsibilities To characterize the drug concentration-time profiles of mAb10933 and mAb10987 in serum and selected pharmacokinetic (PK) parameters.

To assess the immunogenicity of mAb10933 and mAb10987

To evaluate the safety and tolerability of mAb10933+mAb10987 following subcutaneous (SC) administration in seropositive subjects To estimate the incidence and severity of symptomatic SARS-CoV-2 infection over time, including the period following study drug treatment, in mAb10933+mAb10987-treated seronegative and seropositive subjects compared with placebo-treated subjects Additional Cohort A1 Secondary Objective To evaluate the efficacy of mAb10933+mAb10987 compared to placebo in preventing asymptomatic or symptomatic SARS-CoV-2 infection confirmed by RT-qPCR Cohort B: SARS-CoV-2 RT-qPCR Positive at Baseline Cohort B and Cohort B1 Secondary Objectives—objectives for Cohort B and Cohort B1 are for all subjects irrespective of their serology status (positive or negative) at baseline (by central lab test).

To evaluate the efficacy of mAb10933+mAb10987 compared to placebo in preventing development of:

Symptomatic SARS-CoV-2 infection (strict-term)

Symptomatic SARS-CoV-2 infection (broad-term)

To evaluate the impact of mAb10933+mAb10987 compared to placebo on the duration of signs and symptoms in subjects with symptomatic SARS-CoV-2 infection confirmed by RT-qPCR To evaluate the impact of mAb10933+mAb10987 compared to placebo on SARS-CoV-2 RT-qPCR test results To evaluate the impact of mAb10933+mAb10987 compared to placebo in SARS-CoV-2 infection:
On health care utilization
On absenteeism from daily responsibilities To characterize the drug concentration-time profiles of mAb10933 and mAb10987 and selected PK parameters in serum To assess the immunogenicity of mAb10933 and mAb10987

To evaluate the safety and tolerability of mAb10933+mAb10987 following SC administration To estimate the incidence and severity of symptomatic SARS-CoV-2 infection over time, including the period following study drug treatment, in mAb10933+mAb10987-treated seronegative and seropositive subjects compared with placebo-treated subjects Study Design: This was a phase 3 randomized, double-blind, placebo-controlled study in adults, adolescents, and children with household contact exposure to individuals with SARS-CoV-2 infection. All subjects in the study were household contacts with close exposure to the first household member known to be infected with SARS-CoV-2 (index case) but who were themselves asymptomatic (having no active respiratory or non-respiratory symptoms consistent with COVID-19) at the time of screening. The index case had a diagnosis of SARS-CoV-2 infection using a diagnostic test, e.g., RT-PCR, antigen testy, or other test format. Randomization was performed by individual study subjects, not by households. Approximately 2200 adult and adolescent (≥12 years) plus 100 pediatric patients (<12 years) were enrolled.

Screening/Baseline (day 1)—Randomization was performed on an individual subject basis, however all subjects randomized were given a household identification number in the case that multiple members of the same household were enrolled and received study drug. This ensured that correlation among subjects within the same household could be considered in the statistical analysis. Randomization was performed by site and stratified for assignment of treatment group by test results (positive, negative, or unavailable) of a local diagnostic assay for SARS-CoV-2 (e.g., molecular assay such as RT-PCR assay for SARS-CoV-2 or a SARS-CoV-2 antigen test) from appropriate samples, e.g., nasopharyngeal (NP), oropharyngeal (OP), nasal, or saliva, and age group (≥12 to <18, ≥18 to <50, or ≥50) (yes vs no). For pediatric subjects (<12 years), the weight group (≥20 kg, ≥10 kg to <20 kg, and <10 kg) was used as an additional stratification factor. The local diagnostic assay for SARS-CoV-2 must have been considered acceptable for clinical use by local standards.

Statistical analyses were conducted separately in each cohort which were based on central lab determination of viral positivity and serological status. Subjects were randomized in a 1:1 allocation ratio to 1 of 2 treatment groups (placebo or mAB10933+mAb10987 [1200 mg (600 mg of each mAb subcutaneously (SC)]). This study was preceded by safety review of data from other studies: a safety sentinel group of 30 patients with COVID-19 dosed with mAb10933+mAb10987 2400 mg IV, mAb10933+mAb10987 8000 mg IV or placebo in the leading phase 1 studies of mAb10933+mAb10987 in the treatment of COVID-19 patients.

Sentinel Group (day 1 to day 4)—Enrollment in this study was carried out in 2 phases: Sentinel group of approximately 30 adult subjects, irrespective of allocation to cohort A or cohort B.

Subjects were monitored for safety on-site for a minimum of 4 hours after administration of the first dose of study drug and then daily via visits to the study site or phone calls for the first 4 days (96 hours). Because mAb10933+mAb10987 had already cleared an adult sentinel safety group at higher doses administered IV, the sentinel group in this study focused on safety evaluation for injection site reactions and hypersensitivity reactions, and data were reviewed before progressing with enrollment of additional study subjects. The blinded safety data review was led by a designated member of the Regeneron clinical team (generally either the medical monitor or the clinical trial manager). Following a conclusion of the blinded safety data review that the study could proceed, the study resumed enrollment.

Pediatric Sentinel Subjects and Staggered Enrollment/Dosing—approximately 100 pediatric subjects across all weight-tiered dose ranges are enrolled. However, since the enrollment of pediatric subjects (<12 years) ends once enrollment of adult and adolescent subjects is complete, the number of pediatric subjects may be adjusted. Enrollment of pediatric subjects in this study is carried out in 2 phases:

A sentinel group comprises 12 pediatric subjects (by subject number assigned by IWRS; irrespective of allocation to cohort A1 or cohort B1) in 3 weight groups (≥20 kg; 10 kg to 20 kg; <10 kg). Each weight group has 4 subjects randomized 1:1. After all 4 subjects in a weight group complete the sentinel review, enrollment of subjects in that weight group proceeds. Pediatric subjects are monitored for safety on-site for a minimum of 2 hours after administration of study drug and then daily via visits to the study site or phone calls for the first 4 days (96 hours). Because REGN10933+REGN10987 has already cleared an adult safety sentinel cohort at higher doses administered IV in previous studies and the adult safety sentinel in this study, the pediatric sentinel group in this study is focused on safety evaluation for injection site reactions and hypersensitivity reactions. Data is reviewed before progressing with enrollment of additional pediatric subjects. The blinded safety data review is led by a designated member of the Regeneron clinical team (generally either the medical monitor or the clinical trial manager). Following a conclusion of the blinded safety data review that the study may proceed for a weight group, the enrollment of pediatric subjects in that weight group resumes until approximately 25 subjects per each weight group (<10 kg, 10 kg to 20 kg, ≥20 kg) are enrolled.

The PK data from approximately the first 20 subjects per weight group was evaluated to confirm that the dose for the weight group is providing the expected exposure. Once a dose was confirmed, enrollment beyond 25 subjects for this weight group continued. If dosing for a particular group needed to be adjusted, the new dose for that weight group was applied and the next 20 subjects from that weight group who received the new dose were examined for exposure.

After subjects provide informed consent, they were assessed for study eligibility. The screening visit and randomization visits should occur on the same day. If needed, a remote visit occurred to sign the ICF and collect medical history and concomitant medication use, on the day prior to, but within 24 hours of study drug administration, so that the in person screening and randomization visit could be abbreviated, due to COVID-19 considerations. Study drug administration must have occurred within 96 hours of collection of the index cases' positive SARS-CoV-2 diagnostic test sample. On day 1, prior to randomization, a local molecular diagnostic assay for SARS-CoV-2 from appropriate samples was performed. The results of these assays were used as stratification factors for randomization to treatment groups (placebo or mAb10933+mAb10987). The requirement for a local diagnostic assay for SARS-CoV-2 was waived when the results were not expected to be available in a timely manner for randomization. Nasopharyngeal (NP) swab sample (swabbing through both nostrils) for central lab testing of SARS-CoV-2 RT-qPCR and blood sample for central lab serology was also collected and sent to central lab on the same day as collection. On day 1, after completing baseline assessments and sample collection, all subjects received a single-dose of study drug.

Efficacy Assessment Period (day 1 to day 29)—Efficacy, safety, sample collections, and other study assessments were performed at specified time points throughout the efficacy assessment period (EAP). If subjects were able to travel and could do so while maintaining social distancing guidelines, subsequent site visits were conducted; alternatively, telemedicine visits, phone calls, mobile units or home health nurses may have been utilized. Throughout the study, biological samples were obtained by adequately trained and delegated study personnel at study locations where appropriate personal protective equipment (PPE) were available to be used.

Subjects were instructed to contact the study site staff for any new or changing symptoms or signs possibly related to COVID-19, including fever. The investigator recommended that subjects (themselves or by their parent/guardian) measured their temperature daily during the EAP, approximately at the same time, and also every time when the subject felt feverish, chills, or sick. Subjects and/or their parent/guardian may have received automated reminders (e.g., text messages to mobile phones; implemented as soon as technologically feasible and when subjects confirms to opt in) in between the weekly visits to prompt them to contact the study site staff as needed.

At each weekly visit, NP swab sample was collected for SARS-CoV-2 RT-qPCR to be tested at a central lab. The investigator or designee contacted each subject weekly (site visit or telemedicine) to assess the subject's general health, and to document all AEs in general, and any signs and symptoms associated with SARS-CoV-2 infection since the last contact.

Any subject who developed fever, an acute respiratory illness or other symptoms that they felt could be related to COVID-19 should have alerted the study staff immediately. If the investigator or designee suspects SARS-CoV-2 infection, a NP swab sample should have been collected and sent for central lab testing. The subject may also have been asked to provide a blood sample if it corresponds to a scheduled visit.

Subjects with laboratory confirmed SARS-CoV-2 infection during the EAP should have been informed as soon as possible and should have undergone medical isolation to prevent contact with others to reduce the risk of further transmission. Since the subjects were likely isolated, the study visits, assessments and sample collections occurred through a variety of methods.

For all subjects who had a confirmed SARS-CoV-2 infection, they continued to be tested (sample collection weekly) until 2 consecutive confirmed negative SARS-CoV-2 RT-qPCR test results are achieved 24 hours apart. This testing may have continued through the EAP and into the Follow-up period.

Subjects presenting with acute illness should have been medically managed according to local standard of care as per the discretion of the treating physician. If a subject was hospitalized for suspected SARS-CoV-2 infection, every effort should have been made by the site personnel to collect, as soon as possible, nasal swab and/or saliva samples for central lab SARS-CoV-2 RT-qPCR testing.

Follow-up Period (day 30 to day 225)—Subjects who remained SARS-CoV-2 RT-qPCR negative throughout the EAP completed the end of the EAP and entered the Follow-up Period to be followed for 7 months.

Subjects who became SARS-CoV-2 RT-qPCR positive during the EAP continued to have weekly NP swab samples for SARS-CoV-2 RT-qPCR testing until 2 confirmed negative SARS-CoV-2 RT-qPCR test results were achieved at least 24 hours apart, even after they completed the EAP and entered the study Follow-up Period to be followed for 7 months. In such situations, these visits for sample collection should have been characterized as unscheduled visits. At each scheduled visit, the investigator or designee contacted each subject (site visit or telemedicine) to assess and document the subject's general health, AEs in general and signs and symptoms associated with SARS-CoV-2 infection since the last contact, as described for the EAP.

Study Duration: For each subject, there were 3 study periods: a 1-day screening/baseline period, a 1-month EAP, and a 7-month follow-up period after the end of the EAP.

Study Population: The study population comprised asymptomatic, healthy adults (≥18 years), adolescents (≥12 years to <18 years), and children (<12 years) who were household contacts to the first household member with a diagnosis of SARS-CoV-2 infection (index case).

Cohorts and Sample Size—Cohort A: Approximately 1980 adult and adolescent subjects with a negative SARS-CoV-2 RT-qPCR at baseline were enrolled. Cohort B: Approximately 220 adult and adolescent subjects with a positive SARS-CoV-2 RT-qPCR at baseline were enrolled. Cohort A1: Approximately 90 pediatric subjects (<12 years) with a negative SARS-CoV-2 RT-qPCR at baseline are enrolled. Cohort B1: Approximately 10 pediatric subjects (<12 years) with a positive SARS-CoV-2 RT-qPCR at baseline are enrolled.

Inclusion Criteria: A subject must have met the following criteria to be eligible for inclusion in the study:
1. Adult subjects 18 years of age (irrespective of weight) and above at the signing of informed consent or adolescent subjects ≥12 to <18 years of age, or pediatric subjects <12 years of age at the signing of the assent (parent/guardian sign the informed consent);
2. Asymptomatic household contact with sustained exposure to an individual with a positive SARS-CoV-2 RT-PCR assay (index case). To be included in the study, subjects must be randomized within 96 hours of collection of the index cases' positive SARS-COV-2 diagnostic test sample;
3. Subject anticipates living in the same household with the index case until study day 29;
4. Is judged by the investigator to be in good health based on medical history and physical examination at screening/baseline, including subjects who are healthy or have a chronic, stable medical condition;
5. Willing and able to comply with study visits and study-related procedures/assessments;

6. Provide informed consent signed by study subject or legally acceptable representative.

Exclusion Criteria: A subject who met any of the following criteria were excluded from the study:

1. Subject-reported history of prior positive SARS-CoV-2 RT-PCR test or positive SARS-CoV-2 serology test at any time before the screening;
2. Subject has lived with individuals who have had previous SARS CoV-2 infection or currently lives with individuals who have SARS-CoV-2 infection, with the exception of the index case, the first individual known to be infected in the household;
3. Active respiratory or non-respiratory symptoms consistent with COVID-19;
4. History of respiratory illness with sign/symptoms of SARS CoV-2 infection, in the opinion of the investigator within prior 6 months to screening;
5. Nursing home resident;
6. Any physical examination findings, and/or history of any illness, concomitant medications or recent live vaccines that, in the opinion of the study investigator, might confound the results of the study or pose an additional risk to the subject by their participation in the study;
7. Current hospitalization or was hospitalized (i.e., >24 hours) for any reason within 30 days of the screening visit;
8. Has a history of significant multiple and/or severe allergies (e.g., latex gloves), or has had an anaphylactic reaction to prescription or non-prescription drugs or food. This is to avoid possible confounding of the safety analysis and not due to any presumed increased risk of these individuals to a reaction to the investigational product;
9. Treatment with another investigational agent in the last 30 days or within 5 half-lives of the investigational drug, whichever is longer, prior to the screening visit;
10. Received an investigational or approved SARS-CoV-2 vaccine;
11. Received investigational or approved passive antibodies for SARS-CoV-2 infection prophylaxis (e.g., convalescent plasma or sera, monoclonal antibodies, hyperimmune globulin);
12. Use of hydroxychloroquine/chloroquine for prophylaxis/treatment of SARS-CoV-2, or anti-SARS viral agents (e.g., remdesivir) within 60 days of screening (use of hydroxychloroquine/chloroquine for other purposes is allowed);
13. Member of the clinical site study team and/or immediate family;

Study Treatments: Adult and adolescent subjects (≥12 years) received mAb10987 and mAb10933 1200 mg (600 mg of each mAb)/SC/single dose on day 1, or a matching solution SC/single dose on day 1. Pediatric subjects (<12 years of age) receive a SC/single dose on day 1 by weight-tiered groups (an intramuscular formulation may be used for pediatric subjects <10 kg):

TABLE 8

Pediatric Subjects Weight-Tiered Groups

| Weight-Tiered Group | mAb10987 + mAb10933 as a SC Single Dose on Day 1 | |
|---|---|---|
| | Total | per mAb |
| ≥40 kg | 1200 mg | 600 mg |
| ≥20 to <40 kg | 792 mg | 396 mg |
| ≥0 to <20 kg | 408 mg | 204 mg |
| ≥5 to <10 kg | 144 mg | 72 mg |
| ≥2.5 to <5 kg | 96 mg | 48 mg |
| <2.5 kg | 48 mg | 24 mg |

Endpoints: Primary and secondary endpoints were specified for each cohort, as defined below. Symptomatic SARS-CoV-2 infection was determined by a positive central lab SARS-CoV-2 RT-qPCR result during the EAP with signs/symptoms occurring within ±14 days of a positive RT-qPCR. The definitions for "strict-term" and "broad-term" signs/symptoms of SARS-CoV-2 infection are noted above. The endpoints are for subjects who were seronegative at baseline (based on central lab test), unless otherwise noted.

Primary Endpoints

Cohort A and Cohort A1: SARS-CoV-2 RT-qPCR Negative at Baseline

Cohort A Primary Efficacy Endpoints
  Proportion of subjects who had a RT-qPCR confirmed SARS-CoV-2 infection (either asymptomatic or symptomatic) during the efficacy assessment period (EAP).

Cohort A and Cohort A1 Primary Safety Endpoint
  Proportion of subjects with treatment-emergent adverse events (TEAEs) and severity of TEAEs Secondary Endpoints Cohort A and Cohort A1: SARS-CoV-2 RT-qPCR Negative at Baseline Cohort A and Cohort A1 Secondary Efficacy Endpoints
  Proportion of subjects who had a symptomatic RT-qPCR confirmed SARS-CoV-2 infection (broad term) during the EAP
  Proportion of subjects who had a positive SARS-CoV-2 RT-qPCR and the absence of signs and symptoms (strict term) during the EAP
  Proportion of subjects who had a positive SARS-CoV-2 RT-qPCR and the absence of signs and symptoms (broad term) during the EAP
  Number of days of symptomatic SARS-CoV-2 infection (strict-term) from the first day of the first sign or symptom until the last day of the last sign or symptom associated with the first positive SARS-CoV-2 RT-PCR that occurs during the EAP
  Number of days of symptomatic SARS-CoV-2 infection (broad-term) from the first day of the first sign or symptom until the last day of the last sign or symptom associated with the first positive SARS-CoV-2 RT-PCR that occurs during the EAP
  Time-weighted average of viral shedding ($\log_{10}$ copies/mL) from the first positive SARS-CoV-2 RT-qPCR in nasopharyngeal (NP) swab sample (that had an onset during the EAP) until the visit within the window including 22 days after the positive test during the EAP
  Maximum SARS-CoV-2 RT-qPCR $\log_{10}$ viral copies/mL in NP swab sample among individuals with ≥1 RT-qPCR positive that has an onset during the EAP
  Area under the curve (AUC) in viral shedding ($\log_{10}$ copies/mL) from the first positive SARS-CoV-2 RTqPCR in NP swab sample until the first confirmed negative test, that has an onset during the EAP Number of medically attended visits in emergency rooms or urgent care centers related to a RT-qPCR confirmed SARS-CoV-2 infection that has an onset during the EAP Proportion of subjects requiring medically attended visits in emergency rooms or urgent care centers related to a RT-qPCR confirmed SARS-CoV-2 infection that has an onset during the EAP Proportion of subjects hospitalized related to a RT-qPCR confirmed SARS-CoV-2 infection that has an onset during the EAP Number of days of hospital and intensive care unit (ICU) stay in subjects hospitalized for a RT-qPCR confirmed SARS-CoV-2 infection that has an onset during the EAP Number of days missed for daily responsibilities, including work (employed adults) or school (students), daycare or family obligations/responsibilities (childcare or eldercare) due to a RT-qPCR confirmed SARS-CoV-2 infection that has an onset during the EAP Additional Cohort A1 Secondary Efficacy Endpoint Proportion of subjects who have a positive SARS-CoV-2 RT-qPCR confirmed infection (based on central lab test) during the EAP Cohort A and Cohort A1 Secondary Safety Endpoints Proportion of baseline seropositive subjects (based on central lab test) with TEAEs and severity of TEAEs Incidence and severity of symptomatic SARS-CoV-2 infection in seronegative and seropositive subjects (based on central lab test) in both the EAP and follow up period Cohort A and Cohort A1 Pharmacokinetic and Immunogenicity Endpoints Concentrations of mAb10933+mAb10987 in serum over time and selected PK parameters in both seronegative and seropositive subjects (based on central lab test)

Immunogenicity as measured by anti-drug antibodies (ADA) and neutralizing antibodies (Nabs) to mAb10933+mAb10987 over time in both seronegative and seropositive subjects (based on central lab test)

Cohort B and Cohort B1: SARS-CoV-2 RT-qPCR Positive at Baseline

Cohort B Secondary Efficacy Endpoints

Proportion of subjects who subsequently developed signs and symptoms (strict term) of symptomatic SARS-CoV-2 during the EAP within 14 and 28 days of a positive RT-qPCR Proportion of subjects who subsequently developed signs and symptoms (broad term) of symptomatic SARS-CoV-2 infection during the EAP within 14 and 28 days of a positive RT-qPCR Number of days of symptomatic SARS-CoV-2 infection (strict-term)

Number of days of symptomatic SARS-CoV-2 infection (broad-term)

Time-weighted average change from baseline in viral shedding ($\log_{10}$ copies/mL) in NP swab samples until day 23

Area under the curve (AUC) in viral shedding ($\log_{10}$ copies/mL) in NP swab samples until the first confirmed negative test Maximum SARS-CoV-2 RT-qPCR $\log_{10}$ viral copies/mL in NP swab sample Number of medically attended visits in emergency rooms or urgent care centers related to RT-q PCR confirmed SARS-CoV-2 infection Proportion of subjects requiring medically attended visits in emergency rooms or urgent care centers related to a RT-qPCR confirmed SARS-CoV-2 infection Proportion of subjects hospitalized related to a RT-qPCR confirmed SARS-CoV-2 infection Number of days of hospital and ICU stay in subjects hospitalized for a RT-qPCR confirmed SARS-CoV-2 infection Number of days missed for daily responsibilities, including work (employed adults) or school (students), or family obligations/responsibilities (childcare or eldercare) due to a RT-qPCR confirmed SARS-CoV-2 infection Cohort B and Cohort B1 Secondary Safety Endpoints Proportion of subjects with treatment-emergent adverse events (TEAEs) and severity of TEAEs in both seronegative and seropositive subjects (based on central lab test)

Incidence of symptomatic SARS-CoV-2 infection as evidence to monitor ADE, in seronegative and seropositive subjects (based on central lab test) in both the EAP and follow up period Cohort B and Cohort B1 Pharmacokinetic and Immunogenicity Endpoints Concentrations of mAb10933+mAb10987 in serum over time and selected PK parameters in both seronegative and seropositive subjects (based on central lab test)

Immunogenicity as measured by anti-drug antibodies (ADA) and neutralizing antibodies (Nabs) to mAb10933+mAb10987 over time in both seronegative and seropositive subjects (based on central lab test)

Procedures and Assessments:

Efficacy Procedures:

Nasopharyngeal Swab SARS-CoV-2 RT-qPCR Test (Central Lab): Nasopharyngeal swab samples were collected from subjects to determine presence or absence of SARS-CoV-2 virus and to determine the relative quantitation of viral RNA shedding.

COVID-19 Symptomology (Broad Terms and Strict Terms): During each scheduled or unscheduled visit/contact, the investigator queried the subject and/or subject's parent or guardian about adverse events the subject was experiencing or had experienced since the last visit/contact (e.g., within the prior week if it's a weekly scheduled visit) and asked about all of the signs and symptoms associated with these adverse events including the start date, end date and severity of each.

Medically Attended Visits: Subjects and/or their parent/guardian (as appropriate) who became SARS-CoV-2 RT-qPCR positive were queried on any SARS-CoV-2 infection-related medically attended visits to the ED, UCC, or hospitalization. The assessment of medically attended visits to ED, UCC or hospitalization was performed from the time the subject first became SARS-CoV-2 RT-qPCR positive or from the time they developed symptoms suspected to be COVID-19 (later confirmed by RT-qPCR positive results) until the subject had 2 negative tests OR COVID-19 related symptoms had resolved (whichever lasts longer) or until the end of study visit.

Absenteeism Assessment: Subjects and/or their parent/guardian who were or became SARS-CoV-2 RT-PCR positive during the EAP were queried on any SARS-CoV-2 infection-related absenteeism. Data included absenteeism, defined as number of days missed for daily responsibilities, including work (employed adults) or school (matriculating students), daycare or family obligations/responsibilities (childcare or eldercare) due to COVID-19.

Safety Procedures:

Targeted Physical Examination and Vital Signs: The targeted physical examination and vital signs included measurements of temperature, blood pressure (measured after the subject had been resting quietly for at least 5 minutes and may be obtained from a seated or supine position), pulse rate, and respiratory rate, and examination of the oropharynx, skin, heart, lungs and any other system(s) depending on any complaints or concerns expressed by the subjects.

Laboratory Testing: samples for blood chemistry, hematology, and urinalysis were collected and analyzed. For all women of childbearing potential, a urine pregnancy test was performed onsite and any positive urine pregnancy test was confirmed with a serum pregnancy test at the central laboratory.

Other Procedures:

Drug concentration and Immunogenicity measurements: Dense sample and sparse sample collection for drug concentration measurement was performed in subsets of subjects. Samples for anti-drug antibody (ADA) assessment were collected at various times throughout the study.

Serological Assays for Endogenous Anti-SARS-CoV-2 Antibodies: In order to assess the impact of baseline humoral immunity/antibody response to SARS-CoV-2 on mAb10933+mAb10987 efficacy to prevent SARS-CoV-2 infection, serum anti-SARS-CoV-2 was measured at baseline, including but not limited to those which detect antibodies against the S protein and/or the N protein and/or neutralization assays. Samples were collected from adult and pediatric subjects (<18 years).

Exploratory Pharmacodynamic/Biomarker and Serum/Plasma Samples for Research: Samples for assessment of pharmacodynamic and exploratory research were collected from adult and adolescent subjects.

Pharmacogenomic Analysis (Optional): Adult and adolescent subjects may have participated in an optional genomics sub-study (separate informed consent required). Blood sample for RNA and DNA were collected for this substudy.

Statistical Plan:

Primary Efficacy Analysis (Cohort A)—The primary efficacy endpoint is analyzed in the FAS-A population. In order to account for the correlation among subjects within a household and control the associated type 1 error inflation, a generalized linear model was used to estimate the odds ratio between the treatment groups by using the generalized estimation equation (GEE) approach. This model estimated a single within-household correlation coefficient.

A subject was considered to be RT-qPCR positive if any of their results were positive. Otherwise, they were considered negative. If a subject's infection status could not be determined due to all missing RT-qPCR results, the following rules were applied to the primary analysis. If all post-baseline RT-qPCR results were missing, this subject was considered as having a positive RT-qPCR. If a subject had at least 1 COVID-19 sign and symptom (strict-term) within ±14 days of the planned visit with missing RT-qPCR result, this subject was considered as having a positive RT-qPCR.

Safety Analysis—Safety and tolerability were summarized by tabulation of treatment-emergent adverse events (TEAEs).

Results—An exploratory analysis was conducted on the first 409 evaluable subjects enrolled in the trial, who were randomized to receive passive vaccination with mAb10933 and mAb10987 (collectively referred to here as REGEN-COV™) (1,200 mg via subcutaneous injections) or placebo. These 409 evaluable participants who enrolled early in the trial did not have COVID-19 at baseline and were "seronegative", meaning they did not have existing antibodies in their blood to SARS-CoV-2. Individuals were eligible for the trial if they had a household member with COVID-19. Participants were tested weekly by nasopharyngeal swab. The results confirmed the ability of REGEN-COV to prevent asymptomatic and symptomatic COVID-19 infections as the primary endpoint.

Preliminary Results:

Passive vaccination with REGEN-COV™ resulted in 100% prevention of RT-PCR positive symptomatic infection (8/223 placebo vs. 0/186 REGEN-COV™; odds ratio 0.00 (confidence interval 0.00, 0.69)), and 48% lower overall rates of infection (symptomatic and asymptomatic) (23/223 placebo vs. 10/186 REGEN-COV™; odds ratio 0.49 (confidence interval 0.20, 1.12)) (Table 9, below).

TABLE 9

Preliminary Results

| Endpoint | Placebo n/N (%) | REGEN-COV (1200 mg SC) n/N (%) | Odds ratio | 95% confidence interval |
|---|---|---|---|---|
| PCR+ All Infections (all swab types) | 23/223 (10.3%) | 10/186 (5.4%) | 0.49 | 0.20, 1.12 |
| PCR+ All Infections (NP swab only) | 21/212 (9.9%) | 9/179 (5.0%) | ND | ND |
| 'Broad term' Symptomatic infections | 8/223 (3.6%) | 0/186 (0%) | 0.00 | 0.00, 0.69 |
| 'CDC term' Symptomatic infections | 7/223 (3.1%) | 0/186 (0%) | ND | ND |
| 'Strict term' Symptomatic infections | 5/223 (2.2%) | 0/186 (0%) | ND | ND |
| High virus PCR+ (>$10^6$ copies/mL) | 12/212 (5.7%) | 0/179 (0%) | 0.00 | 0.00, 0.41 |
| High virus PCR+ (>$10^4$ copies/mL) | 13/212 (6.1%) | 0/179 (0%) | 0.00 | 0.00, 0.37 |
| High virus PCR+ (>$10^3$ copies/mL) | 19/212 (9.0%) | 8/179 (4.5%) | 0.48 | 0.18, 1.17 |

ND: Not determined

The lower number of infections occurring with REGEN-COV™ therapy were all asymptomatic, with decreased peak virus levels and short duration of viral shedding.

Infections occurring in the placebo group had, on average, more than 100-fold higher peak viral load.

Infections in the REGEN-COV™ group lasted no more than 1 week, while approximately 40% of infections in the placebo group lasted 3-4 weeks (FIG. 30).

No infections in the REGEN-COV™ group had high viral loads (>10^4 copies/mL) compared to 62% in the infected placebo group (13/21 placebo vs. 0/9 REGEN-COV™).

REGEN-COV™ was associated with a reduction of overall infections and complete elimination of high viral load infections (>$10^4$) in evaluable subjects Level of RT-qPCR at the time of infection decreased between placebo and REGEN-COV™ groups (Table 10, below).

TABLE 10

Level of RT-qPCT

| Level of RT-qPCR at time of infection (only from NP swab available subjects) | Placebo n/N (%) | REGEN-COV (1200 mg SC) n/N (%) |
|---|---|---|
| qPCR (All) | 21/212 (9.9%) | 9/179 (5.0%) |
| qPCR >$10^3$ | 19/212 (9.0%) | 8/179 (4.5%) |
| qPCR >$10^4$ | 13/212 (6.1%) | 0/179 (0%) |
| qPCR >$10^5$ | 12/212 (5.7%) | 0/179 (0%) |

REGEN-COV™ was associated with lower disease burden:
  Fewer total viral shedding weeks (44 weeks placebo vs. 9 weeks REGEN-COV™)
  Fewer total high viral shedding weeks (>10^4 copies/mL) (22 weeks placebo vs. 0 weeks REGEN-COV™)
  Fewer total symptomatic weeks (21 weeks placebo vs. 0 weeks REGEN-COV™).
REGEN-COV™ was well tolerated, with a similar proportion of participants experiencing at least one serious adverse event: placebo, 4/286 and REGEN-COV™, 3/267. None were deemed related to study treatment. Injection site reactions were similar: placebo, 1.4%; REGEN-COV™, 2.6%.

Among the first 409 participants, approximately 49% were Hispanic and 13% were African American. On average, participants were 43 years of age, approximately 46% were male and 54% were female.

Results: Phase 3 Prevention Trial (2069A)—this trial showed 81.4% reduced risk of symptomatic SARS-CoV-2 infections with subcutaneous administration of REGEN-COV™ (casirivimab with imdevimab) (FIG. 72). REGEN-COV had rapid onset, with 72% protection against symptomatic infections in the first week, rising to 93% in subsequent weeks. Among individuals who still experienced symptomatic infections, those who received REGEN-COV cleared the virus more rapidly and had markedly shorter symptom duration (93.1% reduction in the total number of weeks with symptoms with REGEN-COV, corresponding to a 2-week reduction in mean duration of symptoms per symptomatic infection participant). Relative reduction in the risk of any infection (symptomatic or asymptomatic) with REGEN-COV was 66.4%, and there was an 82.3% reduction in the total number of weeks of any infection with REGEN-COV, corresponding to an approximate 1-week reduction per infected participant in mean duration of any infection. Relative reduction in the risk of incidence of high viral load infection with REGEN-COV was 85.8%. There was an 89.6% reduction in the total number of weeks of high viral load infection with REGEN-COV, corresponding to an approximate 6-day mean reduction per infected participant in duration of high viral load infection.

This trial met its primary and key secondary endpoints, showing that REGEN-COV reduced the risk of symptomatic infections by 81% in those who were not infected when they entered the trial. In particular, the phase 3, double-blind, placebo-controlled trial assessed the effect of REGEN-COV on individuals without any COVID-19 symptoms who lived in the same household as an individual who tested positive to SARS-CoV-2 within the prior 4 days. It included 1,505 people who were not infected with SARS-CoV-2 at baseline and received either 1 dose of REGEN-COV (1,200 mg) or placebo, administered as subcutaneous injections The data suggest that REGEN-COV, which retains its potency against emerging COVID-19 variants, can complement widespread vaccination strategies, particularly for those at high risk of infection. Despite standard precautions to reduce transmission, nearly 10% of those living with an infected individual developed symptomatic infections if they did not receive REGEN-COV. Convenient subcutaneous administration of REGEN-COV could help control outbreaks in high-risk settings where individuals have not yet been vaccinated, including individual households and group living settings. Moreover, there remain significant numbers of people who have not been vaccinated and will need immediate protection because of a high-risk exposure, where traditional vaccines cannot be employed at such a late stage. The data presented in this study show that REGEN-COV could be extremely effective in this setting. In addition, there will be many individuals who may not respond to vaccines, such as those who are immunocompromised, including those with and receiving treatment for solid organ transplants, and certain cancers and immune diseases. The rapid protection of REGEN-COV, together with the possibility that it can be used for chronic prophylaxis, may provide an important solution in this setting as well.

TABLE 11

Summary: Key Results from Phase 3 Prevention Trial in Symptomatic SARS-CoV-2 Infections[1]

| | REGEN-COV (single 1,200 mg dose) n = 753 | Placebo n = 752 |
|---|---|---|
| Risk of symptomatic SARS-CoV-2 infections Through day 29 (primary endpoint) | | |
| Risk reduction | 81% (p <0.0001) | |
| # of patients with events | 11 (2%) | 59 (9%) |
| Within 1 week | | |
| Risk reduction | 72% (p = 0.0002) | |
| # of patients with events | 9 (1.2%) | 32 (4.3%) |
| Post-1 week | | |
| Risk reduction | 93% (p <0.0001) | |
| #of patients with events | 2 (0.3%) | 27 (3.6%) |
| Symptoms and viral load | | |
| Total weeks with symptoms | | |
| Risk reduction | 93% (p <0.0001) | |
| Total # of weeks | 13 | 188 |
| # of weeks with symptoms (average) in symptomatic individuals | 1 | 3 |
| Total weeks with high viral load (>$10^4$ copies/mL) | | |
| Risk reduction | 90% (p <0.0001) | |
| Total # of weeks | 14 | 136 |
| # of weeks with high viral load (average) in qPCR positive subjects | 0.4 | 1.3 |

[1]Based on the seronegative modified Full Analysis Set population, which includes all randomized subjects with a negative SARS-CoV-2 RT-qPCR test and with a negative SARS-CoV-2 antibody test at randomization

TABLE 12

Detailed primary and key secondary efficacy endpoints*

| | Placebo (n = 752) | REGEN-COV 1200 mg SC (n = 753) |
|---|---|---|
| Proportion of participants who have a symptomatic RT-qPCR-confirmed SARS-CoV-2 infection (broad-term)† | | |
| n/N (%) | 59/752 (7.8) | 11/753 (1.5) |
| Relative risk reduction | — | 81.4% |
| Odds ratio (95% CI) | — | 0.17 (0.09, 0.33) |
| P-value¶ | — | <0.0001 |
| Proportion of participants with viral load >$10^4$ copies/mL‡ | | |
| n/N (%) | 85/749 (11.3) | 12/745 (1.6) |
| Relative risk reduction | — | 85.8% |
| Odds ratio (95% CI) | — | 0.13 (0.07, 0.24) |
| P-value¶ | — | <0.0001 |
| Number of weeks of symptomatic RT-qPCR-confirmed SARS-CoV-2 infection (broad-term) | | |
| Total number of weeks | 187.7 | 12.9 |
| Total duration (weeks) per 1000 participants | 249.6 | 17.1 |
| Reduction‖ | — | 93.1% |
| P-value§ | — | <0.0001 |
| Per-symptomatic participant duration of symptomatic infection, mean (SD), weeks | 3.2 (2.68) | 1.2 (0.99) |
| Number of weeks of high viral load (>$10^4$ copies/mL)‡ | | |
| Total number of weeks | 136.0 | 14.0 |
| Total duration (weeks) of per 1000 participants | 181.6 | 18.8 |
| Reduction‖ | — | 89.6% |
| P-value§ | — | <0.0001 |
| Per-infected participant duration of high viral load, mean (SD), weeks | 1.3 (0.87) | 0.4 (0.60) |
| Number of weeks of any RT-qPCR-confirmed SARS-CoV-2 infection (symptomatic or asymptomatic) | | |
| Total number of weeks | 231.0 | 41.0 |
| Total duration (weeks) per 1000 participants | 307.2 | 54.4 |
| Reduction‖ | — | 82.3% |
| P-value | — | <0.0001 |
| Per-infected participant duration of any infection, mean (SD), weeks | 2.2 (1.07) | 1.1 (0.42) |
| Proportion of participants who have of any RT-qPCR-confirmed SARS-CoV-2 infection (symptomatic or asymptomatic) | | |
| n/N (%) | 107/752 (14.2) | 36/753 (4.8) |
| Relative risk reduction | — | 66.4% |
| Odds ratio (95% CI) | — | 0.31 (0.21, 0.46) |
| P-value | — | <0.0001 |

*Key secondary endpoints and are presented in order of the hierarchy testing sequence †Primary endpoint ‡For viral load endpoints n = 749 (placebo) and n = 745 (REGEN-COV 1200 mg SC).

§Based on a stratified Wilcoxon rank sum test (Van Elteren test) with region (US vs ex-US) and age group (12 to <50 vs ≥50 years) as strata.

‖Based on the normalized weeks per 1000 participants.

SC, subcutaneous;

SD, standard deviation.

Adverse events (AEs) occurred in 20% (n=265) of REGEN-COV participants and 29% (n=379) of placebo participants, and serious AEs occurred in 1% (n=10) of REGEN-COV participants and 1% (n=15) of placebo participants. There were 0 REGEN-COV participants and 4 placebo participants who experienced COVID-19 hospitalizations or emergency room visits. No individuals from either group withdrew from the trial due to AEs, and none of the deaths in the trial (2 REGEN-COV, 2 placebo) were attributed to COVID-19 or study drug.

TABLE 13

Treatment-emergent adverse events occurring in ≥2% of participants in the overall study period

| Preferred Term, n (%) | Placebo (n = 1306) | REGEN-COV 1200 mg Sc (n = 1311) |
|---|---|---|
| COVID-19 | 112 (8.6) | 15 (1.1) |
| Asymptomatic COVID-19 | 108 (8.3) | 54 (4.1) |
| Headache | 46 (3.5) | 24 (1.8) |
| Injection site reaction | 19 (1.5) | 55 (4.2) |

SC, subcutaneous.

To qualify for the REGEN-COV joint Regeneron/NIAID program, all participants entered the program without any COVID-19 symptoms (asymptomatic) and lived in the same household as an individual who tested positive to SARS-CoV-2 within the prior 4 days. All participants were tested for SARS-CoV-2 at baseline using a RT-qPCR test from nasopharyngeal swabs. Participants with a negative test result joined the Phase 3 prevention trial (2069A) and participants with a positive test result joined the Phase 3 treatment trial (2069B), discussed below.

All participants were then randomized (1:1) to receive either 1 dose of REGEN-COV (1,200 mg) or placebo, administered via 4 SC injections. Among participants enrolled in the trial, 31% were Latino/Hispanic and 9% were Black/African American. In total, 31% of participants had at least one known factor that put them at high risk of suffering severe consequences from COVID-19, as defined in the REGEN-COV fact sheet. In addition, 33% were obese and 38% were aged ≥50 years (median age: 43 years; range: 12-92 years).

Expanded Results: Phase 3 Treatment Trial in Recently Infected Asymptomatic Patients (2069B)—this trial showed significantly reduced progression to symptomatic COVID-19. The results of this second phase 3 assessed recently infected asymptomatic patients, evaluating REGEN-COV™ (casirivimab with imdevimab) 1,200 mg administered via subcutaneous (SC) administration. REGEN-COV reduced the overall risk of progressing to symptomatic COVID-19 by 31% (primary endpoint), and by 75% after the third day. The trial also demonstrated that REGEN-COV shortened symptom duration and markedly reduced viral levels. This trial was jointly run with the National Institute of Allergy and Infectious Diseases (NIAID), part of the National Institutes of Health (NIH). The trial enrolled 207 individuals without any COVID-19 symptoms who tested positive to SARS-CoV-2 at baseline, and were randomized to receive either 1 dose of REGEN-COV (1,200 mg) or placebo.

Because COVID-19 transmission often occurs in people who do not yet have symptoms, the results of this study demonstrated that REGEN-COV can be used in such patients with a more convenient subcutaneous administration.

This second phase 3 trial met all primary and key secondary endpoints. In addition to reducing the risk of symptomatic infections, the total number of weeks patients experienced symptoms was nearly cut in half (45%) with REGEN-COV, and the viral burden was reduced by more than 90%. Researchers also found that no participants who received REGEN-COV required COVID-19 related hospitalizations or visits to the emergency room, compared to 6 in the placebo group. Treatment with REGEN-COV 1200 mg subcutaneous (SC) resulted in a 31.5% relative risk reduction in progression from asymptomatic to symptomatic infection during the efficacy assessment period (29/100 [29.0%] vs 44/104 [42.3%] for placebo; p=0.0380), with a more pronounced effect 3 days or longer following REGEN-COV administration (76.4% relative risk reduction) (FIG. 73). Among the 73 household contacts who developed a symptomatic infection, the number of weeks with symptoms was reduced 45.3% (per 1000 participants) with REGEN-COV vs placebo; this corresponded to an approximate 1-week reduction in mean number of weeks of symptoms per symptomatic participant. There was a 39.7% reduction in the number of weeks of high viral load, which equated to an approximately 2-day reduction per participant. A higher proportion of participants in the placebo group had ≥1 treatment-emergent adverse event vs participants in the REGEN-COV group, consistent with the higher number of COVID-19-related events in those receiving placebo.

The data built on the results discussed in Examples 2 and 7 in non-hospitalized COVID-19 patients. The phase 3 outcomes trial in high-risk symptomatic outpatients showed that REGEN-COV (2,400 mg and 1,200 mg administered intravenously [IV]) reduced hospitalization or death by 70% (Example 2). The Phase 2 virology trial in low-risk outpatients showed that all REGEN-COV doses studied had similar efficacy in rapidly reducing viral load (IV: 2,400 mg, 1,200 mg, 600 mg and 300 mg; SC: 1,200 mg and 600 mg) (Example 7).

These Phase 3 data provide even more evidence that REGEN-COV, this time given to asymptomatic patients via convenient injections, can change the course of COVID-19 infection in non-hospitalized patients, and prevent asymptomatic patients from becoming symptomatic, and rapidly lower their viral load.

TABLE 14

Summary of Primary and Key Secondary Efficacy Endpoints

| | Placebo (N = 104) | REGEN-COV 1200 mg SC (N = 100) |
|---|---|---|
| Participants who subsequently develop signs and symptoms (broad-term) within 14 days of a positive RT-qPCR at baseline or during the EAP* | | |
| n (%) | 44 (42.3) | 29 (29.0) |
| Relative risk reduction (total) | — | 31.4% |
| Odds ratio (95% CI) | — | 0.54 (0.30 to 0.97) |
| P value† | — | 0.0380 |

TABLE 14-continued

Summary of Primary and Key Secondary Efficacy Endpoints

|  | Placebo (N = 104) | REGEN-COV 1200 mg SC (N = 100) |
|---|---|---|
| Relative risk reduction after day 3 (days 4-29 only) [O] | — | 75% |
| P value† | — | 0.0014 |
| n (%) | 5 (7%) | 22 (27%) |
| Number of weeks of symptomatic SARS-CoV-2 infection (broad-term) within 14 days of a positive RT-qPCR at baseline or during the EAP‡ | | |
| Total weeks | 170.3 | 89.6 |
| Total weeks per 1000 participants | 1637.4 | 895.7 |
| Reduction | — | 45.3% |
| P value§ | — | 0.0273 |
| Weeks per symptomatic participant, mean (SD) | 3.9 (4.5) | 3.1 (4.1) |
| Weeks per participant, mean (SD) | 1.6 (3.5) | 0.9 (2.6) |
| Number of weeks of high viral load (>4 $\log_{10}$ copies/mL) in NP swab samples during the EAP‡ | | |
| Total weeks | 82 | 48 |
| Total weeks per 1000 participants | 811.9 | 489.8 |
| Reduction | — | 39.7% |
| P value§ | — | 0.0010 |
| Weeks per participant, mean (SD) | 0.8 (0.8) | 0.5 (0.7) |
| COVID-19 related hospitalizations or emergency room visits[X] | | |
| Risk Reduction | — | 100% |
| Nominal p value | — | 0.029 |
| Number of patients with events (%) | 0 (0%) | 6 (6%) |

\* Primary endpoint.
†Based on logistic regression model adjusted by region (US vs ex-US) and age group (12 to <50 vs ≥50 years of age).
‡Key secondary endpoints, presented in order of the hierarchical testing sequence.
§Based on stratified Wilcoxon rank sum test (van Elteren test) with region (US vs ex-US) and age group (12 to <50 vs ≥50 years of age) as strata.
CI, confidence interval;
EAP, efficacy assessment period;
NP, nasopharyngeal;
RT-qPCR, quantitative reverse transcription polymerase chain reaction;
SC, subcutaneous,
SD, standard deviation.
[O] Does not include results from days 1-3, when events were similar between treatment groups
[X] Not part of statistical hierarchy, so p-value is nominal Adverse events (AEs) occurred in 33% (n=52) of REGEN-COV patients and 48% (n=75) of placebo patients, and serious AEs occurred in 0% (n=0) of REGEN-COV patients and 3% (n=4) of placebo patients. No patients from either group withdrew from the trial due to AEs, and there were no deaths.

TABLE 15

Overview of Treatment-Emergent Adverse Events During the Overall Study Period

| n (%) | Placebo (N = 156) | REGEN-COV 1200 mg SC (N = 155) |
|---|---|---|
| TEAEs | 109 | 67 |
| TEAEs not related to COVID-19 | 42 | 26 |
| Grade ≥3 TEAE | 5 | 1 |
| Serious TEAEs | 4 | 0 |
| AESIs* | 0 | 0 |
| TEAEs resulting in study drug withdrawal | 0 | 0 |
| TEAEs resulting in death | 0 | 0 |
| Participants with ≥1 TEAE | 75 (48.1) | 52 (33.5) |
| Participants with ≥1 TEAEs not related to COVID-19 | 25 (16.0) | 17 (11.0) |
| Participants with ≥1 grade ≥3 TEAE | 4 (2.6) | 1 (0.6) |
| Participants with ≥1 serious TEAE | 4 (2.6) | 0 |

TABLE 15-continued

Overview of Treatment-Emergent Adverse Events During the Overall Study Period

| n (%) | Placebo (N = 156) | REGEN-COV 1200 mg SC (N = 155) |
|---|---|---|
| Participants with ≥1 AESI* | 0 | 0 |
| Participants with ≥1 TEAE resulting in study drug withdrawal | 0 | 0 |
| Participants with ≥1 TEAE resulting in death | 0 | 0 |

*Grade ≥3 injection site reaction or hypersensitivity reaction.
AESI, adverse events of special interest;
SC, subcutaneous;
TEAE, treatment-emergent adverse events.

To qualify for this clinical trial, all participants entered the program without any COVID-19 symptoms (asymptomatic) and lived in the same household as an individual who tested positive to SARS-CoV-2 within the prior 4 days. All participants were tested for SARS-CoV-2 at baseline using a RT-qPCR test from nasopharyngeal swabs. Participants with a negative test result joined the Phase 3 prevention trial (2069A), discussed above, and participants with a positive test result joined the Phase 3 treatment trial (2069B).

All participants were then randomized (1:1) to receive either 1 dose of REGEN-COV (1,200 mg) or placebo, administered via 4 SC injections. Among participants enrolled in the trial, 35% were Latino/Hispanic and 5% were Black/African American. In total, 32% had at least 1 known factor that put them at high risk of suffering severe consequences from COVID-19, as defined in the REGEN-COV fact sheet. In addition, 32% were obese and 34% were aged ≥50 years (median age: 41 years; range: 12-87 years).

The results of these two phase 3 trials (2069A and 2069B) is also illustrated in FIG. 59, FIG. 60, FIG. 61, FIG. 62, FIG. 63, FIG. 64, FIG. 65, FIG. 66, FIG. 67, FIG. 68, FIG. 69, FIG. 70, and FIG. 71.

Example 5. Efficacy of Anti-SARS-CoV-2 Spike Glycoprotein Antibodies in SARS-CoV-2 Infected Rhesus Macaques and Golden Hamsters As the animal models of COVID-19 are still being actively developed, no single model has emerged as being more relevant for human disease. Indeed, based on the diverse manifestations of COVID-19 in humans, multiple animal models may be needed to mimic various settings of human SARS-CoV-2 infection. In the following studies, two different models that capture diverse pathology of SARS-CoV-2 infection were used. The rhesus macaque model is widely used to assess efficacy of therapeutics and vaccines and displays a transient mild course of the disease. On the contrary, the golden hamster model manifests a much more severe form of the disease, accompanied by severe lung pathology. Assessment of the efficacy of anti-SARS-CoV-2 spike glycoprotein antibodies in both of these models allows for comparative performance of the antibodies in diverse disease settings to more comprehensively understand the mechanisms by which antibody therapies may limit viral load and pathology in infected individuals.

In the studies discussed in this example, the anti-SARS-CoV-2 spike glycoprotein antibodies administered to the animals was a combination therapeutic composed of two potent neutralizing antibodies (mAb10987+mAb10933) targeting non-overlapping residues on the SARS-CoV-2 spike protein, and the following assays and procedures were used:

(I) Quantitative RT-PCR Assay for SARS-CoV-2 RNA. The amounts of RNA copies per mL bodily fluid or per gram tissue were determined using a qRT-PCR assay. The qRT-PCR assay utilized primers and a probe specifically designed to amplify and bind to a conserved region of nucleocapsid gene of coronavirus. The signal was compared to a known standard curve and calculated to give copies per mL. For the qRT-PCR assay, viral RNA was first isolated from nasal wash using the Qiagen MinElute virus spin kit (cat. no. 57704). For tissues it was extracted with RNA-STAT 60 (Tel-test"B")/chloroform, precipitated and resuspended in RNAse-free water. To generate a control for the amplification reaction, RNA was isolated from the applicable SARS-CoV-2 stock using the same procedure. qPCR assay was performed with Applied Biosystems 7500 Sequence detector and amplified using the following program: 48° C. for 30 minutes, 95° C. for 10 minutes followed by 40 cycles of 95° C. for 15 seconds, and 1 minute at 55° C. The number of copies of RNA per mL was calculated by extrapolation from the standard curve and multiplying by the reciprocal of 0.2 mL extraction volume. This gave a practical range of 50 to $5\times10^8$ RNA copies per mL for nasal washes or per gram of tissue. Primers/probe sequences:

```
2019-nCoV_N1-F:
                                       (SEQ ID NO: 63)
5'-GAC CCC AAA ATC AGC GAA AT-3'

2019-nCoV_N1-R:
                                       (SEQ ID NO: 64)
5'-TCT GGT TAC TGC CAG TTG AAT CTG-3'

2019-nCoV_N1-P:
                                       (SEQ ID NO: 65)
5'-FAM-ACC CCG CAT TAC GTT TGG TGG ACC-BHQ1-3'.
```

(II) Quantitative RT-PCR Assay for SARS-CoV-2 subgenomic RNA. SARS-CoV-2 E gene subgenomic mRNA (sgRNA or sgmRNA) was assessed by RT-PCR using primers and probes known in the art. Briefly, to generate a standard curve, the SARS-CoV-2 E gene sgRNA was cloned into a pcDNA3.1 expression plasmid; this insert was transcribed using an AmpliCap-Max T7 High Yield Message-Maker Kit (Cellscript) to obtain RNA for standards. Prior to RT-PCR, samples collected from challenged animals or standards were reverse-transcribed using Superscript III VILO (Invitrogen) according to the manufacturer's instructions. A Taqman custom gene expression assay (ThermoFisher Scientific) was designed using the sequences targeting the E gene sgRNA20. Reactions were carried out on a QuantStudio 6 and 7 Flex Real-Time PCR System (Applied Biosystems) according to the manufacturer's specifications. Standard curves were used to calculate sgRNA in copies per ml or per swab; the quantitative assay sensitivity was 50 copies per ml or per swab. This gave a practical range of 50 to 5×10^7 RNA copies per mL for nasal washes, and for tissues the viral loads are given per gram. Subgenomic RNA Primers:

```
SG-F:
                                      (SEQ ID NO: 66)
CGATCTTGTAGATCTGTTCCTCAAACGAAC

SG-R:
                                      (SEQ ID NO: 67)
ATATTGCAGCAGTACGCACACACA

PROBE:
                                      (SEQ ID NO: 68)
FAM-ACACTAGCCATCCTTACTGCGCTTCG-BHQ
```

(III) Cells and Virus. Vero E6 cells (VERO C1008, catalog number NR-596, BEI resources) were grown in Dulbecco's modified essential media (DMEM; Gibco) with 10% heat-inactivated fetal bovine serum (FBS; Gibco) at 37° C. with 5% $CO_2$. SARS-CoV-2 isolate USA-WA1/2020 (BEI resources NR-52281, GenBank accession number MN985325.1) was used to generate the animal exposure stock. A fourth cell-culture passage (P4) of SARS-CoV-2 was obtained and propagated. The fourth cell-culture passage (P4) stock virus obtained from BEI was passaged one time to generate a master stock by infecting Vero E6 cells at a multiplicity of infection (MOI) of approximately 0.001 in DMEM containing 2% FBS; viral supernatant was harvested at 3 days post infection. The P5 stock was used to generate the exposure stock by infecting Vero E6 cells at an MOI of 0.02 in DMEM containing 2% FBS; viral supernatant was harvested at three days post infection. The stock has been confirmed to be SARS-CoV-2 via deep sequencing and confirmed to be free of adventitious agents. The viral titer was determined to be $2.1 \times 10^6$ PFU/mL.

(IV) RNA extraction for viral load determination via RT-qPCR. Samples were inactivated using TRIzol LS Isolation Reagent (Invitrogen): 250 μL of test sample were mixed with 750 μL TRIzol LS. Inactivation controls were prepared with each batch of samples. Prior to extraction, $1 \times 10^3$ pfu of MS2 phage (*Escherichia coli* bacteriophage MS2, ATCC) was added to each sample to assess extraction efficiency RNA extraction was performed using the EpMotion M5073c Liquid Handler (Eppendorf) and the Nucleo-Mag Pathogen kit (Macherey-Nagel). Extraction controls were prepared with each batch of samples. After processing, the presence of the eluate was confirmed and the extracted RNA was stored at −80° C.±10° C.

(V) Determination of Viral load via RT-qPCR. 5 μL RNA samples were used in duplex RT-qPCR reactions detecting both SARS-CoV-2 and MS2 phage. Two assays were used to assess SARS-CoV-2 present in the samples. The CDC-developed 2019-nCoV_N1 assay was used to target a region of the N gene. SARS-CoV-2_N1 probe (ACCCCGCAT-TACGTTTGGTGGACC; SEQ ID NO: 69) was labeled with 6-FAM fluorescent dye. The forward primer sequence used was: GACCCCAAAATCAGCGAAAT (SEQ ID NO: 63), and the reverse primer sequence used was: TCTGGT-TACTGCCAGTTGAATCTG (SEQ ID NO: 64). A secondary qPCR assay to measure subgenomic RNA was also performed to target a region of the E (Envelope) gene.

The probe was also labeled with 6-FAM fluorescent dye (ACACTAGCCATCCTTACTGCGCTTCG; SEQ ID NO: 68). The forward primer sequence was: CGATCTCTTGTA-GATCTGTTCTC (SEQ ID NO: 70), and the reverse primer sequence was: ATATTGCAGCAGTACGCACACA (SEQ ID NO: 71). The MS2 probe was labeled with VIC fluorescent dye. Both assays used the TaqPath™ 1-Step RT-qPCR Master Mix, CG (ThermoFisher) and were performed on a QuantStudio 3 instrument (Applied Biosystems). QuantStudio Design and Analysis Software (Applied Biosystems) was used to run and analyze the results. Cycling parameters were set as follows: Hold stage 2 min at 25° C., 15 min at 50° C., 2 min at 95° C. PCR stage: 45 cycles (N1 assay) or 40 cycles (E assay) of 3 sec at 95° C., 30 sec at 60° C. The average Ct value for MS2 phage was calculated for all processed samples and SARS-CoV-2 quantification only performed in samples in which the MS2 Ct value was lower than Average MS2+5%.

(VI) Histopathology. Necropsies were conducted and selected tissue samples (tracheobronchial lymph node, nasal cavity, trachea, heart, liver, spleen, kidney, and all 4 right lung lobes) were collected. Tissues were fixed by immersion in 10% neutral-buffered formalin for a minimum of fourteen days, then trimmed, routinely processed, and embedded in paraffin. Sections of the paraffin-embedded tissues were cut at 5 μm thick, and histology slides were deparaffinized, stained with hematoxylin and eosin (H&E), cover slipped, and labeled. Slides were blindly evaluated by a board-certified veterinary pathologist.

(VII) Virus RNA Sequencing. 10 μl of RNA combined with 25 ng Human Universal Reference RNA (Agilent) was purified by PureBeads (Roche Sequencing). cDNA synthesis was performed using SuperScript™ IV First-Strand Synthesis System (Thermal Fisher) following vendor's protocol. Then one half of cDNA (10 ul) was used to generate libraries using Swift Normalase™ Amplicon Panel (SNAP) SARS-CoV-2 Panel (Swift Biosciences) following vendor's protocol. Sequencing was run on NextSeq (Illumina) by multiplexed paired-read run with 2×150 cycles.

(VIII) RNAseq data analysis. RNAseq analysis was performed using Array Studio software package platform (Omicsoft). Quality of paired-end RNA Illumina reads was assessed using the "raw data QC of RNA-Seq data suite." Minimum and maximum read length, total nucleotide number, and GC % were calculated. Overall quality reports were generated summarizing the quality of all reads in each sample, along each base pair. Swift amplicon bulk RNA-seq reads were aligned to the SARS-COV-2 reference genome Wuhan-Hu-1 (MN908947) using Omicsoft Sequence Aligner (OSA) version 4. The alignments were sorted by read name, and primers were clipped by the complementary Swiftbiosciences primerclip software (v0.3.8). Reads were trimmed by quality score using default parameters (when aligner encountered nucleotide in the read with a quality score of 2 or less, it trimmed the remainder of the read). OSA outputs were analyzed and annotated using Summarize Variant Data and Annotate Variant Data packages (Omicsoft). The rest of the analysis focused on the genome section encoding the Spike protein. Using custom scripts, target coverage was summarized for each sample and SNPs calling was calculated. The frequencies of viral mutations inferred from the sequencing reads were calculated if mutated reads were higher than 1% relative to total number reads.

Figure 1A:
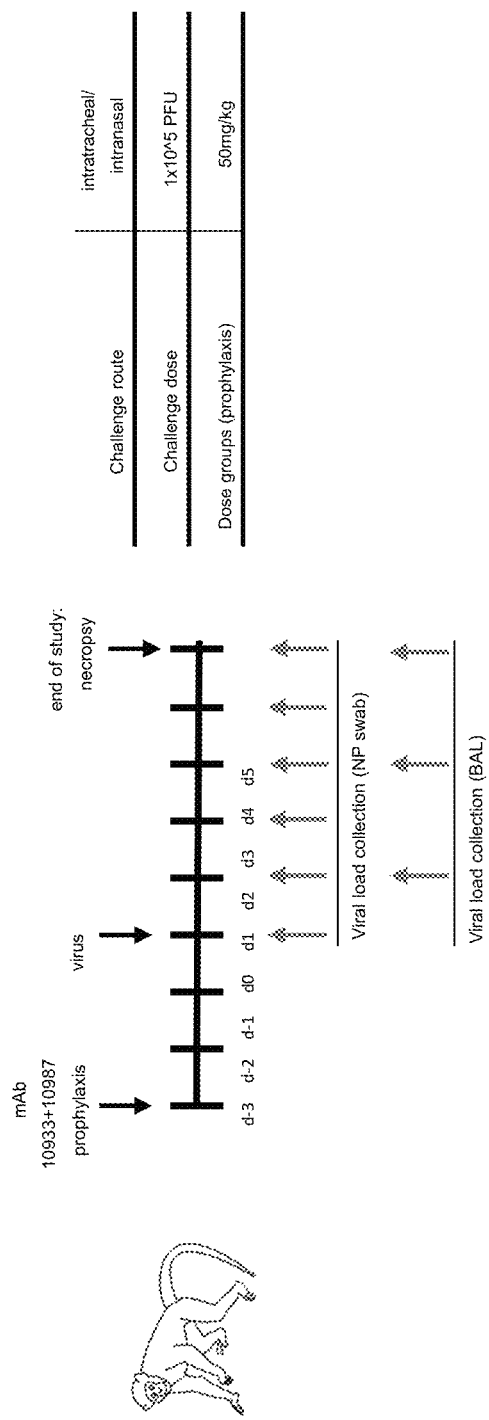
FIG. 1A and FIG. 1B illustrate the overview of a study design evaluating the prophylactic efficacy of anti-SARS-CoV-2 spike glycoprotein antibodies in a rhesus macaque model of SARS-CoV-2 infection (FIG. 1A), and the impact of anti-SARS-CoV-2 spike glycoprotein antibody prophylaxis on viral genomic RNA (gRNA) and subgenomic RNA (sgRNA) in nasopharyngeal swabs and bronchioalveolar lavage (BAL) fluid (FIG. 1B).
Figure 1B:
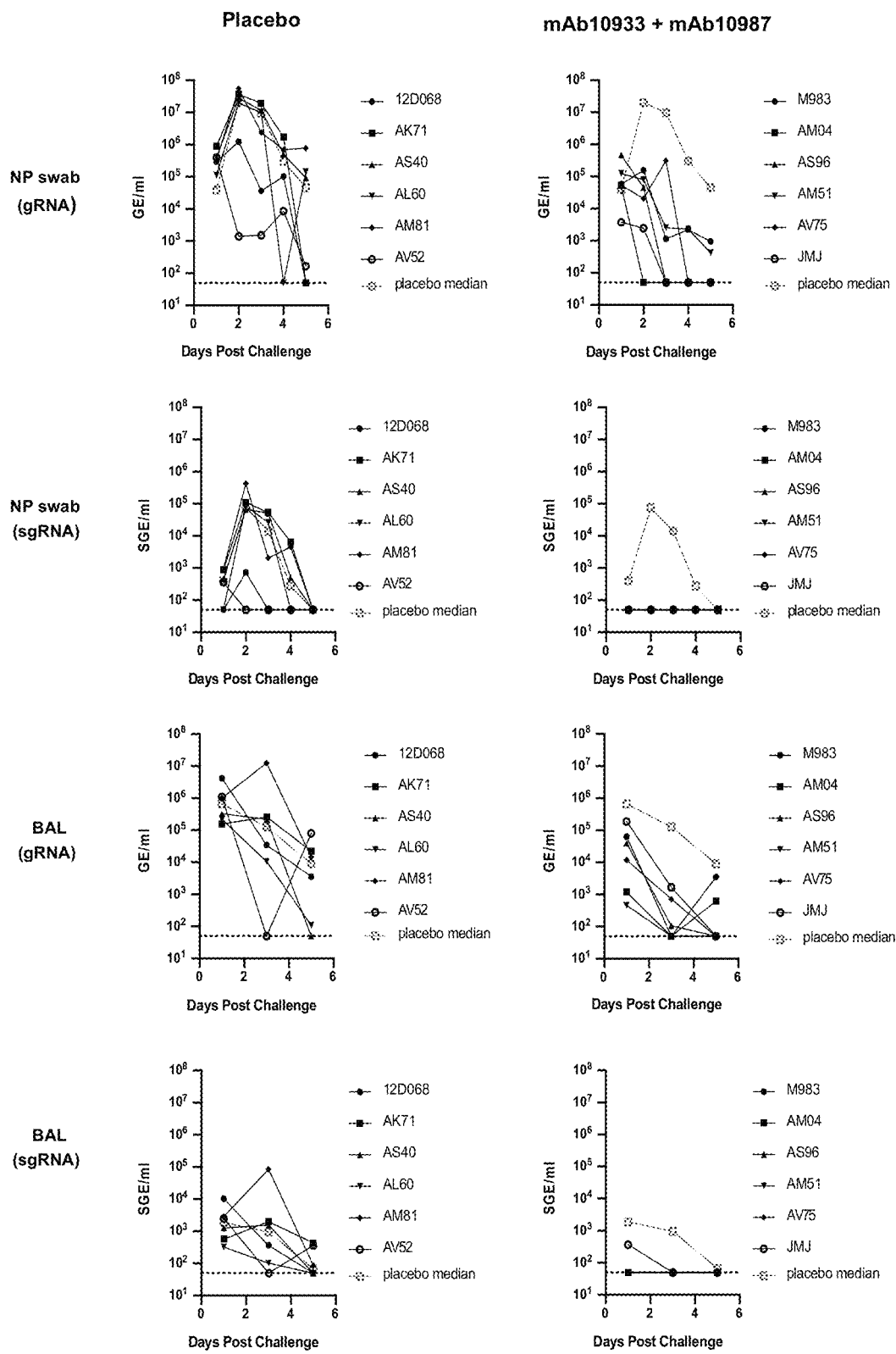

Part A—Efficacy of Anti-SARS-CoV-2 Spike Glycoprotein Antibodies in SARS-CoV-2 Infected Rhesus Macaques To determine the ability of the spike antibodies to protect rhesus macaques from SARS-CoV-2 challenge, the impact of high-dose antibody administration prior to challenge with the virus was assessed. A total of 12 naïve rhesus macaques of Indian origin (purpose bred, *Macaca mulatta*) were used in this study. Animals were distributed to treatment groups based on age distribution. The animals were dosed with 50 mg/kg dose of anti-SARS-CoV-2 spike glycoprotein antibodies through intravenous administration and challenged with 1×10^5 PFU of virus through intranasal and intratracheal routes 3 days post antibody dosing. Due to the relatively transient nature of the SARS-CoV-2 infection in the rhesus macaque model, the in-life portion of the study was limited to 5 days. To determine the impact of antibody prophylaxis on viral load in upper and lower airways, nasopharyngeal swabs were collected on a daily basis as well as Bronchoalveolar lavage (BAL) fluid on days 1, 3, and 5 post-challenge (FIG. 1A). Both genomic and subgenomic RNA were measured to assess the impact of antibody prophylaxis on the dynamics of viral replication. The kinetics of viral replication in placebo treated animals mirrored those previously reported, with peak in viral load on day 2 post-challenge, followed by a rapid decrease, although the majority of animals were still positive for viral RNA in nasal swabs on day 5. Kinetics of sgRNA in nasal swabs and BAL were similar to those of gRNA indicating that both forms of RNA are likely associated with viral replication in this model, although sgRNA levels were significantly lower than gRNA levels with approximately a 2-log difference. In animals that received antibody prophylaxis, a decreased viral load across all measurement, including nasal swabs and BAL, was observed, suggesting that antibodies administered prophylactically can reduce viral load in both upper and lower airways (FIG. 1B). This contrasts with the previously reported impact on viral load in remdesivir treated animals, where reduced viral load could only be observed in lower airways with no differences in nasal viral RNA levels.

Figure 2A:
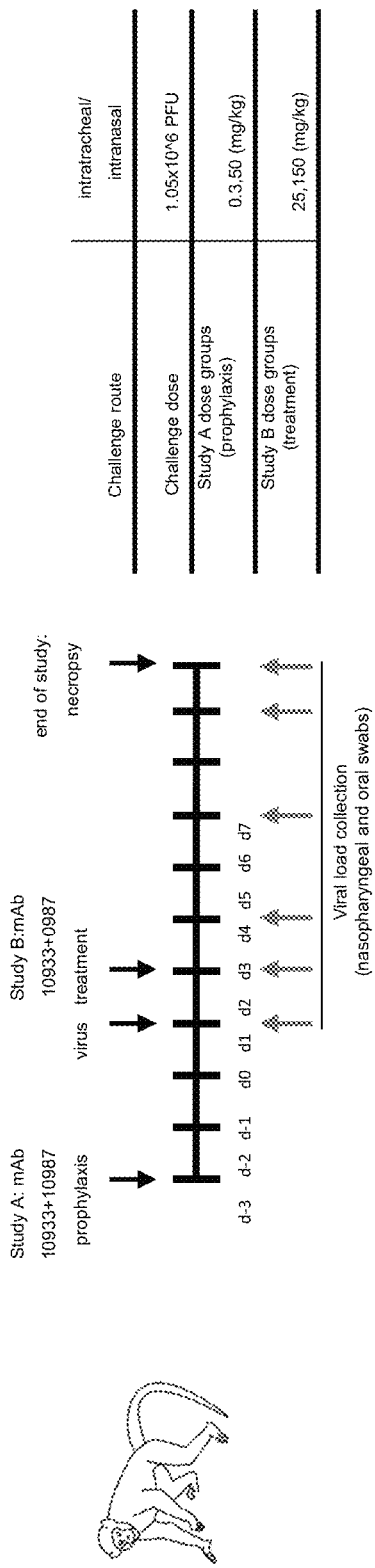
FIG. 2A, FIG. 2B, FIG. 2C and FIG. 2D illustrate the overview of a study design evaluating prophylactic and therapeutic efficacy of anti-SARS-CoV-2 spike glycoprotein antibodies in a rhesus macaque model of SARS-CoV-2 infection (FIG. 2A), the impact of anti-SARS-CoV-2 spike glycoprotein antibody prophylaxis on viral gRNA and sgRNA in nasopharyngeal swabs and oral swabs (FIG. 2B), the impact of anti-SARS-CoV-2 spike glycoprotein antibody treatment on viral gRNA and sgRNA in nasopharyngeal swabs and oral swabs (FIG. 2C), and representative images of histopathology in lungs of treated and placebo animals (FIG. 2D).
Figure 2B:
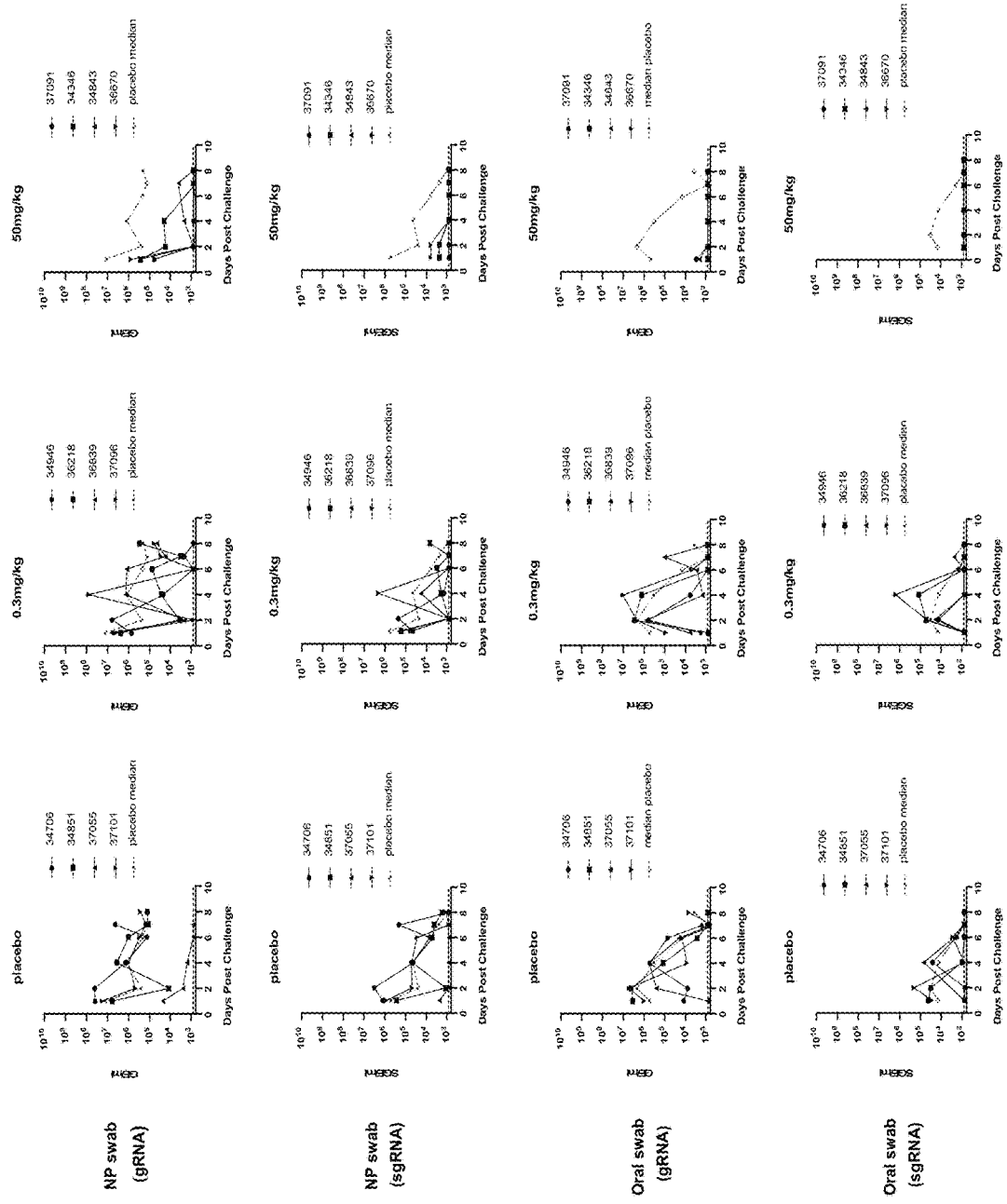

Part B—Efficacy of Anti-SARS-CoV-2 Spike Glycoprotein Antibodies in SARS-CoV-2 Infected Rhesus Macaques and Assessment of Putative Escape Mutants A second prophylaxis study including both a high dose and a low dose group confirmed the ability of high dose anti-SARS-CoV-2 spike glycoprotein antibodies to minimize virus replication even when animals were challenged with a higher dose of virus (1.05×10^6 PFU) (FIG. 2A and FIG. 2B). Twenty-four (24) rhesus macaques (13 female and 11 males) were used in this study, and randomly assigned to one of six groups. Animals were obtained from the Southwest National Primate Research Center (SNPRC) colony and were between 2.5 and 6 years of age and approximately 3 to 10 kg at the time of study enrollment. On Study Day 0, each animal was exposed at an Animal BioSafety Level 4 (ABSL-4) laboratory with a targeted dose of 1.05×10^6 PFU of SARS-CoV-2 in a total volume of 500 µl (5.25×10^5 PFU in 250 µl via intranasal route and 5.25×10^5 PFU in 250 µl via intratracheal route). Intranasal delivery was via a mucosal atomization device (Teleflex Intranasal Mucosal Atomization Device LMA MAD Nasal Device), which allowed for IN delivery of atomized particles 30-100 microns in size, which model droplet transmission. Intratracheal delivery used a Tracheal Mucosal Atomization Device (Teleflex Laryngo-Tracheal Mucosal Atomization Device LMA MADGIC). On Day −3 relative to exposure, prophylactic group animals were sedated and received treatment. On Day 1 (post virus exposure), therapeutic group animals were sedated and received treatment. Treatment was administered via intravenous injection over the course of approximately 90 seconds.

In this study, an increased impact of antibody treatment on viral load in oral swabs versus nasopharyngeal swabs was observed, indicating that antibody treatment may impact multiple physiological sources of virus replication differentially. At a low dose of 0.3 mg/kg, no protective effect of the antibodies was observed, with antibody treated animals displaying similar viral kinetics to placebo animals in both nasal and oral swabs.

Figure 2C:
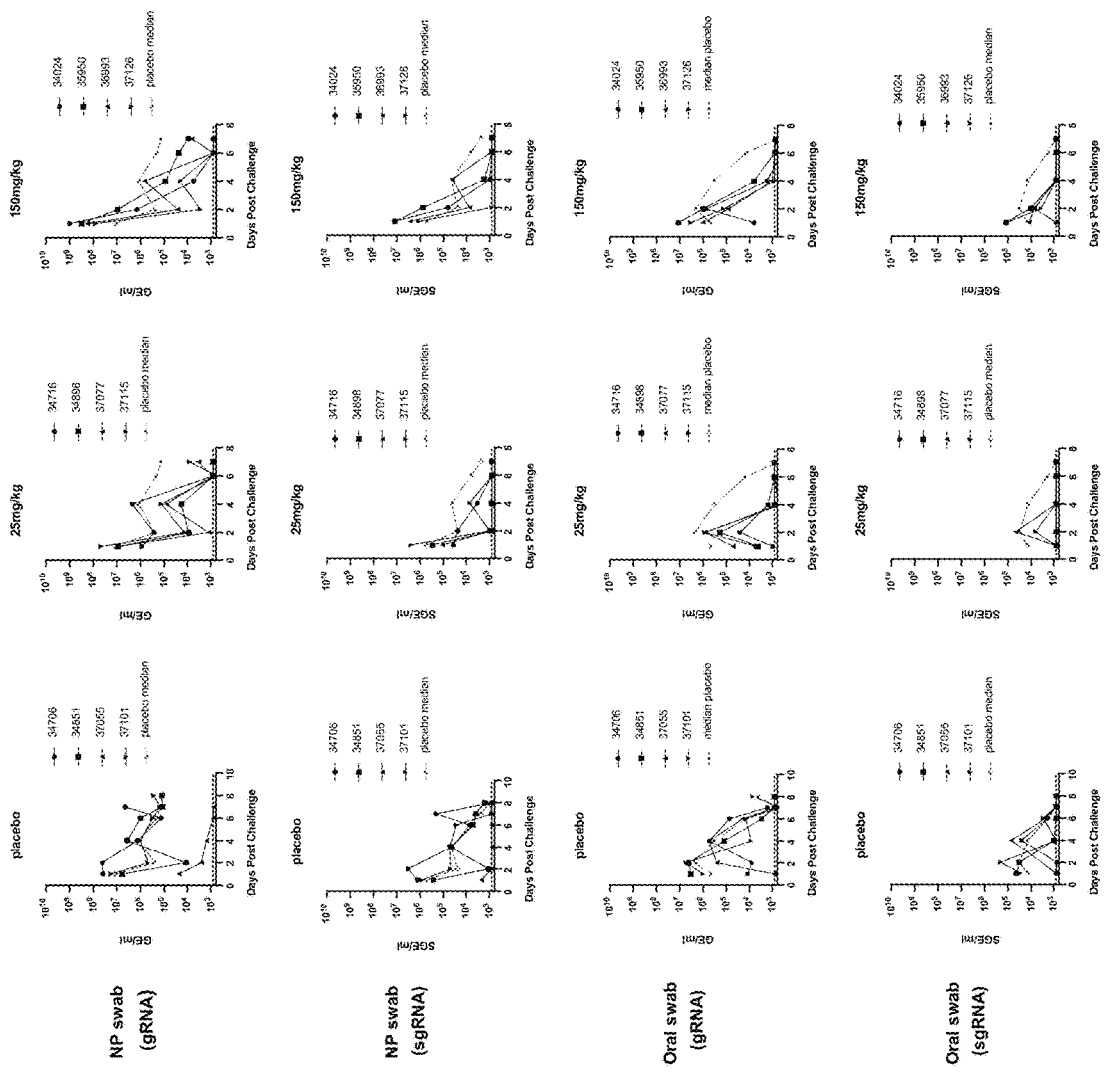

In addition, the impact of anti-SARS-CoV-2 spike glycoprotein antibodies in the treatment setting by dosing animals challenged with 1×10^6 PFU of SARS-CoV-2 virus 1-day post-infection (FIG. 2A) was assessed. By day 1 post-challenge the animals already reached peak viral load as measured by both genomic and subgenomic RNA, mimicking a likely clinical scenario, since it has been shown that most SARS-CoV-2 infected individuals reach peak viral loads relatively early in the disease course and often prior or just at start of symptom onset. Relative to placebo treated animals, anti-SARS-CoV-2 spike glycoprotein antibody-treated animals displayed faster viral clearance in both nasopharyngeal and oral swabs sample, including both genomic and subgenomic RNA samples (FIG. 2C). Similar to the prophylaxis group, the drop in viral load appeared more dramatic in oral swabs versus NP swabs. Due to the small group sizes and higher day 1 viral load in the 150 mg/kg group, no statistical conclusions regarding dose response in this study could be made. The animals in the 150 mg/kg group displayed approximately 1-log higher titers on day 1, at the time of antibody administration, therefore potentially masking enhanced effect of a higher dose of the antibodies. Similar impact of antibody treatment was observed on genomic and subgenomic RNA for both NP and oral samples, indicating that the antibody treatment directly limited viral replication in these animals (FIG. 2C).

Figure 2D:
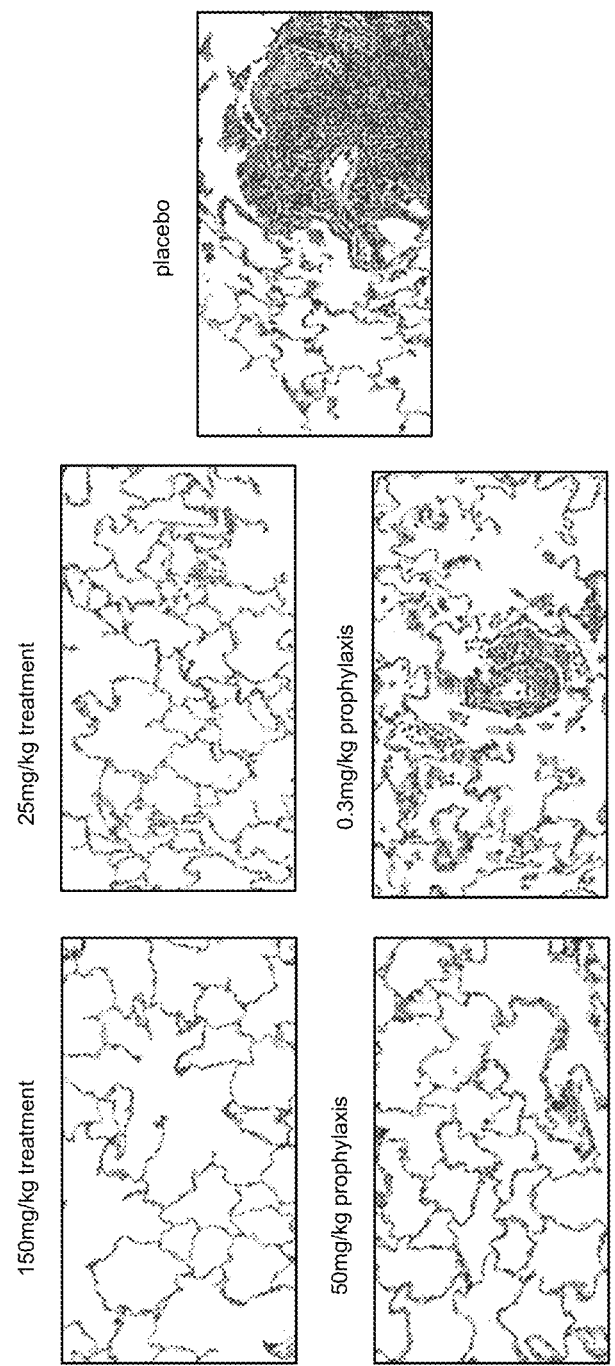

Pathology analyses of lungs of infected animals revealed that all four placebo monkeys showed evidence of lung injury characterized in three monkeys by interstitial pneumonia (FIG. 2D), with minimal to mild infiltration of mononuclear cells (lymphocytes and macrophages) in the septa, perivascular space, and/or pleura. In these three animals, the distribution of lesions was multifocal and involved 2-3 of the 4 lung lobes. Accompanying these changes were alveolar infiltration of lymphocytes, increased alveolar macrophages, and syncytial cells. Type II pneumocyte hyperplasia was also observed in occasional alveoli. In the fourth placebo monkey, lung injury was limited to type II pneumocyte hyperplasia, suggestive of a reparative process secondary to inflammation. Overall, the histological lesions observed in the placebo animals were consistent with an acute SARS-CoV-2 infection.

In the prophylactic groups, 3 of 4 animals in the low-dose combo and 1 of 4 animals in the high-dose combo groups showed evidence of interstitial pneumonia (Table 16) that was generally minimal and with fewer histological features compared to the placebo group. In the one affected high-dose combo animal, only 1 of the 4 lung lobes had a minimal lesion. In the therapeutic treatment groups, 2 of 4 low-dose and 2 of 4 high-dose combo animals showed evidence of interstitial pneumonia. In all affected low and high dose animals, only 1 of 4 lung lobes had lesions. The incidence of this interstitial pneumonia (number of animals as well as number of lung lobes affected) and the severity were reduced in both prophylactic and therapeutic treatment modalities, compared to placebo. Table 16, below, shows the pathology scores in individual animals treated with either anti-SARS-CoV-2 spike glycoprotein antibodies or placebo.

TABLE 16

Pathology analysis in rhesus macaque lungs.

| | Prophylaxis | | | | | | | | | | | |
|---|---|---|---|---|---|---|---|---|---|---|---|---|
| Group | placebo | | | | 0.3 mg/kg | | | | 50 mg/kg | | | |
| Animal No. | 1 | 2 | 3 | 4 | 5 | 6 | 7 | 8 | 9 | 10 | 11 | 12 |
| No of lobes examined | 4 | 4 | 4 | 4 | 4 | 4 | 4 | 4 | 4 | 4 | 4 | 4 |
| No of lobes with inflammation | 2 | 1 | 0 | 3 | 2 | 0 | 2 | 3 | 1 | 0 | 0 | 0 |
| Inflammation | | | | | | | | | | | | |
| Septa | 1 | 1 | 0 | 1 | 1 | 0 | 1 | 1 | 1 | 0 | 0 | 0 |
| Alveoli | 1 | 1 | 0 | 1 | 1 | 0 | 1 | 1 | 1 | 0 | 0 | 0 |
| Perivascular | 1 | 1 | 0 | 2 | 1 | 0 | 1 | 0 | 0 | 0 | 0 | 0 |
| Pleura | 0 | 1 | 0 | 1 | 1 | 0 | 1 | 0 | 0 | 0 | 0 | 0 |
| Syncytial cells | 0 | 0 | 0 | 1 | 0 | 0 | 0 | 0 | 1 | 0 | 0 | 0 |
| Hyperplasia, Type II cells | 0 | 1 | 1 | 1 | 0 | 0 | 0 | 1 | 0 | 0 | 0 | 0 |
| Increased alveolar macrophages | 1 | 1 | 1 | 1 | 1 | 1 | 1 | 1 | 0 | 0 | 1 | 1 |

| | Treatment | | | | | | | | | | | |
|---|---|---|---|---|---|---|---|---|---|---|---|---|
| Group | placebo | | | | 25 mg/kg | | | | 150 mg/kg | | | |
| Animal No. | 1 | 2 | 3 | 4 | 5 | 6 | 7 | 8 | 9 | 10 | 11 | 12 |
| No of lobes examined | 4 | 4 | 4 | 4 | 4 | 4 | 4 | 4 | 4 | 4 | 4 | 4 |
| No of lobes with inflammation | 2 | 1 | 0 | 3 | 0 | 1 | 1 | 0 | 1 | 0 | 1 | 0 |
| Inflammation | | | | | | | | | | | | |
| Septa | 1 | 1 | 0 | 1 | 0 | 1 | 1 | 0 | 1 | 0 | 2 | 0 |
| Alveoli | 1 | 1 | 0 | 1 | 0 | 0 | 1 | 0 | 0 | 0 | 1 | 0 |
| Perivascular | 1 | 1 | 0 | 2 | 0 | 0 | 0 | 0 | 0 | 0 | 1 | 0 |
| Pleura | 0 | 1 | 0 | 1 | 0 | 0 | 1 | 0 | 0 | 0 | 1 | 0 |
| Syncytial cells | 0 | 0 | 0 | 1 | 0 | 0 | 1 | 0 | 0 | 0 | 1 | 0 |
| Hyperplasia, Type II cells | 0 | 1 | 1 | 1 | 0 | 0 | 1 | 0 | 0 | 0 | 1 | 0 |
| Increased alveolar macrophages | 1 | 1 | 1 | 1 | 0 | 1 | 1 | 1 | 1 | 1 | 1 | 1 |

Figure 3A:
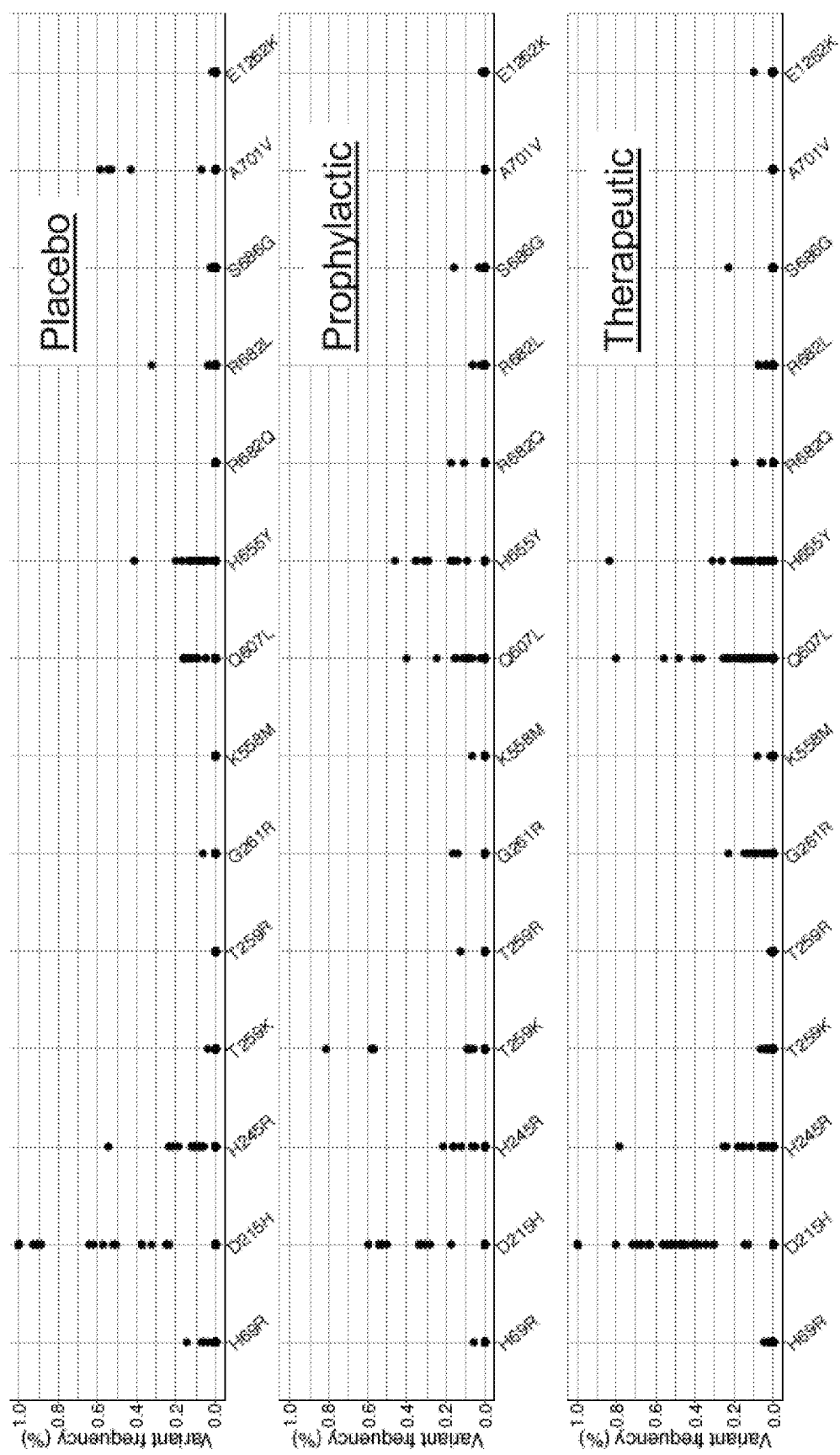
Figure 3B:
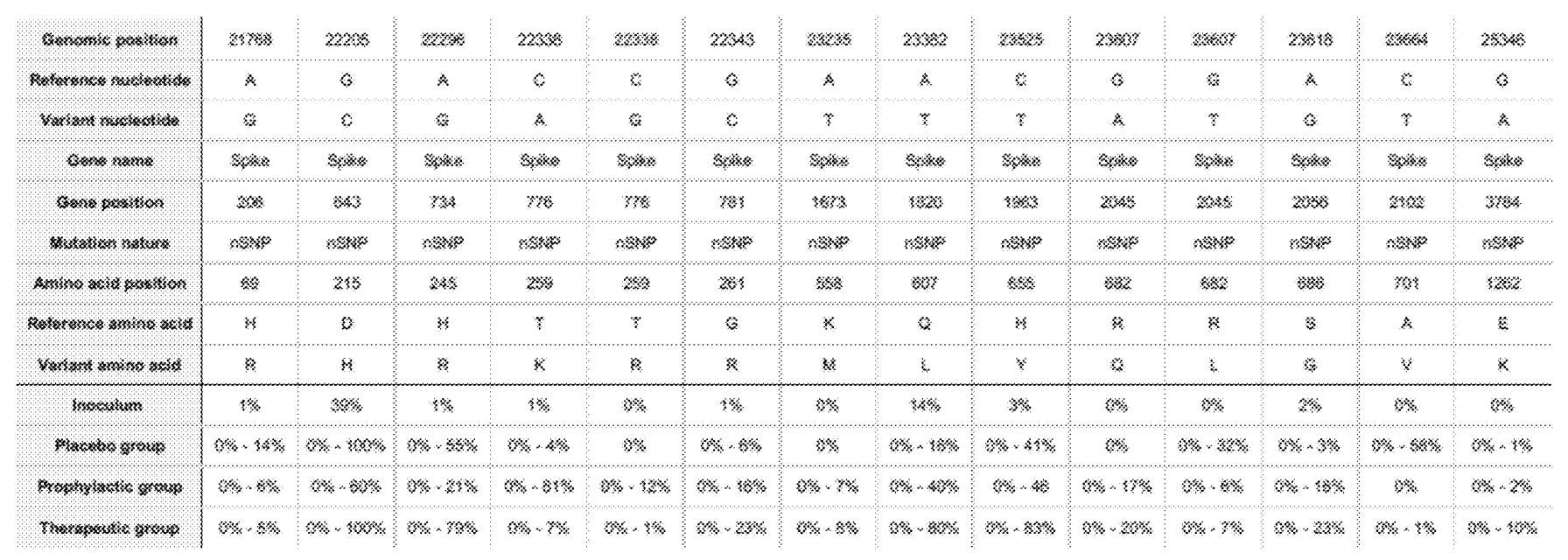

The use of two antibodies that target non-overlapping sites on the spike protein has been demonstrated to safeguard against selection of escape mutants, which were readily detectable with single antibody treatment. To assess whether any signs of putative escape mutants could be observed in an in vivo setting with authentic SARS-CoV-2 virus, RNAseq analysis was performed on all RNA samples obtained from all animals in this study. Analysis of the spike gene sequence identified mutations in animal samples that were not present in the inoculum virus (FIG. 3A and FIG. 3B) further indicating that the virus was actively replicating in those animals. Mutations unique to treated animals were not observed, as all identified mutations were either present in the inoculum or in both treated and placebo animals indicating that they were likely selected as part of virus replication in the animals and were not specifically associated with antibody treatment.

Part C—Efficacy of Anti-SARS-CoV-2 Spike Glycoprotein Antibodies in SARS-CoV-2 Infected Golden Hamsters A total of 50 golden hamsters, male and female, 6-8 weeks old were used in this study. Animals were weighed prior to the start of the study. The animals were monitored twice daily for signs of COVID-19 disease (ruffled fur, hunched posture, labored breathing, a.o.) during the study period. Body weights were measured once daily during the study period. Antibodies were dosed through intraperitoneal (IP) injection. Animals were challenged with $5.6 \times 10^4$ PFU of (USA-WA1/2020 (NR-52281; BEI Resources) by administration of 0.05 ml of viral inoculum dropwise into each nostril. Tissues were sampled for viral load assays by collecting two small pieces (0.1-0.2 gram each) from the lung (total of 4 pieces, 2 per tissue).

Figure 4A:
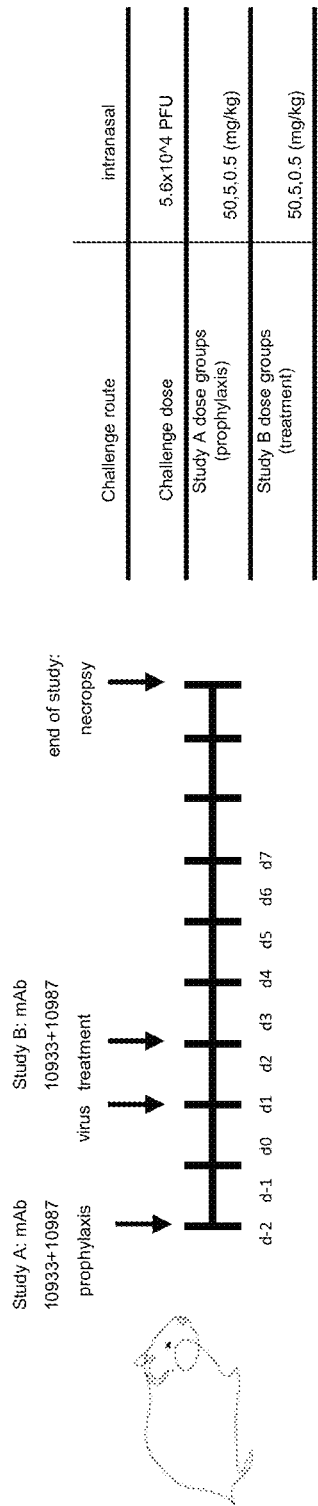
FIG. 4A, FIG. 4B and FIG. 4C illustrate the overview of a study design evaluating the therapeutic and prophylactic efficacy of anti-SARS-CoV-2 spike glycoprotein antibodies in a golden Syrian hamster model of SARS-CoV-2 infection (FIG. 4A), the impact of anti-SARS-CoV-2 spike glycoprotein antibody treatment or prophylaxis on weight loss (FIG. 4B), and the impact of anti-SARS-CoV-2 spike glycoprotein antibody therapy on levels of gRNA and sgRNA in lungs.
Figure 4B:
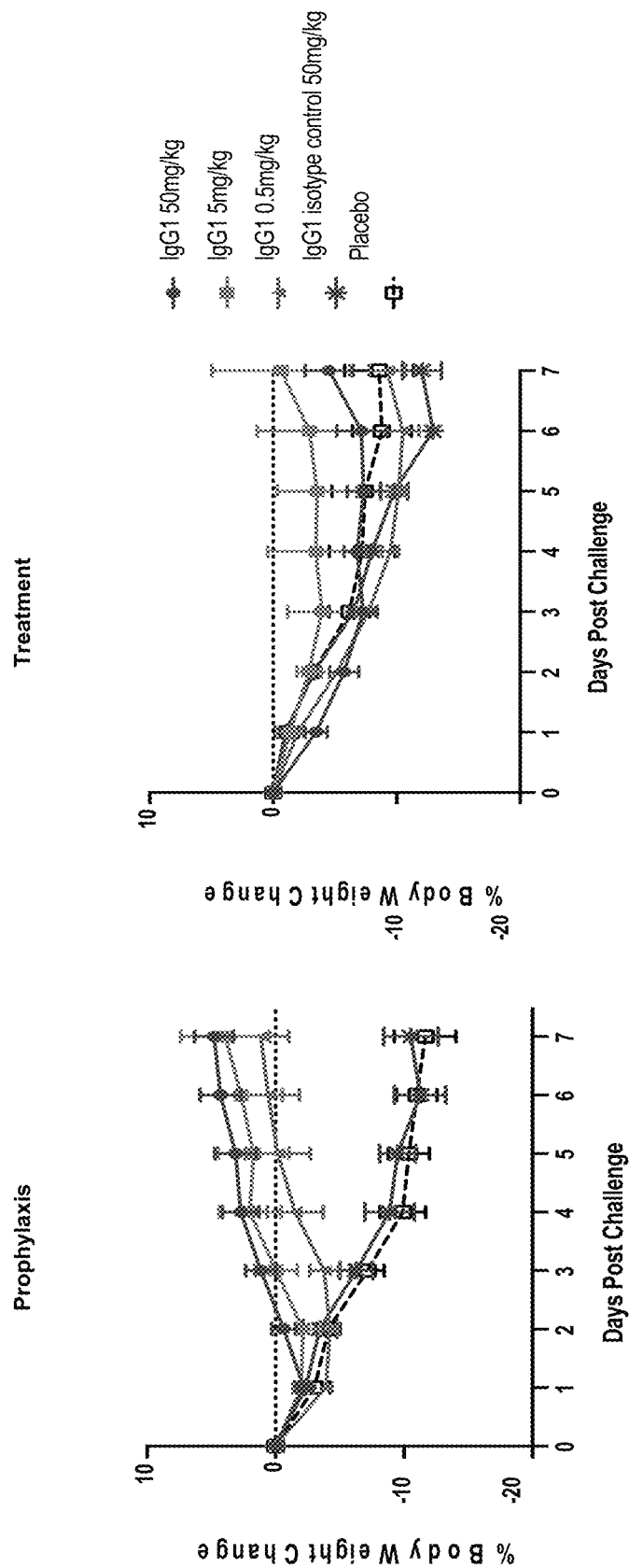
Figure 4C:
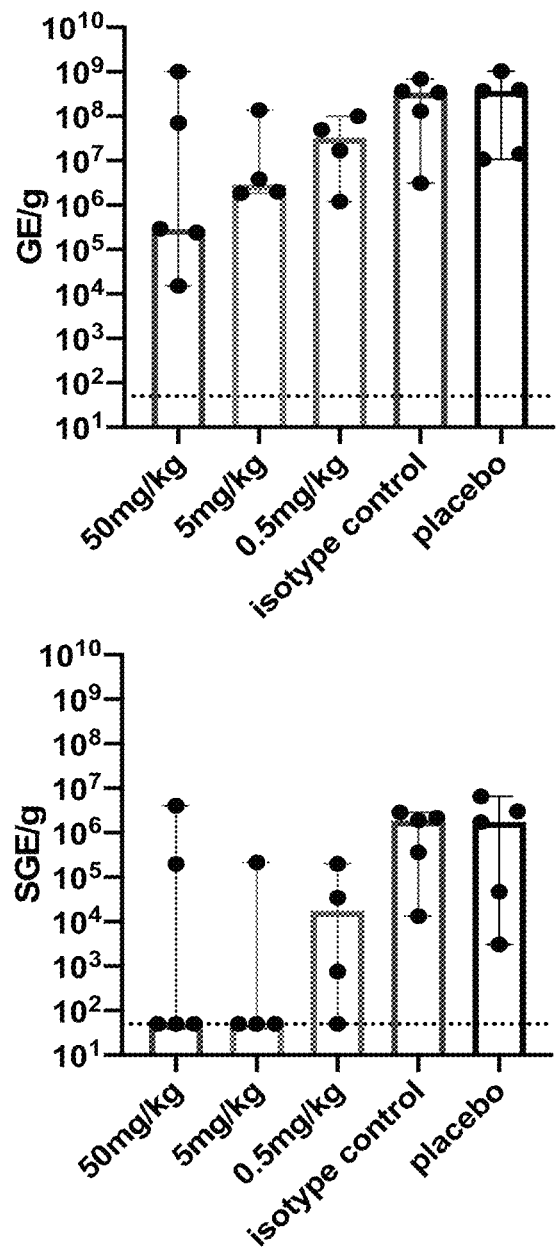

Unlike rhesus macaques which present with a mild clinical course of disease when infected with SARS-CoV-2 and may mimic mild human disease, the golden hamster model was more severe, with animals demonstrating readily observable clinical disease, including rapid weight loss accompanied by very high viral load in lungs, as well as severe lung pathology. Thus, this model may more closely mimic more severe disease in humans. Prophylaxis of hamsters 2 days before challenge with $5.6 \times 10^4$ PFU dose of SARS-CoV-2 virus resulted in dramatic protection from weight loss at all doses of antibody given (from 50 mg/kg to 0.5 mg/kg). This protection was accompanied by decreased viral load in the lungs at the end of the study. High gRNA and sgRNA levels in the lungs of a few treated animals were observed; however, these individual animals did not show any less protection from weight loss than the animals with much lower viral loads. One explanation may be that antibody treatment may provide additional therapeutic benefit in this model not directly associated with viral load decrease. Alternatively, it is possible that increased viral RNA may not necessarily be associated with infectious virus. As viral replication and lung pathology in the hamster model occur very rapidly, the treatment setting represents a high bar for demonstrating therapeutic efficacy. A clear therapeutic benefit in animals treated with 50 mg/kg and 5 mg/kg doses of anti-SARS-CoV-2 spike glycoprotein antibodies 1-day post viral challenge (FIG. 4B) was observed. Although the 5 mg/kg treated group showed fastest recovery at the end of the study, this was likely due to lower day 1 weight loss in this group of animals and not truly an enhanced benefit of a lower dose (FIG. 4B).

Results

The in vivo efficacy of the anti-SARS-CoV-2 antibody combination in two animal models, one mild and one severe, in both prophylactic and treatment settings, was assessed in these studies. Efficacy was demonstrated in both models, as measured by reduced viral load in the upper and lower airways as well as by limited weight loss in the hamster model. The impact of antibody prophylaxis on viral RNA levels in nasal and oral swabs may indicate potential to not only prevent disease in the exposed individual but also to limit transmission.

Importantly, no signs of worsening of either viral load or pathology in presence of antibodies at either high or low doses in either animal model was observed. The potential for antibody dependent enhancement of disease (ADE) is a concern for antibody-based therapeutics and vaccines. ADE of virus infection can occur when antibodies bind to virus particles and increase infectivity as a result of internalization of the antibody/virus complex via interaction of the antibody Fc domain with Fc gamma receptors (FCGRs). Antibody-dependent enhancement may result in infection of cell types expressing FCGR, potentially leading to either enhanced viral replication, increased inflammation, or more severe disease. In vitro ADE studies demonstrated that mAb10987 alone or in combination with mAb10933 mediated entry of pVSV SARS-CoV-2 S pseudoparticles into FCGR2+ Raji and FCGR1+/FCGR2+ THP1 cells, but not any of the other FCGR+ tested cell lines (FCGR2+ IM9 and K562, and FCGR1+/FCGR2+ U937), or the FCGR-negative control cell line (Ramos). mAb10933 alone did not mediate entry of pVSV SARS-CoV-2 S pseudoparticles into any of the tested cell lines (R10933-PH-20101). These data demonstrate that mAb10987 may have the ability to enhance viral entry into certain FCGR+ cells in vitro. However, in vivo, circulating IgG may compete with anti SARS-CoV-2 S protein mAbs for binding to FCGRs, such that antibody mediated viral entry may be dampened. This is supported by the in vivo animal model studies, in which no evidence of enhanced disease was shown. In conclusion, the data presented in this example offers convincing evidence that an antibody-based therapy (e.g., using an antibody cocktail of mAb10987+ mAb10933) offers a clinical benefit in both prevention and treatment settings of COVID-19 disease.

Example 6. Clinical Evaluation of Repeated Doses of Anti-SARS-CoV-2 Spike Glycoprotein Antibodies in Adult Volunteers The below-described clinical study is a phase 1, randomized, double-blind, placebo-controlled study assessing the safety, tolerability, pharmacokinetics, and immunogenicity of repeated subcutaneous doses of anti-spike (S) SARS-CoV-2 monoclonal antibodies (mAb10933+mAb10987) in adult volunteers.

Study Objectives: The primary and secondary objectives of the study are set forth below.

Primary objectives—The primary objectives are:
To assess the occurrence of adverse events of special interest (AESIs) in subjects treated with repeated subcutaneous (SC) doses of mAb10933+mAb10987 compared to placebo (In this study, AESIs are defined as grade 3 or greater (NCI-CTCAE Grading v5.0) injection site reactions or hypersensitivity reactions including, but not limited to, anaphylaxis, laryngeal/pharyngeal edema, severe bronchospasm, chest pain, seizure, and severe hypotension)
To assess the concentrations of mAb10933 and mAb10987 in serum over time after single and repeated SC administration Secondary objectives—The secondary objectives are:
To assess the safety and tolerability of repeated SC doses of mAb10933+mAb10987 compared to placebo
To assess attainment of target concentrations of mAb10933 and mAb10987 in serum after single and repeated SC administration
To assess the immunogenicity of mAb10933 and mAb10987

Exploratory objectives—The exploratory objectives are:
To assess the occurrence of COVID-19 in subjects receiving repeated SC doses of mAb10933+mAb10987 compared to placebo
To assess the occurrence of SARS-CoV-2 seroconversion
To identify biomarkers and genomic factors associated with the safety and exposure of mAb10933+ mAb10987 and/or SARS-CoV-2 infection Study Design: This study is a phase 1, randomized, double-blind, placebo-controlled study in adult volunteers, designed to assess the safety and tolerability of multiple subcutaneous (SC) doses of mAb10933+mAb10987. Subjects are randomized in a 3:1 ratio to receive up to 6 SC doses of mAb10933+mAb10987 combination therapy or placebo.

Study Duration: The study comprises 3 periods: a screening/baseline period of up to 7 days, a treatment period of 24 weeks (or shorter if a subject develops a symptomatic SARS-CoV-2 infection), and a 28-week follow-up period (potentially longer if subject develops symptomatic COVID-19).

Study Population: The study includes approximately 940 subjects. Subjects include male and female adult volunteers 18 to 90 years of age who are healthy or have chronic but stable and well-controlled medical condition(s), and are negative at screening for SARS-CoV-2 infection.

Inclusion Criteria: A subject meets the following criteria to be eligible for inclusion in the study:
1. 18 years to 90 years of age (inclusive) at the signing of informed consent
2. Is healthy or has chronic medical condition(s) that is stable and well controlled as per the opinion of the investigator and is not likely to require medical intervention through the end of study
3. Stable medication for co-morbid condition(s) for at least 6 months prior to screening
4. Willing and able to comply with study visits and study-related procedures, including compliance with site precautionary requirements related to SARS-CoV-2 infection and transmission
5. Willing and able to provide signed informed consent Exclusion Criteria: A subject meeting any of the following criteria will be excluded from the study:
1. Positive diagnostic test for SARS-CoV-2 infection ≤72 hours prior to randomization (This test is done as part of screening. The sample for the test should be collected ≤72 hours within randomization, and the result should be reviewed and confirmed negative prior to dosing).
2. Subject-reported clinical history of COVID-19 as determined by investigator
3. Subject-reported history of prior positive diagnostic test for SARS-CoV-2 infection
4. Active respiratory or non-respiratory symptoms suggestive or consistent with COVID-19
5. Medically attended acute illness, systemic antibiotics use, or hospitalization (ie, >24 hours) for any reason within 30 days prior to screening
6. Clinically significant abnormal laboratory results at screening as defined by 1 or more of the following (may be repeated once):
   HbA1c ≥8.0%
   Hemoglobin <10 g/dL
   Absolute neutrophil count <1.5×109/L
   Platelet count <75×109/L
   Serum creatinine >1.5× upper limit of normal (ULN) or estimated glomerular filtration rate ≤60 mL/min/1.73 m2
   Hepatic function abnormalities defined as 1 or more of the following:
   Aspartate aminotransferase (AST) and/or alanine aminotransferase (ALT), and/or alkaline phosphatase (ALP) >2×ULN
   Total bilirubin >1×ULN
7. Acute exacerbation of a chronic pulmonary condition (eg, chronic obstructive pulmonary disease [COPD], asthma exacerbations) in the past 6 months prior to screening
8. Abnormal blood pressure (BP) at screening, as defined by diastolic BP >100 mm Hg and/or systolic BP >160 mm Hg. Blood pressure measurements may be repeated once at screening
9. History of heart failure hospitalization, diagnosis of a myocardial infarction, stroke, transient ischemic attack, unstable angina, percutaneous or surgical revascularization procedure (coronary, carotid, or peripheral vascular), or intracardiac device placement (e.g., pacemaker) within 12 months prior to screening
10. Cancer requiring treatment currently or in the past 5 years, except for non-melanoma skin cancer or cervical/anus in-situ
11. History of significant multiple and/or severe allergies (eg, latex gloves), or has had an anaphylactic reaction to prescription or non-prescription drugs or food. This is to avoid potential confounding of the safety data and not due to a particular safety risk.
12. Treatment with another investigational drug in the last 30 days or within 5 half-lives of the investigational drug, whichever is longer, prior to screening
13. Received investigational or approved SARS-CoV-2 vaccine
14. Received investigational or approved passive antibodies for SARS-CoV-2 infection prophylaxis (e.g., convalescent plasma or sera, monoclonal antibodies, hyperimmune globulin)
15. Use of remdesivir, intravenous immunoglobulin (IVIG), or other anti-SARS viral agents within 2 months prior to screening
16. Regular alcohol consumption of 21 drinks per week
17. Member of the clinical site study team and/or immediate family
18. Pregnant or breastfeeding women
19. Women of childbearing potential (WOCBP)* who are unwilling to practice highly effective contraception prior to the initial dose/start of the first treatment, during the study, and for at least 8 months after the last dose. Highly effective contraceptive measures include:
a. Stable use of combined (estrogen and progestogen containing) hormonal contraception (oral, intravaginal, transdermal) or progestogen-only hormonal contraception (oral, injectable, implantable) associated with inhibition of ovulation initiated 2 or more menstrual cycles prior to screening
b. Intrauterine device (IUD) or intrauterine hormone-releasing system (IUS)
c. Bilateral tubal ligation
* WOCBP are defined as women who are fertile following menarche until becoming postmenopausal, unless permanently sterile. Permanent sterilization methods include hysterectomy, bilateral salpingectomy, and bilateral oophorectomy.
A postmenopausal state is defined as no menses for 12 months without an alternative medical cause. A high follicle stimulating hormone (FSH) level in the postmenopausal range may be used to confirm a postmenopausal state in women not using hormonal contraception or hormonal replacement therapy. However, in the absence of 12 months of amenorrhea, a single FSH measurement is insufficient to determine the occurrence of a postmenopausal state. The above definitions are according to the Clinical Trial Facilitation Group (CTFG) guidance. Pregnancy testing and contraception are not required for women with documented hysterectomy or tubal ligation.
20. Sexually active men who are unwilling to use the following forms of medically acceptable birth control during the study drug follow-up period and for 8 months after the last dose of study drug: vasectomy with medical assessment of surgical success OR consistent use of a condom. Sperm donation is prohibited during the study and for up to 8 months after the last dose of study drug.

Study Treatments: In the study, treatment includes co-administered mAb10933+mAb10987 1200 mg (600 mg+600 mg)/subcutaneous (SC)/Q4W (once monthly), or placebo/SC/Q4W (once monthly).

Endpoints: Primary, secondary, and exploratory endpoints are as defined below.

Primary endpoints—The primary endpoints are:
Incidence of AESIs that occur within 4 days of SC administration of mAb10933+mAb10987 or placebo at baseline and days 29, 57, 85, 113, and 141
Concentration of mAb10933 and mAb10987 in serum over time Secondary endpoints—The secondary endpoints are:
Proportion of subjects with treatment-emergent adverse events (TEAEs) and severity of TEAEs through the end of study
Proportion of subjects who achieve or exceed target concentration in serum (20 µg/mL) of mAb10933 and mAb10987 at the end of each 4-week dosing interval of mAb109333+mAb10987
Immunogenicity as measured by anti-drug antibodies (ADA) to mAb10933 and mAb10987 over time Exploratory endpoints—The exploratory endpoints are:
Incidence and severity of symptomatic SARS-CoV-2 infection during the treatment and follow-up periods
Proportion of baseline anti-SARS-CoV-2 seronegative subjects with post-baseline positive serology (anti-N protein) through the end of study Procedures and Assessments:

Procedures performed only at screening—Screening procedures include medical history (including chronic medical conditions), demographics (including age, sex, race, weight, height), and an assessment for SARS-CoV-2 infection (by a central laboratory RT-PCR of nasopharyngeal [NP] swab or by an approved or authorized diagnostic assay performed according to the site's standards and procedures).

Procedure performed at baseline—Subjects undergo a baseline RT-PCR assessment for SARS-CoV-2 infection by a central laboratory NP swab.

Safety procedures and assessments—Subjects are asked to report all adverse events (AEs) experienced and concomitant medications from the time of informed consent until their last study visit. Targeted physical examinations, vital signs, clinical laboratory tests, and clinical evaluations are performed. During the treatment period, subjects are followed up for AEs approximately 24 hours and 2 weeks after each study drug administration. In subjects who develop symptoms/signs of COVID-19 during the treatment period or the follow-up period, an assessment for SARS-CoV-2 infection is performed (by a central laboratory RT-PCR of NP swab or by an approved or authorized diagnostic assay performed according to the site's standards and procedures).

Pharmacokinetics, immunogenicity, and serology—Blood samples are collected to assess concentrations of mAb10933 and mAb10987 in serum, immunogenicity of mAb10933 and mAb10987, and anti-SARS-CoV-2 serology.

Statistical Plan:

Approximately 940 subjects (705 subjects in the mAb10933+mAb10987 group and 235 subjects in the placebo group) will be enrolled by the end of the study. Assuming that approximately 80% of previously enrolled subjects reconsent to the extended treatment period per protocol amendment 3, approximately 856 subjects are expected to be randomized in the 6-month treatment schedule (642 subjects in the mAb10933+mAb10987 group and 214 subjects in the placebo group).

Based on prior experience with subcutaneous (SC) administered monoclonal antibodies (mAbs), the expected rates of injection site reactions (ISRs) and hypersensitivity reactions are approximately 10% and <1%, respectively. If the observed number of subjects with ISRs is ≤54, with a sample size of 705 subjects in the mAb10933+mAb10987 group, the risk of ISRs >10% would be ruled out. Similarly, ≥1% risk of hypersensitivity reactions (grade ≥3) would be ruled out if such events occur in less than 2 subjects in the study.

Results—This study demonstrates that multiple subcutaneous (SC) doses of mAb10933+mAb10987 are safe and well-tolerated.

Example 7. Clinical Evaluation of Virologic Efficacy of Anti-SARS-CoV-2 Spike Glycoprotein Antibodies Across Different Dose Regimens in Outpatients with SARS-CoV-2 Infection The below-described clinical study is a phase 2, randomized, double-blind, placebo-controlled, parallel group study to assess the dose response profile of single intravenous (IV) or single subcutaneous (SC) doses of mAb10933+mAb10987 in outpatients with SARS-CoV-2 infection.

Study Objectives: The primary and secondary objectives of the study are set forth below.

Primary objective—The primary objective was to assess the virologic efficacy of mAb10933+mAb10987 across different intravenous and subcutaneous doses compared to placebo.

Secondary objectives—The secondary objectives were:
To evaluate additional indicators of virologic efficacy of mAb10933+mAb10987 compared to placebo
To evaluate the safety and tolerability of mAb10933+mAb10987 compared to placebo
To assess the concentrations of mAb10933 and mAb10987 in serum over time
To assess the immunogenicity of mAb10933 and mAb10987

Exploratory objectives—The exploratory objectives were:
To explore the occurrence of all-cause hospitalizations, emergency room (ER) visits, or deaths in patients treated with mAb10933+mAb10987 compared to those treated with placebo
To explore the occurrence of COVID-19-related medically-attended visits (MAVs) in patients treated with mAb10933+mAb10987 compared to those treated with placebo (a COVID-19-related medically-attended visit will be defined as follows: hospitalization, ER visit, urgent care visit, physician's office visit, or telemedicine visit, with the primary reason for the visit being COVID-19)
To assess viral genetic variation in patients with a positive SARS-CoV-2 quantitative reverse transcription polymerase chain reaction (RT-qPCR)
To explore relationships between mAb10933+mAb10987 exposure and selected efficacy endpoints, safety endpoints, and/or biomarkers Study Design: This study is a randomized, double-blind, placebo-controlled, parallel group study to assess the dose response profile of single intravenous (IV) or single subcutaneous (SC) doses of REGN10933+REGN10987 in outpatients with SARS-CoV-2 infection. An overview of the study is shown in FIG. 57.

Eligible patients were randomized to receive a single dose of mAb10933+mAb10987 or placebo by IV or SC route. On the day of dosing, patients had NP swabs taken for SARS-CoV-2 RT-qPCR testing and blood drawn for safety, drug concentration, immunogenicity, and serologic analyses. After study drug administration, patients had a post-dose blood collection (either at the end of intravenous infusion or at least 1 hour after subcutaneous administration). Patients were monitored for at least 1 hour after study drug administration and then released from the study site, if medically appropriate.

Information related to safety and COVID-19-related medically-attended visits were recorded during planned study visits. Patients also were asked to notify study personnel as soon as possible about any medically-attended visits. The TEAEs that were collected during the study may differ according to different periods of the study schedule. Refer to the safety reporting section in the protocol for more information on reporting of TEAEs and treatment-emergent laboratory abnormalities.

Patients had NP swabs and blood samples collected every other day for the first week of the study. Additional NP swab samples were collected once-weekly for 2 more weeks to assess potential persistence of viral load. A phone visit occurred during the fourth week for collection of safety information.

After the first month, patients had visits approximately once-monthly for 4 additional months. The penultimate visit was in-person to collect blood samples for drug concentration and immunogenicity. The final visit (EOS) was a phone call.

Study Duration: The duration of the study was 170 days for each patient.

Study Population: This study enrolled adult, non-hospitalized patients who had a positive diagnostic test for SARS-CoV-2. The protocol called for up to approximately 1400 patients to be enrolled by the end of the study.

Inclusion Criteria: A patient must have met the following criteria to be eligible for inclusion in the study:

14. Is male or female ≥18 years of age (or country's legal age of adulthood) at randomization Note: upper age limit may apply; refer to other inclusion criteria.

15. Has SARS-CoV-2-positive diagnostic test from a sample collected ≤72 hours prior to randomization, using a validated SARS-CoV-2 antigen, RT-PCR, or other molecular diagnostic assay and an appropriate sample such as nasopharyngeal (NP), nasal, oropharyngeal (OP), or saliva Note: Historical record of positive result is acceptable, as long as the sample was collected ≤72 hours prior to randomization.

16. Low-risk symptomatic patient: Has symptoms consistent with COVID-19 (as determined by the investigator) with onset ≤7 days before randomization, and meets all of the following 8 criteria:

a. Age ≤50 b. No obesity, with obesity defined as BMI ≥30 kg/m$^2$ c. Does not have cardiovascular disease or hypertension d. Does not have chronic lung disease or asthma e. Does not have type 1 or type 2 diabetes mellitus f. Does not have chronic kidney disease, with or without dialysis g. Does not have chronic liver disease
h. Is not pregnant
or
Asymptomatic patient: Has had no symptoms consistent with COVID-19 (as determined by the investigator) occurring at any time <2 months prior to randomization
17. Maintains $O_2$ saturation ≥93% on room air
18. Is willing and able to provide informed consent signed by study patient or legally acceptable representative
19. Is willing and able to comply with study procedures, including providing samples for viral shedding testing Exclusion Criteria: A patient who met any of the following criteria was excluded from the study:
1. Was admitted to a hospital for COVID-19 prior to randomization, or is hospitalized (inpatient) for any reason at randomization
2. Has a known positive SARS-CoV-2 serologic test
3. Has a positive SARS-CoV-2 antigen or molecular diagnostic test from a sample collected >72 hours prior to randomization
4. Is immunosuppressed, based on investigator's assessment
   Note: examples include cancer treatment, bone marrow or organ transplantation, immune deficiencies, HIV (if poorly controlled or evidence of AIDS), sickle cell anemia, thalassemia, and prolonged use of immune-weakening medications.
5. Has participated, or is participating, in a clinical research study evaluating COVID-19 convalescent plasma, mAbs against SARS-CoV-2, or intravenous immunoglobulin (IVIG) within 3 months or within 5 half-lives of the investigational product (whichever is longer) prior to the screening visit
6. Prior, current, or planned future use of any of the following treatments: COVID-19 convalescent plasma, mAbs against SARS-CoV-2 (e.g., bamlanivimab), IVIG (any indication), systemic corticosteroids (any indication), or COVID-19 treatments (authorized, approved, or investigational)
   Note: prior use is defined as the past 30 days or within than 5 half-lives of the investigational product (whichever is longer) from screening.
7. Prior use (prior to randomization), current use (at randomization), or planned use (within time period given per CDC guidance but no sooner than 22 days of study drug administration) of any authorized or approved vaccine for SARS-CoV-2
8. Has known active infection with influenza or other non-SARS-CoV-2 respiratory pathogen, confirmed by a diagnostic test
9. Has known allergy or hypersensitivity to components of study drug
10. Has been discharged, or is planned to be discharged, to a quarantine center
11. Has participated, is participating, or plans to participate in a clinical research study evaluating any authorized, approved, or investigational vaccine for SARS-CoV-2
12. Is a member of the clinical site study team or is an immediate family member of the site study team Study Treatments: In the study, treatment included co-administered mAb10933+mAb10987 via intravenous or subcutaneous administration as a single dose selected from:
IV Single Dose
   Co-administered mAb10933+mAb10987 combination therapy intravenous (IV) single dose:
   2400 mg (1200 mg per monoclonal antibody [mAb])
   1200 mg (600 mg per mAb)
   600 mg (300 mg per mAb)
   300 mg (150 mg per mAb)
   Placebo IV single dose
SC Single Dose
   Co-administered mAb10933+mAb10987 combination therapy subcutaneous (SC) single dose
   1200 mg (600 mg per mAb)
   600 mg (300 mg per mAb)
   Placebo SC single dose Endpoints: Primary, secondary, and exploratory endpoints were as defined below.

Primary endpoints—The primary endpoint was time-weighted average daily change from baseline in viral load ($\log_{10}$ copies/mL) from day 1 to day 7, as measured by RT-qPCR in NP swab samples, in patients who had a central-lab determined RT-qPCR positive test and were seronegative at baseline Secondary endpoints—The secondary endpoints were:
   Time-weighted average daily change from baseline in viral load ($\log_{10}$ copies/mL) from day 1 to day 5
   Time-weighted average daily change from baseline in viral load ($\log_{10}$ copies/mL) in patients with high viral load ($>10^4$ copies/mL, $>10^5$ copies/mL, $>10^6$ copies/mL, $>10^7$ copies/mL) from day 1 to day 7
   Time-weighted average daily change from baseline in viral load ($\log_{10}$ copies/mL) in patients with high viral load ($>10^4$ copies/mL, $>10^5$ copies/mL, $>10^6$ copies/mL, $>10^7$ copies/mL) from day 1 to day 5
   Proportion of patients with high viral load ($>10^4$ copies/mL, $>10^5$ copies/mL, $>10^6$ copies/mL, $>10^7$ copies/mL) at each visit
   Proportion of patients with viral loads below the limit of detection at each visit
   Proportion of patients with viral loads below the lower limit of quantitation at each visit
   Time-weighted average daily change from baseline in cycle threshold (Ct) from day 1 to day 7, as measured by RT-qPCR in NP samples
   Time-weighted average daily change from baseline in Ct from day 1 to day 5, as measured by RT-qPCR in NP samples
   Change from baseline in Ct at each visit, as measured by RT-qPCR in NP samples
   Change from baseline in viral load at each visit, as measured by RT-qPCR in NP samples
   Proportion of patients with treatment-emergent SAEs through day 29
   Proportion of patients with infusion-related reactions (grade ≥2) through day 4
   Proportion of patients with injection-site reactions (grade ≥3) through day 4
   Proportion of patients with hypersensitivity reactions (grade ≥2) through day 29
   Concentrations of mAb10933 and mAB10987 in serum over time
   Immunogenicity as measured by anti-drug antibodies (ADAs) and neutralizing antibodies (NAbs) to mAb10933 and mAb10987

Exploratory endpoints—The exploratory endpoints were:
   Cumulative incidence (through day 29 and day 169) of COVID-19-related medically-attended visits or all-cause mortality
   Cumulative incidence (through day 29 and day 169) of COVID-19-related hospitalizations, emergency room visits, or all-cause mortality Cumulative incidence (through day 29 and day 169) of COVID-19-related hospitalizations or all-cause mortality Cumulative incidence (through day 29 and day 169) of COVID-19-related emergency room visits or all-cause mortality Proportion of patients (through day 29 and day 169) with ≥1 COVID-19-related medically-attended visit or all-cause mortality Proportion of patients (through day 29 and day 169) with ≥1 COVID-19-related medically-attended visit by type of visits (hospitalization, emergency room visit, urgent care, physician's office visit, and/or telemedicine visit)

Proportion of patients (through day 29 and day 169) with ≥2 COVID-19-related medically-attended visits or all-cause mortality Days of hospitalization due to COVID-19

Proportion of patients (by day 29 and day 169) admitted to an intensive care unit (ICU) due to COVID-19

Proportion of patients (by day 29 and day 169) requiring supplemental oxygen due to COVID-19

Proportion of patients (by day 29 and day 169) requiring mechanical ventilation due to COVID-19

Total number of COVID-19-related MAVs through day 29 and 169

Cumulative incidence (through day 29 and day 169) of all-cause hospitalizations, emergency room visits, or mortality All-cause mortality by day 29 and day 169

Proportion of patients with treatment-emergent SAEs through day 169

Procedures and Assessments:

Procedures and Assessment included:

NP swabs for SARS-CoV-2 RT-qPCR

COVID-19-related medically-attended visits

TEAEs, treatment-emergent SAEs, and treatment-emergent AESIs (grade ≥2 infusion-related reactions, grade ≥3 injection-site reactions, grade ≥2 hypersensitivity reactions, and any TEAE that led to a hospitalization or emergency room visit, regardless of whether the visit is related to COVID-19)

Targeted concomitant medications, safety labs, vital signs, and pregnancy status Statistical Plan:

The primary virologic efficacy variable was the time-weighted average change from baseline in viral load from day 1 to day 7, as measured by RT-qPCR in NP swab samples. The primary analysis was conducted in the seronegative modified full analysis set (mFAS) population.

The mFAS included all randomized patients with a positive central-lab determined SARS-CoV-2 RT-qPCR result from NP swab samples at randomization and was based on the treatment received (as treated). The seronegative mFAS was the subset of patients in the mFAS population who were seronegative at baseline.

Results—This study demonstrates that different intravenous and subcutaneous doses of mAb10933+mAb10987 provide virologic efficacy compared to placebo (FIG. 74). All tested doses met the primary endpoint, rapidly and significantly reducing patients' viral load ($\log_{10}$ copies/mL) compared to placebo (p≤0.001). With an initial cohort of 816 patients, this study showed significant and comparable virologic reduction through day 7 in patients who were SARS-CoV-2 PCR+ and seronegative at baseline across all 6 REGEN-COV dose levels tested. Although there were minor numerical differences in mean viral reduction between the 2400 mg arm and other treatment arms, these were deemed neither statistically different nor clinically meaningful. Indeed, REGEN-COV significantly and substantially reduced viral load across all dose levels tested, down to as low as single doses of 300 mg intravenous or 600 mg subcutaneous (FIG. 47). Moreover, these results were comparable to those of Example 2, despite the lower doses in this study (FIG. 48 and FIG. 51; Example 2 study labeled as "2067" and this study labeled as "20145"). There were also dose-proportional increases in REGEN-COV serum concentrations in IV and SC patients (FIG. 75). The treatment was generally well-tolerated, with no fatalities and only two serious adverse events, both of which were assessed as not related to COVID-19 or REGEN-COV (FIG. 49 and FIG. 50). Summaries of the demographics and baseline characteristics for seronegative intravenous and subcutaneous patients (modified full analysis set) are shown in FIG. 45 and FIG. 46, respectively.

TABLE 17

Time-weighted average daily change from baseline (Day 1) to Day 7 in viral load ($\log_{10}$ copies/mL) in patients who are PCR-positive and seronegative at baseline

| | Prespecified testing hierarchy | | |
|---|---|---|---|
| Comparison | LS mean | 95% CI | p-value |
| REGEN-COV 2400 mg IV (n = 61) vs. pooled placebo (n = 74) | −0.71 | (−1.05, −0.38) | <0.0001 |
| REGEN-COV 1200 mg IV (n = 67) vs. pooled placebo (n = 74) | −0.56 | (−0.89, −0.24) | 0.0007 |
| REGEN-COV 1200 mg IV (n = 71) vs. pooled placebo (n = 74) | −0.56 | (−0.87, −0.24) | 0.0007 |
| REGEN-COV 600 mg IV (n = 66) vs. pooled placebo (n = 74) | −0.66 | (−0.99, −0.34) | <0.0001 |
| REGEN-COV 600 mg IV (n = 71) vs. pooled placebo (n = 74) | −0.56 | (−0.88, −0.24) | 0.0006 |
| REGEN-COV 300 mg IV (n = 76) vs. pooled placebo (n = 74) | −0.57 | (−0.88, −0.25) | 0.0004 |

CI, confidence interval;
IV, intravenous;
LS, least-squares;
PCR, polymerase chain reaction;
SC, subcutaneous The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A method for improving one or more clinical parameters of COVID-19, the method comprising administering a therapeutic composition to a subject in need thereof, wherein the therapeutic composition comprises at least one antigen-binding molecule that binds a surface protein of SARS-CoV-2, wherein the at least one antigen-binding molecule is an anti-SARS-CoV-2 spike glycoprotein antibody or antigen-binding fragment thereof comprising three heavy chain complementarity determining regions (HCDRs) and three light chain complementarity determining regions (LCDRs), HCDR1, HCDR2, HCDR3, LCDR1, LCDR2, and LCDR3 contained within a heavy chain variable region (HCVR) and light chain variable region (LCVR) amino acid sequence pair comprising the amino acid sequences selected from the group consisting of SEQ ID NOs: 2 and 10, SEQ ID NOs: 22 and 30, and SEQ ID NOs: 42 and 50.

2. The method of claim 1, wherein the subject is a human patient with laboratory-confirmed SARS-CoV-2 and one or more COVID-19 symptoms.

3. The method of claim 2, wherein the one or more COVID-19 symptoms comprise fever, cough, or shortness of breath.

4. The method of claim 2 or claim 3, wherein the subject is selected from the group consisting of: (a) a human COVID-19 patient requiring low-flow oxygen supplementation; (b) a human COVID-19 patient requiring high-intensity oxygen therapy but not on mechanical ventilation; and (c) a human COVID-19 patient requiring mechanical ventilation.

5. The method of claim 1, wherein the subject is hospitalized due to one or more COVID-19 symptoms.

6. The method of claim 1, wherein the subject is an outpatient.

7. A method for preventing a SARS-CoV-2 infection or COVID-19 in a subject, the method comprising administering a prophylactic composition to the subject, wherein the prophylactic composition comprises at least one antigen-binding molecule that binds a surface protein of SARS-CoV-2, wherein the at least one antigen-binding molecule is an anti-SARS-CoV-2 spike glycoprotein antibody or antigen-binding fragment thereof comprising three heavy chain complementarity determining regions (HCDRs) and three light chain complementarity determining regions (LCDRs), HCDR1, HCDR2, HCDR3, LCDR1, LCDR2, and LCDR3, contained within a heavy chain variable region (HCVR) and light chain variable region (LCVR) amino acid sequence pair comprising the amino acid sequences selected from the group consisting of SEQ ID NOs: 2 and 10, SEQ ID NOs: 22 and 30, and SEQ ID NOs: 42 and 50.

8. The method of claim 7, wherein the subject is an uninfected individual at high risk of SARS-CoV-2 infection.

9. The method of claim 8, wherein the subject at high risk of SARS-CoV-2 infection is a healthcare worker, a first responder, or a household member of an individual with a positive test for a SARS-CoV-2 infection.

10. The method of claim 1 or claim 7, wherein the therapeutic or prophylactic composition comprises a first antigen-binding molecule that binds a first epitope on a surface protein of SARS-CoV-2, and a second antigen-binding molecule that binds a second epitope on a surface protein of SARS-CoV-2, wherein the first epitope and the second epitope are structurally non-overlapping.

11. The method of claim 10, wherein the therapeutic or prophylactic composition further comprises a third antigen-binding molecule that binds a third epitope on a surface protein of SARS-CoV-2, wherein the third epitope is structurally non-overlapping with the first epitope and the second epitope.

12. The method of claim 1 or claim 7, wherein the therapeutic or prophylactic composition comprises a first antigen-binding molecule that binds a first epitope on a surface protein of SARS-CoV-2, and a second antigen-binding molecule that binds a second epitope on a surface protein of SARS-CoV-2, wherein the first antigen-binding molecule and the second antigen-binding molecule are capable of simultaneously binding the surface protein of SARS-CoV-2.

13. The method of claim 12, wherein the first antigen-binding molecule is a first anti-SARS-CoV-2 spike glycoprotein antibody or antigen-binding fragment thereof comprising six complementarity determining regions, HCDR1, HCDR2, HCDR3, LCDR1, LCDR2, and LCDR3, contained within a heavy chain variable region (HCVR) and light chain variable region (LCVR) amino acid sequence pair comprising the amino acid sequences of SEQ ID NOs: 2 and 10, and the second antigen-binding molecule is a second anti-SARS-CoV-2 spike glycoprotein antibody or antigen-binding fragment thereof comprising six complementarity determining regions, HCDR1, HCDR2, HCDR3, LCDR1, LCDR2, and LCDR3, contained within a heavy chain variable region (HCVR) and light chain variable region (LCVR) amino acid sequence pair comprising the amino acid sequences of SEQ ID NOs: 22 and 30.

14. The method of claim 12, wherein the therapeutic or prophylactic composition further comprises a third antigen-binding molecule that binds a third epitope on a surface protein of SARS-CoV-2, wherein the first antigen-binding molecule, the second antigen-binding molecule, and the third antigen-binding molecule are capable of simultaneously binding the surface protein of SARS-CoV-2.

15. The method of claim 10, wherein:

a) the first antigen-binding molecule comprises three heavy chain complementarity determining regions (CDRs) (HCDR1, HCDR2 and HCDR3) contained within a heavy chain variable region (HCVR) comprising the amino acid sequence set forth in SEQ ID NO: 2, and three light chain complementarity determining regions (CDRs) (LCDR1, LCDR2 and LCDR3) contained within a light chain variable region (LCVR) comprising the amino acid sequence set forth in SEQ ID NO: 10; and b) the second antigen-binding molecule comprises three heavy chain complementarity determining regions (CDRs) (HCDR1, HCDR2 and HCDR3) contained within a heavy chain variable region (HCVR) comprising the amino acid sequence set forth in SEQ ID NO: 22, and three light chain complementarity determining regions (CDRs) (LCDR1, LCDR2 and LCDR3) contained within a light chain variable region (LCVR) comprising the amino acid sequence set forth in SEQ ID NO: 30.

16. The method of claim 10, wherein the surface protein of SARS-CoV-2 is a spike (S) protein comprising a receptor binding domain comprising an amino acid sequence at least 80% identical to SEQ ID NO: 59.

17. The method of claim 1 or claim 7, wherein the heavy chain CDRs and the light chain CDRs, HCDR1, HCDR2, HCDR3, LCDR1, LCDR2, and LCDR3, comprise the amino acid sequences, respectively, selected from the group consisting of SEQ ID NOs: 4, 6, 8, 12, 14, and 16; 24, 26, 28, 32, 34, and 26; and 44, 46, 48, 52, 34, and 54.

18. The method of claim 17, wherein the anti-SARS-CoV-2 spike glycoprotein antibody or antigen-binding fragment comprises a HCVR/LCVR amino acid sequence pair comprising the amino acid sequences selected from the group consisting of SEQ ID NOs: 2 and 10, SEQ ID NOs: 22 and 30, and SEQ ID NOs: 42 and 50.

19. The method of claim 1 or claim 7, wherein the anti-SARS-CoV-2 spike glycoprotein antibody comprises a human IgG heavy chain constant region.

20. The method of claim 19, wherein the anti-SARS-CoV-2 spike glycoprotein antibody comprises a heavy chain constant region of IgG1 or IgG4 isotype.

21. The method of claim 19, wherein the anti-SARS-CoV-2 spike glycoprotein antibody comprises a heavy chain and light chain amino acid sequence pair selected from the group consisting of SEQ ID NOs: 18 and 20, SEQ ID NOs: 38 and 40, and SEQ ID NOs: 56 and 58.

22. The method of claim 10, wherein the first antigen-binding molecule is a first anti-SARS-CoV-2 spike glycoprotein antibody or antigen-binding fragment thereof comprising six complementarity determining regions, HCDR1, HCDR2, HCDR3, LCDR1, LCDR2, and LCDR3, contained within a heavy chain variable region (HCVR) and light chain variable region (LCVR) amino acid sequence pair comprising the amino acid sequences of SEQ ID NOs: 2 and 10, and the second antigen-binding molecule is a second anti-SARS-CoV-2 spike glycoprotein antibody or antigen-binding fragment thereof comprising six complementarity determining regions, HCDR1, HCDR2, HCDR3, LCDR1, LCDR2, and LCDR3, contained within a heavy chain variable region (HCVR) and light chain variable region (LCVR) amino acid sequence pair comprising the amino acid sequences of SEQ ID NOs: 22 and 30.

23. The method of claim 22, wherein the first anti-SARS-CoV-2 spike glycoprotein antibody or antigen-binding fragment comprises six complementarity determining regions, HCDR1, HCDR2, HCDR3, LCDR1, LCDR2, and LCDR3, comprising the amino acid sequences, respectively, of SEQ ID NOs: 4, 6, 8, 12, 14, and 16, and the second anti-SARS-CoV-2 spike glycoprotein antibody or antigen-binding fragment comprises six complementarity determining regions, HCDR1, HCDR2, HCDR3, LCDR1, LCDR2, and LCDR3, comprising the amino acid sequences, respectively, of SEQ ID NOs: 24, 26, 28, 32, 34, and 36.

24. The method of claim 23, wherein the first anti-SARS-CoV-2 spike glycoprotein antibody or antigen-binding fragment comprises a HCVR and LCVR amino acid sequence pair comprising the amino acid sequences of SEQ ID NOs: 2 and 10N/10n, and the second anti-SARS-CoV-2 spike glycoprotein antibody or antigen-binding fragment comprises a HCVR and LCVR amino acid sequence pair comprising the amino acid sequences of SEQ ID NOs: 22 and 30.

25. The method of claim 22, wherein the first and the second anti-SARS-CoV-2 spike glycoprotein antibodies comprises human IgG heavy chain constant regions.

26. The method of claim 25, wherein the first and the second anti-SARS-CoV-2 spike glycoprotein antibodies comprises heavy chain constant regions of IgG1 or IgG4 isotype.

27. The method of claim 25, wherein the first anti-SARS-CoV-2 spike glycoprotein antibody comprises a heavy chain comprising the amino acid sequence of SEQ ID NO: 18 and a light chain comprising the amino acid sequence of SEQ ID NO: 20, and the second anti-SARS-CoV-2 spike glycoprotein antibody comprises a heavy chain comprising the amino acid sequence of SEQ ID NO: 38 and a light chain comprising the amino acid sequence of SEQ ID NO: 40.

28. The method of claim 1 or claim 7, wherein the antigen-binding molecule is an anti-SARS-CoV-2 spike glycoprotein antibody or antigen-binding fragment thereof comprising six complementarity determining regions, HCDR1, HCDR2, HCDR3, LCDR1, LCDR2, and LCDR3, contained within a heavy chain variable region (HCVR) comprising the amino acid sequence of SEQ ID NO: 42 and light chain variable region (LCVR) comprising the amino acid sequence of SEQ ID NO: 50.

29. The method of claim 28, wherein the anti-SARS-CoV-2 spike glycoprotein antibody or antigen-binding fragment comprises six complementarity determining regions, HCDR1, HCDR2, HCDR3, LCDR1, LCDR2, and LCDR3, comprising the amino acid sequences, respectively, of SEQ ID NOs: 44, 46, 48, 52, 34, and 54.

30. The method of claim 29, wherein the anti-SARS-CoV-2 spike glycoprotein antibody or antigen-binding fragment comprises a HCVR comprising the amino acid sequence of SEQ ID NO: 42, and a LCVR comprising the amino acid sequence of SEQ ID NOs: 50.

31. The method of claim 28, wherein the anti-SARS-CoV-2 spike glycoprotein antibody comprises a human IgG heavy chain constant region.

32. The method of claim 31, wherein the anti-SARS-CoV-2 spike glycoprotein antibody comprises a heavy chain constant region of IgG1 or IgG4 isotype.

33. The method of claim 31, wherein the anti-SARS-CoV-2 spike glycoprotein antibody comprises a heavy chain comprising the amino acid sequence of SEQ ID NO: 56, and a light chain comprising the amino acid sequence of SEQ ID NO: 58.

34. The method of claim 1 or claim 7, wherein the therapeutic composition comprises 1 mg to 10 g of the antigen-binding molecule(s).

35. The method of claim 1 or claim 7, wherein the therapeutic composition comprises about 1.2 g of mAb10933 and about 1.2 g of mAb10987.

36. The method of claim 1 or claim 7, wherein the therapeutic composition comprises about 150 mg of mAb10933 and about 150 mg of mAb10987.

37. The method of claim 1 or claim 7, wherein the therapeutic composition comprises about 300 mg of mAb10933 and about 300 mg of mAb10987.

38. The method of claim 1 or claim 7, wherein the therapeutic composition comprises about 600 mg of mAb10933 and about 600 mg of mAb10987.

39. The method of claim 1 or claim 7, wherein the therapeutic composition comprises from 150 mg to 1200 mg of mAb10933 and from 150 mg to 1200 mg of mAb10987.

40. The method of claim 1 or claim 7, wherein the therapeutic or prophylactic composition is administered to the subject by intravenous infusion or subcutaneous injection.

41. The method of claim 1, wherein, following administration of the therapeutic composition, the subject exhibits one or more efficacy parameters selected from the group consisting of:
   (a) reduction from baseline in SARS-CoV-2 viral shedding;
   (b) at least 1 point improvement in clinical status using a 7-point ordinal scale;
   (c) reduction or elimination of need for oxygen supplementation;
   (d) reduction or elimination of need for mechanical ventilation;
   (e) prevention of COVID-19-related mortality;
   (f) prevention of all-cause mortality; and
   (g) change in serum concentration of one or more disease-related biomarkers.

42. The method of claim 41, wherein the 7-point ordinal scale is:
   [1] Death;
   [2] Hospitalized, requiring invasive mechanical ventilation or extracorporeal membrane oxygenation;
   [3] Hospitalized, requiring non-invasive ventilation or high flow oxygen devices;
   [4] Hospitalized, requiring supplemental oxygen;
   [5] Hospitalized, not requiring supplemental oxygen—requiring ongoing medical care (COVID-19-related or otherwise);
   [6] Hospitalized, not requiring supplemental oxygen—no longer requires ongoing medical care; and
   [7] Not hospitalized.

43. The method of claim 41 or 42, wherein the one or more efficacy parameters are measured 21 days after administration of a first dose of the therapeutic composition.

44. The method of claim 41, wherein the reduction from baseline in SARS-CoV-2 viral shedding is determined by real-time quantitative PCR (RT-qPCR) in nasopharyngeal swab samples, nasal samples, or saliva samples.

45. The method of claim 41, wherein the change in serum concentration of one or more disease-related biomarkers is a change in c-reactive protein, lactate dehydrogenase, D-dimer, or ferritin.

46. The method of claim 1, further comprising administering an additional therapeutic agent to the subject.

47. The method of claim 46, wherein the additional therapeutic agent is an antiviral compound.

48. The method of claim 47, wherein the antiviral compound is remdesivir.

49. The method of claim 46, wherein the additional therapeutic agent is an IL-6 or IL-6R blocker.

50. The method of claim 49, wherein the additional therapeutic agent is tocilizumab or sarilumab.

51. The method of claim 46, wherein the additional therapeutic agent is a steroid.

52. The method of claim 1 or claim 7, wherein the subject is seronegative for SARS-CoV-2 infection.

53. A method for improving one or more clinical parameters of a SARS-CoV-2 infection, the method comprising administering a therapeutic composition to a subject with a SARS-CoV-2 infection, wherein the therapeutic composition comprises a first anti-SARS-CoV-2 spike glycoprotein antibody or antigen-binding fragment thereof comprising three heavy chain complementarity determining regions (HCDRs) and three light chain complementarity determining regions (LCDRs) contained within a heavy chain variable region (HCVR) and light chain variable region (LCVR) amino acid sequence pair comprising the amino acid sequences of SEQ ID NOs: 2 and 10N/10n, and a second anti-SARS-CoV-2 spike glycoprotein antibody or antigen-binding fragment thereof comprising three HCDRs and three LCDRs contained within an HCVR and an LCVR amino acid sequence pair comprising the amino acid sequences of SEQ ID NOs: 22 and 30, wherein a time to alleviate at least one clinical parameter of a SARS-CoV-2 infection in a population of seronegative subjects administered said therapeutic composition is shorter than that of a comparable population of seronegative subjects administered a placebo.

54. A method for improving one or more clinical parameters of a SARS-CoV-2 infection, the method comprising administering a therapeutic composition to a subject with a SARS-CoV-2 infection, wherein the therapeutic composition comprises a first anti-SARS-CoV-2 spike glycoprotein antibody or antigen-binding fragment thereof comprising three heavy chain complementarity determining regions (HCDRs) and three light chain complementarity determining regions (LCDRs) contained within a heavy chain variable region (HCVR) and light chain variable region (LCVR) amino acid sequence pair comprising the amino acid sequences of SEQ ID NOs: 2 and 10, and a second anti-SARS-CoV-2 spike glycoprotein antibody or antigen-binding fragment thereof comprising three HCDRs and three LCDRs contained within an HCVR and an LCVR amino acid sequence pair comprising the amino acid sequences of SEQ ID NOs: 22 and 30, wherein a time to alleviate at least one clinical parameter of a SARS-CoV-2 infection in a population of seronegative subjects administered said therapeutic composition is shorter than that of a comparable population of seropositive subjects.

55. A method for improving one or more clinical parameters of a SARS-CoV-2 infection, the method comprising administering a therapeutic composition to a subject with a SARS-CoV-2 infection, wherein the therapeutic composition comprises a first anti-SARS-CoV-2 spike glycoprotein antibody or antigen-binding fragment thereof comprising three heavy chain complementarity determining regions (HCDRs) and three light chain complementarity determining regions (LCDRs) contained within a heavy chain variable region (HCVR) and light chain variable region (LCVR) amino acid sequence pair comprising the amino acid sequences of SEQ ID NOs: 2 and 10, and a second anti-SARS-CoV-2 spike glycoprotein antibody or antigen-binding fragment thereof comprising three HCDRs and three LCDRs contained within an HCVR and an LCVR amino acid sequence pair comprising the amino acid sequences of SEQ ID NOs: 22 and 30, wherein said therapeutic composition reduces viral load through 7 days post-administration (Day 7) in a population of subjects as compared to the day of administration (Day 0).

56. The method of claim 55, wherein the time-weighted-average reduction from baseline nasopharyngeal (NP) viral load through Day 7 in a seronegative population of subjects is at least 0.86 log 10 copies/mL more in patients treated with 0.6 g of the first anti-SARS-CoV-2 spike glycoprotein antibody and 0.6 g of the second anti-SARS-CoV-2 spike glycoprotein antibody, as compared to a comparable population of subjects treated with a placebo, wherein the p value is <0.0001.

57. The method of claim 55, wherein the reduction from baseline nasopharyngeal (NP) viral load through Day 7 in a seronegative population of subjects is at least 1.04 log 10 copies/mL more in patients treated with 1.2 g of the first anti-SARS-CoV-2 spike glycoprotein antibody and 1.2 g of the second anti-SARS-CoV-2 spike glycoprotein antibody, as compared to a comparable population of subjects treated with a placebo, wherein the p value is <0.0001.

58. The method of claim 55, wherein the average reduction from baseline nasopharyngeal (NP) viral load through Day 7 in the population of subjects is at least 0.71 log 10 copies/mL more in patients treated with 0.6 g of the first anti-SARS-CoV-2 spike glycoprotein antibody and 0.6 g of the second anti-SARS-CoV-2 spike glycoprotein antibody, as compared to a comparable population of subjects treated with a placebo, wherein the p value is <0.0001.

59. The method of claim 55, wherein the average reduction from baseline nasopharyngeal (NP) viral load through Day 7 in the population of subjects is a 0.86 log 10 copies/mL more in patients treated with 1.2 g of the first anti-SARS-CoV-2 spike glycoprotein antibody and 1.2 g of the second anti-SARS-CoV-2 spike glycoprotein antibody, as compared to a comparable population of subjects treated with a placebo, wherein the p value is <0.0001.

60. A method for improving one or more clinical parameters of a SARS-CoV-2 infection, the method comprising administering a therapeutic composition to a subject with a SARS-CoV-2 infection, wherein the therapeutic composition comprises a first anti-SARS-CoV-2 spike glycoprotein antibody or antigen-binding fragment thereof comprising three heavy chain complementarity determining regions (HCDRs) and three light chain complementarity determining regions (LCDRs) contained within a heavy chain variable region (HCVR) and light chain variable region (LCVR) amino acid sequence pair comprising the amino acid sequences of SEQ ID NOs: 2 and 10, and a second anti-SARS-CoV-2 spike glycoprotein antibody or antigen-binding fragment thereof comprising three HCDRs and three LCDRs contained within an HCVR and an LCVR amino acid sequence pair comprising the amino acid sequences of SEQ ID NOs: 22 and 30, wherein said therapeutic composition reduces viral load in a population of subjects.

61. The method of claim 60, wherein administration of said therapeutic composition comprises administering 0.6 g of the first anti-SARS-CoV-2 spike glycoprotein antibody and 0.6 g of the second anti-SARS-CoV-2 spike glycoprotein antibody, and wherein said administering produces a mean reduction in viral load at day 7 post-administration compared to baseline viral load measured at day 0 pre-administration of at least 3.00 log 10 copies/mL.

62. The method of claim 61, wherein said reduction is at least 3.50 log 10 copies/mL.

63. The method of claim 61, wherein said reduction is at least 3.90 log 10 copies/mL.

64. The method of claim 60, wherein administration of said therapeutic composition comprises administering 1.2 g of the first anti-SARS-CoV-2 spike glycoprotein antibody and 1.2 g of the second anti-SARS-CoV-2 spike glycoprotein antibody, and wherein said administering produces a mean reduction in viral load at day 7 post-administration compared to baseline viral load measured at day 0 pre-administration of at least 3.50 log 10 copies/mL.

65. The method of claim 61, wherein said reduction is at least 3.75 log 10 copies/mL.

66. The method of claim 61, wherein said reduction is at least 4.09 log 10 copies/mL.

67. A method for improving one or more clinical parameters of a SARS-CoV-2 infection, the method comprising administering a therapeutic composition to a subject with a SARS-CoV-2 infection, wherein the therapeutic composition comprises a first anti-SARS-CoV-2 spike glycoprotein antibody or antigen-binding fragment thereof comprising three heavy chain complementarity determining regions (HCDRs) and three light chain complementarity determining regions (LCDRs) contained within a heavy chain variable region (HCVR) and light chain variable region (LCVR) amino acid sequence pair comprising the amino acid sequences of SEQ ID NOs: 2 and 10, and a second anti-SARS-CoV-2 spike glycoprotein antibody or antigen-binding fragment thereof comprising three HCDRs and three LCDRs contained within an HCVR and an LCVR amino acid sequence pair comprising the amino acid sequences of SEQ ID NOs: 22 and 30, wherein said therapeutic composition reduces time to symptom alleviation by a median of 4 days in a population of subjects treated with 0.6 g of the first anti-SARS-CoV-2 spike glycoprotein antibody and 0.6 g of the second anti-SARS-CoV-2 spike glycoprotein antibody or 1.2 g of the first anti-SARS-CoV-2 spike glycoprotein antibody and 1.2 g of the second anti-SARS-CoV-2 spike glycoprotein antibody, as compared to a comparable population of subjects treated with a placebo.

68. The method of claim 60 or claim 67, wherein said subjects and/or population of subjects comprises subjects not hospitalized for COVID-19.

* * * * *

UNITED STATES PATENT AND TRADEMARK OFFICE
CERTIFICATE OF CORRECTION

PATENT NO. : 11,999,777 B2
APPLICATION NO. : 17/337396
DATED : June 4, 2024
INVENTOR(S) : Samit Ganguly et al.

It is certified that error appears in the above-identified patent and that said Letters Patent is hereby corrected as shown below:

In the Claims

Claim 24:
Column 218, Line 18:
"2 and 10N/10n"
Should read:
--2 and 10--

Claim 53:
Column 220, Line 22:
"2 and 10N/10n"
Should read:
--2 and 10--

Signed and Sealed this
Sixteenth Day of July, 2024

Katherine Kelly Vidal
*Director of the United States Patent and Trademark Office*